US009938323B2

(12) United States Patent
Grunewald et al.

(10) Patent No.: US 9,938,323 B2
(45) Date of Patent: Apr. 10, 2018

(54) AMATOXIN DERIVATIVES AND CONJUGATES THEREOF AS INHIBITORS OF RNA POLYMERASE

(71) Applicant: NOVARTIS AG, Basel (CH)

(72) Inventors: Jan Grunewald, San Diego, CA (US);
Yunho Jin, San Diego, CA (US);
Weijia Ou, San Diego, CA (US);
Tetsuo Uno, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/524,197

(22) PCT Filed: Nov. 5, 2015

(86) PCT No.: PCT/IB2015/058537
§ 371 (c)(1),
(2) Date: May 3, 2017

(87) PCT Pub. No.: WO2016/071856
PCT Pub. Date: May 12, 2016

(65) Prior Publication Data
US 2017/0355731 A1    Dec. 14, 2017

Related U.S. Application Data

(60) Provisional application No. 62/076,023, filed on Nov. 6, 2014.

(51) Int. Cl.
| *A61K 38/00* | (2006.01) |
| *C07K 7/64* | (2006.01) |
| *C07K 16/22* | (2006.01) |
| *C07K 16/30* | (2006.01) |

(52) U.S. Cl.
CPC ........... *C07K 7/64* (2013.01); *C07K 16/22* (2013.01); *C07K 16/30* (2013.01); *C07K 2319/30* (2013.01)

(58) Field of Classification Search
None
See application file for complete search history.

(56) References Cited

FOREIGN PATENT DOCUMENTS

| EP | 2774624 A1 | 10/2014 |
| EP | 2683409 B1 | 12/2014 |
| WO | 2009114950 A1 | 9/2009 |
| WO | 2010115629 A2 | 10/2010 |
| WO | 2011014973 A2 | 2/2011 |
| WO | 2012016186 A2 | 2/2012 |
| WO | 2012041504 A1 | 4/2012 |
| WO | 2012119787 A1 | 9/2012 |
| WO | 2013104613 A1 | 7/2013 |
| WO | 2014009025 A1 | 1/2014 |
| WO | 2014043403 A1 | 3/2014 |
| WO | 2014135282 A1 | 9/2014 |
| WO | 2014141094 A1 | 9/2014 |
| WO | 2016142049 A1 | 9/2016 |

OTHER PUBLICATIONS

Zhao, et al., "Synthesis of a Cytotoxic Amanitin for Biorthogonal Conjugation", ChemBioChem, 2015, pp. 1420-1425, vol. 16, Wiley-VCH Verlag GmbH & Co.
Adair, et al., "Antibody-drug conjugates—a perfect synergy", Expert Opin. Biol. Ther., 2012, pp. 1191-1206, vol. 12, No. 9, Informa UK, Ltd.
Flygare, et al., "Antibody-Drug Conjugates for the Treatment of Cancer", Chem. Biol. Drug. Des., 2013, pp. 113-121, vol. 81, John Wiley & Sons A/S.
Jackson, et al., "Using the Lessons Learned from the Clinic to Improve the Preclinical Development of Antibody Drug Conjugates", Pharm. Res., 2014, pp. 1-12.
(Continued)

*Primary Examiner* — Jeanette Lieb
(74) *Attorney, Agent, or Firm* — Daniel E. Raymond; Genomics Institute of the Novartis Research Foundation

(57) ABSTRACT

The invention disclosed herein relates to cytotoxic cyclic peptides of Formula (I), methods of inhibiting RNA polymerase with such cyclic peptides, immunoconjugates comprising such cyclic peptides (i.e Antibody Drug Conjugates), pharmaceutical compositions comprising such cyclic peptides immunoconjugates, compositions comprising such cyclic peptides immunoconjugates with a therapeutic co-agent and methods of treatment using such cyclic peptides immunoconjugates:

Formula (I)

23 Claims, 7 Drawing Sheets

(56) References Cited

OTHER PUBLICATIONS

Konig, et al., "Chemistry of Peptides and Proteins", Proceeding sof the Sixth USSR-FRG Symposium on Chemistry of Peptides and PRoteins, Sep. 1-5, 1987.

Moldenhauer, et al., "Therapeutic Potential of Amanitin-Conjugated Anti-Epithelial Cell Adhesion Molecule Monoclonal Antibody Against Pancreatic Cacinoma", JNCI, Apr. 18, 2012, pp. 622-634, vol. 104, Issue 8, Oxford University Press.

Senter, et al., "The discovery and development of brentuximab vedotin for use in relapsed Hogkin lymphoma and systemic anaplastic large cell lymphoma", Nature Biotechnology, Jul. 6372012, pp. 631-637, vol. 30, Nature America, Inc.

AMATOXIN DERIVATIVES AND CONJUGATES THEREOF AS INHIBITORS OF RNA POLYMERASE

CROSS-REFERENCE TO RELATED APPLICATIONS

This application is a 371 U.S. national phase application of international application number PCT/IB2015/058537 filed 5 Nov. 2015, which claims the benefit of U.S. Provisional Application No. 62/076,023, filed 6 Nov. 2014, which is incorporated by reference herein in its entirety.

FIELD OF THE INVENTION

The invention relates to amatoxins and conjugates of amatoxins to a target-binding moiety, e.g. an antibody, and the use of such conjugates to treat cancer.

BACKGROUND

Amatoxins are cyclic peptides comprised of eight amino acid units which can be prepared synthetically, or can be isolated from a variety of mushroom species, such as *Amanita phalloides* (green death cap mushroom), *Amanita bisporigera* (destroying angel), *Amanita ocreata* (destroying angel), *Amanita virosa* (destroying angel), *Amanita bisporigera* (fool's mushroom), *Lepiota brunneo-incamata* (deadly dapperling), *Conocybe filaris* and *Galerina marginata*.

There are currently ten known members of the Amatoxin Family: alpha-Amanitin, beta-Amanitin, gamma-Amanitin, epsilon-Amanitin, Amanullin, Amanullinic acid, Amaninamide, Amanin and Proamanullin. Different mushroom species contain varying amounts of different Amatoxin family members.

Amatoxins are potent and selective inhibitors of RNA polymerase II, a vital enzyme in the synthesis of messenger RNA (mRNA), microRNA, and small nuclear RNA (snRNA). By inhibiting the synthesis of mRNA, Amatoxins thereby stop cell metabolism by inhibiting transcription and protein biosynthesis, which results in cellular apoptosis. Consequently Amatoxins stop cell growth and proliferation.

Alpha-amanitin, is known to be an extremely potent inhibitor of eukaryotic RNA polymerase II (EC2.7.7.6) and to a lesser degree, RNA polymerase III, thereby inhibiting transcription and protein biosynthesis. Wieland (1983) Int. J. Pept. Protein Res. 22(3):257-276. Alpha-amanitin binds non-covalently to RNA polymerase II and dissociates slowly, making enzyme recovery unlikely.

The use of antibody-drug conjugates (ADCs) for the targeted delivery of cell proliferation inhibitors and/or cytotoxic agents to specific cells has been the focus of significant research. Antibody-Drug Conjugate, Methods in Molecular Biology, Vol. 1045, Editor L. Ducry, Humana Press (2013). ADCs include an antibody selected for its ability to bind to a cell targeted for therapeutic intervention, linked to a drug selected for its cytostatic or cytotoxic activity. Binding of the antibody to the targeted cell thereby delivers the drug to the site where its therapeutic effect is needed. Many antibodies that recognize and selectively bind to targeted cells, like cancer cells, have been disclosed for use in ADCs, and many methods for attaching payload (drug) compounds such as cytotoxins to antibodies have also been described. In spite of the extensive work on ADCs, though, only a few classes of cell proliferation inhibitors have been used extensively as ADC payloads. Even though the first ADC approved for use in humans in the U.S. was launched in 2000 (and later withdrawn from the market), a decade later only a few chemical classes of drug compounds (maytansinoids, auristatins, calicheamycins and duocarmycins) had reached clinical trials as payloads for ADCs. *Antibody-Drug Conjugates: the Next Generation of Moving Parts*, A. Lash, *Start-Up*, December 2011, 1-6.

The use of amatoxins as cytotoxic moieties in ADC's for tumour therapy was explored in 1981 (Davis & Preston, Science 1981, 213, 1385-1388) by coupling an anti-Thy 1.2 antibody to alpha-amanitin using a linker attached to the 7' position of the indole ring via diazotation. Morris & Venton (Morris & Venton, Int. J. Peptide Protein Res. 1983, 21 419-430) also demonstrated that substitution at the 7' position resulted in a derivative which maintained cytotoxic activity.

Patent application EP 1 859 811 A 1 (published Nov. 28, 2007) described the direct conjugation (i.e. without a linker structure) of albumin or a monoclonal antibody (HEA125, OKT3, or PA-1) to the gamma C-atom of amatoxin amino acid 1 of beta-amanitin. The inhibitory effect of these conjugates on the proliferation of breast cancer cells (MCF-7), Burkitt's lymphoma cells (Raji), and Tlymphoma cells (Jurkat) was shown. The use of linkers was suggested, however no such constructs were exemplified and no details regarding linker attachment sites on Amatoxins were provided.

Patent applications WO 2010/115629 and WO 2010/115630 (both published Oct. 14, 2010) describe conjugates, where antibodies, such as antiEpCAM antibodies such as humanized antibody huHEA125, are coupled to amatoxins via (i) the gamma C-atom of amatoxin amino acid 1, (ii) the 6' C-atom of amatoxin amino acid 4, or (iii) via the delta C-atom of amatoxin amino acid 3, in each case either directly or via a linker between the antibody and the amatoxins. The inhibitory effects of these conjugates on the proliferation of breast cancer cells (cell line MCF-7), pancreatic carcinoma (cell line Capan-1), colon cancer (cell line Colo205) and cholangiocarcinoma (cell line OZ) were shown.

Patent applications WO 2012/119787 (published Sep. 13, 2012) describes conjugating a target-binding moiety via a linker attached to the amatoxin indole nitrogen. The cytotoxic activity of such conjugates on a HER2-positive tumor cell line in vitro was disclosed.

Patent applications WO 2014/043403 (published Mar. 20, 2014) describes conjugating a target-binding moiety via a linker attached to the 7' position of the amatoxin indole. The cytotoxic activity of such conjugates on Herceptin and IgG1 in MDA-MB-468 cells was disclosed. Also, the cytotoxic activity of such conjugates on Herceptin in PC3, HCC-1954 and MDA-MB-46 cells was disclosed.

In view of the toxicity of amatoxins, particularly for liver cells, it is important that ADC's comprising a linked amatoxin remain highly stable in plasma prior to the release of the amatoxin after internalization into the target cells. In this regard, improvements of the conjugate stability may have drastic consequences for the therapeutic window and the safety of the amatoxin conjugates for therapeutic approaches. Thus, given the widely acknowledged value of ADCs as therapeutics for treating cancer there remains a need for the stable delivery of potent RNA polymerase inhibitors to the target cells prior to internalization of the RNA polymerase inhibitors.

SUMMARY OF THE INVENTION

The invention provided herein includes cytotoxic cyclic peptides of formula (I), which are analogs of alpha-amanitin and beta-amanitin, and methods of using such cytotoxic cyclic peptides as the drug component of an antibody-drug conjugate (ADC). The present invention includes novel cytotoxic cyclic peptides and the use of such novel cytotoxic cyclic peptides as payloads for ADCs. The invention further includes methods and intermediates useful for incorporating such novel cytotoxic cyclic peptides into ADCs.

The invention further includes immunoconjugates comprising such cyclic peptides (i.e Antibody Drug Conjugates), pharmaceutical compositions comprising such cyclic peptides immunoconjugates and compositions comprising such cyclic peptides immunoconjugates with a therapeutic co-agent.

The invention further includes methods of inhibiting RNA polymerase using such immunoconjugates comprising such cyclic peptides and methods of treating cell proliferation diseases using such immunoconjugates comprising such cyclic peptides.

In one aspect the cytotoxic cyclic peptides of the invention, or stereoisomer and pharmaceutically acceptable salts thereof, have the structure of Formula (A)

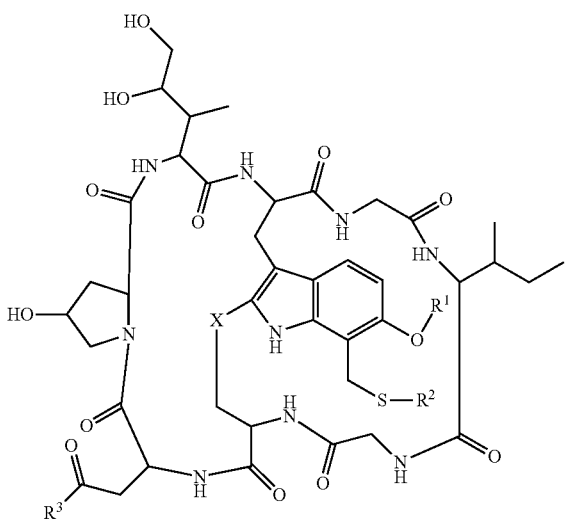

Formula (A)

wherein:
X is S(=O), S(=O)$_2$ or S;
R$^1$ is H or —CH$_3$; R$^2$ is -L$_1$L$_2$R$^4$, -L$_3$R$^6$ or —(CH$_2$)$_m$X$_3$(CH$_2$)$_m$R$^4$; R$^3$ is —NH$_2$ or —OH; L$_1$ is —(CH$_2$)$_m$NR$^5$C(=O)—,

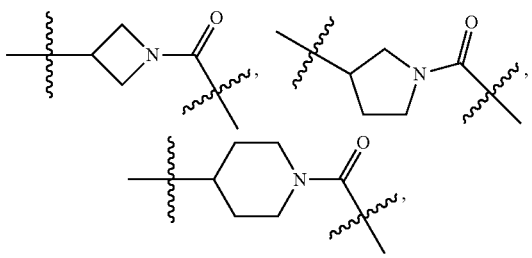

—(CH$_2$)$_m$X$_3$(CH$_2$)$_m$—, —(CH$_2$)$_m$NR$^5$—,

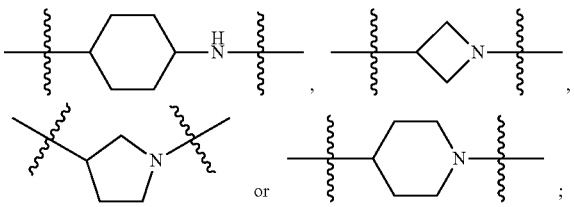

L$_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)NR$^5$C(=O)(CH$_2$)$_m$—, —(CH$_2$)$_m$C(=O)NR$^5$(CH$_2$)$_m$(O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$)$_n$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$(O(CH$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$— or —(CH$_2$)$_m$X$_3$(CH$_2$)$_m$NR$^5$C(=O)—, wherein:
X₁ is 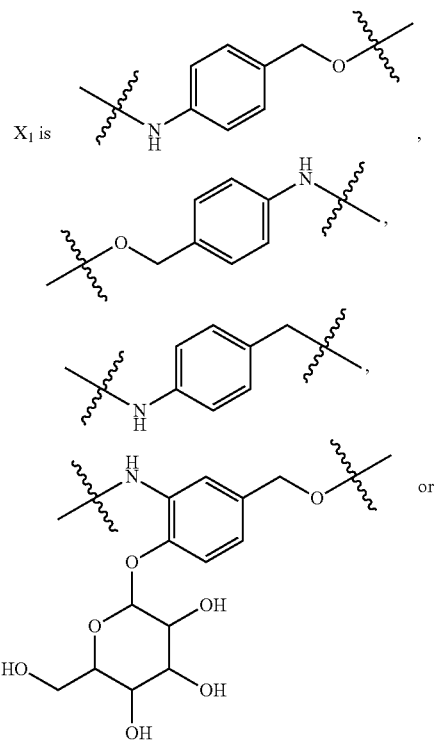
X₂ is 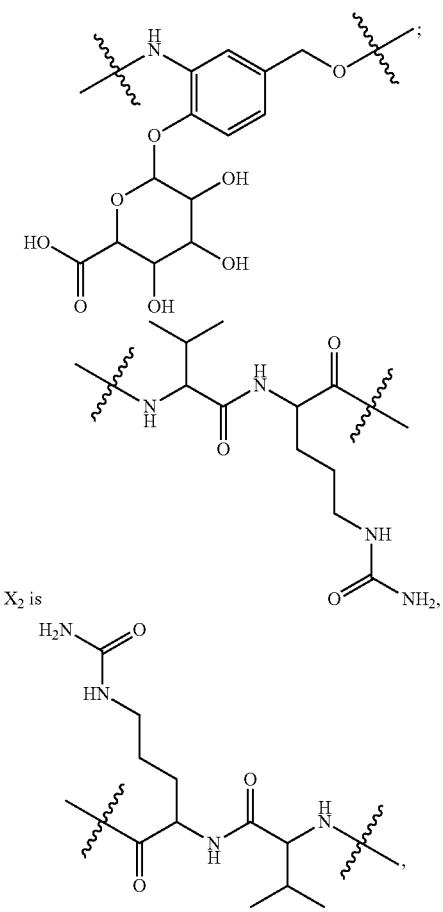
X₃ is 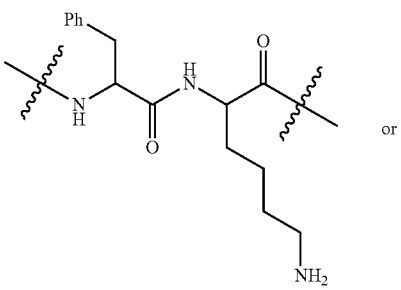 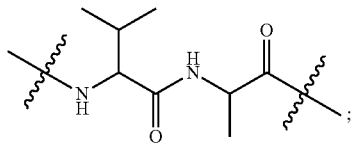, and
X₄ is 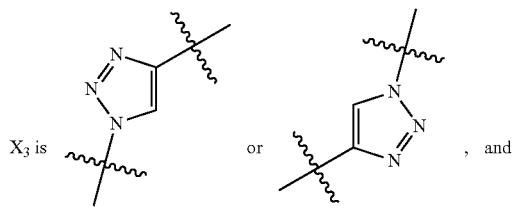;
L₃ is —(CH₂)$_m$NR⁵C(=O)—;
R⁴ is
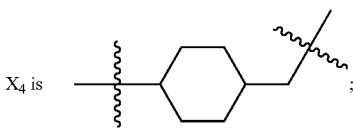
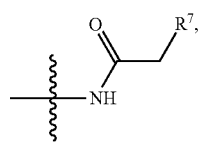
—NR₅C(=O)CH=CH₂, —N₃,
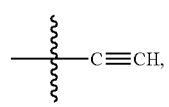 [SMILES: *C#C]
SH, —S(=O)₂(CH=CH₂), —(CH₂)₂S(=O)₂(CH=CH₂), —NR⁵S(=O)₂(CH=CH₂), —NR⁵C(=O)CH₂R⁷, —NR⁵C(=O)CH₂Br, —NR⁵C(=O)CH₂I, —NHC(=O)CH₂Br, —NHC(=O)CH₂I, —ONH₂, —C(=O)NHNH₂,

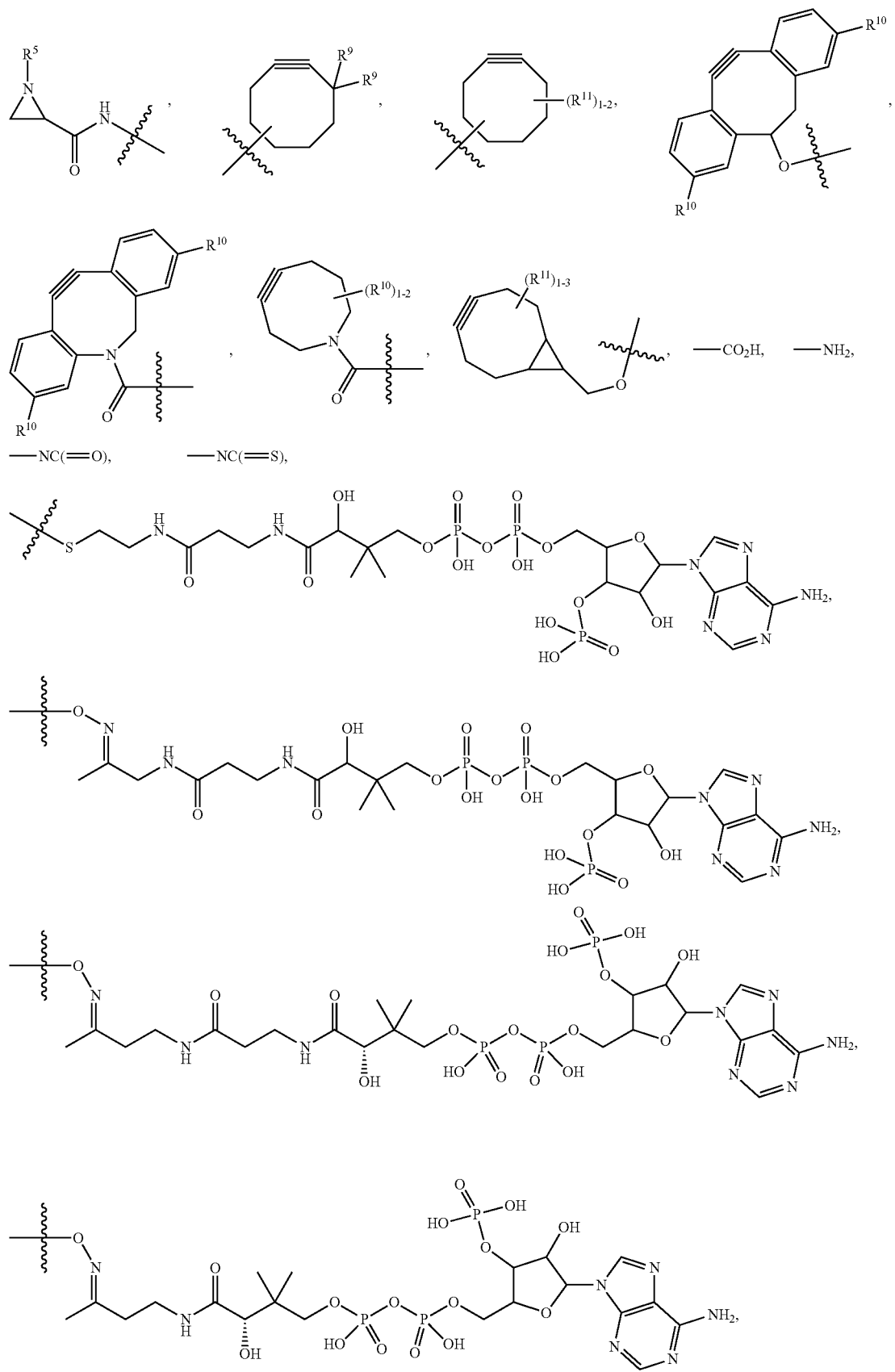

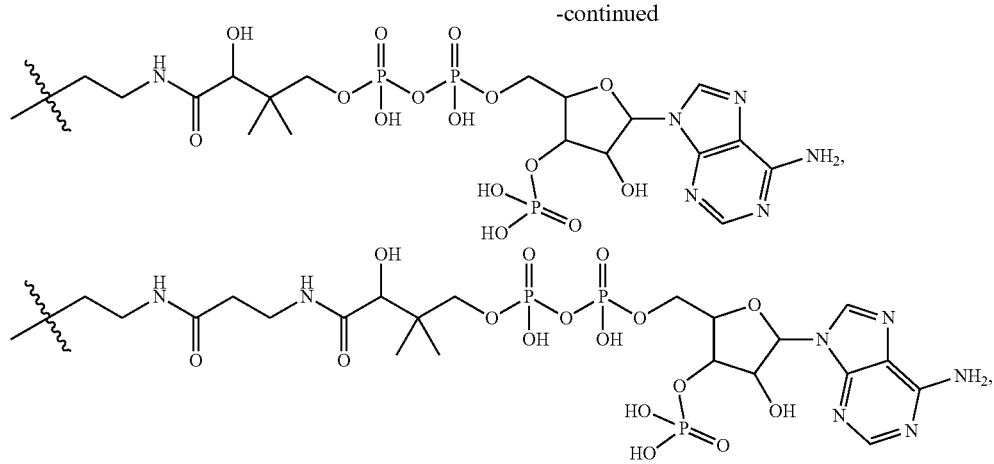
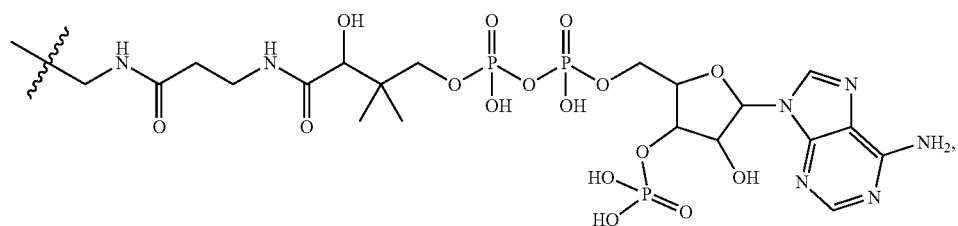
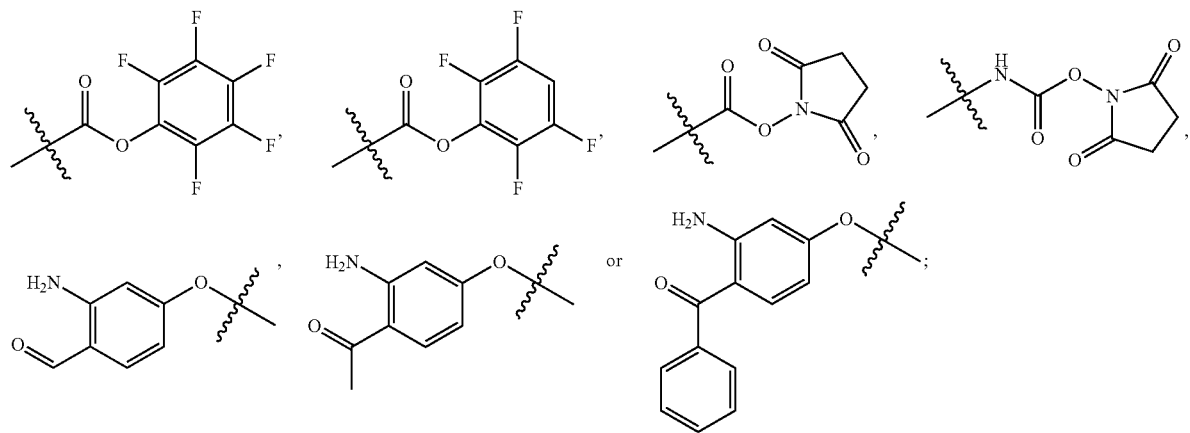
each R[5] is independently selected from H and $C_1$-$C_6$alkyl;
R[6] is
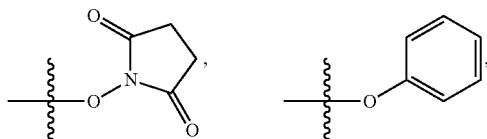
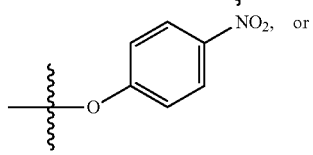
-continued
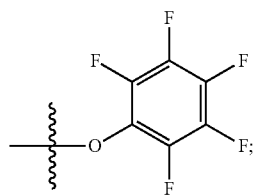

$R^7$ is —S(CH$_2$)$_n$CHR$^8$NHC(=O)R$^5$ or

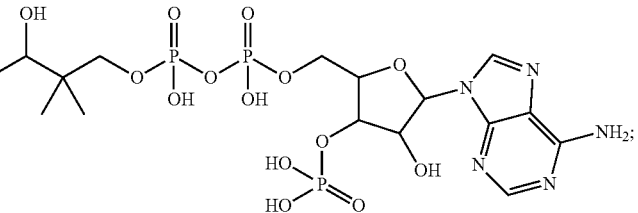

$R^8$ is $R^5$ or —C(=O)OR$^5$;
each $R^9$ is independently selected from H, C$_1$-C$_6$alkyl, F, Cl, and —OH;
each $R^{10}$ is independently selected from H, C$_1$-C$_6$alkyl, F, Cl, —NH$_2$, —OCH$_3$, —OCH$_2$CH$_3$, —N(CH$_3$)$_2$, —CN, —NO$_2$ and —OH;
each $R^{11}$ is independently selected from H, C$_{1-6}$alkyl, fluoro, benzyloxy substituted with —C(=O)OH, benzyl substituted with —C(=O)OH, C$_{1-4}$alkoxy substituted with —C(=O)OH and C$_{1-4}$alkyl substituted with —C(=O)OH;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.

In one aspect the cytotoxic cyclic peptides of the invention, or stereoisomer and pharmaceutically acceptable salts thereof, have the structure of Formula (I)

Formula (I)

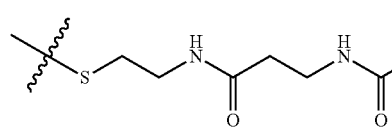

wherein:
$R^1$ is H or —CH$_3$; $R^2$ is -L$_1$L$_2$R$^4$, -L$_3$R$^6$ or —(CH$_2$)$_m$X$_3$(CH$_2$)$_m$R$^4$; $R^3$ is —NH$_2$ or —OH;
$L_1$ is —(CH$_2$)$_m$NR$^5$C(=O)—, -continued —(CH$_2$)$_m$X$_3$(CH$_2$)$_m$—, —(CH$_2$)$_m$NR$^5$—, or $L_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O $-(CH_2)_mC(R^5)_2NR^5-$, $-(CH_2)_mX_3(CH_2)_mNR^5-$, $-(CH_2)_mX_3(CH_2)_m(O(CH_2)_m)_nNR^5-$, $-(CH_2)_mNR^5-$, $-(CH_2)_mC(=O)NR^5(CH_2)_m(O(CH_2)_m)_nNR^5-$, $-(CH_2)_m(O(CH_2)_m)_nNR^5-$, $-(CH_2CH_2O)_n(CH_2)_m-$, $-(CH_2)_m(OCH_2CH_2)_n-$, $-(CH_2)_mO(CH_2)_m-$, $-(CH_2)_mS(=O)_2-$, $-(CH_2)_mC(=O)NR^5(CH_2)_mS(=O)_2-$, $-(CH_2)_mX_3(CH_2)_mS(=O)_2-$, $-(CH_2)_mX_2X_1C(=O)-$, $-(CH_2)_m(O(CH_2)_m)_nC(=O)X_2X_1C(=O)-$, $-(CH_2)_m(O(CH_2)_m)_nX_2X_1C(=O)-$, $-(CH_2)_mX_3(CH_2)_mX_2X_1C(=O)-$, $-(CH_2)_mX_3(CH_2)_m(O(CH_2)_m)_nX_2X_1C(=O)-$, $-(CH_2)_mX_3(CH_2)_mC(=O)NR^5(CH_2)_mNR^5C(=O)-$, $-(CH_2)_mX_3(CH_2)_mC(=O)NR^5(CH_2)_mC(=O)-$, $-(CH_2)_mX_3(CH_2)_mC(=O)NR^5(CH_2)_m(O(CH_2)_m)_nC(=O)-$, $-(CH_2)_mC(=O)X_2X_1C(=O)NR^5(CH_2)_m-$, $-(CH_2)_mX_3(O(CH_2)_m)_nC(=O)-$, $-(CH_2)_mNR^5C(=O)((CH_2)_mO)_n(CH_2)_m-$, $-(CH_2)_m(O(CH_2)_m)_nC(=O)NR^5(CH_2)_m-$, $-(CH_2)_mNR^5C(=O)NR^5(CH_2)_m-$ or $-(CH_2)_mX_3(CH_2)_mNR^5C(=O)-$, wherein:

$X_1$ is

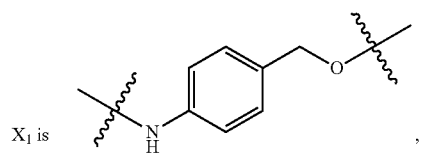

,

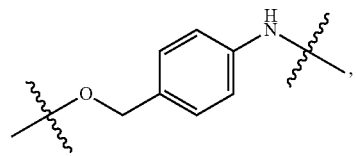

,

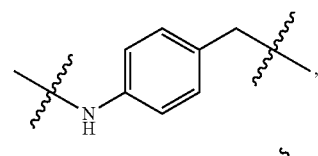

,

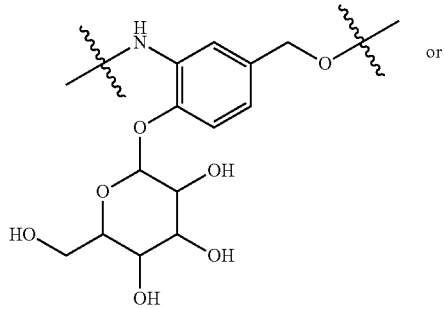

or

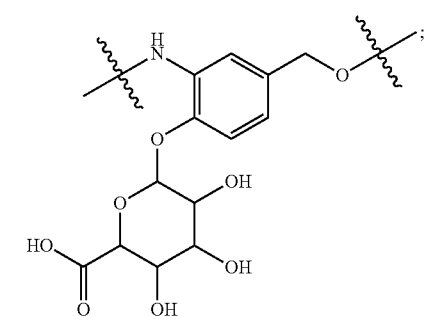

;

$X_2$ is

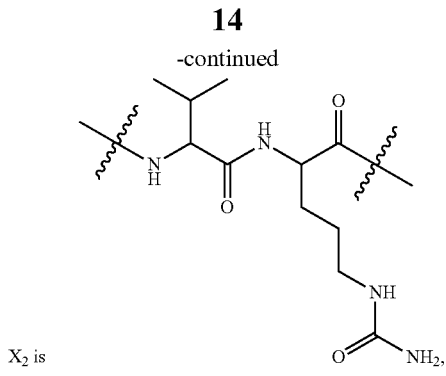

,

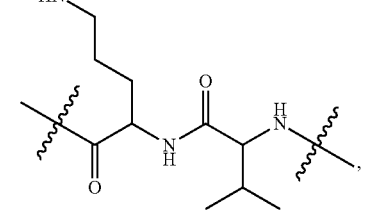

,

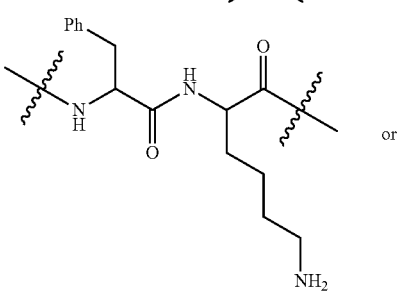

or

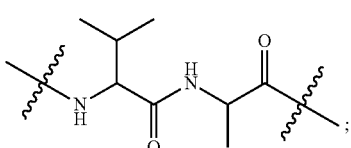

;

$X_3$ is 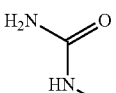 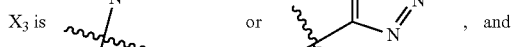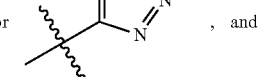, and $X_4$ is 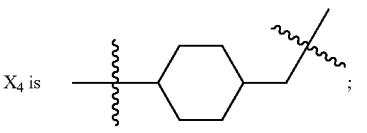;

$L_3$ is $-(CH_2)_mNR^5C(=O)-$;
$R^4$ is

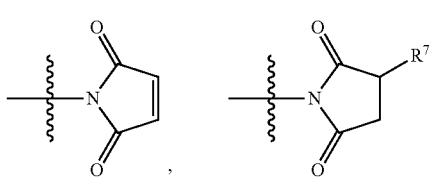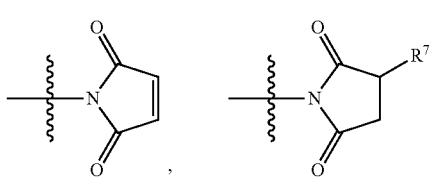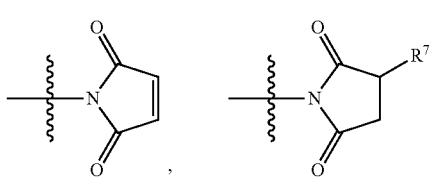,

-continued
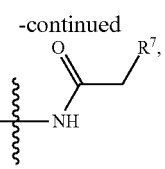
—NR5C(=O)CH=CH2, —N3,
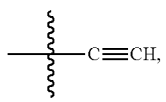 [SMILES: *C#C]
SH, —S(=O)2(CH=CH2), —(CH2)2S(=O)2(CH=CH2), —NR5S(=O)2(CH=CH2), —NR5C(=O)CH2R7, —NR5C(=O)CH2Br, —NR5C(=O)CH2I, —NHC(=O)CH2Br, —NHC(=O)CH2I, —ONH2, —C(=O)NHNH2,
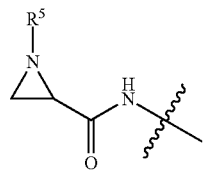 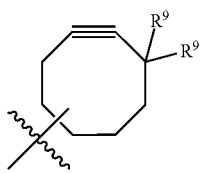
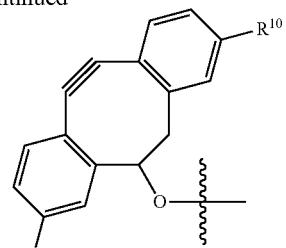
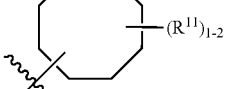
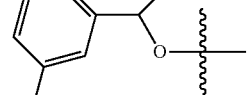
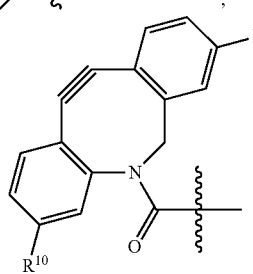
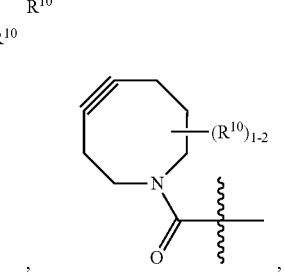
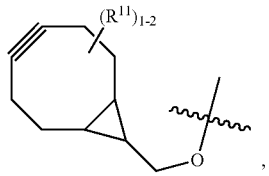
—CO2H, —NH2, —NC(=O), —NC(=S),
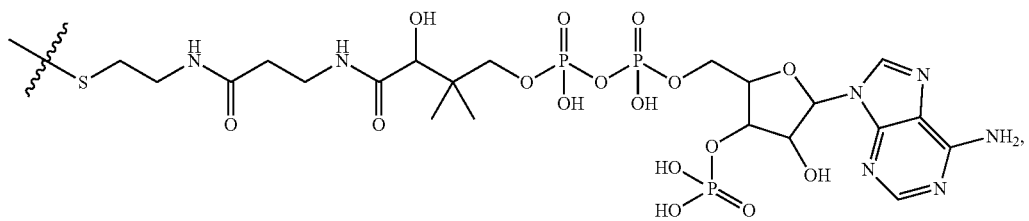 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]
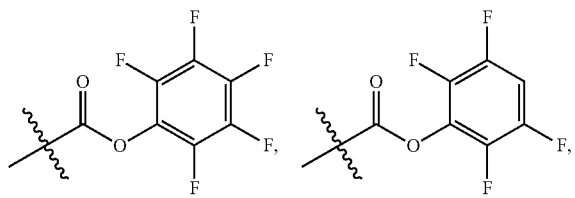
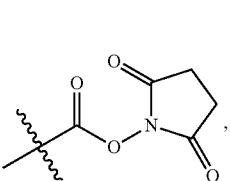
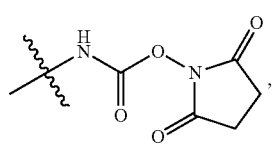
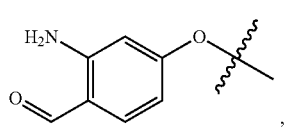
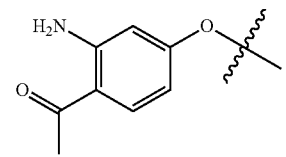
or
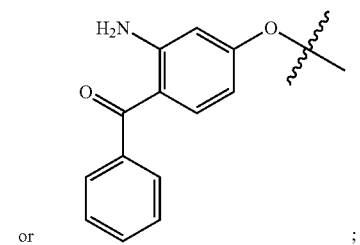
;

each R⁵ is independently selected from H and C₁-C₆alkyl;

R⁶ is

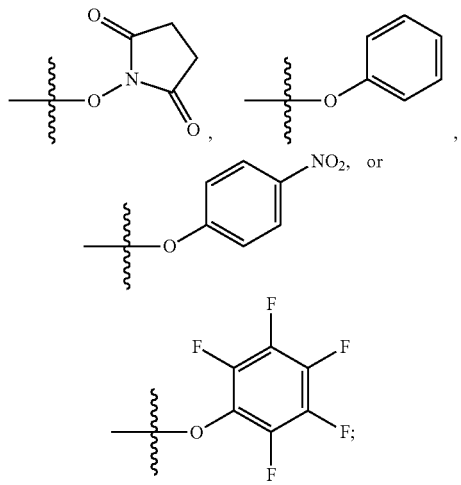

R⁷ is —S(CH₂)ₙCHR⁸NHC(=O)R⁵ or

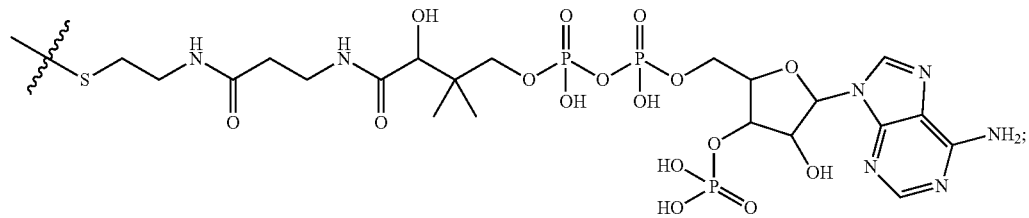 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]

R⁸ is R⁵ or —C(=O)OR⁵;

each R⁹ is independently selected from H, C₁-C₆alkyl, F, Cl, and —OH;

each R¹⁰ is independently selected from H, C₁-C₆alkyl, F, Cl, —NH₂, —OCH₃, —OCH₂CH₃, —N(CH₃)₂, —CN, —NO₂ and —OH;

each R¹¹ is independently selected from H, C₁₋₆alkyl, fluoro, benzyloxy substituted with —C(=O)OH, benzyl substituted with —C(=O)OH, C₁₋₄alkoxy substituted with —C(=O)OH and C₁₋₄alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments the cytotoxic cyclic peptides of the invention, or stereoisomer and pharmaceutically acceptable salts thereof, have the structure of Formula (I)

Formula (I)

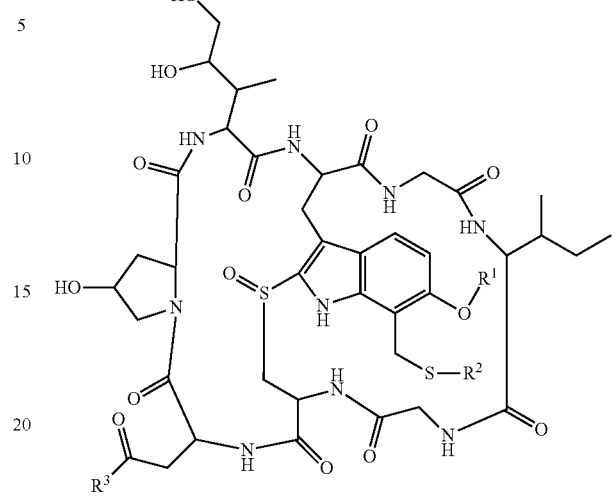

wherein:
R¹ is H or —CH₃; R² is -L₁L₂R⁴, -L₃R⁶ or —(CH₂)ₘX₃(CH₂)ₘR⁴; R³ is —NH₂ or —OH;
L₁ is —(CH₂)ₘNR⁵C(=O)—,

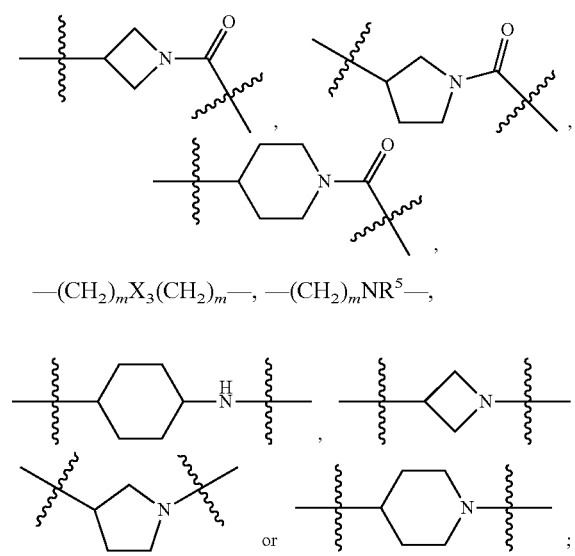

—(CH₂)ₘX₃(CH₂)ₘ—, —(CH₂)ₘNR⁵—,

L₂ is —(CH₂)ₘ—, —NR⁵(CH₂)ₘ—, —(CH₂)ₘNR⁵C(=O)(CH₂)ₘ—, —X₄—, —(CH₂)ₘNR⁵C(=O)X₄—, —(CH₂)ₘNR⁵C(=O)—, —((CH₂)ₘO)ₙ(CH₂)ₘ—, —((CH₂)ₘO)ₙ

$-(CH_2)_mX_3(CH_2)_m-$, $-NR^5((CH_2)_mO)_nX_3(CH_2)_m-$, $-X_1X_2C(=O)(CH_2)_m-$, $-(CH_2)_n(O(CH_2)_m)_n-$, $-(CH_2)_mNR^5(CH_2)_m-$, $-(CH_2)_mNR^5C(=O)(CH_2)_m-$, $-(CH_2)_mX_3(CH_2)_m-$, $-(CH_2)_mC(=O)NR^5(CH_2)_mNR^5C(=O)(CH_2)_m-$, $-(CH_2)_mC(=O)-$, $-(CH_2)_mNR^5(CH_2)_mC(=O)X_2X_1C(=O)-$, $-(CH_2)_mX_3(CH_2)_mC(=O)X_2X_1C(=O)-$, $-(CH_2)_mC(=O)NR^5(CH_2)_m-$, $-(CH_2)_mC(=O)NR^5(CH_2)_mX_3(CH_2)_m-$, $-(CH_2)_mX_3(CH_2)_mNR^5C(=O)(CH_2)_m-$, $-(CH_2)_mX_3(CH_2)_mC(=O)NR^5(CH_2)_m-$, $-(CH_2)_mO)_n(CH_2)_mNR^5C(=O)(CH_2)_m-$, $-(CH_2)_mC(=O)NR^5(CH_2)_m(O(CH_2)_m)_n-$, $-(CH_2)_m(O(CH_2)_m)_nC(=O)-$, $-(CH_2)_mNR^5(CH_2)_mC(=O)-$, $-(CH_2)_mC(=O)NR^5(CH_2)_mNR^5C(=O)-$, $-(CH_2)_m(O(CH_2)_m)_nX_3(CH_2)_m-$, $-(CH_2)_mX_3((CH_2)_mO)_n(CH_2)_m-$, $-(CH_2)_mX_3(CH_2)_mC(=O)-$, $-(CH_2)_mC(=O)NR^5(CH_2)_mO)_n(CH_2)_mX_3(CH_2)_m-$, $-(CH_2)_mX_3(CH_2)_m(O(CH_2)_m)_nNR^5C(=O)(CH_2)_m-$, $-(CH_2)_mX_3(CH_2)_m(O(CH_2)_m)_nC(=O)-$, $-(CH_2)_mX_3(CH_2)_m(O(CH_2)_m)_n-$, $-(CH_2)_mC(=O)NR^5(CH_2)_mC(=O)-$, $-(CH_2)_mC(=O)NR^5(CH_2)_m(O(CH_2)_m)_nC(=O)-$, $-((CH_2)_mO)_n(CH_2)_mNR^5C(=O)(CH_2)_m-$, $-(CH_2)_mC(=O)NR^5(CH_2)_mC(=O)NR^5(CH_2)_m-$, $-(CH_2)_mNR^5C(=O)(CH_2)_mNR^5C(=O)(CH_2)_m-$, $-(CH_2)_mX_3(CH_2)_mC(=O)NR^5-$, $-(CH_2)_mNR^5-$, $-(CH_2)_mX_3-$, $-C(R^5)_2(CH_2)_m-$, $-(CH_2)_mC(R^5)_2NR^5-$, $-(CH_2)_mC(=O)NR^5(CH_2)_mNR^5-$, $-(CH_2)_mC(=O)NR^5(CH_2)_mNR^5C(=O)NR^5-$, $-(CH_2)_mC(=O)X_2X_1C(=O)-$, $-C(R^5)_2(CH_2)_mNR^5C(=O)(CH_2)_m-$, $-(CH_2)_mC(=O)NR^5(CH_2)_mC(R^5)_2NR^5-$, $-C(R^5)_2(CH_2)_mX_3(CH_2)_m-$, $-(CH_2)_mX_3(CH_2)_mC(R^5)_2NR^5-$, $-C(R^5)_2(CH_2)_mOC(=O)NR^5(CH_2)_m-$, $-(CH_2)_mNR^5C(=O)O(CH_2)_mC(R^5)_2NR^5-$, $-(CH_2)_mX_3(CH_2)_mNR^5-$, $-(CH_2)_mX_3(CH_2)_m(O(CH_2)_m)_nNR^5-$, $-(CH_2)_m NR^5-$, $-(CH_2)_mC(=O)NR^5(CH_2)_m(O(CH_2)_m)_n NR^5-$, $-(CH_2)_m(O(CH_2)_m)_nNR^5-$, $-(CH_2CH_2O)_n(CH_2)_m-$, $-(CH_2)_m(OCH_2CH_2)_n-$, $-(CH_2)_mO(CH_2)_m-$, $-(CH_2)_mS(=O)_2-$, $-(CH_2)_mC(=O)NR^5(CH_2)_mS(=O)_2-$, $-(CH_2)_mX_3(CH_2)_mS(=O)_2-$, $-(CH_2)_mX_2X_1C(=O)-$, $-(CH_2)_m(O(CH_2)_m)_nC(=O)X_2X_1C(=O)-$, $-(CH_2)_m(O(CH_2)_m)_nX_2X_1C(=O)-$, $-(CH_2)_mX_3(CH_2)_mX_2X_1C(=O)-$, $-(CH_2)_mX_3(CH_2)_m(O(CH_2)_m)_nX_2X_1C(=O)-$, $-(CH_2)_mX_3(CH_2)_mC(=O)NR^5(CH_2)_mNR^5C(=O)-$, $-(CH_2)_mX_3(CH_2)_mC(=O)NR^5(CH_2)_mC(=O)-$, $-(CH_2)_mX_3(CH_2)_mC(=O)NR^5(CH_2)_m(O(CH_2)_m)_nC(=O)-$, $-(CH_2)_mC(=O)X_2X_1C(=O)NR^5(CH_2)_m-$, $-(CH_2)_mX_3(O(CH_2)_m)_nC(=O)-$, $-(CH_2)_mNR^5C(=O)((CH_2)_mO)_n(CH_2)_m-$, $-(CH_2)_m(O(CH_2)_m)_nC(=O)NR^5(CH_2)_m-$, $-(CH_2)_mNR^5C(=O)NR^5(CH_2)_m-$ or $-(CH_2)_mX_3(CH_2)_mNR^5C(=O)-$,
wherein:

$X_1$ is

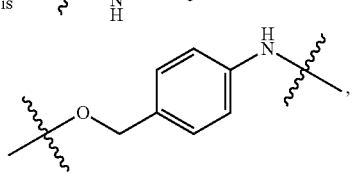

,

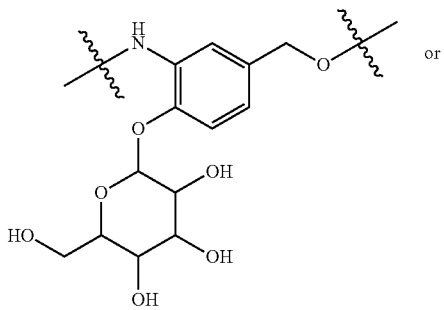 or

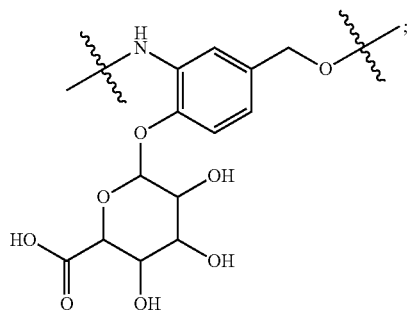;

$X_2$ is

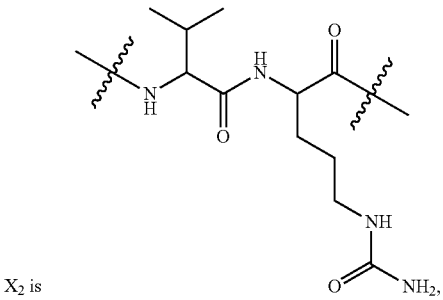

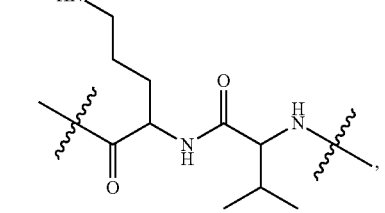 or

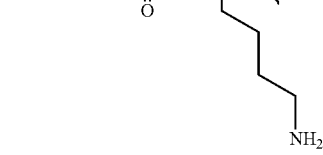

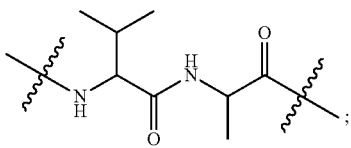;

-continued
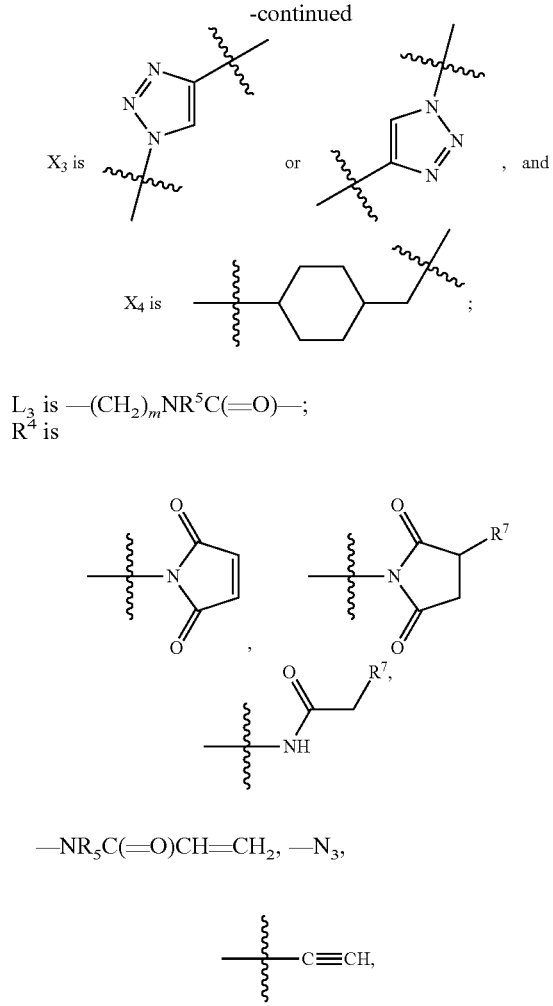
$X_3$ is ... or ..., and
$X_4$ is ...;
$L_3$ is —(CH$_2$)$_m$NR$^5$C(=O)—;
$R^4$ is
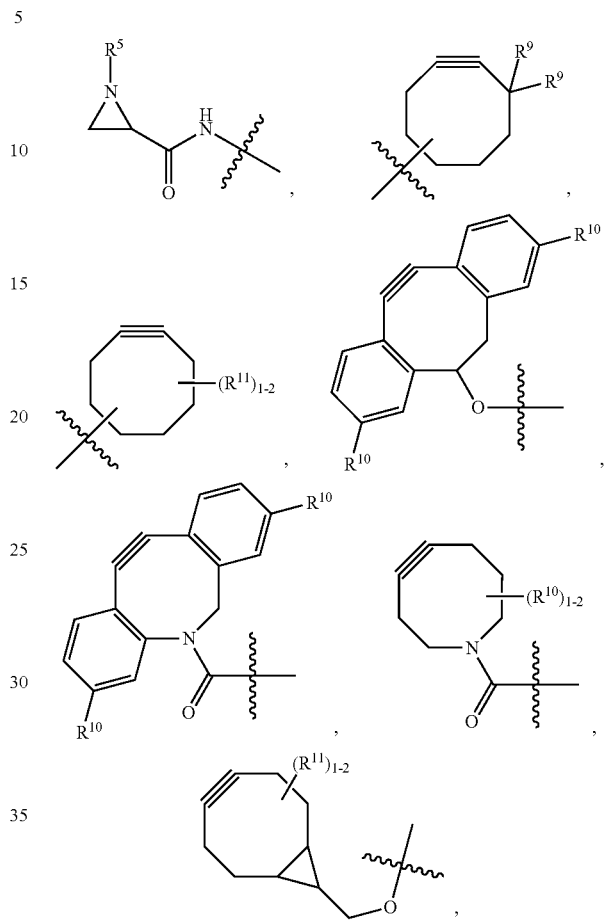
—NR$_5$C(=O)CH=CH$_2$, —N$_3$,
SH, —S(=O)$_2$(CH=CH$_2$), —(CH$_2$)$_2$S(=O)$_2$(CH=CH$_2$), —NR$^5$S(=O)$_2$(CH=CH$_2$), —NR$^5$C(=O)CH$_2$R$^7$, —NR$^5$C(=O)CH$_2$Br, —NR$^5$C(=O)CH$_2$I, —NHC(=O)CH$_2$Br, —NHC(=O)CH$_2$I, —ONH$_2$, —C(=O)NHNH$_2$,
—CO$_2$H, —NH$_2$, —NC(=O), —NC(=S),
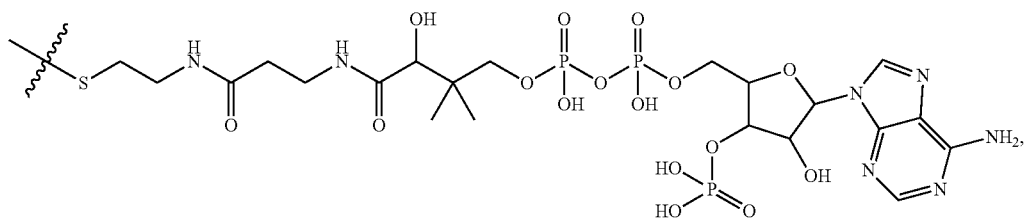
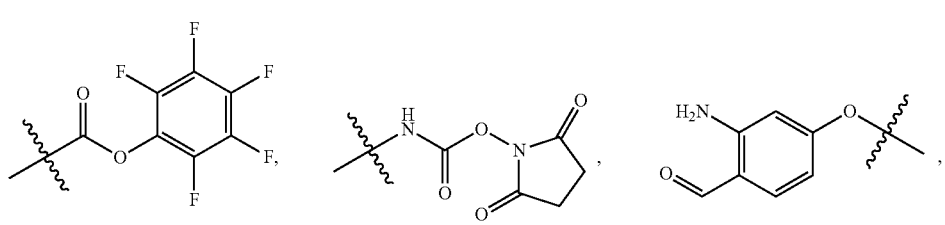

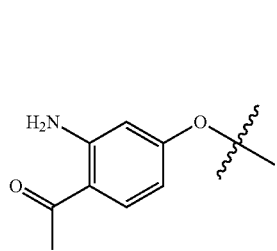 or 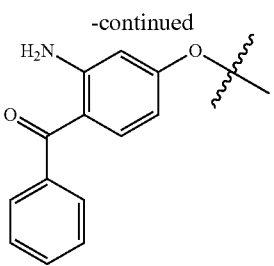 ;

each R⁵ is independently selected from H and $C_1$-$C_6$alkyl;
R⁶ is

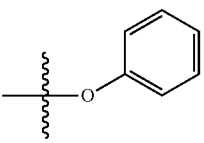

R⁷ is —S(CH$_2$)$_n$CHR⁸NHC(=O)R⁵ or

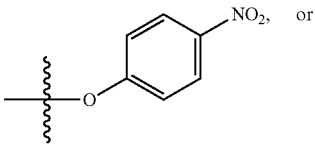

R⁸ is R⁵ or —C(=O)OR⁵;

each R⁹ is independently selected from H, $C_1$-$C_6$alkyl, F, Cl, and —OH;

each $R^{10}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments of this aspect of the cytotoxic cyclic peptides having the structure of Formula (I), are cytotoxic cyclic peptides having the structure of Formula (Ia):

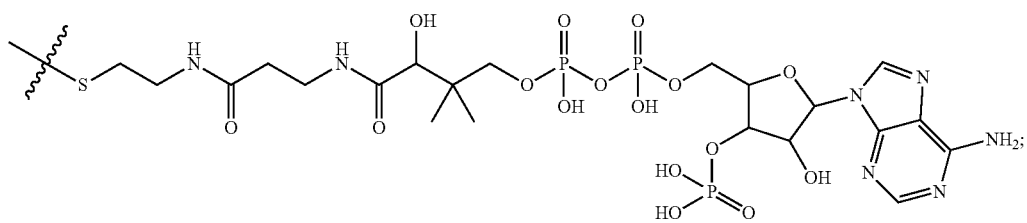

Formula (Ia)

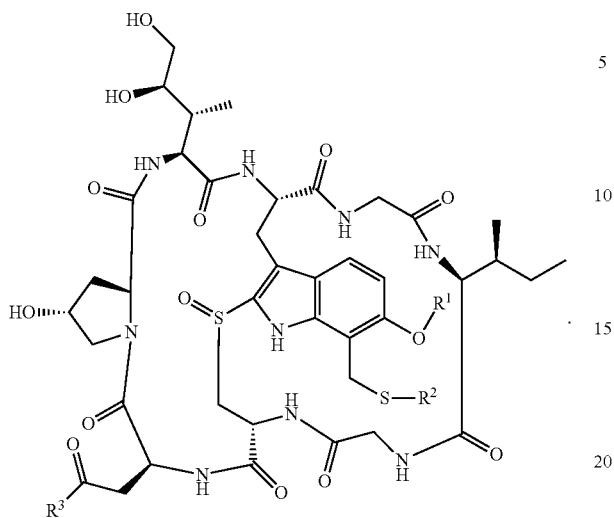

In certain embodiments of such cytotoxic cyclic peptides of Formula (I) and Formula (Ia):
$R^1$ is H or —$CH_3$; $R^2$ is -$L_1L_2R^4$, -$L_3R^6$ or —$(CH_2)_mX_3(CH_2)_mR^4$; $R^3$ is —$NH_2$ or —OH;
$L_1$ is —$(CH_2)_mNR^5C(=O)$—,

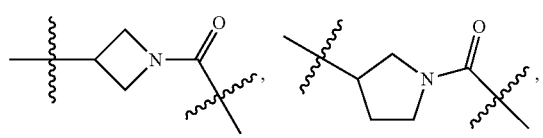

or —$(CH_2)_mX_3(CH_2)_m$—;
$L_2$ is —$(CH_2)_m$—, —$NR^5(CH_2)_m$—, —$(CH_2)_mNR^5C(=O)(CH_2)_m$—, —$X_4$—, —$(CH_2)_mNR^5C(=O)X_4$—, —$(CH_2)_mNR^5C(=O)$—, —$((CH_2)_mO)_n(CH_2)_m$—, —$((CH_2)_mO)_n(CH_2)_mX_3(CH_2)_m$—, —$NR^5((CH_2)_mO)_nX_3(CH_2)_m$— or —$X_1X_2C(=O)(CH_2)_m$—,
wherein:
$X_1$ is

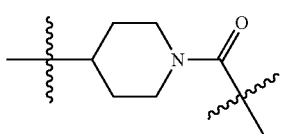

;

$X_2$ is

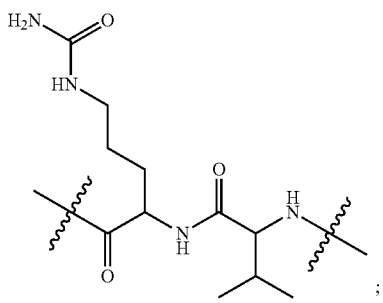 [SMILES: *NC(C(=O)NC(CCCNC(N)=O)C(*)=O)C(C)C]

;

$X_3$ is

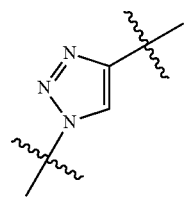 [SMILES: *c1cn(*)nn1]

and $X_4$ is

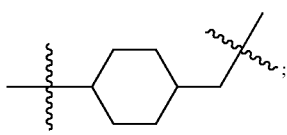 [SMILES: *CC1CCC(*)CC1]

;

$L_3$ is —$(CH_2)_mNR^5C(=O)$—; $R^4$ is

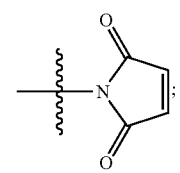 [SMILES: *N1C(=O)C=CC1=O]

;

$R^6$ is

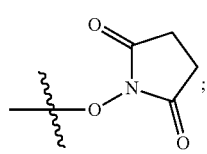 [SMILES: *ON1C(=O)CCC1=O]

;

each $R^5$ is independently selected from H and $C_1$-$C_6$alkyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.
In certain embodiments of such cytotoxic cyclic peptides of Formula (I) and Formula (Ia):
$R^1$ is H or —$CH_3$; $R^2$ is -$L_1L_2R^4$, -$L_3R^6$ or —$(CH_2)_mX_3(CH_2)_mR^4$; $R^3$ is —$NH_2$ or —OH;

$L_1$ is —$(CH_2)_m NR^5C(=O)$—,

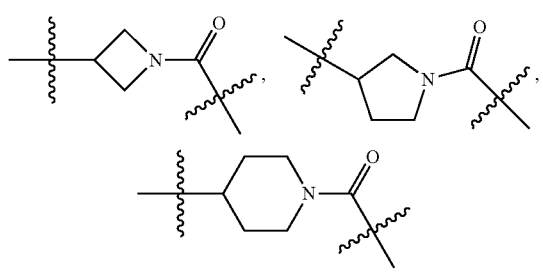

or —$(CH_2)_m X_3(CH_2)_m$—;

$L_2$ is —$(CH_2)_m$—, —$NR^5(CH_2)_m$—, —$(CH_2)_m NR^5C(=O)(CH_2)_m$—, —$X_4$—, —$(CH_2)_m NR^5C(=O)X_4$—, —$(CH_2)_m NR^5C(=O)$—, —$((CH_2)_m O)_n(CH_2)_m$—, —$((CH_2)_m O)_n(CH_2)_m X_3(CH_2)_m$—, —$NR^5((CH_2)_m O)_n X_3(CH_2)_m$—, —$NR^5((CH_2)_m O)_n(CH_2)_m X_3(CH_2)_m$— or —$X_1 X_2C(=O)(CH_2)_m$—, wherein:

$X_1$ is

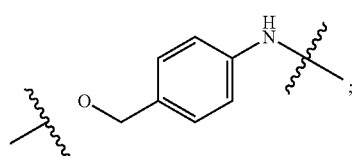

$X_2$ is

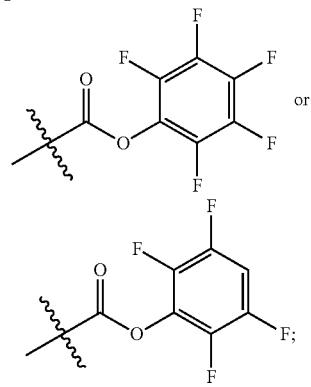

$X_3$ is

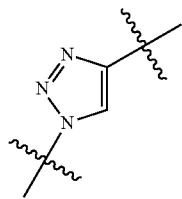 [SMILES: *c1cn(*)nn1]

and $X_4$ is

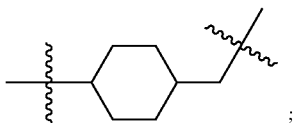 [SMILES: *CC1CCC(*)CC1]

$L_3$ is —$(CH_2)_m NR^5C(=O)$— or —$(CH_2)_m NR^5C(=O)(CH_2)_m C(=O)$—;

$R^4$ is

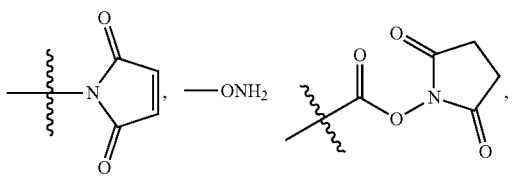

$R^6$ is

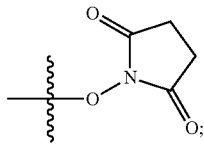 [SMILES: *ON1C(=O)CCC1=O]

each $R^5$ is independently selected from H and $C_1$-$C_6$alkyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.

In certain embodiments of such cytotoxic cyclic peptides of Formula (I) and Formula (Ia):

$R^1$ is H or —$CH_3$; $R^2$ is -$L_1 L_2 R^4$, -$L_3 R^6$ or —$(CH_2)_m X_3(CH_2)_m R^4$; $R^3$ is —$NH_2$ or —OH;

$L_1$ is —$(CH_2)_m NR^5C(=O)$—,

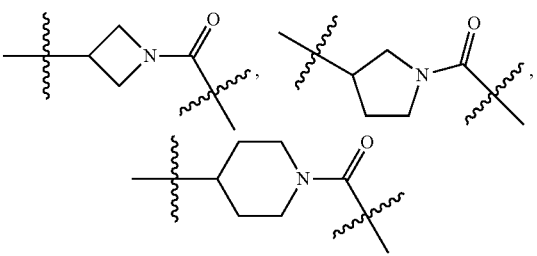

or (CH$_2$)$_m$X$_3$(CH$_2$)$_m$—;
L$_2$ is —(CH$_2$)$_m$—, —NR$^5$(CH$_2$)$_m$—, —(CH$_2$)$_m$NR$^5$C(=O)(CH$_2$)$_m$—, —X$_4$, —(CH$_2$)$_m$NR$^5$C(=O)X$_4$, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$— or —X$_1$X$_2$C(=O)(CH$_2$)$_m$—,
wherein:
X$_1$ is

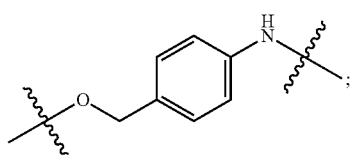 [SMILES: *Nc1ccc(CO*)cc1]

X$_2$ is

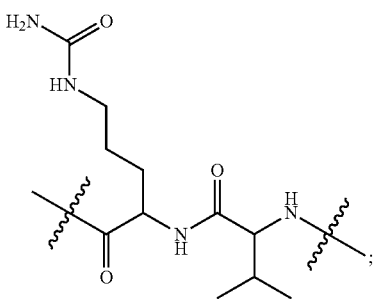 [SMILES: *NC(C(=O)NC(CCCNC(N)=O)C(*)=O)C(C)C]

X$_3$ is

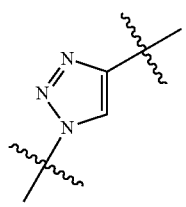 [SMILES: *c1cn(*)nn1]

and X$_4$ is

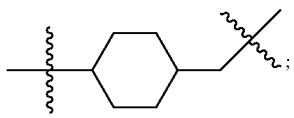 [SMILES: *CC1CCC(*)CC1]

L$_3$ is —(CH$_2$)$_m$NR$^5$C(=O)— or —(CH$_2$)$_m$NR$^5$C(=O)(CH$_2$)$_m$C(=O)—;
R$^4$ is

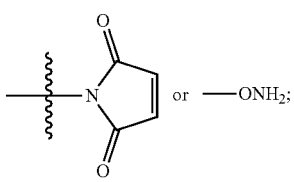 or —ONH$_2$;

R$^6$ is 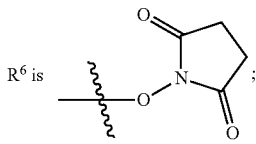;

each R$^5$ is independently selected from H and C$_1$-C$_6$alkyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.

In preferred embodiments of any of the aforementioned cytotoxic cyclic peptides of Formula (I) and Formula (Ia):
R$^2$ is

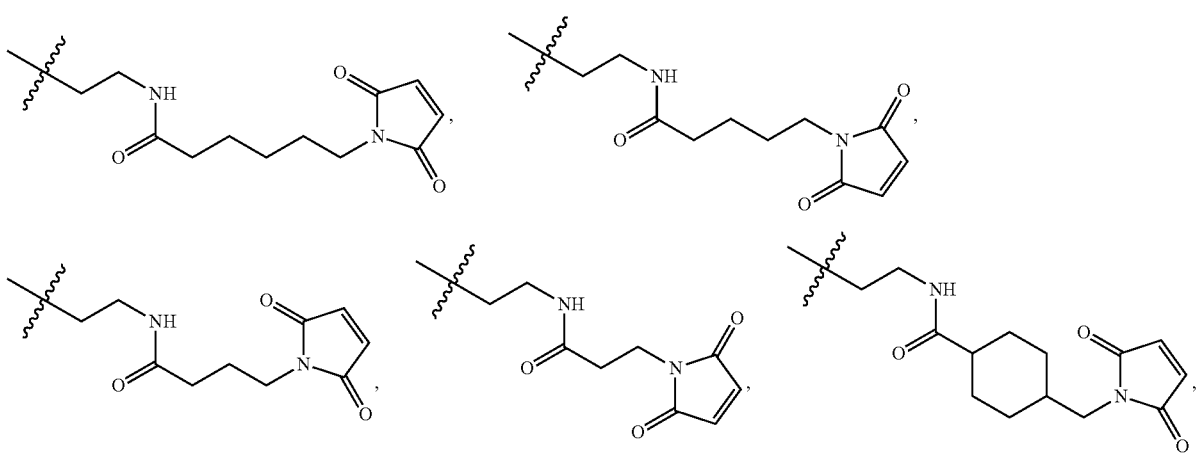

-continued
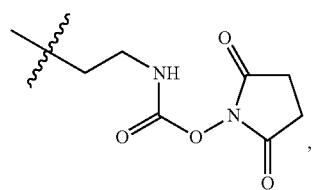 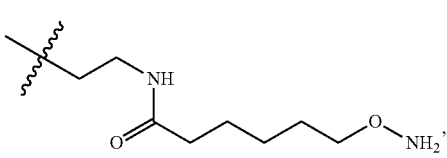
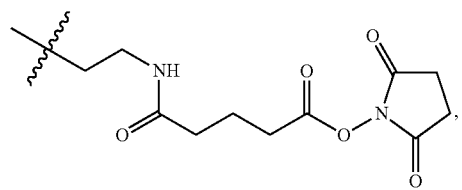 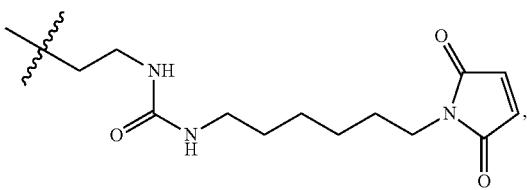
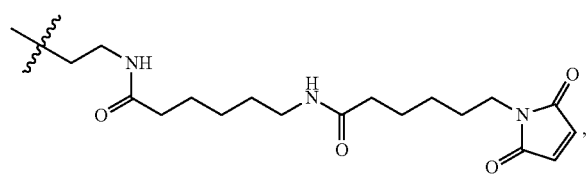 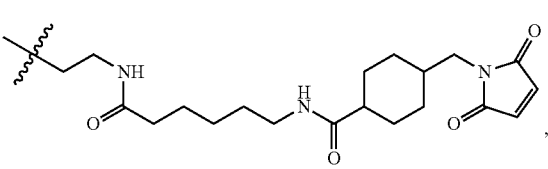
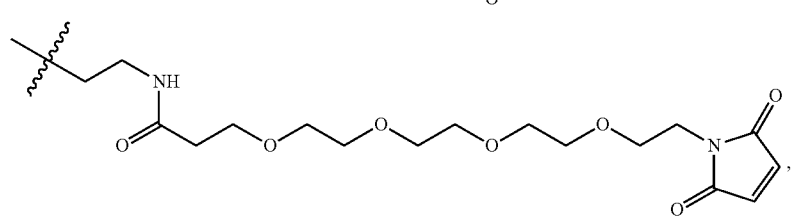
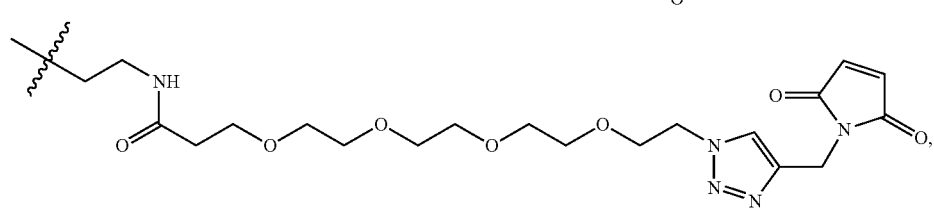
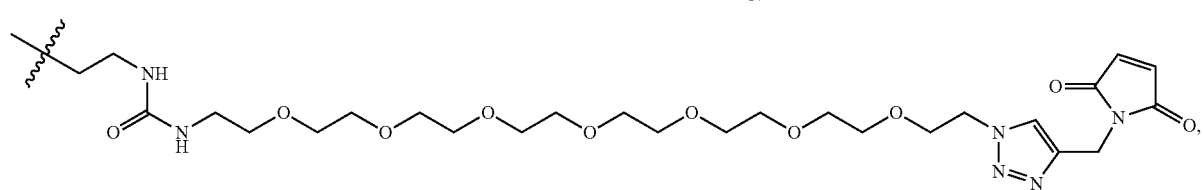
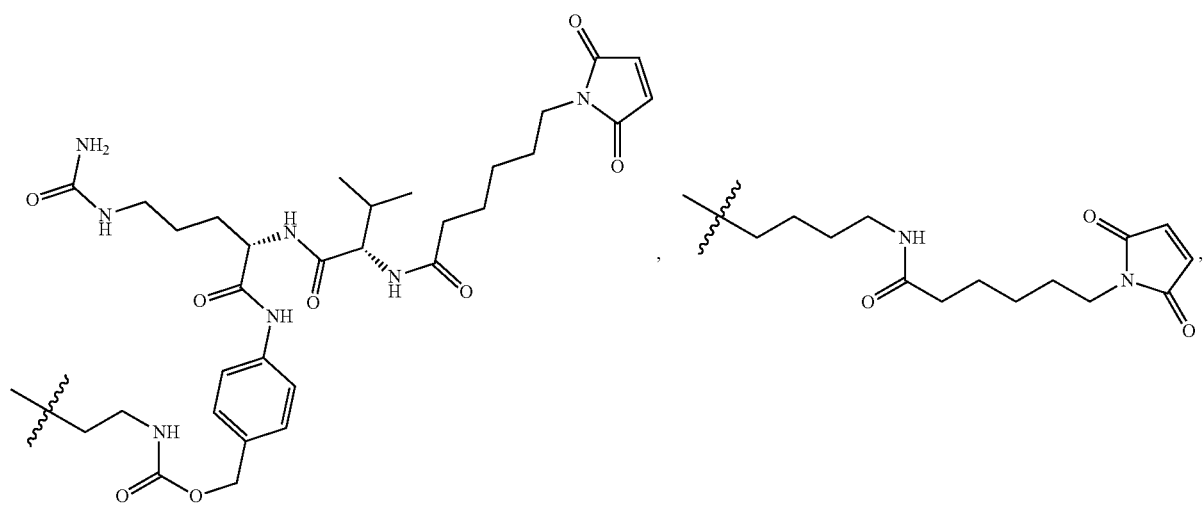

-continued
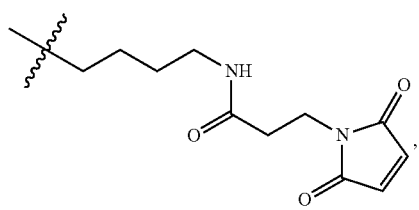
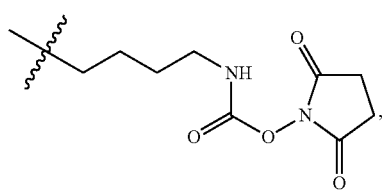
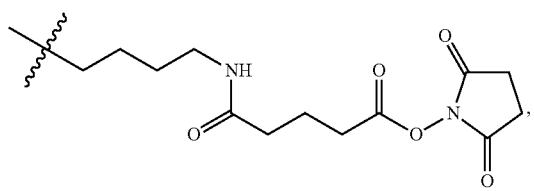
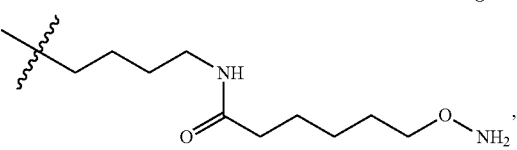
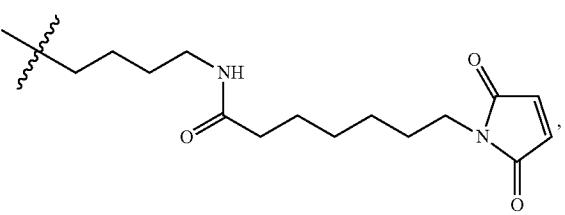
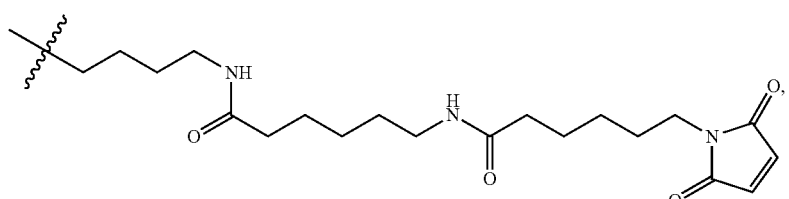
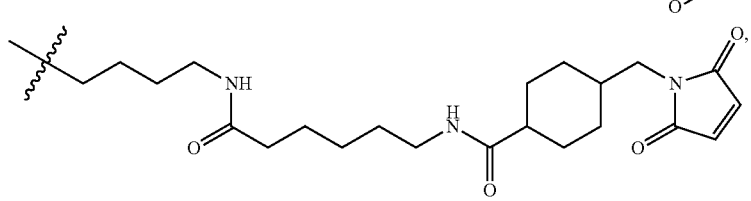
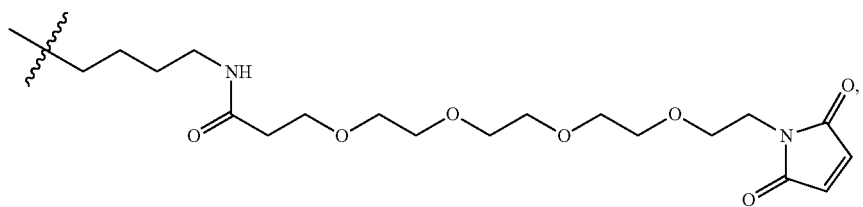
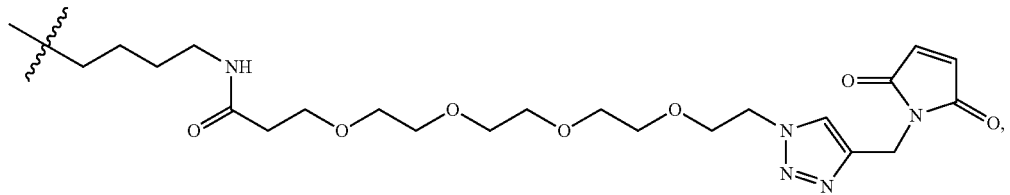
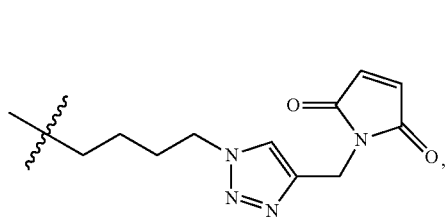
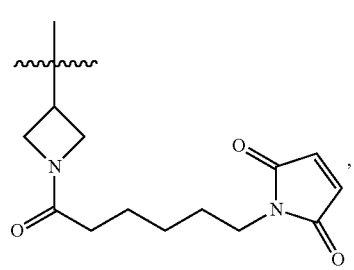
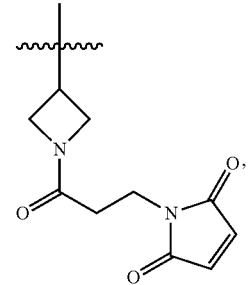

-continued
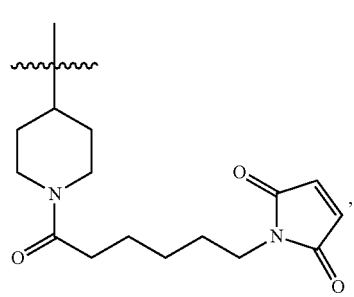
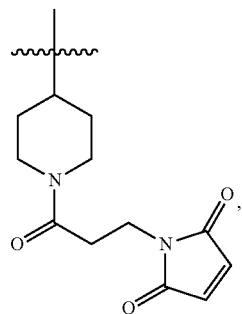
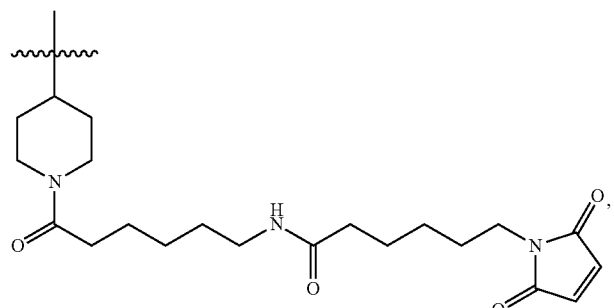
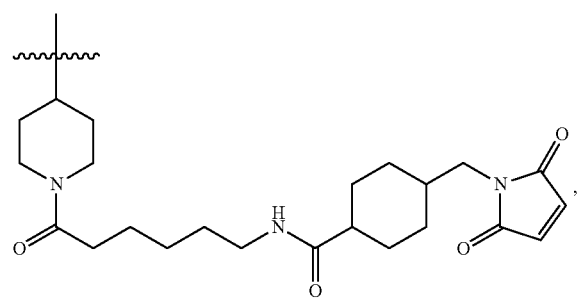
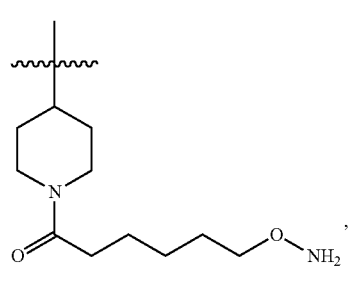
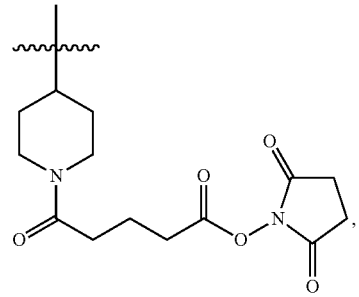
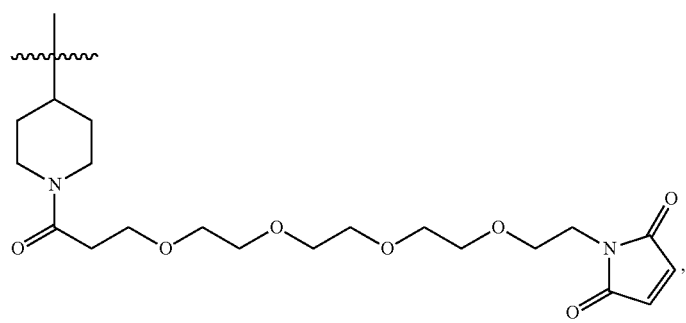
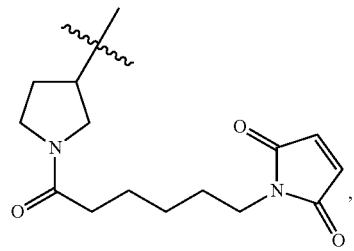
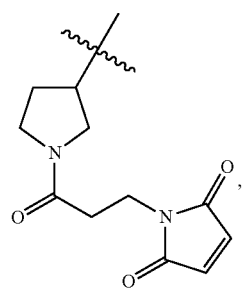
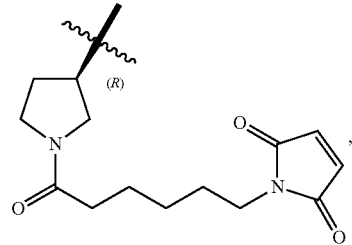
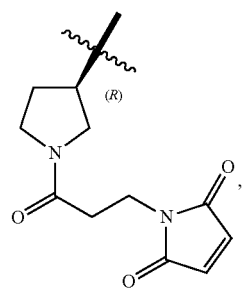

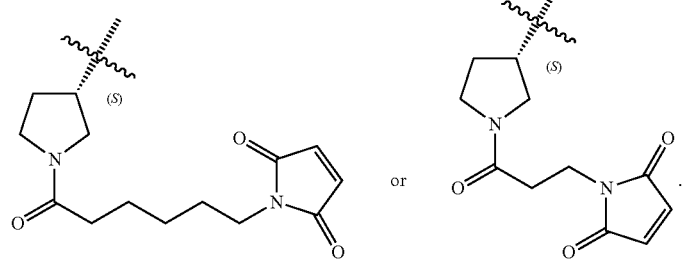
In certain embodiments of any of the aforementioned cytotoxic cyclic peptides of Formula (I) and Formula (Ia): $R^2$ is
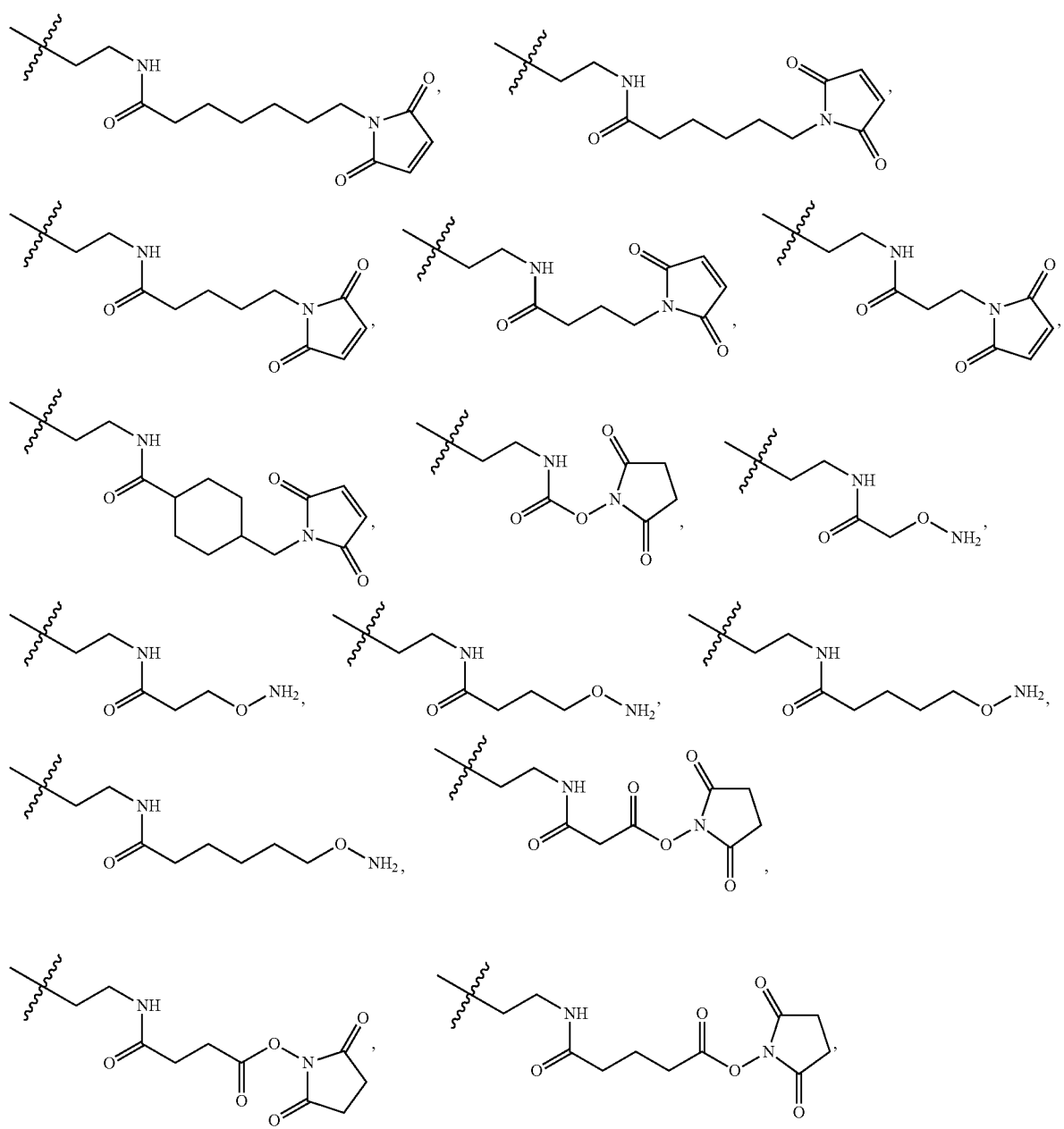

-continued
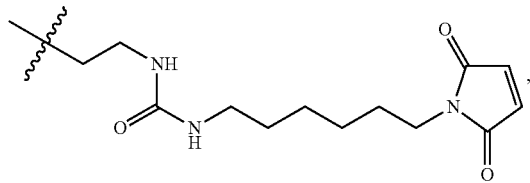 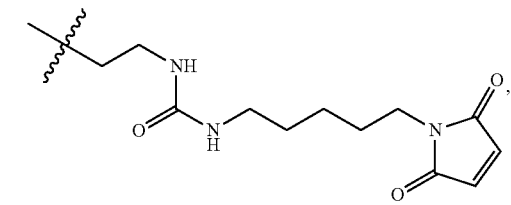
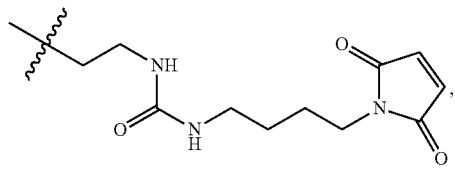 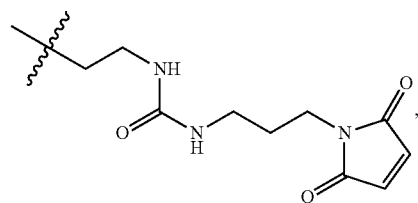
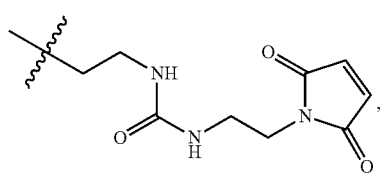 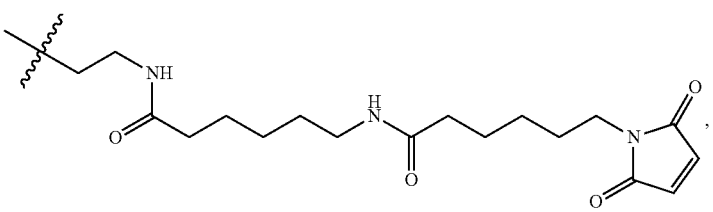
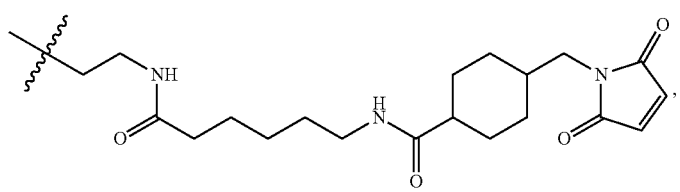
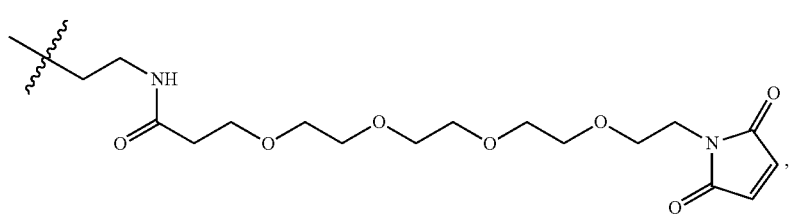
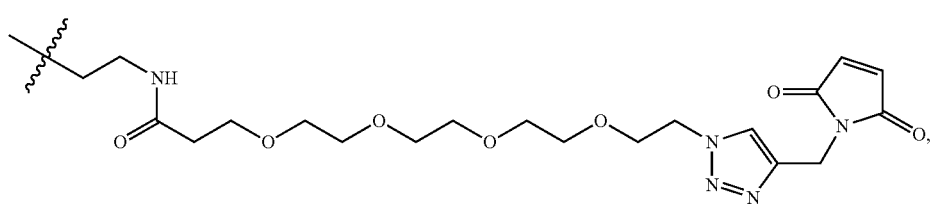
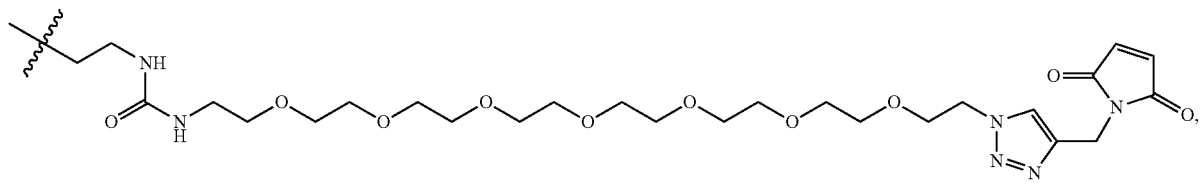

or
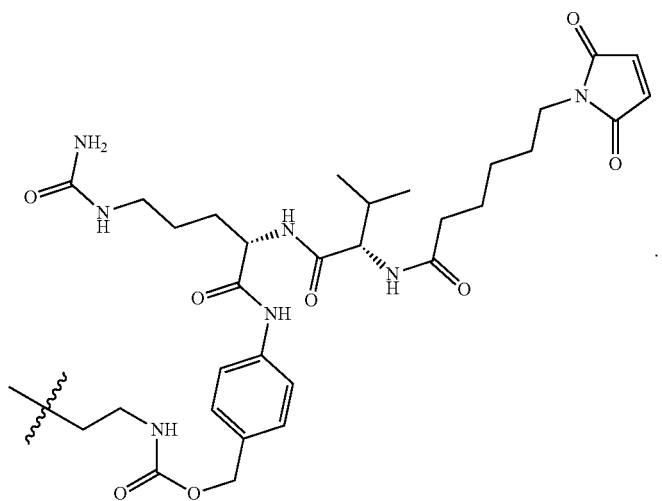
In certain embodiments of any of the aforementioned cytotoxic cyclic peptides of Formula (I) and Formula (Ia): $R^2$ is
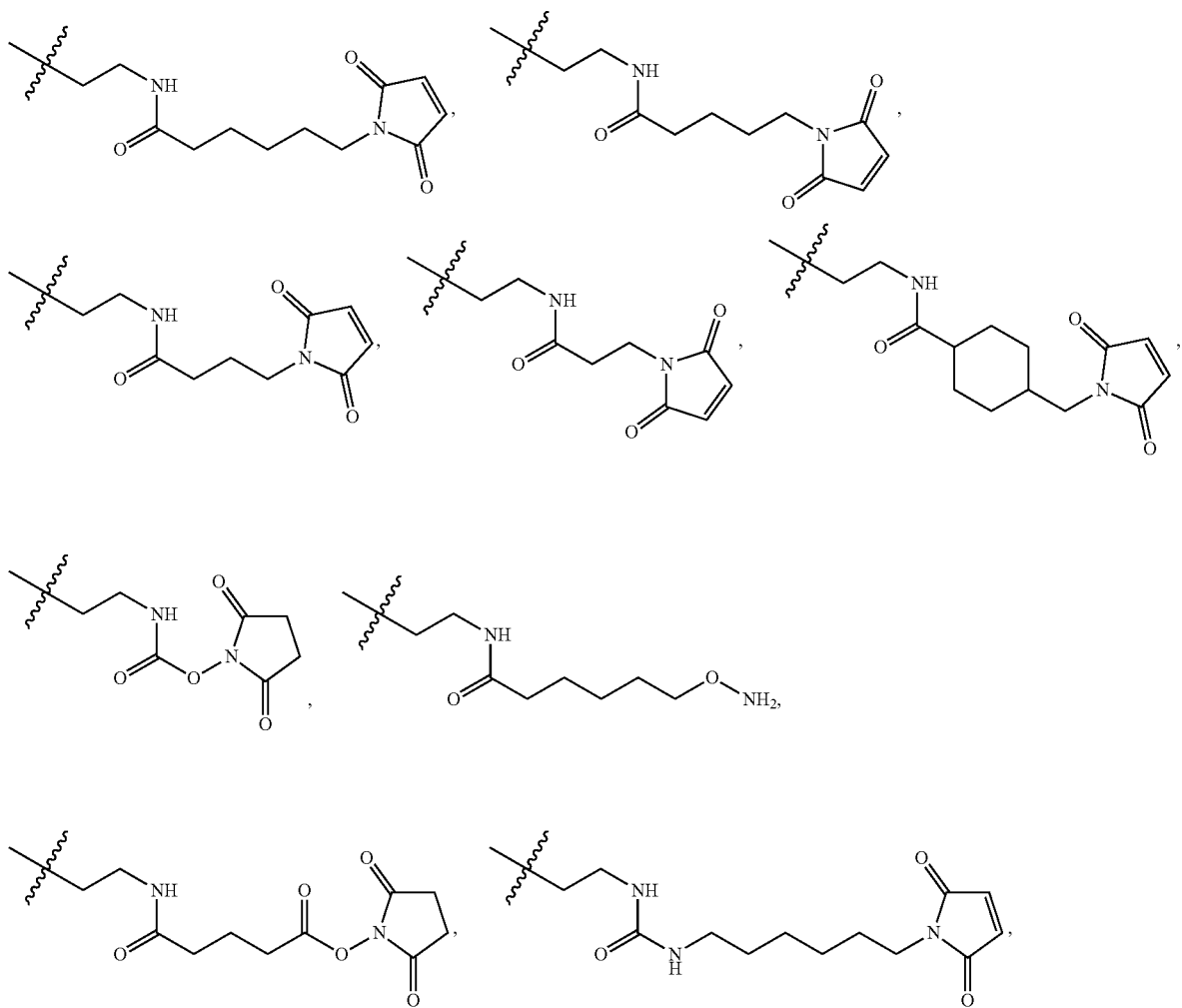

-continued
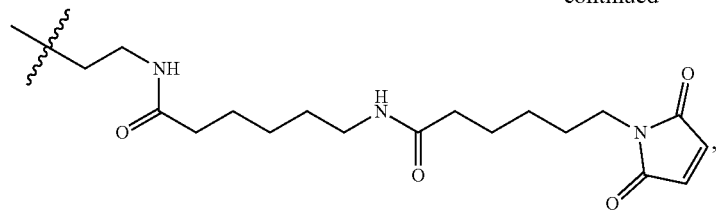
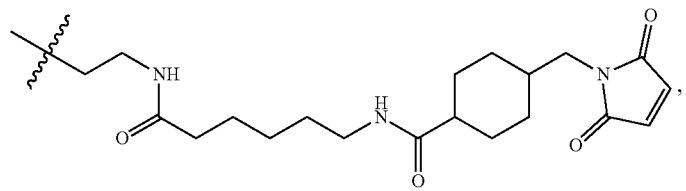
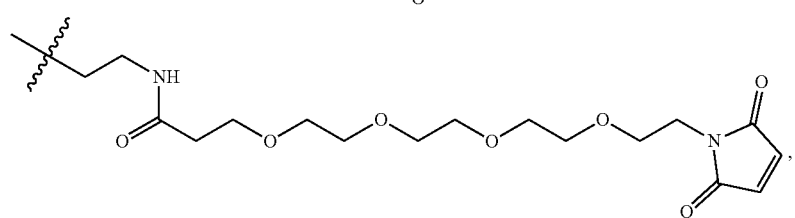
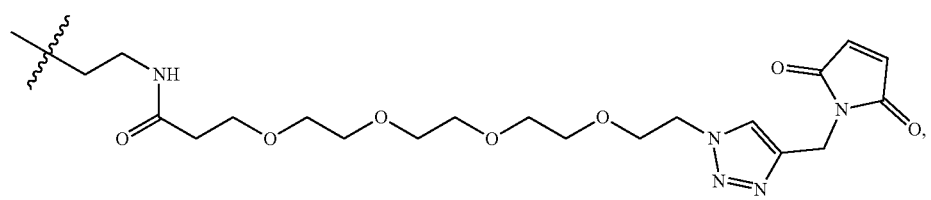
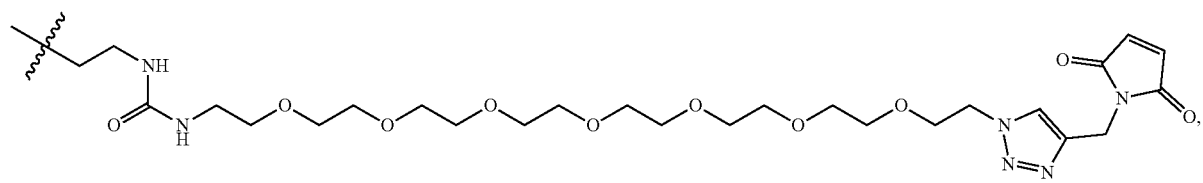
or
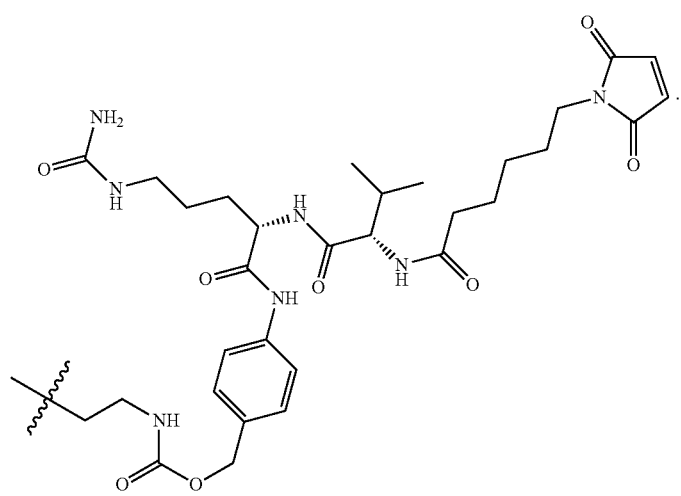

In certain embodiments of any of the aforementioned cytotoxic cyclic peptides of Formula (I) and Formula (Ia):
R² is
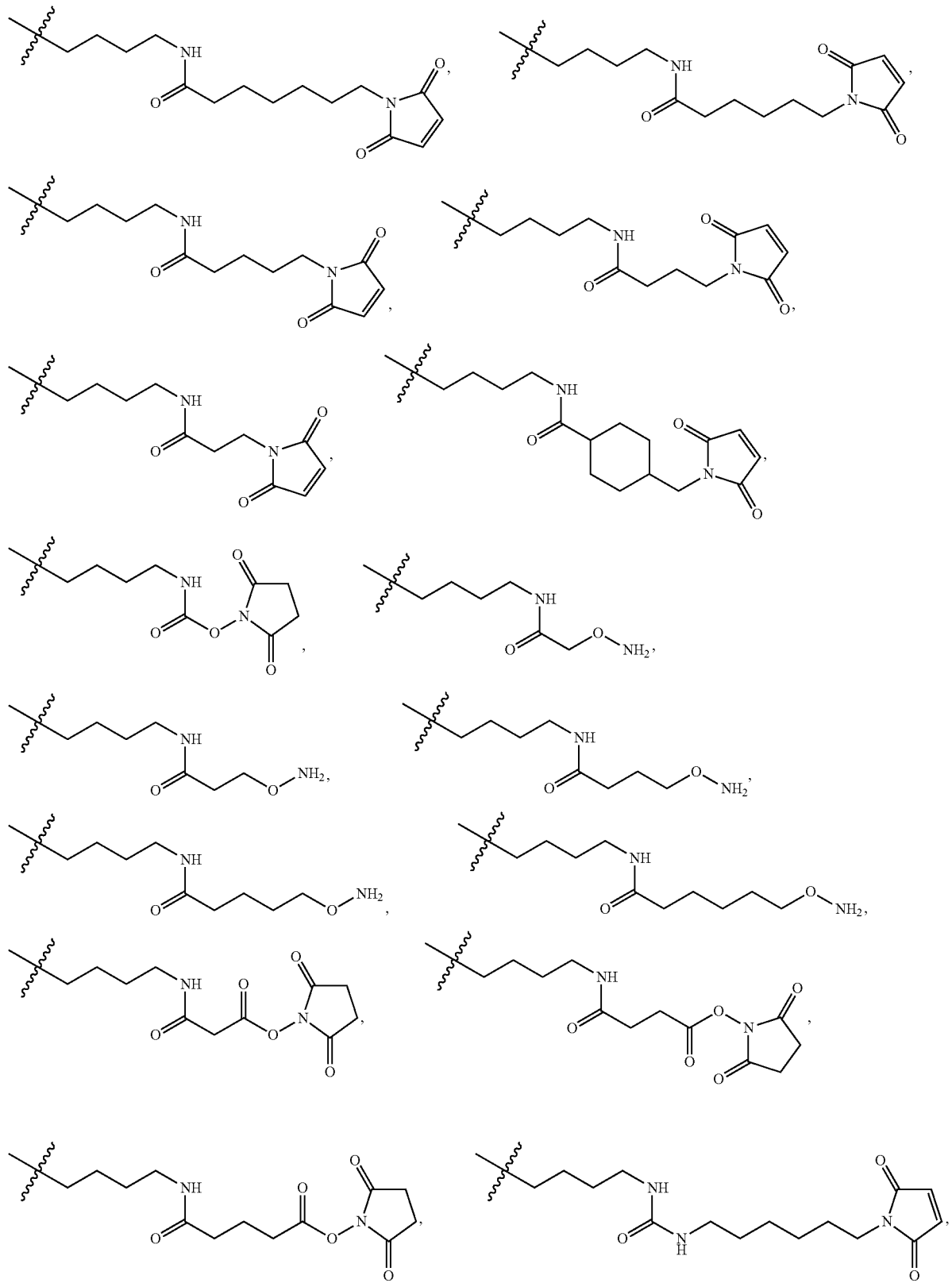

-continued
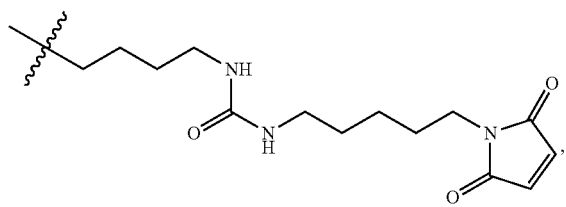
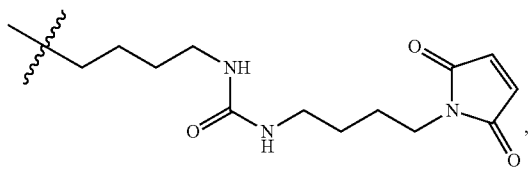
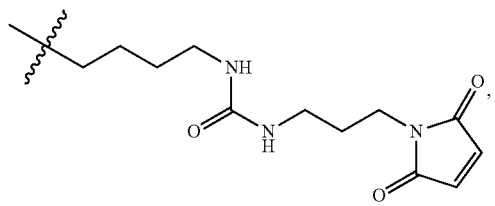
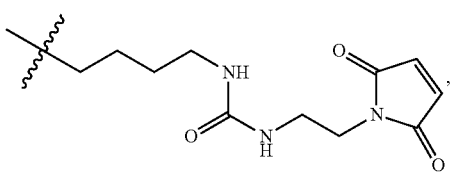
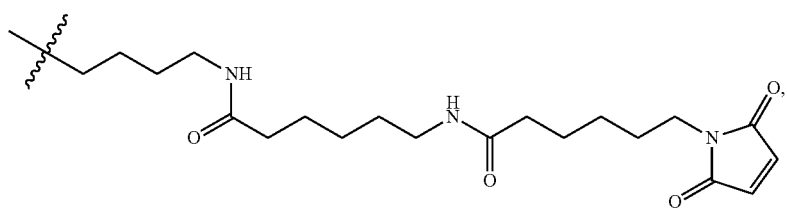
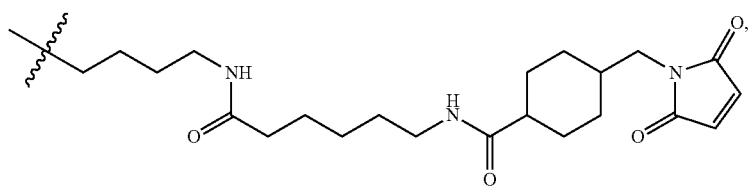
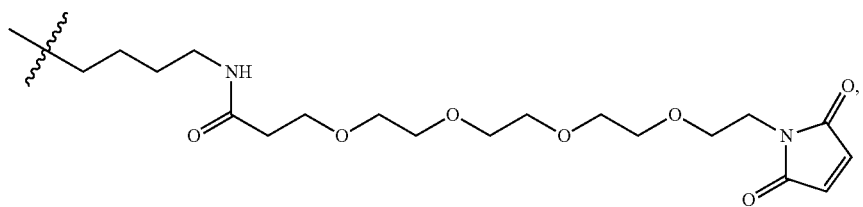
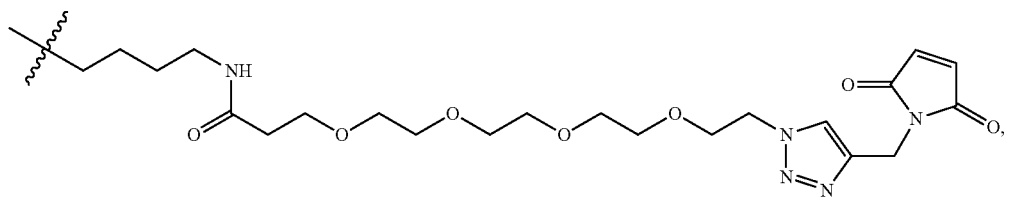
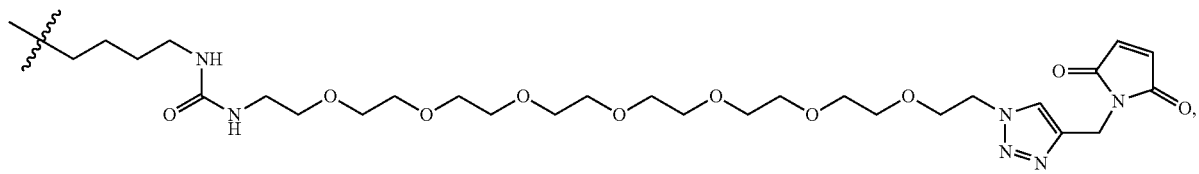

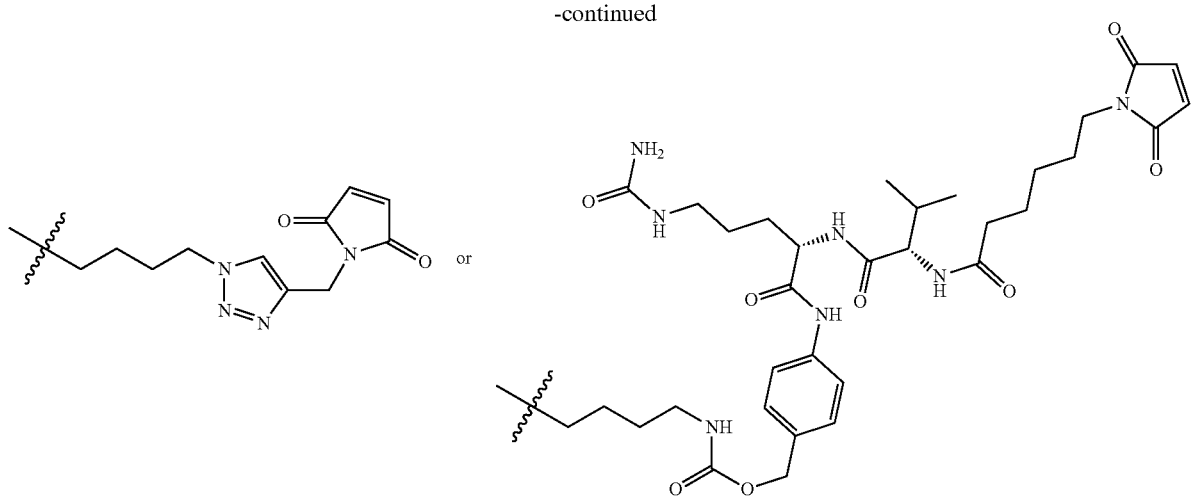
In certain embodiments of any of the aforementioned cytotoxic cyclic peptides of Formula (I) and Formula (Ia):
R² is
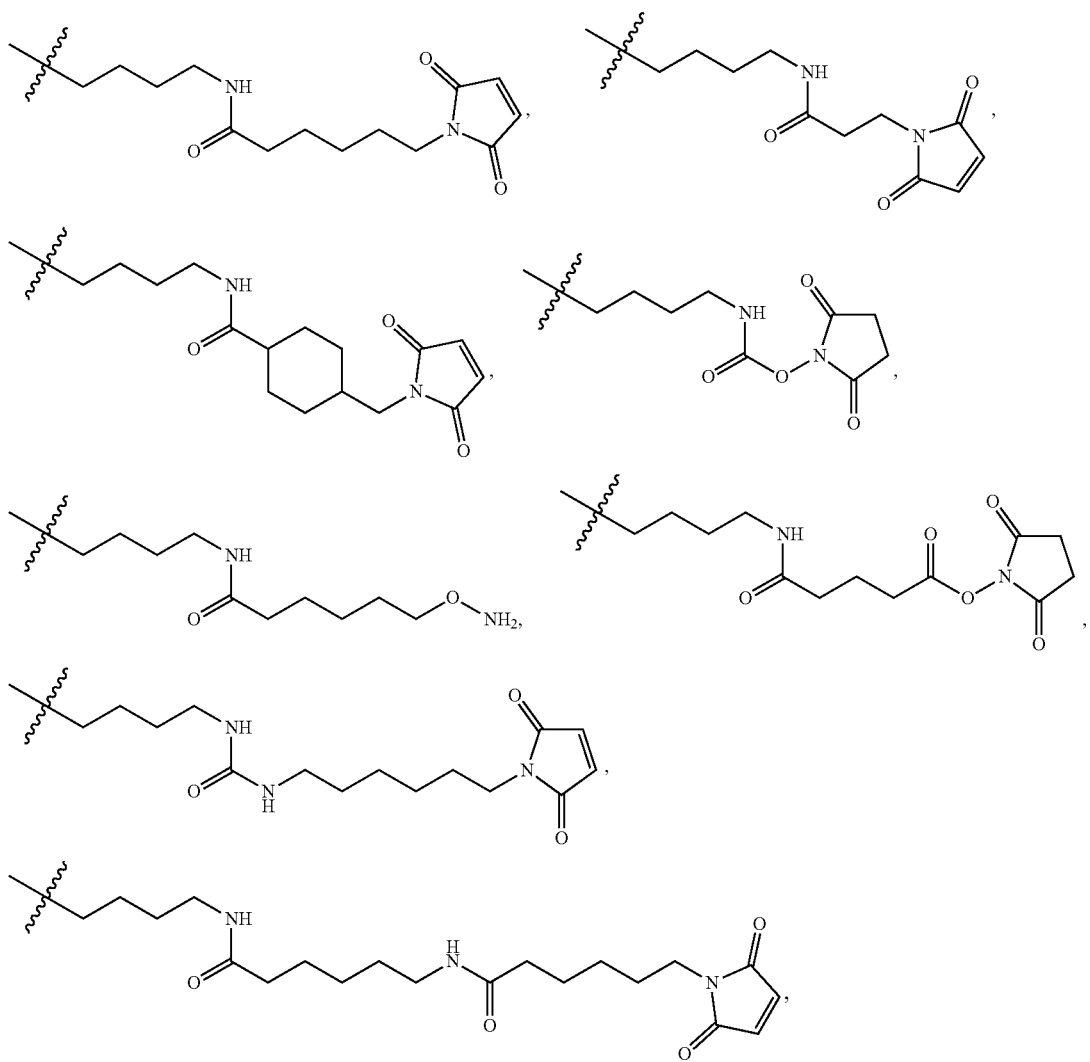

-continued
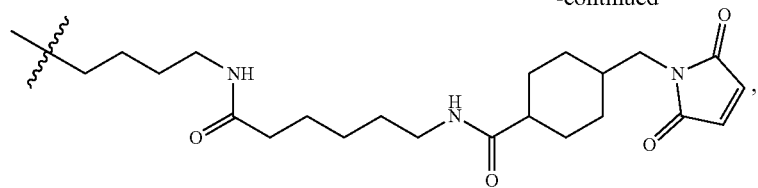
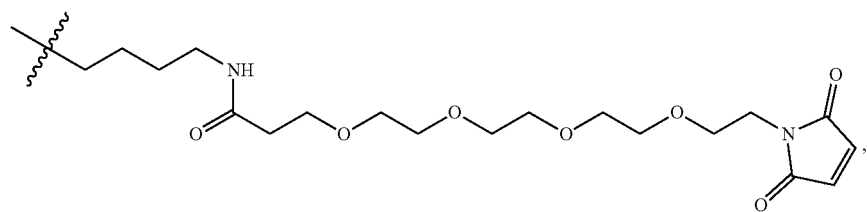
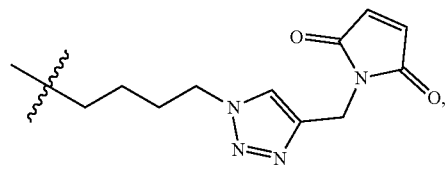
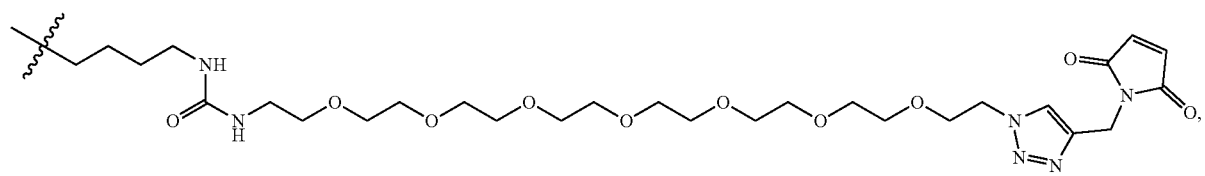
or
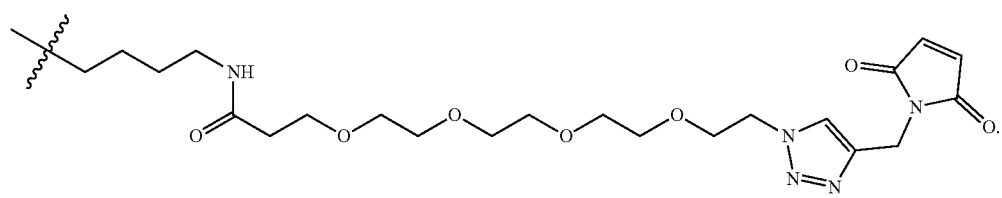
In certain embodiments of any of the aforementioned cytotoxic cyclic peptides of Formula (I) and Formula (Ia):
$R^2$ is
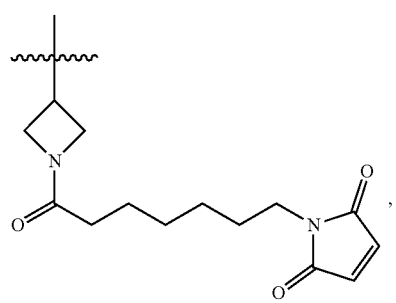 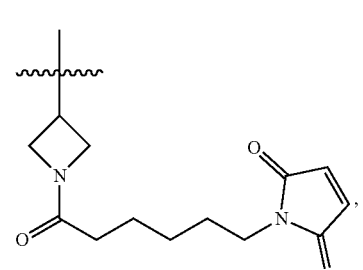 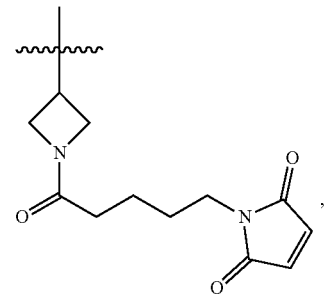

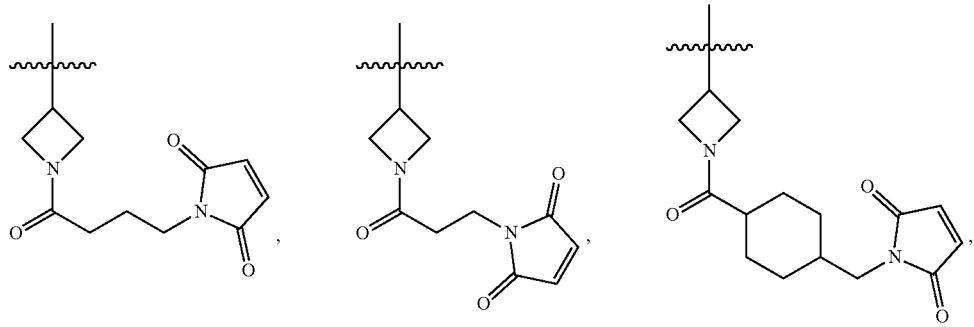,
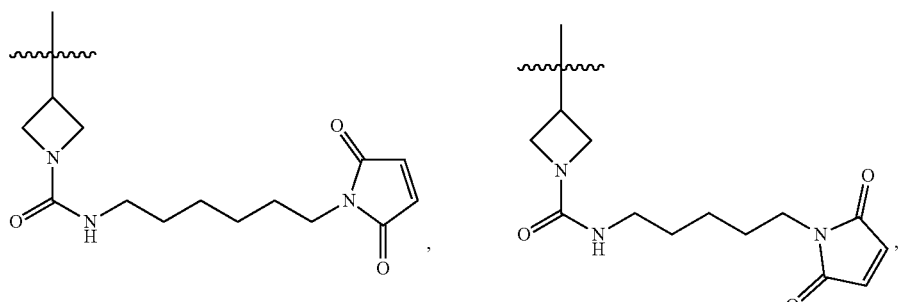,
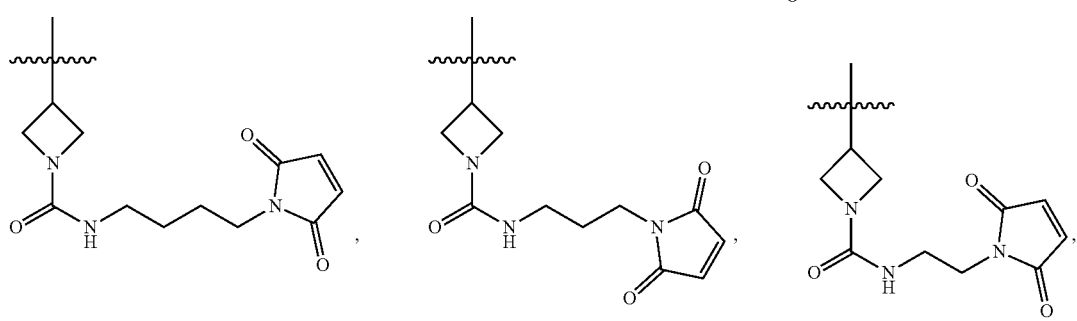,
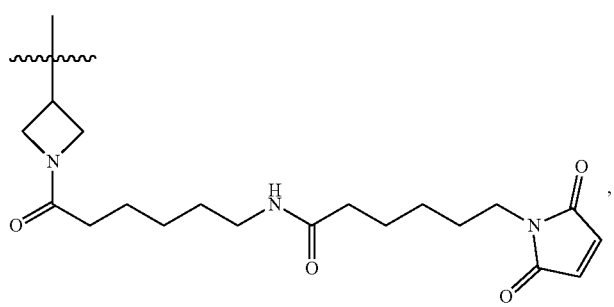,
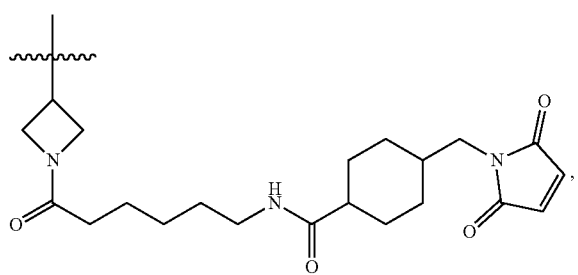

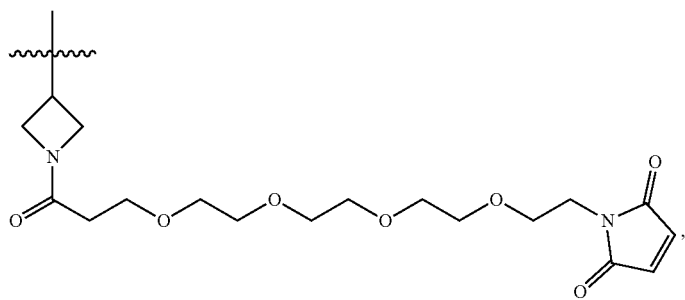
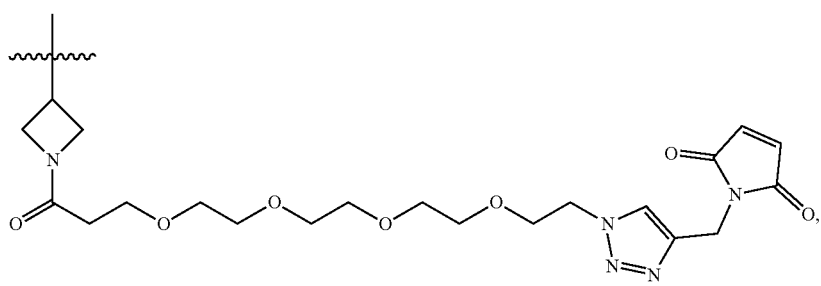
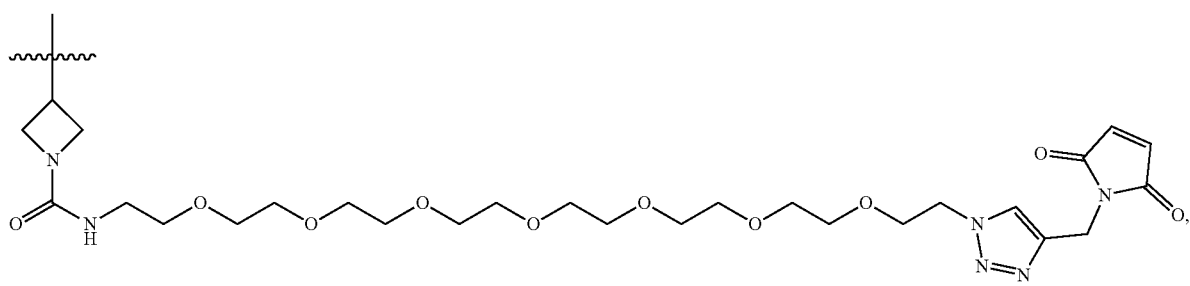
or
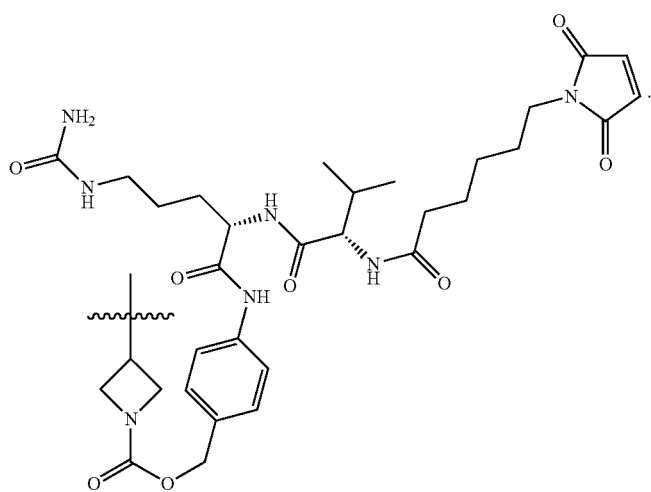

In certain embodiments of any of the aforementioned cytotoxic cyclic peptides of Formula (I) and Formula (Ia):
R² is
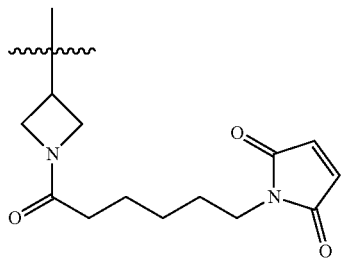 or 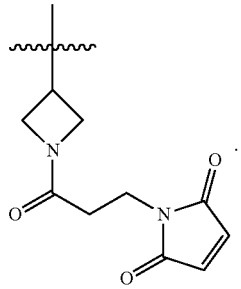
In certain embodiments of any of the aforementioned cytotoxic cyclic peptides of Formula (I) and Formula (Ia):
R² is
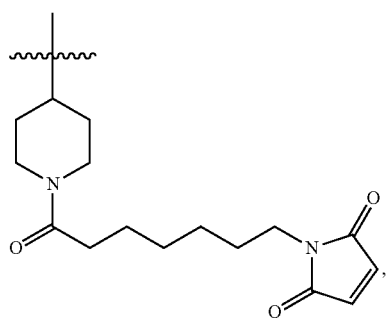 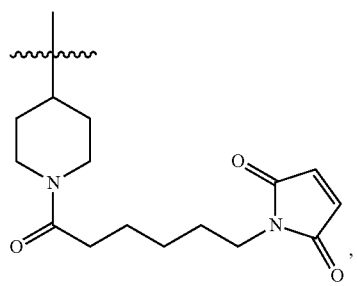 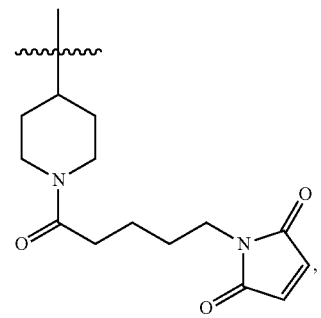
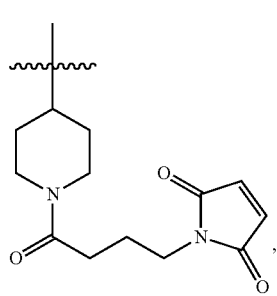 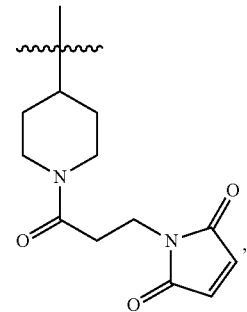 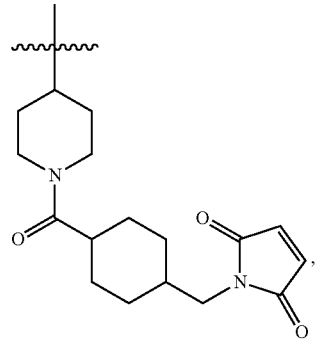
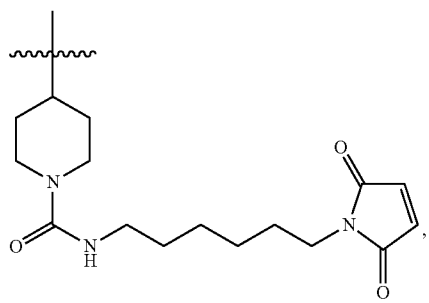 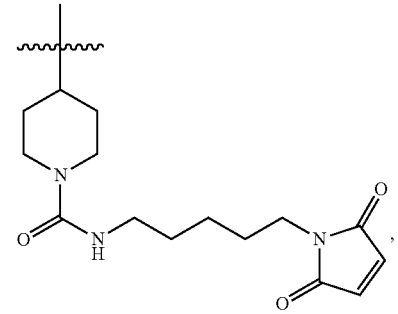
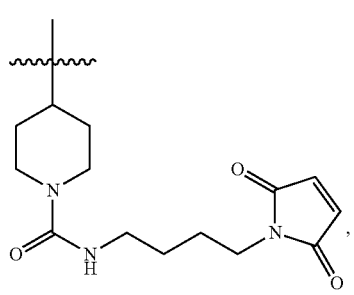 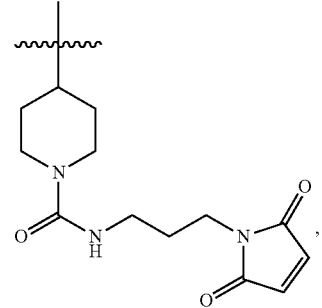 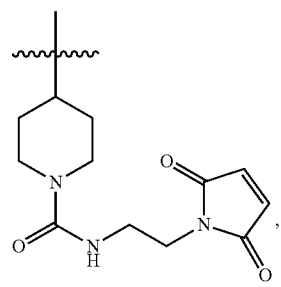

59 60
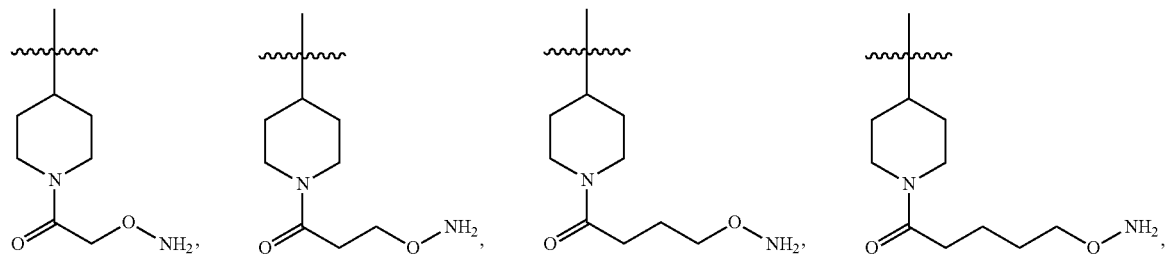
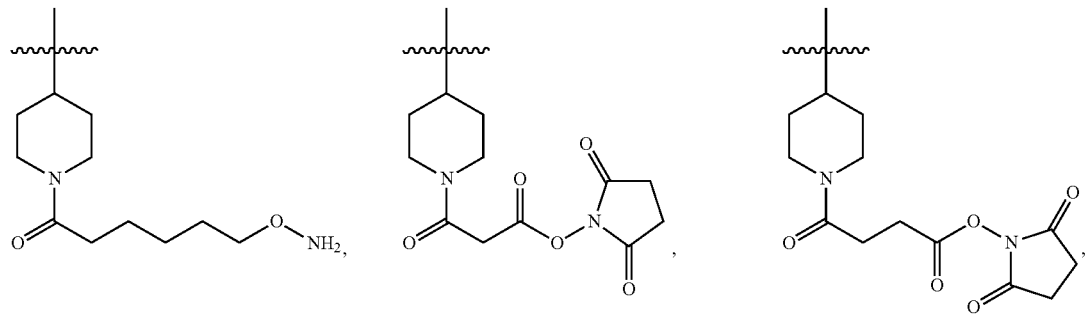
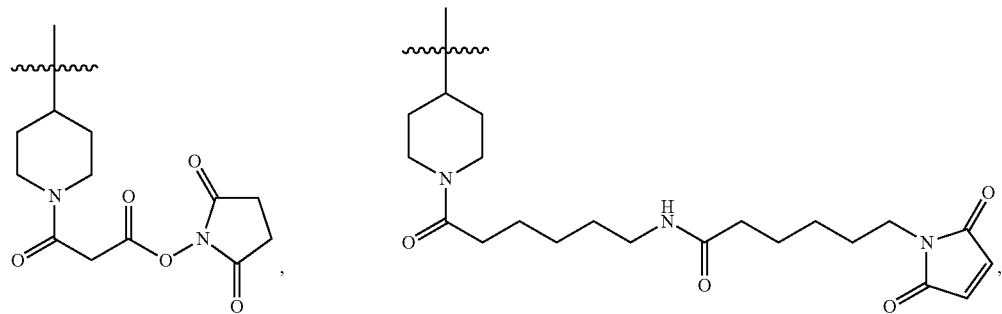 [SMILES: *C1CCN(C(=O)CC(=O)ON2C(=O)CCC2=O)CC1 ; *C1CCN(C(=O)CCCCCNC(=O)CCCCCN2C(=O)C=CC2=O)CC1]
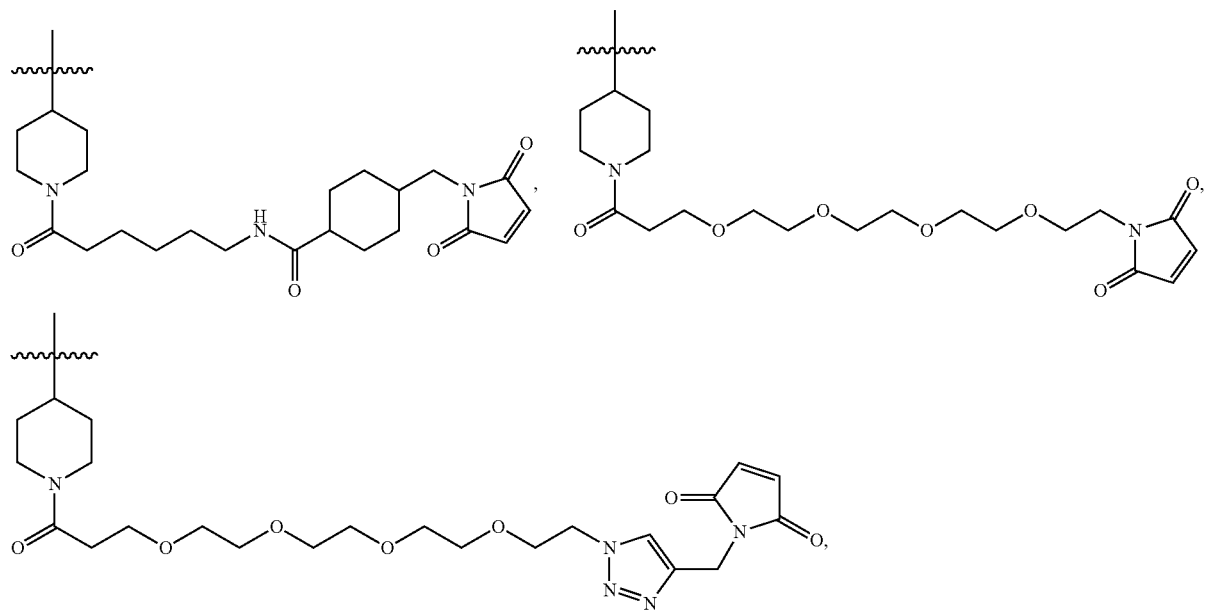

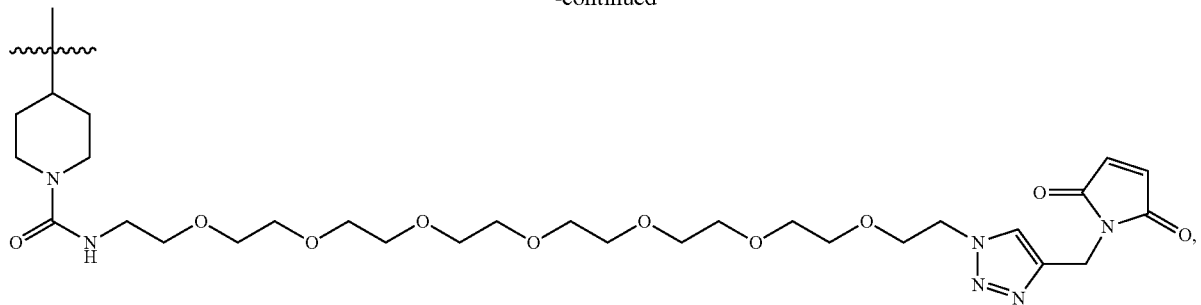
or
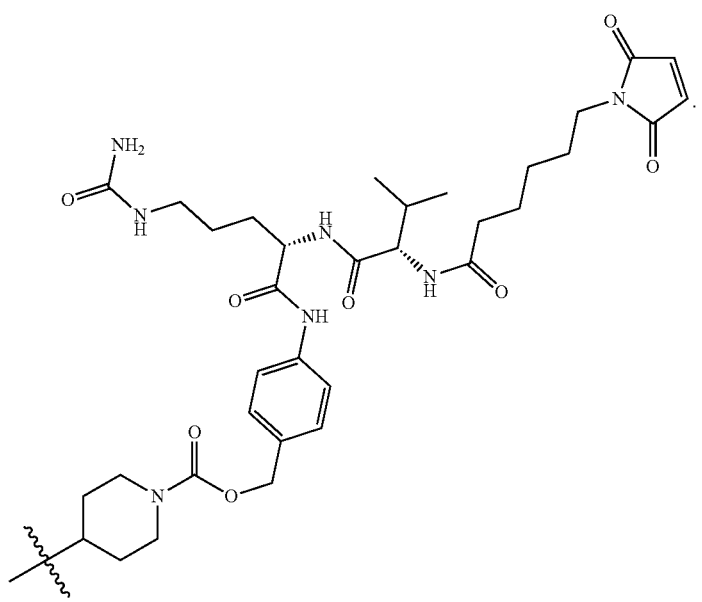
In certain embodiments of any of the aforementioned cytotoxic cyclic peptides of Formula (I) and Formula (Ia): $R^2$ is
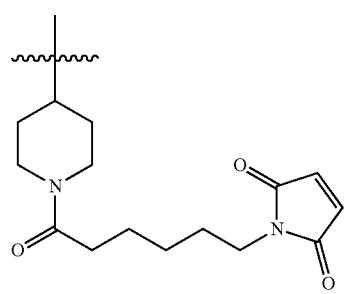
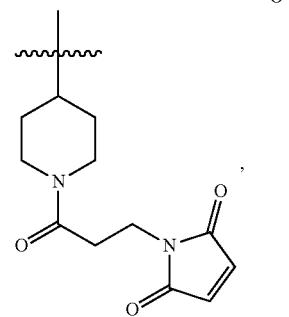
-continued
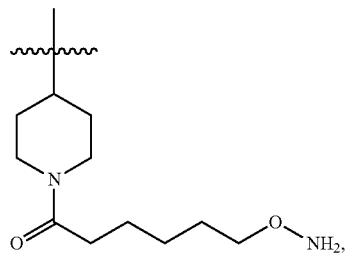

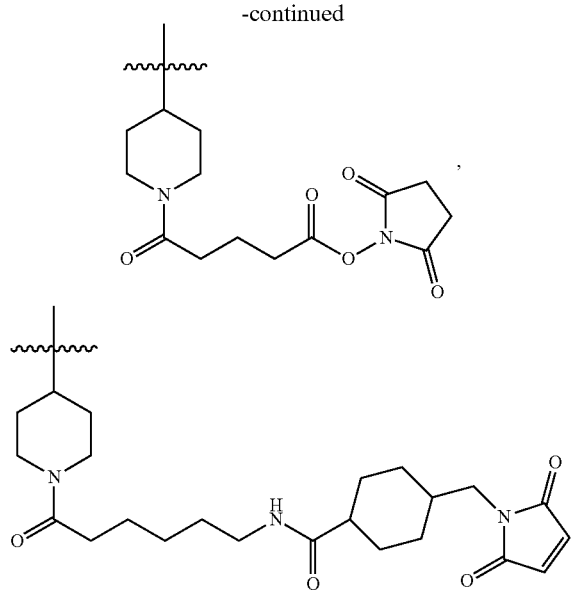
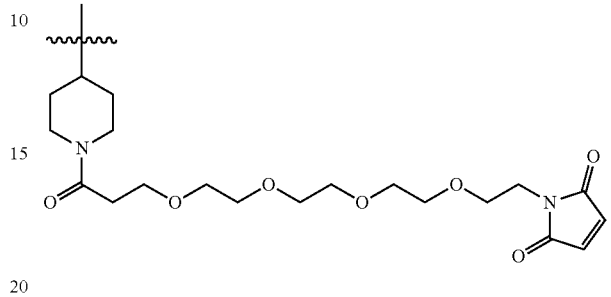
In certain embodiments of any of the aforementioned cytotoxic cyclic peptides of Formula (I) and Formula (Ia):
R² is
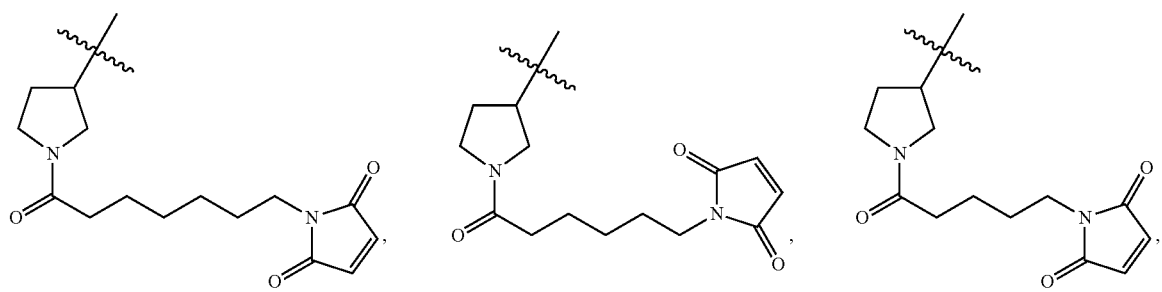
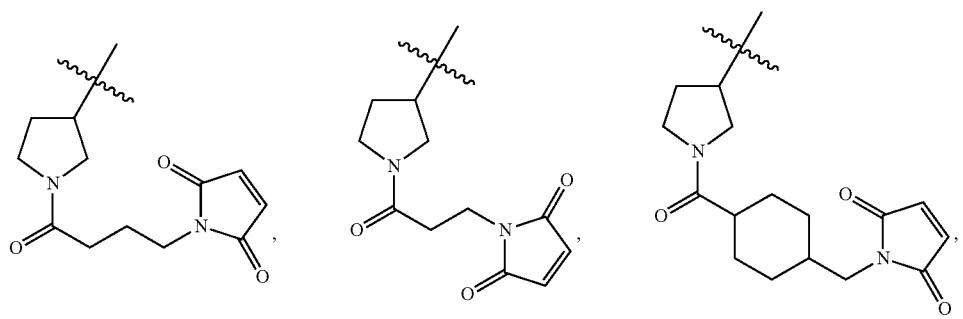
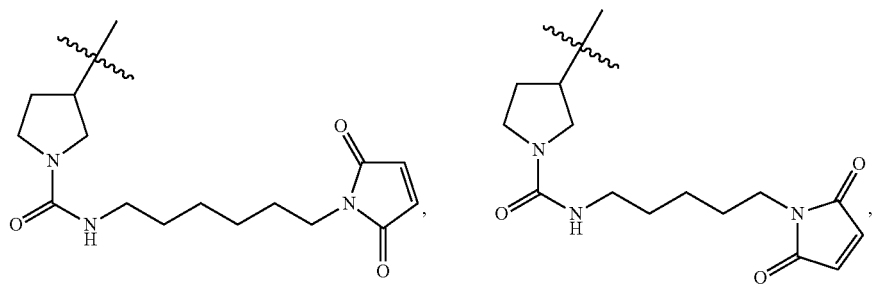

-continued
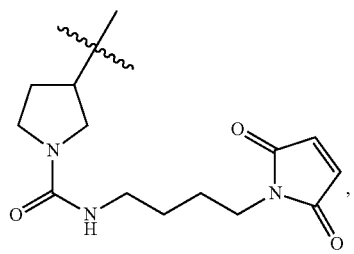 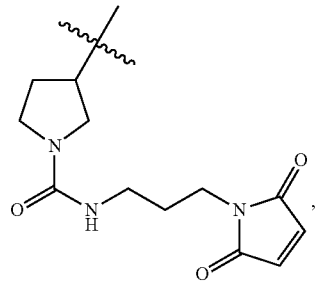 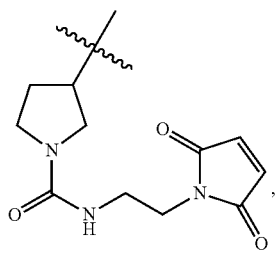
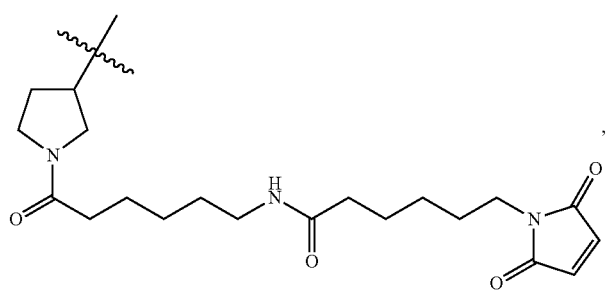 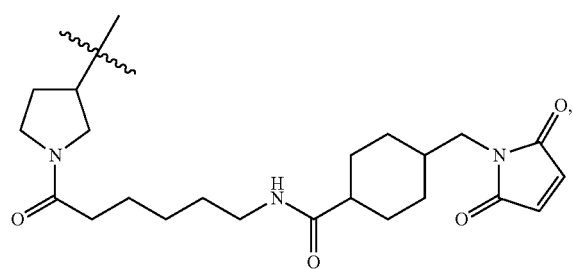
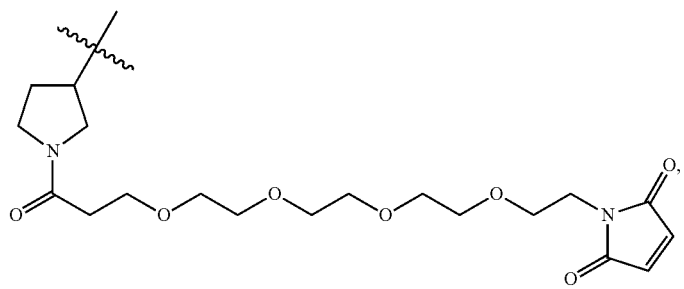
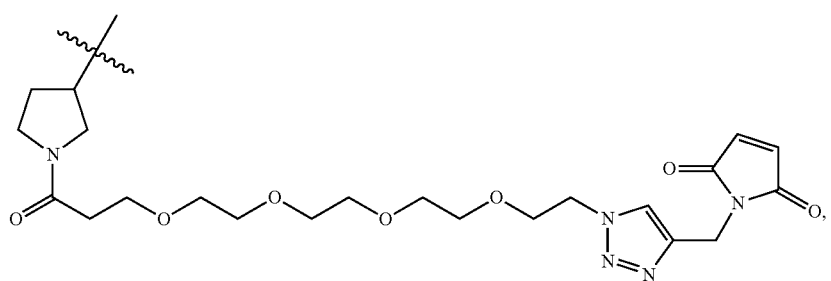
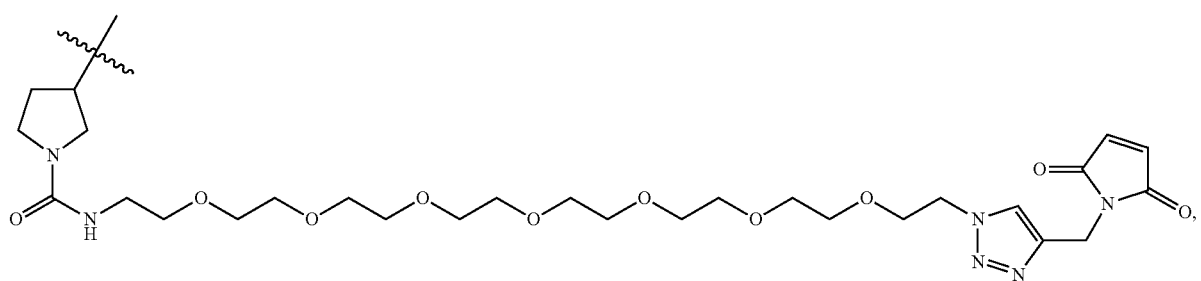

or
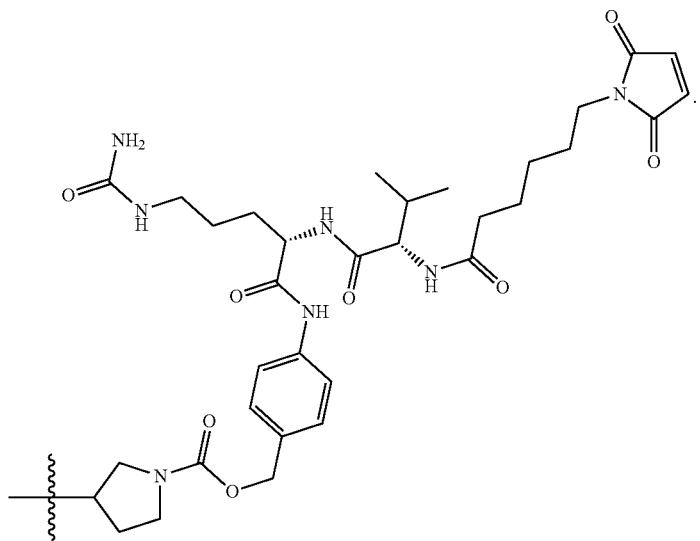
In certain embodiments of any of the aforementioned cytotoxic cyclic peptides of Formula (I) and Formula (Ia): R² is
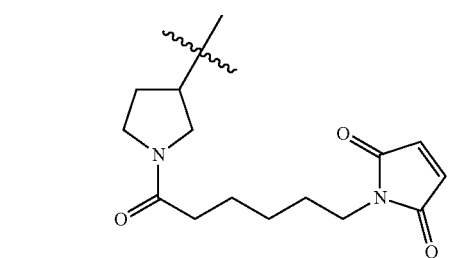 or 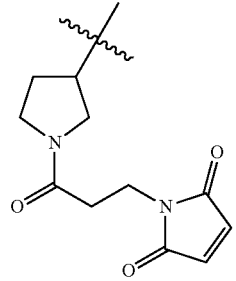
In certain embodiments of any of the aforementioned cytotoxic cyclic peptides of Formula (I) and Formula (Ia): R² is
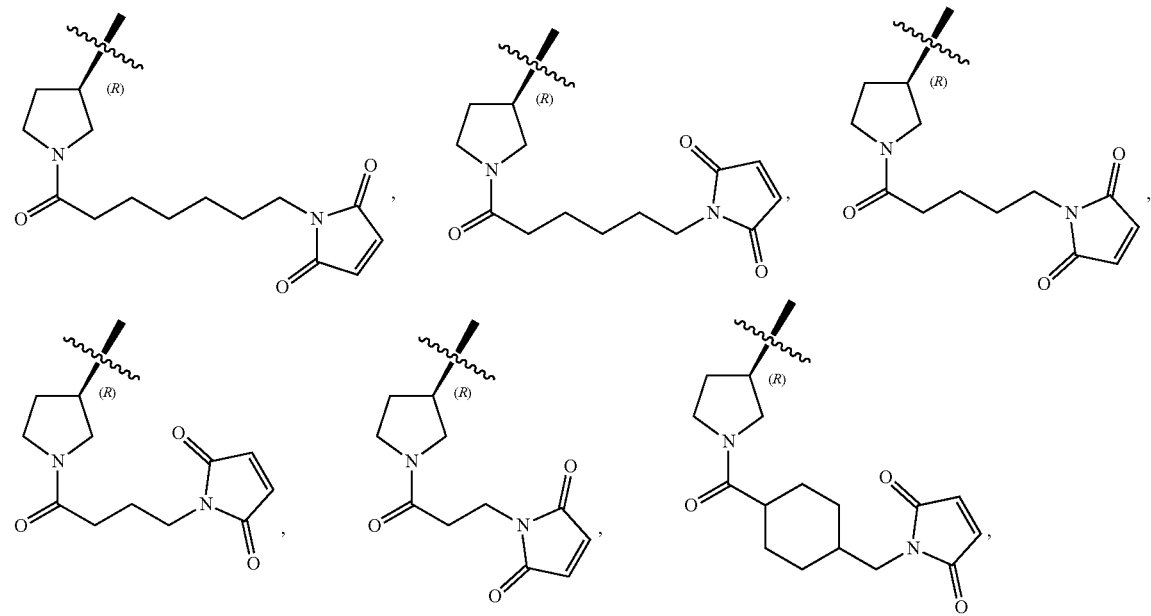

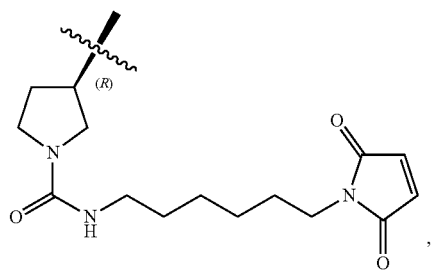,
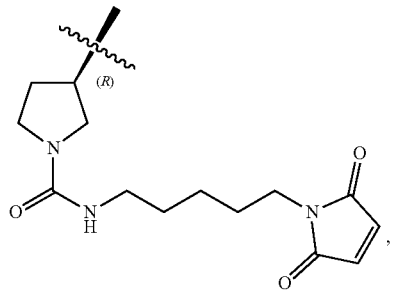,
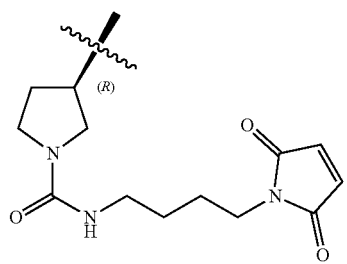,
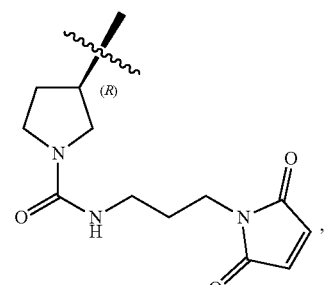,
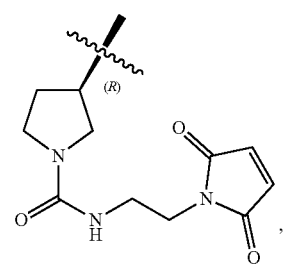,
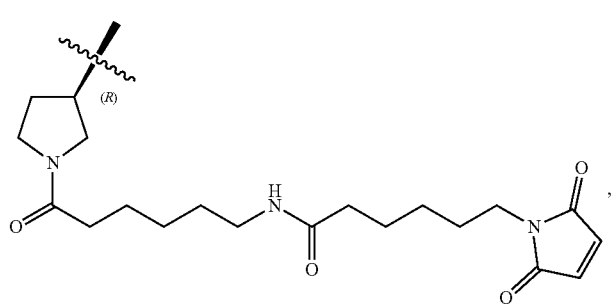,
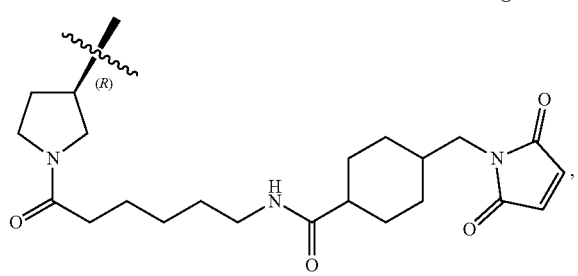,
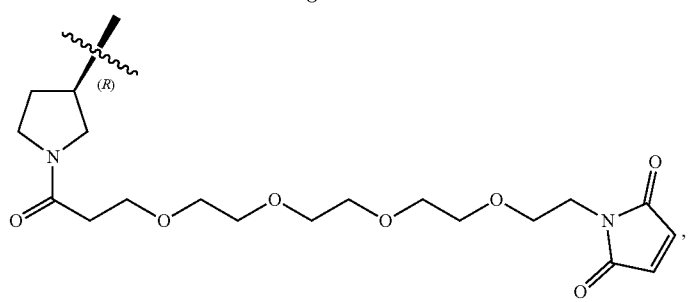,
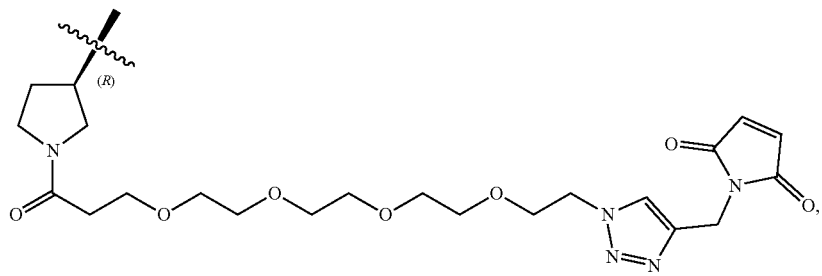,

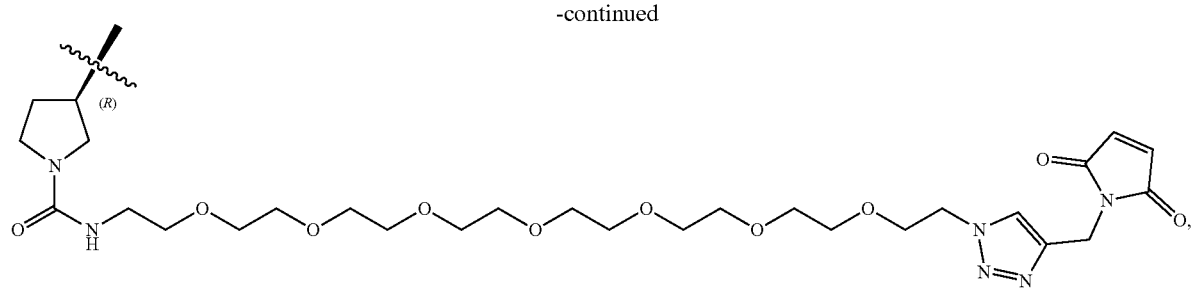
or
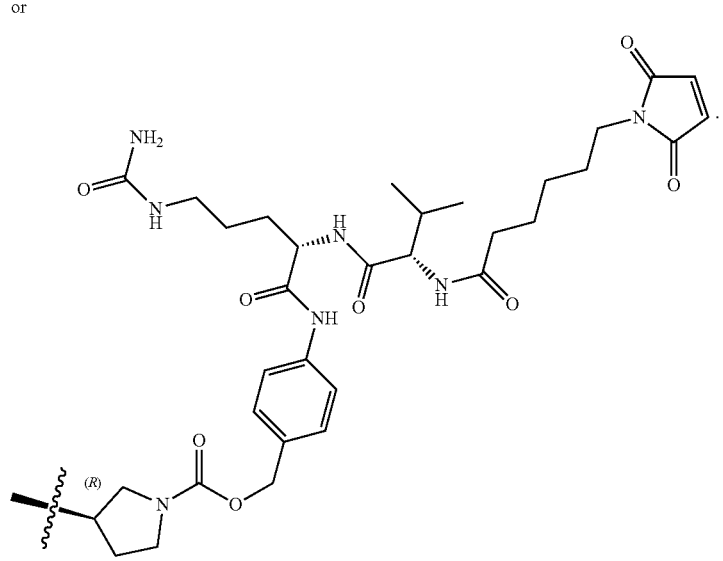
In certain embodiments of any of the aforementioned cytotoxic cyclic peptides of Formula (I) and Formula (Ia): $R^2$ is
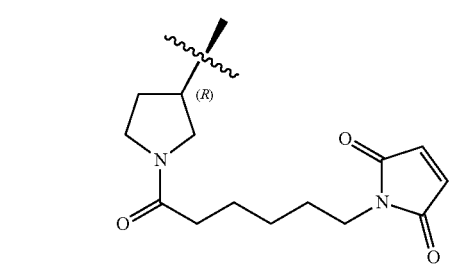
or
-continued
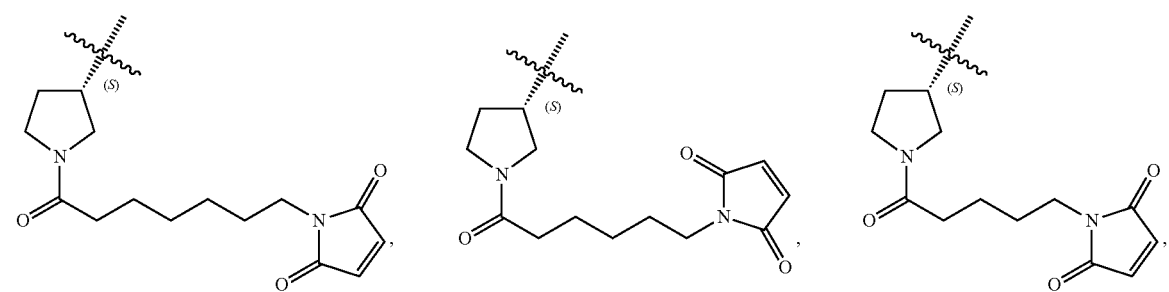
In certain embodiments of any of the aforementioned cytotoxic cyclic peptides of Formula (I) and Formula (Ia): $R^2$ is

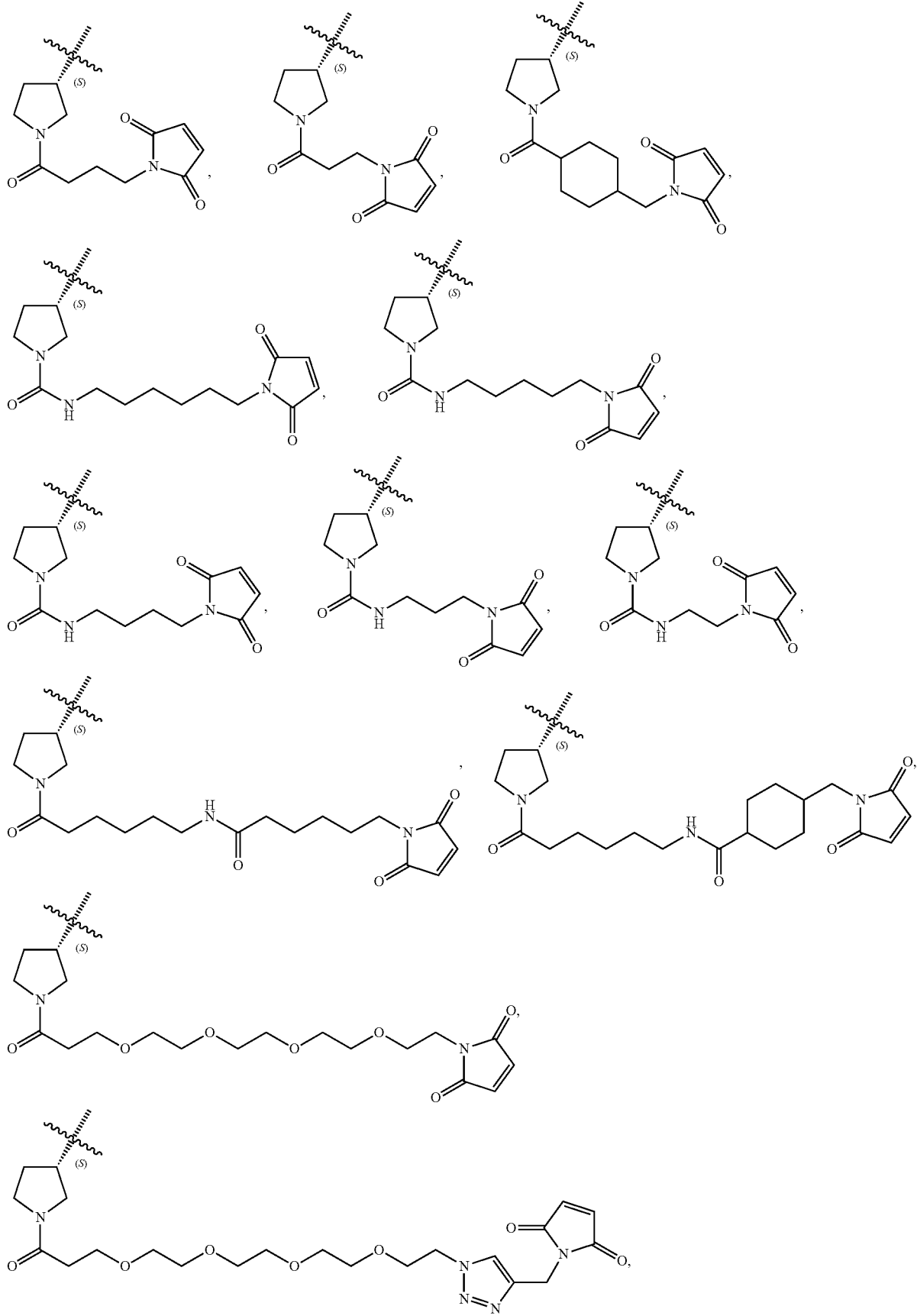

-continued
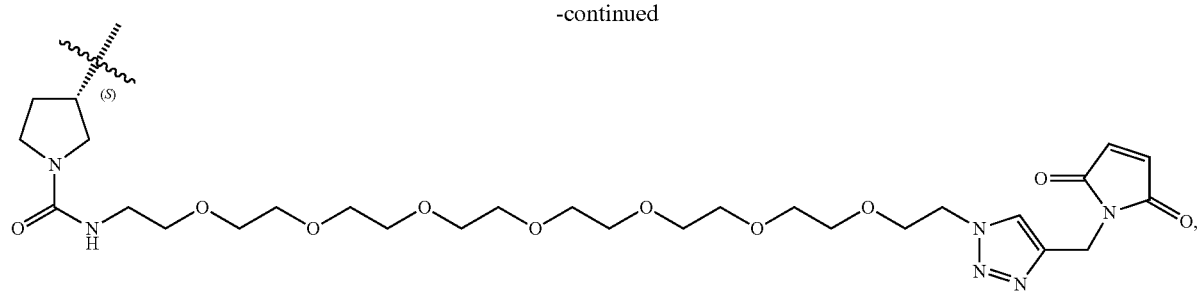
or
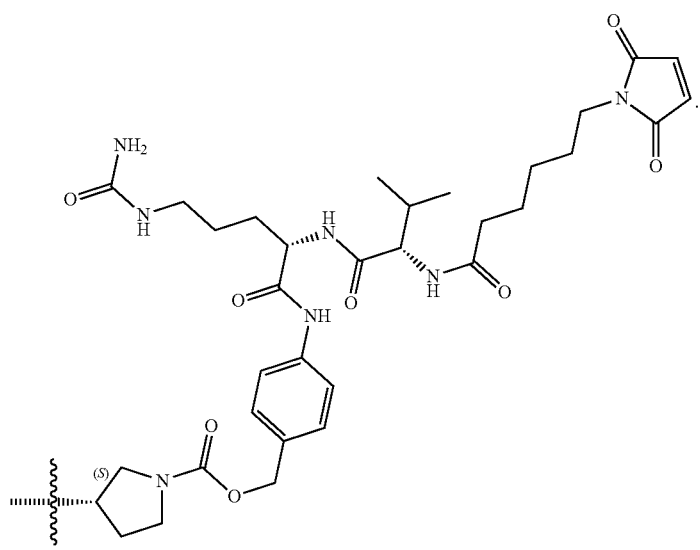
In certain embodiments of any of the aforementioned cytotoxic cyclic peptides of Formula (I) and Formula (Ia): $R^2$ is
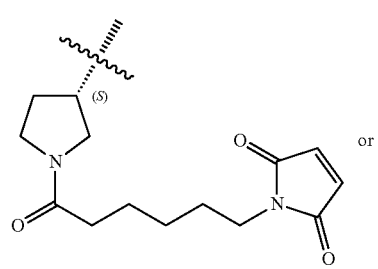 or 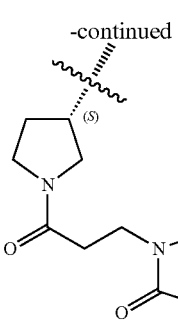
-continued
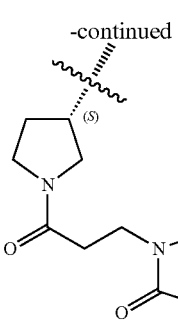
In certain embodiments of any of the aforementioned cytotoxic cyclic peptides of Formula (I) and Formula (Ia): $R^2$ is
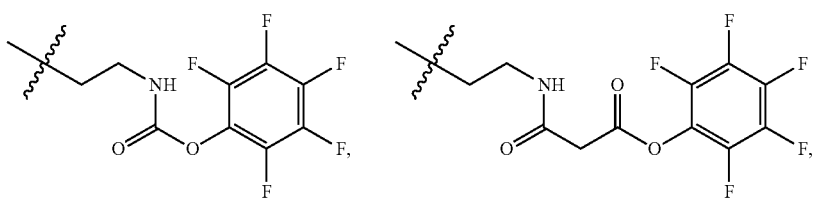

-continued
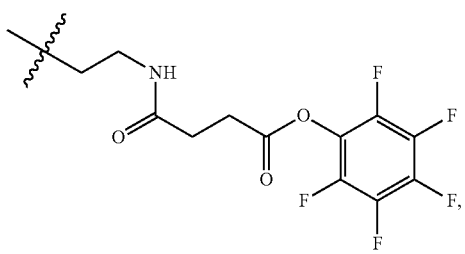
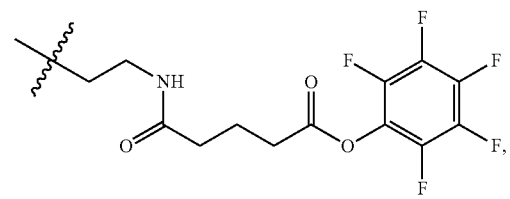
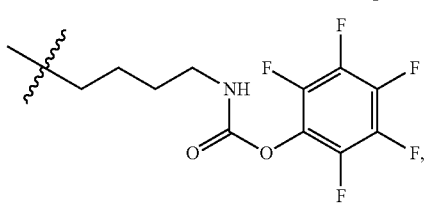
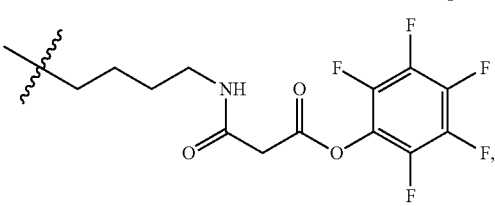
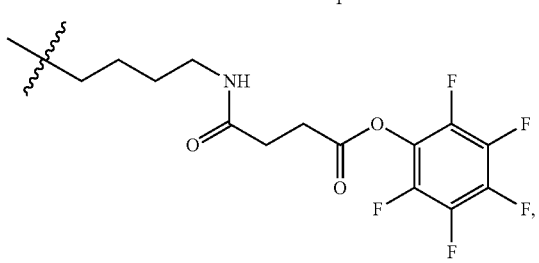
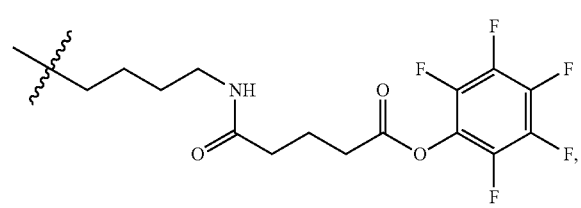
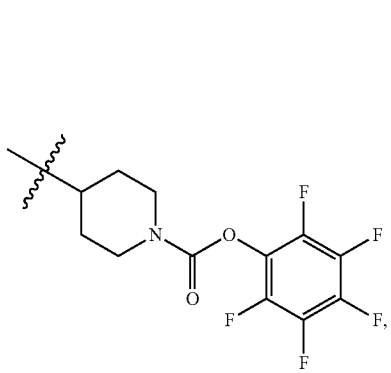
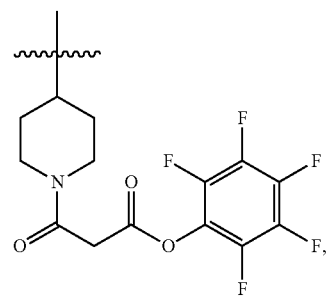
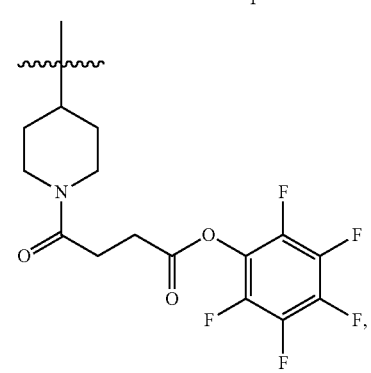
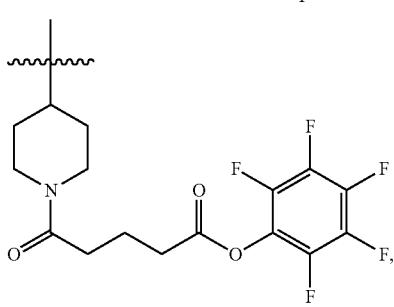
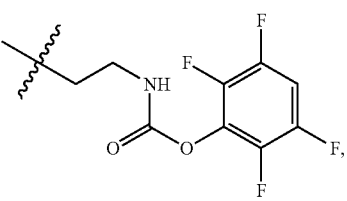
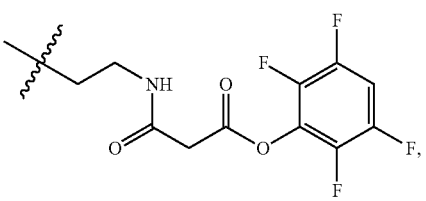
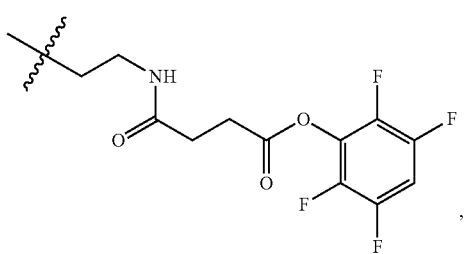

-continued
79
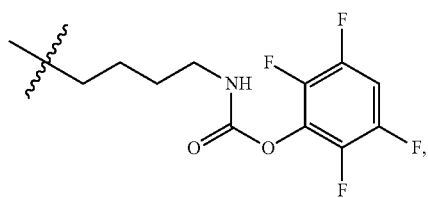
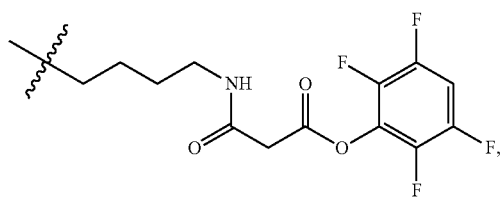
80
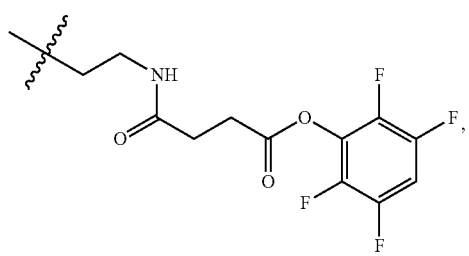
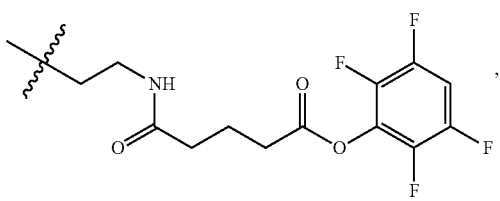
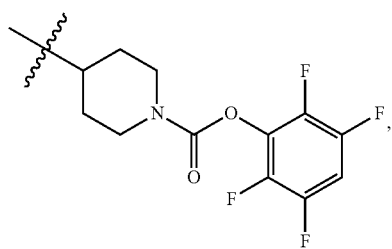
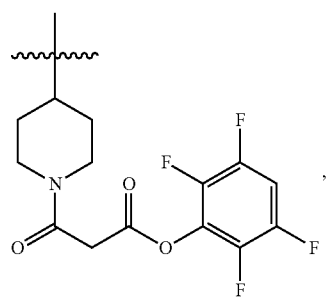
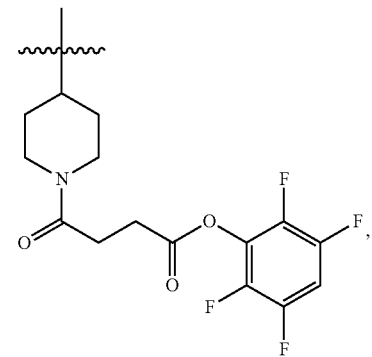
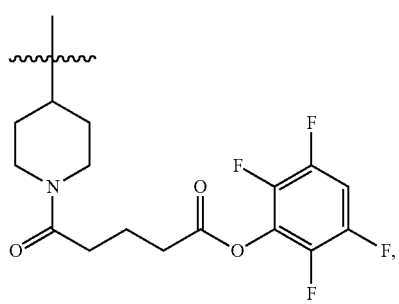
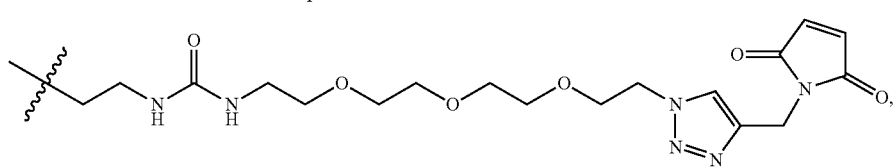
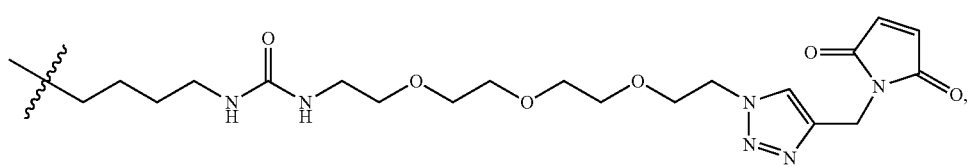
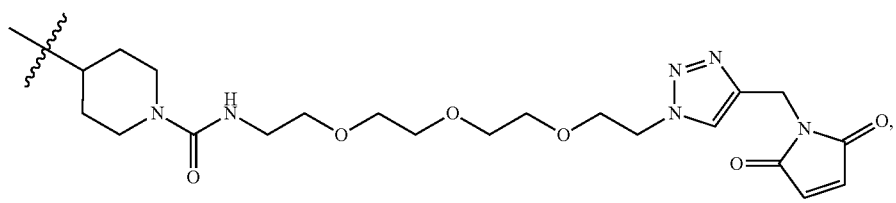

-continued
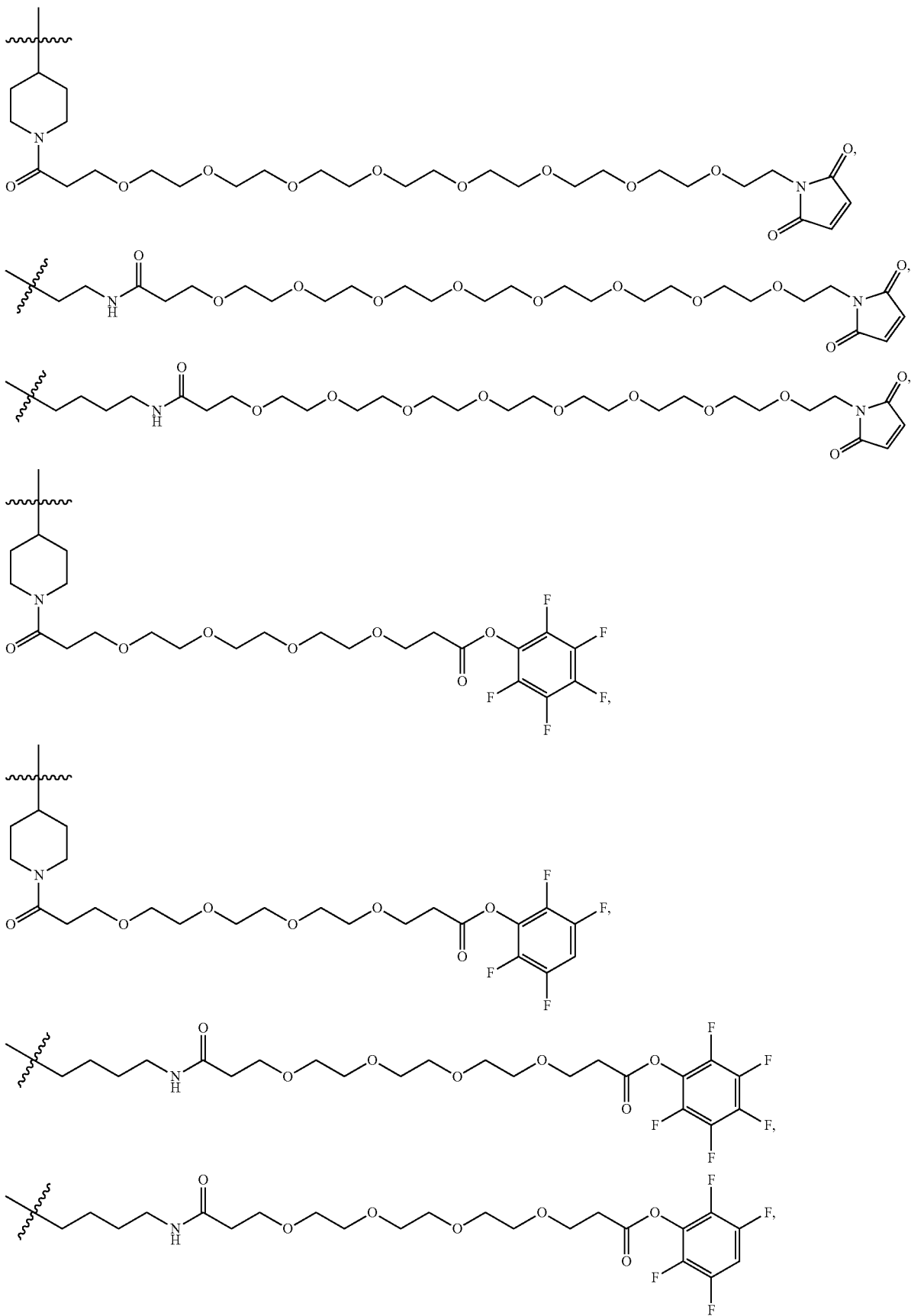

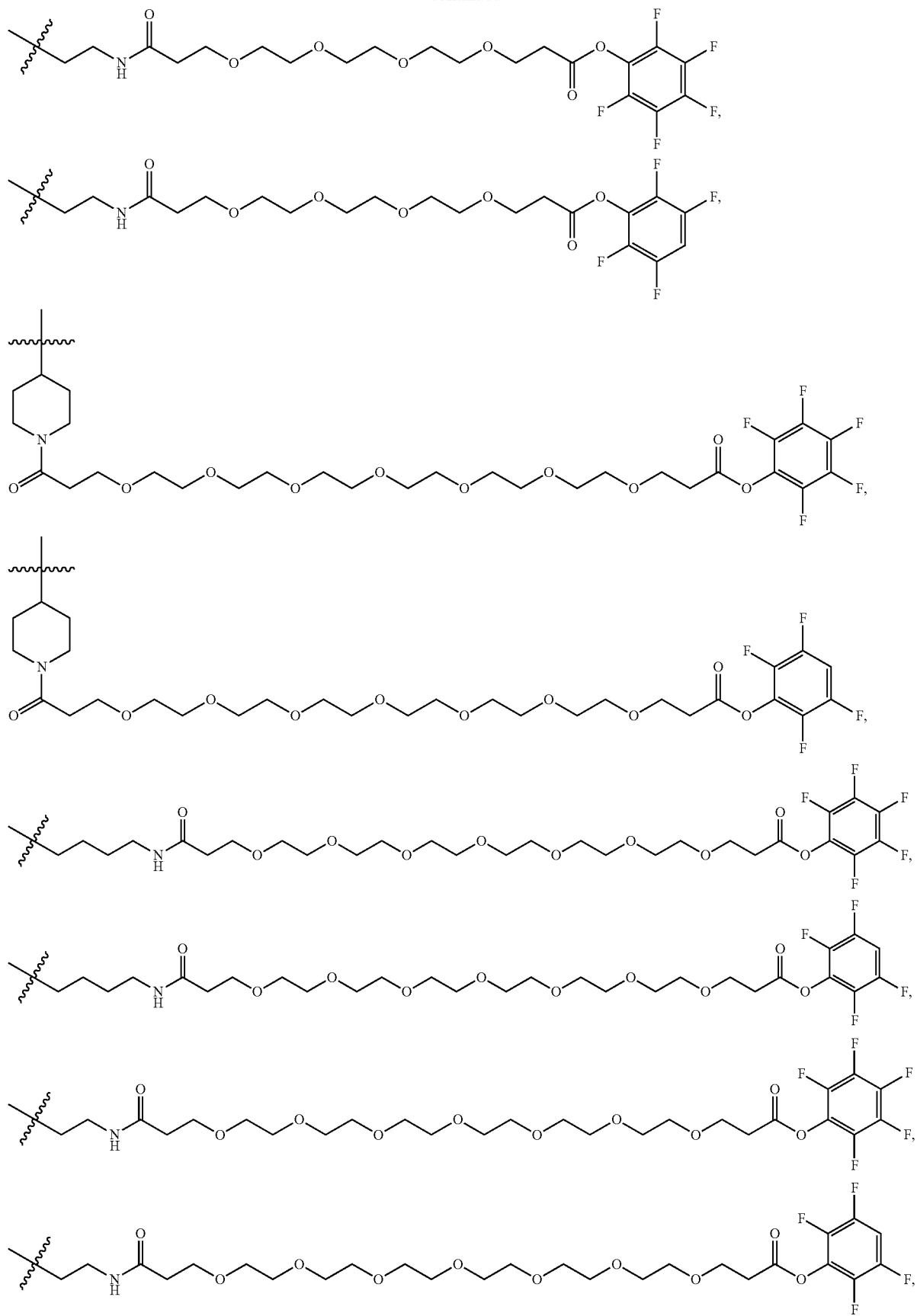

-continued

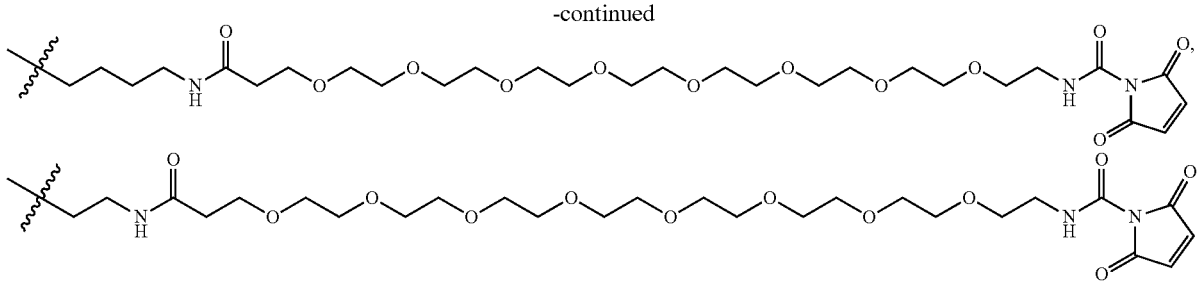

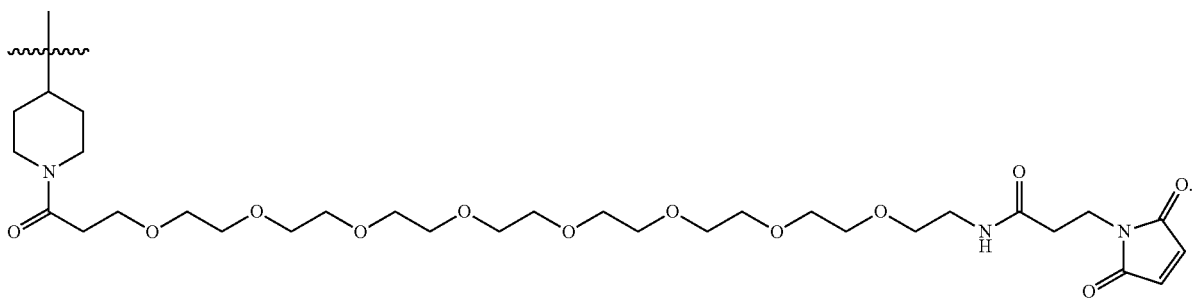

or

In certain embodiments of any of the aforementioned cytotoxic cyclic peptides of Formula (I) and Formula (Ia) $R^1$ is —CH$_3$, while in certain other embodiments of any of the aforementioned cytotoxic cyclic peptides of Formula (I) and Formula (Ia) $R^1$ is H.

In certain embodiments of any of the aforementioned cytotoxic cyclic peptides of Formula (I) and Formula (Ia) $R^3$ is —NH$_2$, while in certain other embodiments of any of the aforementioned cytotoxic cyclic peptides of Formula (I) and Formula (Ia) $R^3$ is —OH.

In certain embodiments of any of the aforementioned cytotoxic cyclic peptides of Formula (I) and Formula (Ia), the cytotoxic cyclic peptides of Formula (I) and Formula (Ia) is selected from:

6'O-methyl-7'C-((2-(2-(maleimido)ethanecarboxamido)ethylthio)methyl)-α-Amanitin;
6'O-methyl-7'C-((2-(3-(maleimido)propanecarboxamido) ethylthio)methyl)-α-Amanitin;
6'O-methyl-7'C-((2-(4-(maleimido)butanecarboxamido)ethylthio)methyl)-α-Amanitin;
6'O-methyl-7'C-((2-(5-(maleimido)pentanecarboxamido) ethylthio)methyl)-α-Amanitin;
6'O-methyl-7'C-(2-((4-((maleimido)methyl)cyclohexanecarboxamido)ethylthio)methyl)-α-Amanitin;
6'O-methyl-7'C-((2-(5-(5-(maleimido)pentanecarboxamido) pentanecarboxamido)ethylthio)methyl)-α-Amanitin;
6'O-methyl-7'C-((2-(6-(4-((maleimido)methyl)cyclohexanecarboxamido)hexanecarboxamido)ethylthio)methyl)-α-Amanitin;
6'O-methyl-7'C-((2-(14-(maleimido)-3,6,9,12-tetraoxatetradecancarboxamido)ethylthio)methyl)-α-Amanitin;
6'O-methyl-7'C-((2-(14-((4-maleimido)methyl-1H-1,2,3-triazol-1-yl)-3,6,9,12-tetraoxatetradecancarboxamido) ethylthio)methyl)-α-Amanitin;
6'O-methyl-7'C-(2-((2,5-dioxopyrrolidin-1-yl)oxycarbonylamino)ethylthiomethyl)-α-Amanitin;
6'-O-methyl-7'-C-((2-(3-(6-(maleimido)hexyl)ureido)ethylthio)methyl)-α-Amanitin;
6'-O-methyl-7'C-(MC-Val-Cit-PABC-(2-aminoethyl)thiomethyl-)-α-Amanitin;
6'O-methyl-7'C-((2-(3-(23-((4-maleimido)methyl-1H-1,2,3-triazol-1-yl)-3,6,9,12,15,18,21-heptaoxatricosyl) ureido) ethylthio)methyl)-α-Amanitin;
6'O-methyl-7'C-((2-(4-(maleimido)ethanecarboxamido)butylthio)methyl)-α-Amanitin;
6'O-methyl-7'C-((4-(5-(maleimido)pentanecarboxamido) butylthio)methyl)-α-Amanitin;
6'O-methyl-7'C-(4-((2,5-dioxopyrrolidin-1-yl)oxycarbonylamino)butylthiomethyl)-α-Amanitin;
6'O-methyl-7'C-((4-(4-((maleimido)methyl)cyclohexanecarboxamido)butylthio)methyl)-α-Amanitin;
6'O-methyl-7'C-((4-(3-(6-(maleimido)hexyl)ureido)butylthio)methyl)-α-Amanitin;
6'O-methyl-7'C-((4-(5-(5-(maleimido)pentanecarboxamido) pentanecarboxamido)butylthio)methyl)-α-Amanitin;
6'O-methyl-7'C-((4-(5-(4-((maleimido)methyl)cyclohexanecarboxamido)pentanecarboxamido)butylthio)methyl)-α-Amanitin;
6'O-methyl-7'C-((4-(14-(maleimido)-3,6,9,12-tetraoxatetradecancarboxamido)butylthio)methyl)-α-Amanitin;
6'O-methyl-7'C-((4-(14-((4-maleimido)methyl-1H-1,2,3-triazol-1-yl)-3,6,9,12-tetraoxatetradecancarboxamido)butylthio)methyl)-α-Amanitin;
6'O-methyl-7'C-((4-(3-(23-((4-maleimido)methyl-1H-1,2,3-triazol-1-yl)-3,6,9,12,15,18,21-heptaoxatricosyl) ureido) butylthio)methyl)-α-Amanitin;
7'C-((2-(5-(maleimido)pentanecarboxamido)ethylthio) methyl)-α-Amanitin;
6'O-methyl-7'C-((1-(3-(maleimido)propanoyl)-azetidin-3-thio)methyl)-α-Amanitin;
6'O-methyl-7'C-((1-(6-(maleimido)hexanoyl)-azetidin-3-thio)methyl)-α-Amanitin;
6'O-methyl-7'C-((1-(3-(maleimido)propanoyl)-piperidine-4-thio)methyl)-α-Amanitin;
6'O-methyl-7'C-((1-(6-(maleimido)hexanoyl)-piperidine-4-thio)methyl)-α-Amanitin;
6'O-methyl-7'C—((N-(4-((maleimido)methyl)cyclohexanecarbonyl)piperidine-4-thio)methyl)-α-Amanitin;
6'O-methyl-7'C-((1-(6-(6-(maleimido)hexanamido) hexanoyl)-piperidine-4-thio)methyl)-α-Amanitin;

6'O-methyl-7'C-((1-(6-(4-((maleimido)methyl)cyclohexanecarboxamido)hexanoyl)-piperidine-4-thio)methyl)-α-Amanitin;

6'O-methyl-7'C-((1-(15-(maleimido)-4,7,10,13-tetraoxapentadecanoyl)-piperidine-4-thio)methyl)-α-Amanitin;

6'O-methyl-7'C—(R)—(N-(3-(maleimido)propanoyl)pyrrolidine-3-thio)methyl -α-Amanitin;

6'O-methyl-7'C—(R)—(N-(6-(maleimido)hexanoyl)pyrrolidine-3-thio)methyl -α-Amanitin;

6'O-methyl-7'C—(S)—(N-(3-(maleimido)propanoyl)pyrrolidine-3-thio)methyl -α-Amanitin;

6'O-methyl-7'C—(S)—(N-(6-(maleimido)hexanoyl)pyrrolidine-3-thio)methyl -α-Amanitin;

6'O-methyl-7'C—(N-(6-(maleimido)hexanoyl)pyrrolidine-3-thio)methyl -α-Amanitin;

6'O-methyl-7'C-(((4-(4-maleimido)methyl-1H-1,2,3-triazol-1-yl)butylthio)methyl)-α-Amanitin;

6'O-methyl-7'C-((6-(aminoxy)hexaneamido)-ethylthiomethyl)-□-Amanitin;

6'O-methyl-7'C-((1-(6-(aminooxy) hexanoyl)-piperidine-4-thio)methyl)-α-Amanitin;

6'O-methyl-7'C-((6-(aminoxy)hexaneamido)-butylthiomethyl)-□-Amanitin;

NHS ester of 6'O-methyl-7'C-((2-(3-(carboxy)propanecarboxamido)ethylthio)methyl)-α-Amanitin;

NHS ester of 6'O-methyl-7'C-((4-(3-(carboxy)propanecarboxamido)butylthio)methyl)-α-Amanitin;

NHS ester of 6'O-methyl-7'C-((1-(4-(carboxy)butanoyl)-piperidine-4-thio)methyl)-α-Amanitin, and 6'O-methyl-7'C-((1-(14-((4-maleimido)methyl-1H-1,2,3-triazol-1-yl)-3,6,9,12-tetraoxatetradecancarbonyl)-piperidine-4-thio)methyl)-α-Amanitin.

In other embodiments of any of the aforementioned cytotoxic cyclic peptides of Formula (I) and Formula (Ia), the cytotoxic cyclic peptides of Formula (I) and Formula (Ia) is selected from:

Tetrafluorophenyl ester of 6'O-methyl-7'C-((4-(3-(carboxy)propanecarboxamido)butylthio)methyl)-α-Amanitin;

7'C-((4-(3-(23-((4-maleimido)methyl-1H-1,2,3-triazol-1-yl)-3,6,9,12,15,18,21-heptaoxatricosyl) ureido)butylthio)methyl)-α-Amanitin;

7'C-((4-(14-(maleimido)-3,6,9,12-tetraoxatetradecancarboxamido)butylthio)methyl)-α-Amanitin;

6'O-methyl-7'C-((4-(26-(maleimido)-3,6,9,12,15,18,21,24-octaoxahexacosancarboxamido)butylthio)methyl)-α-Amanitin;

6'O-methyl-7'C-((4-(3-(2-(2-(2-(2-((4-maleimido)methyl-1H-1,2,3-triazol-1-yl)-ethoxy)ethoxy)ethoxy)ethyl)ureido)butylthio)methyl)-α-Amanitin;

6'O-methyl-7'C-((1-(26-(maleimido)-3,6,9,12,15,18,21,24-octaoxahexacosancarboxamido)-piperidine-4-thio)methyl)-α-Amanitin;

Perfluorophenyl ester of 6'O-methyl-7'C-((4-((23-carboxy) 3,6,9,12,15,18,21-heptaoxatricosancarboxamido)butylthio)methyl)-α-Amanitin;

Tetrafluorophenyl ester of 6'O-methyl-7'C-((4-(14-carboxy-3,6,9,12-tetraoxatetradecancarboxamido)butylthio)methyl)-α-Amanitin;

6'O-methyl-7'C-((4-(26-(3-(maleimido)propanamido)-3,6,9,12,15,18,21,24-octaoxahexacosancarboxamido)butylthio)methyl)-α-Amanitin; and Perfluorophenyl ester of 6'O-methyl-7'C-(1-((23-carboxy-3,6,9,12,15,18,21-heptaoxatricosancarbonyl)-piperidine-4-thio)methyl)-α-Amanitin.

In other embodiments of any of the aforementioned cytotoxic cyclic peptides of Formula (I) and Formula (Ia), the cytotoxic cyclic peptides of Formula (I) and Formula (Ia) is selected from:

6'O-methyl-7'C-((2-(3-(23-((4-maleimido)methyl-1H-1,2,3-triazol-1-yl)-3,6,9,12,15,18,21-heptaoxatricosyl)ureido)ethylthio)methyl)-α-Amanitin;

6'O-methyl-7'C-((4-(3-(23-((4-maleimido)methyl-1H-1,2,3-triazol-1-yl)-3,6,9,12,15,18,21-heptaoxatricosyl)ureido)butylthio)methyl)-α-Amanitin, and 6'O-methyl-7'C-((4-(14-(maleimido)-3,6,9,12-tetraoxatetradecancarboxamido)butylthio)methyl)-α-Amanitin.

The present invention provides immunoconjugates, also referred to herein as ADCs, containing cytotoxic cyclic peptides linked to an antigen binding moiety, such as an antibody or antibody fragment. These conjugates comprising cytotoxic cyclic peptides are useful to treat cell proliferation disorders, particularly when the cytotoxic cyclic peptides are linked to an antibody that recognizes cancer cells and thus promotes delivery of the cytotoxic cyclic peptides to a cell targeted for attack. The immunoconjugates are especially useful for treating certain cancers as further detailed herein. Data provided herein demonstrate that these immunoconjugates are effective inhibitors of cell proliferation.

In one aspect of the immunoconjugates of the invention include immunoconjugates of Formula (B):

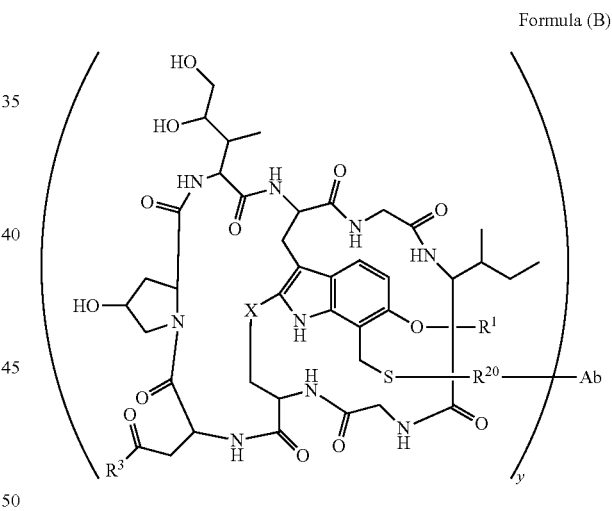

Formula (B)

wherein:

X is S(=O), S(=O)$_2$ or S;

Ab represents an antigen binding moiety;

y is an integer from 1 to 16;

$R^1$ is H or —CH$_3$; $R^3$ is —NH$_2$ or —OH; $R^{20}$ is -L$_1$L$_2$R$^{40}$, -L$_3$R$^{60}$ or —(CH$_2$)$_m$X$_3$(CH$_2$)$_m$R$^{40}$;

L$_1$ is —(CH$_2$)$_m$NR$^5$C(=O)—,

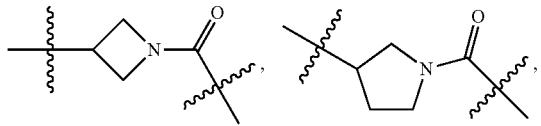

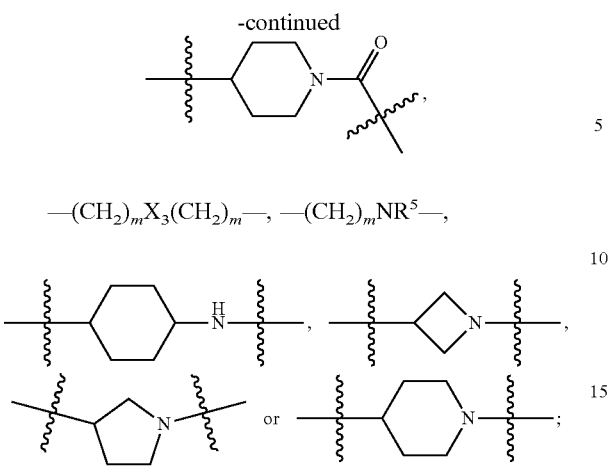

—(CH$_2$)$_m$X$_3$(CH$_2$)$_m$—, —(CH$_2$)$_m$NR$^5$—,

L$_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$O(CH$_2$)$_m$)$_n$—, —(CH$_2$)$_m$NR$^5$(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$R$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$(O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$(O(CH$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$—, or —(CH$_2$)$_m$X$_3$(CH$_2$)$_m$NR$^5$C(=O)—, wherein:

X$_1$ is

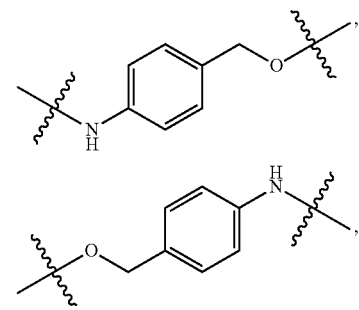

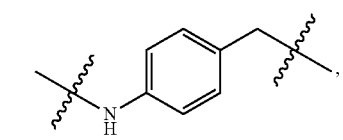

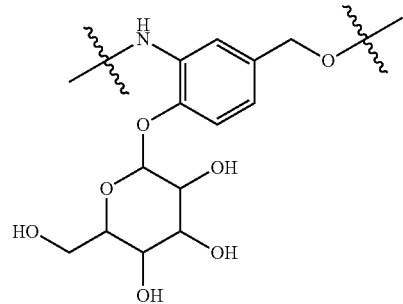

or

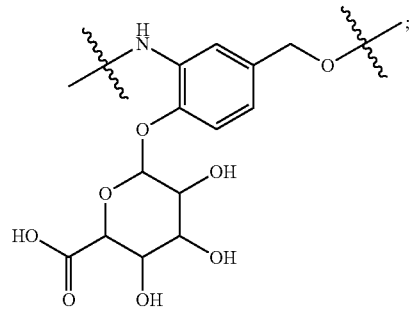

$X_2$ is
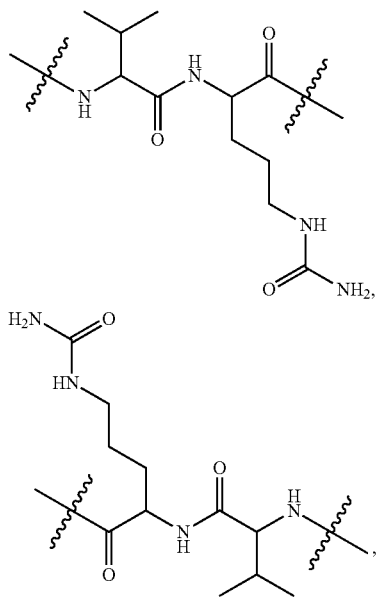
$X_3$ is
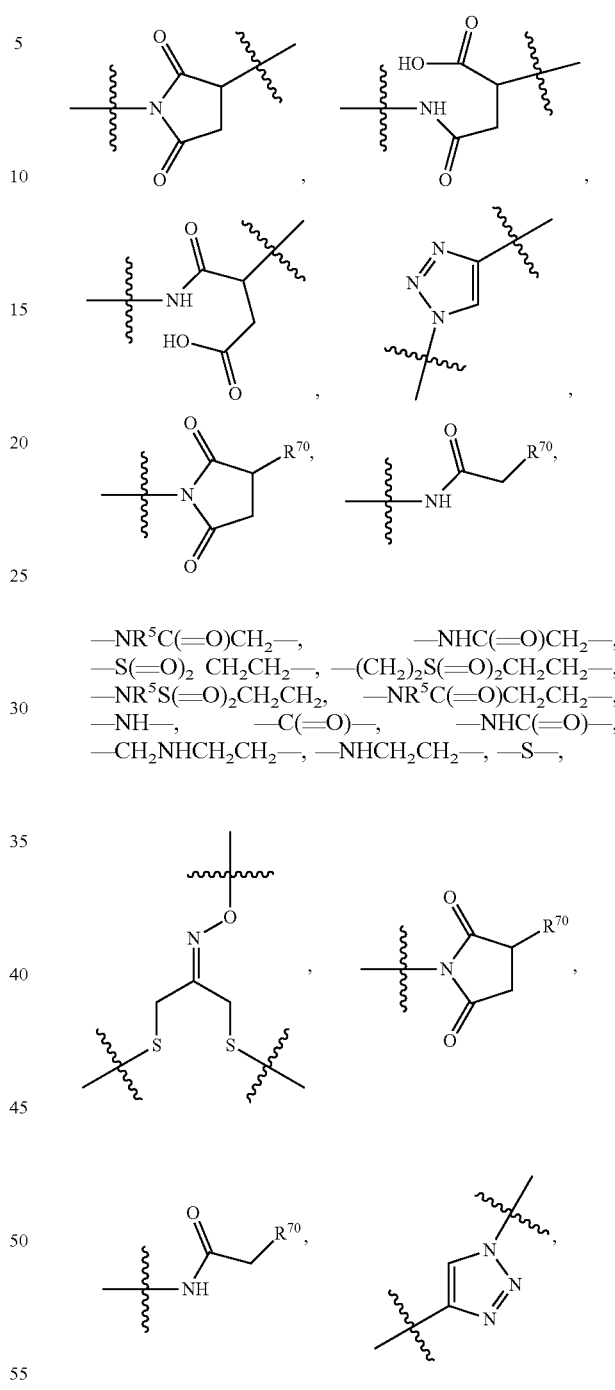
and $X_4$ is
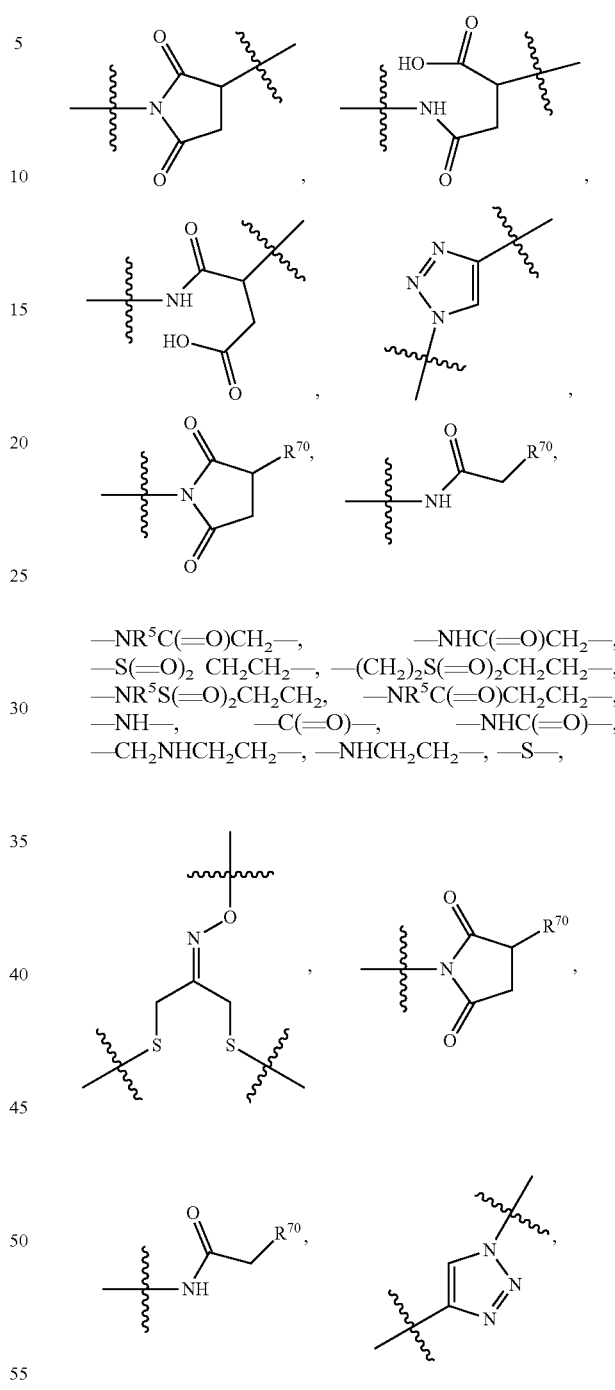
$L_3$ is —(CH$_2$)$_m$NR$^5$C(=O)—;
$R^{40}$ is
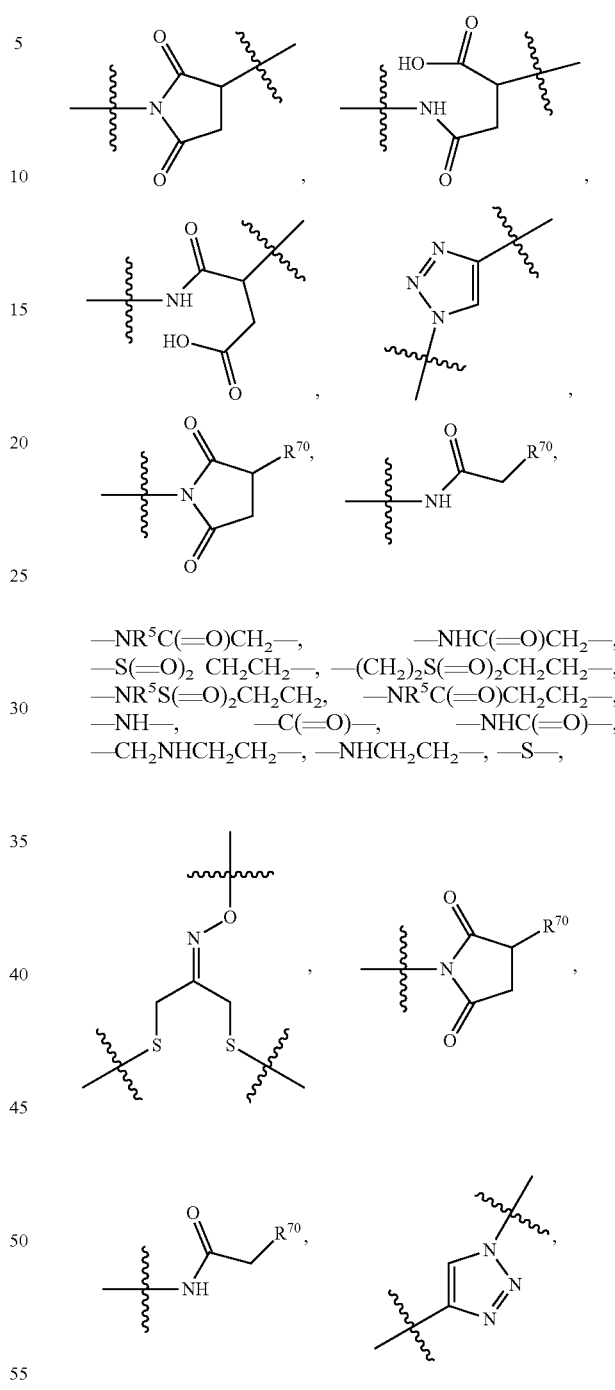
—NR$^5$C(=O)CH$_2$—,  —NHC(=O)CH$_2$—,
—S(=O)$_2$ CH$_2$CH$_2$—, —(CH$_2$)$_2$S(=O)$_2$CH$_2$CH$_2$—,
—NR$^5$S(=O)$_2$CH$_2$CH$_2$, —NR$^5$C(=O)CH$_2$CH$_2$—,
—NH—,  —C(=O)—,  —NHC(=O)—,
—CH$_2$NHCH$_2$CH$_2$—, —NHCH$_2$CH$_2$—, —S—,

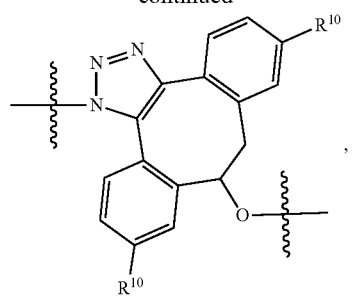,
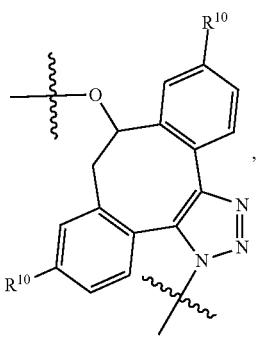,
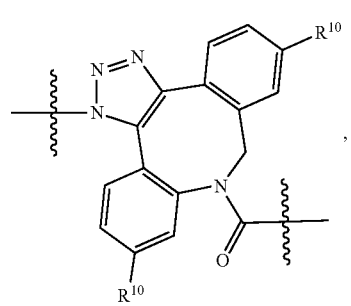,
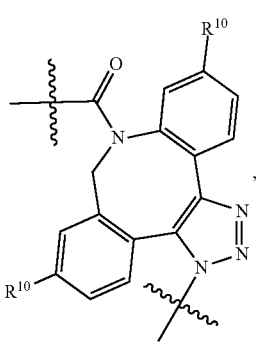,
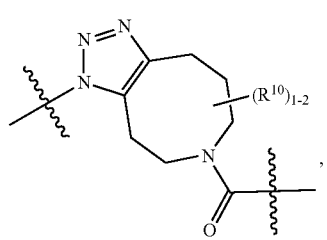,
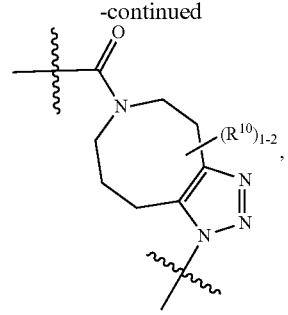,
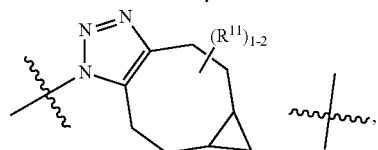,
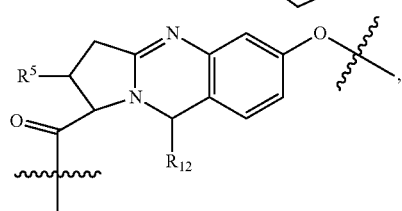,
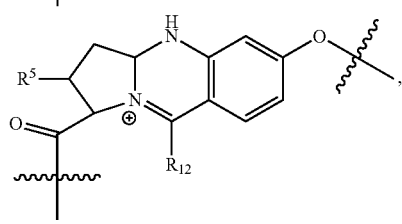,
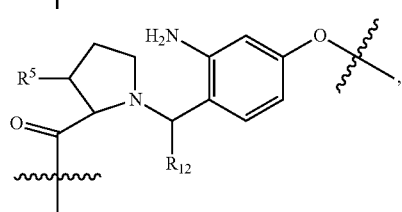,
,
,
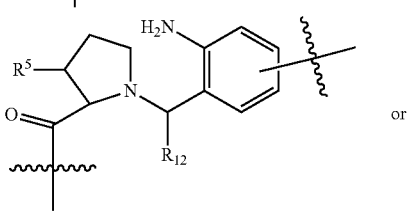 or -continued

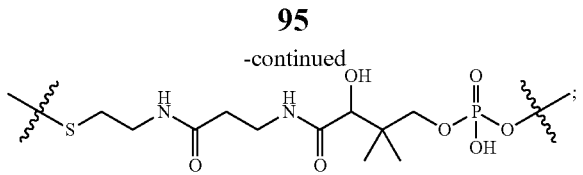

each $R^5$ is independently selected from H and $C_1$-$C_6$alkyl;
$R^{60}$ is —NH—;
$R^{70}$ is

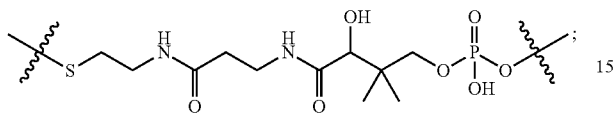

$R^8$ is H, $C_1$-$C_6$alkyl or —C(=O)$OR^5$;
each $R^9$ is independently selected from H, $C_1$-$C_6$alkyl, F, Cl, and —OH;
each $R^{10}$ is independently selected from H, $C_1$-$C_6$alkyl, F, Cl, —$NH_2$, —$OCH_3$, —$OCH_2CH_3$, —N($CH_3$)$_2$, —CN, —$NO_2$ and —OH;
each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each $R^{12}$ is independently selected from H, —$CH_3$ and phenyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.

In one aspect of the immunoconjugates of the invention include immunoconjugates of Formula (II):

Formula (II)

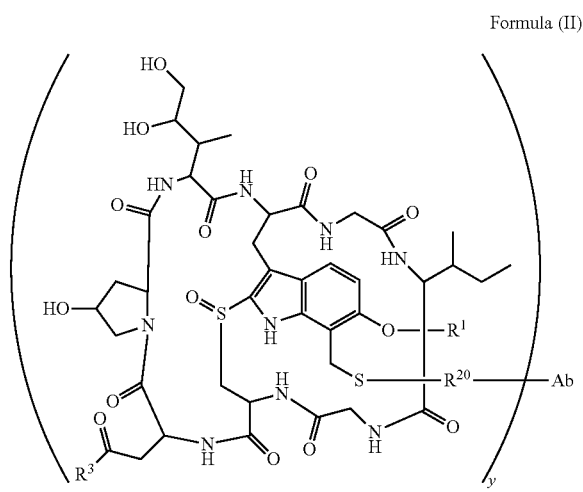

wherein:
Ab represents an antigen binding moiety;
y is an integer from 1 to 16;
$R^1$ is H or —$CH_3$; $R^3$ is —$NH_2$ or —OH; $R^{20}$ is -$L_1L_2R^{40}$, -$L_3R^{60}$ or —($CH_2$)$_m$$X_3$($CH_2$)$_m$$R^{40}$;

$L_1$ is —($CH_2$)$_m$$NR^5$C(=O)—,

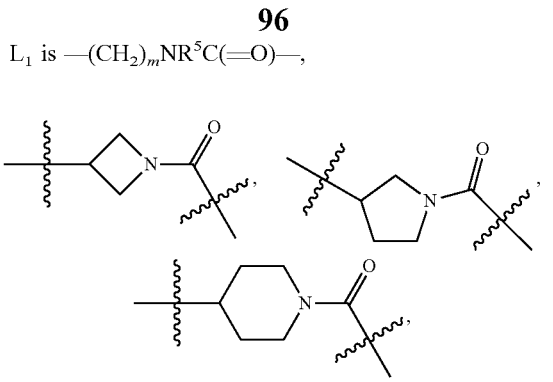

—($CH_2$)$_m$$X_3$($CH_2$)$_m$—, —($CH_2$)$_m$$NR^5$—,

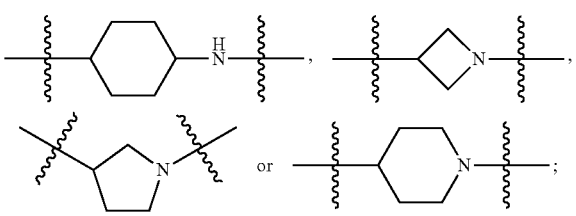

$L_2$ is —($CH_2$)$_m$—, —$NR^5$($CH_2$)$_m$—, —($CH_2$)$_m$$NR^5$C(=O)($CH_2$)$_m$—, —$X_4$, —($CH_2$)$_m$$NR^5$C(=O)$X_4$, —($CH_2$)$_m$$NR^5$C(=O)—, —(($CH_2$)$_m$O)$_n$($CH_2$)$_m$—, —(($CH_2$)$_m$O)$_n$($CH_2$)$_m$$X_3$($CH_2$)$_m$—, —$NR^5$(($CH_2$)$_m$O)$_n$$X_3$($CH_2$)$_m$—, —$X_1X_2$C(=O)($CH_2$)$_m$—, —($CH_2$)$_m$(O($CH_2$)$_m$)$_n$—, —($CH_2$)$_m$$NR^5$($CH_2$)$_m$—, —($CH_2$)$_m$$NR^5$C(=O)($CH_2$)$_m$$X_3$($CH_2$)$_m$—, —($CH_2$)$_m$C(=O)$NR^5$($CH_2$)$_m$$NR^5$C(=O)($CH_2$)$_m$—, —($CH_2$)$_m$C(=O)—, —($CH_2$)$_m$$NR^5$($CH_2$)$_m$C(=O)$X_2X_1$X(=O)—, —($CH_2$)$_m$$X_3$($CH_2$)$_m$C(=O)$X_2X_1$C(=O)—, —($CH_2$)$_m$C(=O)$NR^5$($CH_2$)$_m$—, —($CH_2$)$_m$C(=O)$NR^5$($CH_2$)$_m$$X_3$($CH_2$)$_m$—, —($CH_2$)$_m$$X_3$($CH_2$)$_m$$NR^5$C(=O)($CH_2$)$_m$—, —($CH_2$)$_m$$X_3$($CH_2$)$_m$C(=O)$NR^5$($CH_2$)$_m$—, —($CH_2$)$_m$O)$_n$($CH_2$)$_m$$NR^5$C(=O)($CH_2$)$_m$—, —($CH_2$)$_m$C(=O)$NR^5$($CH_2$)$_m$(O($CH_2$)$_m$)$_n$—, —($CH_2$)$_m$(O($CH_2$)$_m$)$_n$C(=O)—, —($CH_2$)$_m$$NR^5$($CH_2$)$_m$C(=O)—, —($CH_2$)$_m$C(=O)$NR^5$($CH_2$)$_m$$NR^5$C(=O)—, —($CH_2$)$_m$(O($CH_2$)$_m$)$_n$$X_3$($CH_2$)$_m$—, —($CH_2$)$_m$$X_3$(($CH_2$)$_m$O)$_n$($CH_2$)$_m$—, —($CH_2$)$_m$$X_3$($CH_2$)$_m$C(=O)—, —($CH_2$)$_m$C(=O)$NR^5$($CH_2$)$_m$O)$_n$($CH_2$)$_m$$X_3$($CH_2$)$_m$—, —($CH_2$)$_m$$X_3$($CH_2$)$_m$(O($CH_2$)$_m$)$_n$$NR^5$C(=O)($CH_2$)$_m$—, —($CH_2$)$_m$$X_3$($CH_2$)$_m$(O($CH_2$)$_m$)$_n$C(=O)—, —($CH_2$)$_m$$X_3$($CH_2$)$_m$(O($CH_2$)$_m$)$_n$—, —($CH_2$)$_m$C(=O)$NR^5$($CH_2$)$_m$C(=O)—, —($CH_2$)$_m$C(=O)$NR^5$($CH_2$)$_m$(O($CH_2$)$_m$)$_n$C(=O)—, —(($CH_2$)$_m$O)$_n$($CH_2$)$_m$$NR^5$C(=O)($CH_2$)$_m$—, —($CH_2$)$_m$C(=O)$NR^5$($CH_2$)$_m$C(=O)$NR^5$($CH_2$)$_m$—, —($CH_2$)$_m$$NR^5$C(=O)($CH_2$)$_m$$NR^5$C(=O)($CH_2$)$_m$—, —($CH_2$)$_m$$X_3$($CH_2$)$_m$C(=O)$NR^5$—, —($CH_2$)$_m$C(=O)$NR^5$—, —($CH_2$)$_m$$X_3$—, —C($R^5$)$_2$($CH_2$)$_m$—, —($CH_2$)$_m$C($R^5$)$_2$$NR^5$—, —($CH_2$)$_m$C(=O)$NR^5$($CH_2$)$_m$$NR^5$—, —($CH_2$)$_m$C(=O)$NR^5$($CH_2$)$_m$$NR^5$C(=O)$NR^5$—, —($CH_2$)$_m$C(=O)$X_2X_1$C(=O)—, —C($R^5$)$_2$($CH_2$)$_m$$NR^5$C(=O)($CH_2$)$_m$—, —($CH_2$)$_m$C(=O)$NR^5$($CH_2$)$_m$C($R^5$)$_2$$NR^5$—, —C($R^5$)$_2$($CH_2$)$_m$$X_3$($CH_2$)$_m$—, —($CH_2$)$_m$$X_3$($CH_2$)$_m$C($R^5$)$_2$$NR^5$—, —C($R^5$)$_2$ ($CH_2$)$_m$OC(=O)$NR^5$($CH_2$)$_m$—, —($CH_2$)$_m$$NR^5$C(=O)O($CH_2$)$_m$C($R^5$)$_2$$NR^5$—, —($CH_2$)$_m$$X_3$($CH_2$)$_m$$NR^5$—, —($CH_2$)$_m$$X_3$($CH_2$)$_m$(O($CH_2$)$_m$)$_n$$NR^5$—, —($CH_2$)$_m$$NR^5$—, —($CH_2$)$_m$C(=O)$NR^5$($CH_2$)$_m$ (O($CH_2$)$_m$)$_n$$NR^5$—, —($CH_2$)$_m$(O($CH_2$)$_m$)$_n$ $NR^5-$, $-(CH_2CH_2O)_n(CH_2)_m-$, $-(CH_2)_m(OCH_2CH_2)_n-$, $-(CH_2)_mO(CH_2)_m-$, $-(CH_2)_mS(=O)_2-$, $-(CH_2)_mC(=O)NR^5(CH_2)_mS(=O)_2-$, $-(CH_2)_mX_3(CH_2)_mS(=O)_2-$, $-(CH_2)_mX_2X_1C(=O)-$, $-(CH_2)_m(O(CH_2)_m)_nC(=O)X_2X_1C(=O)-$, $-(CH_2)_m(O(CH_2)_m)_nX_2X_1C(=O)-$, $-(CH_2)_mX_3(CH_2)_mX_2X_1C(=O)-$, $-(CH_2)_mX_3(CH_2)_m(O(CH_2)_m)_nX_2X_1C(=O)-$, $-(CH_2)_mX_3(CH_2)_mC(=O)NR^5(CH_2)_mNR^5C(=O)-$, $-(CH_2)_mX_3(CH_2)_mC(=O)NR^5(CH_2)_mC(=O)-$, $-(CH_2)_mX_3(CH_2)_mC(=O)NR^5(CH_2)_m(O(CH_2)_m)_nC(=O)-$, $-(CH_2)_mC(=O)X_2X_1C(=O)NR^5(CH_2)_m-$, $-(CH_2)_mX_3(O(CH_2)_m)_nC(=O)-$, $-(CH_2)_mNR^5C(=O)((CH_2)_mO)_n(CH_2)_m-$, $-(CH_2)_m(O(CH_2)_m)_nC(=O)NR^5(CH_2)_m-$, $-(CH_2)_mNR^5C(=O)NR^5(CH_2)_m-$, or $-(CH_2)_mX_3(CH_2)_mNR^5C(=O)-$, wherein:

$X_1$ is

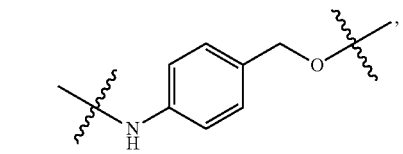


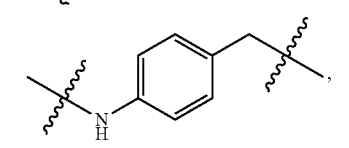

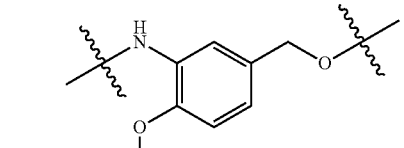

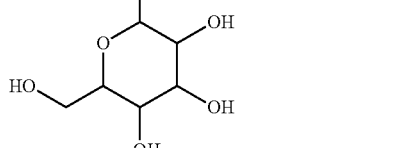

$X_2$ is

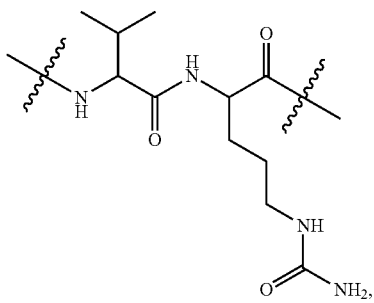

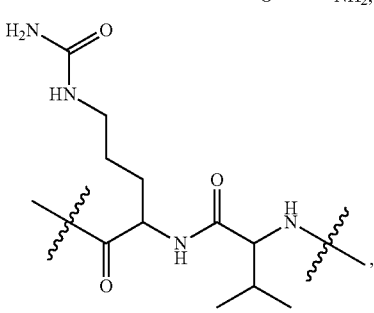

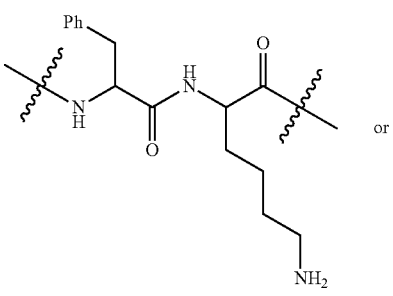

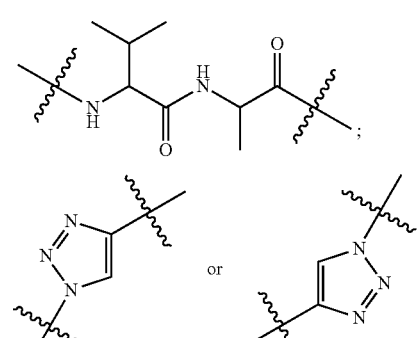

$X_3$ is 

and $X_4$ is

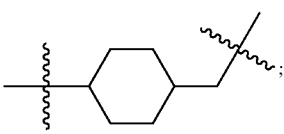 [SMILES: *CC1CCC(*)CC1]

$L_3$ is $-(CH_2)_mNR^5C(=O)-$;

$R^{40}$ is
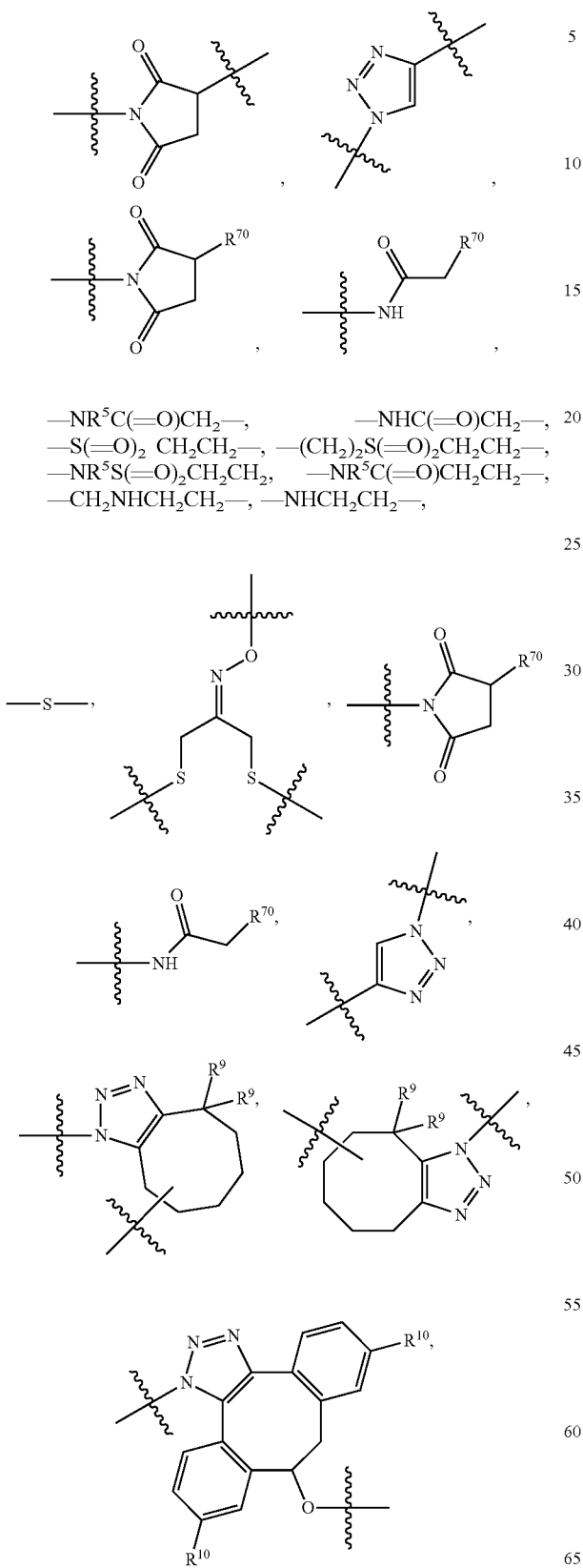
$-NR^5C(=O)CH_2-$, $-NHC(=O)CH_2-$,
$-S(=O)_2\,CH_2CH_2-$, $-(CH_2)_2S(=O)_2CH_2CH_2-$,
$-NR^5S(=O)_2CH_2CH_2$, $-NR^5C(=O)CH_2CH_2$,
$-CH_2NHCH_2CH_2-$, $-NHCH_2CH_2-$,
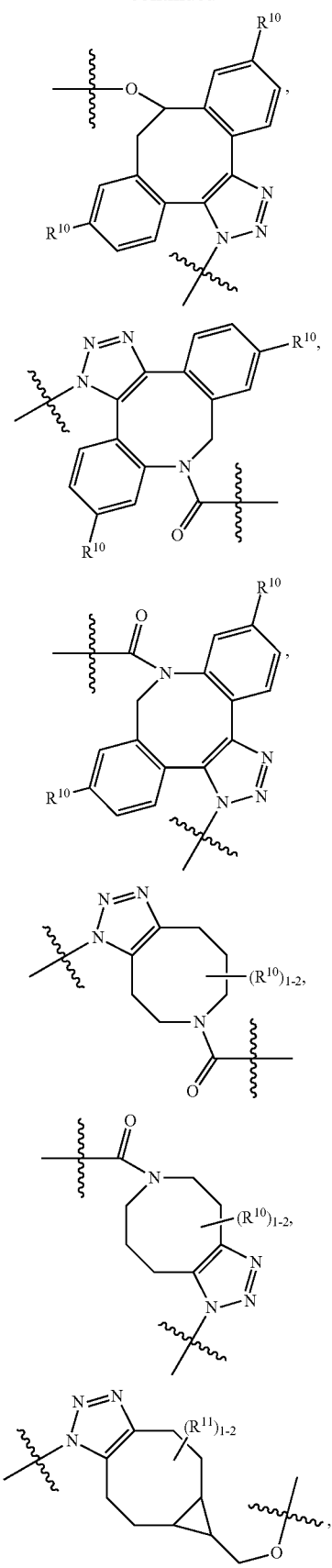

-continued

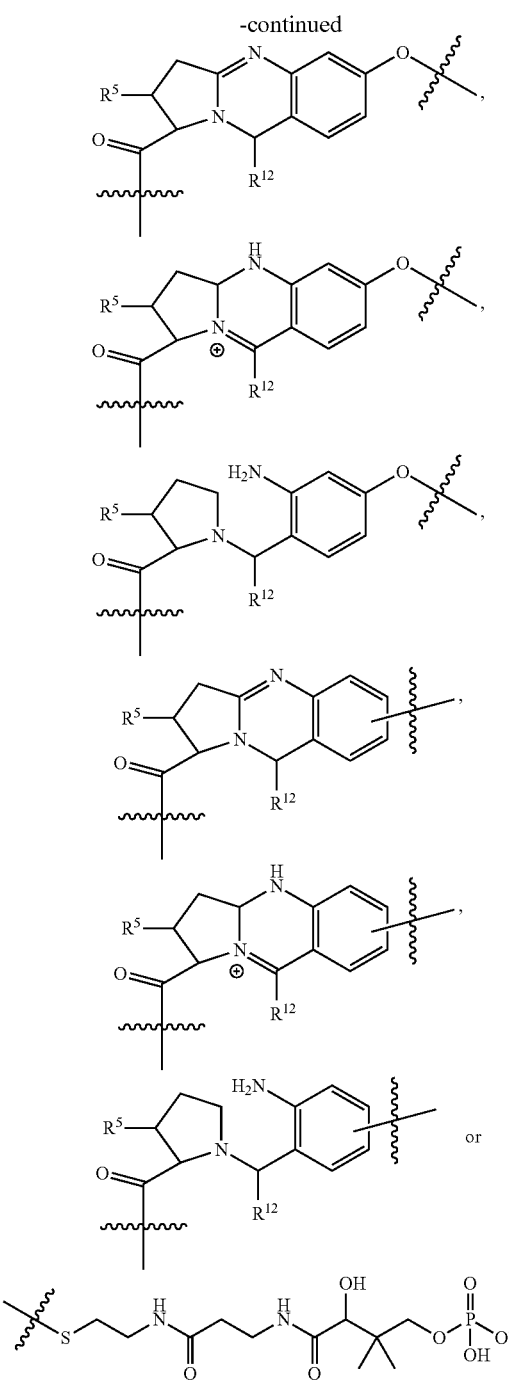

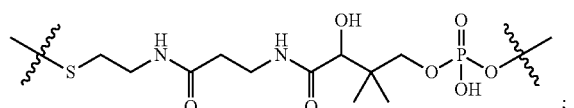

each $R^5$ is independently selected from H and $C_1$-$C_6$alkyl;
$R^{60}$ is —NH—;
$R^{70}$ is

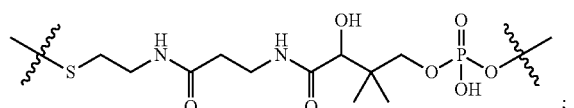

$R^8$ is H, $C_1$-$C_6$alkyl or —C(=O)$OR^5$;
each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{12}$ is independently selected from H, —$CH_3$ and phenyl;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments of this aspect of immunoconjugates having the structure of Formula (II), are immunoconjugates having the structure of Formula (IIa):

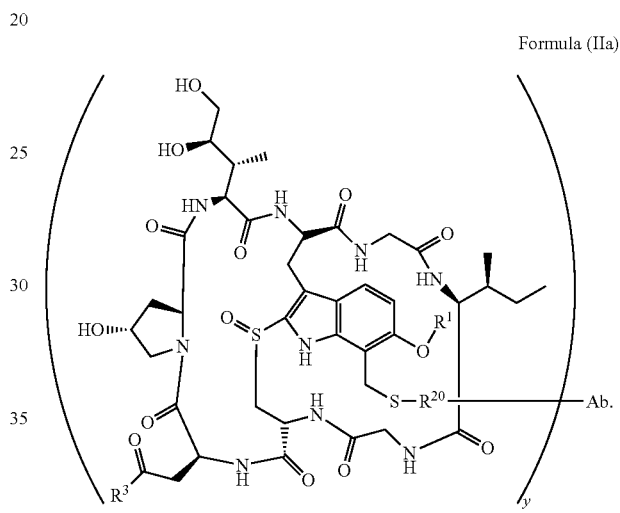

Formula (IIa)

In certain embodiments of such immunoconjugates of Formula (II) and Formula (IIa):

Ab represents an antigen binding moiety;
y is an integer from 1 to 16;
$R^1$ is H or —$CH_3$; $R^3$ is —$NH_2$ or —OH; $R^{20}$ is -$L_1L_2R^{40}$, -$L_3R^{60}$ or —$(CH_2)_mX_3(CH_2)_mR^{40}$;
$L_1$ is —$(CH_2)_mNR^5C(=O)$—,

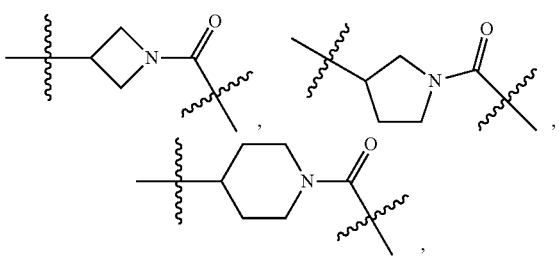

or —$(CH_2)_mX_3(CH_2)_m$—;
$L_2$ is —$(CH_2)_m$—, —$NR^5(CH_2)_m$—, —$(CH_2)_mNR^5C(=O)(CH_2)_m$—, —$X_4$—, —$(CH_2)_mNR^5C(=O)X_4$, —$(CH_2)_mNR^5C(=O)$—, —$((CH_2)_mO)_n(CH_2)_m$—, —$((CH_2)_mO)_n(CH_2)_mX_3(CH_2)_m$—, —$NR^5((CH_2)_mO)_nX_3(CH_2)_m$—, or —$X_1X_2C(=O)(CH_2)_m$—, wherein:

$X_1$ is

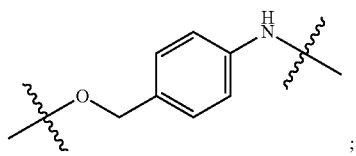 [SMILES: *Nc1ccc(CO*)cc1]

$X_2$ is

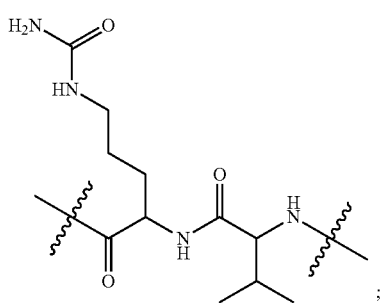 [SMILES: *NC(C(=O)NC(CCCNC(N)=O)C(*)=O)C(C)C]

$X_3$ is

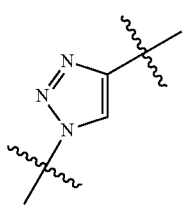 [SMILES: *c1cn(*)nn1]

and $X_4$ is

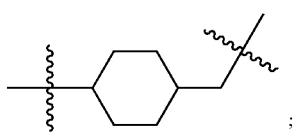

$L_3$ is —$(CH_2)_m NR^5 C(=O)$—; $R^{40}$ is

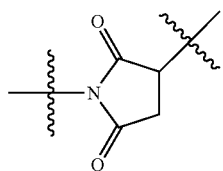

$R^{60}$ is —NH—;
each $R^5$ is independently selected from H and $C_1$-$C_6$alkyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.

In certain embodiments of such immunoconjugates of Formula (II) and Formula (IIa):
Ab represents an antigen binding moiety;
y is an integer from 1 to 16;
$R^1$ is H or —$CH_3$; $R^3$ is —$NH_2$ or —OH; $R^{20}$ is -$L_1 L_2 R^{40}$, -$L_3 R^{60}$ or —$(CH_2)_m X_3 (CH_2)_m R^{40}$;
$L_1$ is —$(CH_2)_m NR^5 C(=O)$—,

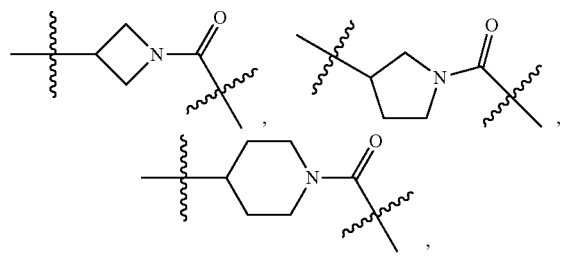

or —$(CH_2)_m X_3 (CH_2)_m$—;
$L_2$ is —$(CH_2)_m$—, —$NR^5(CH_2)_m$—, —$(CH_2)_m NR^5 C(=O)(CH_2)_m$—, —$X_4$—, —$(CH_2)_m NR^5 C(=O) X_4$, —$(CH_2)_m NR^5 C(=O)$—, —$((CH_2)_m O)_n (CH_2)_m$—, —$((CH_2)_m O)_n (CH_2)_m X_3 (CH_2)_m$—, —$NR^5 ((CH_2)_m O)_n X_3 (CH_2)_m$—, —$NR^5 ((CH_2)_m O)_n (CH_2)_m X_3 (CH_2)_m$—, or —$X_1 X_2 C(=O)(CH_2)_m$—,
wherein:

$X_1$ is

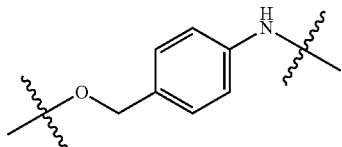

$X_2$ is

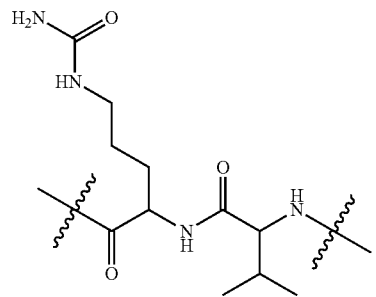

$X_3$ is

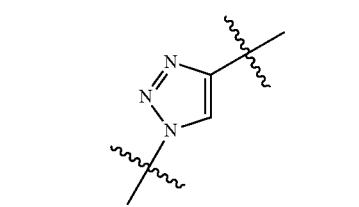 [SMILES: *c1cn(*)nn1]

and X₄ is
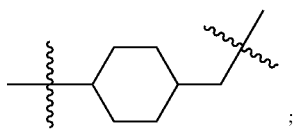
L₃ is —(CH₂)ₘNR⁵C(=O)—;
R⁴⁰ is
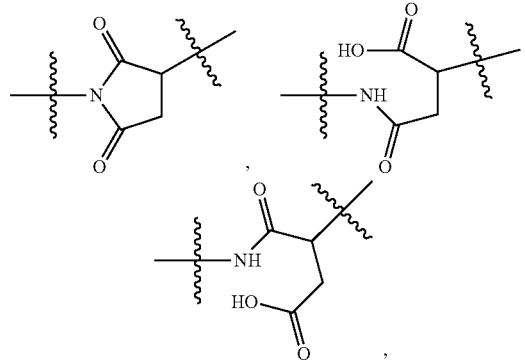
—NH—, —C(=O)—, —NHC(=O)— or
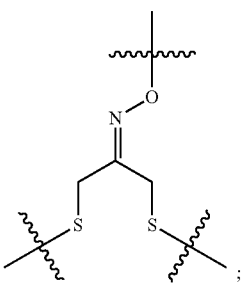 [SMILES: *ON=C(CS*)CS*]
R⁶⁰ is —NH—;
each $R^5$ is independently selected from H and $C_1$-$C_6$alkyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.
In preferred embodiments of any of the aforementioned immunoconjugates of Formula (II) and Formula (IIa):
$R^{20}$ is
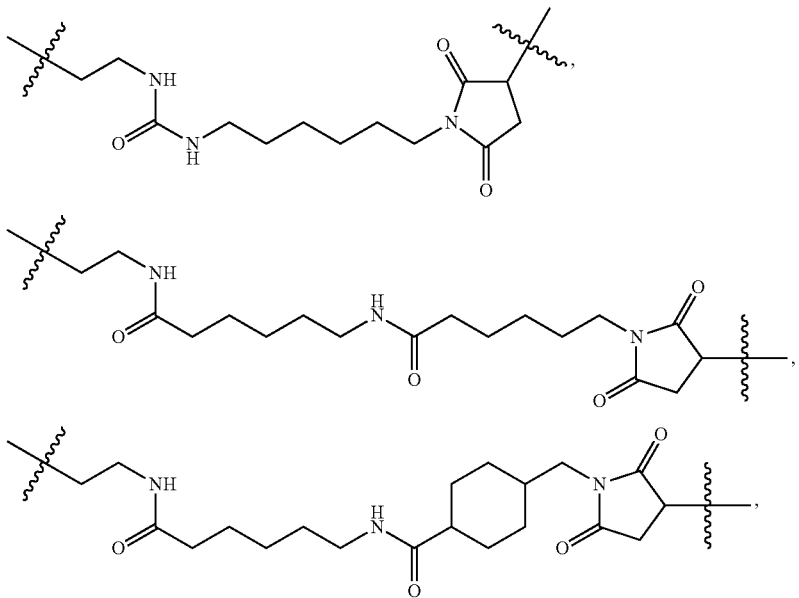
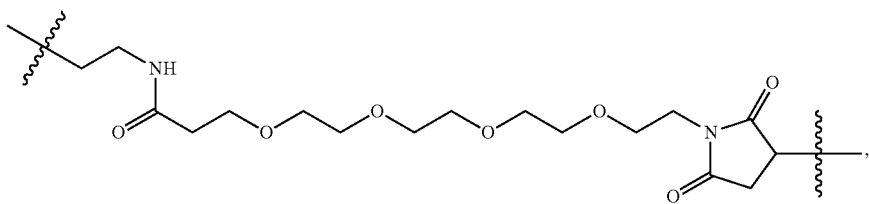

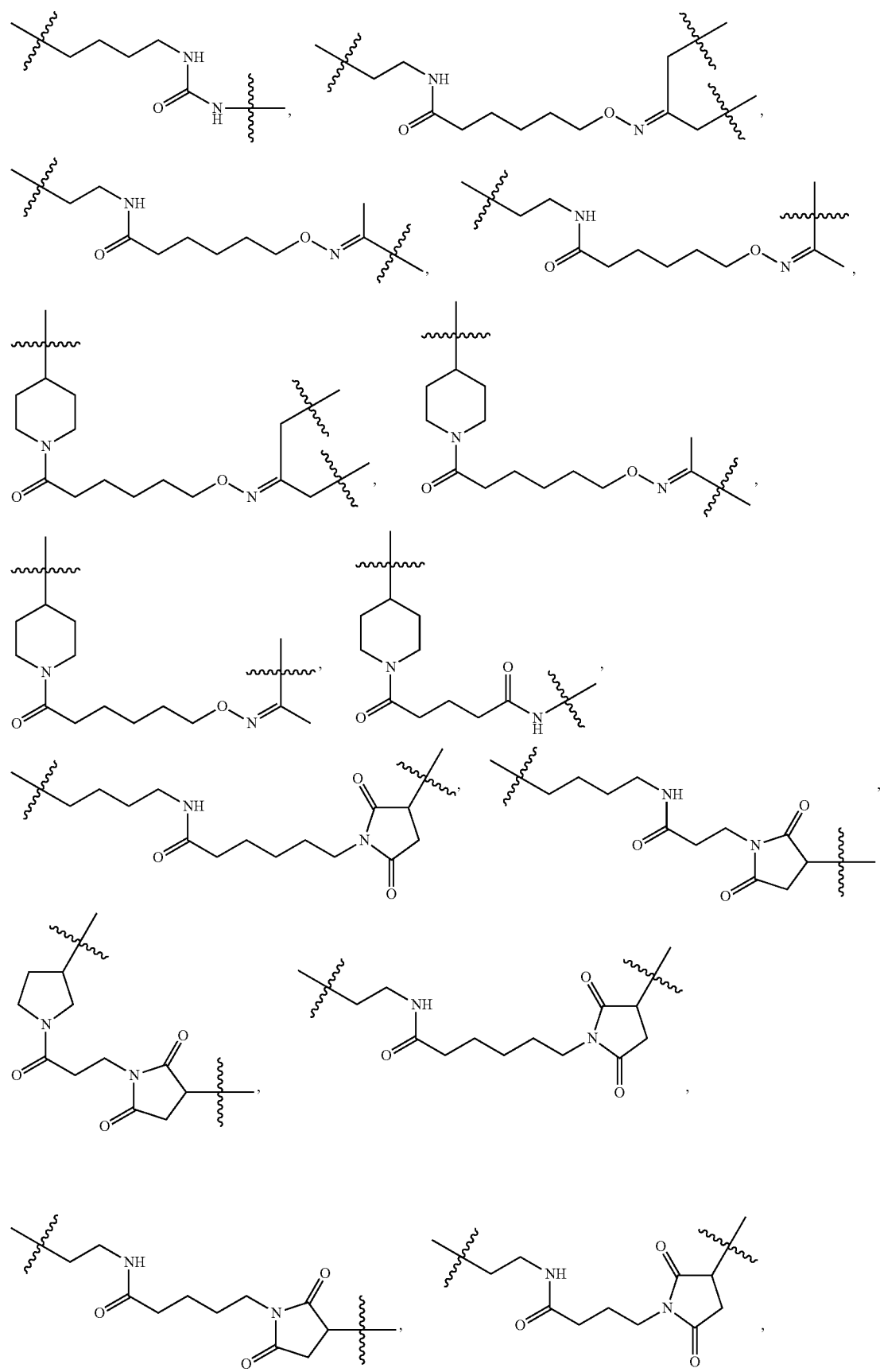

-continued
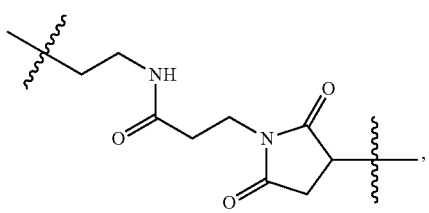
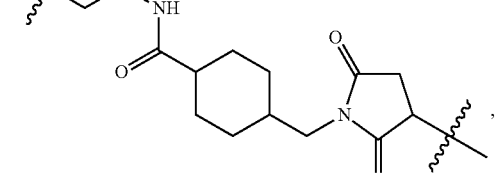
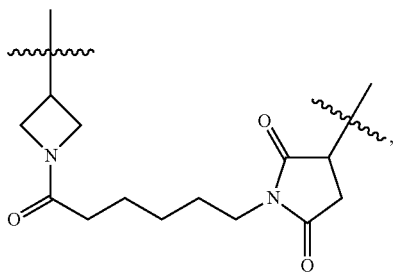
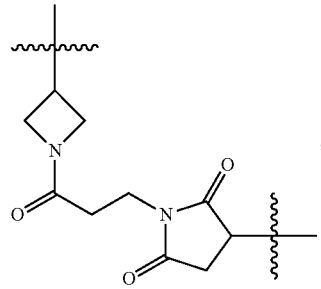
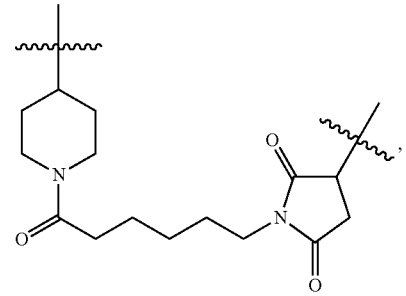
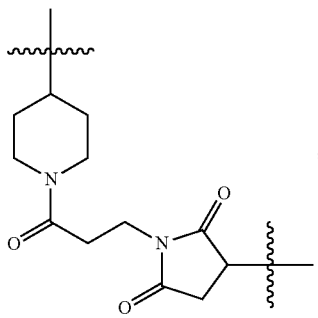
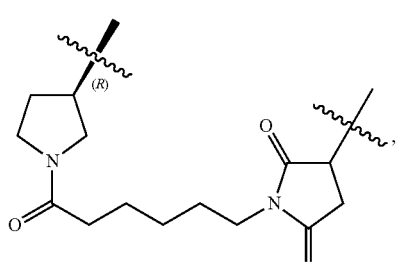
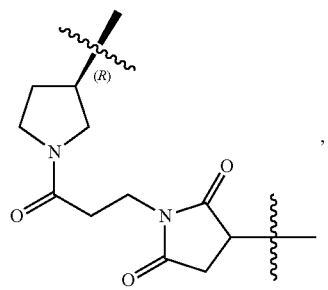
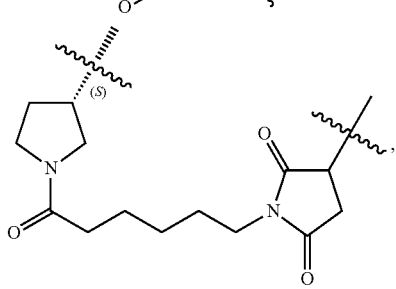
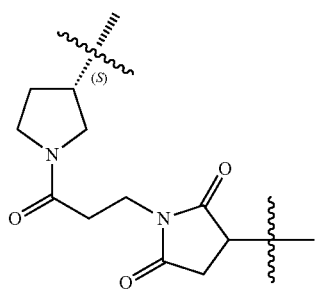
or
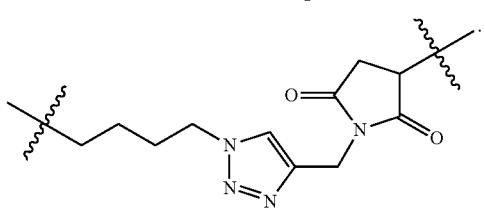
In certain embodiments of any of the aforementioned immunoconjugates of Formula (II) and Formula (Ia): $R^{20}$ is
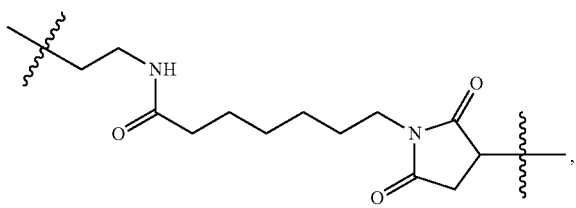
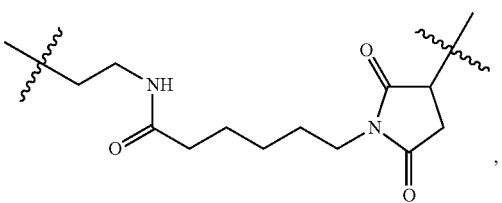

-continued
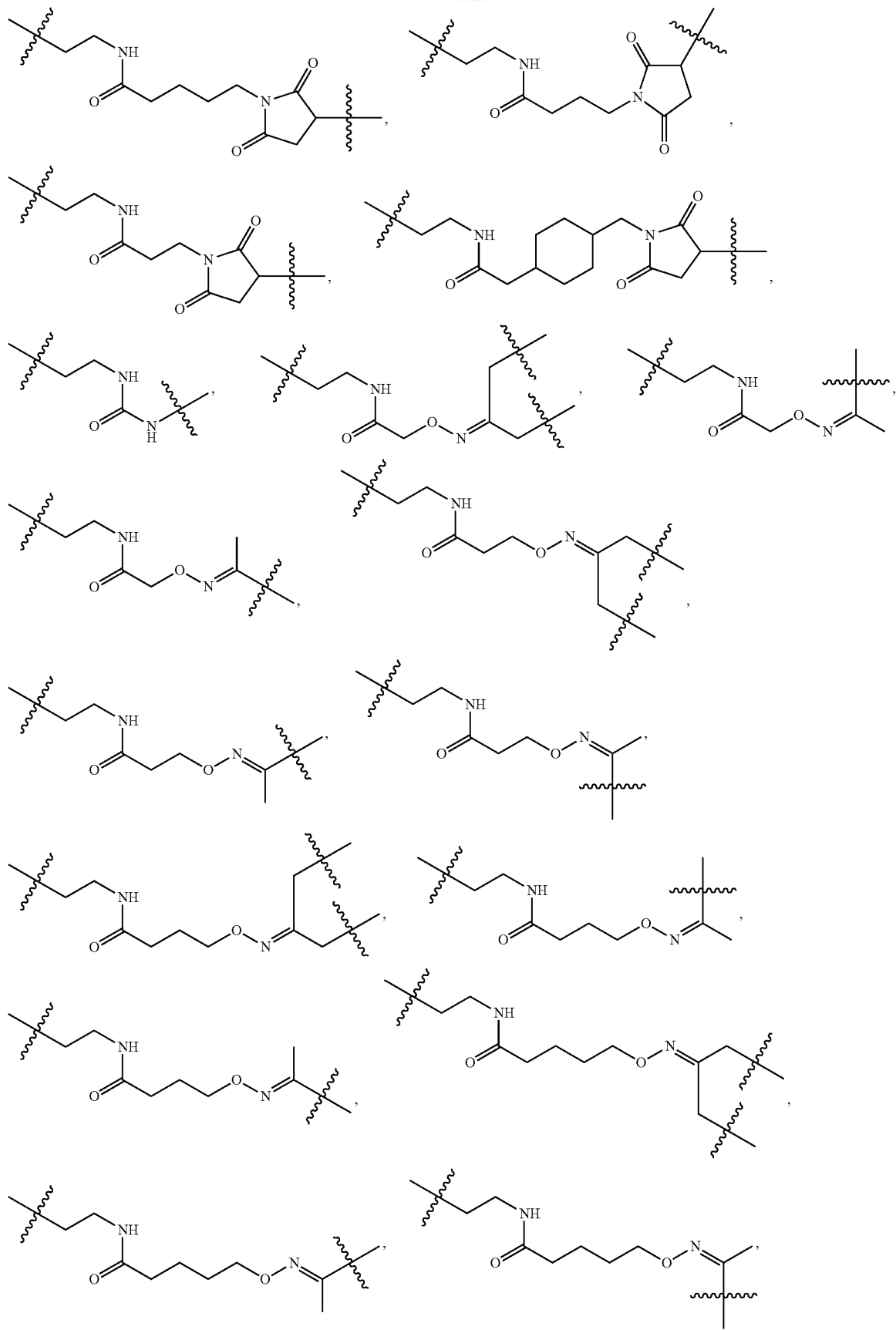

-continued
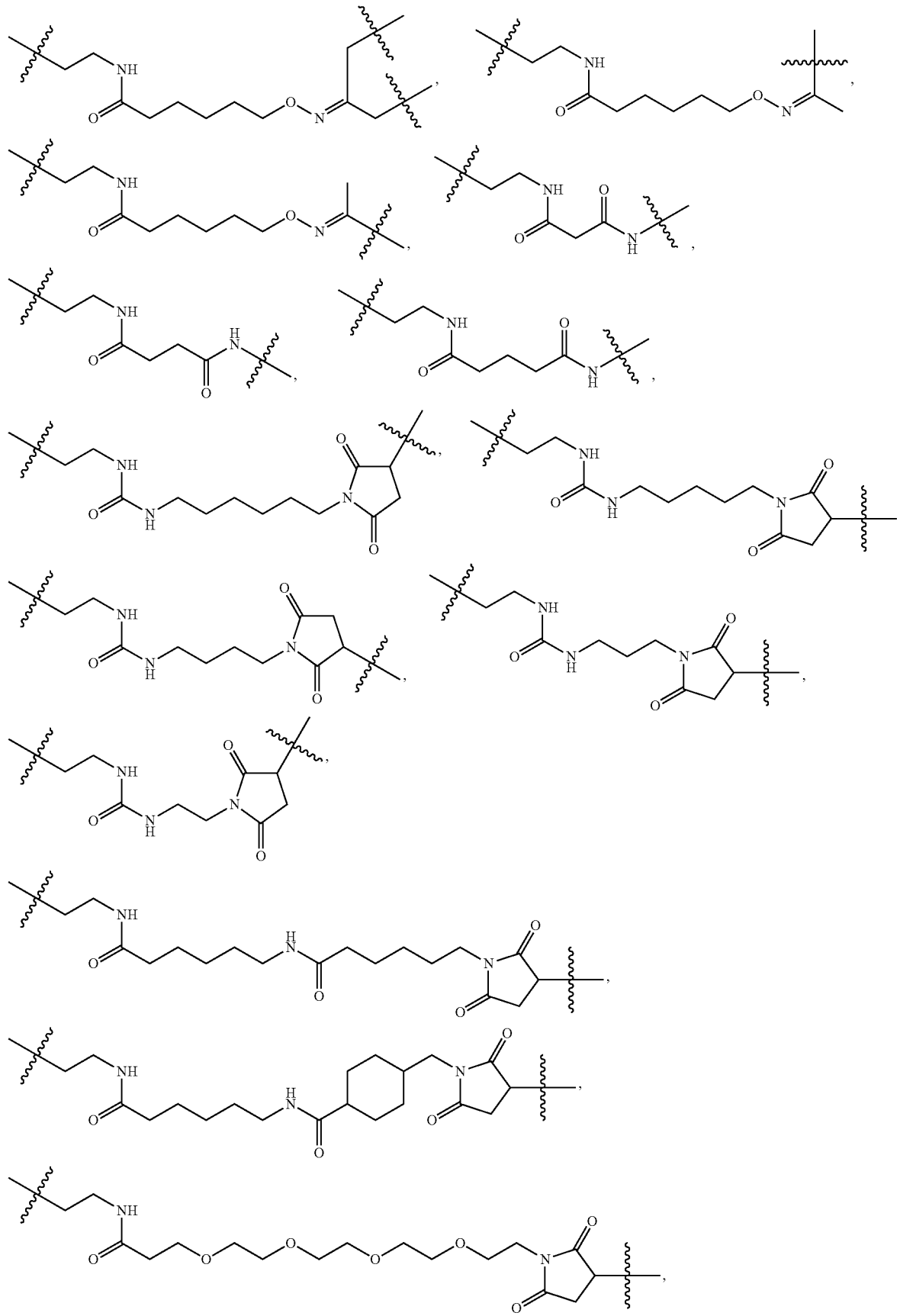

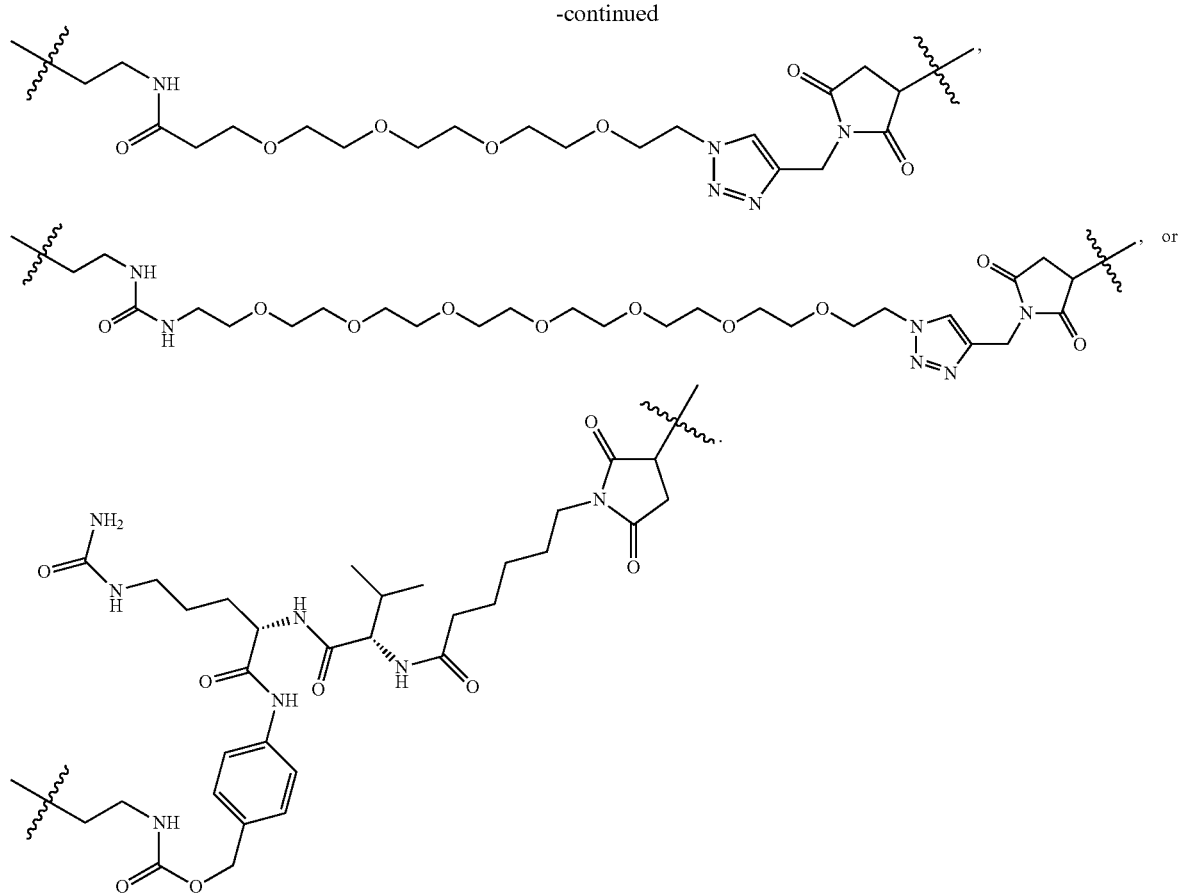
In certain embodiments of any of the aforementioned immunoconjugates of Formula (II) and Formula (IIa):
$R^{20}$ is
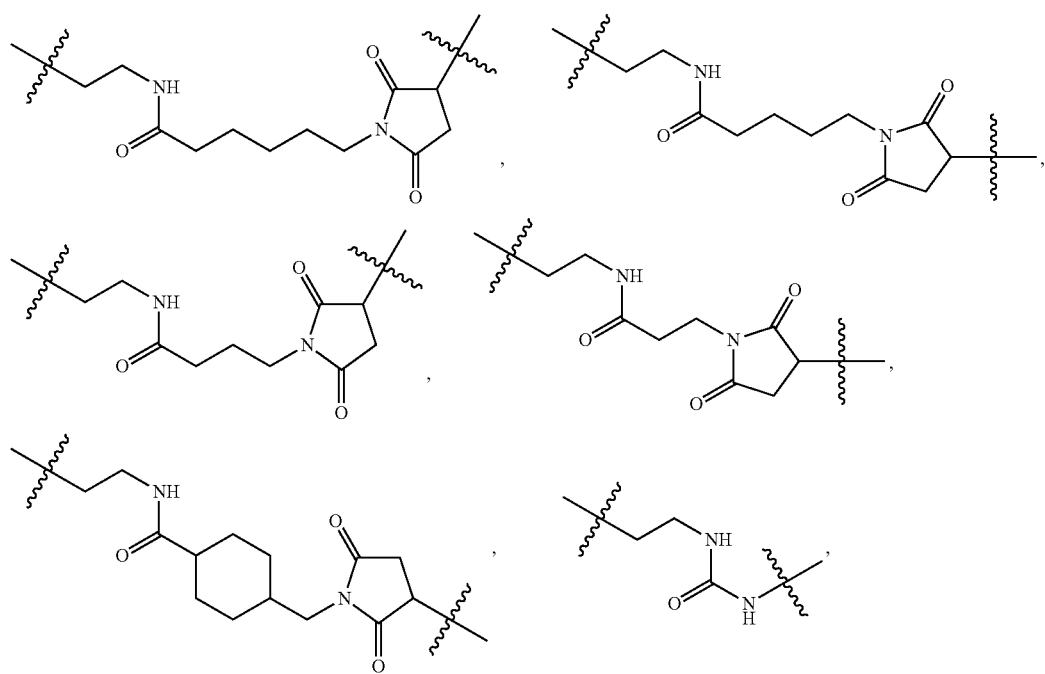

-continued
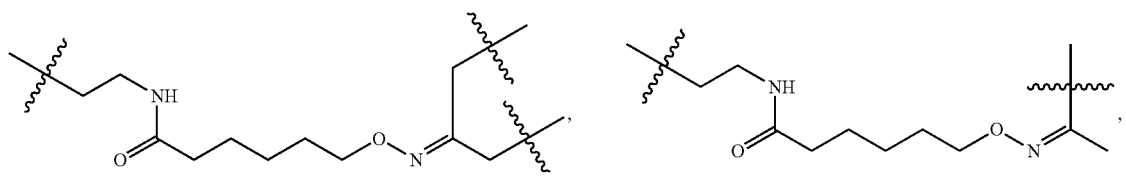
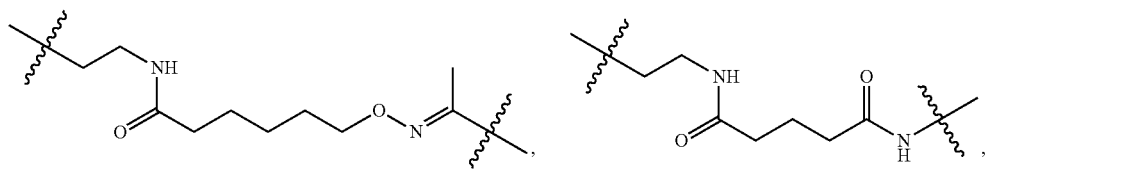
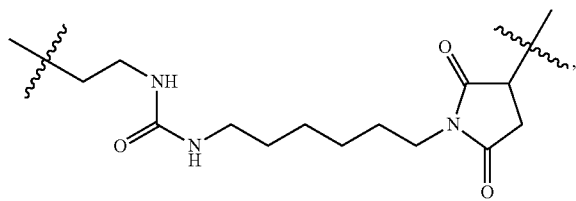
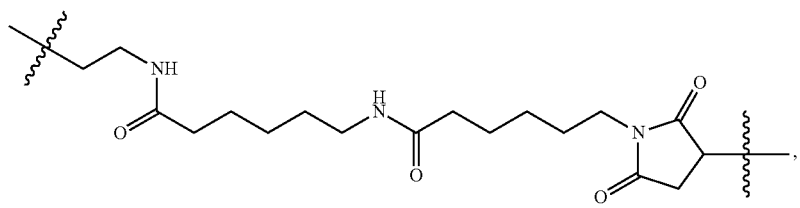
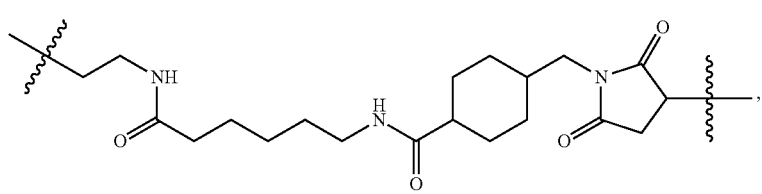
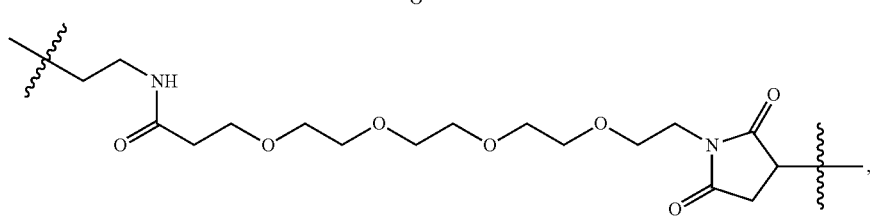
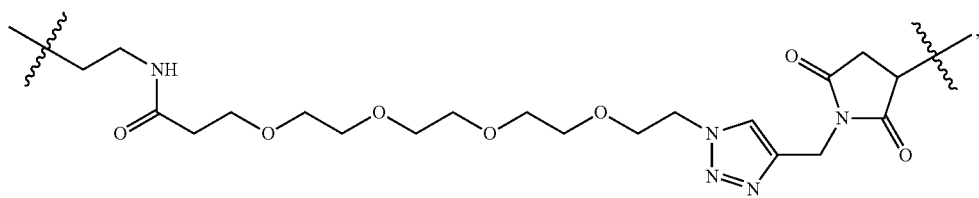
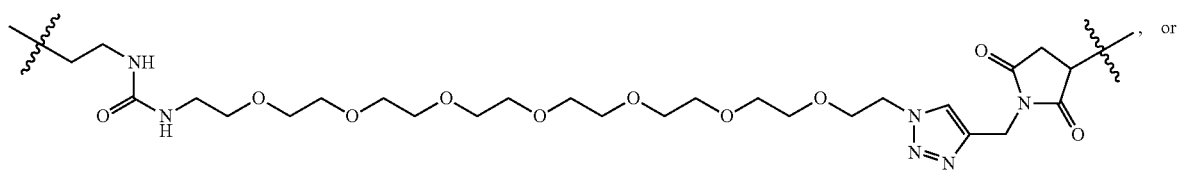

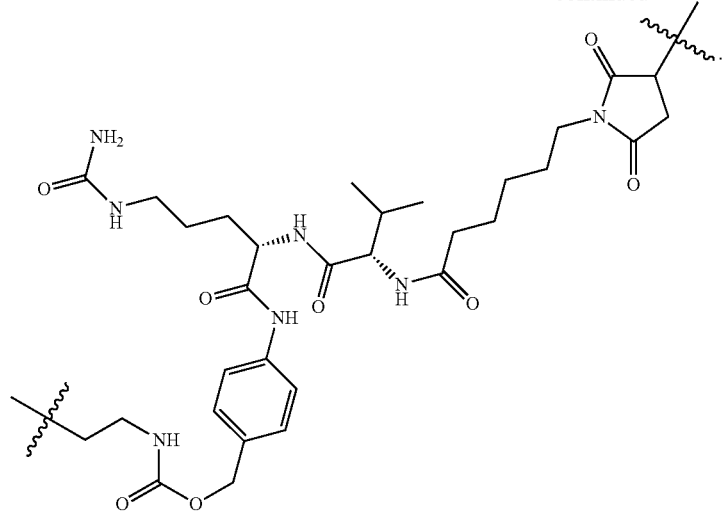
In certain embodiments of any of the aforementioned immunoconjugates of Formula (II) and Formula (IIa): $R^{20}$ is
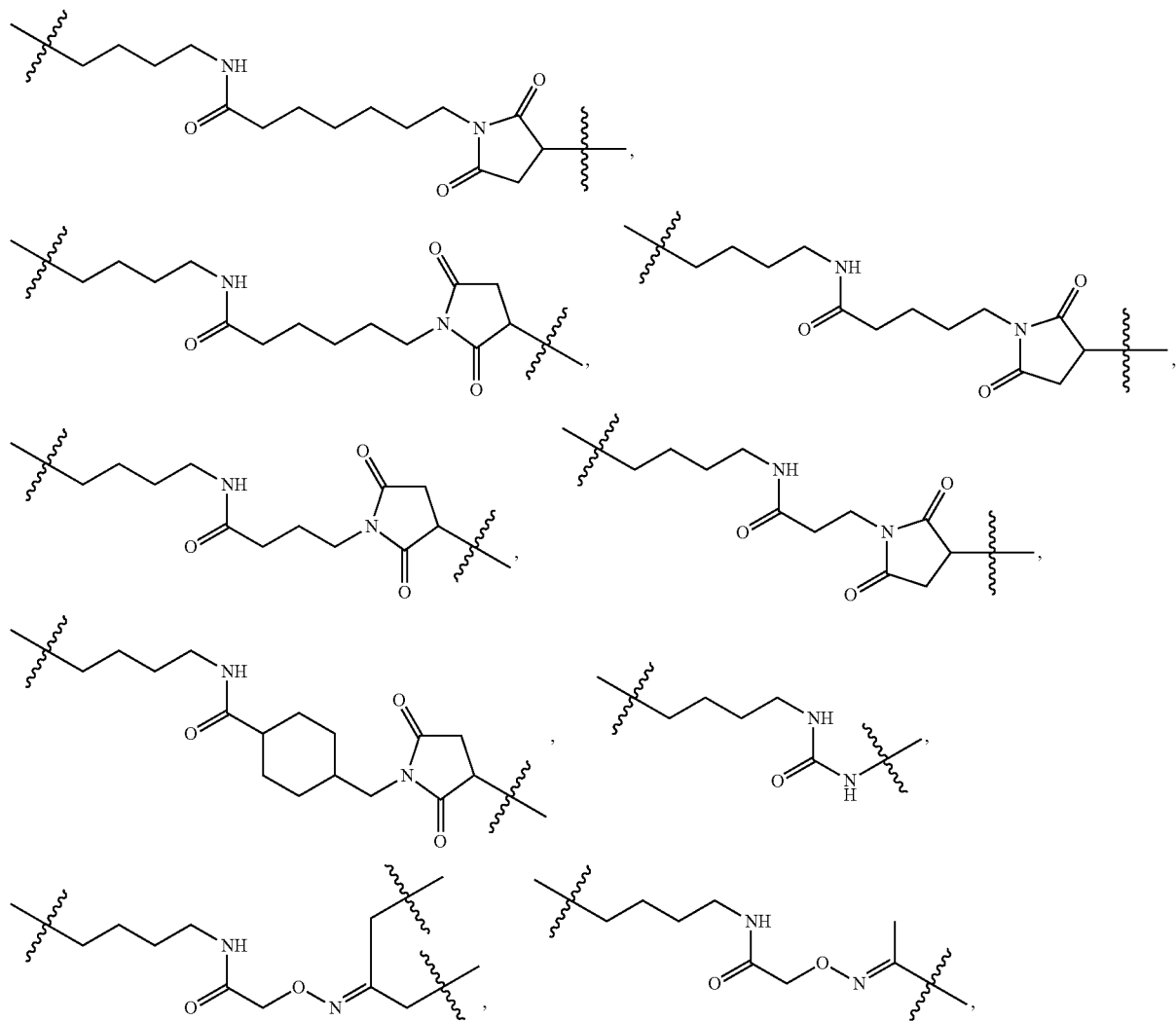

-continued
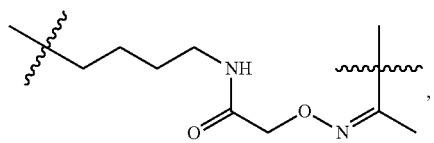
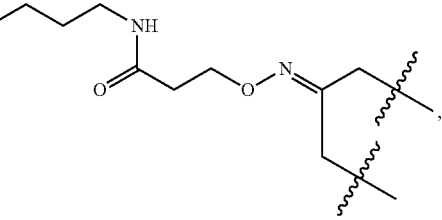
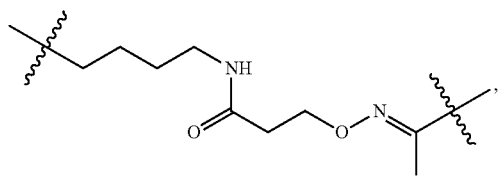
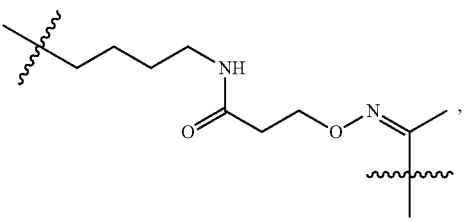
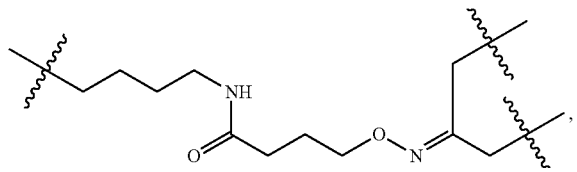
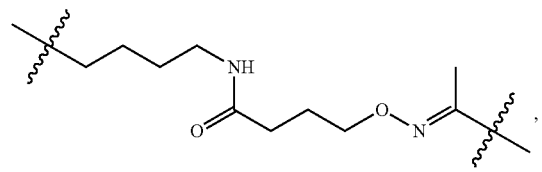
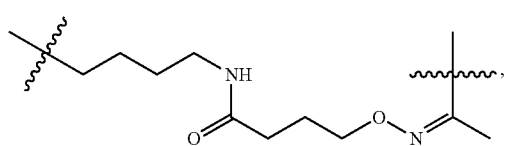
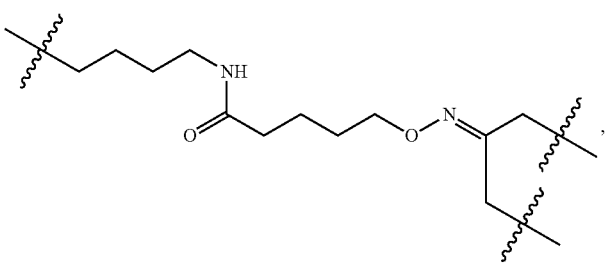
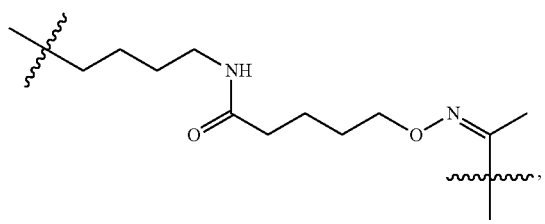
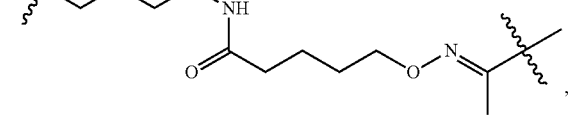
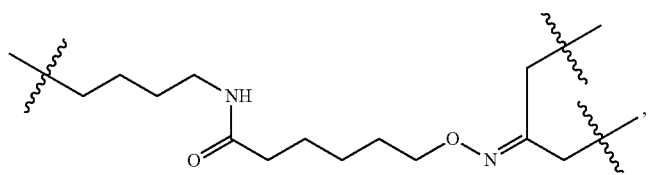
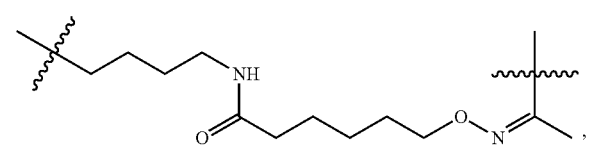
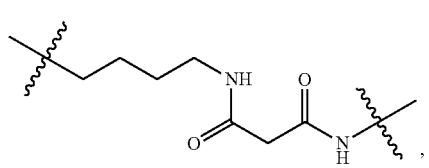
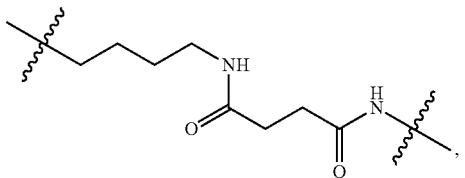

-continued
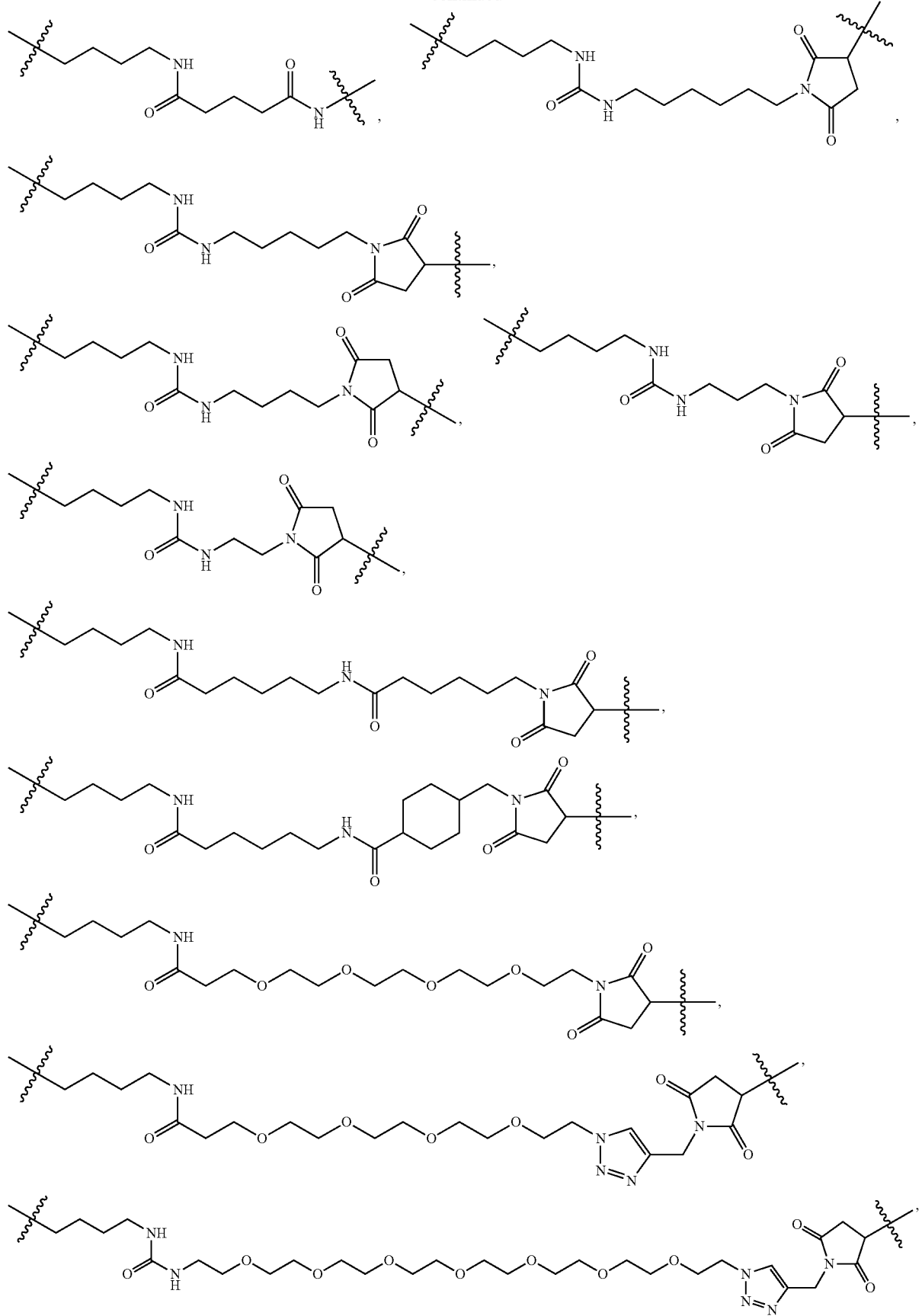

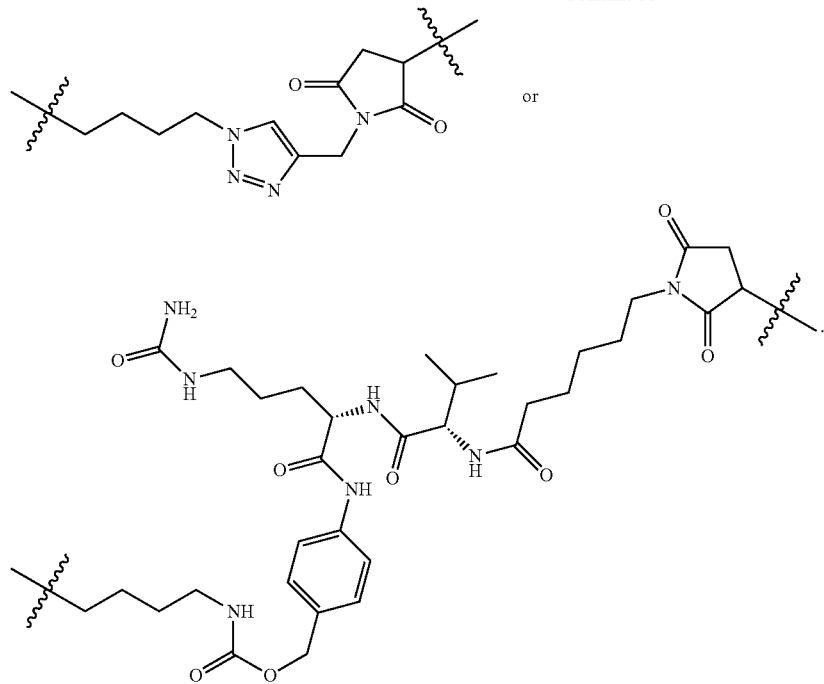
or
In certain embodiments of any of the aforementioned R[20] is immunoconjugates of Formula (II) and Formula (IIa):
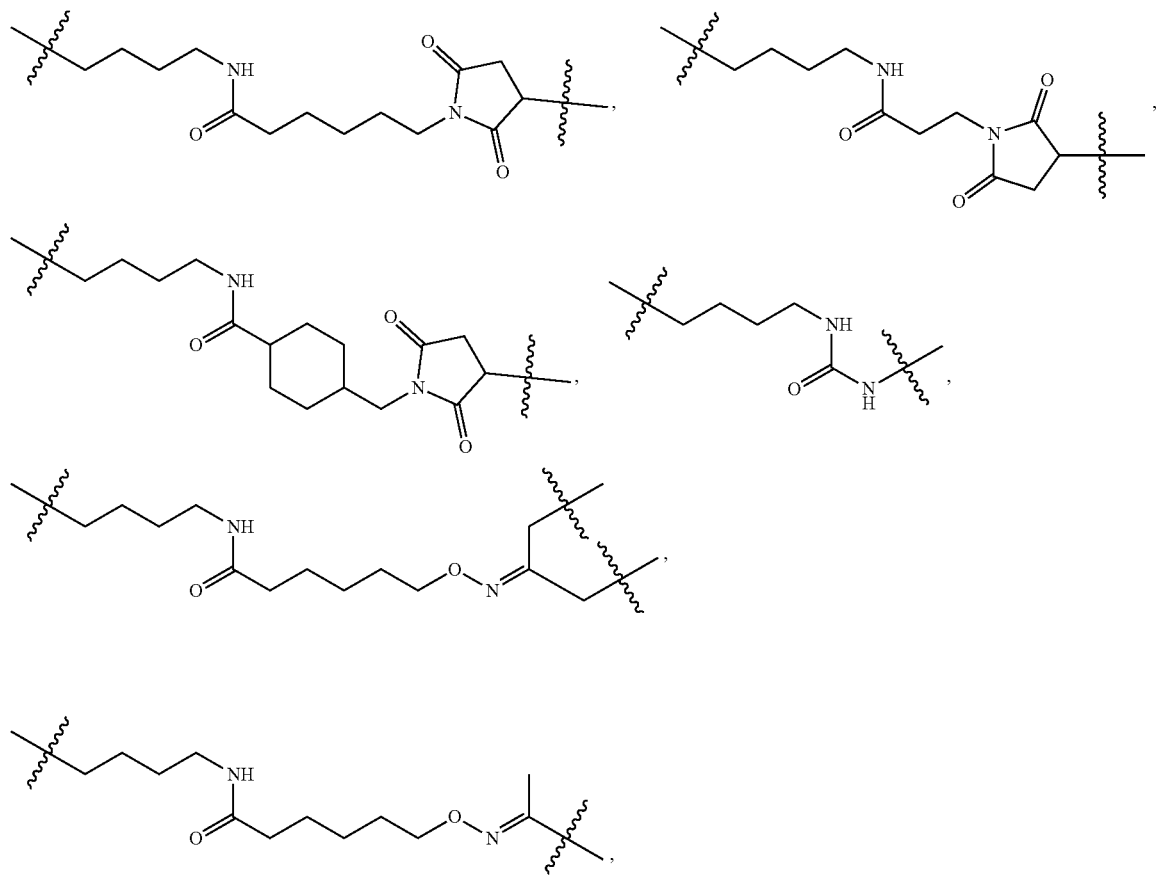

127   128
-continued
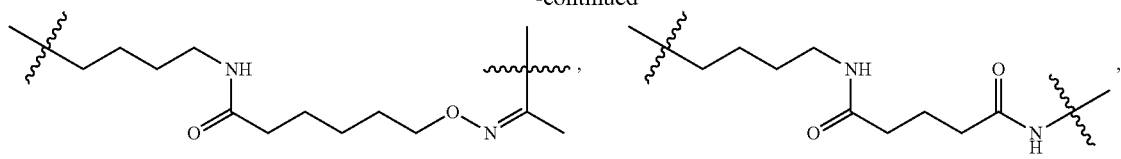
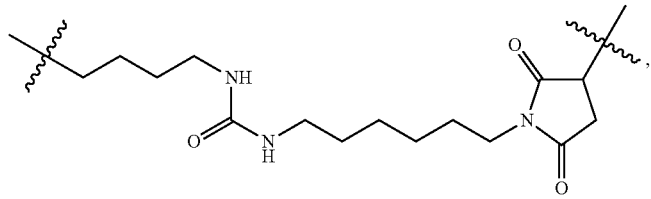
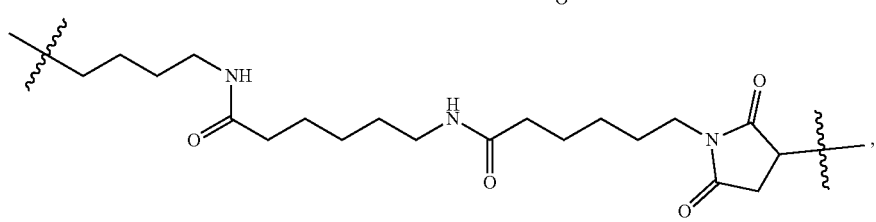
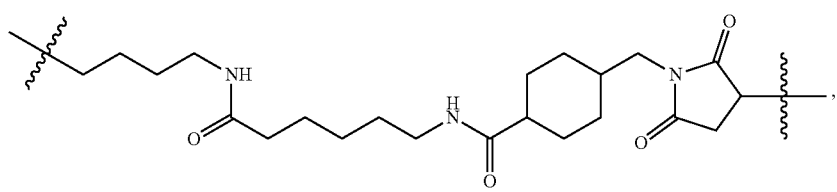
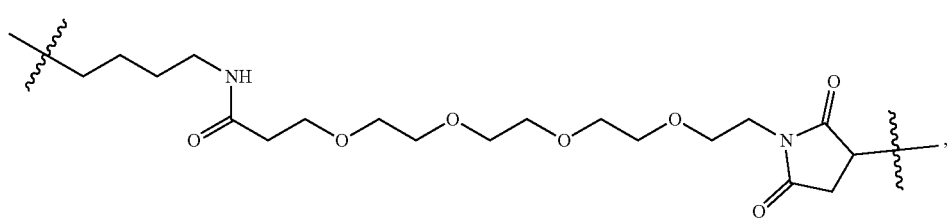
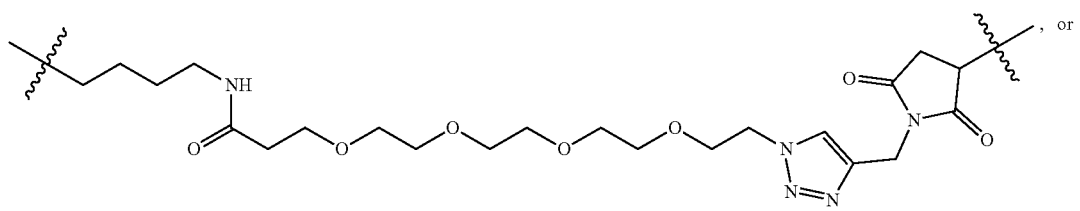, or
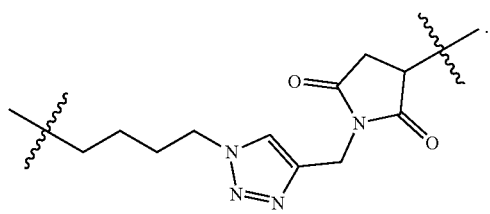.

In certain embodiments of any of the aforementioned immunoconjugates of Formula (II) and Formula (IIa):
$R^{20}$ is
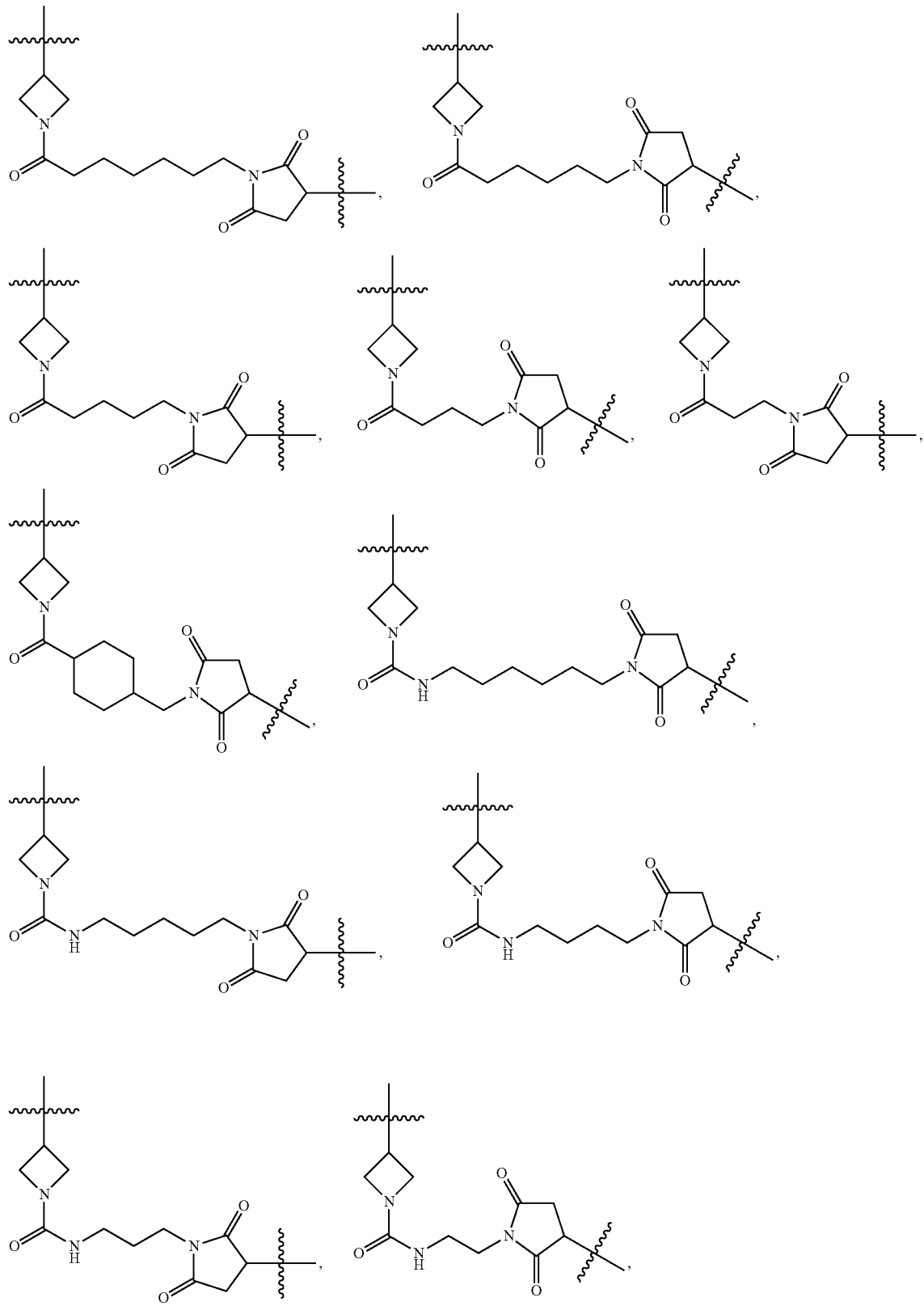

-continued
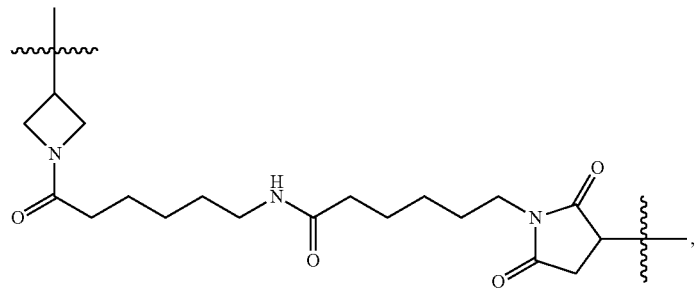
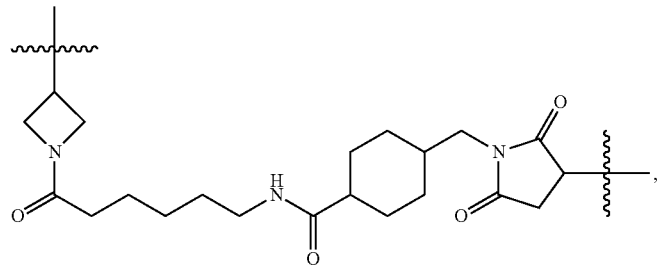
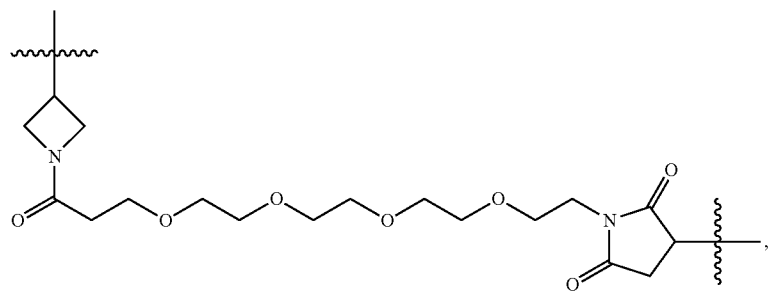
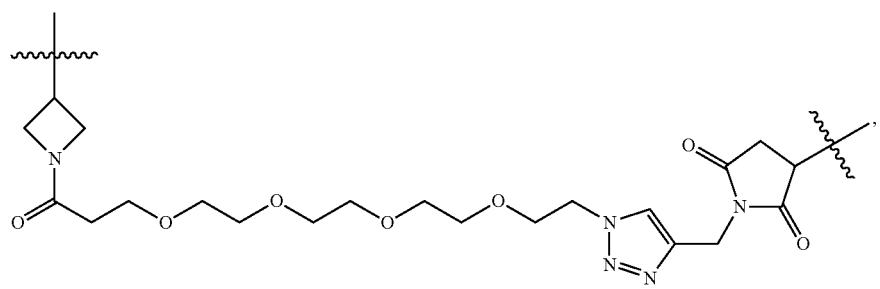
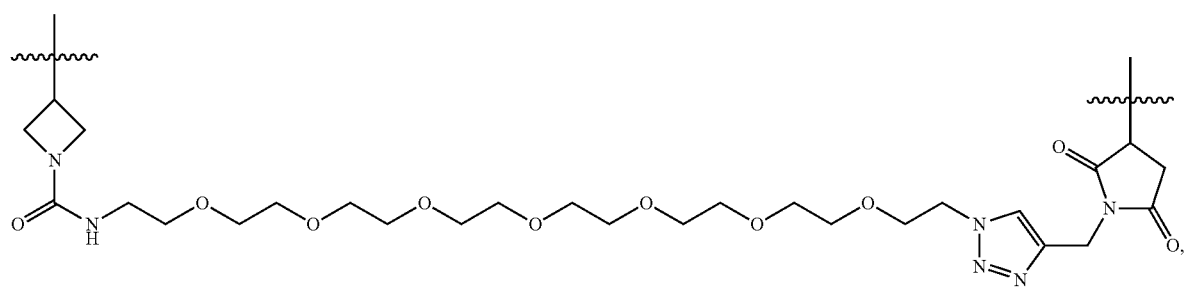

or
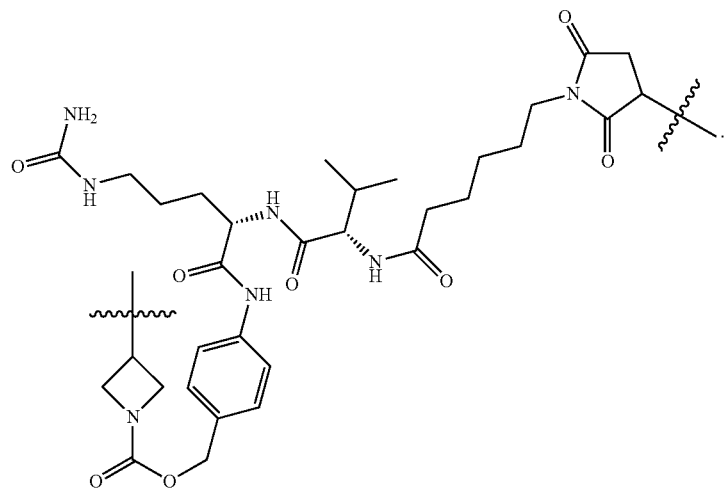 [SMILES: *C1CN(C(=O)OCc2ccc(NC(=O)[C@H](CCCNC(N)=O)NC(=O)[C@@H](NC(=O)CCCCCN3C(=O)CC(*)C3=O)C(C)C)cc2)C1]
In certain embodiments of any of the aforementioned immunoconjugates of Formula (II) and Formula (IIa):
R²⁰ is
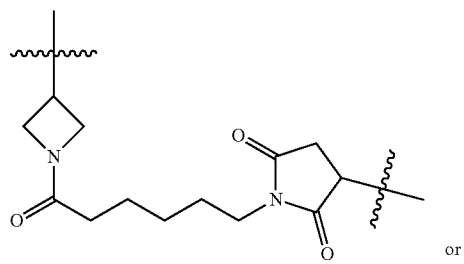 or
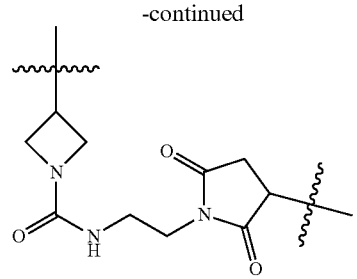
In certain embodiments of any of the aforementioned immunoconjugates of Formula (II) and Formula (IIa):
R²⁰ is
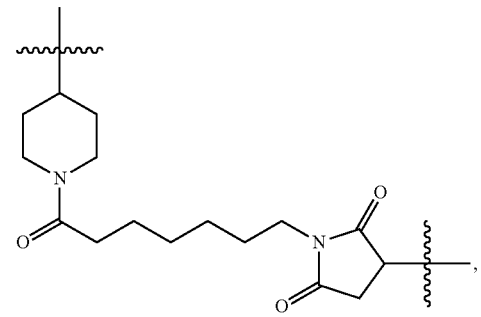
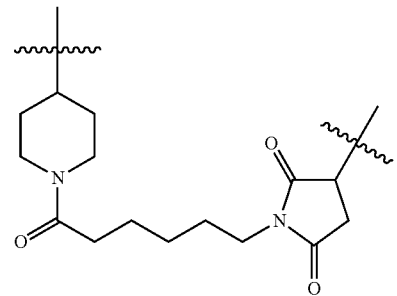
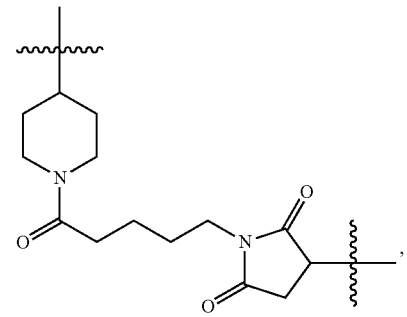
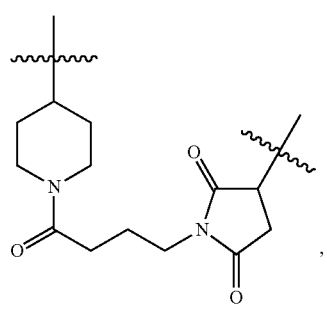
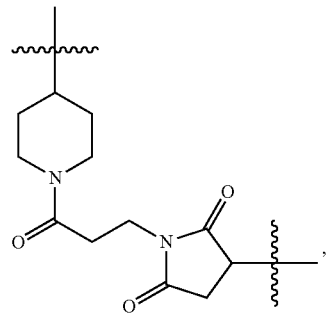

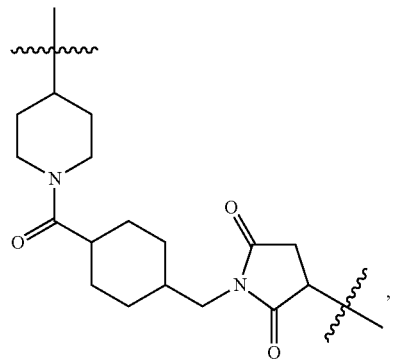
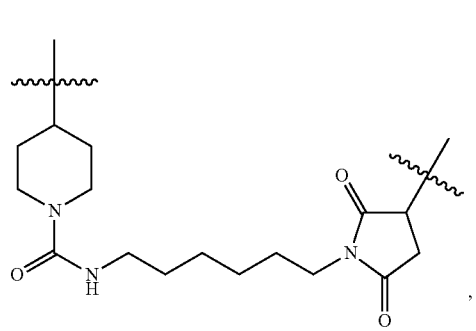
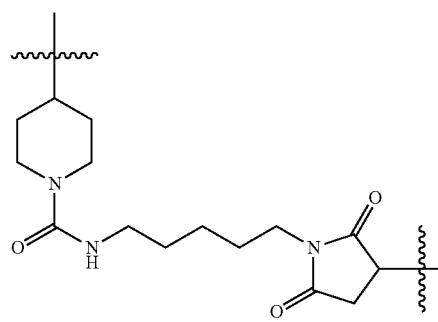
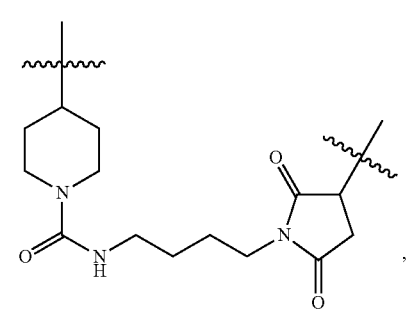
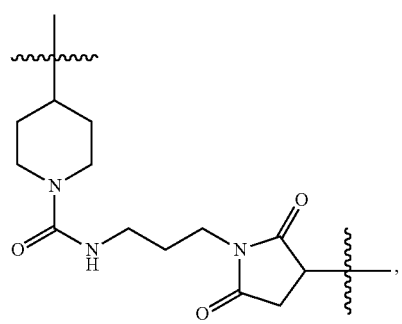
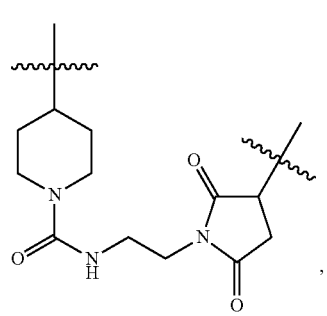
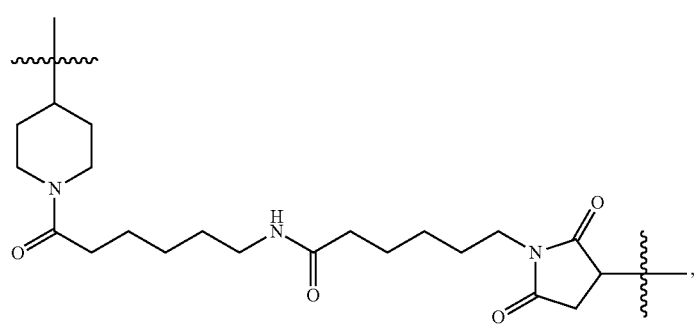
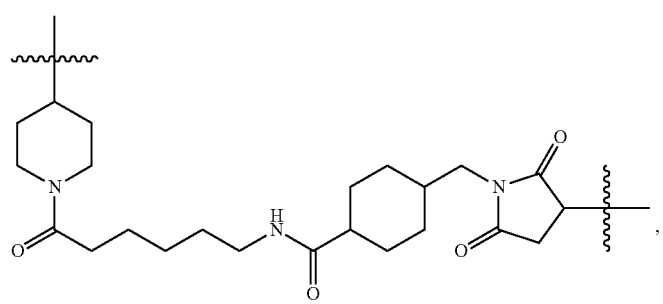
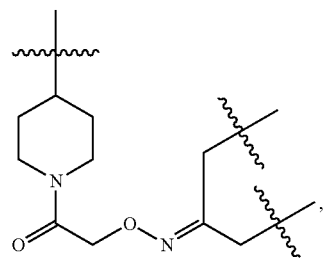

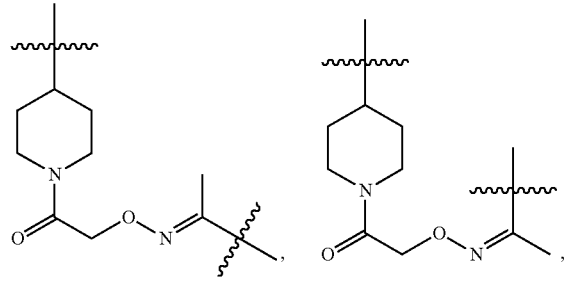 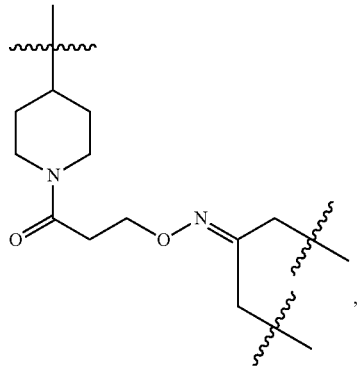
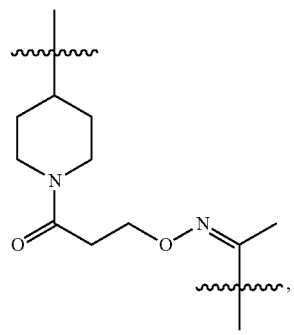 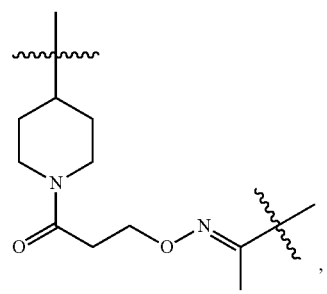 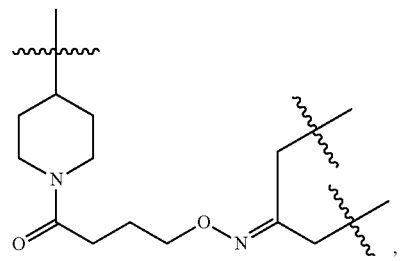
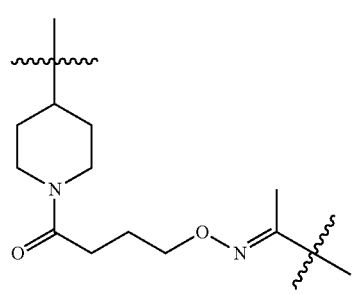 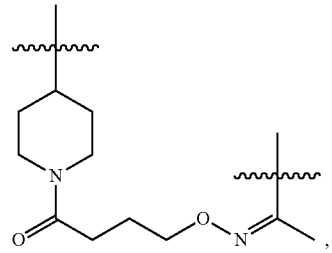 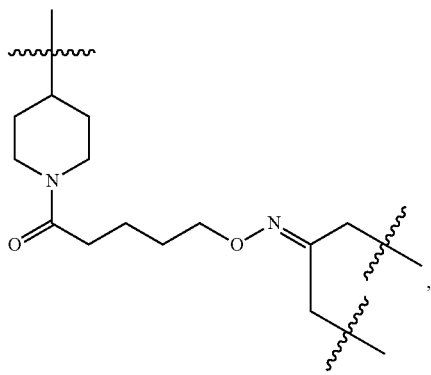
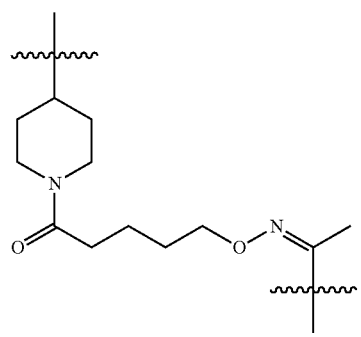 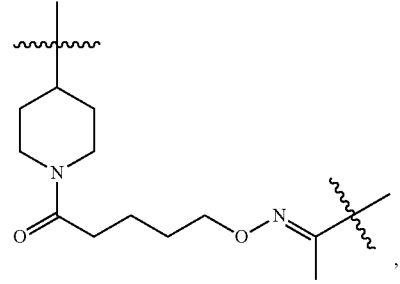
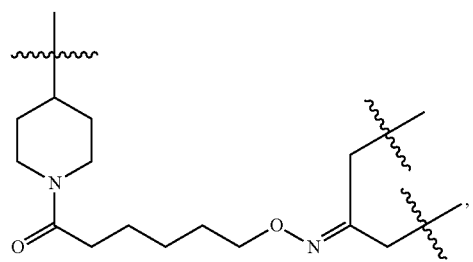 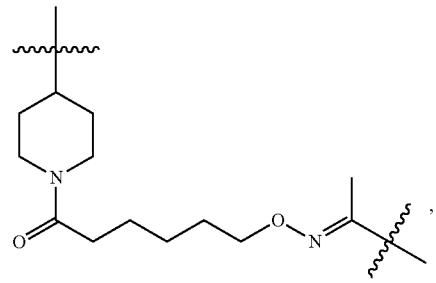

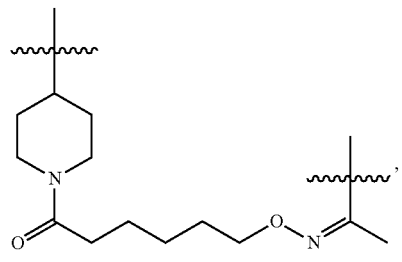
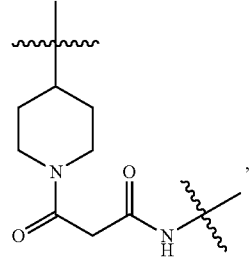
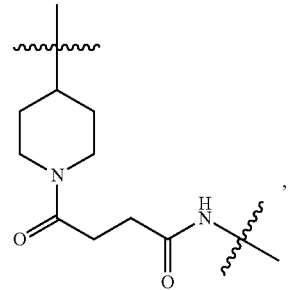
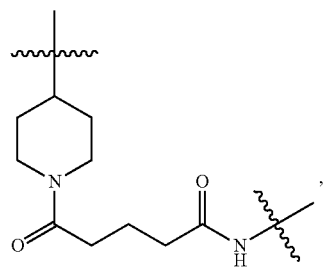
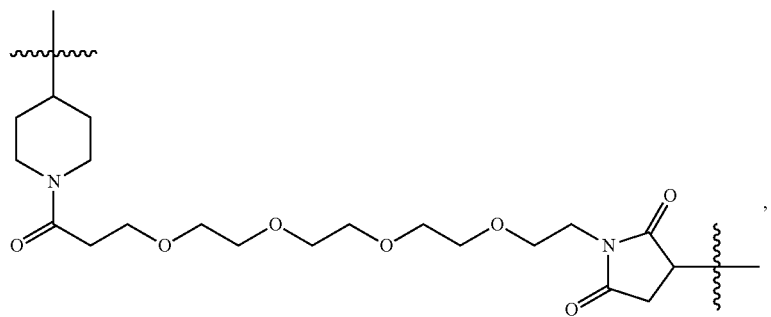
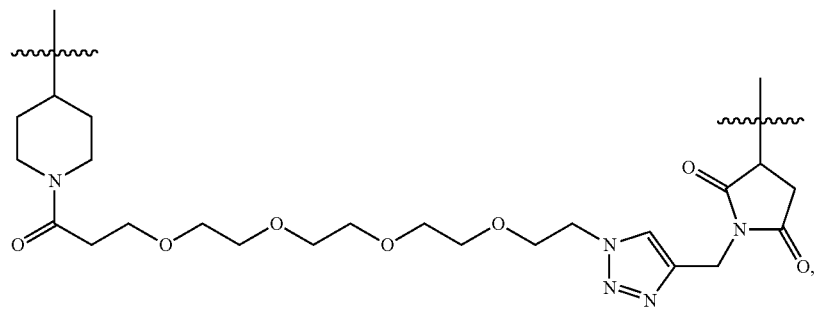
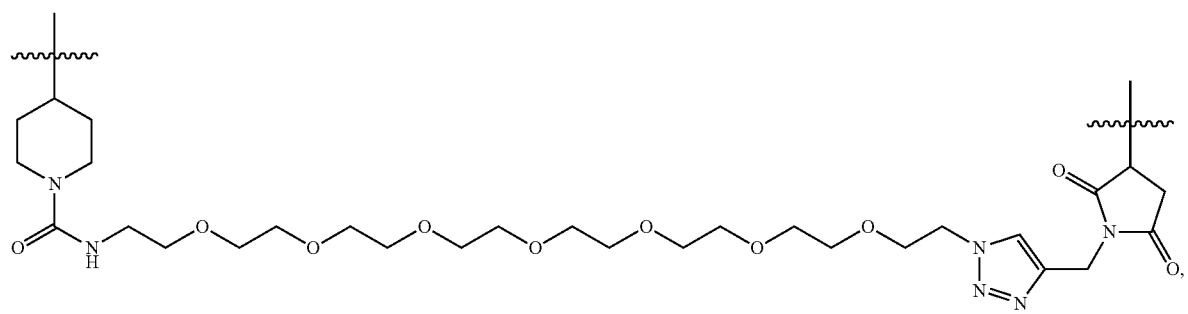

or
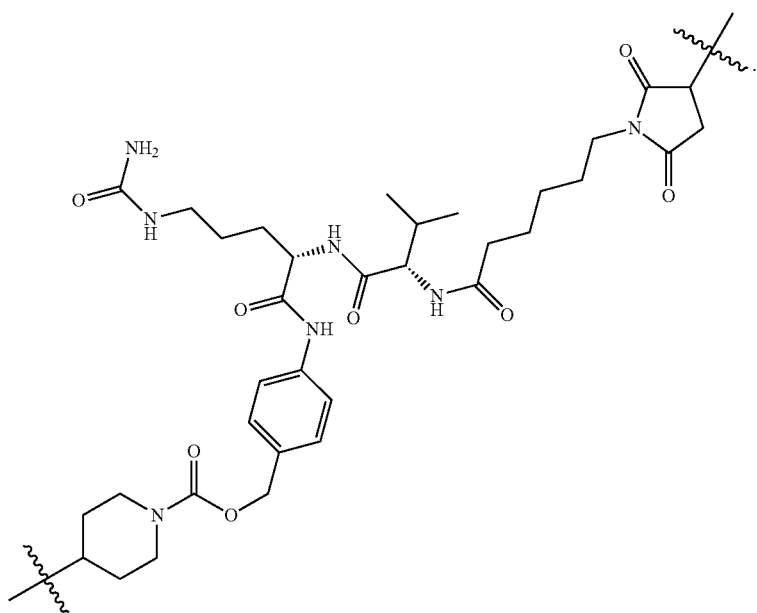
In certain embodiments of any of the aforementioned immunoconjugates of Formula (II) and Formula (IIa):
R$^{20}$ is
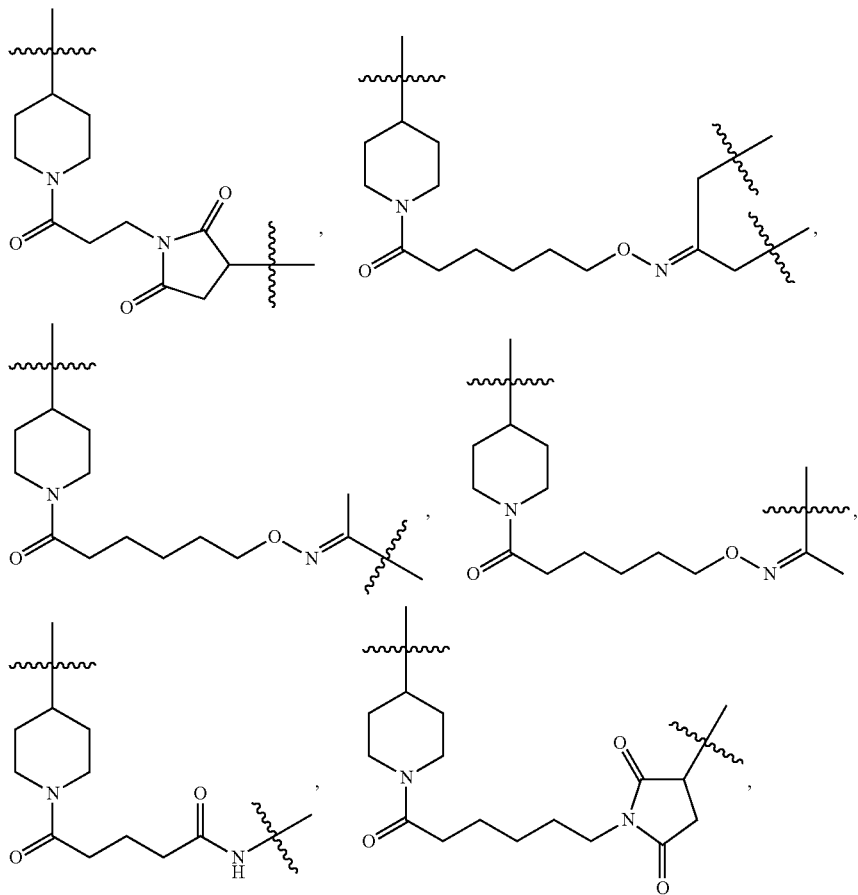

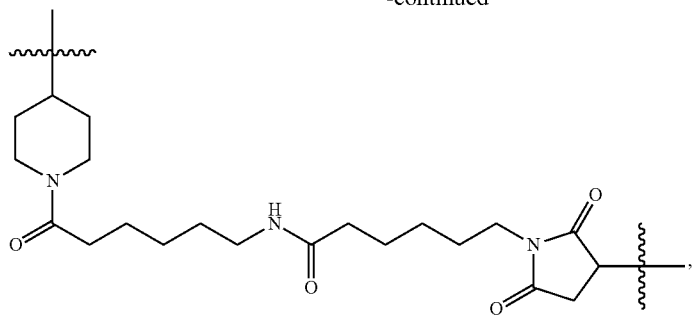
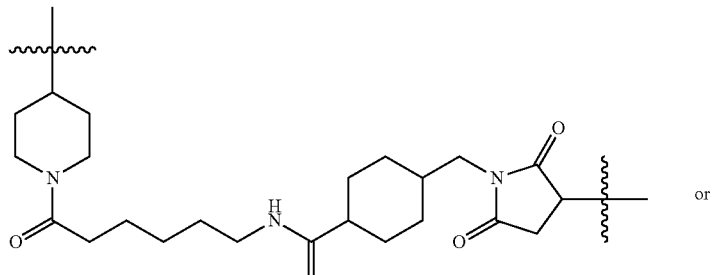
or
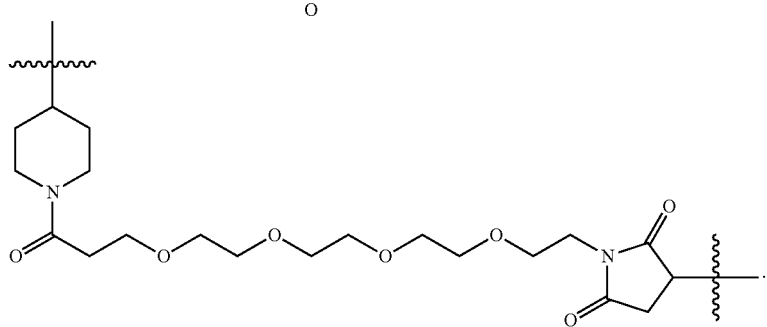
In certain embodiments of any of the aforementioned immunoconjugates of Formula (II) and Formula (IIa):
$R^{20}$ is
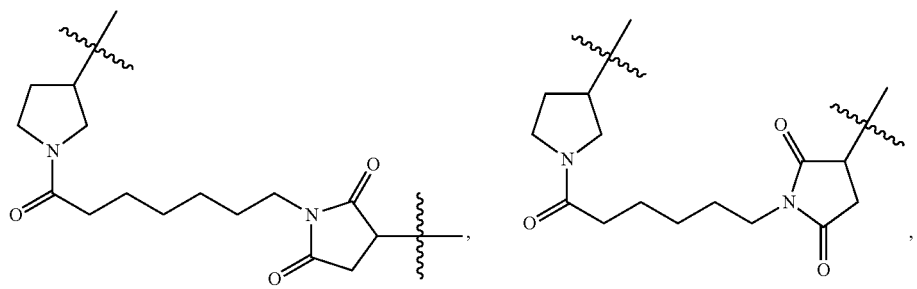
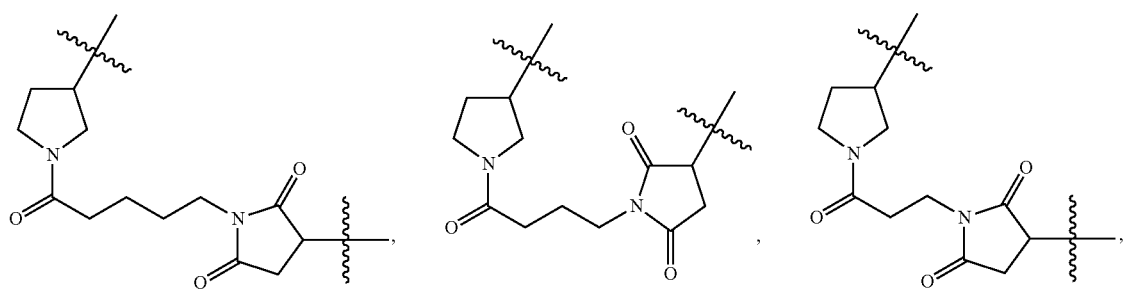

-continued
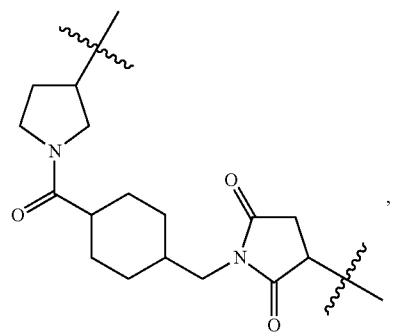 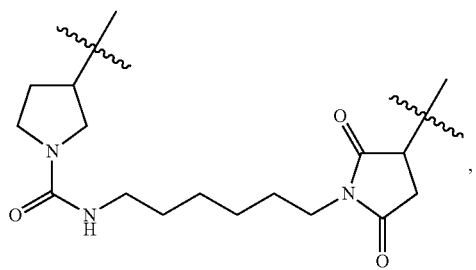
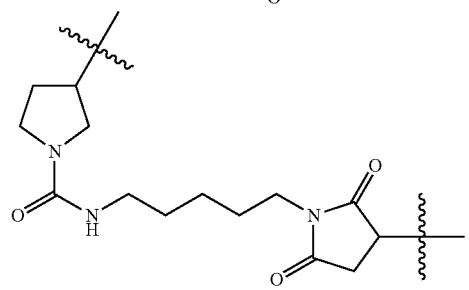 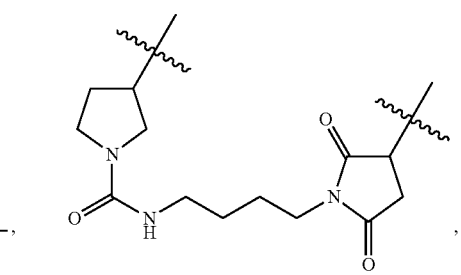
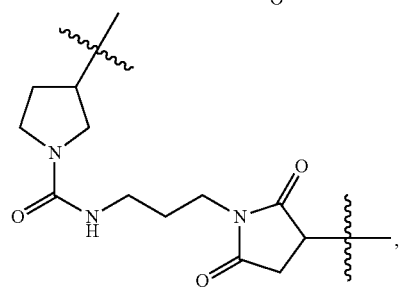 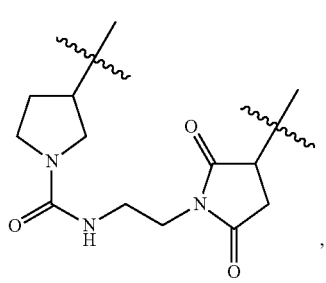
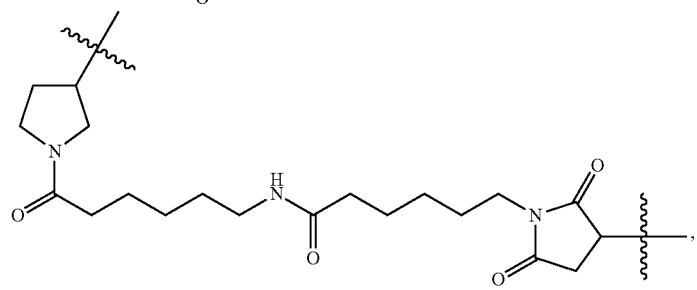
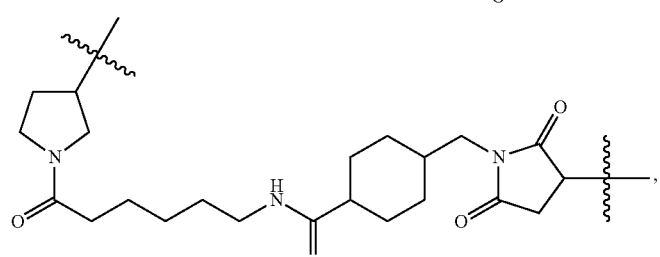
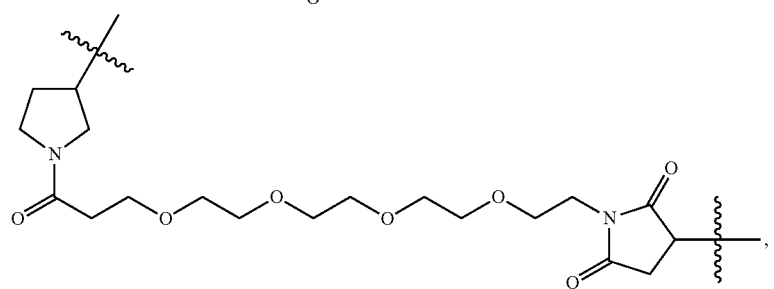

-continued
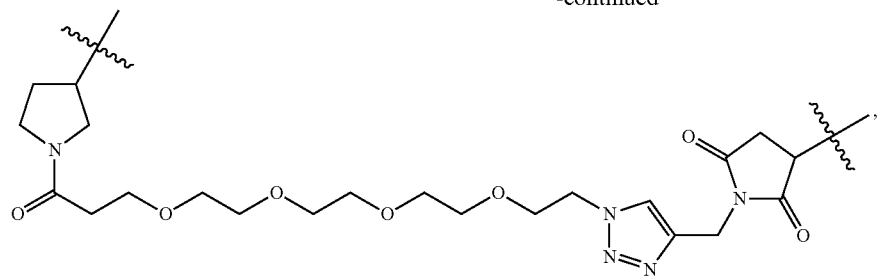
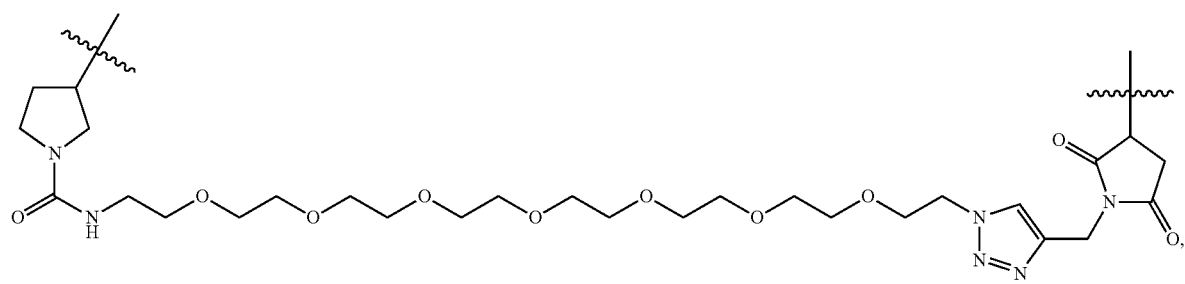
or
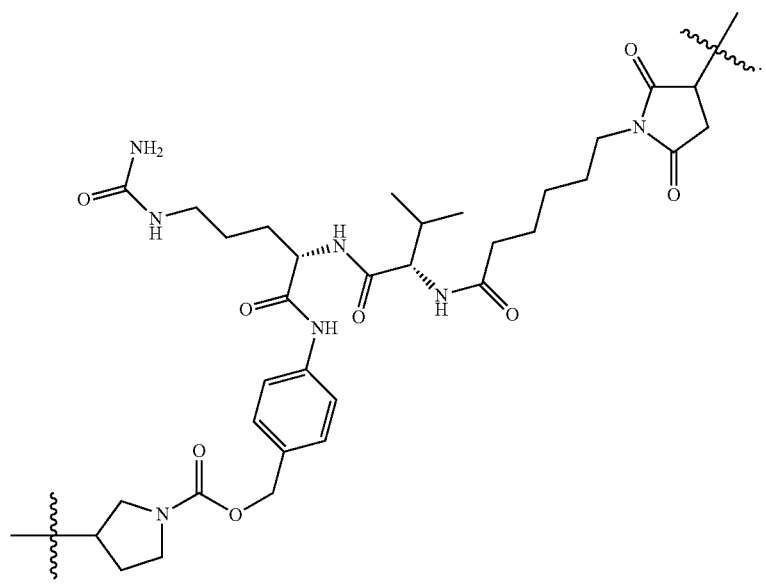
In certain embodiments of any of the aforementioned immunoconjugates of Formula (II) and Formula (IIa):
R$^{20}$ is
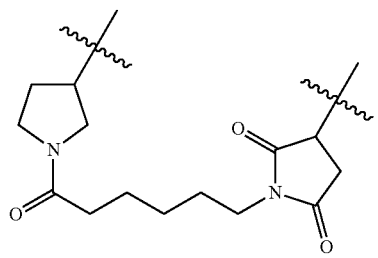
or
-continued
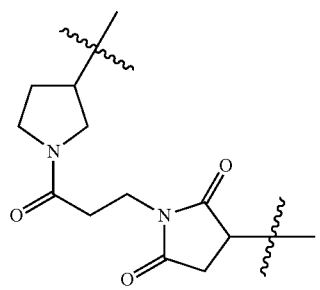

In certain embodiments of any of the aforementioned immunoconjugates of Formula (II) and Formula (IIa):
R[20] is
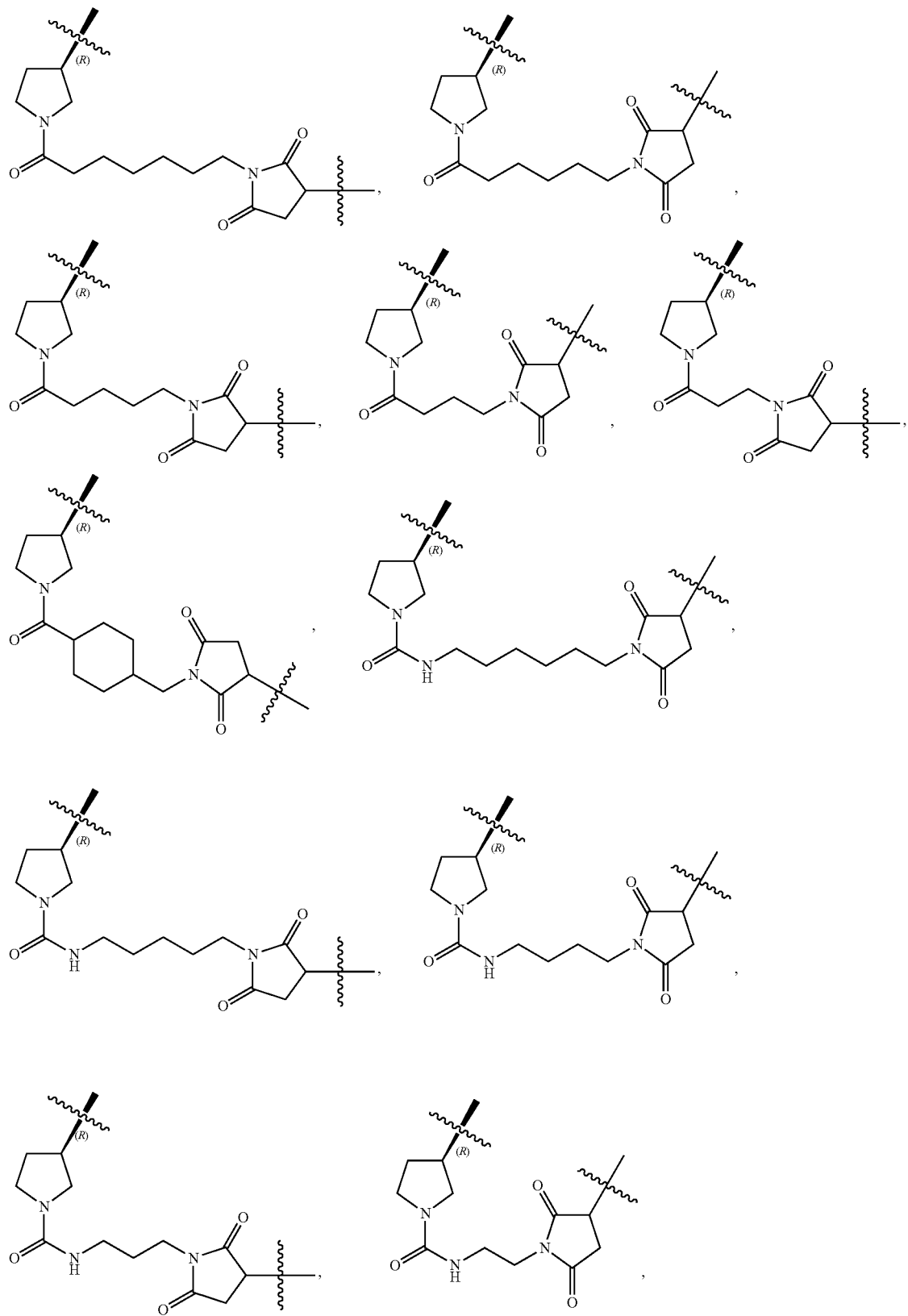

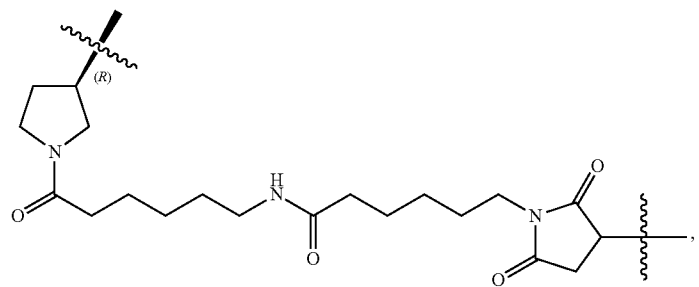
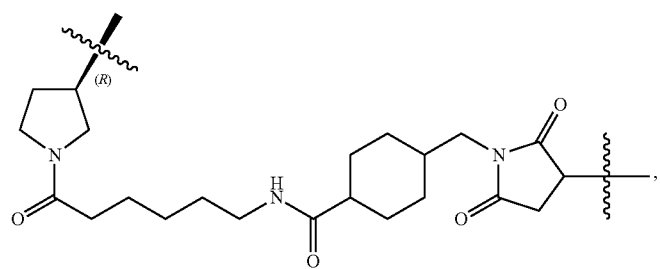
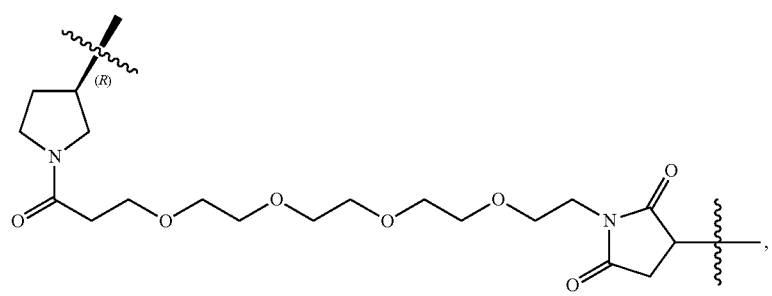
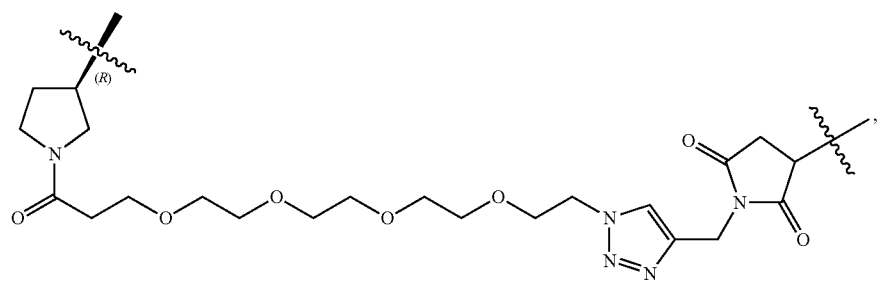
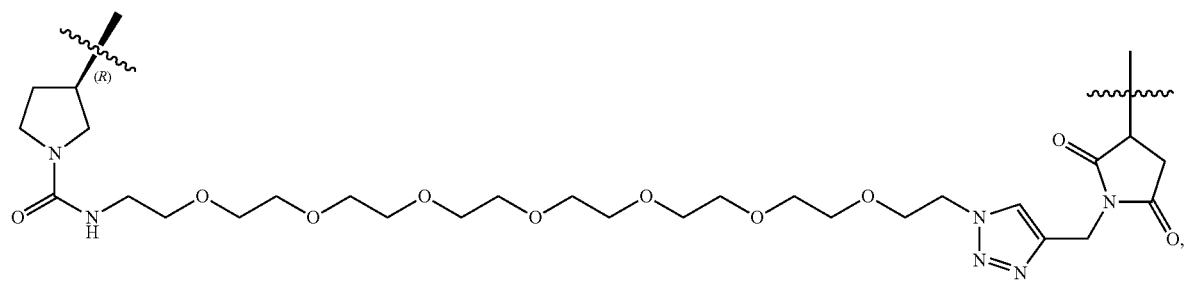

or
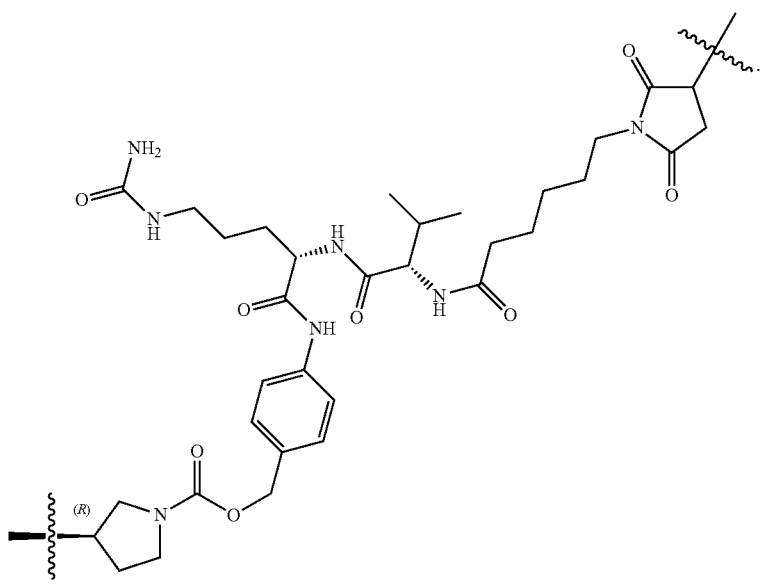
In certain embodiments of any of the aforementioned immunoconjugates of Formula (II) and Formula (IIa):
$R^{20}$ is
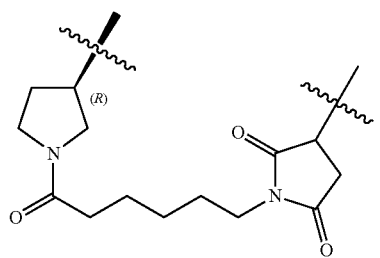 or
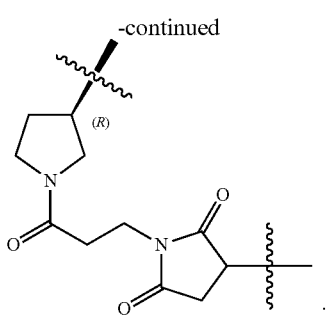.
In certain embodiments of any of the aforementioned immunoconjugates of Formula (II) and Formula (IIa):
$R^{20}$ is
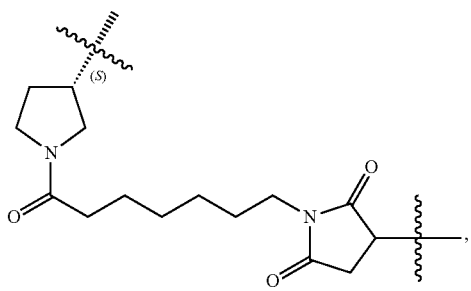, 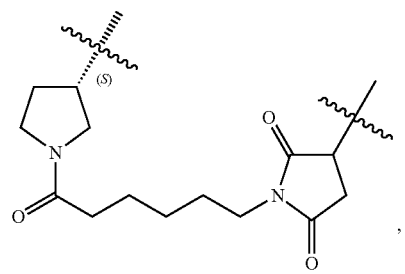,
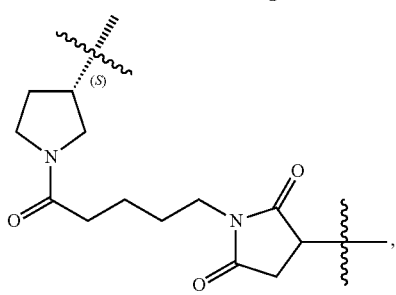, 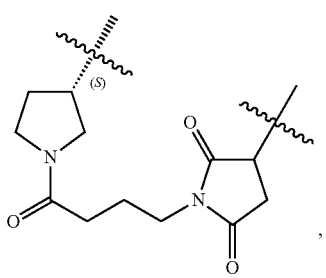, 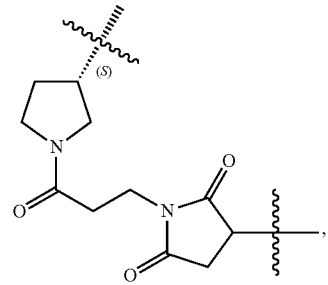, -continued
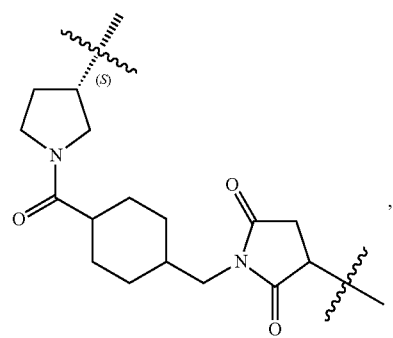 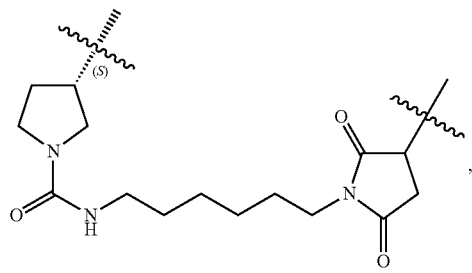
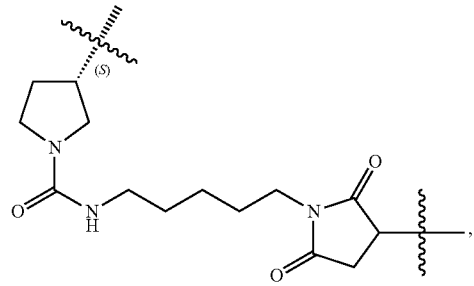 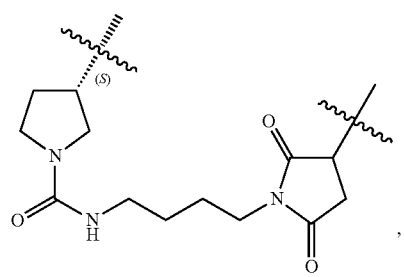
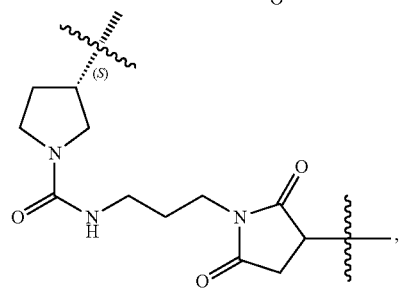 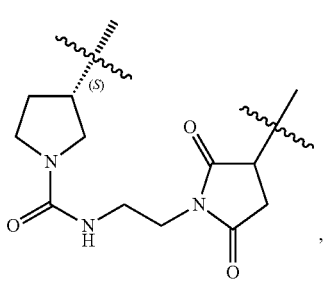
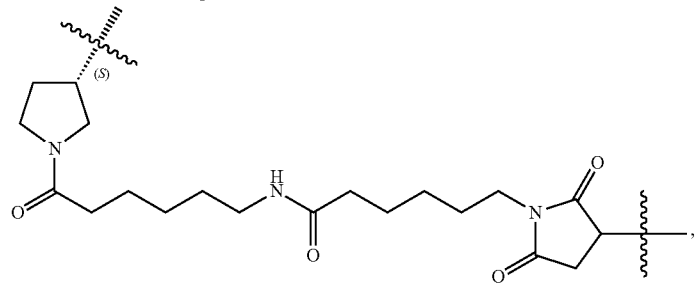
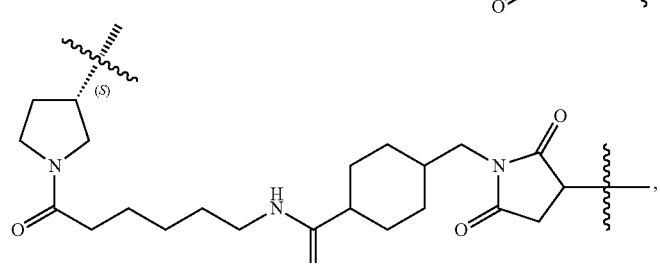
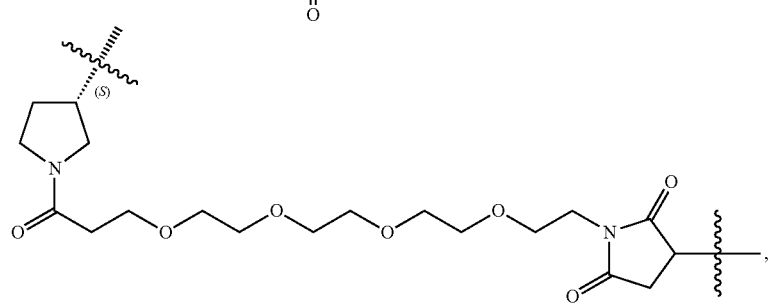

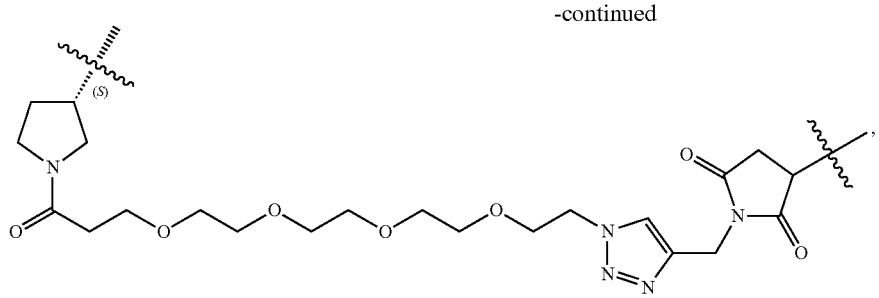
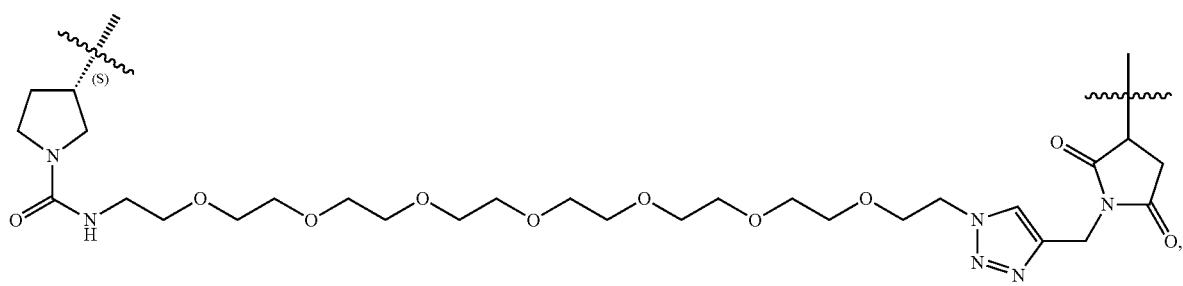
or
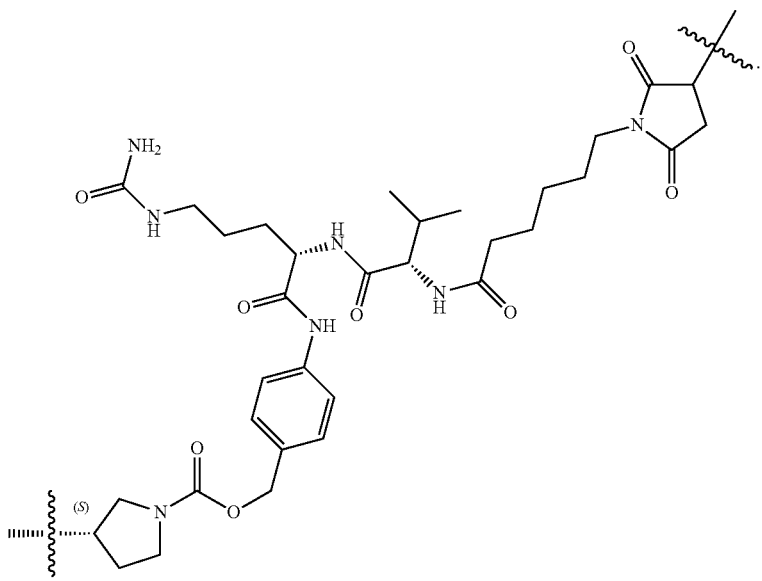
In certain embodiments of any of the aforementioned immunoconjugates of Formula (II) and Formula (IIa): $R^{20}$ is
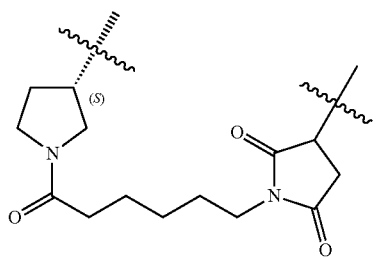
or
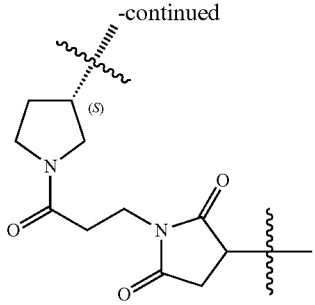
In certain embodiments of any of the aforementioned immunoconjugates of Formula (II) and Formula (IIa): $R^{20}$ is

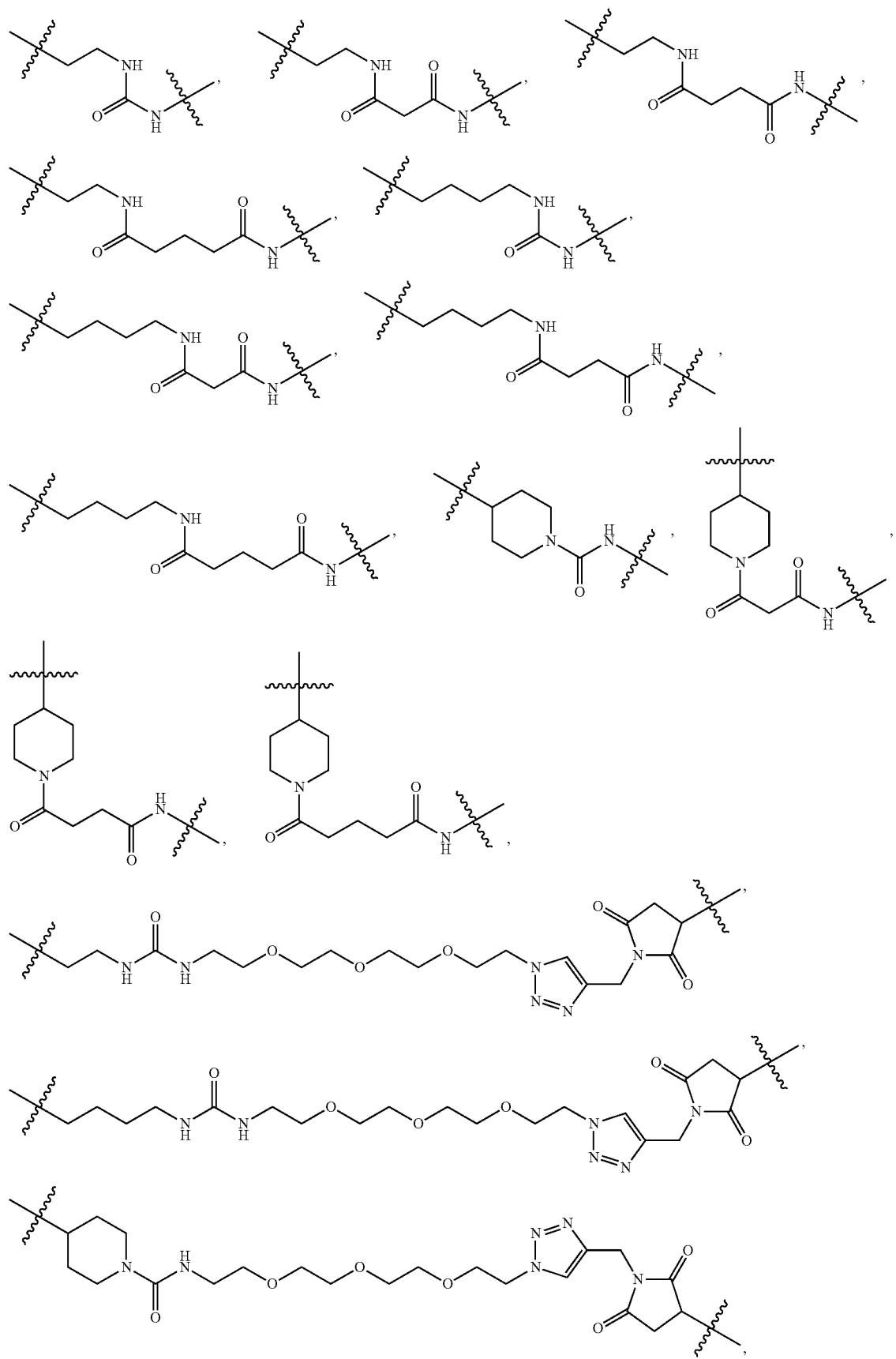

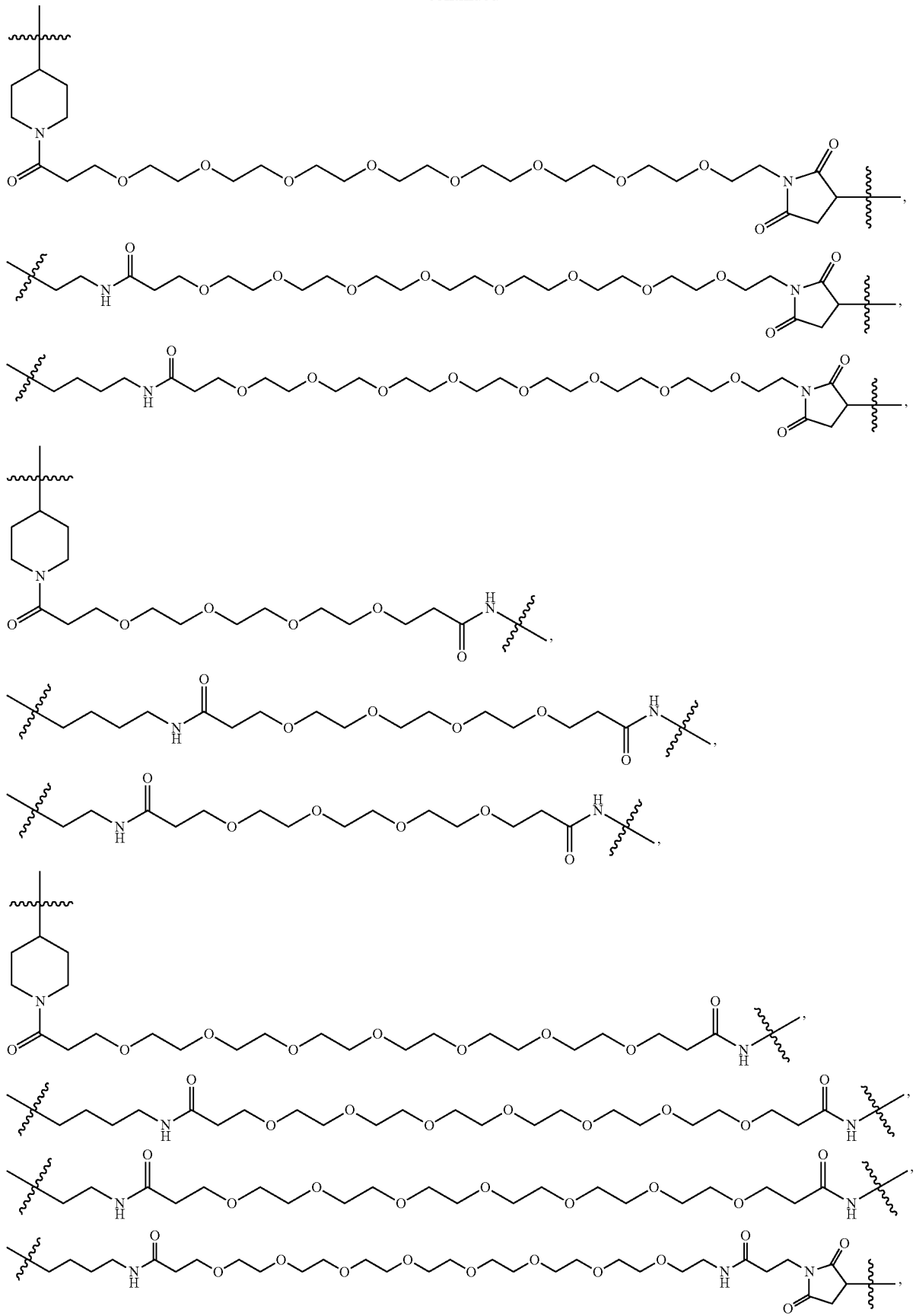

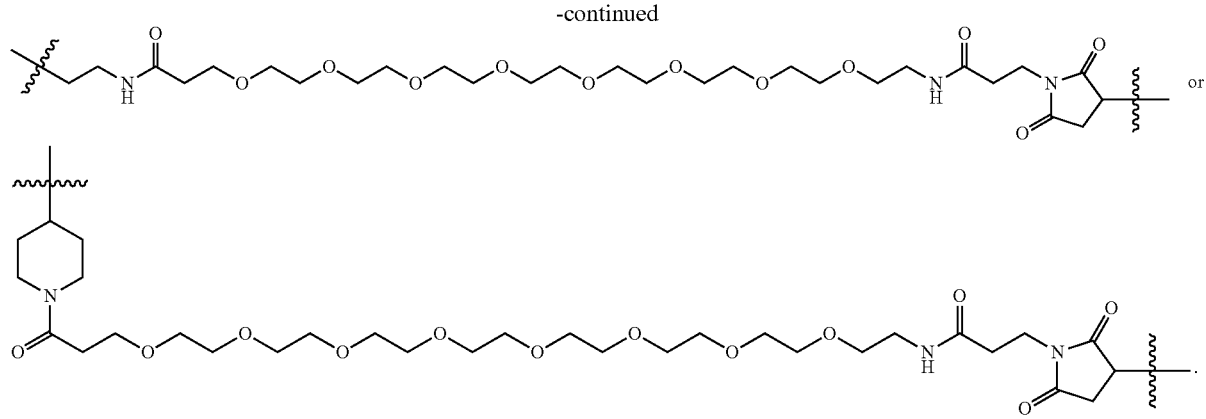

In certain embodiments of any of the aforementioned immunoconjugates of Formula (II) and Formula (IIa), $R^1$ is —$CH_3$, while in certain other embodiments of any of the aforementioned immunoconjugates of Formula (II) and Formula (IIa) $R^1$ is H.

In certain embodiments of any of the aforementioned immunoconjugates of Formula (II) and Formula (IIa) $R^3$ is —$NH_2$, while in certain other embodiments of any of the aforementioned immunoconjugates of Formula (II) and Formula (IIa) $R^3$ is —OH.

In certain embodiments the immunoconjugates of the invention are selected from:

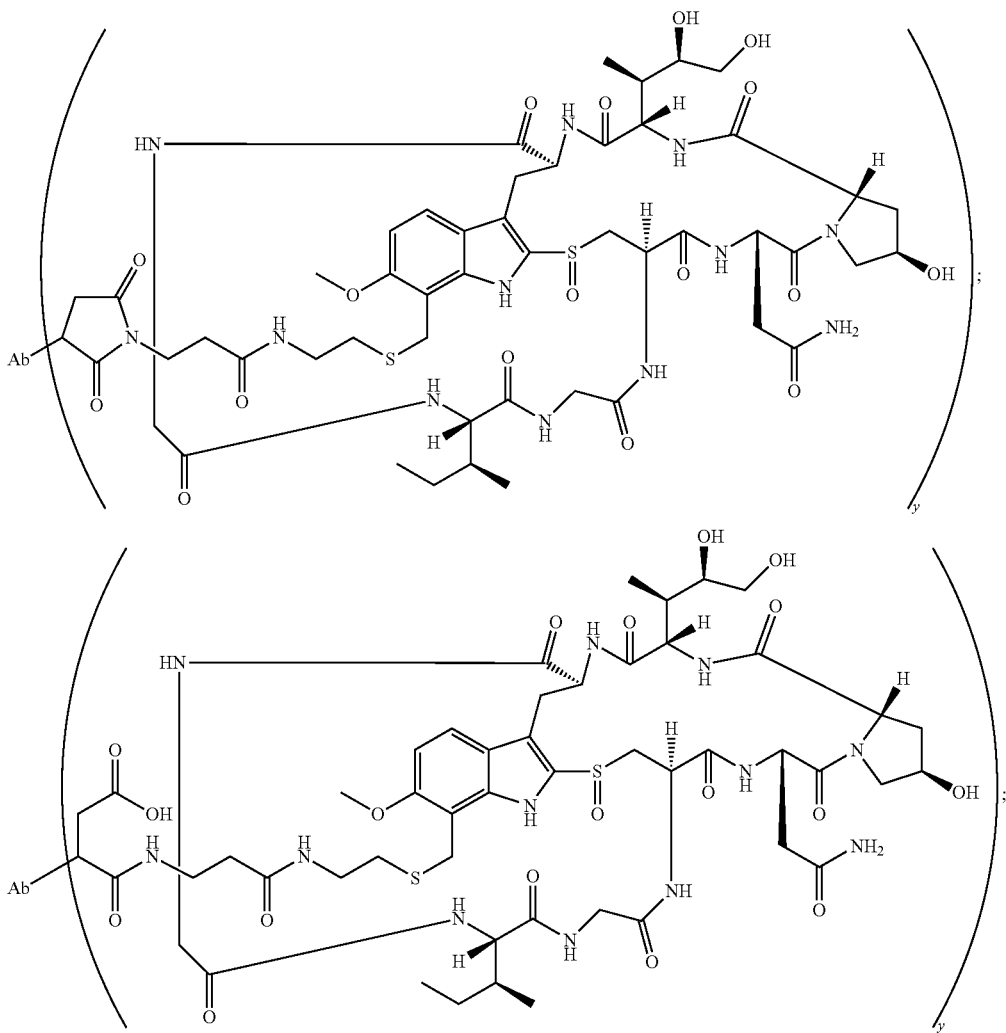

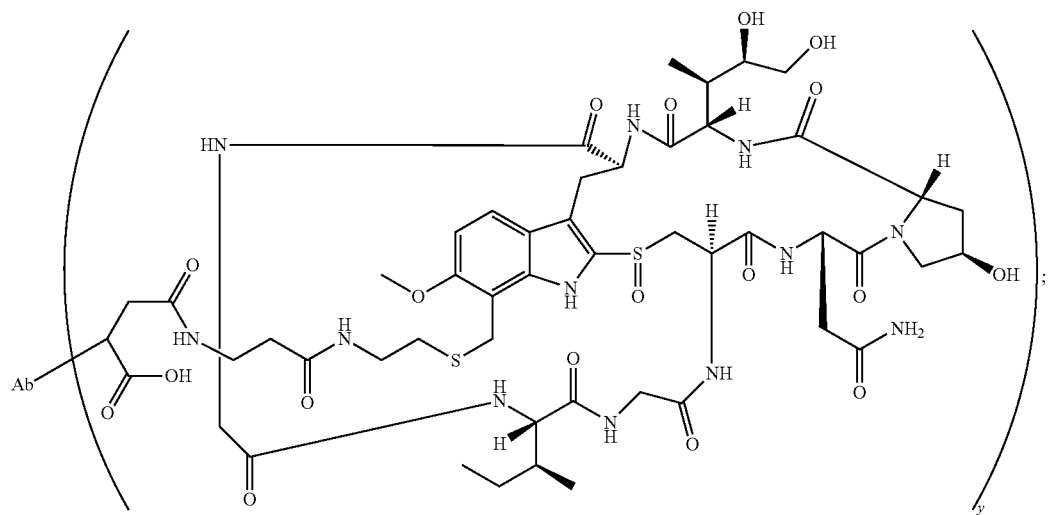
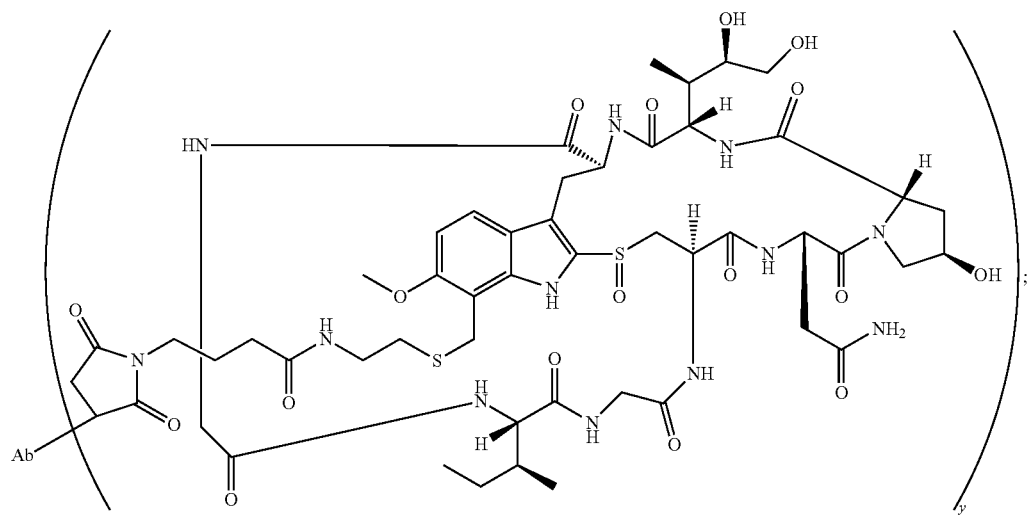
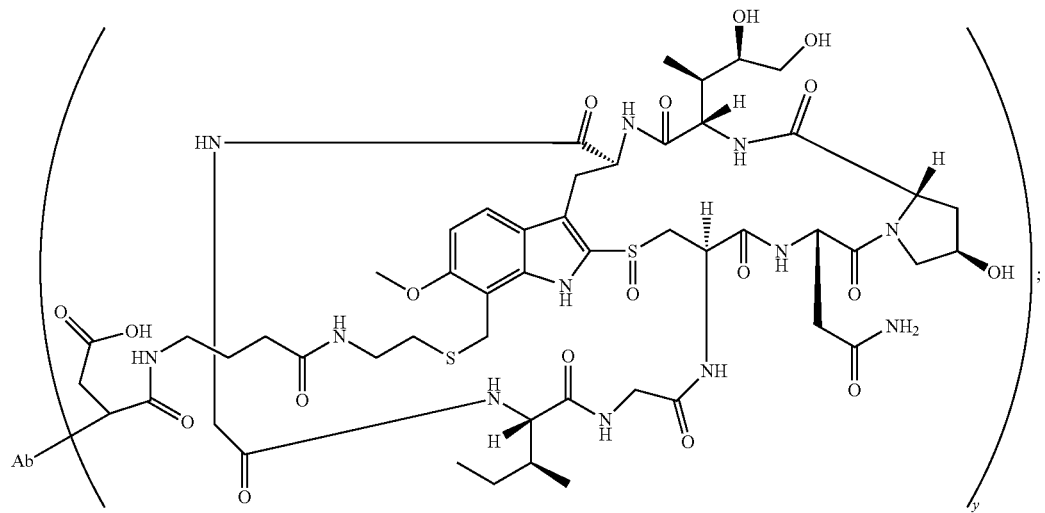

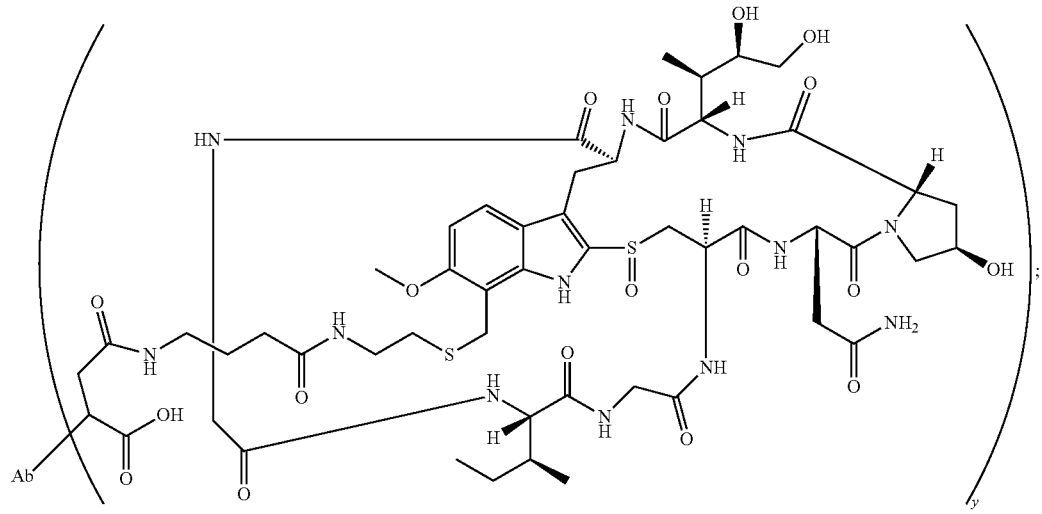
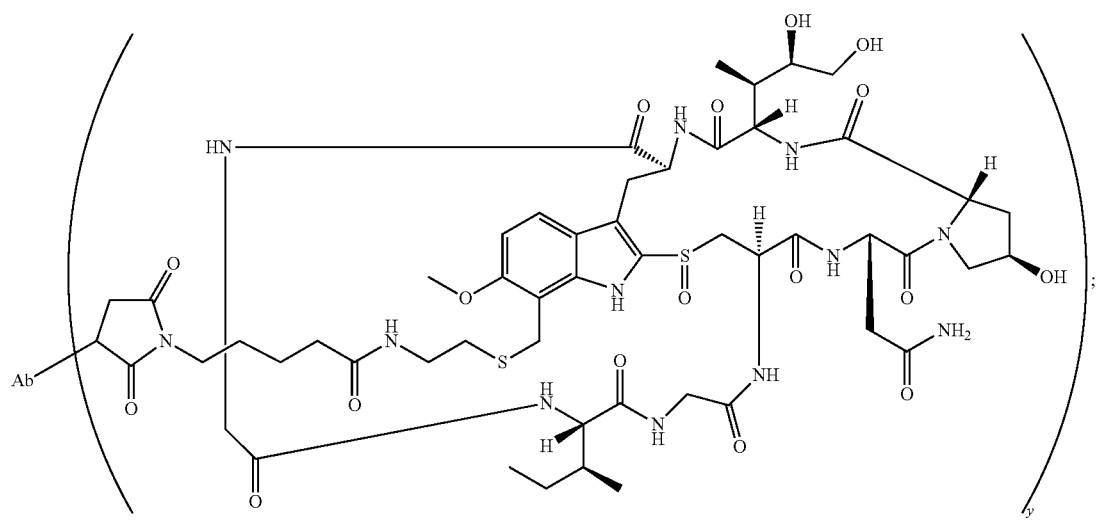
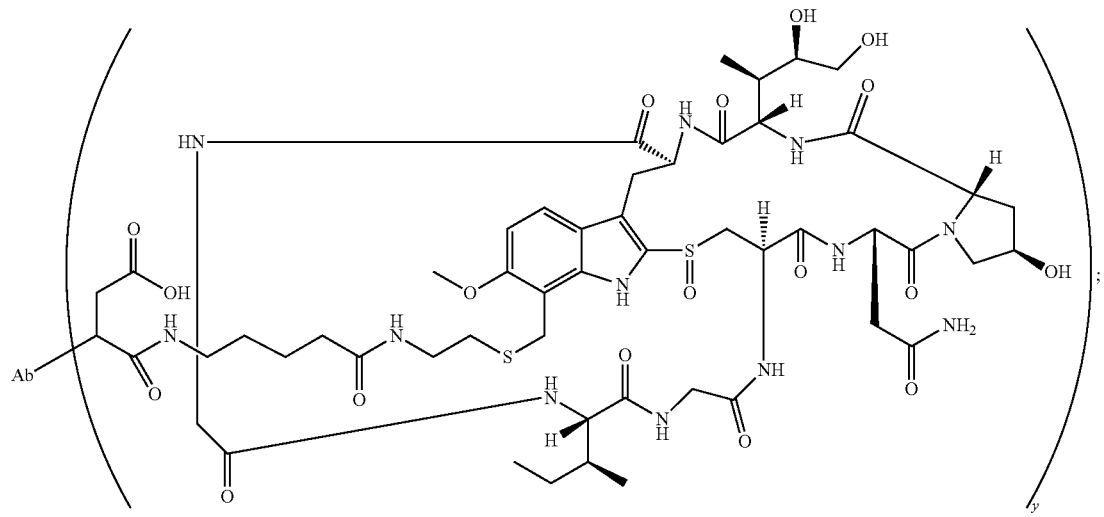

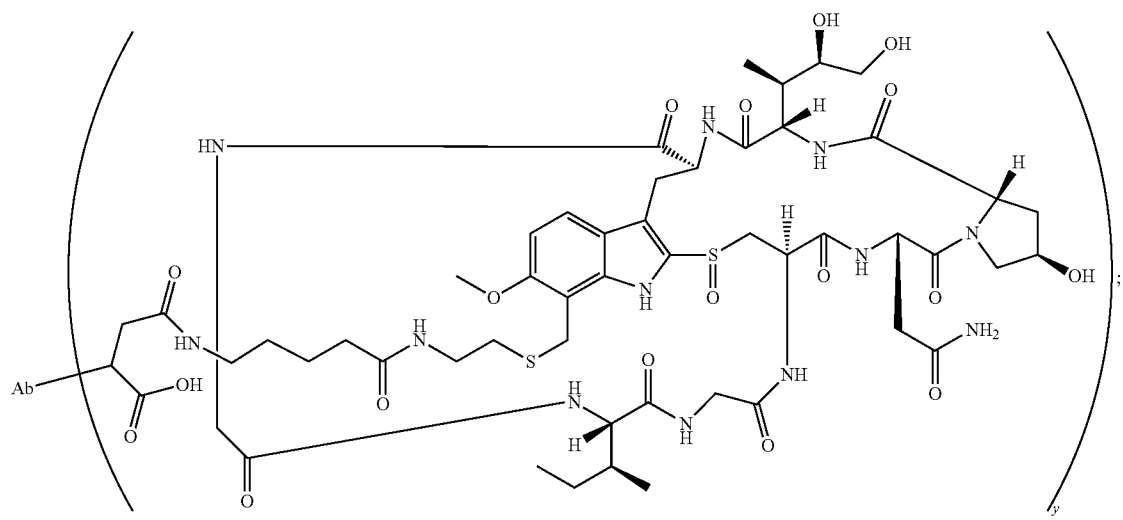
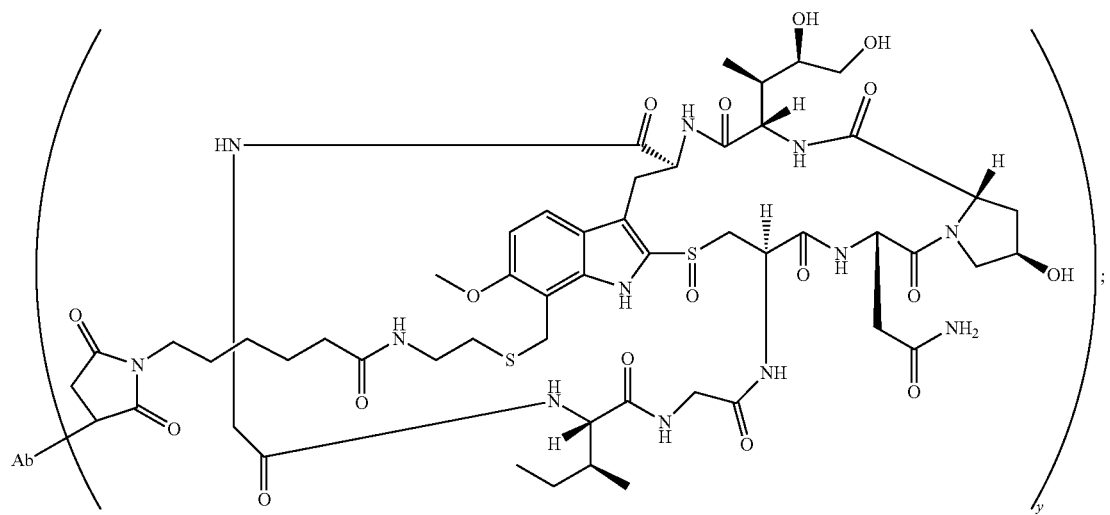
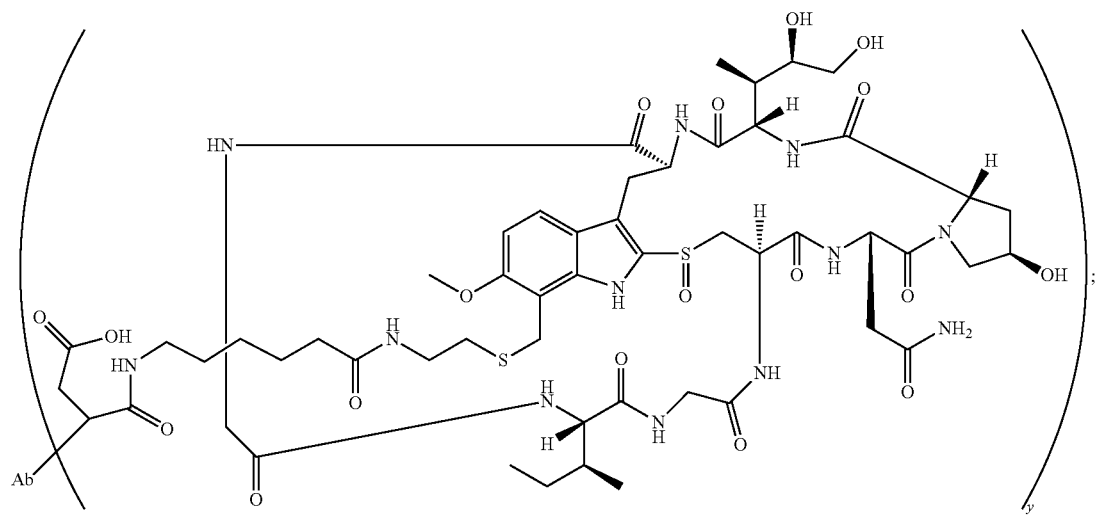

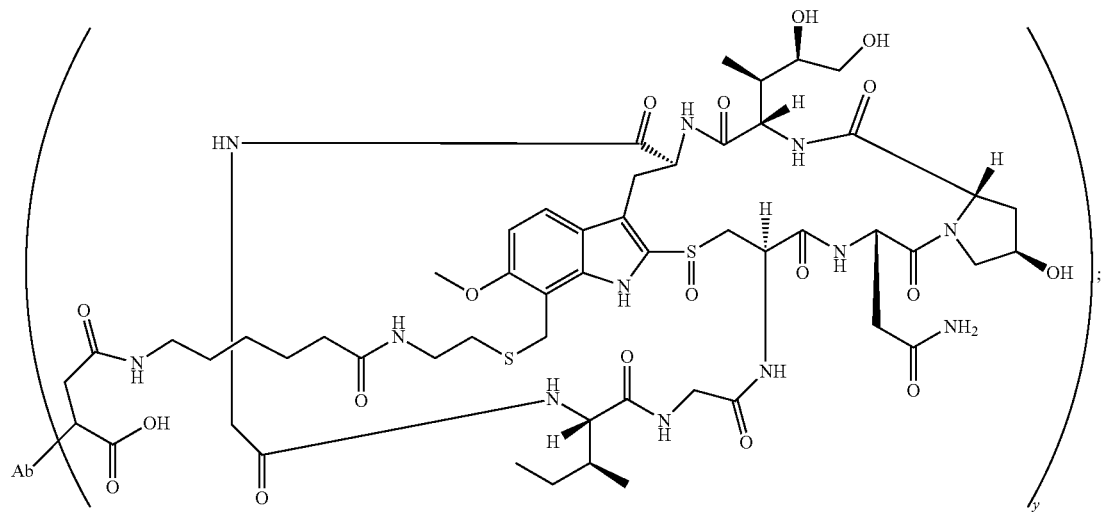
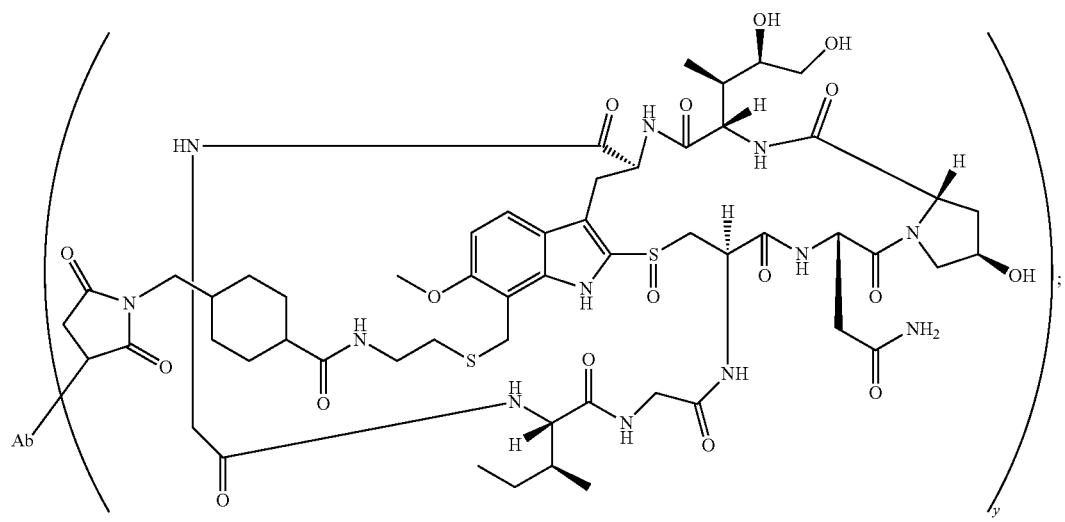
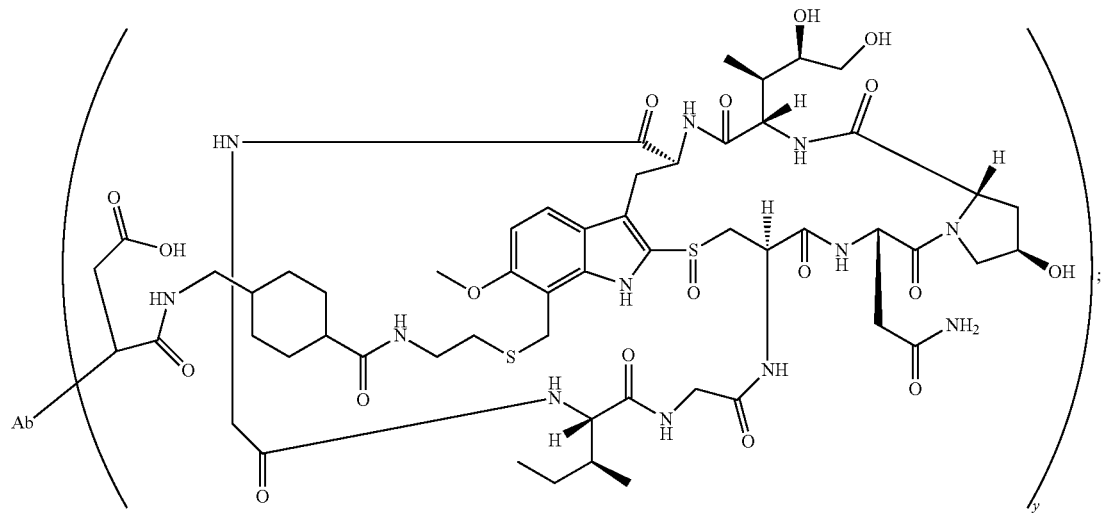

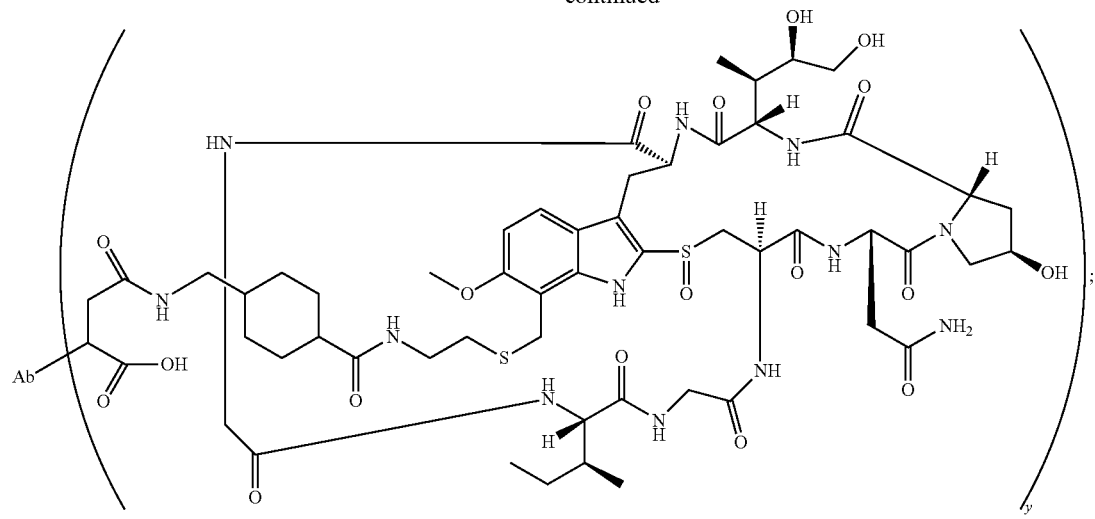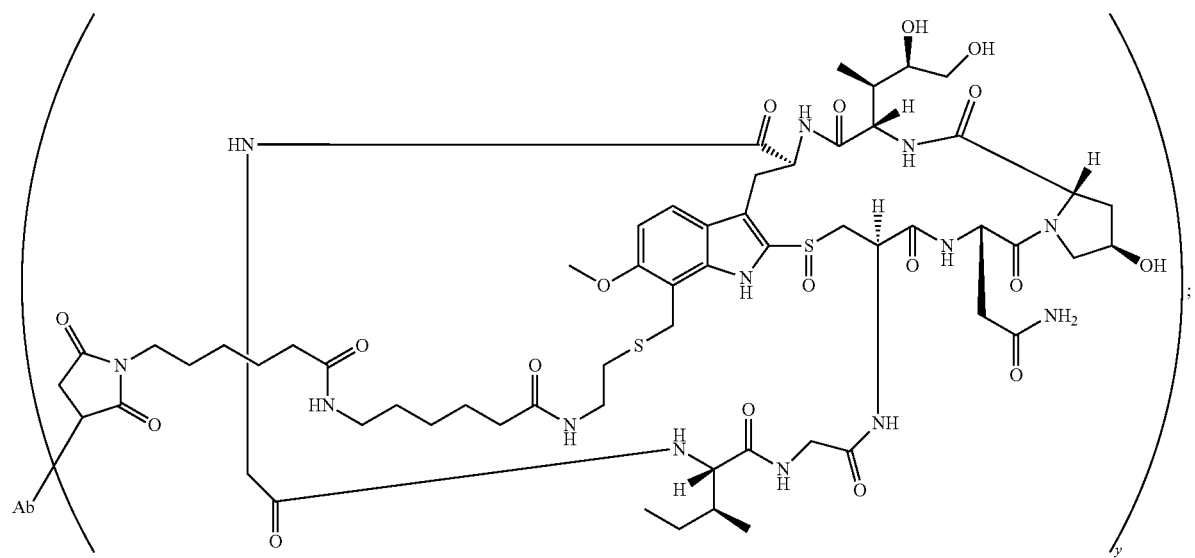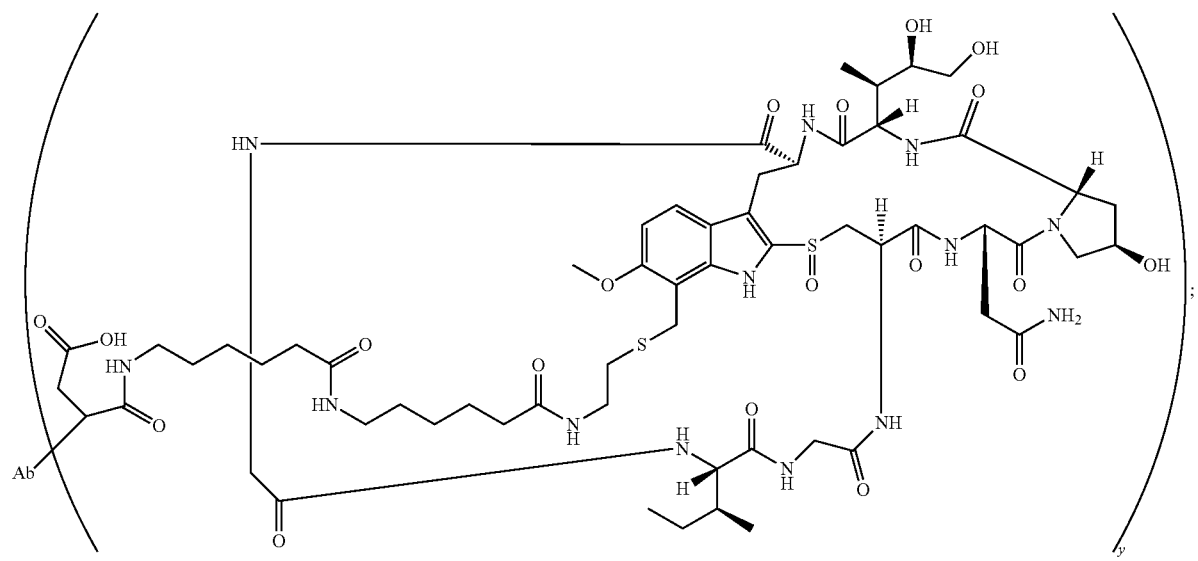

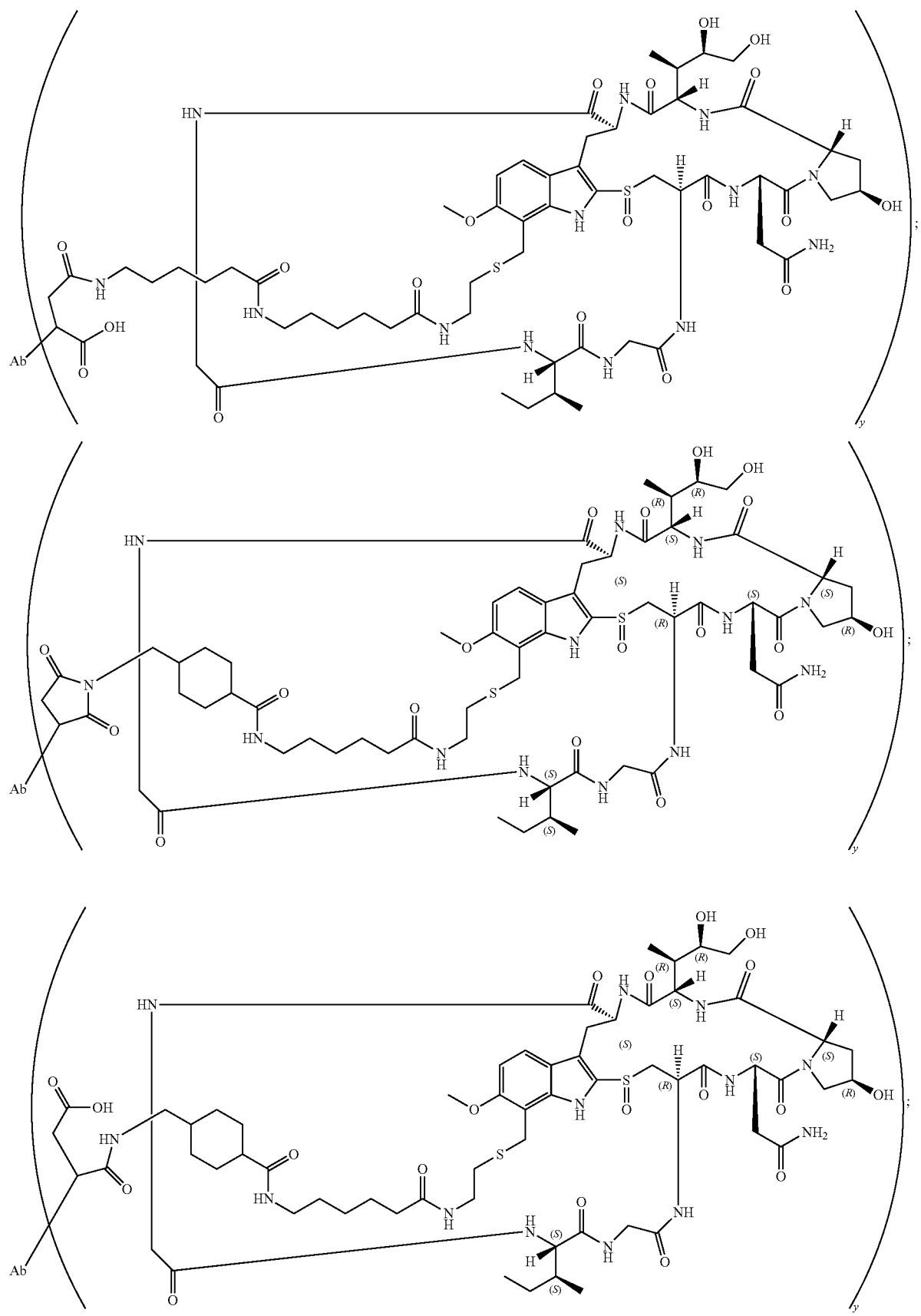

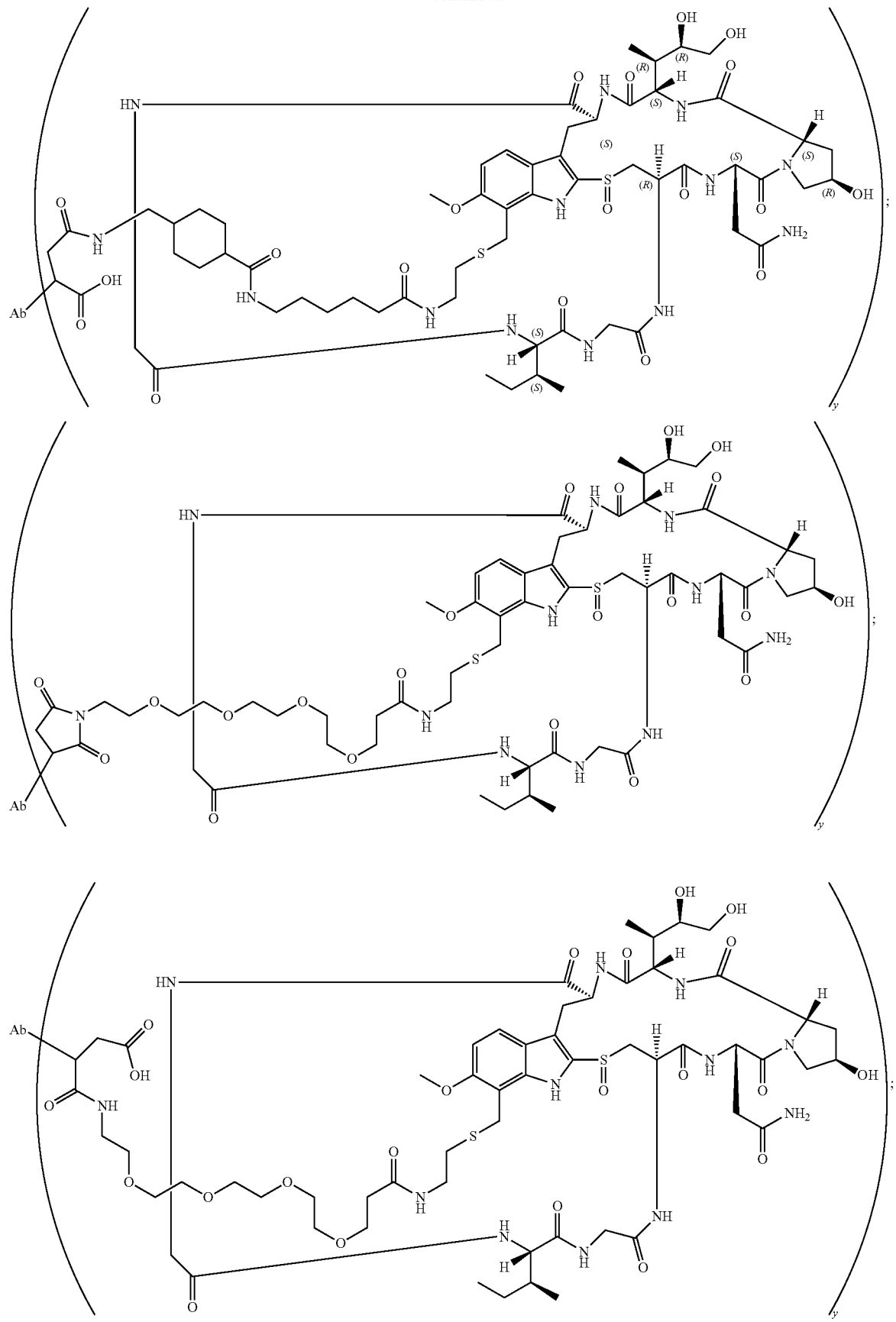

-continued
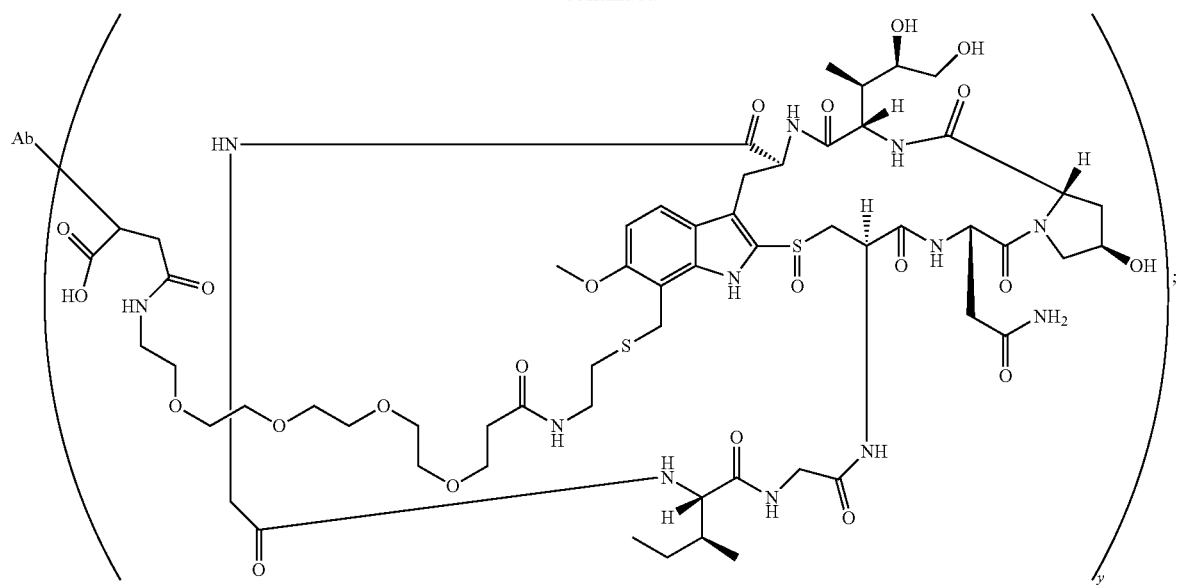
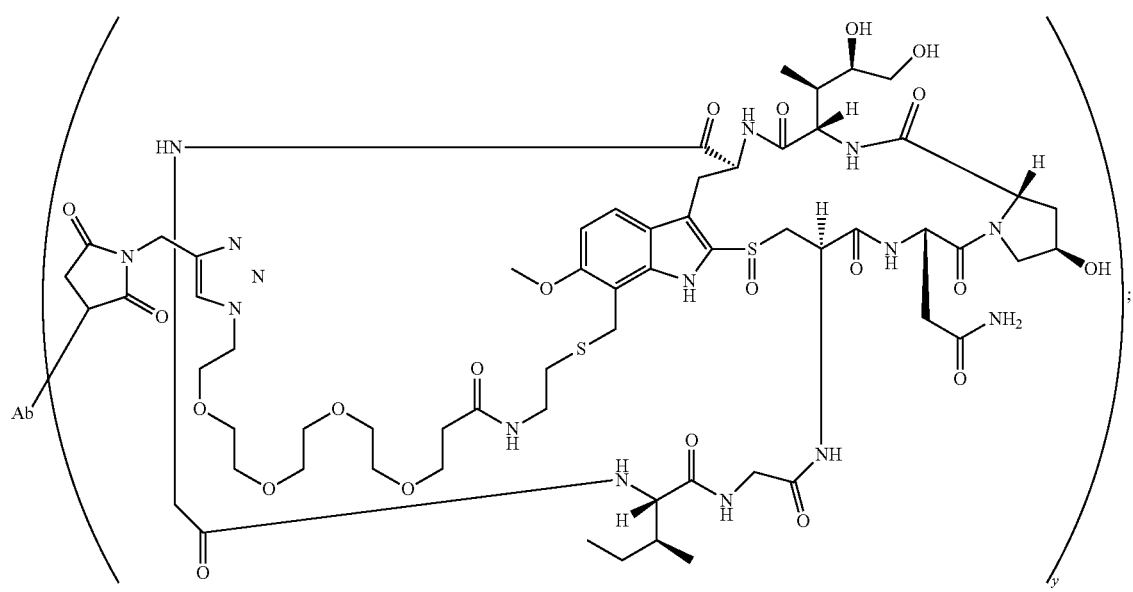


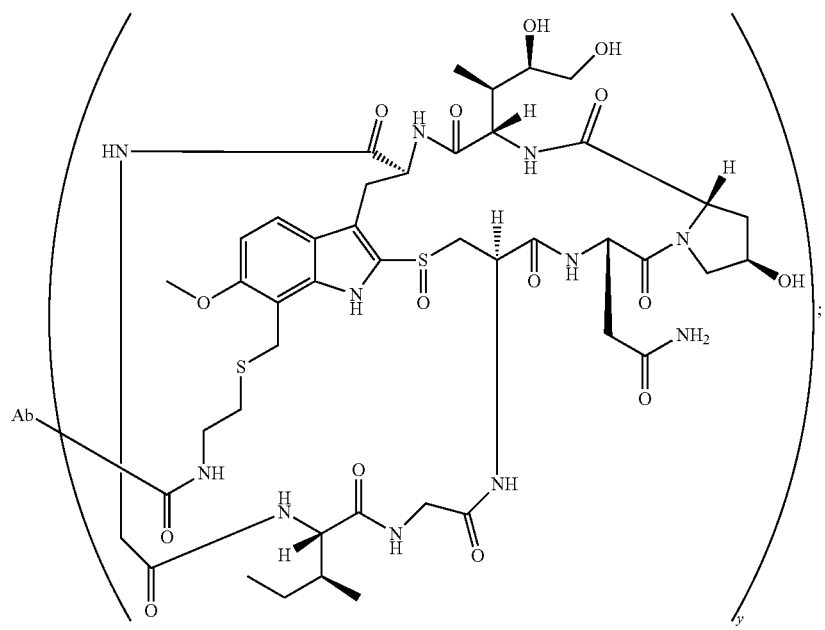

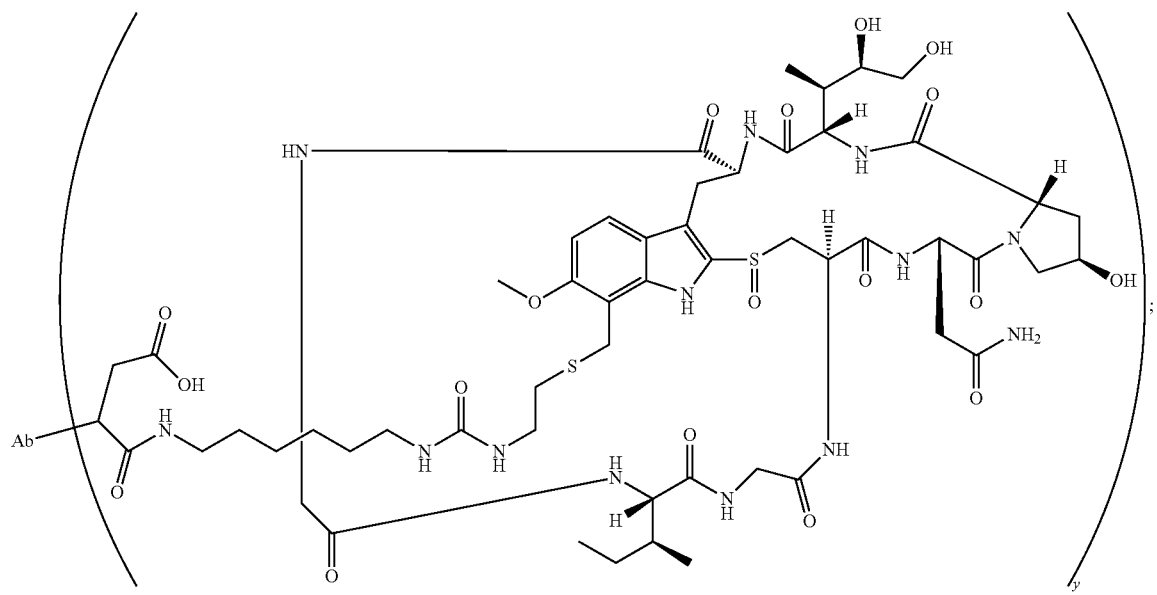
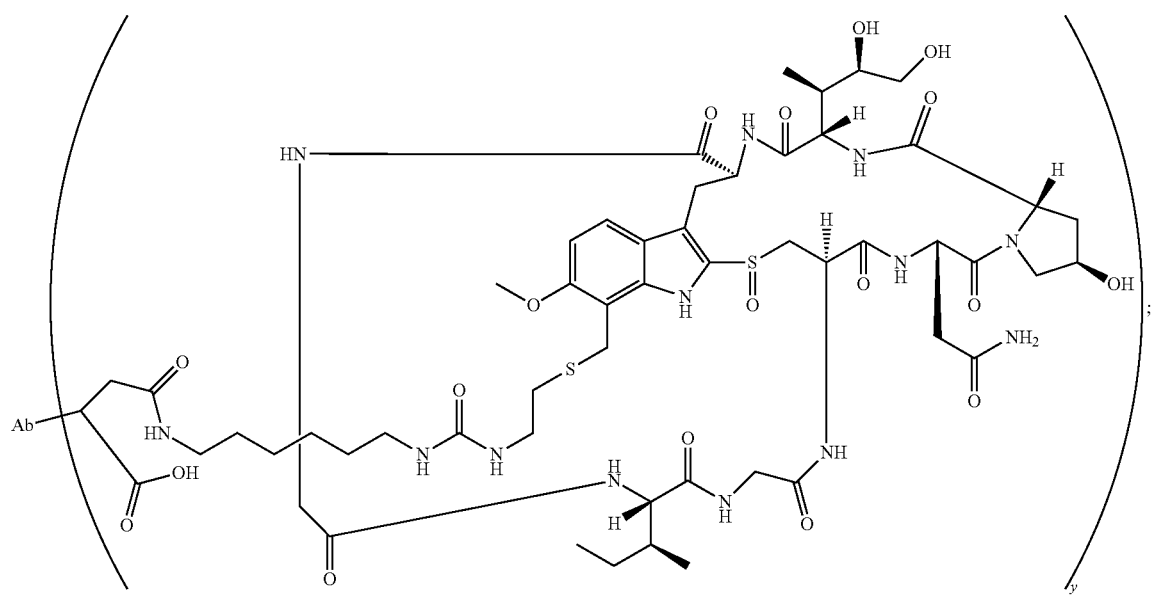

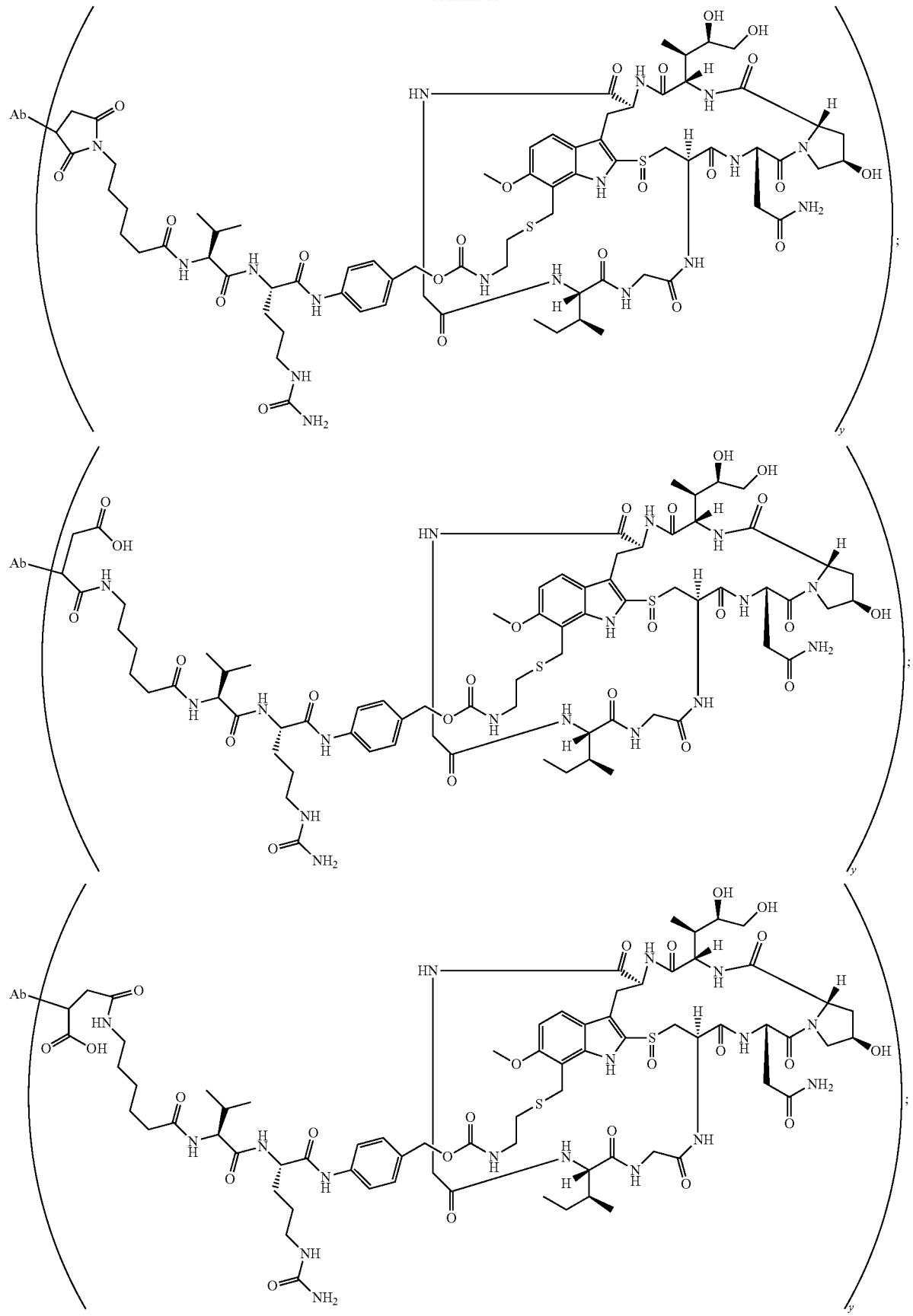


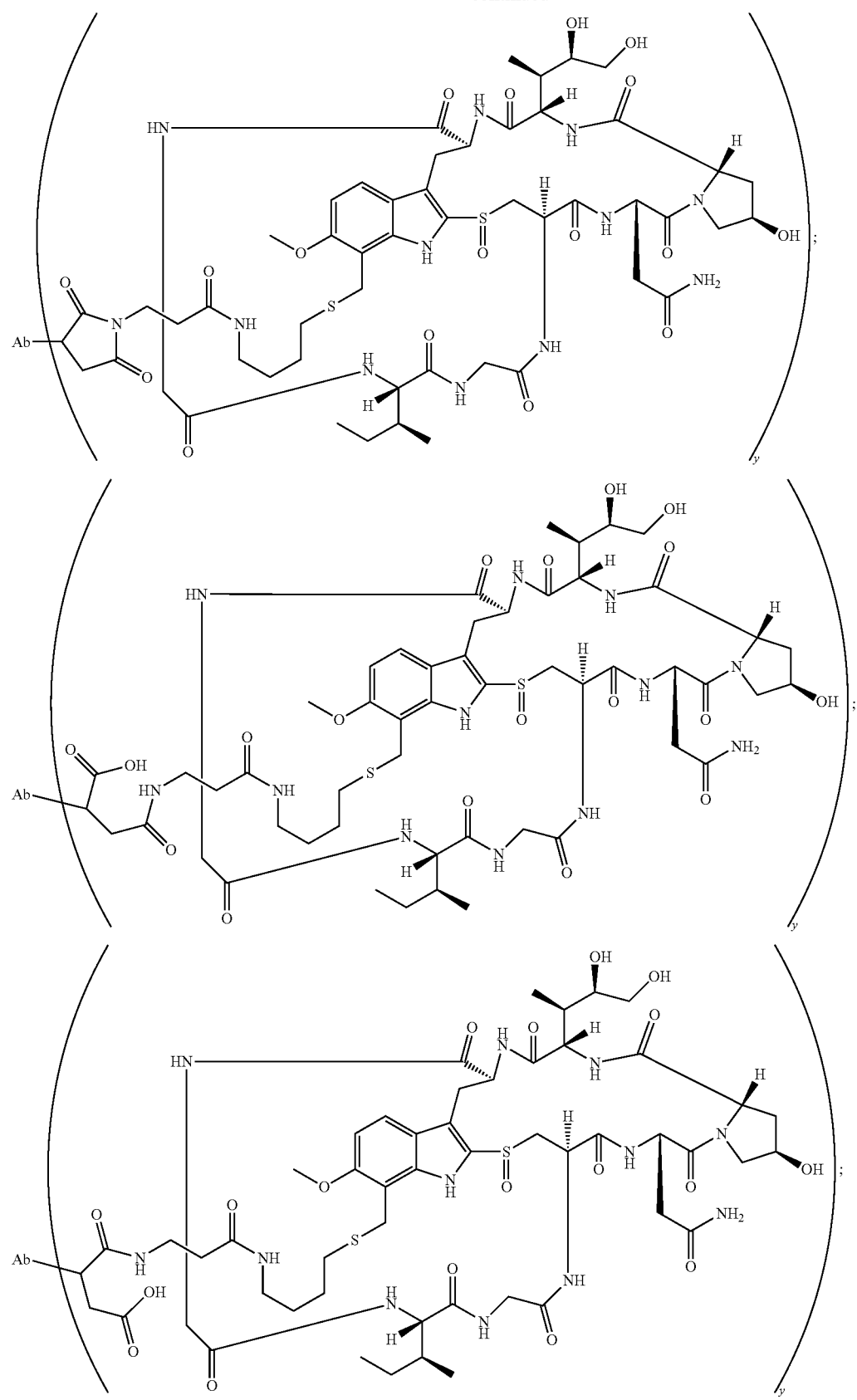

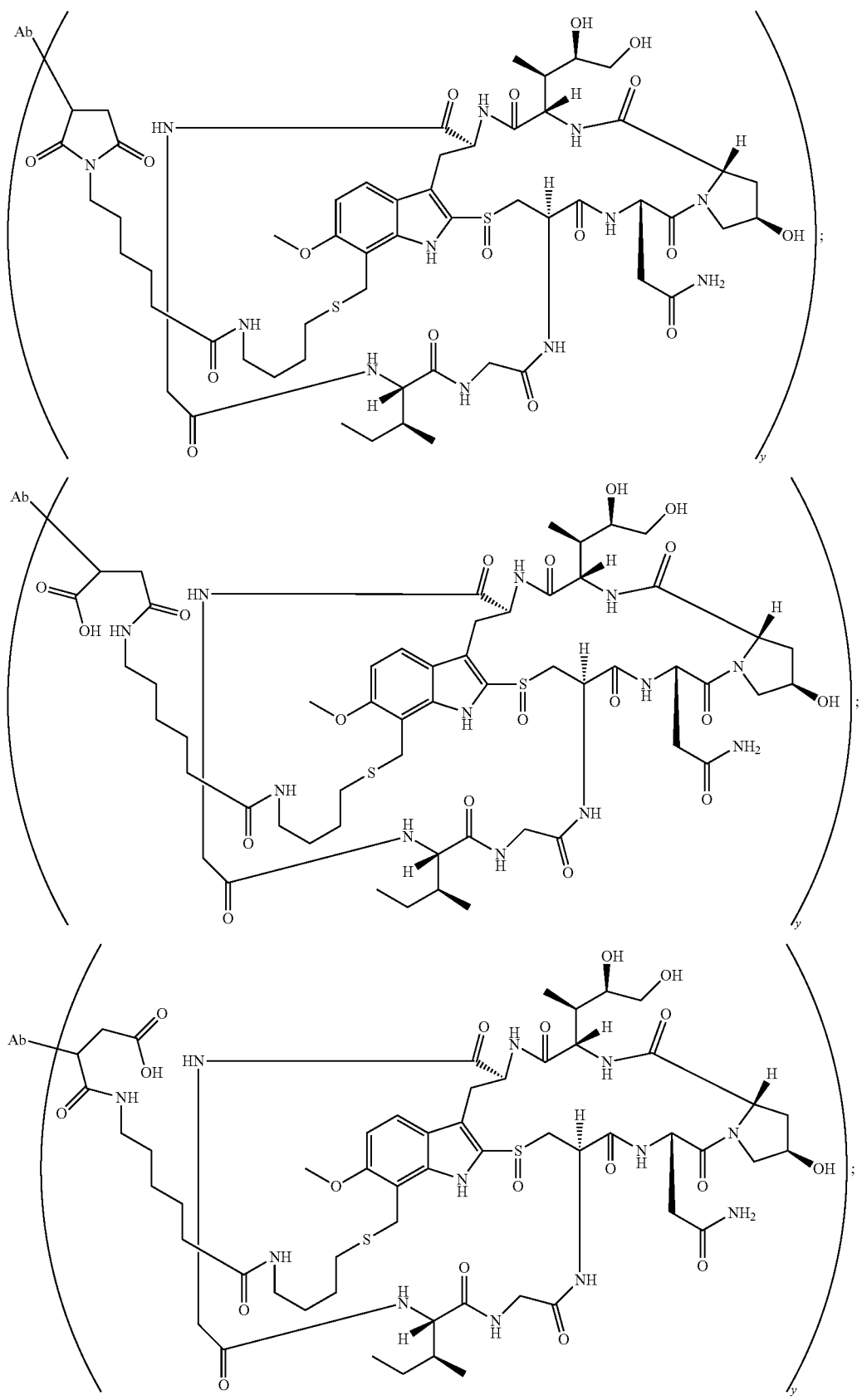

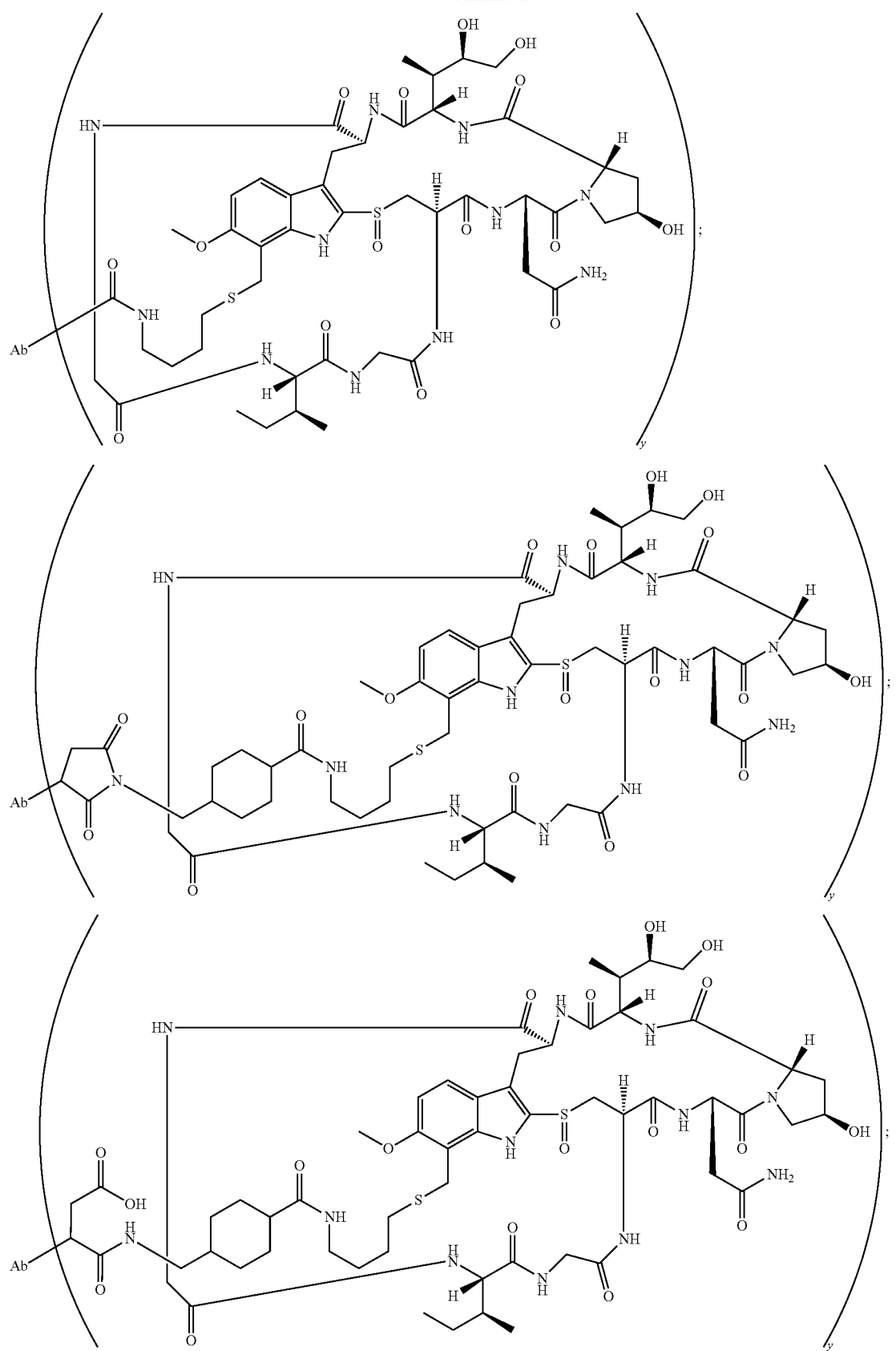

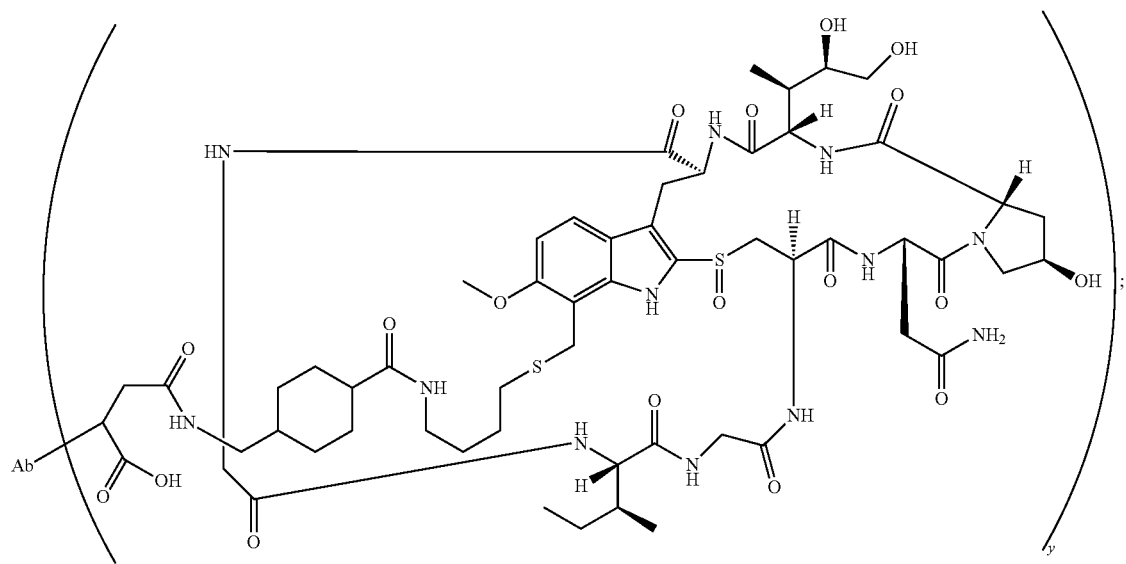
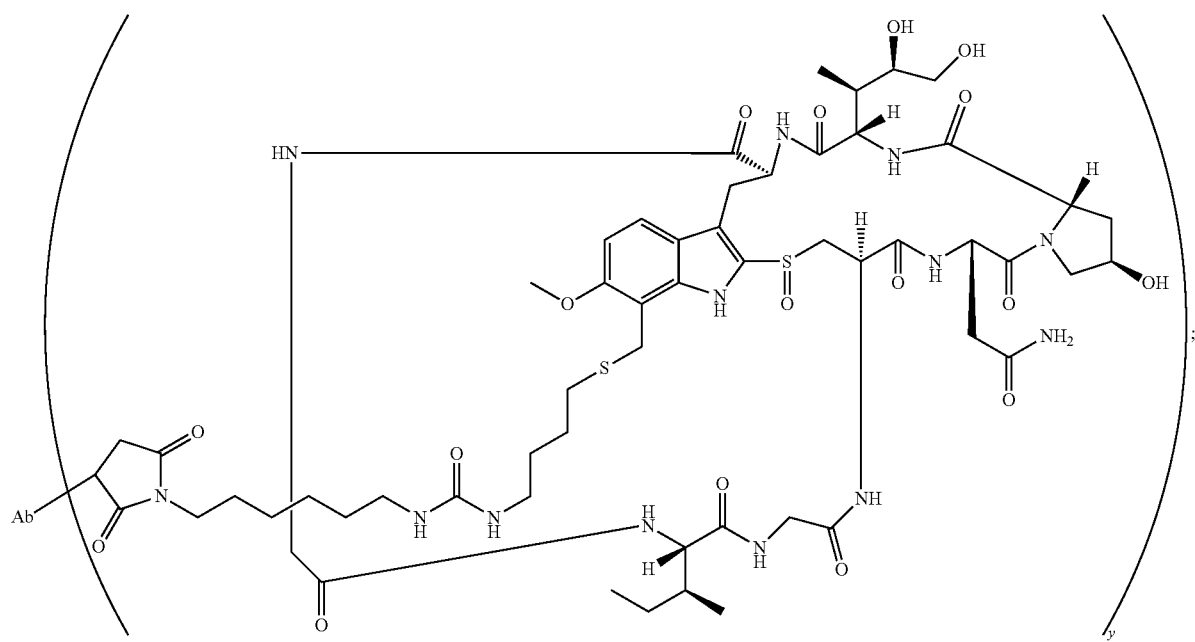

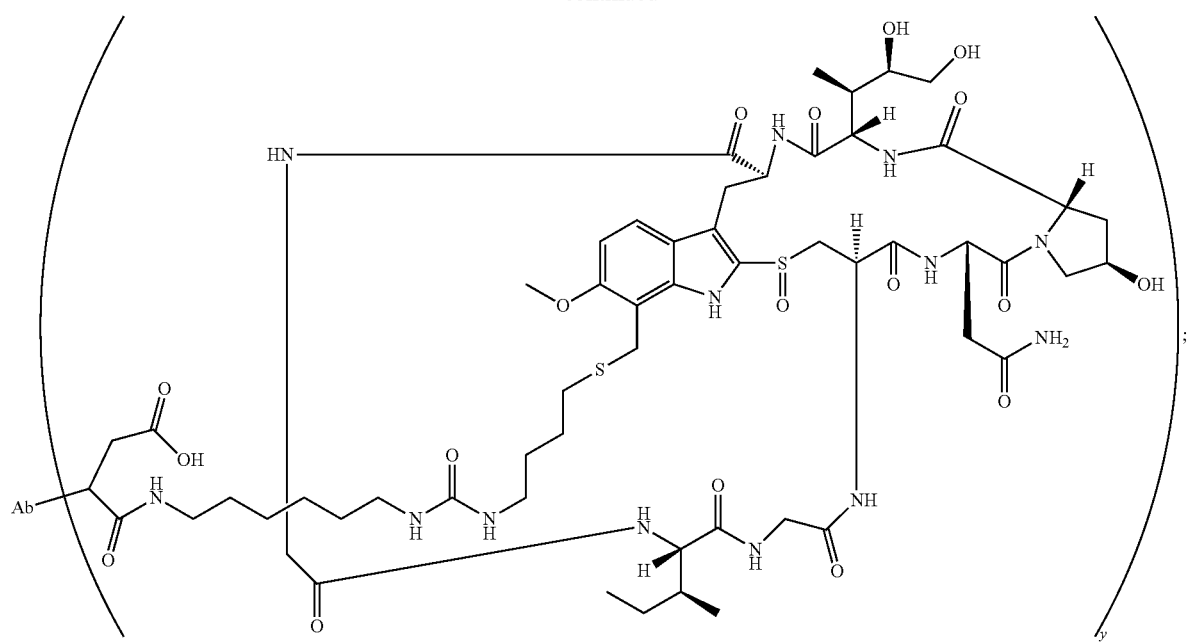
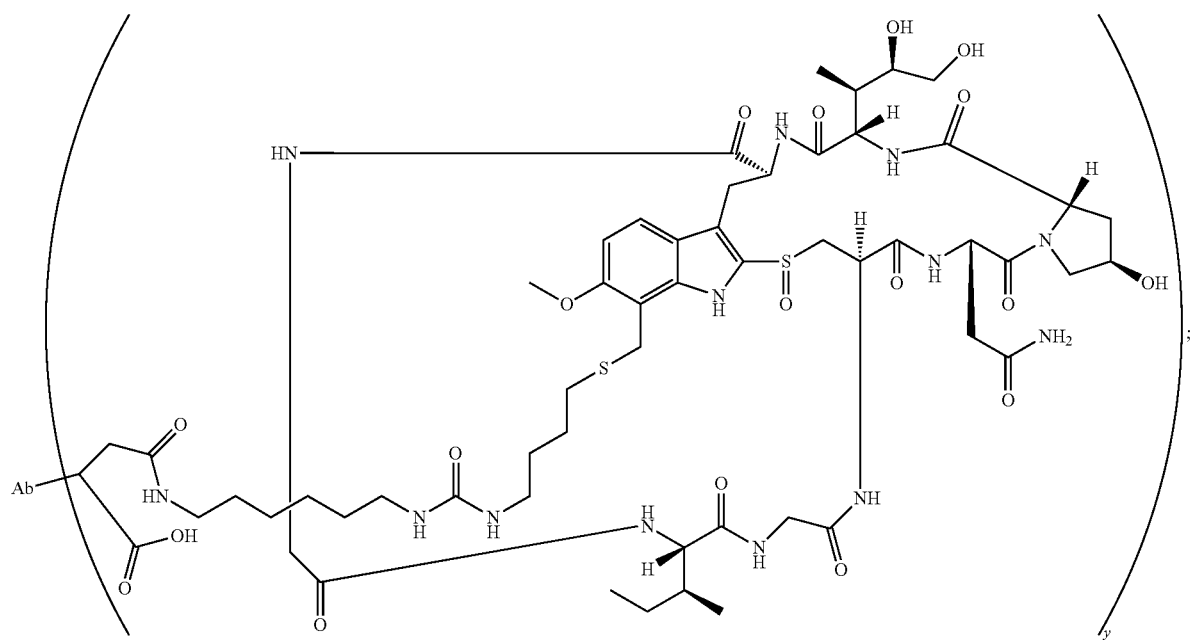

201
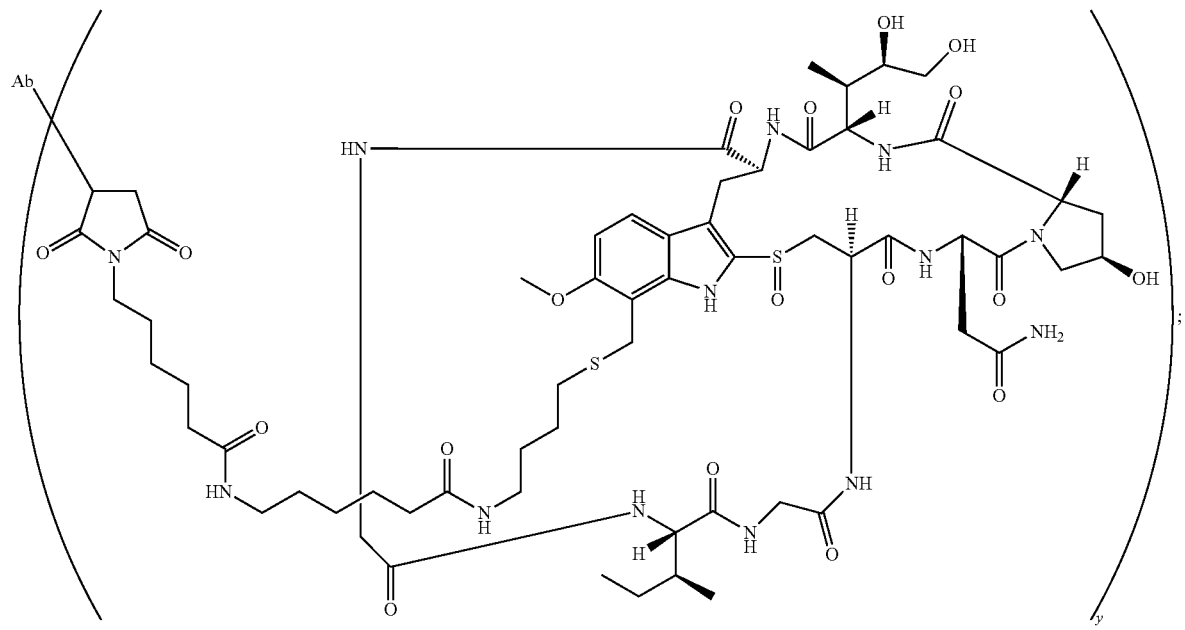
202
-continued
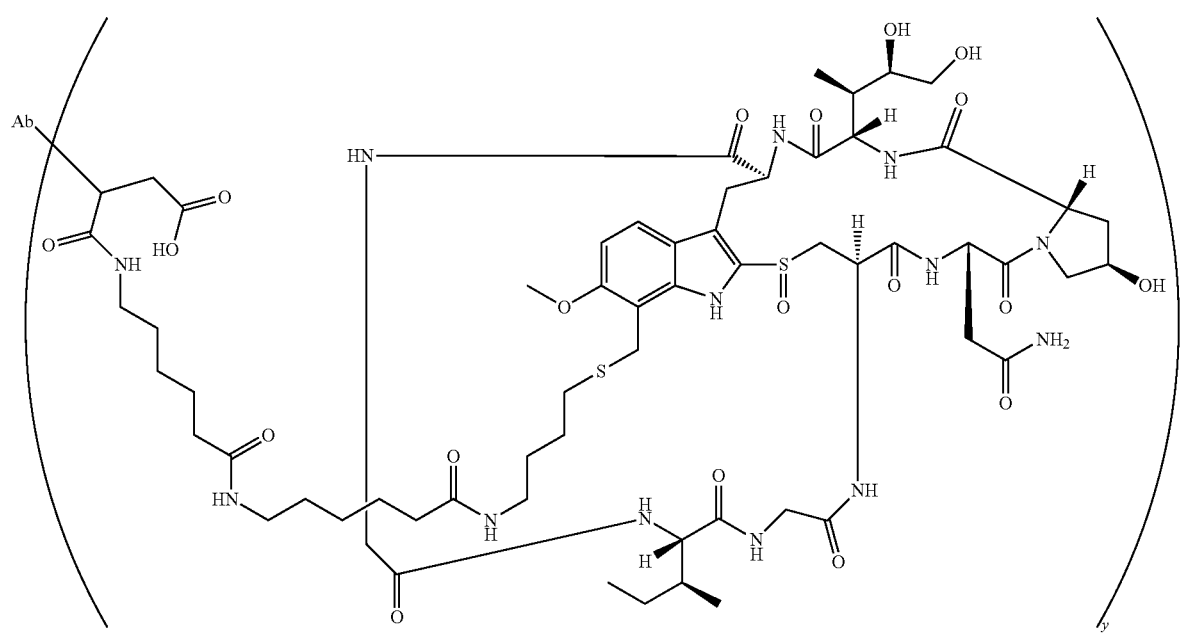

203
204
-continued
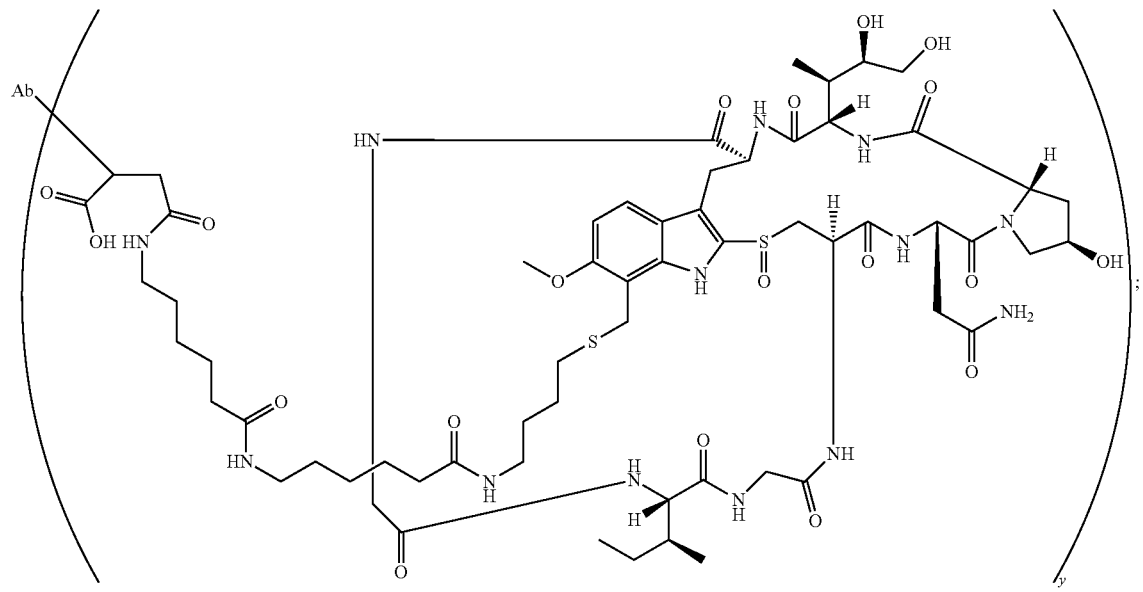
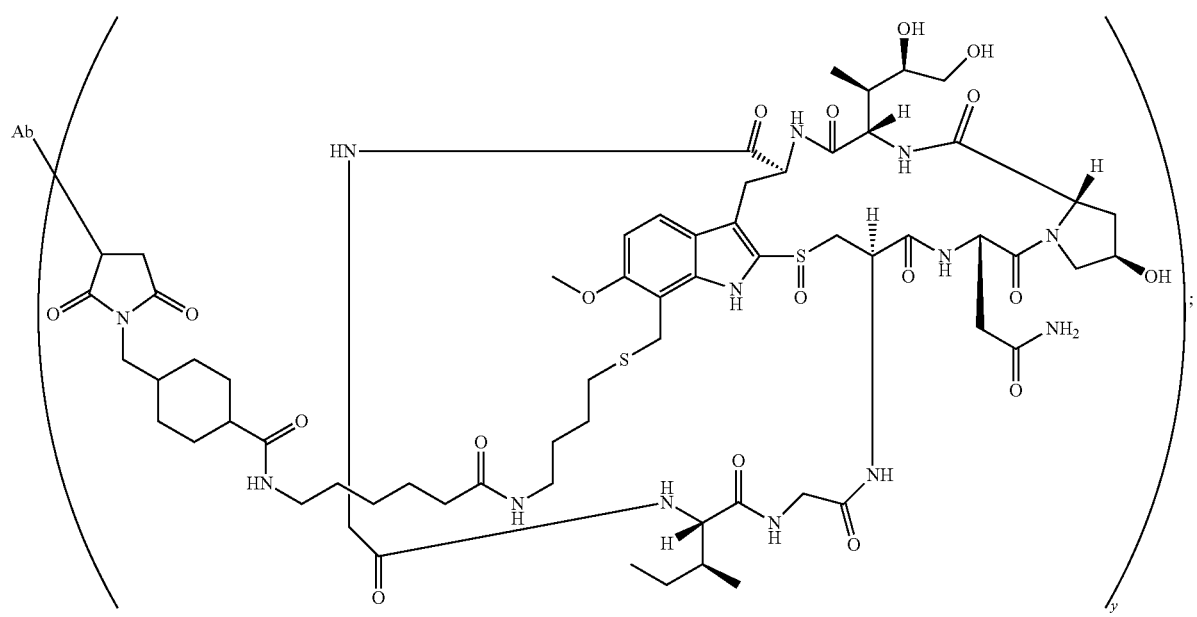

205
206
-continued
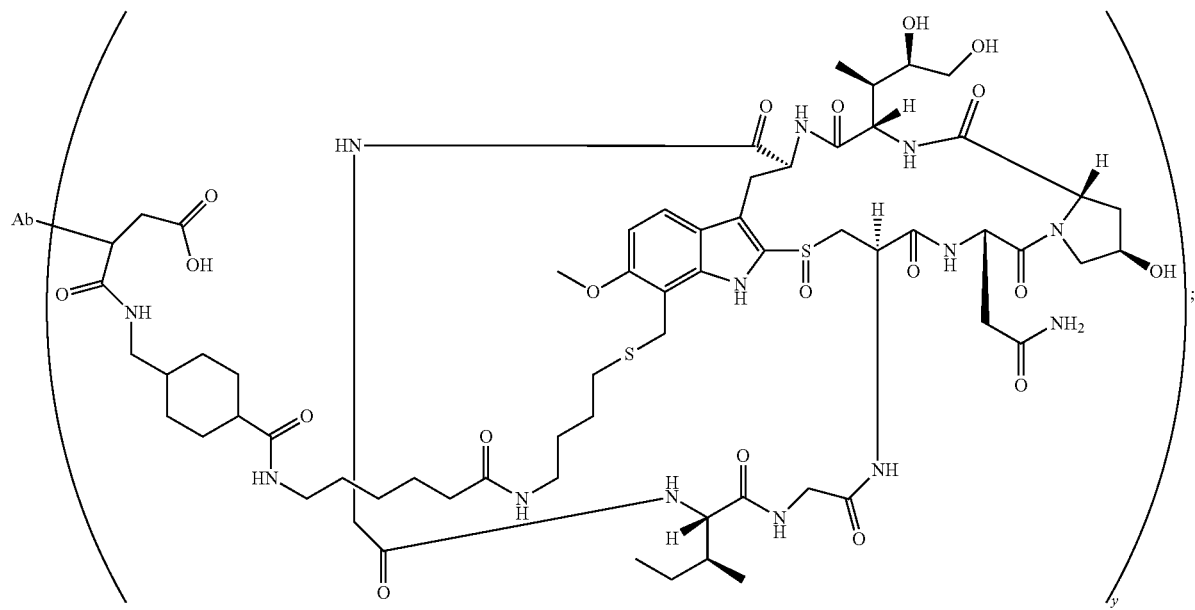

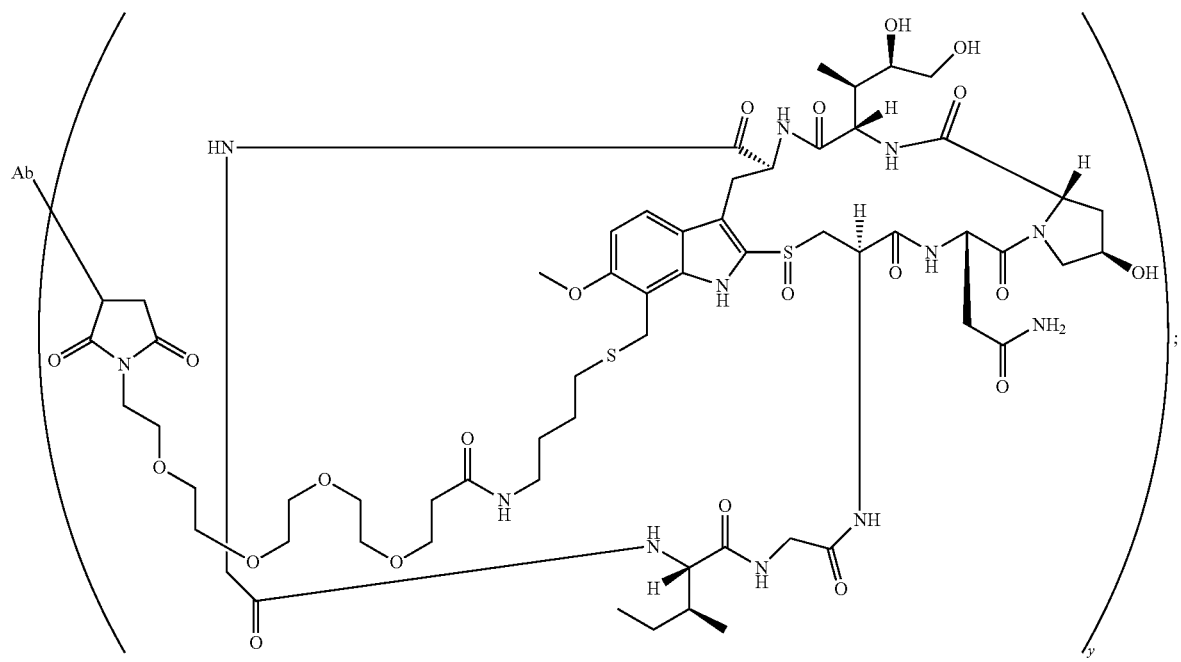
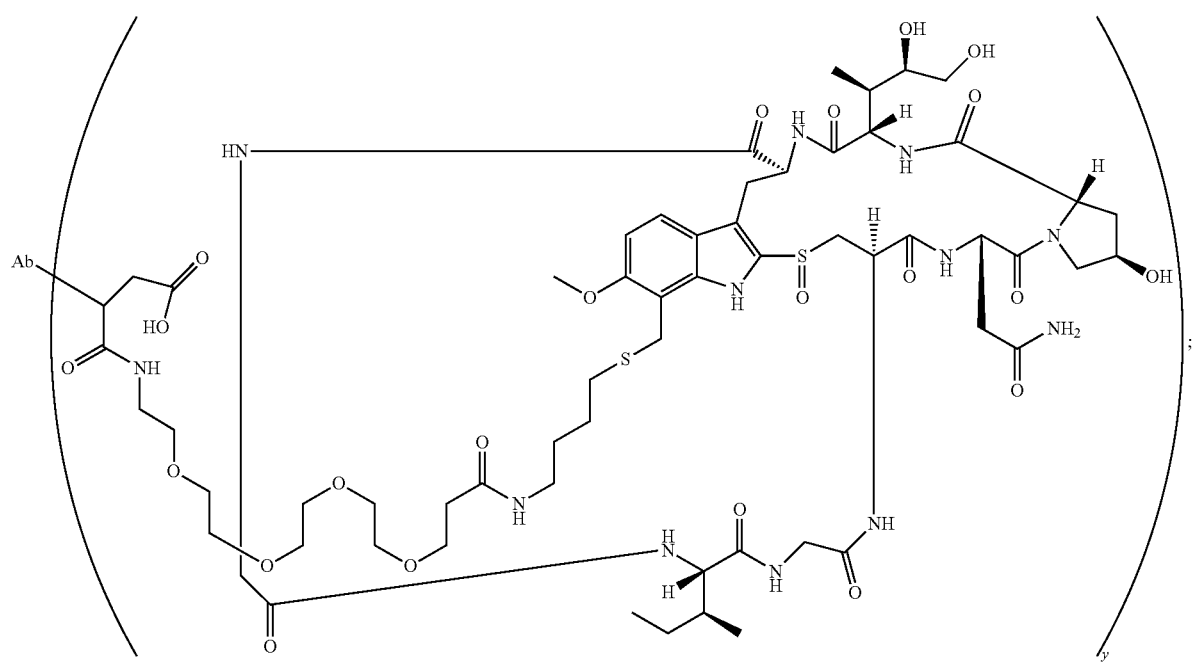

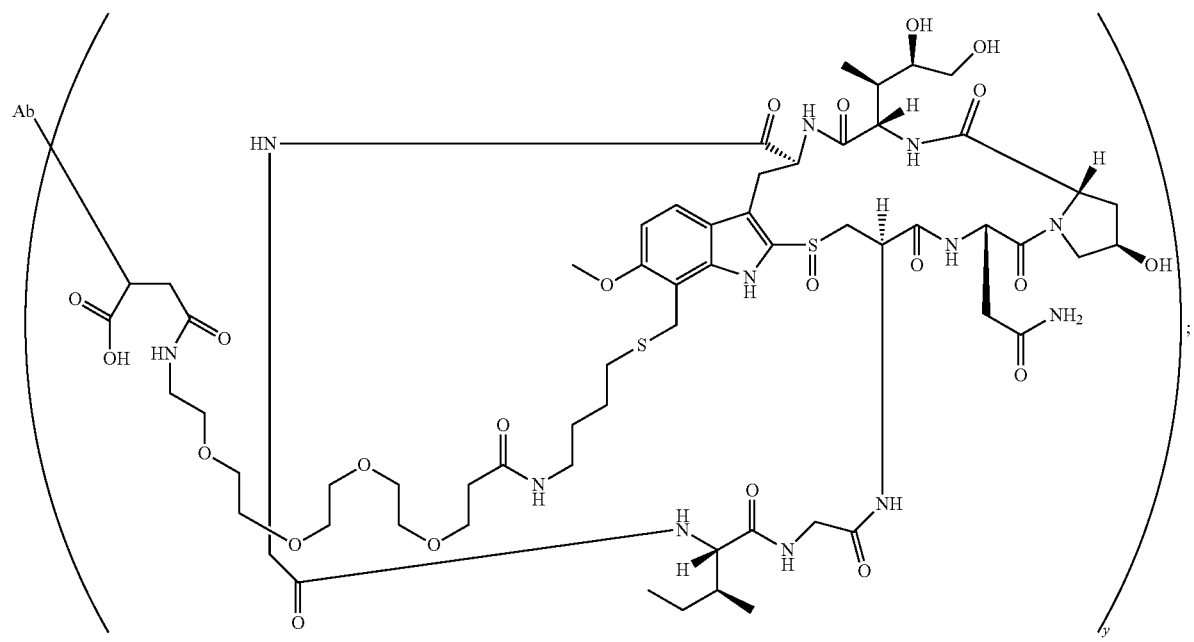
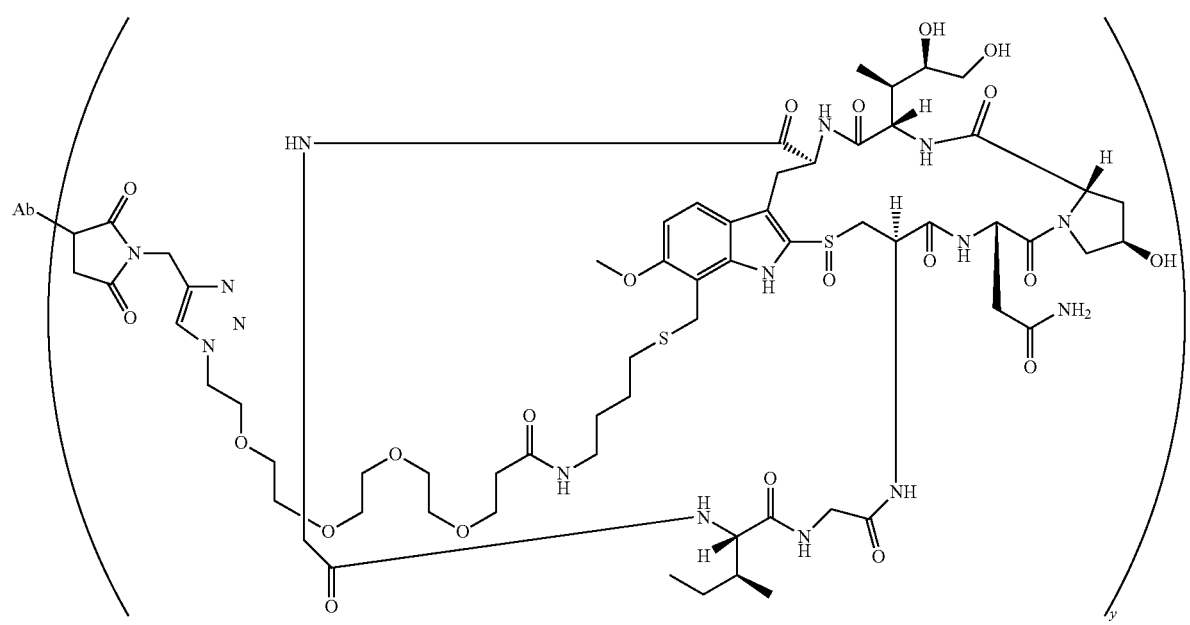

-continued
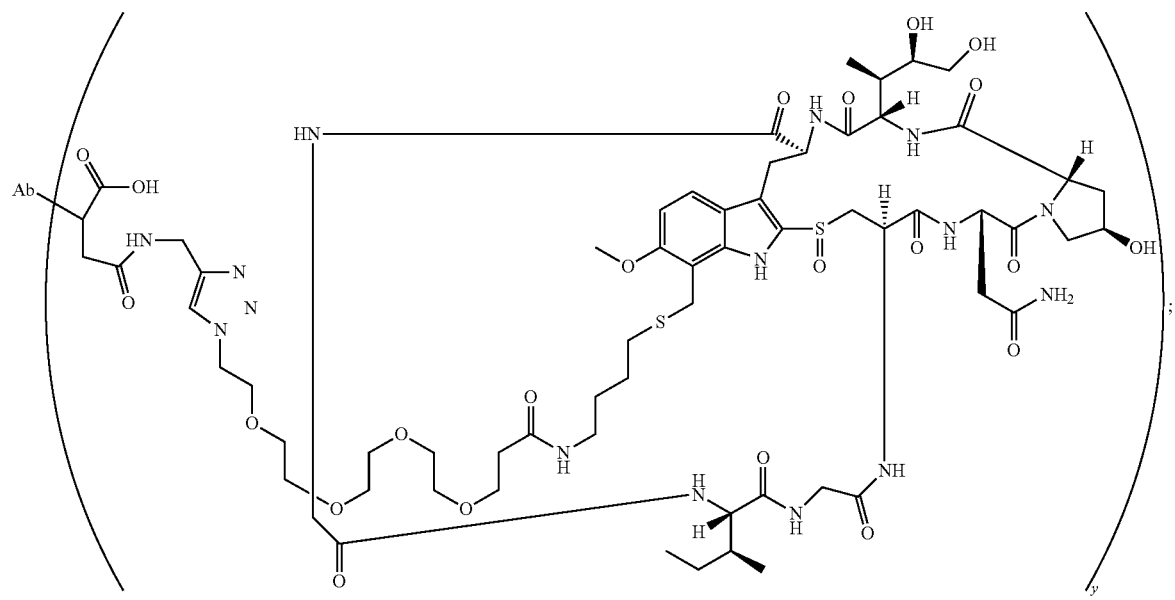
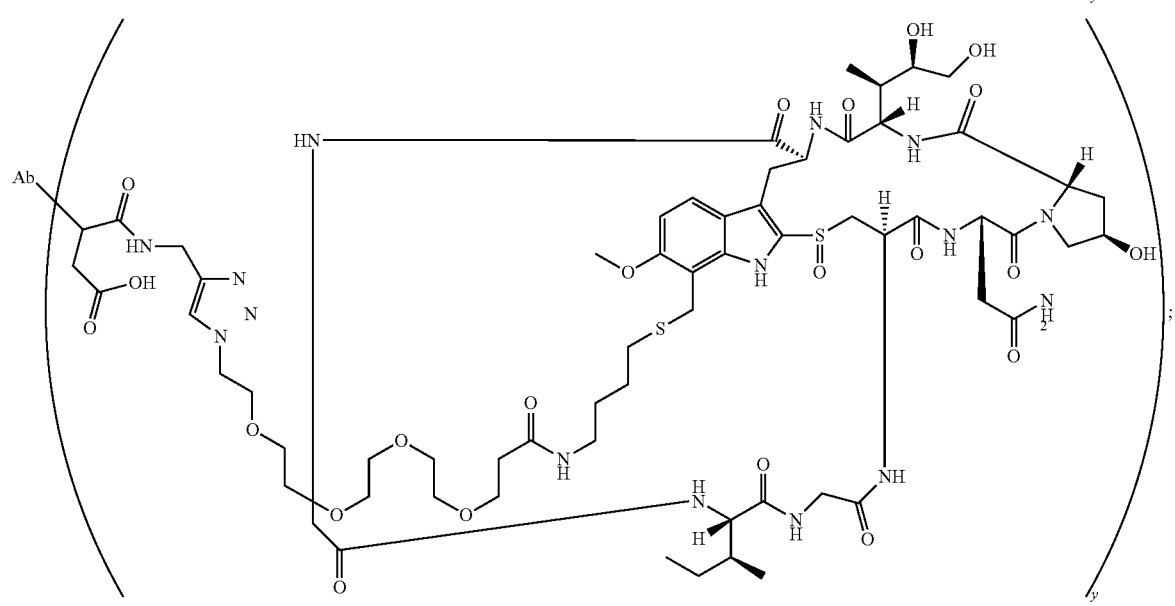
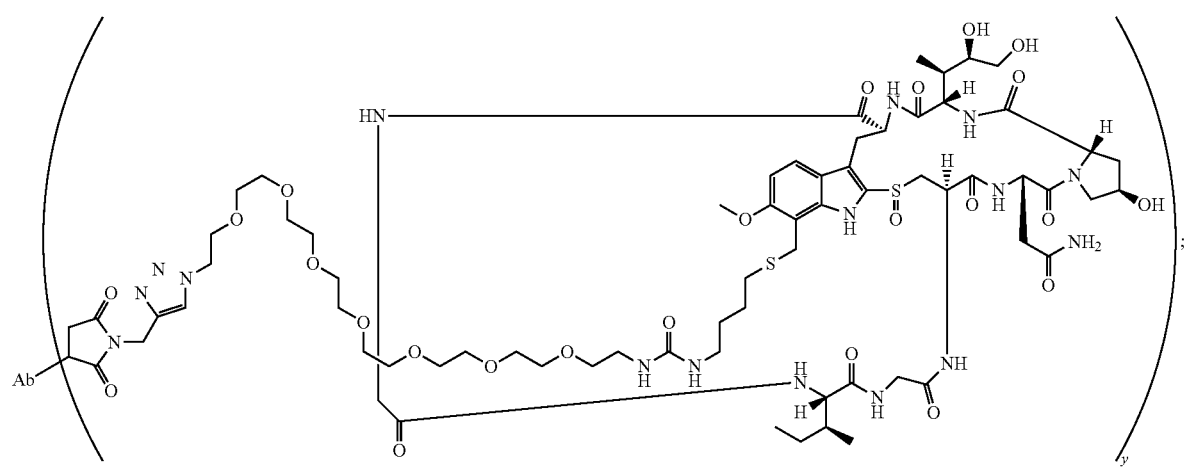

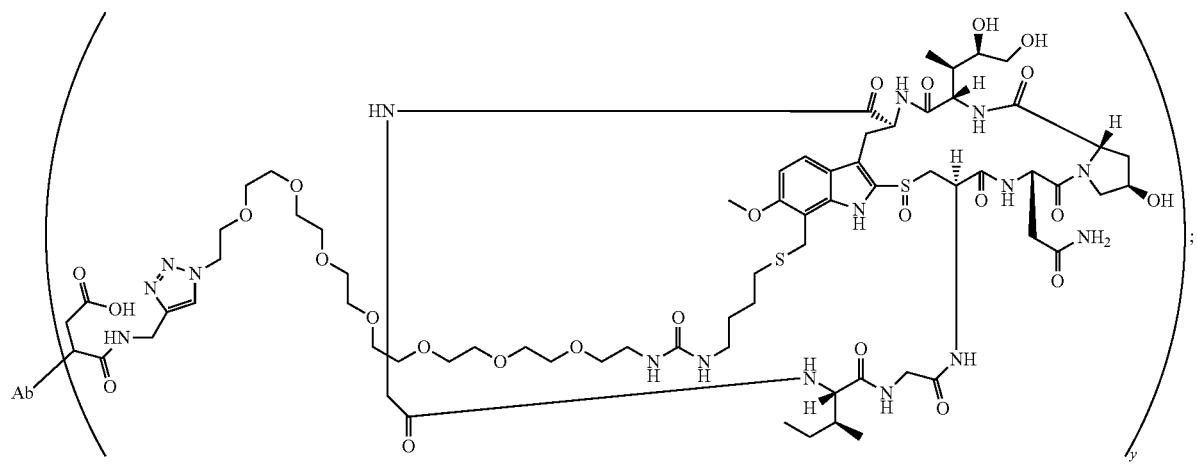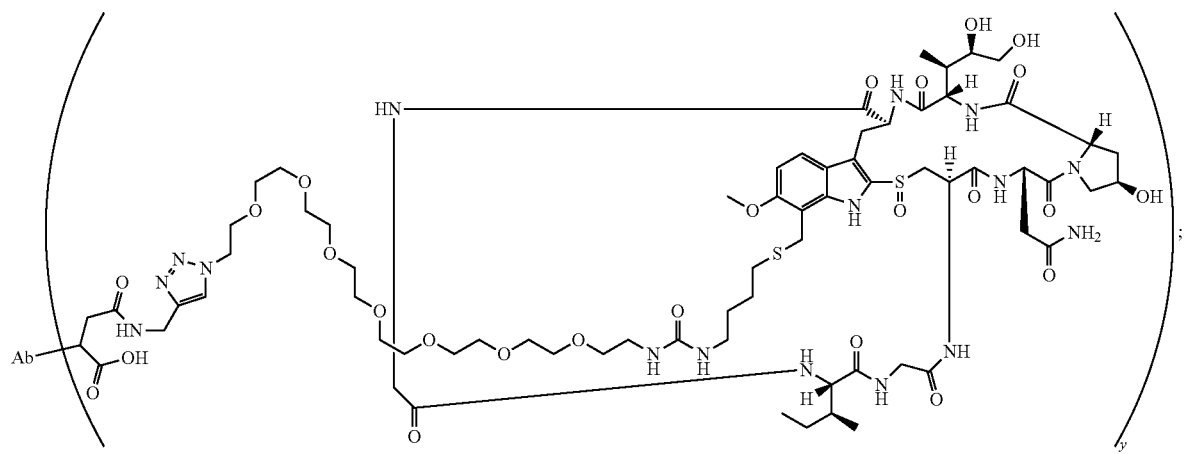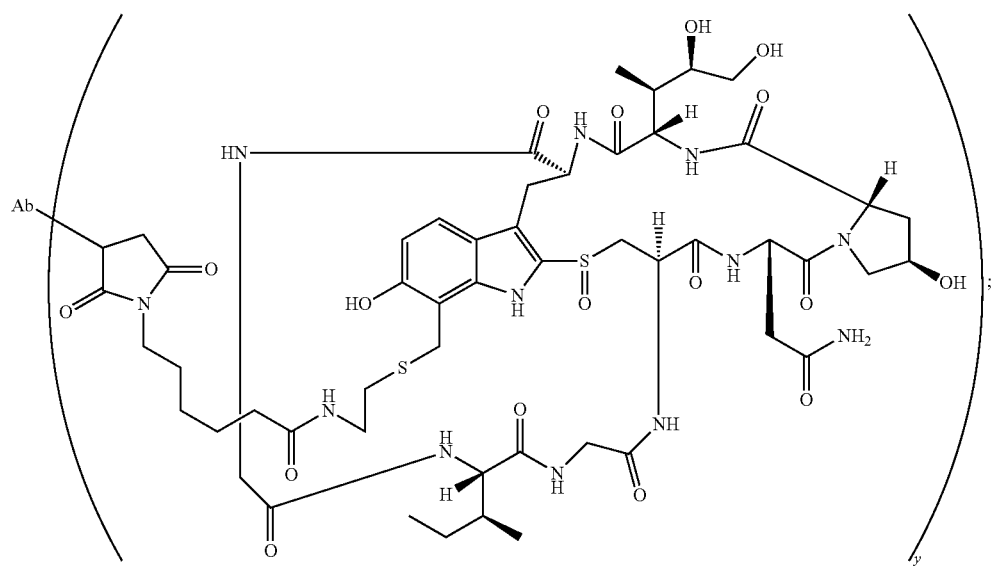

-continued
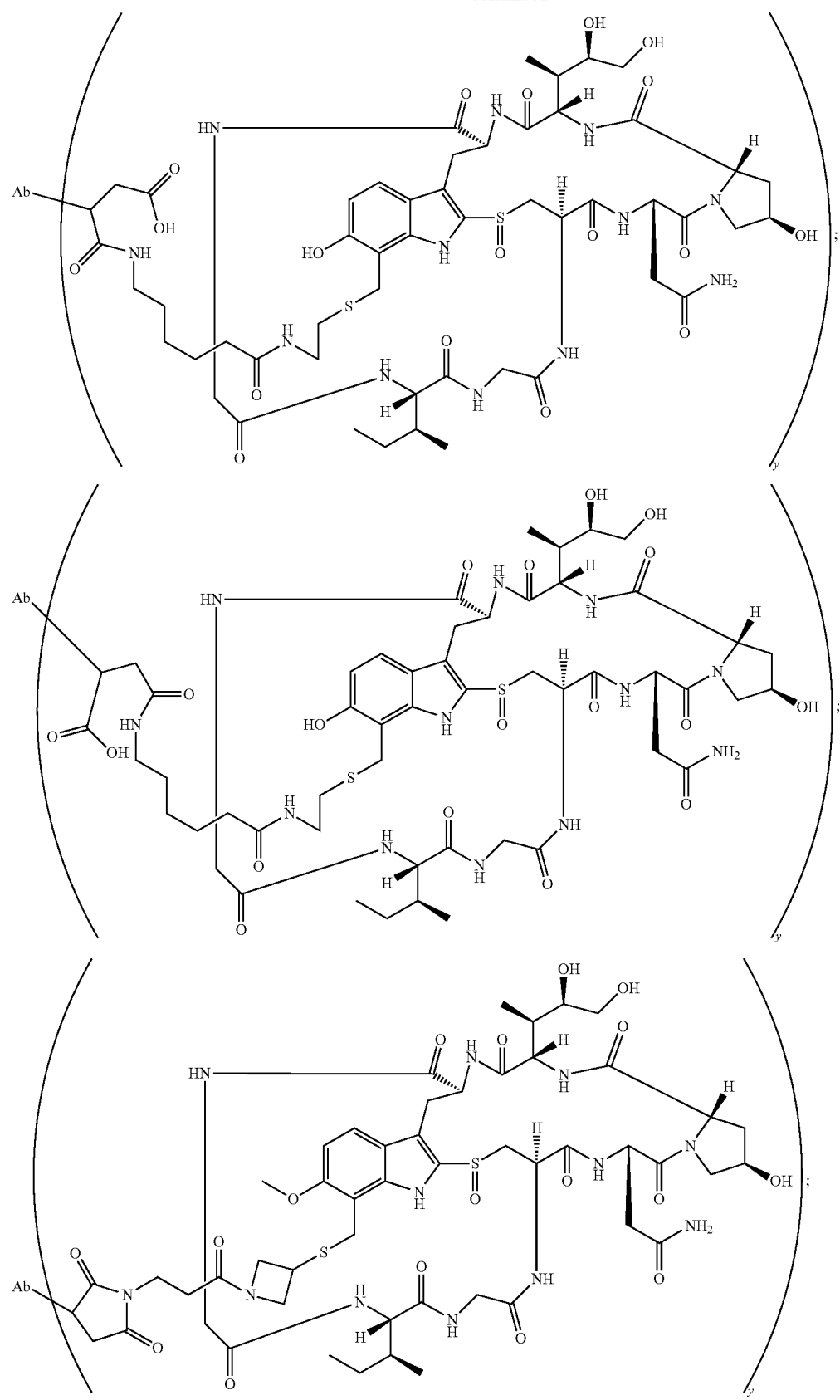

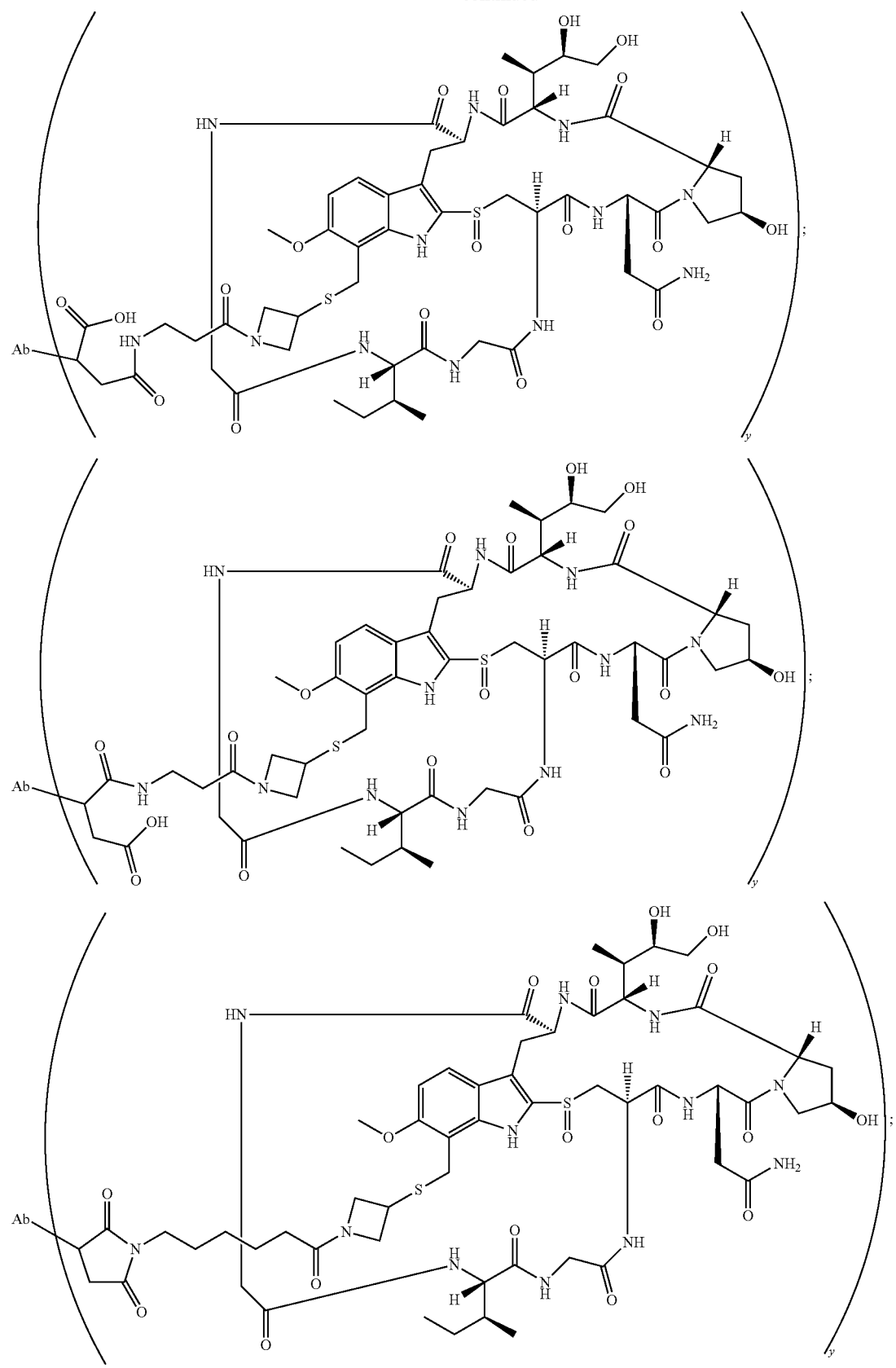

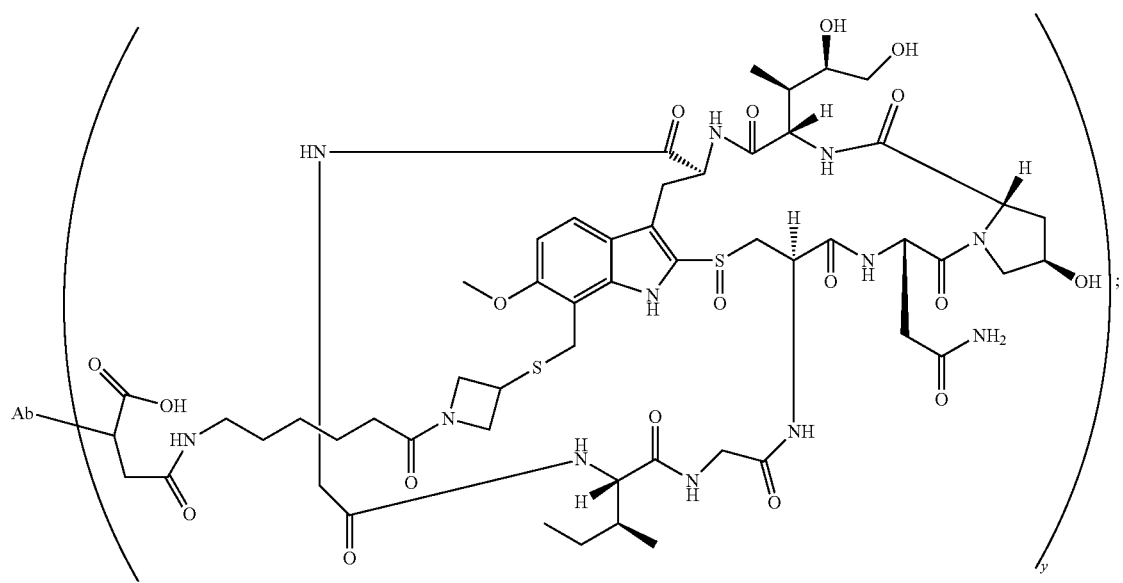
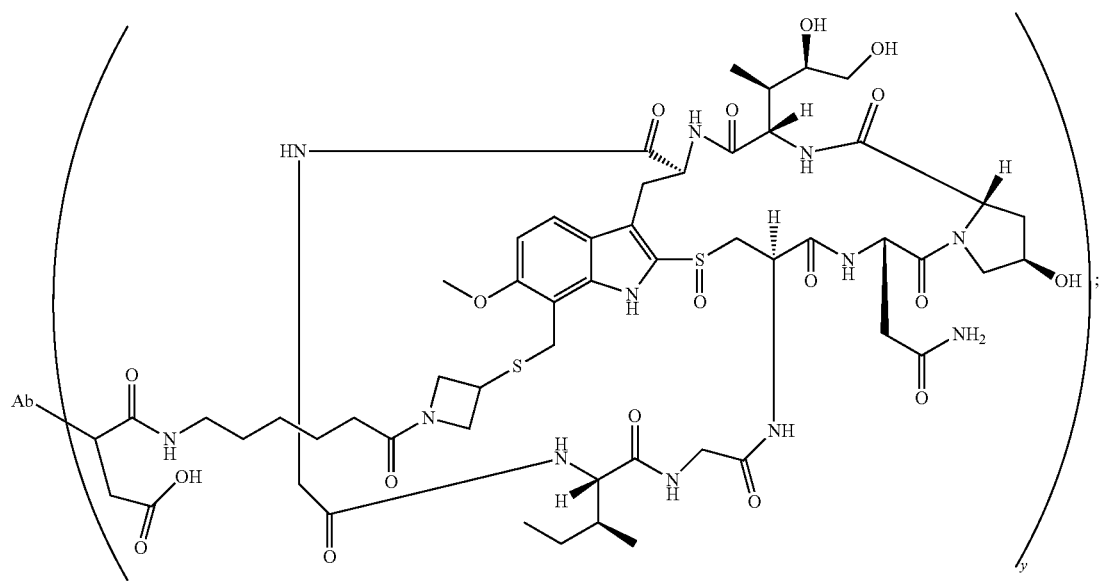

221
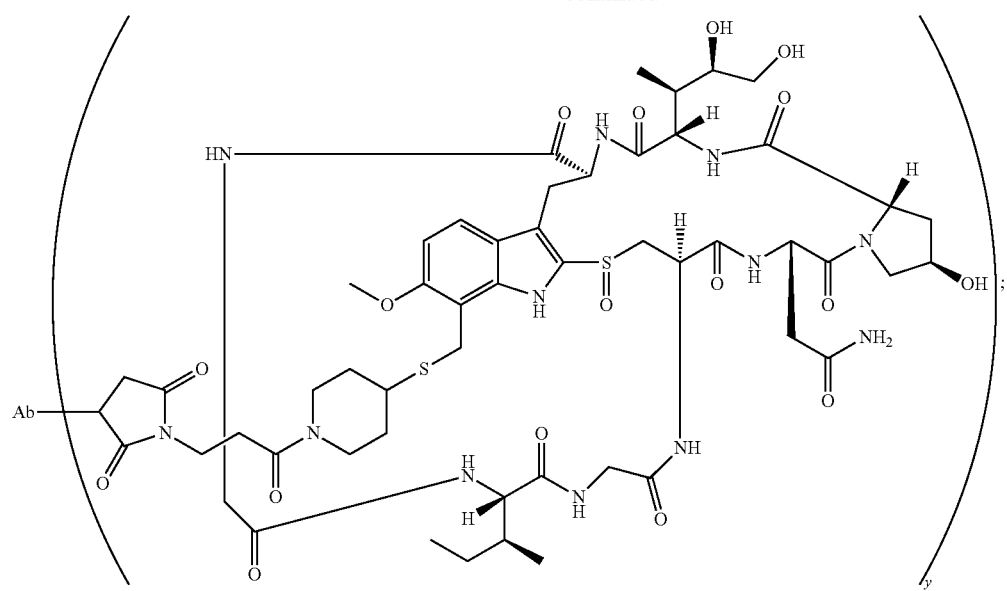
222
-continued
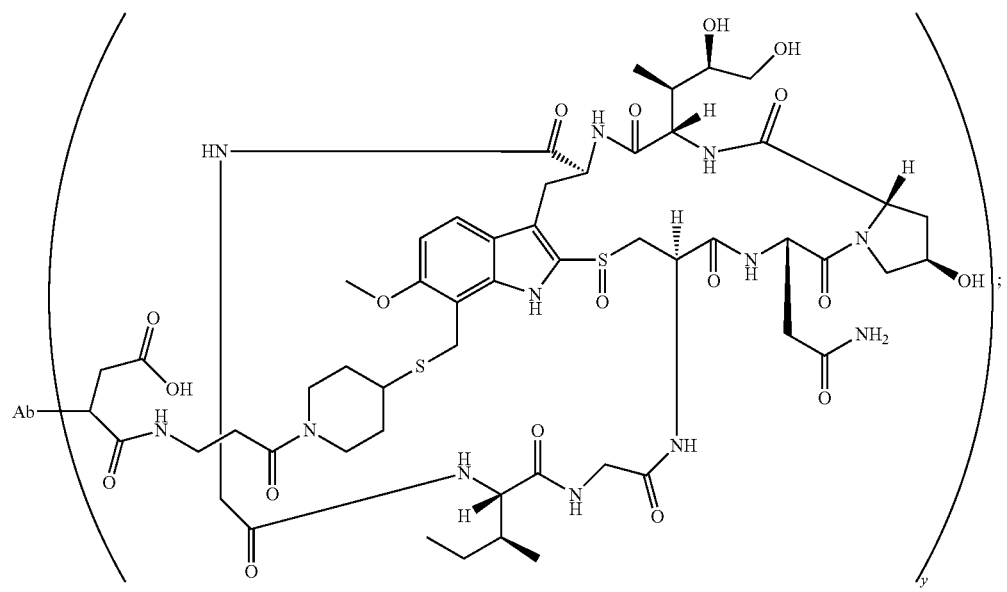

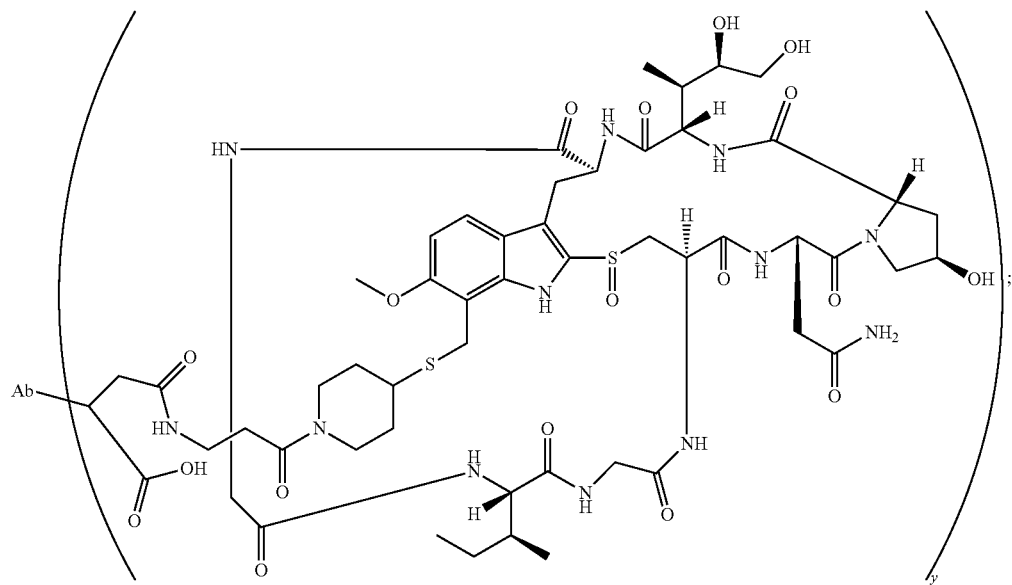
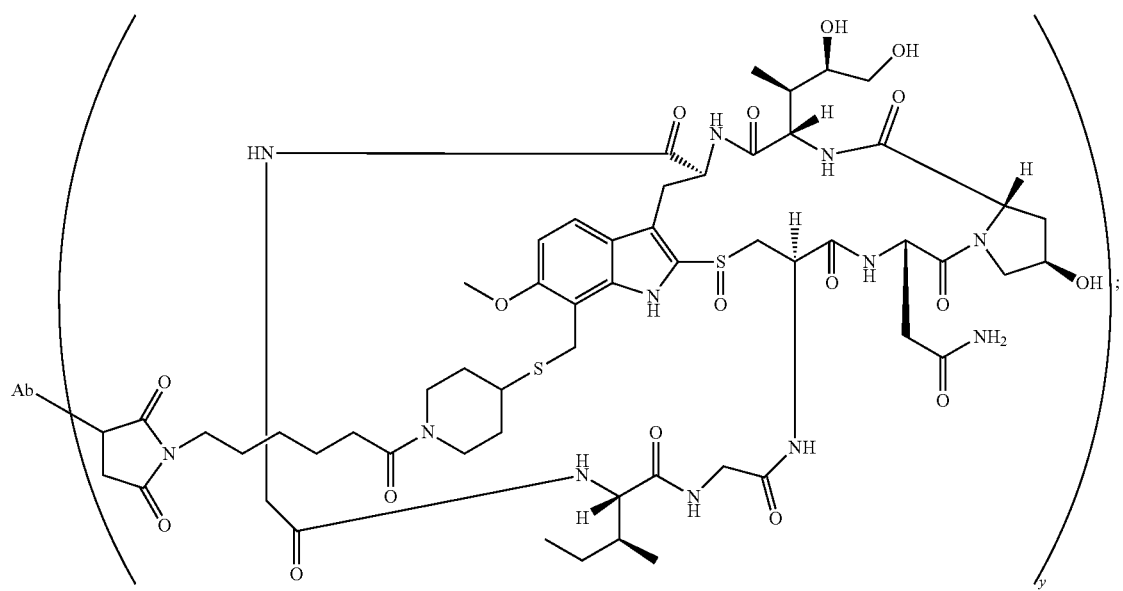

225 226
-continued
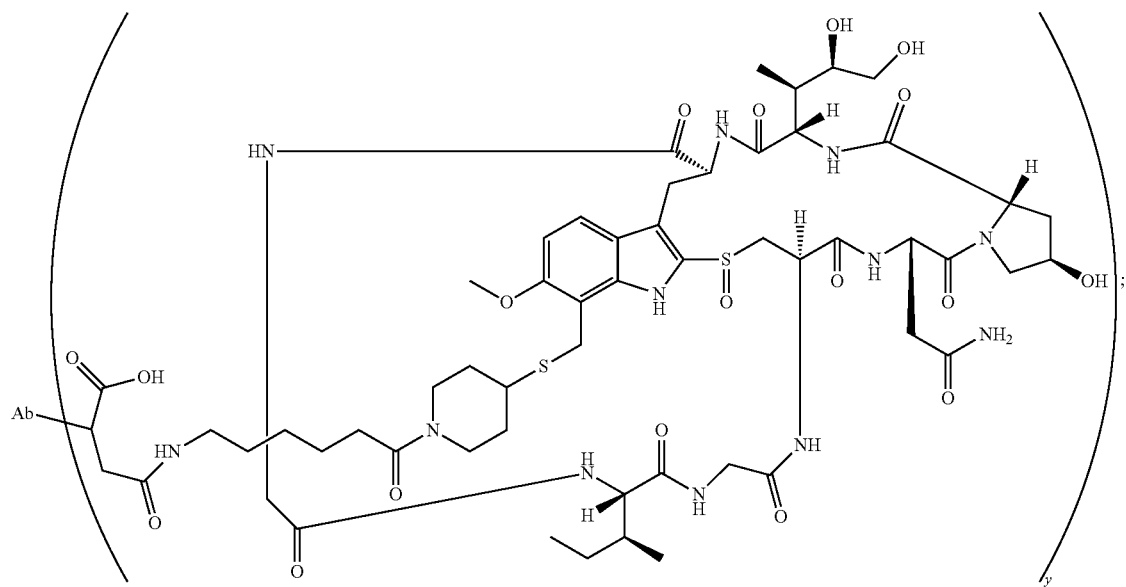
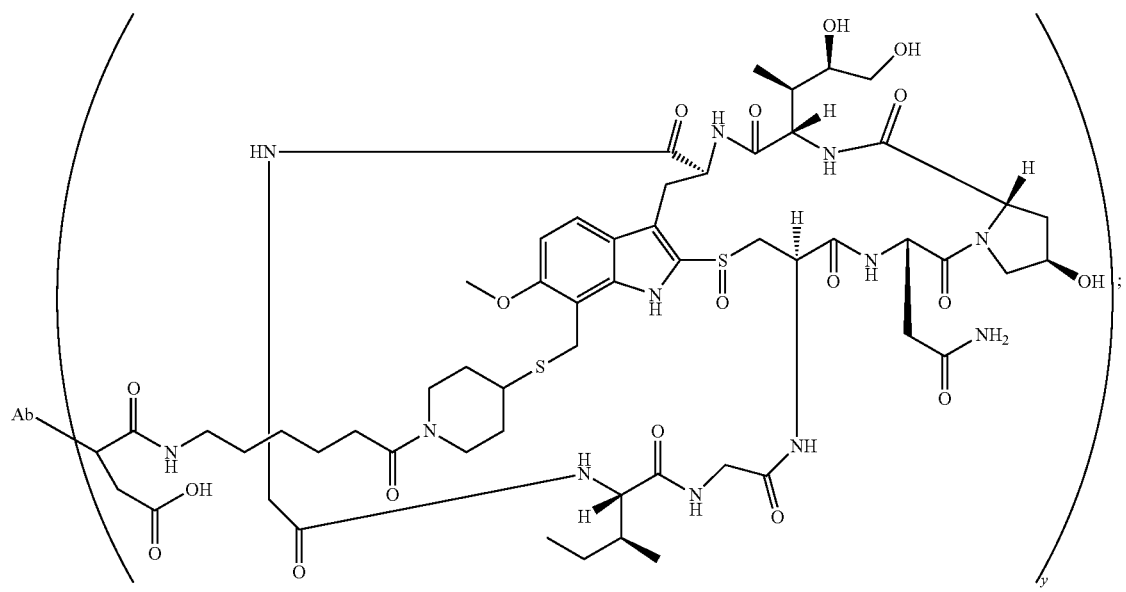

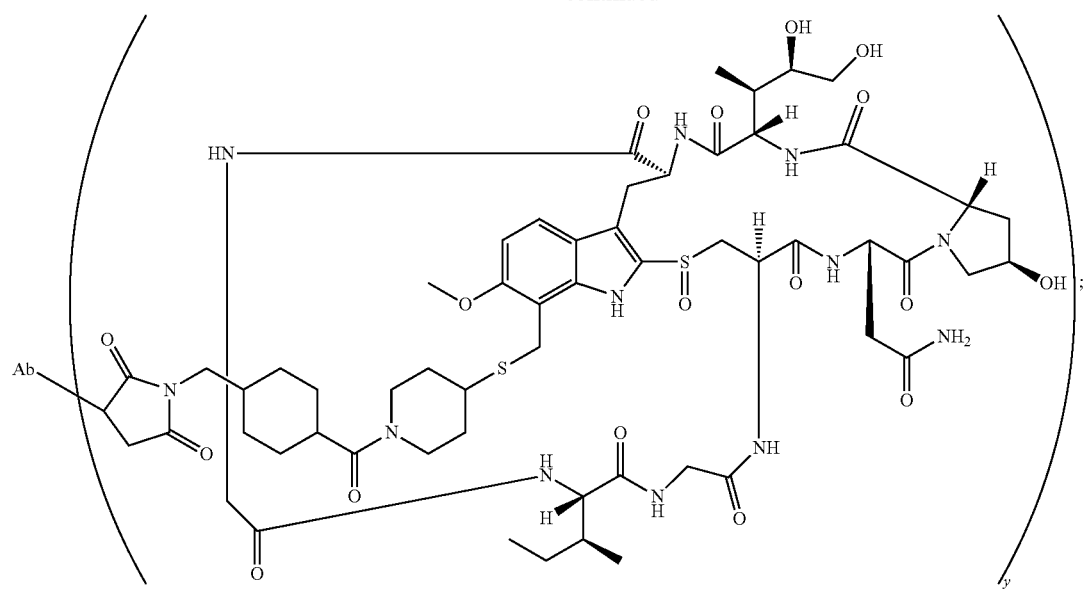
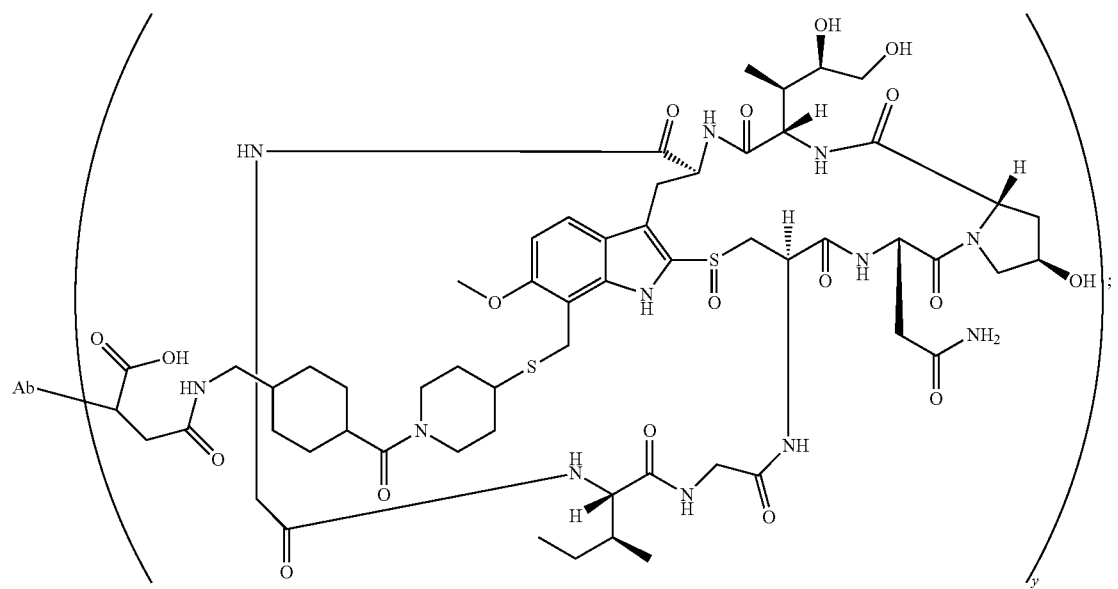

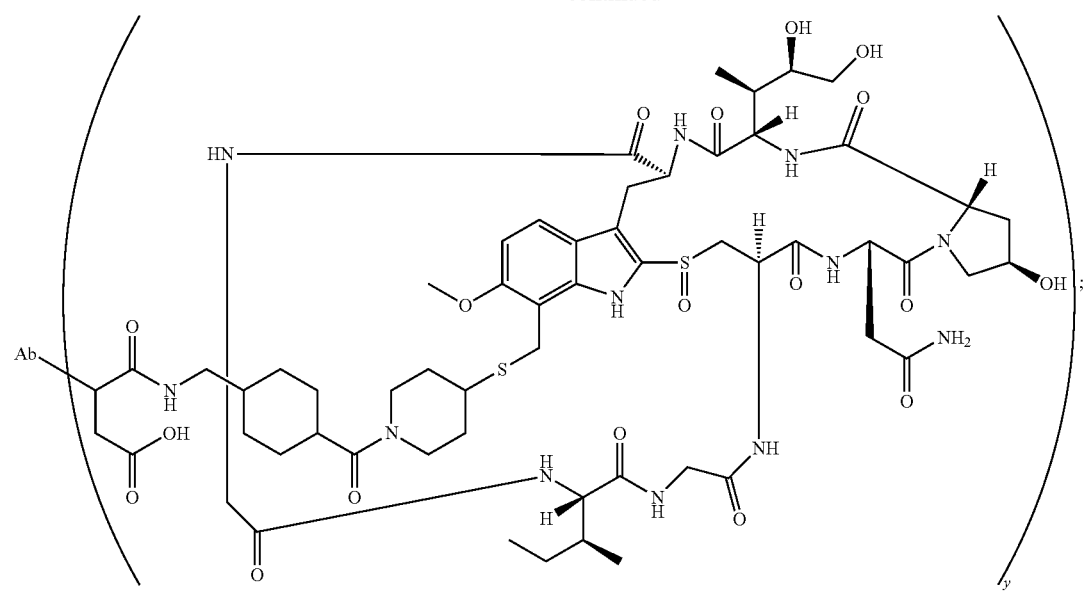
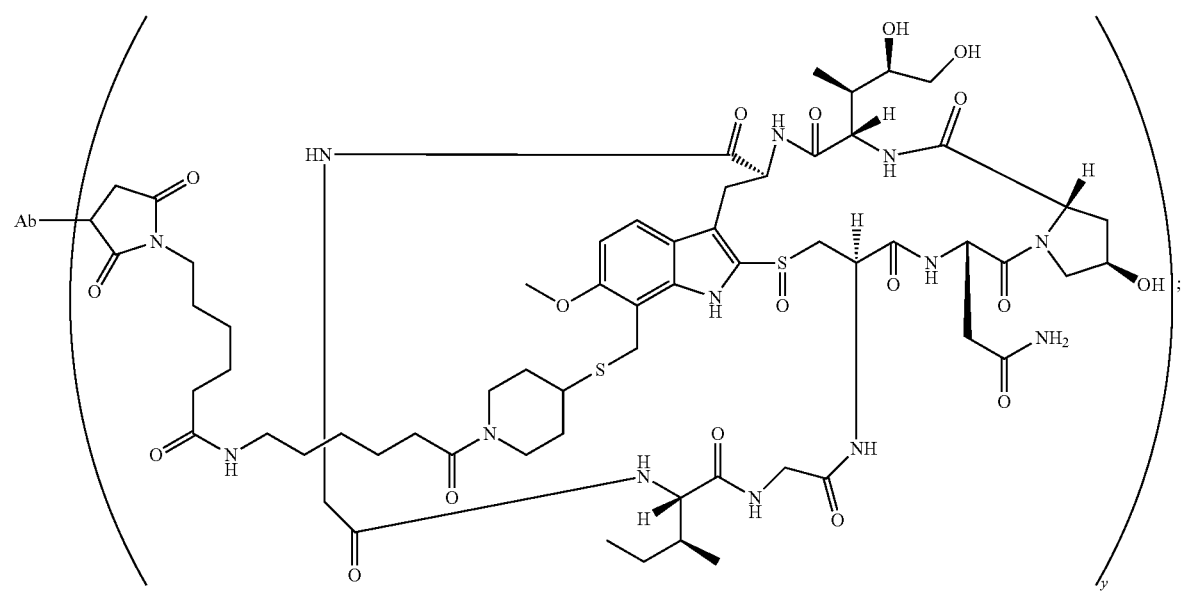

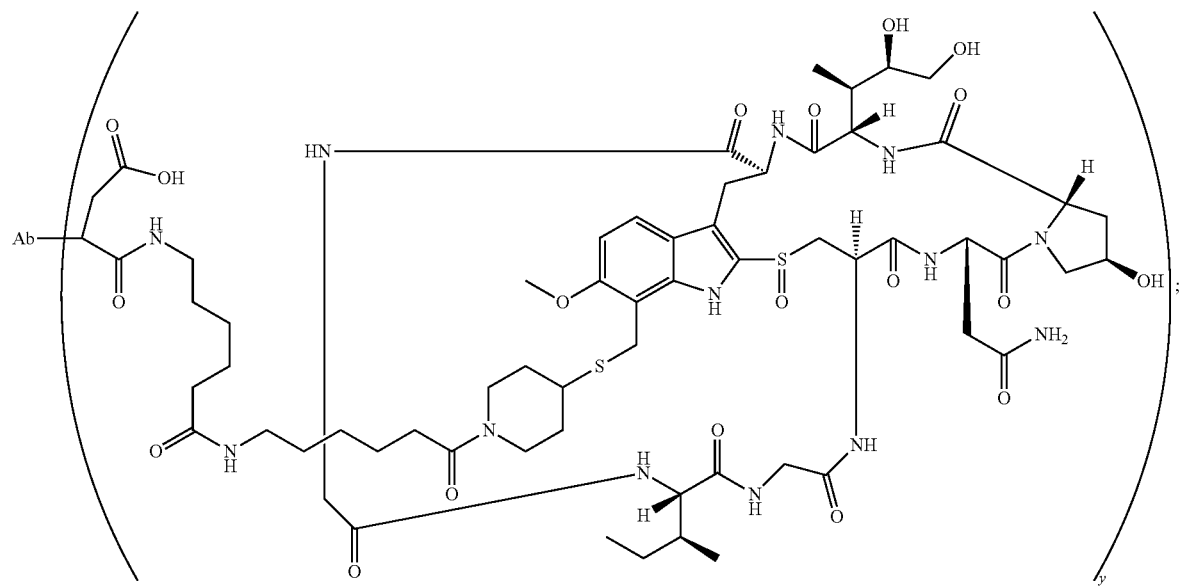
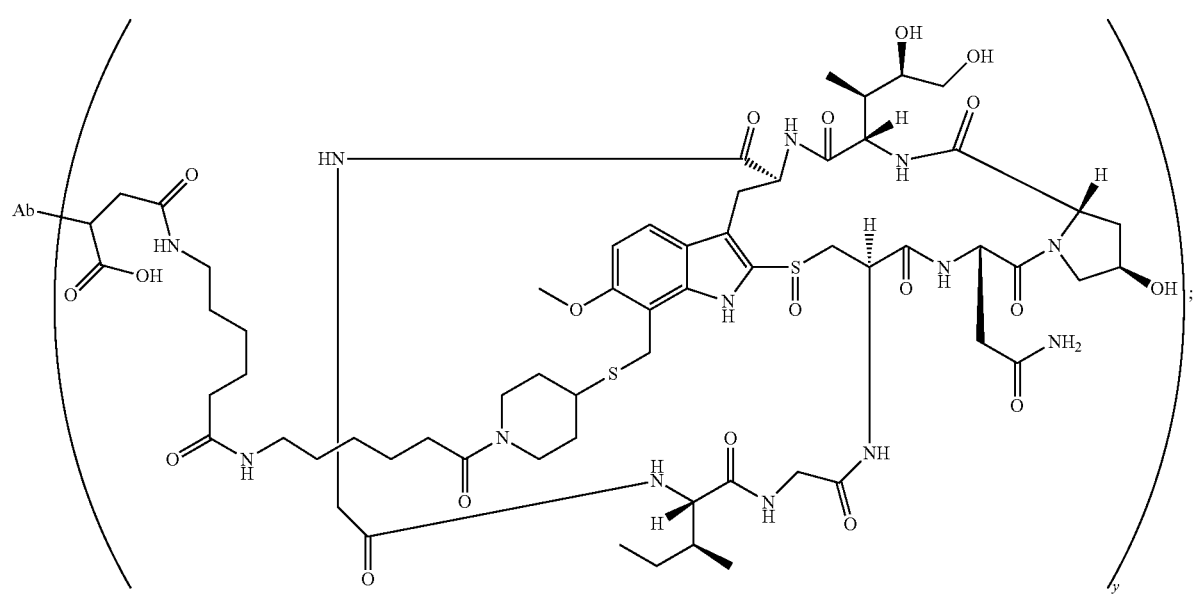

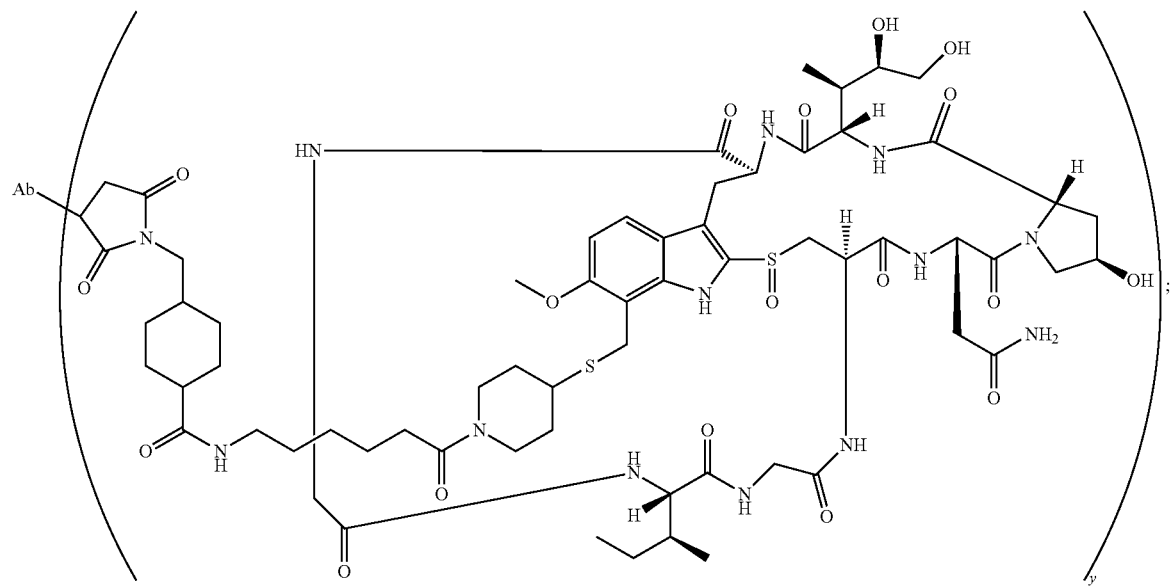
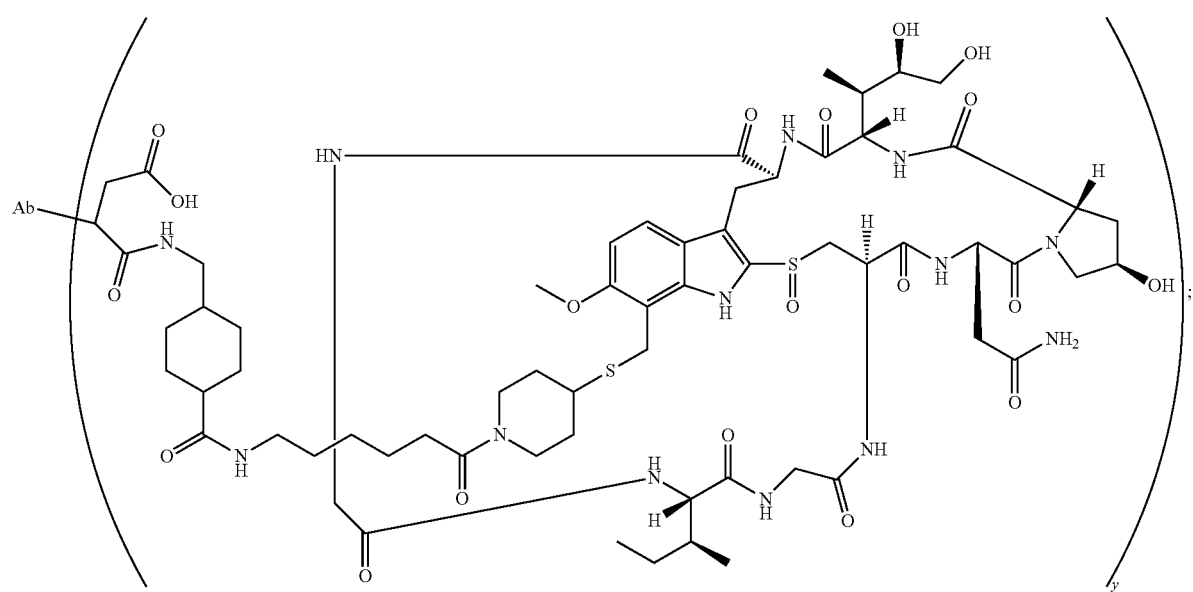

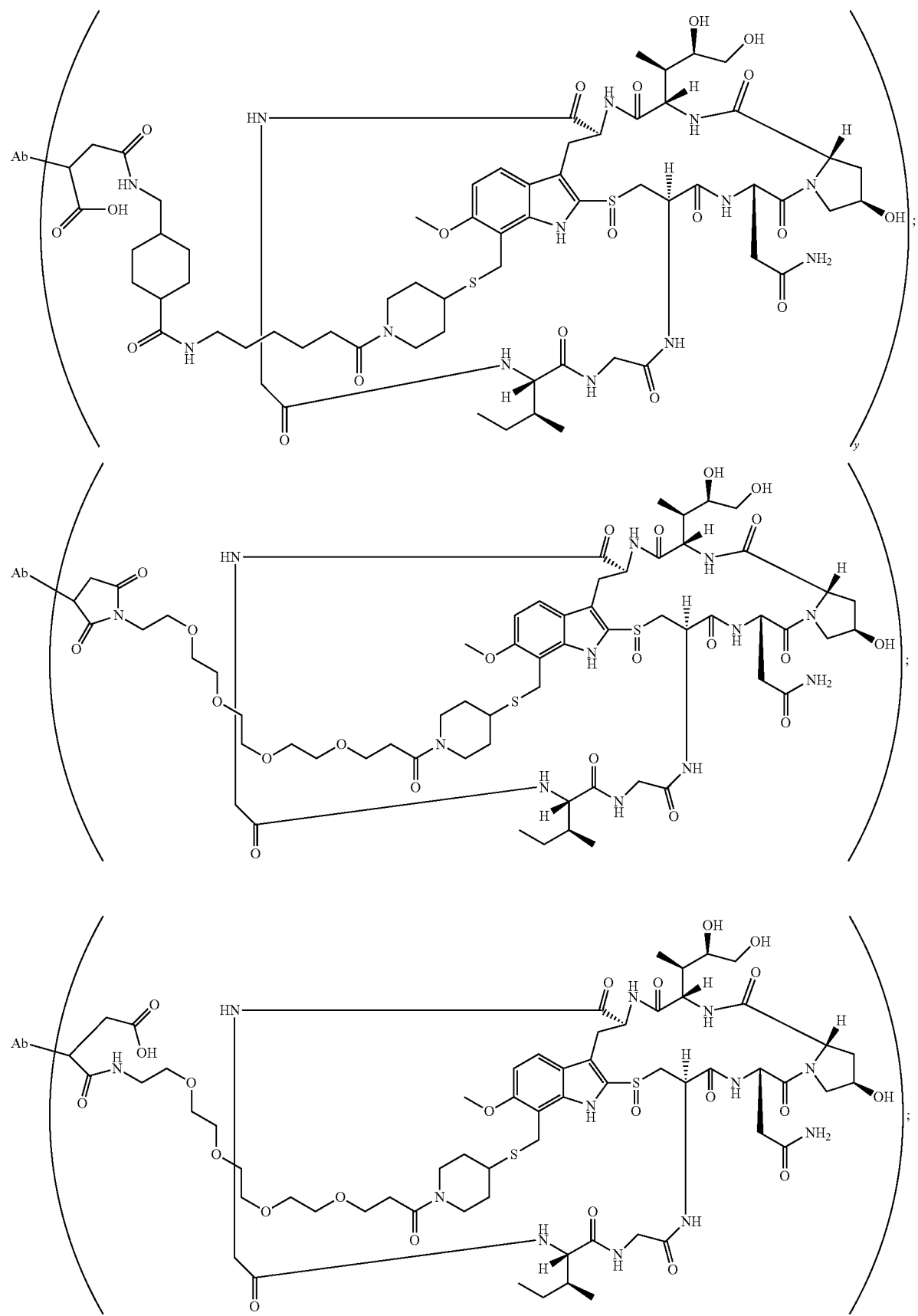

-continued
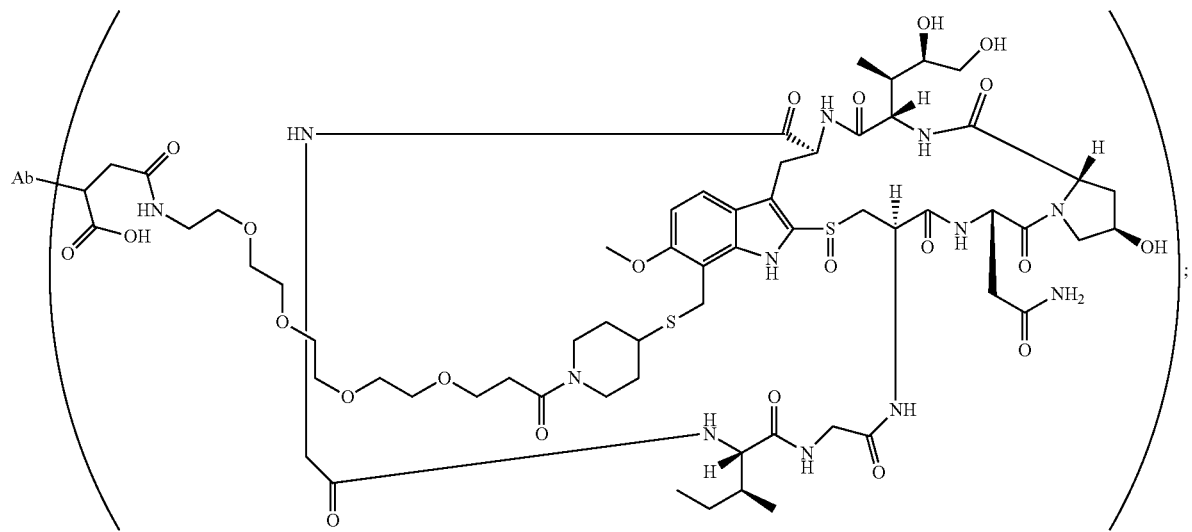
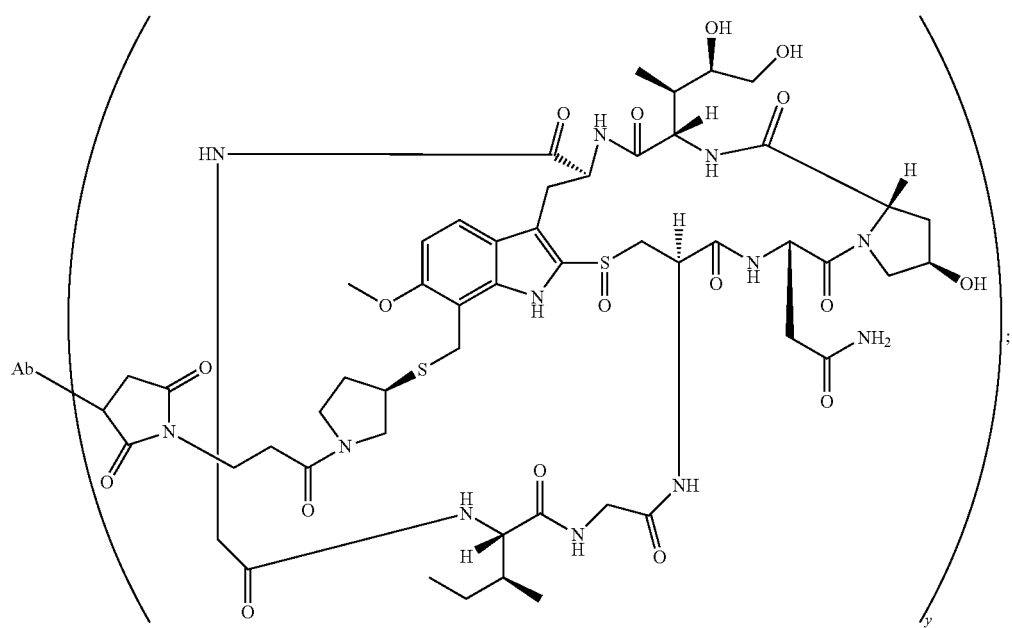

-continued
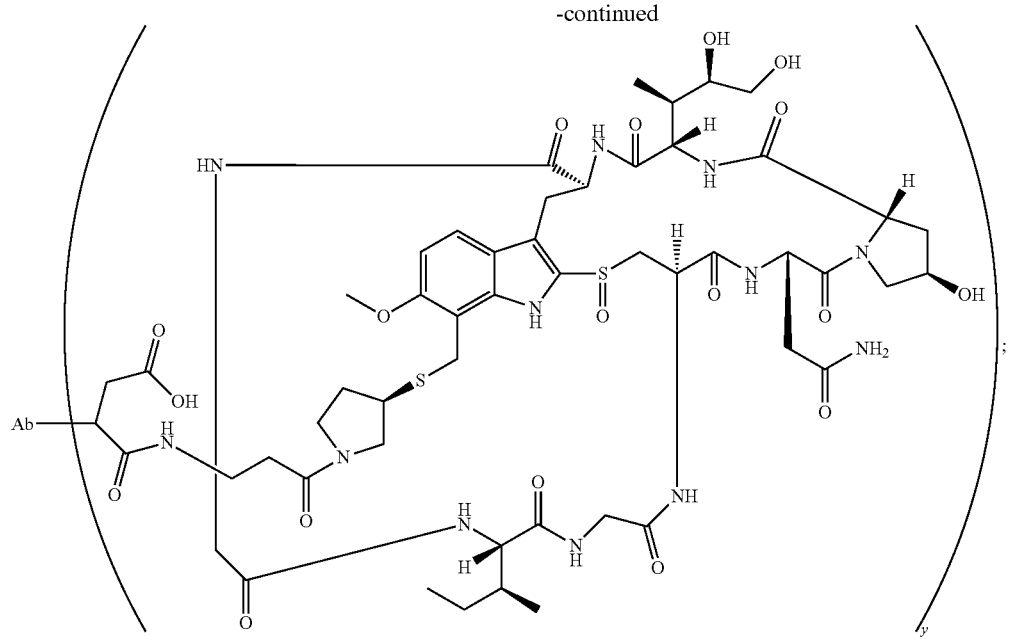
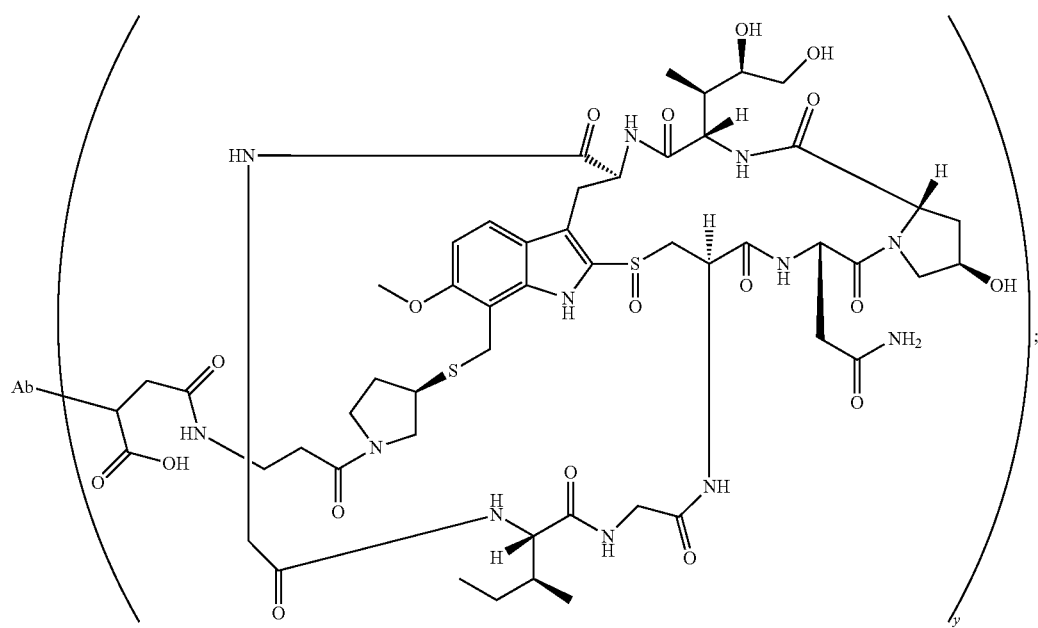

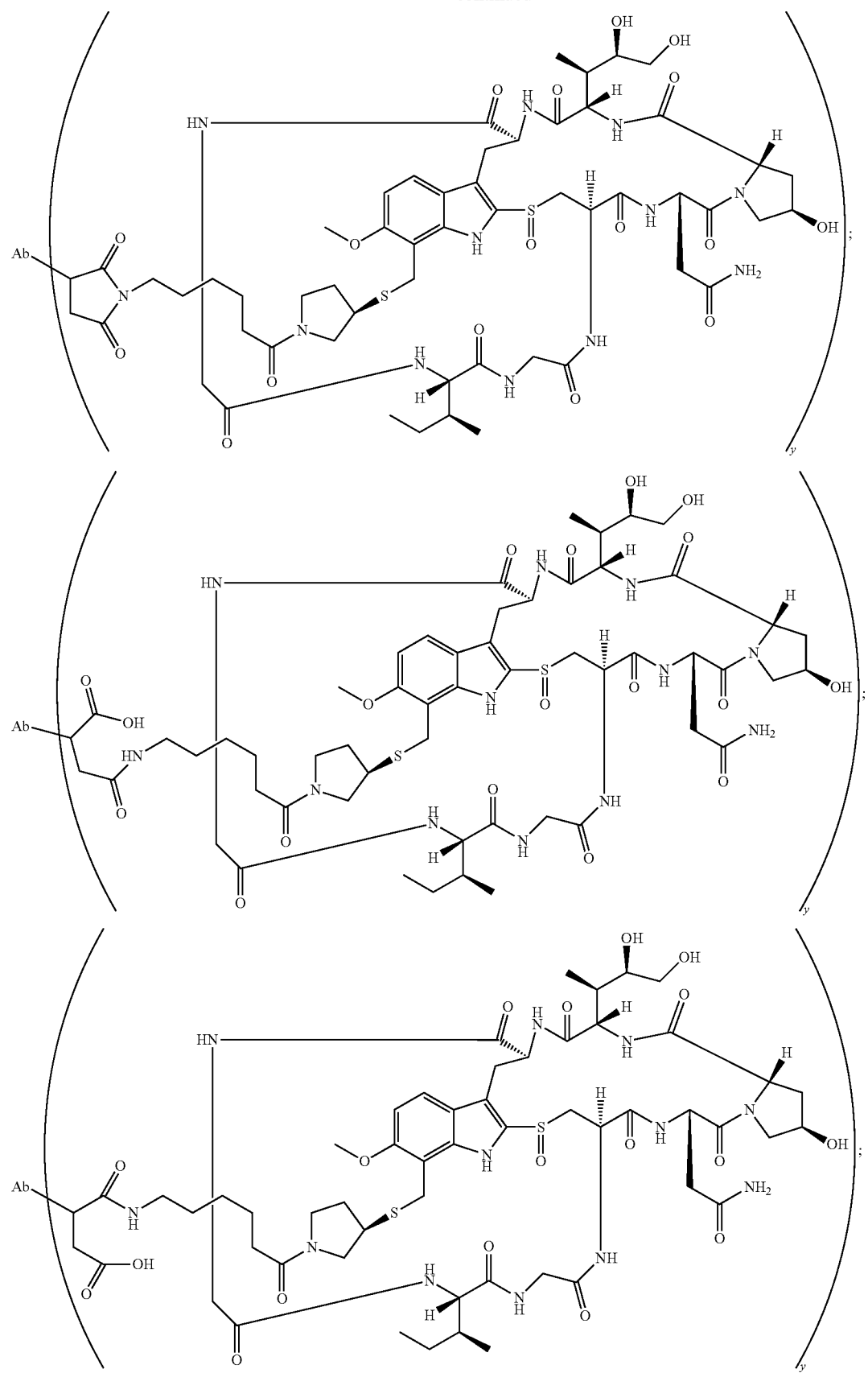

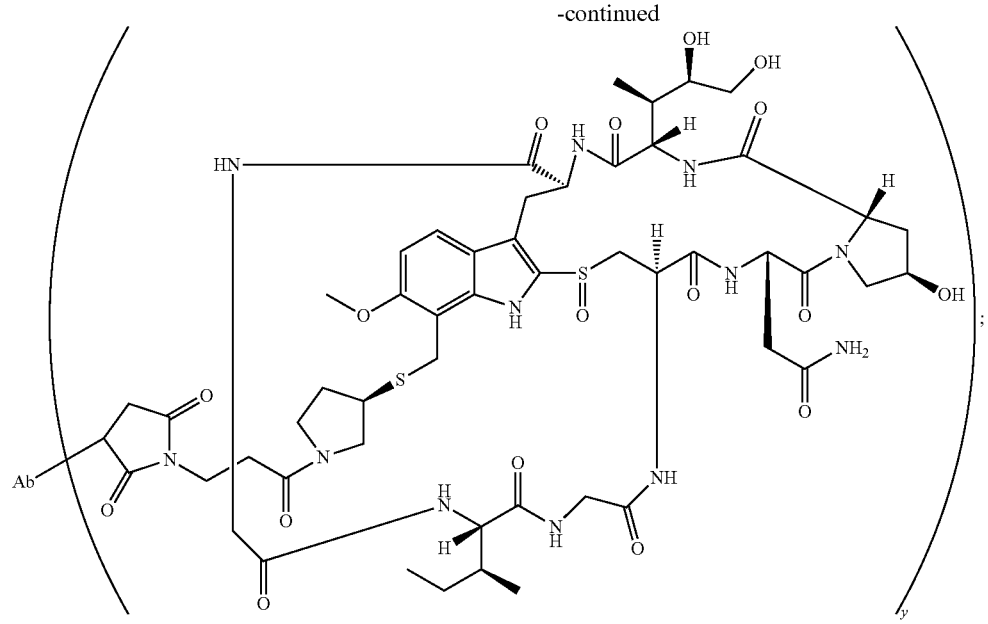
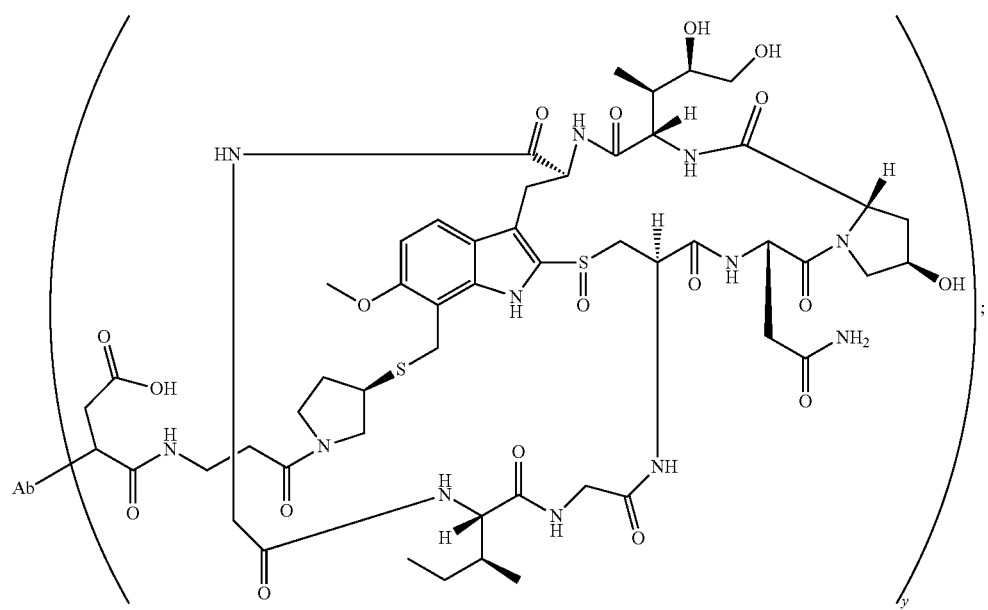

-continued
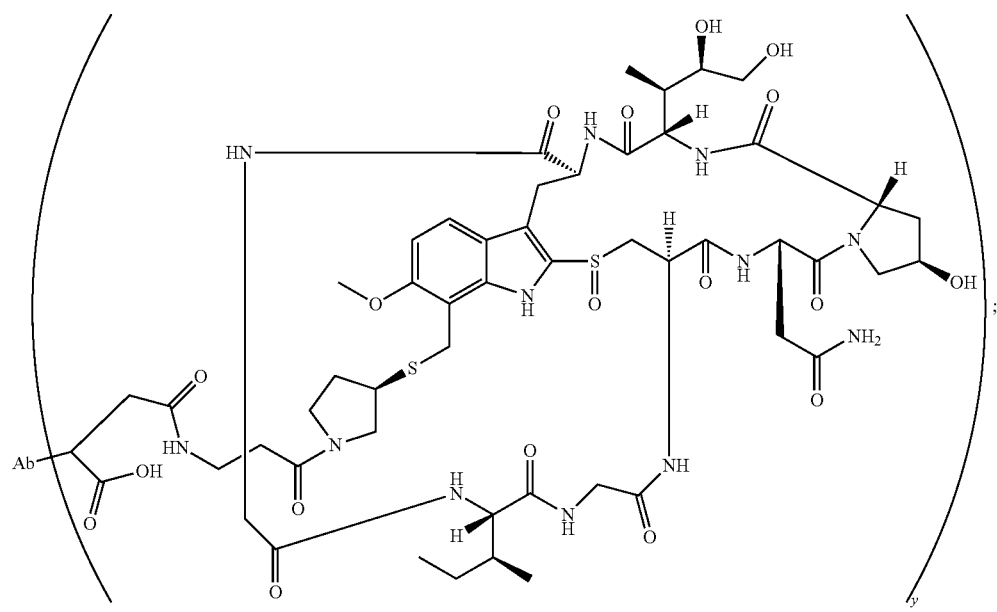
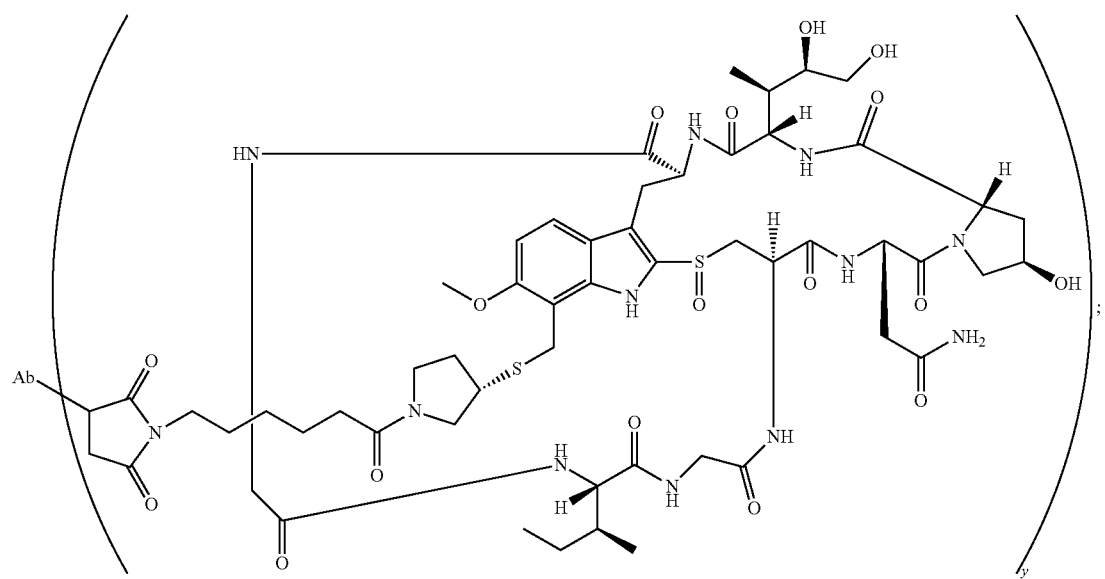

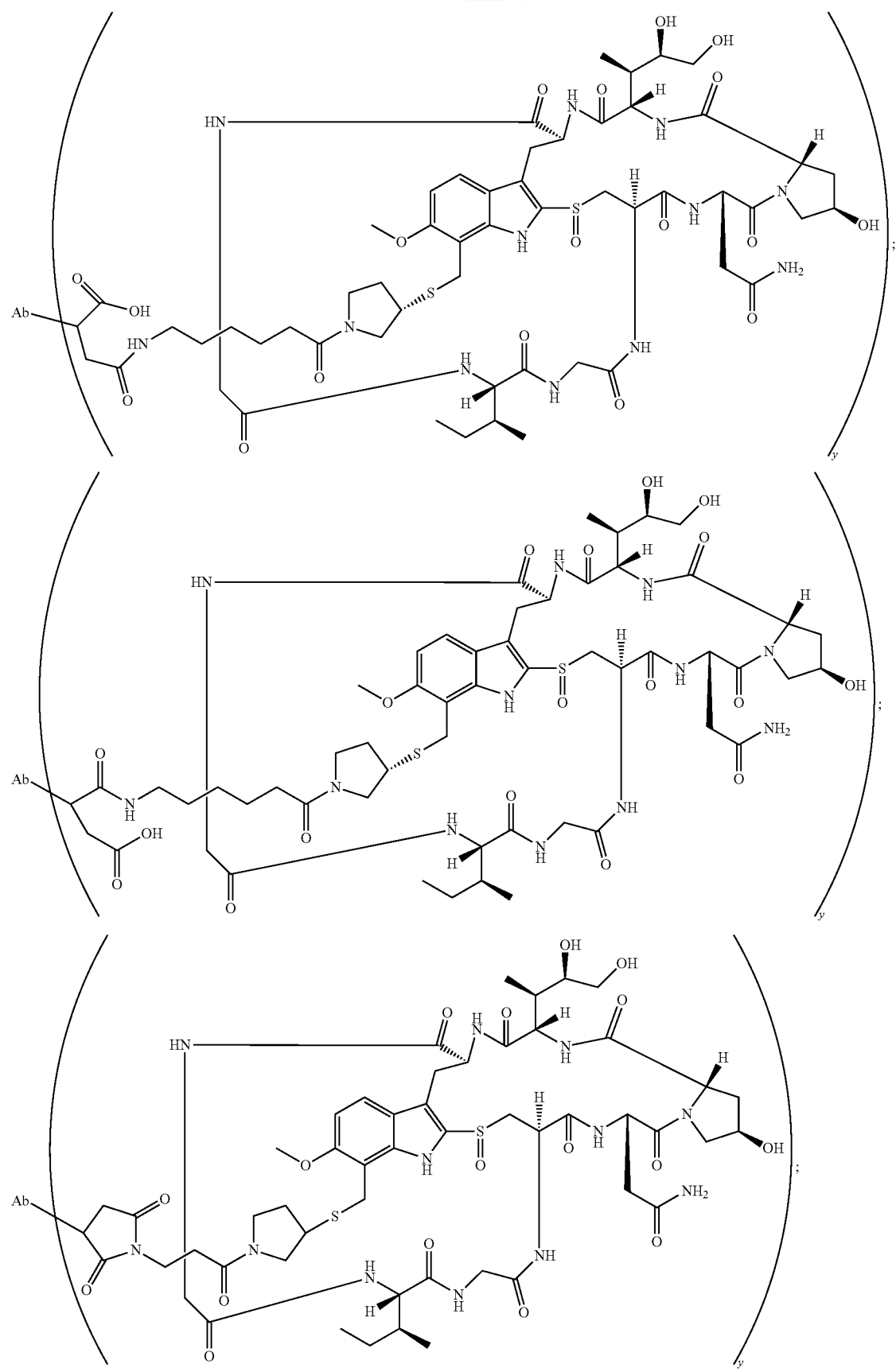

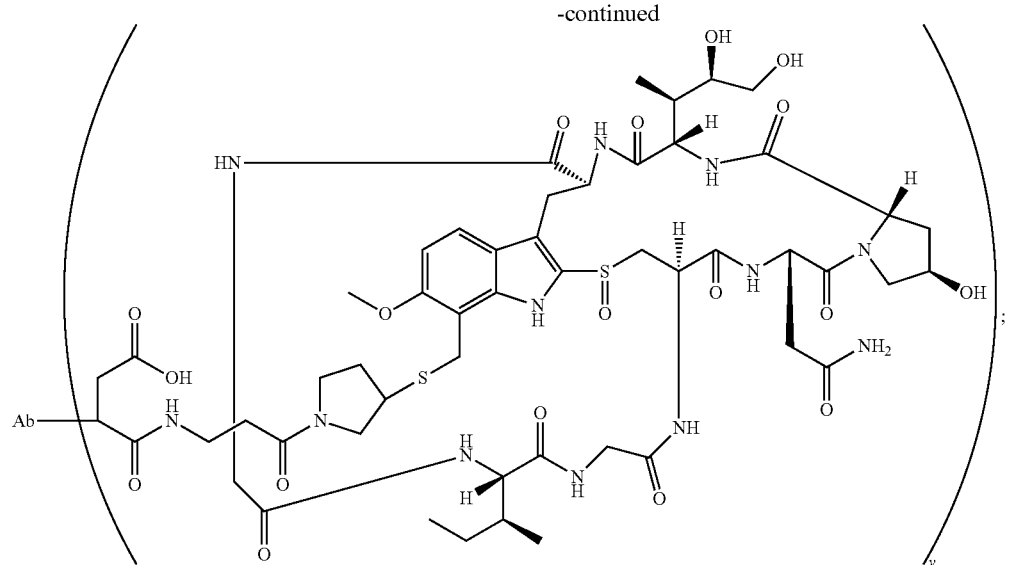
;
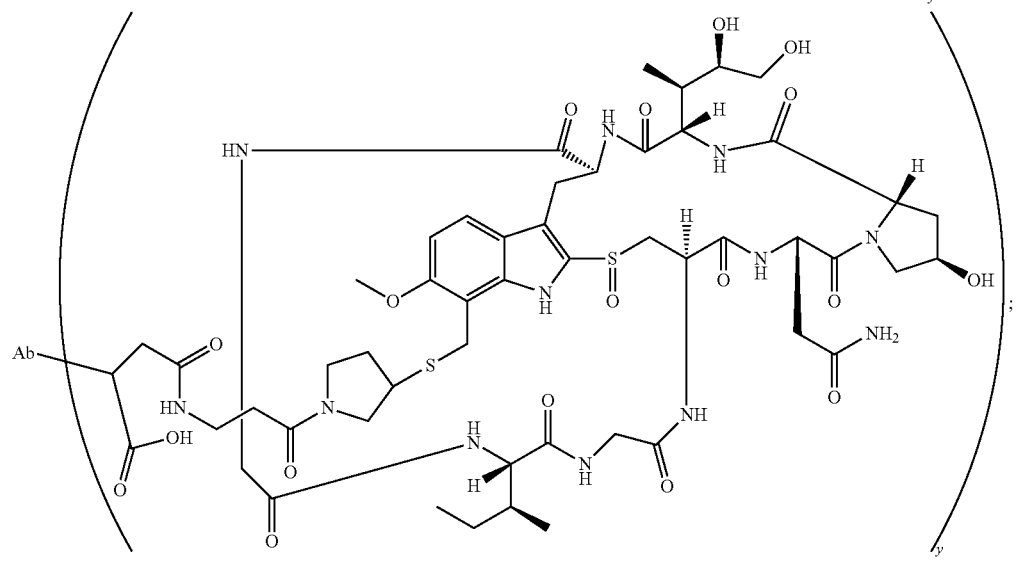
;
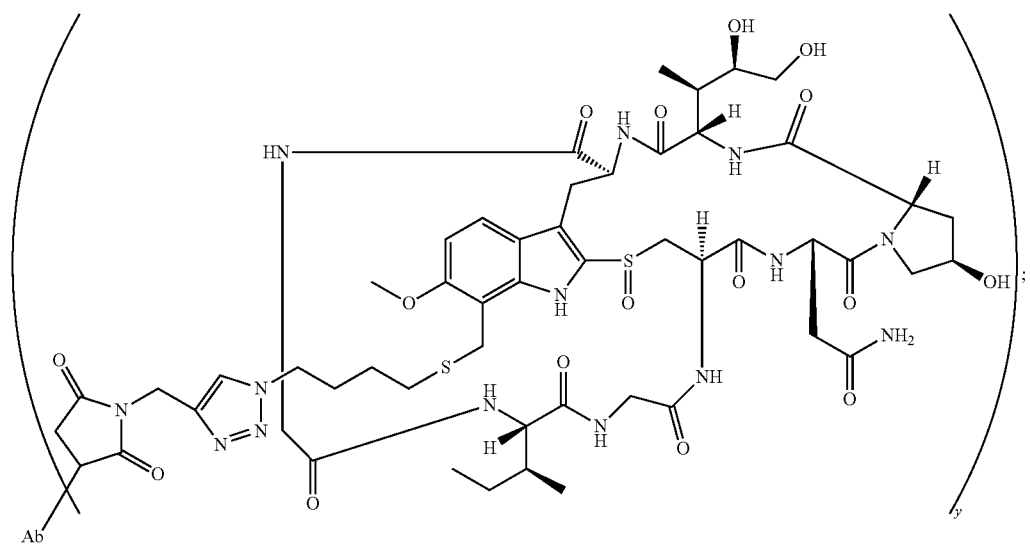
;

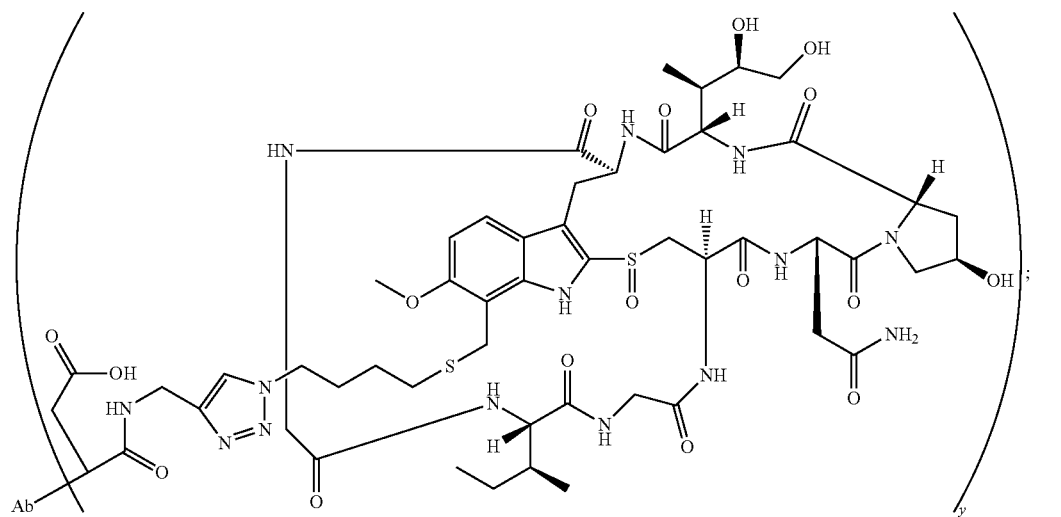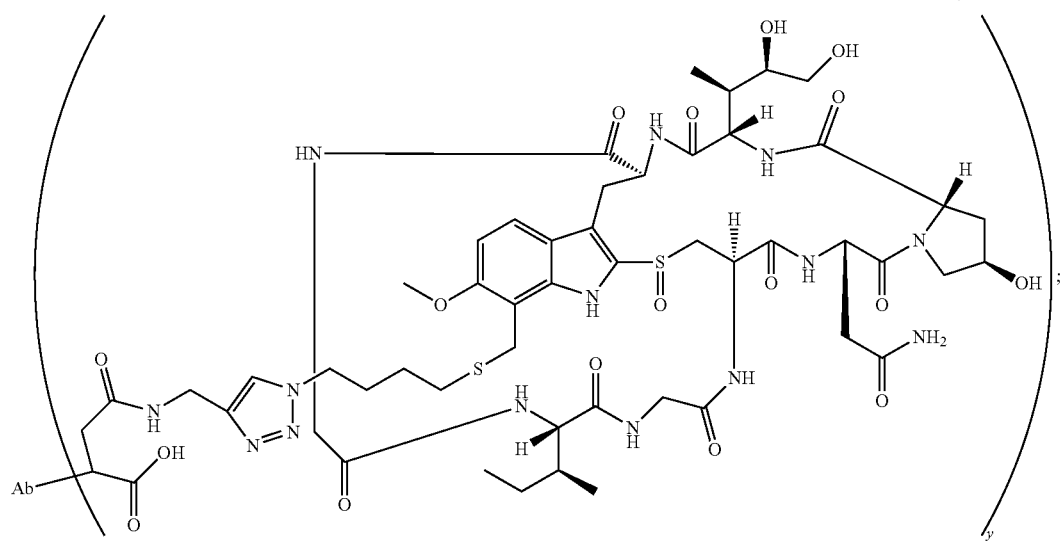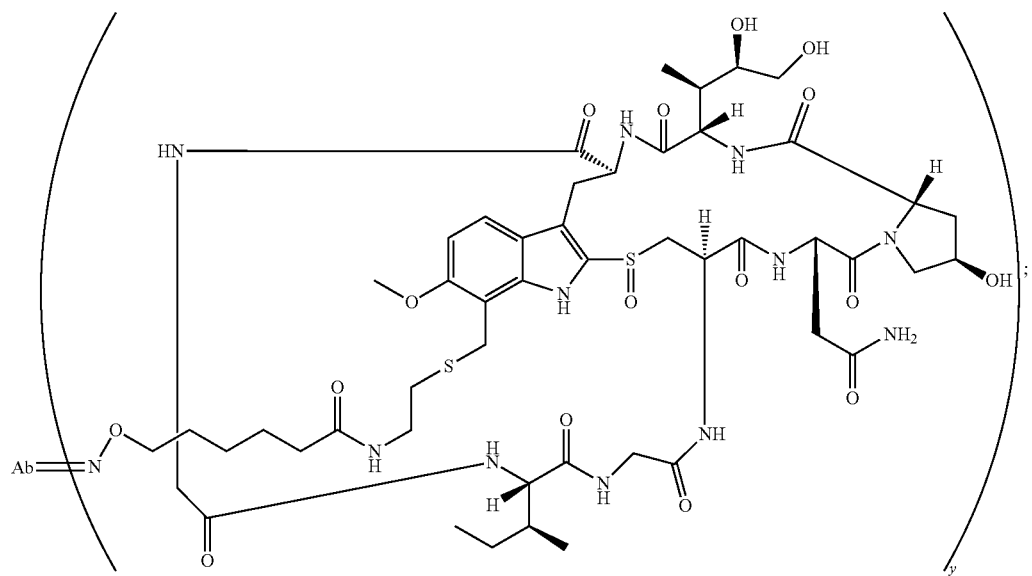

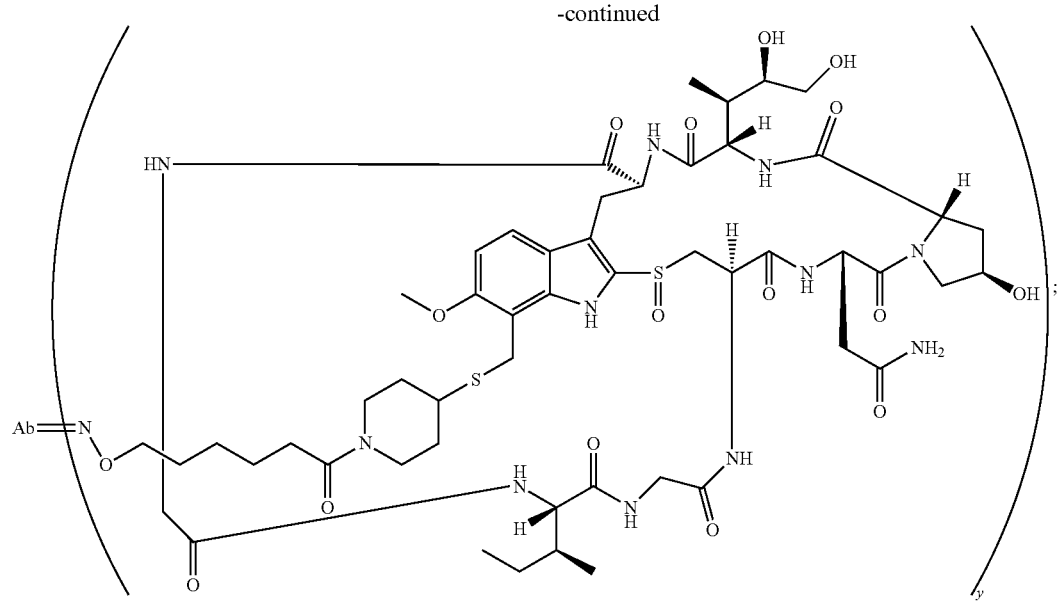
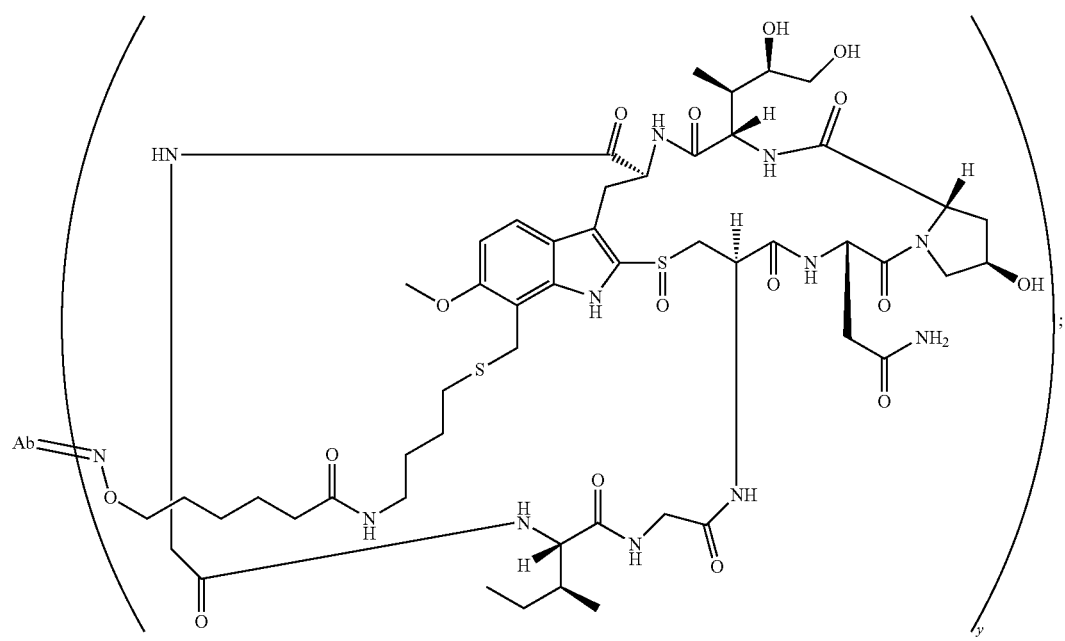

-continued
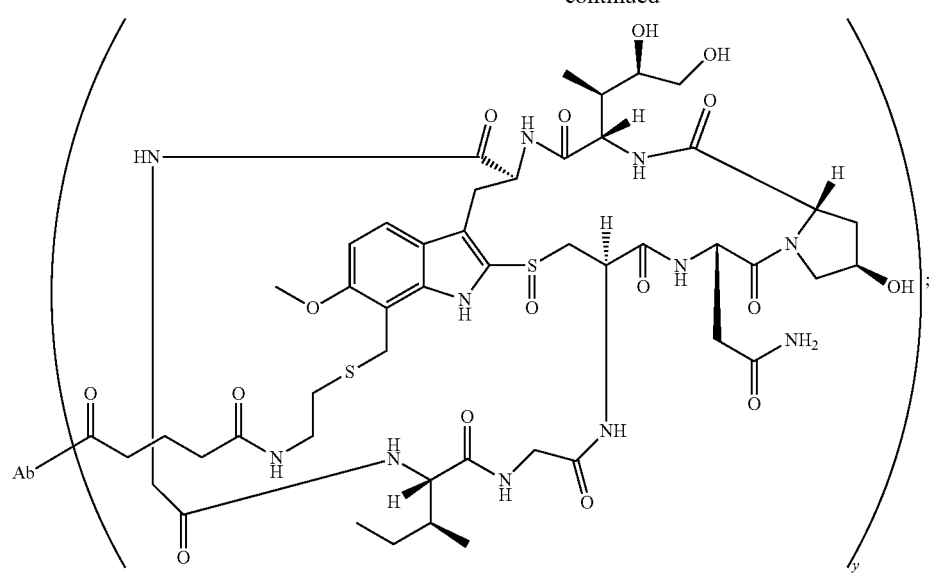
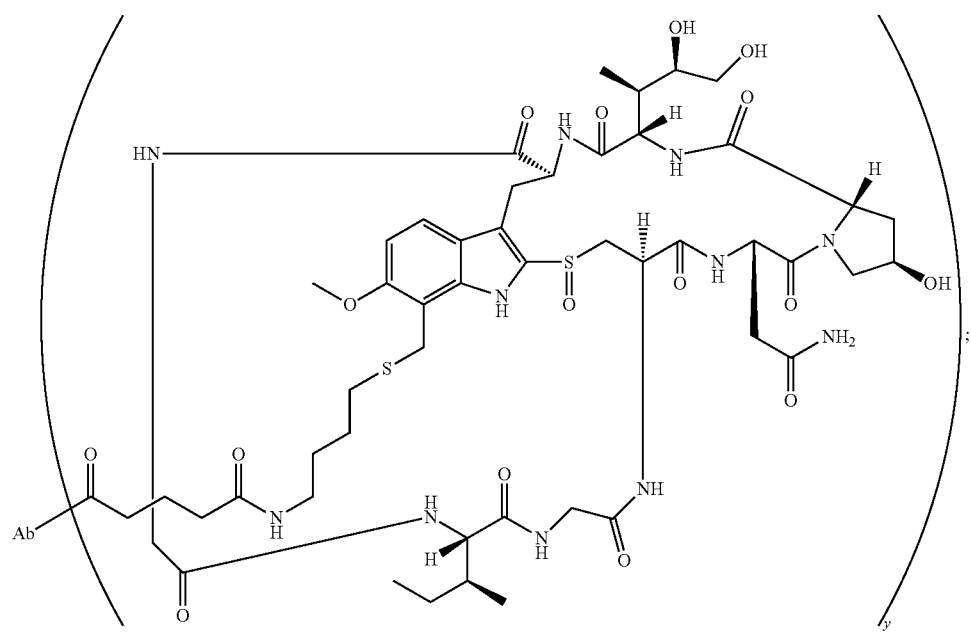

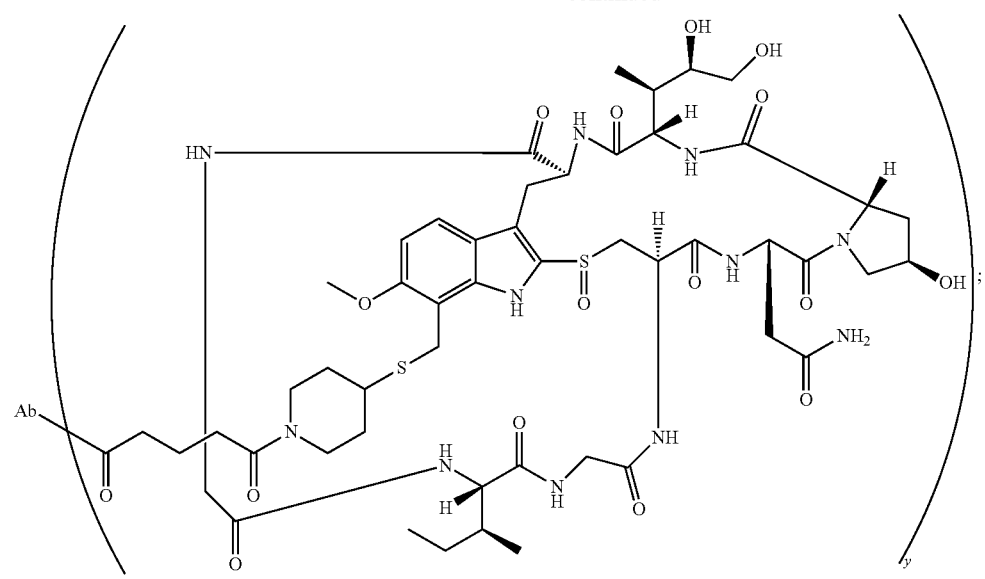
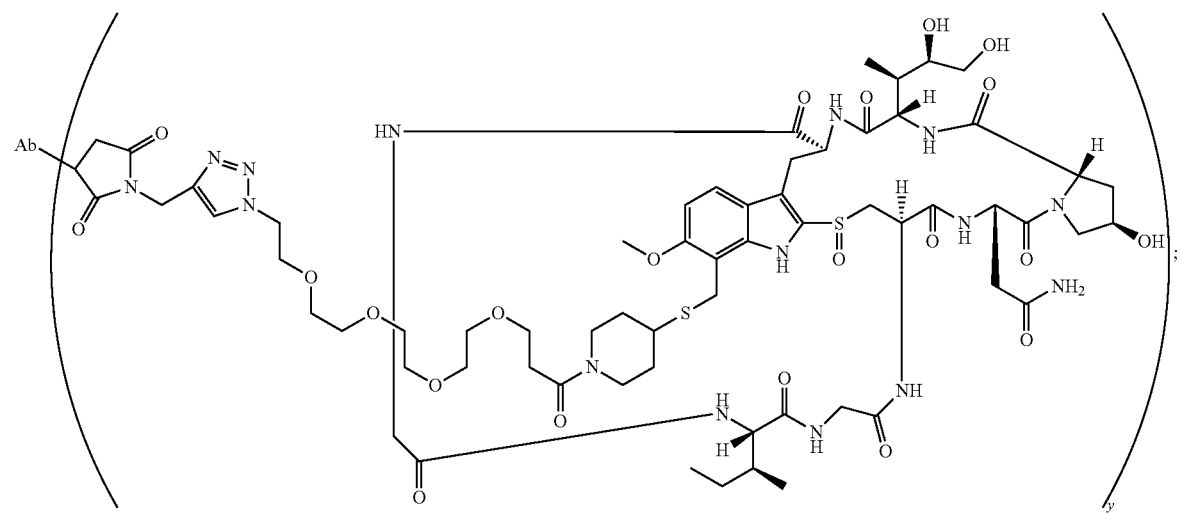
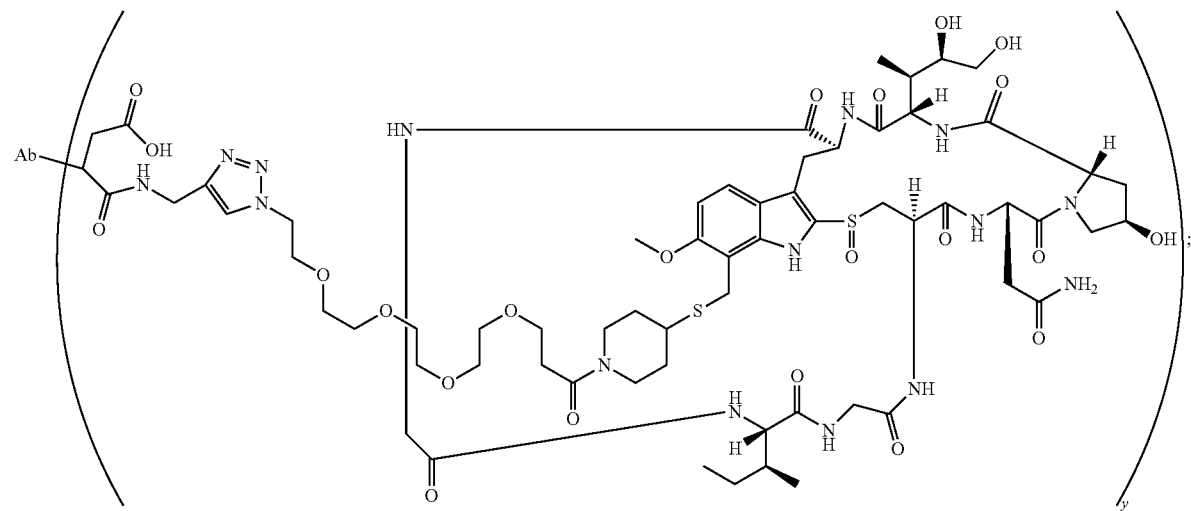

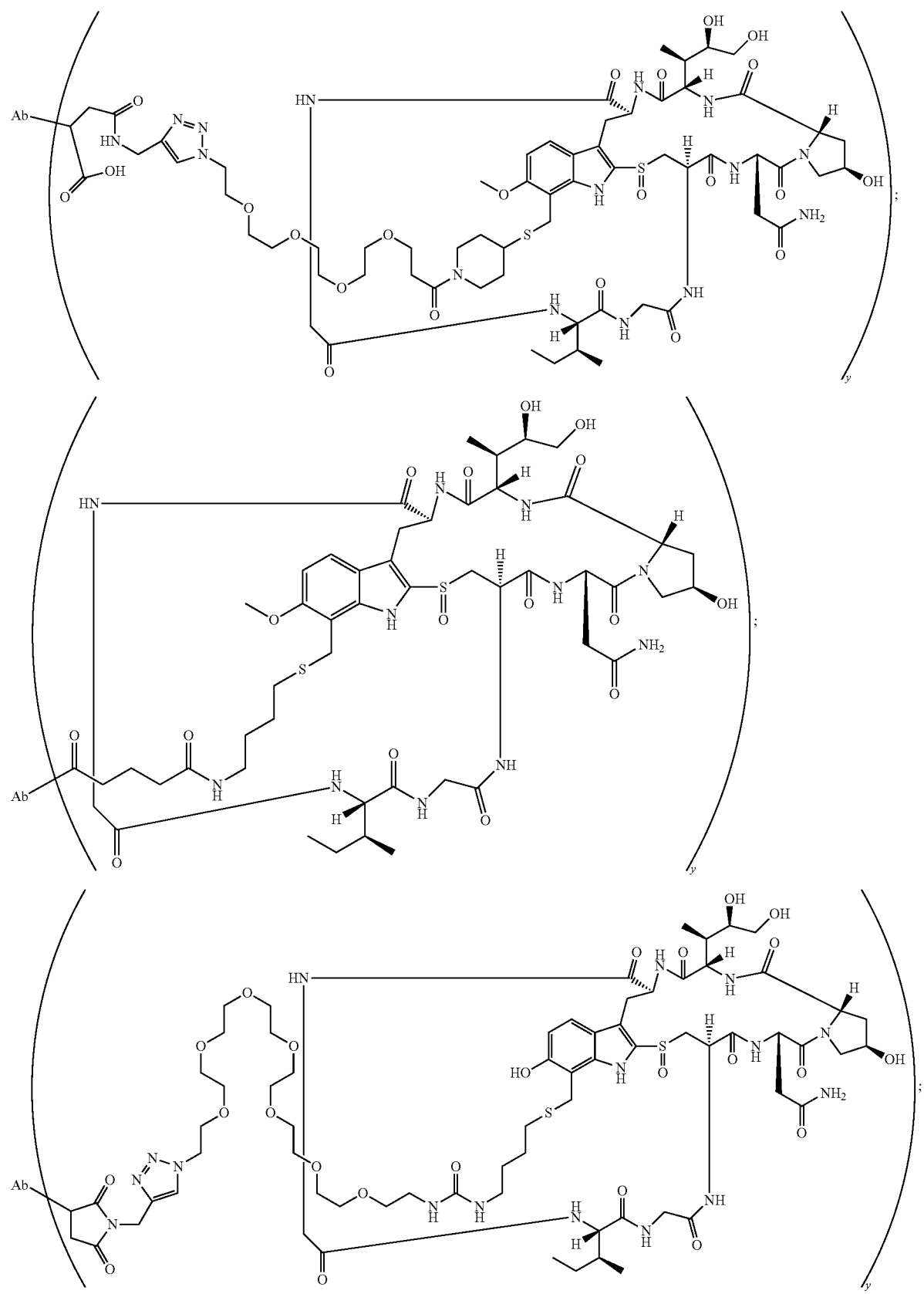

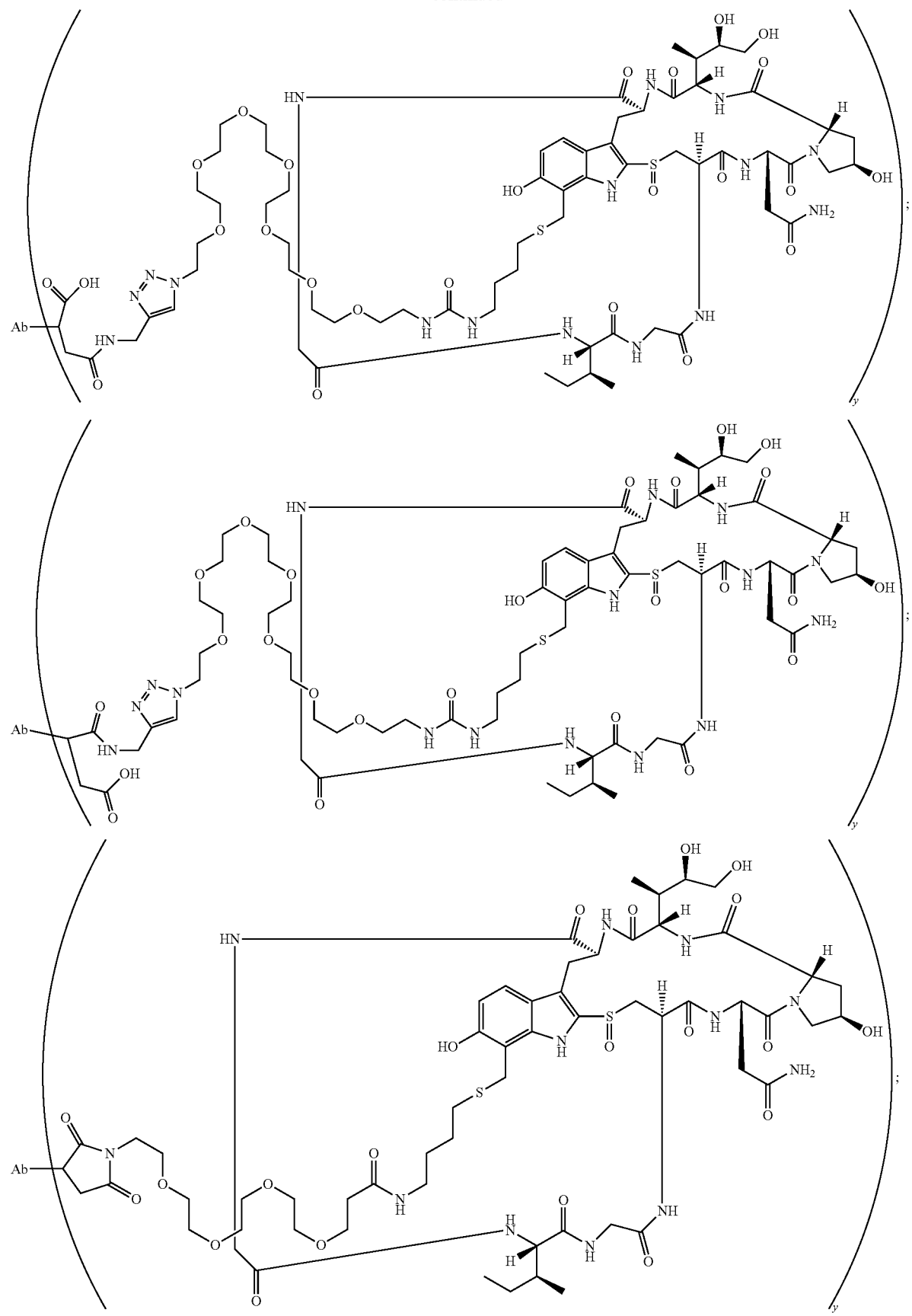

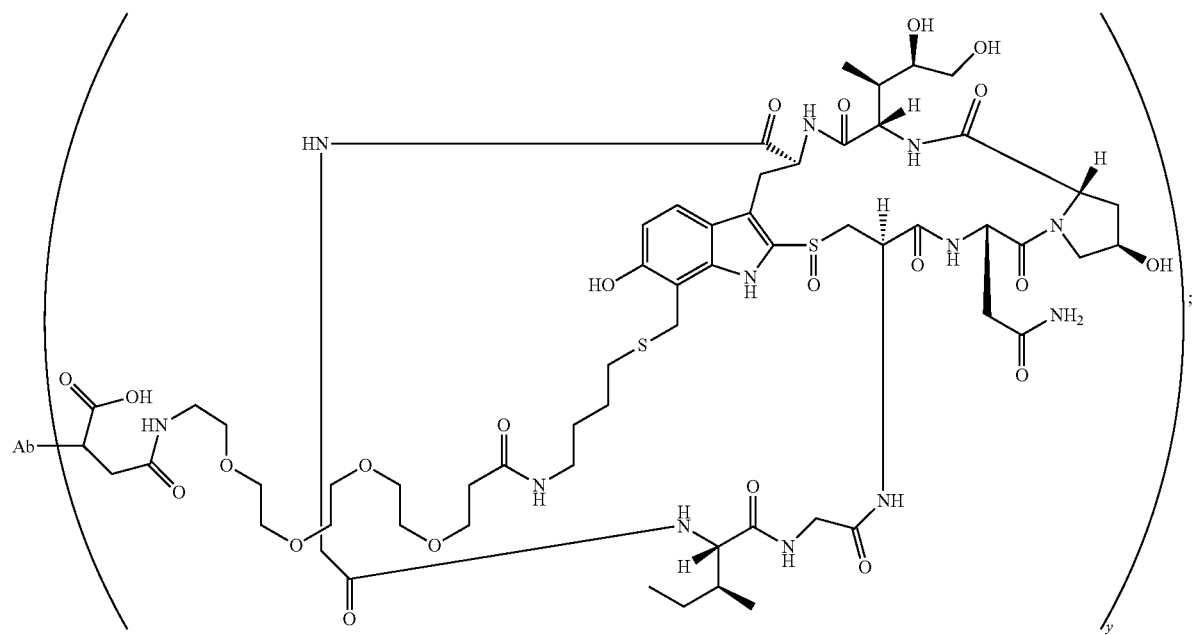
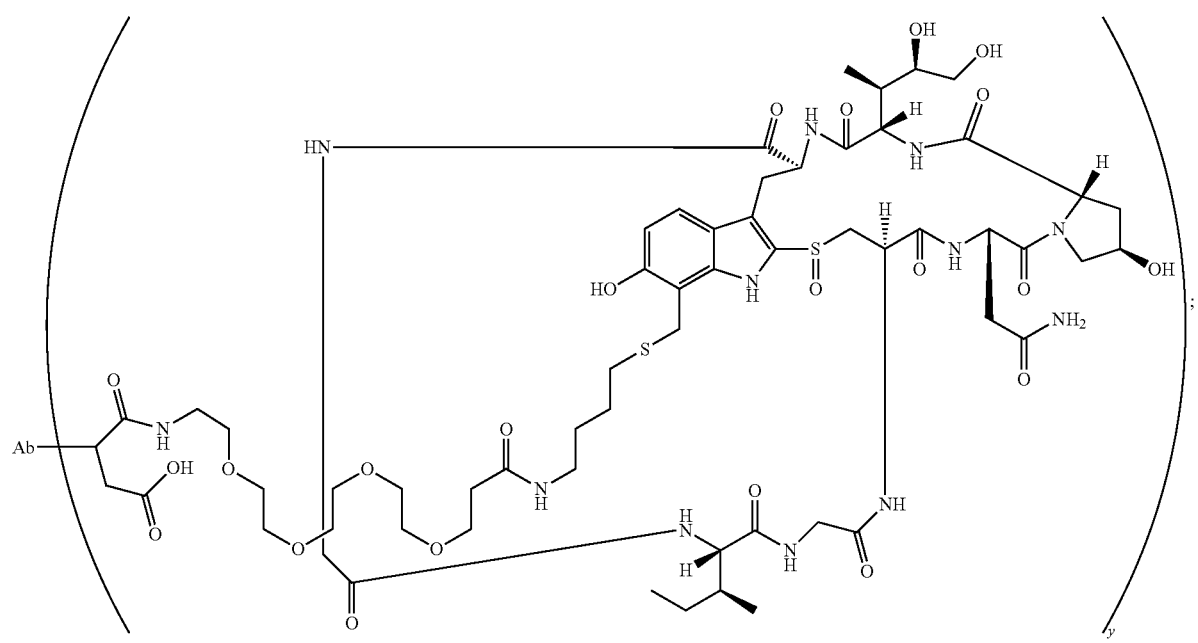

265 266
-continued
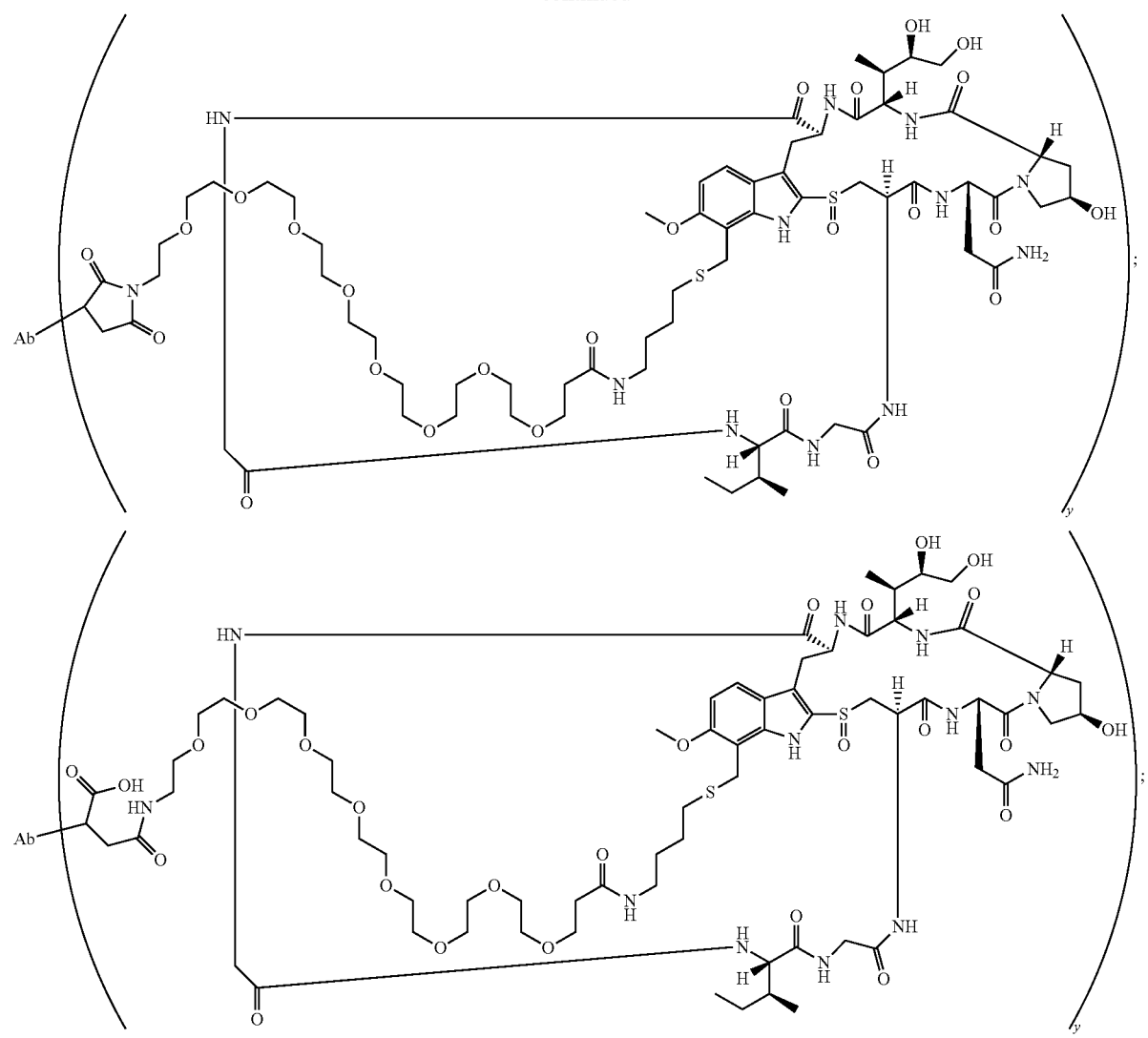
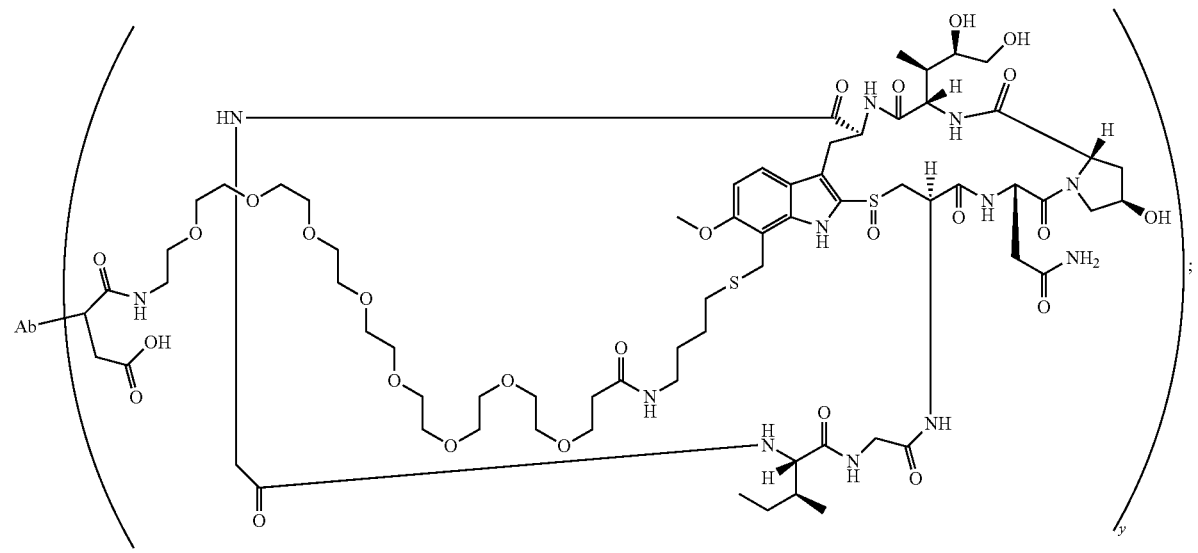

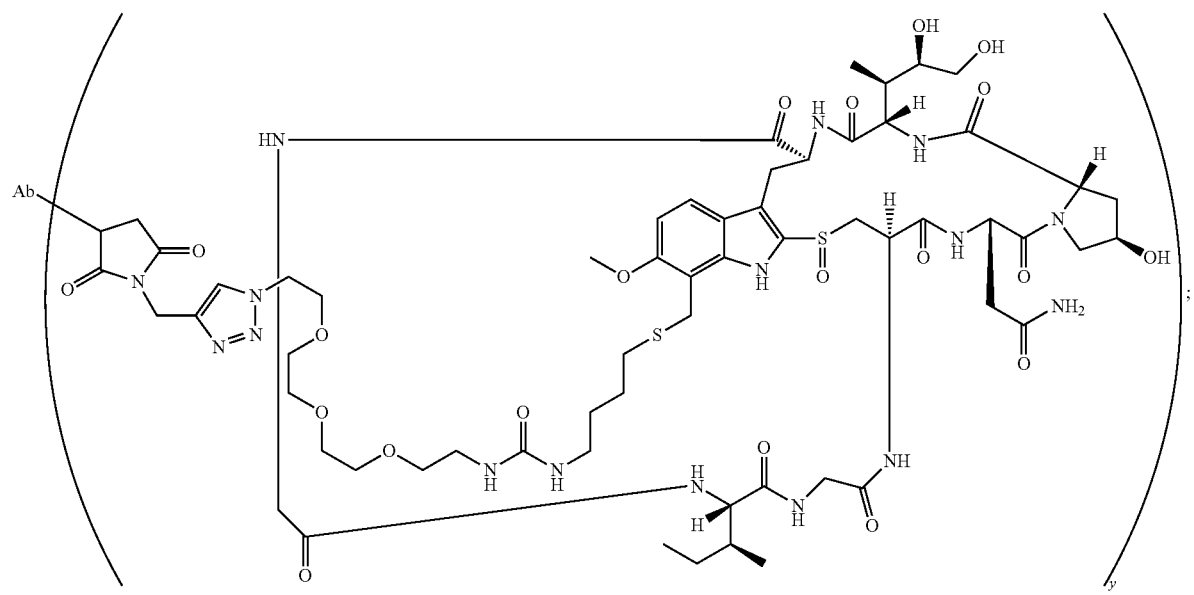

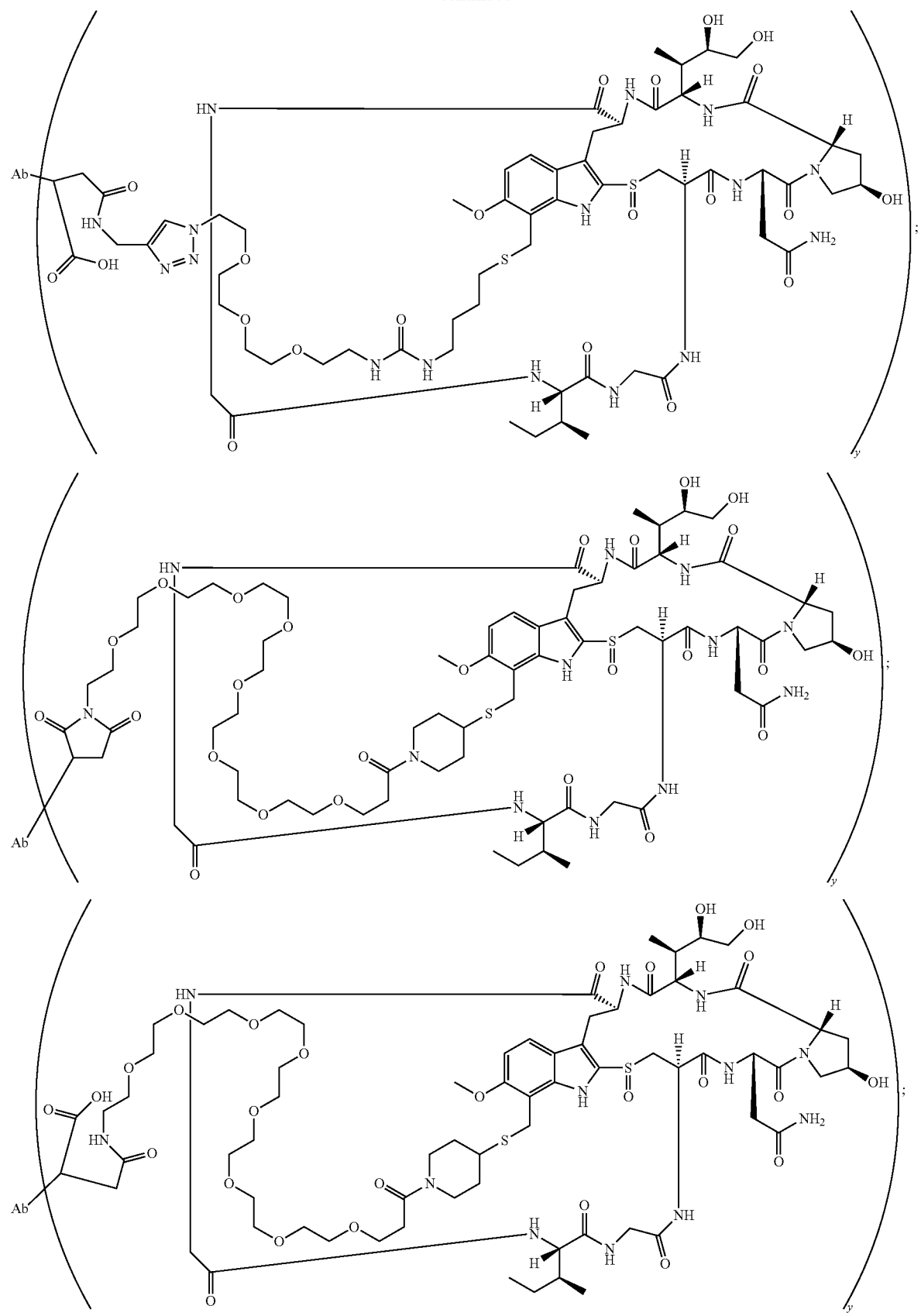

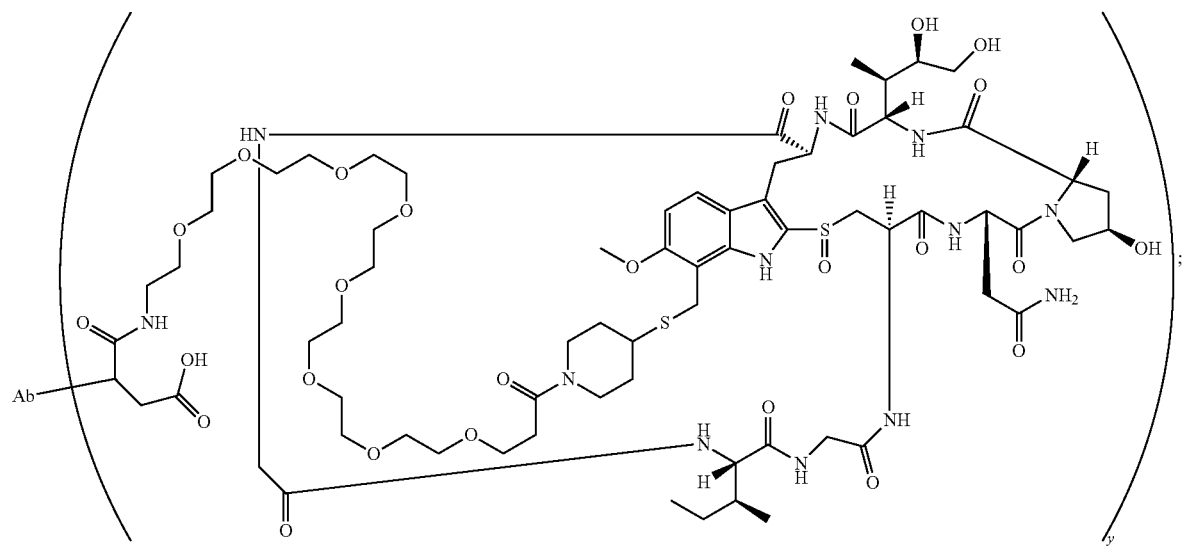
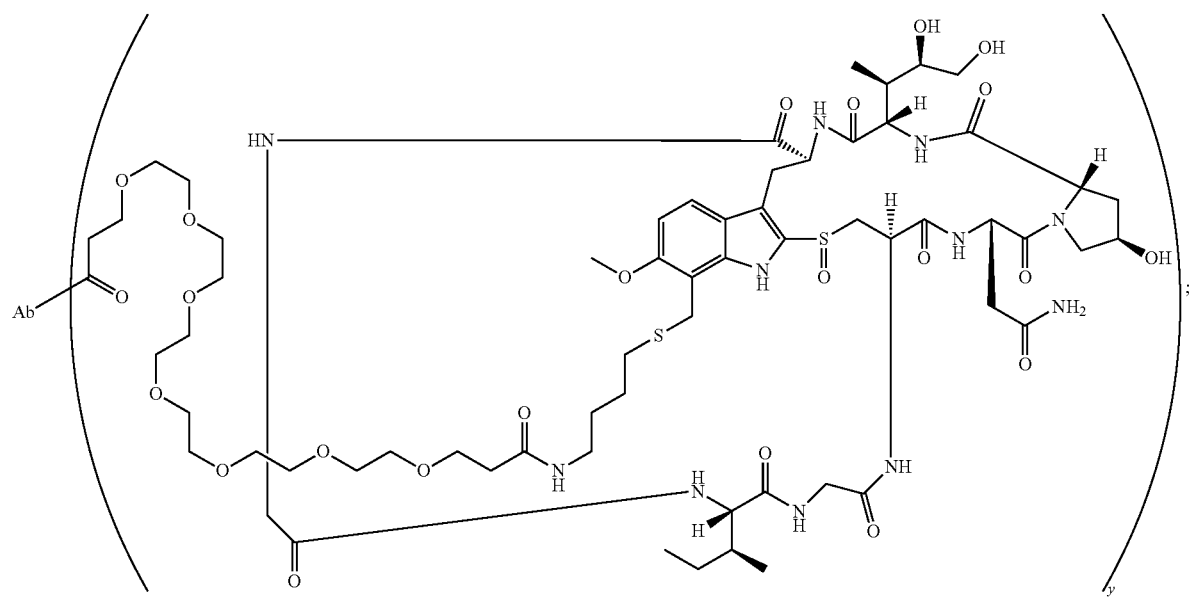

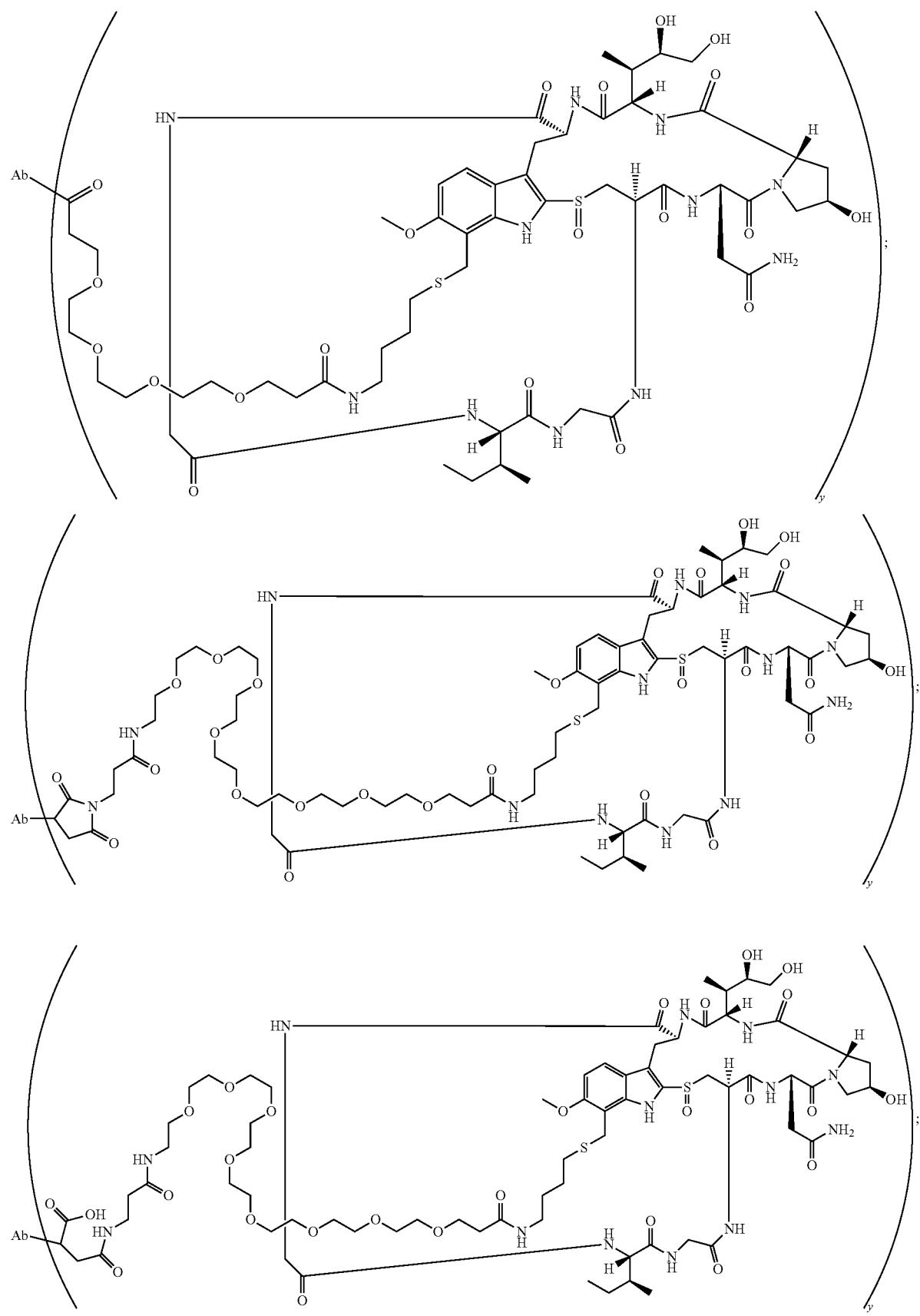

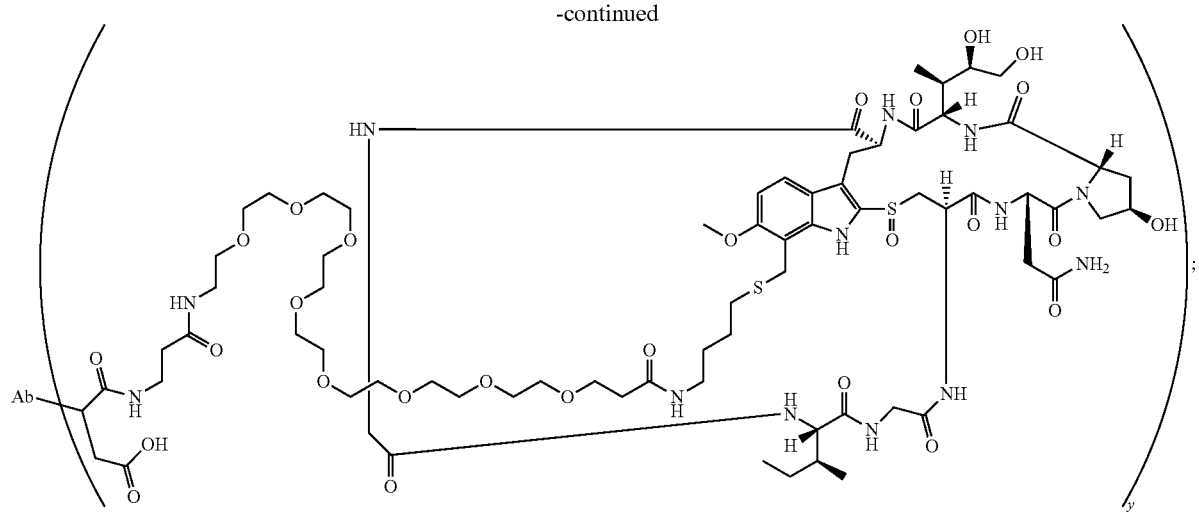

and

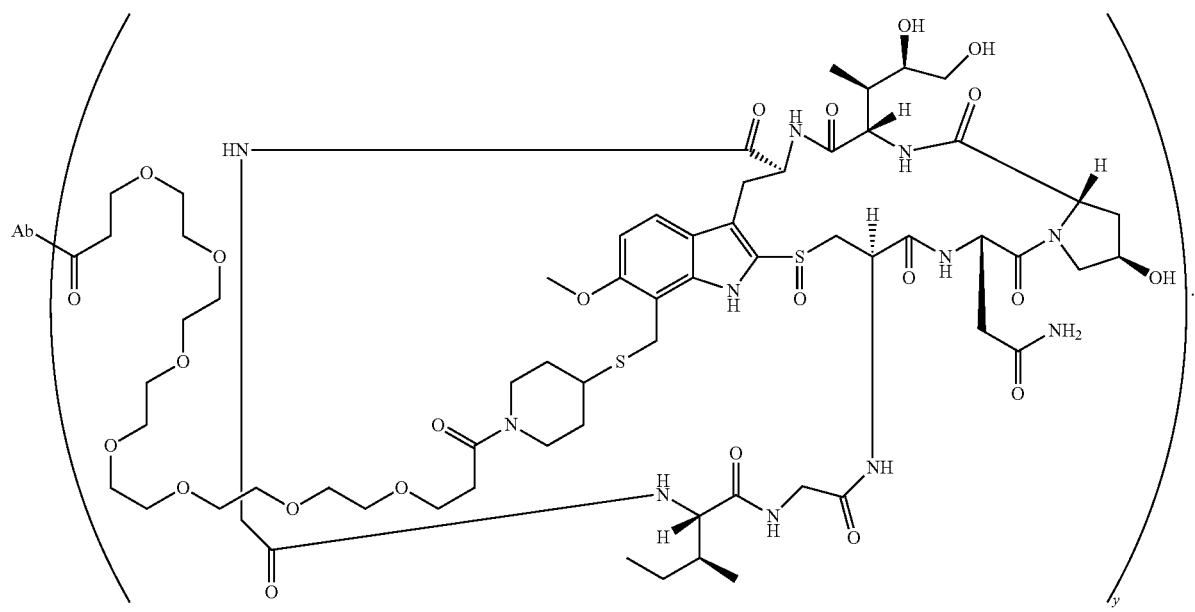

In certain embodiments of any of the aforementioned compounds of Formula (I) and Formula (Ia) and immunoconjugates of Formula (II) and Formula (IIa), each m is independently selected from 1, 2, 3, 4, 5 and 6. In any of the above embodiments, each m is independently selected from 1, 2, 3, 4 and 5. In any of the above embodiments, each m is independently selected from 1, 2, 3 and 4. In any of the above embodiments, each m is independently selected from 1, 2 and 3. In any of the above embodiments, each m is independently selected from 1 and 2.

In certain embodiments of any of the aforementioned compounds of Formula (I) and Formula (Ia) and immunoconjugates of Formula (II) and Formula (IIa), each n is independently selected from 1, 2, 3, 4, 5, 6, 7, 8, 9, 10, 11 and 12. In any of the above embodiments, each n is independently selected from 1, 2, 3, 4, 5, 6, 7, 8, 9, 10 and 11. In any of the above embodiments, each n is independently selected from 1, 2, 3, 4, 5, 6, 7, 8, 9, 10, 11, 12, 13 and 14. In any of the above embodiments, each n is independently selected from 1, 2, 3, 4, 5, 6, 7, 8 and 9. In any of the above embodiments, each n is independently selected from 1, 2, 3, 4, 5, 6, 7 and 8. In any of the above embodiments, each n is independently selected from 1, 2, 3, 4, 5, 6 and 7. In any of the above embodiments, each n is independently selected from 1, 2, 3, 4, 5 and 6. In any of the above embodiments, each n is independently selected from 1, 2, 3, 4 and 5. In any of the above embodiments, each n is independently selected from 1, 2, 3 and 4. In any of the above embodiments, each n is independently selected from 1, 2 and 3. In any of the above embodiments, each n is independently selected from 1 and 2.

In certain embodiments of any of the aforementioned immunoconjugates of Formula (II) and Formula (IIa), each y is independently selected from 1, 2, 3, 4, 5, 6, 7, 8, 9, 10, 11 and 12. In any of the above embodiments, each y is independently selected from 1, 2, 3, 4, 5, 6, 7, 8, 9, 10 and 11. In any of the above embodiments, each y is independently selected from 1, 2, 3, 4, 5, 6, 7, 8, 9 and 10. In any of the above embodiments, each y is independently selected from 1, 2, 3, 4, 5, 6, 7, 8 and 9. In any of the above embodiments, each y is independently selected from 1, 2, 3, 4, 5, 6, 7 and 8. In any of the above embodiments, each y is independently selected from 1, 2, 3, 4, 5, 6 and 7. In any of the above embodiments, each y is independently selected from 1, 2, 3, 4, 5 and 6. In any of the above embodiments, each y is independently selected from 1, 2, 3, 4 and 5. In any of the above embodiments, each y is independently selected from 1, 2, 3 and 4. In any of the above embodiments, each y is independently selected from 1, 2 and 3. In any of the above embodiments, each y is independently selected from 1 and 2.

The invention provides methods for making such immunoconjugates (ADCs) using cytotoxic cyclic peptides of Formula (I) as the payload (drug) to be delivered. In such cytotoxic cyclic peptides the 7' position of the indole ring has been modified with a —$CH_2SH$ moiety which is further modified with linker components ($L_1$ and $L_2$) and a reactive functional group which facilitates connecting the cytotoxic cyclic peptide to the antibody or antigen binding fragment.

In another aspect, the invention provides pharmaceutical compositions comprising an immunoconjugate of Formula (II) or Formula (IIa), admixed with at least one pharmaceutically acceptable carrier or excipient, optionally admixed with two or more pharmaceutically acceptable carriers or excipients, and methods to use these compositions to treat cell proliferation disorders.

In another aspect, the invention provides a method to treat a condition characterized by excessive or undesired cell proliferation, which comprises administering to a subject in need of such treatment an effective amount of an immunoconjugate of Formula (II) or Formula (IIa). The subject for treatment can be a mammal, and is preferably a human. Conditions treatable by the immunoconjugates and methods described herein include various forms of cancer, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

In another aspect, the invention provides the use of an immunoconjugate of Formula (II) or Formula (IIa) in the manufacture of a medicament for the treatment of cancer, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

In another aspect, the invention provides the use of an immunoconjugate of Formula (II) or Formula (IIa) as a medicament.

The invention includes all stereoisomers (including diastereoisomers and enantiomers), tautomers, and isotopically enriched versions thereof (including deuterium substitutions) of the compounds of Formula (I) and immunoconjugates of Formula (II).

The invention also include pharmaceutically acceptable salts of the compounds of Formula (I) and immunoconjugates of Formula (II).

DETAILED DESCRIPTION

Figure 1A:
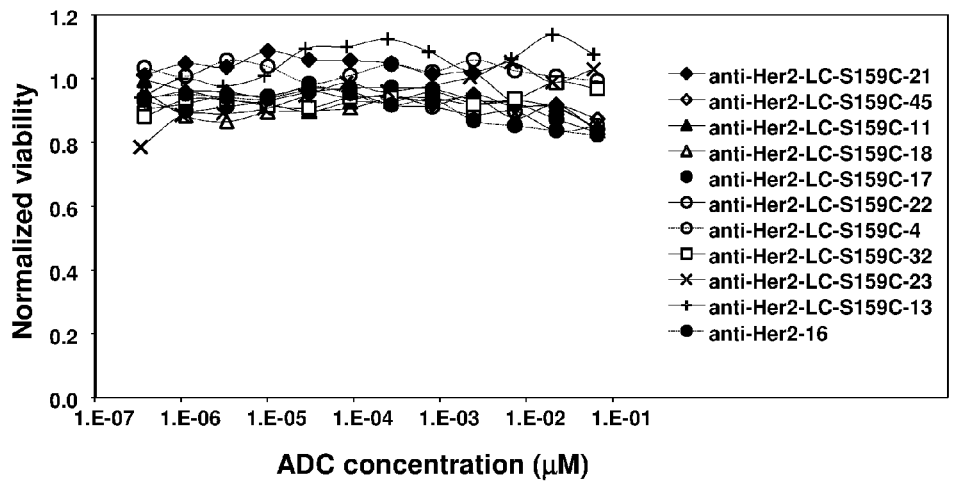
FIG. 1. In vitro cell proliferation assays of anti-Her2 ADCs conjugated through engineered Cys residues: (A) MDA-MB-231 clone 40 cells, (B) MDA-MB-231 clone 16 cells, (C) HCC1954 cells, and (D) JimT-1 cells.
Figure 1B:
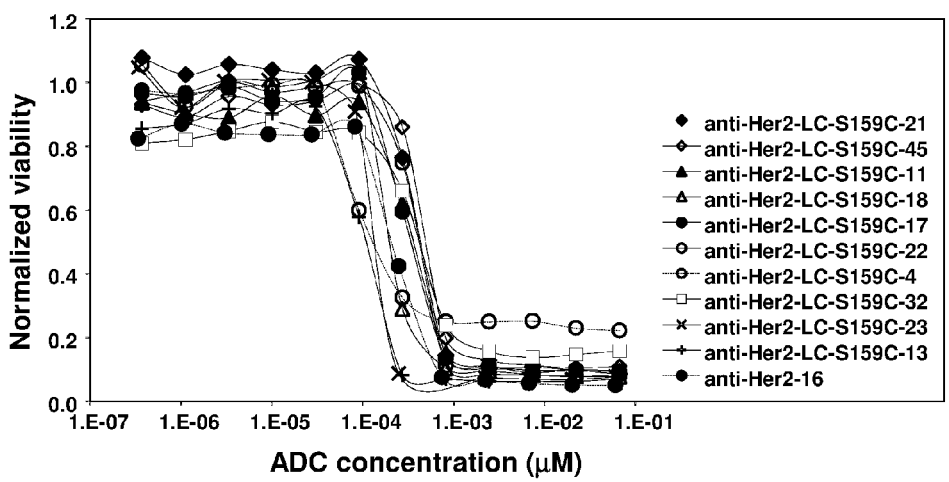
Figure 1C:
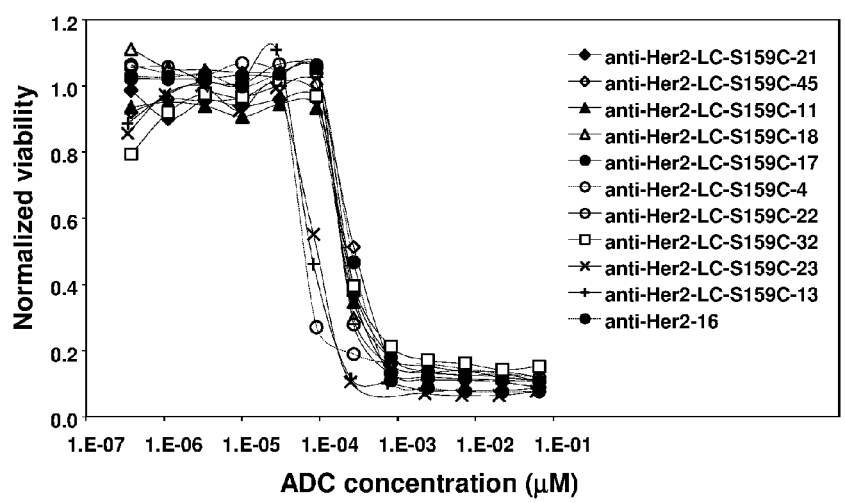
Figure 1D:
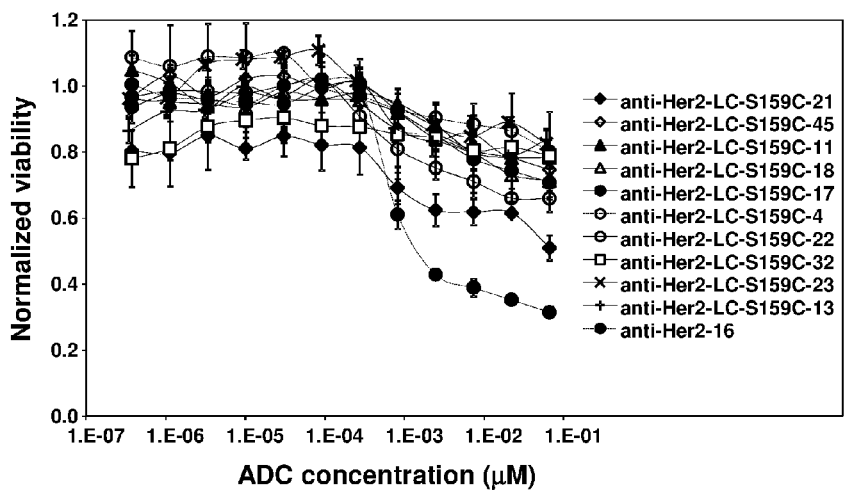
Figure 2A:
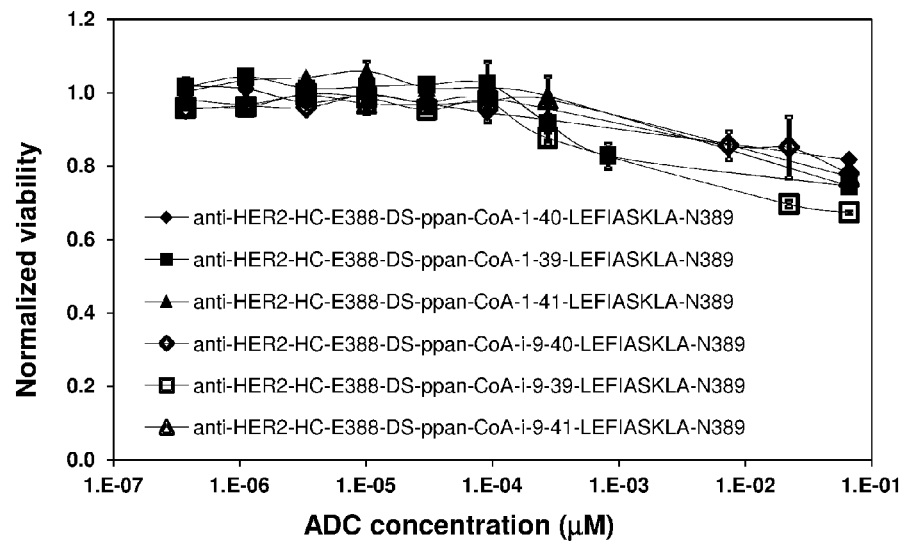
FIG. 2. In vitro cell proliferation assays of anti-Her2 ADCs conjugated enzymatically: (A) JimT-1 cells, (B) A375 cells, (C) NCI-H526 cells, (D) HCC1954 cells, (E) NCI-N87 cells and (F) SK-BR-3 cells.
Figure 2B:
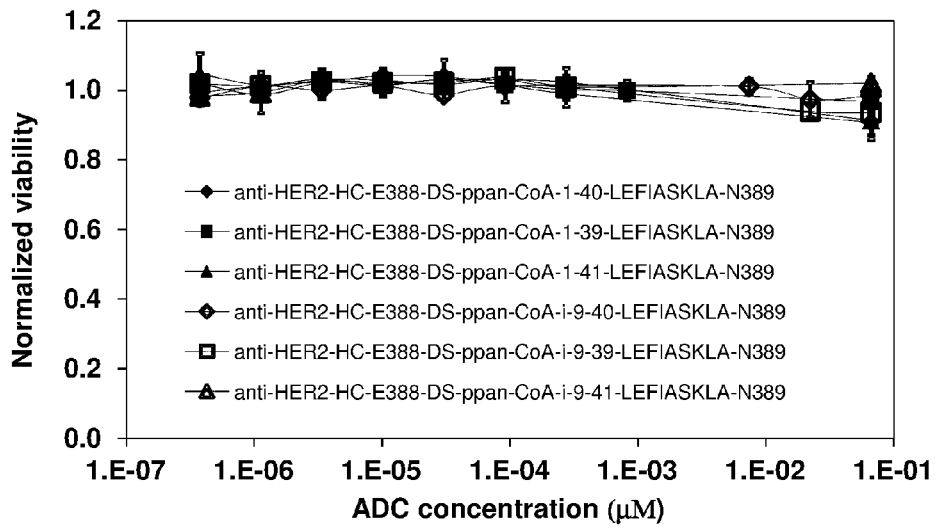
Figure 2C:
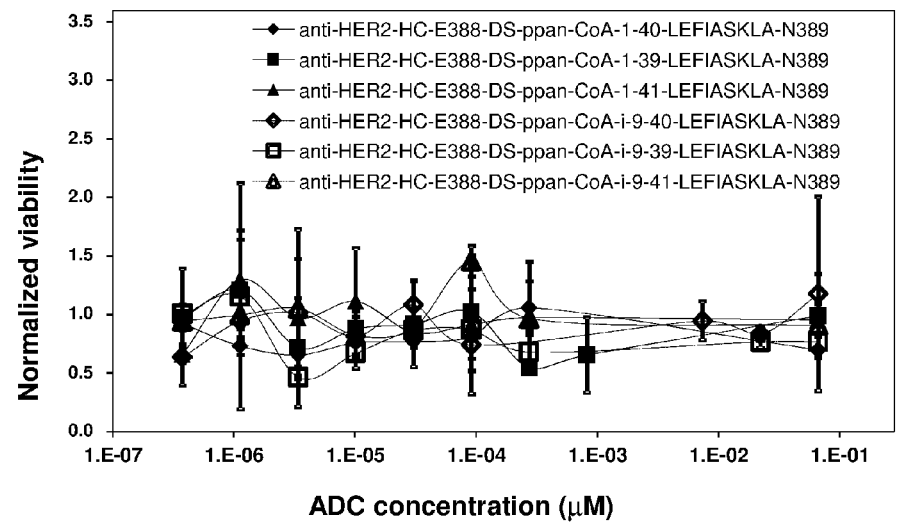
Figure 2D:
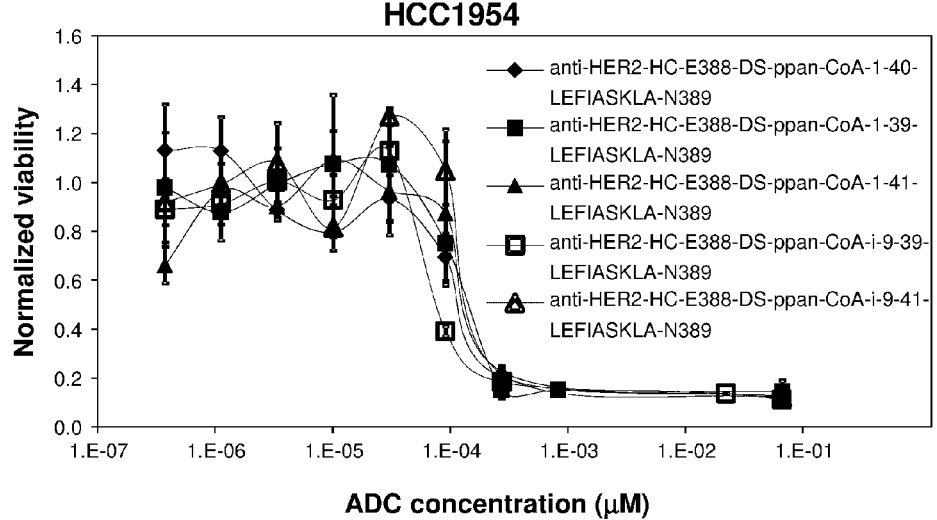
Figure 2E:
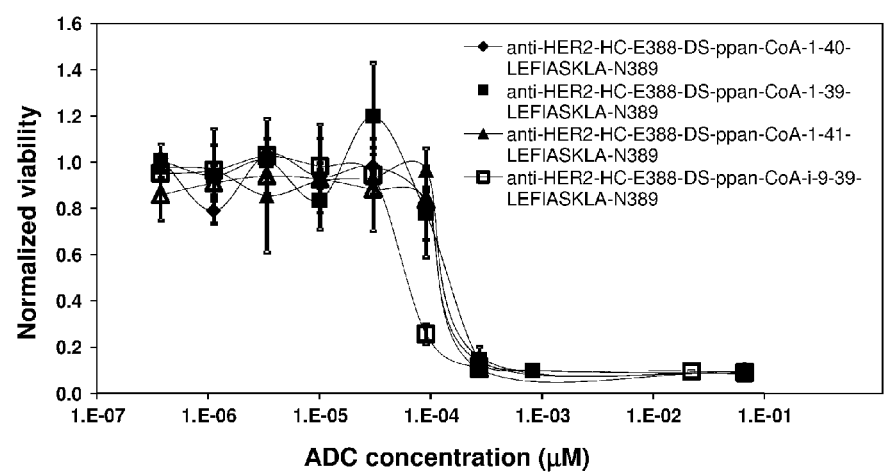
Figure 2F:
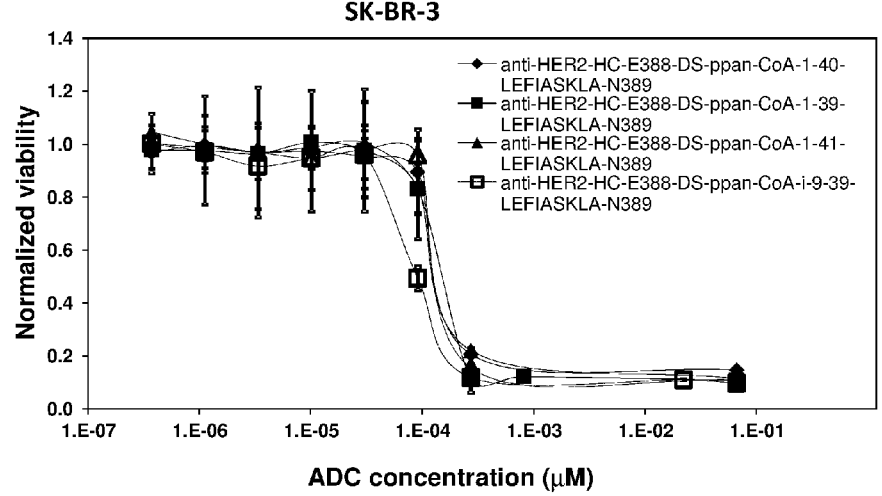

The following definitions apply unless otherwise expressly provided.

The term "amino acid" refers to canonical, synthetic, and unnatural amino acids, as well as amino acid analogs and amino acid mimetics that function in a manner similar to the canonical amino acids. Canonical amino acids are proteinogenous amino acids encoded by the genetic code and include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, as well as selenocysteine, pyrrolysine and pyrroline-carboxy-lysine. Amino acid analogs refer to compounds that have the same basic chemical structure as a canonical amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a canonical amino acid.

The term "antigen binding moiety" as used herein refers to a moiety capable of binding specifically to an antigen, and includes but is not limited to antibodies and antibody fragments.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and $C_L$ domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the invention may include amino acid residues not encoded by human sequences (e.g., mutations introduced by random or site-specific mutagenesis in vitro or by somatic mutation in vivo, or a substitution to promote stability or manufacturing).

The term "humanized" antibody, as used herein, refers to an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

The term "specifically binds" or "selectively binds," when used in the context of describing the interaction between an antigen (e.g., a protein or a glycan) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agents with a particular binding specificity bind to a particular antigen at least ten (10) times the background and do not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The terms "polypeptide" and "protein" are used interchangeably herein to refer to a polymer of amino acid residues. The terms apply to canonical amino acid polymers as well as to non-canonical amino acid polymers. Unless otherwise indicated, a particular polypeptide sequence also implicitly encompasses modified variants thereof.

The term "immunoconjugate" or "antibody-drug-conjugate" as used herein refers to the linkage of an antigen binding moiety such as an antibody or an antigen binding fragment thereof with an cytotoxic peptide of Formula (I). The linkage can be covalent bonds, or non-covalent interactions, and can include chelation. Various linkers, known in the art, can be employed in order to form the immunoconjugate.

The term "cytotoxin", or "cytotoxic agent" as used herein, refer to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein, refers to a chemical moiety that is or can be conjugated to an antibody or antigen binding fragment to form an immunoconjugate, and can include any moiety that is useful to attach to the antibody or antigen binding fragment. For example, "drug moiety" or "payload" includes, but is not limited to, the cytotoxic cyclic peptides described herein. The immunoconjugates of the invention comprise one or more cytotoxic cyclic peptides described herein as a payload, but may also include one or more other payloads. Other payloads include, for example, a drug moiety or payload can be an anti-cancer agent, an anti-inflammatory agent, an antifungal agent, an antibacterial agent, an anti-parasitic agent, an anti-viral agent, or an anesthetic agent. In certain embodiments a drug moiety is selected from an Eg5 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Suitable examples include calicheamycins such as gamma-calicheamycin; and maytansinoids such as DM1, DM3 and DM4. Methods for attaching each of these to a linker compatible with the antibodies and method of the invention are known in the art. See, e.g., Singh et al., (2009) Therapeutic Antibodies: Methods and Protocols, vol. 525, 445-457.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to at least partially alleviate, inhibit, prevent and/or ameliorate a condition, or a disorder or a disease.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

In certain embodiments, the modified immunoconjugates of the invention are described according to a "cytotoxic cyclic peptide-to-antibody" ratio of, e.g., 1, 2, 3, 4, 5, 6, 7, or 8, or 12 or 16; this ratio corresponds to "y" in Formula (II). While this ratio has an integer value for a specific conjugate molecule, it is understood that an average value is typically used to describe a sample containing many molecules, due to some degree of inhomogeneity within a sample of an immunoconjugate. The average loading for a sample of an immunoconjugate is referred to herein as the "drug to antibody ratio," or DAR. In some embodiments, the DAR is between about 1 and about 16, and typically is about 1, 2, 3, 4, 5, 6, 7, or 8. In some embodiments, at least 50% of a sample by weight is compound having the average DAR plus or minus 2, and preferably at least 50% of the sample is a product that contains the average DAR plus or minus 1.5. Preferred embodiments include immunoconjugates wherein the DAR is about 2 to about 8, e.g., about 2, about 3, about 4, about 5, about 6, about 7, or about 8. In these embodiments, a DAR of "about q" means the measured value for DAR is within ±20% of q, or preferably within ±10% of q.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms, unless otherwise stated, e.g., where a specific isomer is identified. Optically active (R)- and (S)-isomers may be prepared using chiral synthons or chiral reagents, or resolved using conventional techniques. If the compound contains a double bond, the substituent may be E or Z configuration. If the compound contains a di-substituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. "Substantially pure" or "substantially free of other isomers" as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The term "thiol-maleimide" as used herein refers to a group formed by reaction of a thiol with maleimide, having this general formula

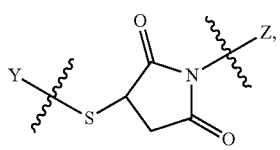

where Y and Z are groups to be connected via the thiol-maleimide linkage and can comprise linker components, antibodies or payloads.

"Cleavable" as used herein refers to a linker or linker component that connects two moieties by covalent connections, but breaks down to sever the covalent connection between the moieties under physiologically relevant conditions, typically a cleavable linker is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linker or linker component attached to the payload, or it may release the payload without any residual part or component of the linker.

"Pcl" as used herein refers to pyrroline carboxy lysine, e.g.,

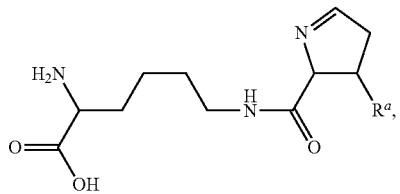

where $R^a$ is H, which has the following formula when incorporated into a peptide:

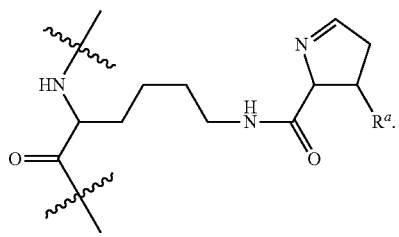

The corresponding compound wherein $R^a$ is methyl is pyrrolysine.

"Non-cleavable" as used herein refers to a linker or linker component that is not especially susceptible to breaking down under physiological conditions, e.g., it is at least as stable as the antibody or antigen binding fragment portion of the immunoconjugate. Such linkers are sometimes referred to as "stable", meaning they are sufficiently resistant to degradation to keep the payload connected to the antigen binding moiety Ab until Ab is itself at least partially degraded, i.e., the degradation of Ab precedes cleavage of the linker in vivo. Degradation of the antibody portion of an ADC having a stable or non-cleavable linker may leave some or all of the linker, and one or more amino acid groups from an antibody, attached to the payload or drug moiety that is delivered in vivo.

The terms "$C_1$-$C_3$alkyl", "$C_2$-$C_3$alkyl", "$C_1$-$C_4$alkyl", "$C_1$-$C_5$alkyl", "$C_1$-$C_6$alkyl" and "$C_2$-$C_6$alkyl", as used herein, refer to a fully saturated branched or straight chain hydrocarbon containing 1-3 carbon atoms, 2-3 carbon atoms, 1-4 carbon atoms, 1-5 carbon atoms, 1-6 carbon atoms or 2-6 carbon atoms, respectively. Non-limiting examples of "$C_1$-$C_3$alkyl" groups include methyl, ethyl, n-propyl and isopropyl. Non-limiting examples of "$C_2$-$C_3$alkyl" groups include ethyl, n-propyl and isopropyl. Non-limiting examples of "$C_1$-$C_4$alkyl" groups include methyl, ethyl, n-propyl, isopropyl, n-butyl, isobutyl, sec-butyl and tert-butyl. Non-limiting examples of "$C_1$-$C_5$alkyl" groups include methyl, ethyl, n-propyl, isopropyl, n-butyl, isobutyl, sec-butyl, tert-butyl, n-pentyl and isopentyl. Non-limiting examples of "$C_1$-$C_6$alkyl" groups include methyl, ethyl, n-propyl, isopropyl, n-butyl, isobutyl, sec-butyl, tert-butyl, n-pentyl, isopentyl and hexyl. Non-limiting examples of "$C_2$-$C_6$alkyl" groups include ethyl, n-propyl, isopropyl, n-butyl, isobutyl, sec-butyl, tert-butyl, n-pentyl, isopentyl and hexyl.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

The terms "$C_1$-$C_3$alkoxy", "$C_2$-$C_3$alkoxy", "$C_1$-$C_4$alkoxy", "$C_1$-$C_5$alkoxy", "$C_1$-$C_6$alkoxy" and "$C_2$-$C_6$alkoxy, as used herein, refer to the groups —O—$C_1$-$C_3$alkyl, —O—$C_2$-$C_3$alkyl, —O—$C_1$-$C_4$alkyl, —O—$C_1$-$C_5$alkyl, —O—$C_1$-$C_6$alkyl and —O—$C_2$-$C_6$alkyl, respectively, wherein the groups "$C_1$-$C_3$alkyl", "$C_2$-$C_3$alkyl", "$C_1$-$C_4$alkyl", "$C_1$-$C_5$alkyl", "$C_1$-$C_6$alkyl" and "$C_2$-$C_6$alkyl" are as defined herein. Non-limiting examples of "$C_1$-$C_3$alkoxy" groups include methoxy, ethoxy, n-propoxy and isopropoxy. Non-limiting examples of "$C_2$-$C_3$alkoxy" groups include ethoxy, n-propoxy and isopropoxy. Non-limiting examples of "$C_1$-$C_4$alkoxy" groups include methoxy, ethoxy, n-propoxy, isopropoxy, n-butoxy, isobutoxy, sec-butoxy and tert-butoxy. Non-limiting examples of "$C_1$-$C_5$alkoxy" groups include methoxy, ethoxy, n-propoxy, isopropoxy, n-butoxy, isobutoxy, sec-butoxy, tert-butoxy, n-pentyloxy and isopentyloxy. Non-limiting examples of "$C_1$-$C_6$alkoxy" groups include methoxy, ethoxy, n-propoxy, isopropoxy, n-butoxy, isobutoxy, sec-butoxy, tert-butoxy, n-pentyloxy, isopentyloxy and hexyloxy. Non-limiting examples of "$C_2$-$C_6$alkoxy" groups include ethoxy, n-propoxy, isopropoxy, n-butoxy, isobutoxy, sec-butoxy, tert-butoxy, n-pentyloxy, isopentyloxy and hexyloxy.

The immunoconjugate naming convention used herein is antibody-Compound Number, where Compound Number refers to the compound of Formula (I) used for conjugation to the particular antibody. By way of example, anti-Her2-LC-S159C-1 describes antibody anti-Her2-LC-S159C conjugated to Compound 1. By way of Example anti-Her2-HC-E388-DS-ppan-CoA-1-40-LEFIASKLA-N389 describes antibody anti-Her2-HC-E388-DSLEFIASKLA-N389 tagged with a ybbR peptide (DSLEFIASKLA) which is coupled to CoA analogue (CoA-1) and then conjugated to Compound 40.

Linkers

A wide variety of linkers for use in ADCs are known (see, e.g., Lash, *Antibody-Drug Conjugates: the Next Generation of Moving Parts, Start-Up*, December 2011, 1-6), and can be used in conjugates within the scope of the invention.

The cytotoxic cyclic peptides provided herein for use as immunoconjugate (ADC) payloads are attached to an antigen binding moiety via a linker, where the linker is selected from -**L$_1$L$_2$-*, -**L$_3$-* and —**(CH$_2$)$_m$X$_3$(CH$_2$)$_m$—*, and the * indicates the point of attachment to the antigen binding moiety. The linker can be attached to the antigen binding moiety at any suitable available position on the antigen binding moiety: typically the linker is attached to an available amino nitrogen atom (i.e., a primary or secondary amine, rather than an amide) or a hydroxylic oxygen atom, or to an available sulfhydryl, such as on a cysteine. Furthermore, the linker, which is selected from -**L$_1$L$_2$-*, -**L$_3$-* and —**(CH$_2$)$_m$X$_3$(CH$_2$)$_m$—*, is attached to the 7' position of the indole of an amatoxin via an —CH$_2$S— group, where the ** of indicates the point of attachment to the sulphur of the —CH$_2$S— group.

The linker, -**L$_1$L$_2$-*, -**L$_3$-* and —**(CH$_2$)$_m$X$_3$(CH$_2$)$_m$—* of compounds of Formula (I), and Formula (Ia) and of immunoconjugates of Formula (II) and Formula (IIa) is a linking moiety used to link an amatoxin to an antigen binding moiety. Linker components L$_1$ and L$_2$ are described herein.

The linker, -**L$_1$L$_2$-*, in Formula (I), Formula (Ia), Formula (II) and Formula (IIa) may be divalent, meaning it can used to link only one payload per linker to an antigen binding moiety, or it can be trivalent an is able to link two payloads per linker to an antigen binding moiety, or it can be polyvalent. Trivalent, tetravalent, and polyvalent linkers can be used to increase the loading of a payload (drug) on an antigen binding moiety (e.g. an antibody), thereby increasing the drug to antibody ratio (DAR) without requiring additional sites on the antibody for attaching multiple linkers. Examples of such linkers given in Bioconjugate Chem., 1999 March-April; 10(2):279-88; U.S. Pat. No. 6,638,499; Clin Cancer Res Oct. 15, 2004 10; 7063; and WO2012/113847A1.

The linker, -**L$_1$L$_2$-*, -**L$_3$-* and —**(CH$_2$)$_m$X$_3$(CH$_2$)$_m$—* of compounds of Formula (I), and Formula (Ia) and of immunoconjugates of Formula (II) and Formula (IIa) can be cleavable or non-cleavable. Cleavable linkers, such as those containing a hydrazone, a disulfide, the dipeptide Val-Cit, and ones containing a glucuronidase-cleavable p-aminobenzyloxycarbonyl moiety, are well known in the art, and can be used. See, e.g., Ducry, et al., *Bioconjugate Chem.*, vol. 21, 5-13 (2010). For the immunoconjugates of comprising a cleavable linker, the linker is substantially stable in vivo until the immunoconjugate binds to or enters a cell, at which point either intracellular enzymes or intracellular chemical conditions (pH, reduction capacity) cleave the linker to free the cytotoxic peptide.

Alternatively, non-cleavable linkers can be used in compounds of Formula (I) and Formula (Ia) and in the immunoconjugates of Formula (II) and Formula (IIa). Non-cleavable linkers lack structural components designed to degrade in cells, and thus their structures can vary substantially. See, e.g., Ducry, et al., *Bioconjugate Chem.*, vol. 21, 5-13 (2010). These immunoconjugates are believed to enter a targeted cell and undergo proteolytic degradation of the antibody rather than linker decomposition; thus at least a portion, or all, of the linker and even some of the antibody or antibody fragment may remain attached to the payload.

The L$_1$ component of linker, -**L$_1$L$_2$-*, of compounds of Formula (I), and Formula (Ia) and of immunoconjugates of Formula (II) and Formula (IIa) is selected from —(CH$_2$)$_m$NR$^5$C(=O)—,

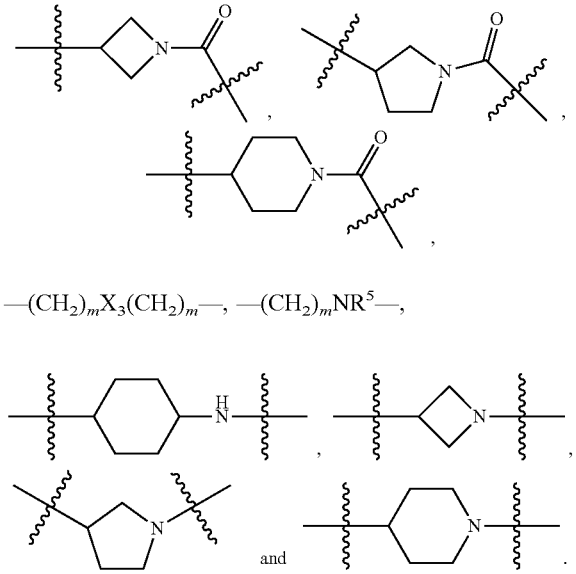

—(CH$_2$)$_m$X$_3$(CH$_2$)$_m$—, —(CH$_2$)$_m$NR$^5$—, and .

The L$_2$ component of linker, -**L$_1$L$_2$-*, of compounds of Formula (I), and Formula (Ia) and of immunoconjugates of Formula (II) and Formula (IIa) can be any suitable linker known in the art, including, but not limited to —(CH$_2$)$_m$—, —NR$^5$(CH$_2$)$_m$—, —(CH$_2$)$_m$NR$^5$C(=O)(CH$_2$)$_m$—, —X$_4$, —(CH$_2$)$_m$NR$^5$C(=O)X$_4$, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)X$_1$X$_2$C(=O)(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$C(=O)NR$^5$(CH$_2$)$_m$X$_3$—, —(CH$_2$)$_m$X$_3$(CH$_2$)$_m$C(=O)NR$^5$(CH$_2$)$_m$—, —(CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$(O(CH$_2$)$_m$)$_n$—, —((C(R$^5$)$_2$)$_m$OC(=O)NR$^5$(CH$_2$)$_m$O(CH$_2$)$_m$—, —(CH$_2$)$_m$(O(CH$_2$)$_m$)$_n$NR$^5$C(=O)O(C(R$^5$)$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NR$^5$(CH$_2$)$_m$C(=O)—, —(CH$_2$)$_m$O(CH$_2$)$_m$NR$^5$C(=O)O((C(R$^5$)$_2$)$_m$—, —(CH$_2$)$_m$C(=O)X$_2$X$_1$C(=O)NR$^5$(CH$_2$)$_m$NR$^5$C(=O)—, —(CH$_2$)$_m$C(=O)NR$^5$(CH$_2$)$_m$ NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$S(CH$_2$)$_m$—; —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —C(R$^5$)$_2$(CH$_2$)$_m$OC(=O)NR$^5$(CH$_2$)$_m$X$_3$(CH$_2$)$_m$—, —(CH$_2$)$_m$X$_3$(CH$_2$)$_m$NR$^5$C(=O)O(CH$_2$)$_m$C(R$^5$)$_2$NR$^5$—, —C(R$^5$)$_2$(CH$_2$)$_m$OC(=O)NR$^5$((CH$_2$)$_m$O)$_n$(CH$_2$)$_m$—, —(CH$_2$)$_m$(O(CH$_2$)$_m$)$_n$NR$^5$C(=O)O(CH$_2$)$_m$C(R$^5$)$_2$NR$^5$—, —C(R$^5$)$_2$(CH$_2$)$_m$OC(=O)NR$^5$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$(O(CH$_2$)$_m$)$_n$NR$^5$—, —(CH$_2$)$_m$(O(CH$_2$)$_m$)$_n$NR$^5$—, —(C(R$_5$)$_2$)$_m$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$C(=O)NR$^5$(CH$_2$)$_m$C(=O)X—, —(CH$_2$)$_2$S(=O)$_2$CH$_2$CH$_2$S—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$—, —(CH$_2$)$_m$X$_3$(CH$_2$)$_m$NR$^5$C(=O) or —(CH$_2$)$_m$X$_3$(CH$_2$)$_m$S(=O)$_2$NR$_5$—, wherein:

X$_1$ is

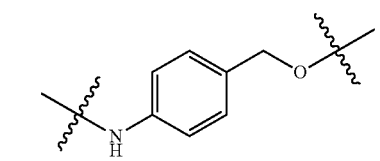

,

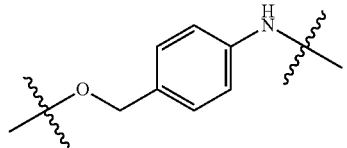

,

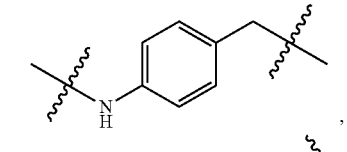

,

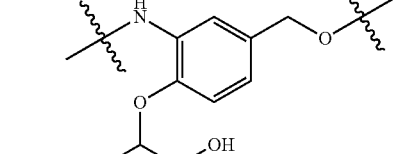

or

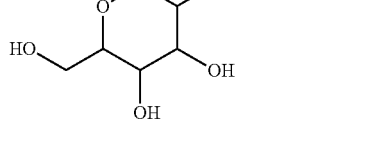

;

X$_2$ is

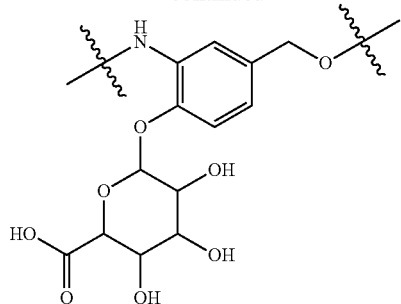

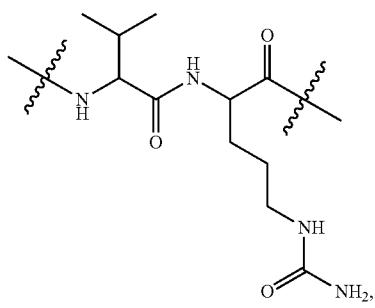

,

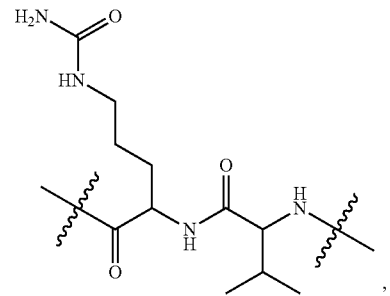

,

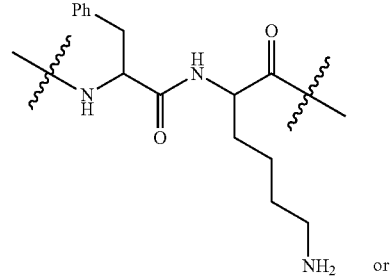

or

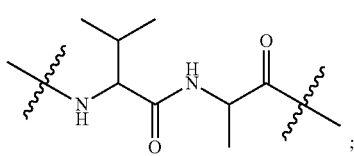

;

$X_3$ is

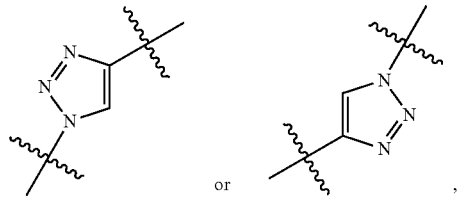 [SMILES: *c1cn(*)nn1 ; *c1cn(*)nn1]

and $X_4$ is

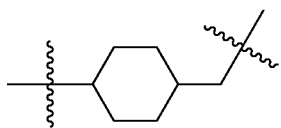

In certain embodiments. the $L_2$ component of linker, -**$L_1L_2$-*, of compounds of Formula (I), and Formula (Ia) and of immunoconjugates of Formula (II) and Formula (IIa) is selected from —$(CH_2)_m$—, —$NR^5(CH_2)_m$—, —$(CH_2)_m NR^5C(=O)(CH_2)_m$—, —$((CH_2)_mO)_n(CH_2)_m$—, —$((CH_2)_mO)_n(CH_2)_mX_3(CH_2)_m$—, —$X_1X_2C(=O)(CH_2)_m$—, —$NR^5((CH_2)_mO)_n(CH_2)_mX_3(CH_2)_m$—, —$((CH_2)_mO)_n(CH_2)_mNR^5C(=O)(CH_2)_m$—, —$(CH_2)_mNR^5C(=O)X_4$— and $X_4$, where $X_4$ is

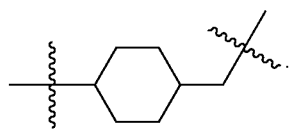 [SMILES: *CC1CCC(*)CC1]

The $L_2$ component of linker, -**$L_1L_2$-*, can comprise thiol-maleimide groups, thioethers, amides, and esters; groups that are easily cleaved in vivo under conditions found in, on or around targeted cells, such as disulfides, hydrazones, dipeptides like Val-Cit, substituted benzyloxycarbonyl groups, and the like; spacers to orient the payload in a suitable position relative to the antigen binding moiety, such as phenyl, heteroaryl, cycloalkyl or heterocyclyl rings, and alkylene chains; and/or pharmacokinetic property-enhancing groups, such as alkylene substituted with one or more polar groups (carboxy, sulfonate, hydroxyl, amine, amino acid, saccharide), and alkylene chains containing one or more —NH— or —O— in place of methylene group(s), such as glycol ethers (—$CH_2CH_2O$—$)_p$ where p is 1-10, which may enhance solubility or reduce intermolecular aggregation, for example.

The linker, -**$L_1L_2$-* can comprise chemical moieties that are readily formed by reaction between two reactive groups. Non-limiting examples of such chemical moieties are given in Table 1.

TABLE 1
| Reactive Group 1 | Reactive Group 2 | Chemical Moiety |
| --- | --- | --- |
| a thiol | a thiol | -S-S- |
| a thiol | a maleimide | 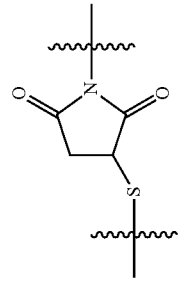 |
| a thiol | a haloacetamide | 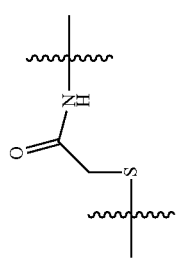 |
| an azide | an alkyne | 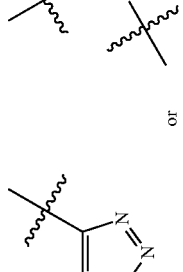 or 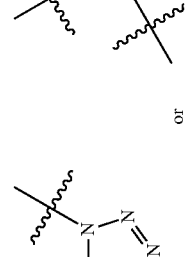 |
| an alkyne | an azide |  or |

TABLE 1-continued

| Reactive Group 1 | Reactive Group 2 | Chemical Moiety |
|---|---|---|
| a cyclooctyne | azide | (structures) |
| an aldehyde | a hydroxylamine | |
| an aldehyde | a hydrazine | |
| an aldehyde | NH₂—NH—C(=O)— | |
| a ketone | a hydroxylamine | |
| a ketone | a hydrazine | |

TABLE 1-continued

| Reactive Group 1 | Reactive Group 2 | Chemical Moiety |
|---|---|---|
| a ketone | NH$_2$—NH—C(=O)— | ![structure] |
| a hydroxylamine | an aldehyde | ![structure] |
| a hydroxylamine | a ketone | ![structure] |
| a hydrazine | an aldehyde | ![structure] |
| a hydrazine | a ketone | ![structure] |
| NH$_2$—NH—C(=O)— | an aldehyde | ![structure] |

TABLE 1-continued
| Reactive Group 1 | Reactive Group 2 | Chemical Moiety |
|---|---|---|
| NH$_2$—NH—C(=O)— | a ketone | 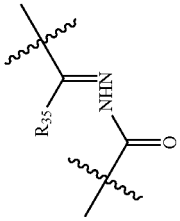 |
| a haloacetamide | a thiol | 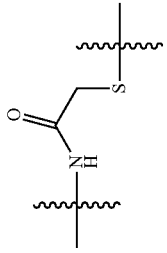 |
| a maleimide | a thiol | 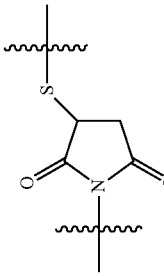 |
| a vinyl sulfone | a thiol | 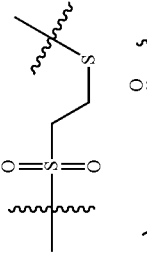 |
| a thiol | a vinyl sulfone | 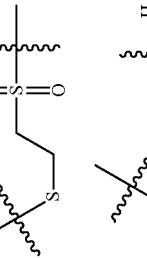 |
| an aziridine | a thiol | 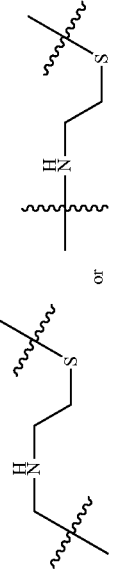 |

TABLE 1-continued
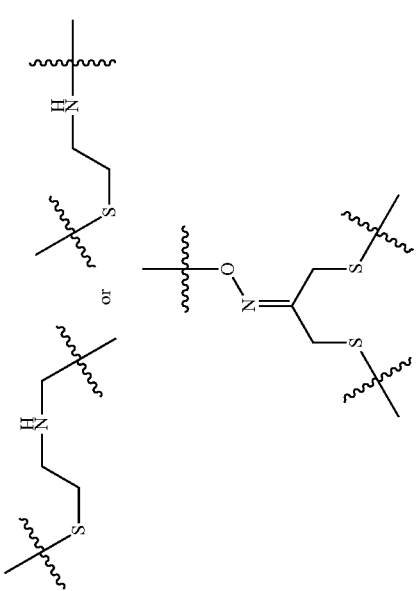

where: $R^{32}$ in Table 1 is H, $C_{1-4}$ alkyl, phenyl, pyrimidine or pyridine; $R^{35}$ in Table 1 is H, $C_{1-6}$alkyl, phenyl or $C_{1-4}$alkyl substituted with 1 to 3 —OH groups; each $R^{36}$ in Table 1 is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH; $R^{37}$ in Table 1 is independently selected from H, phenyl and pyridine; each $R^5$ in Table 1 is independently selected from H or $C_{1-6}$alkyl; $R^{12}$ in Table 1 is H, —CH$_3$ or phenyl; $R^{12}$ in Table 1 is H or nitro.

In addition, $L_2$ of the linker, -**$L_1L_2$-* can be a group shown in Table 2 below:

TABLE 2

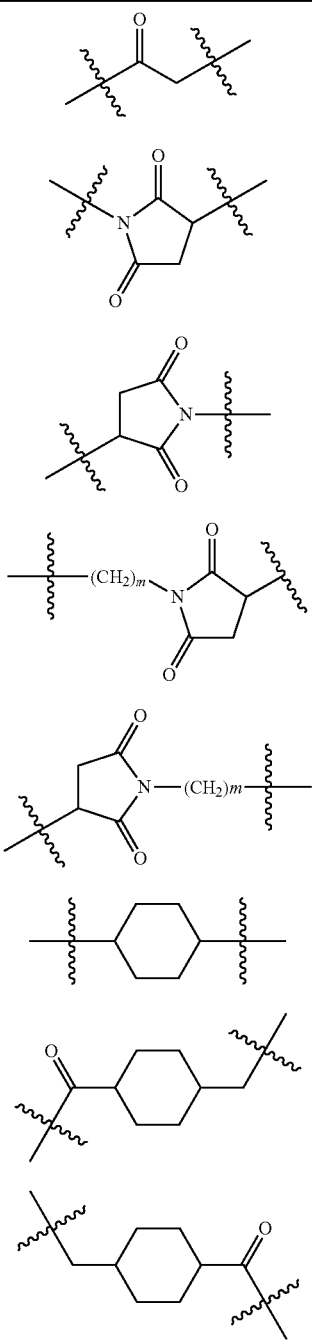

TABLE 2-continued

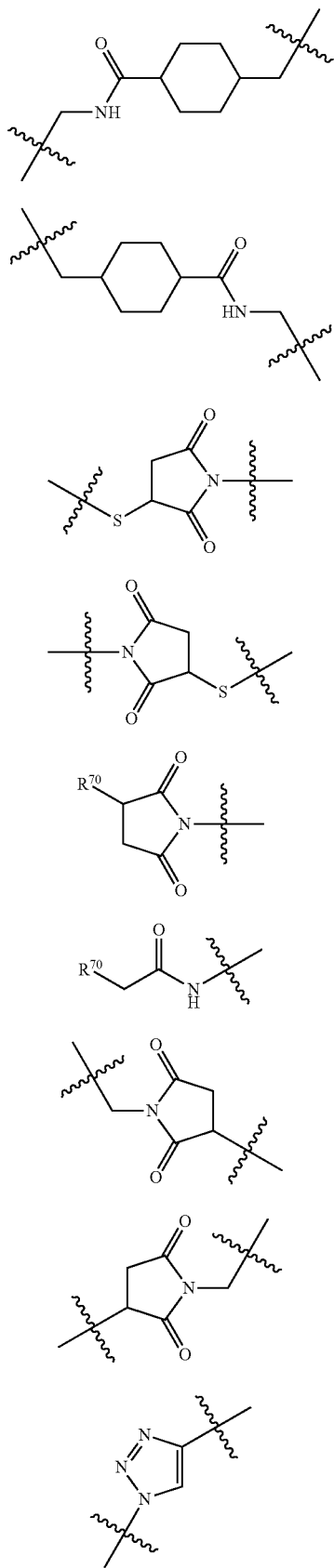

TABLE 2-continued
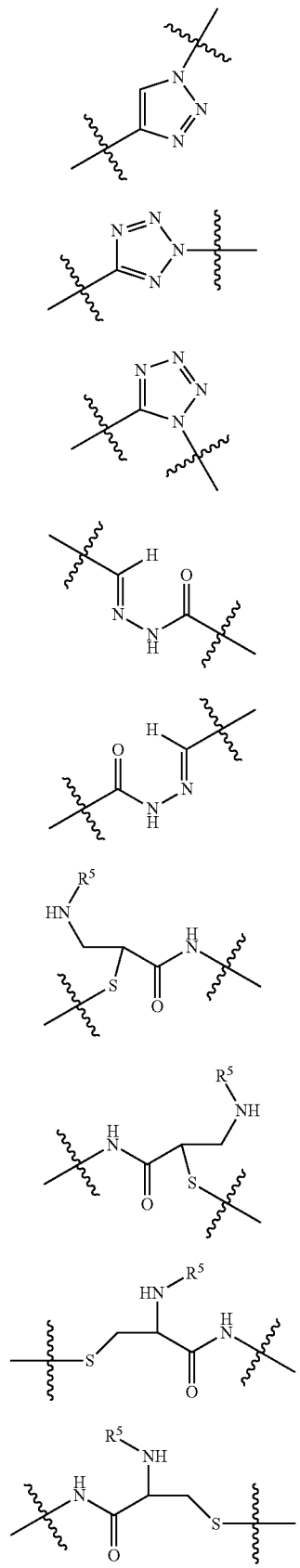
TABLE 2-continued
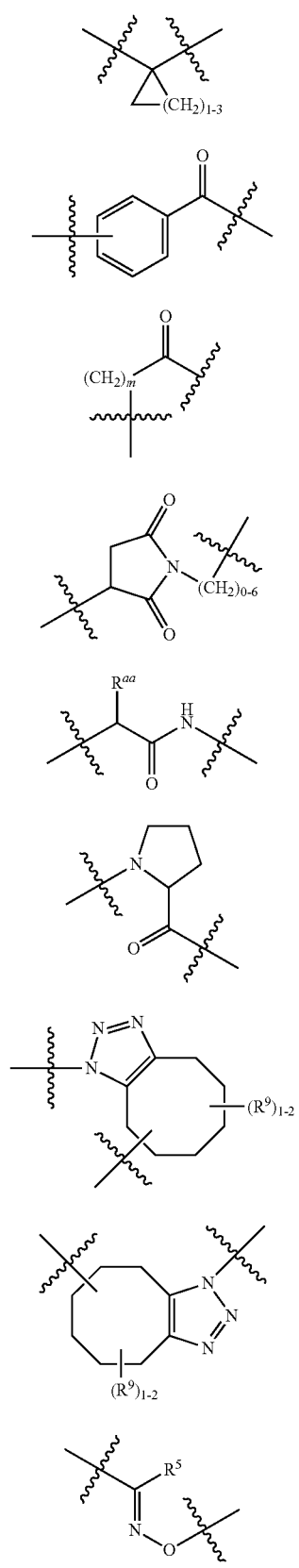

TABLE 2-continued
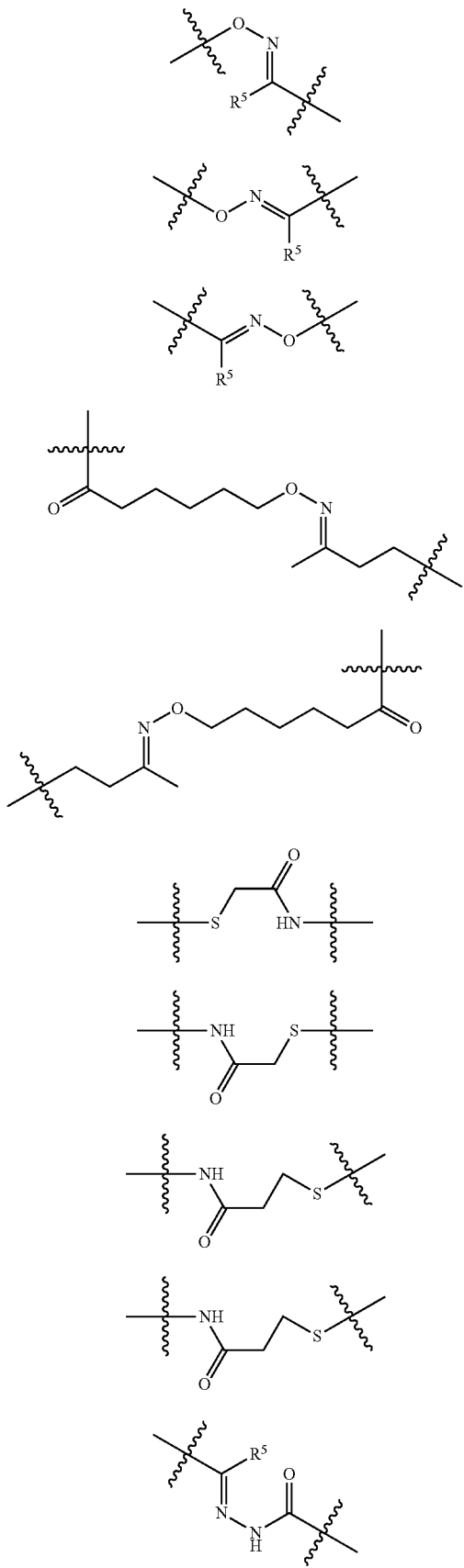
TABLE 2-continued
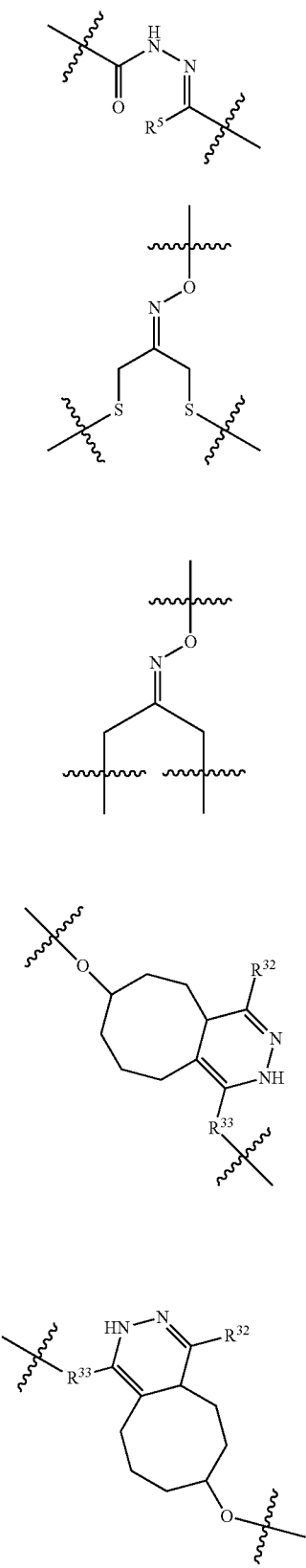

TABLE 2-continued
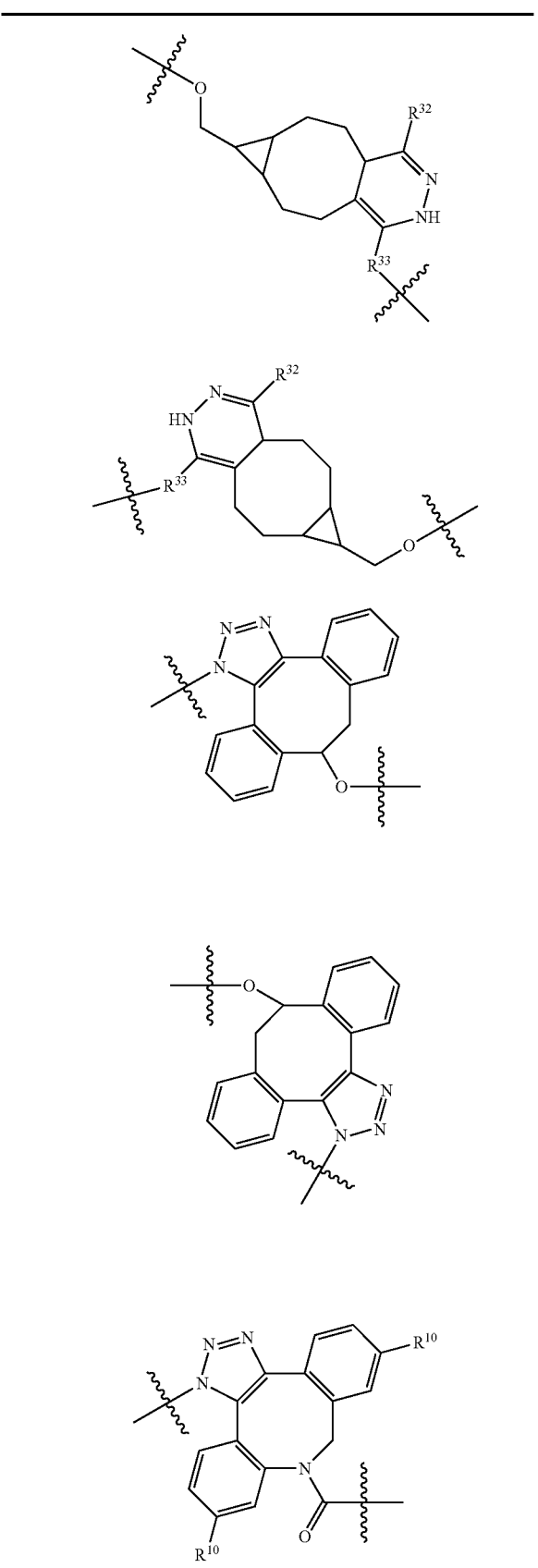
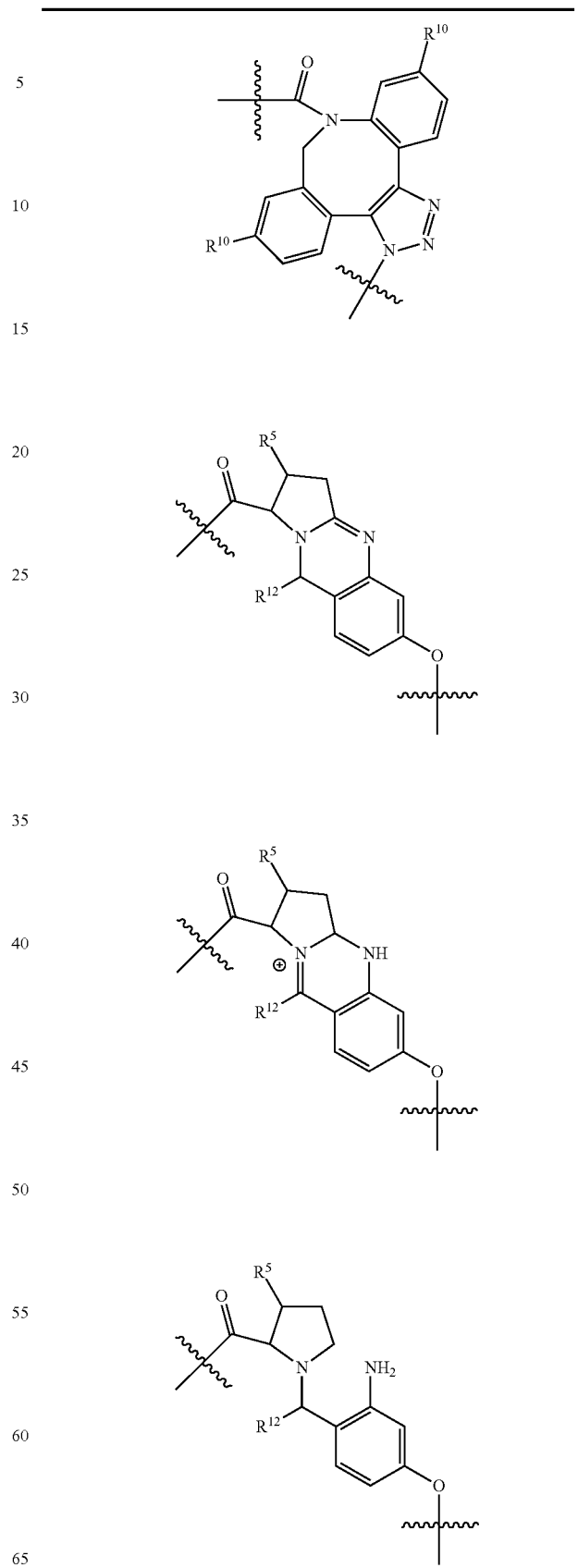

TABLE 2-continued

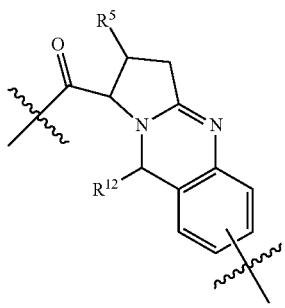

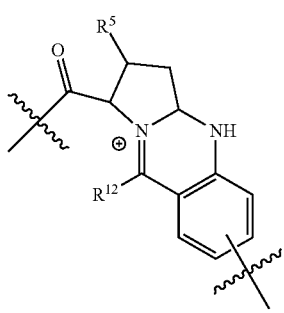

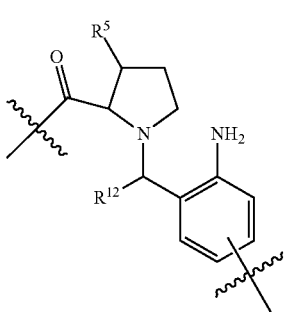

each R⁵ is independently selected from H or $C_{1-6}$alkyl;

each R¹⁰ is independently selected from H, $C_{1-6}$alkyl, F, Cl, —NH₂, —OCH₃, —OCH₂CH₃, —N(CH₃)₂, —CN, —NO₂ and —OH;

R70 is

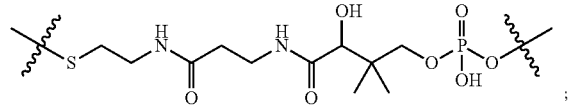 [SMILES: *OP(=O)(O)OCC(C)(C)C(O)C(=O)NCCC(=O)NCCS*]

$R^{aa}$ is H or a side chain of an amino acid selected from alanine, tryptophan, tyrosine, phenylalanine, leucine, isoleucine, valine, asparagine, glutamic acid, glutamine, aspatic acid, histidine, arginine, lysine, cysteine, methionine, serine, threonine, citrulline, ornithine, phenylglycine and t-butylglycine;

R¹² is H, —CH₃ or phenyl;

R³² is independently selected from H, $C_{1-4}$ alkyl, phenyl, pyrimidine and pyridine;

R³³ is independently selected from

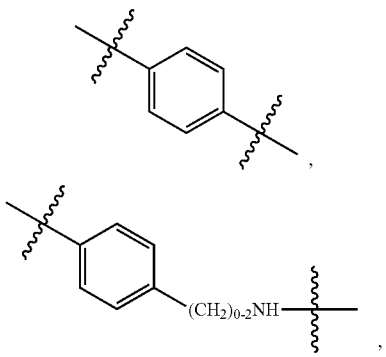

TABLE 2-continued

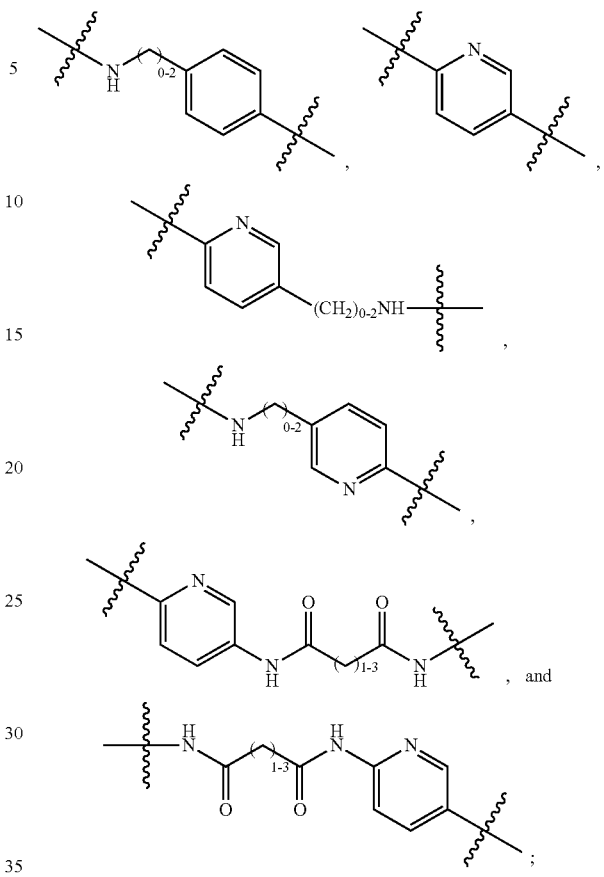

$R^{34}$ is independently selected from H, $C_{1-4}$ alkyl, and $C_{1-6}$ haloalkyl.

In preferred embodiments, linker, -**L₁L₂-*, of immunoconjugates of Formula (II) and Formula (IIa) includes a group formed upon reaction of a reactive functional group with one of the amino acid side chains commonly used for conjugation, e.g., the thiol of cysteine, the free —NH₂ of lysine, a Pcl or Pyl group engineered into an antibody (see e.g., Ou, et al., PNAS 108(26), 10437-42 (2011)) or a

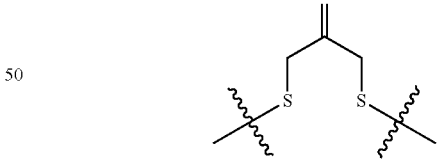

group formed from a disulfide bridge. Such groups formed by reaction with a cysteine residue of the antigen binding moiety include, but are not limited to,

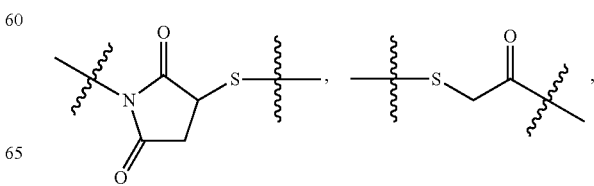

-continued

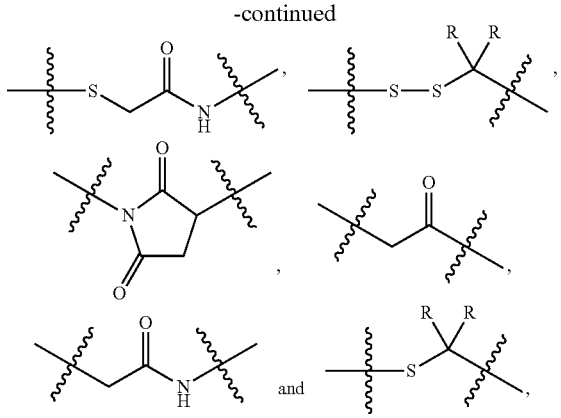

where each R is independently H or $C_{1-4}$ alkyl (preferably methyl). Such groups formed by reaction with the —NH$_2$ of a lysine residue of the antigen binding moiety, where each p is 1-10, and each R is independently H or $C_{1-4}$ alkyl (preferably methyl) include, but are not limited to,

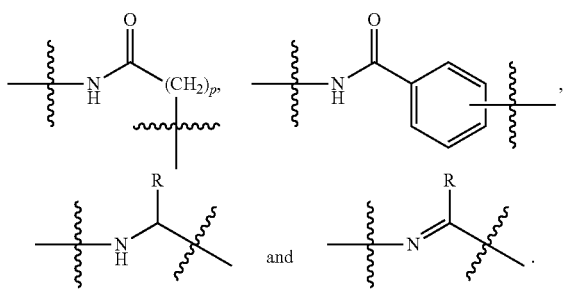

Such groups formed by reaction with a Pcl or Pyl group include, but are not limited to,

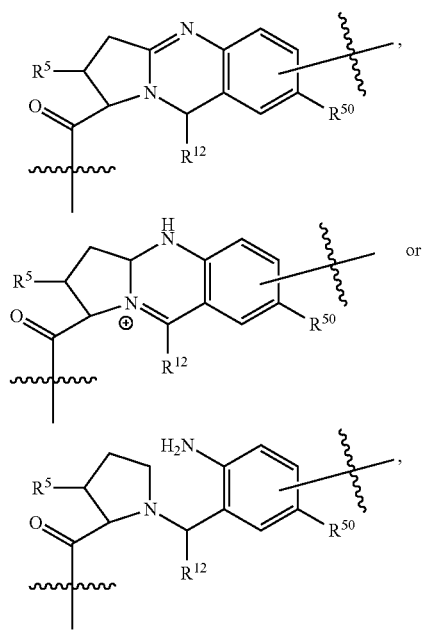

wherein $R^5$ is H or Me, $R^{50}$ is H or nitro, and $R^{12}$ is H, Me or Phenyl, for linking, where the acyl group shown attaches to the lysine portion of a Pcl or Pyl in an engineered antibody. Such a group formed upon reaction of

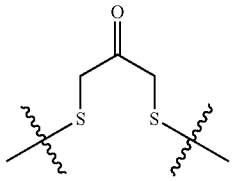 [SMILES: *SCC(=O)CS*]

and a compound of Formula (I) or Formula (Ia) which contains an hydroxylamine is

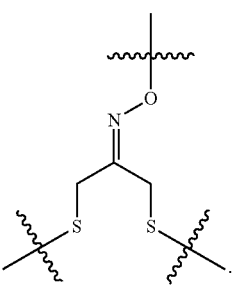 [SMILES: *ON=C(CS*)CS*]

Cytotoxic Cyclic Peptides

The cytotoxic cyclic peptides of the invention, or stereoisomer thereof, and pharmaceutically acceptable salts thereof, are compounds having the structure of Formula (A):

Formula (A)

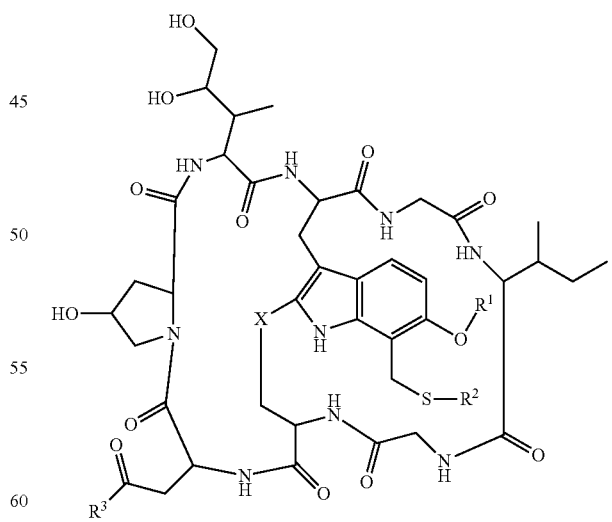

wherein:

X is S(=O), S(=O)$_2$ or S;

$R^1$ is H or —CH$_3$; $R^2$ is -L$_1$L$_2$R$^4$, -L$_3$R$^6$ or —(CH$_2$)$_m$X$_3$(CH$_2$)$_m$R$^4$; $R^3$ is —NH$_2$ or —OH;

$L_1$ is —(CH$_2$)$_m$NR$^5$C(=O)—,

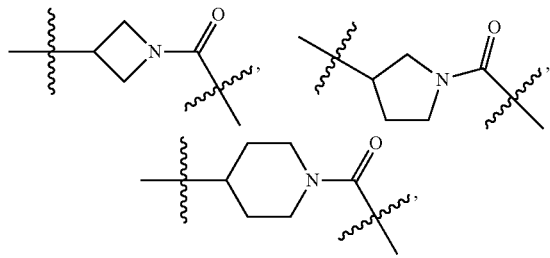

—(CH$_2$)$_m$X$_3$(CH$_2$)$_m$—, —(CH$_2$)$_m$NR$^5$—,

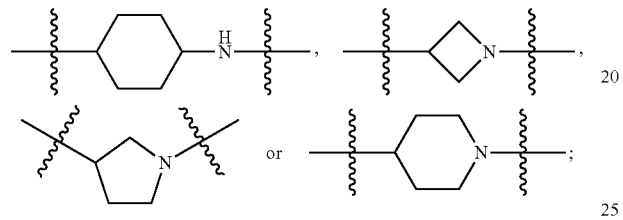

$L_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$—, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)NR$^5$C(=O)(CH$_2$)$_m$—, —(CH$_2$)$_m$C(=O)NR$^5$(CH$_2$)$_m$(O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$)$_n$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$(O(CH$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—,

—(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$—, —(CH$_2$)$_m$—, —(CH$_2$)$_m$(O(CH$_2$)$_m$)C(=O)NR$^5$(CH$_2$)$_m$—, —(CH$_2$)$_m$NR$^5$C(=O)NR$^5$(CH$_2$)$_m$— or —(CH$_2$)$_m$X$_3$(CH$_2$)$_m$NR$^5$C(=O)—, wherein:

$X_1$ is

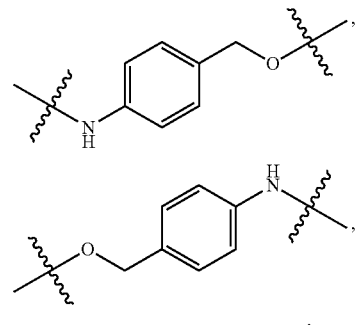

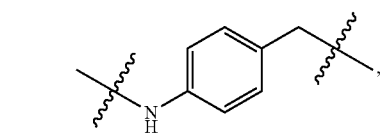

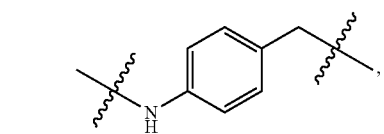

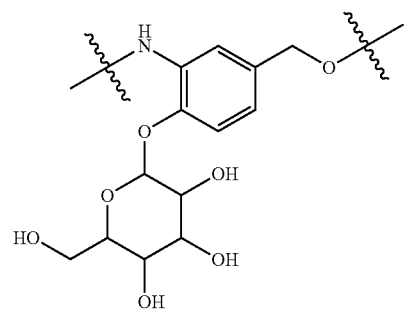

or

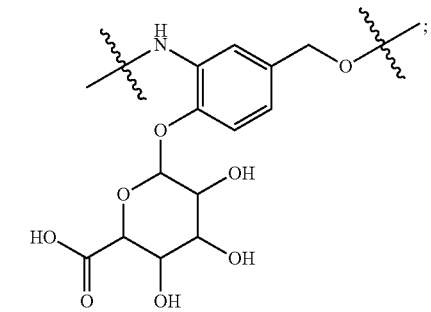

$X_2$ is
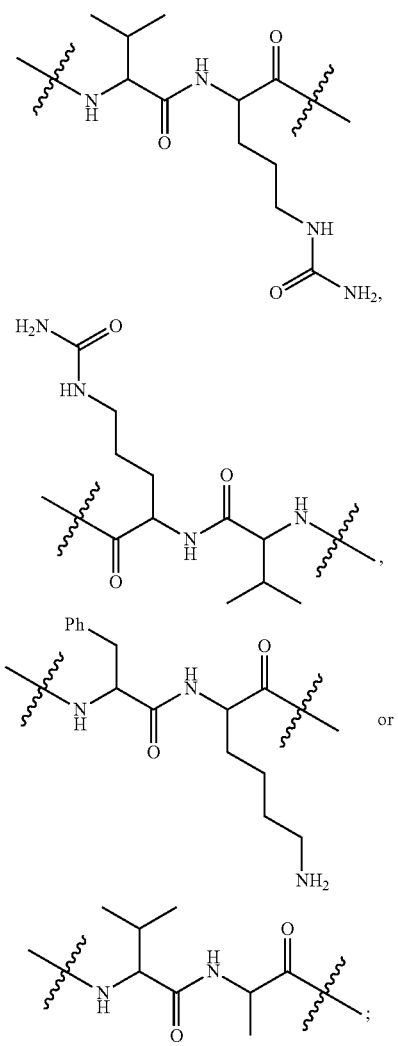
$X_3$ is
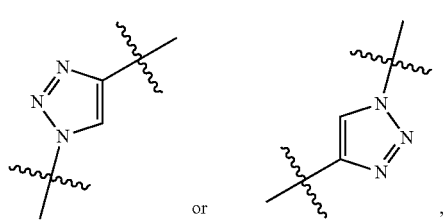 [SMILES: *c1cn(*)nn1 ; *c1cn(*)nn1]
or and $X_4$ is
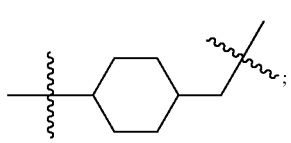 [SMILES: *CC1CCC(*)CC1]
$L_3$ is —$(CH_2)_m NR^5 C(=O)$—;
$R^4$ is
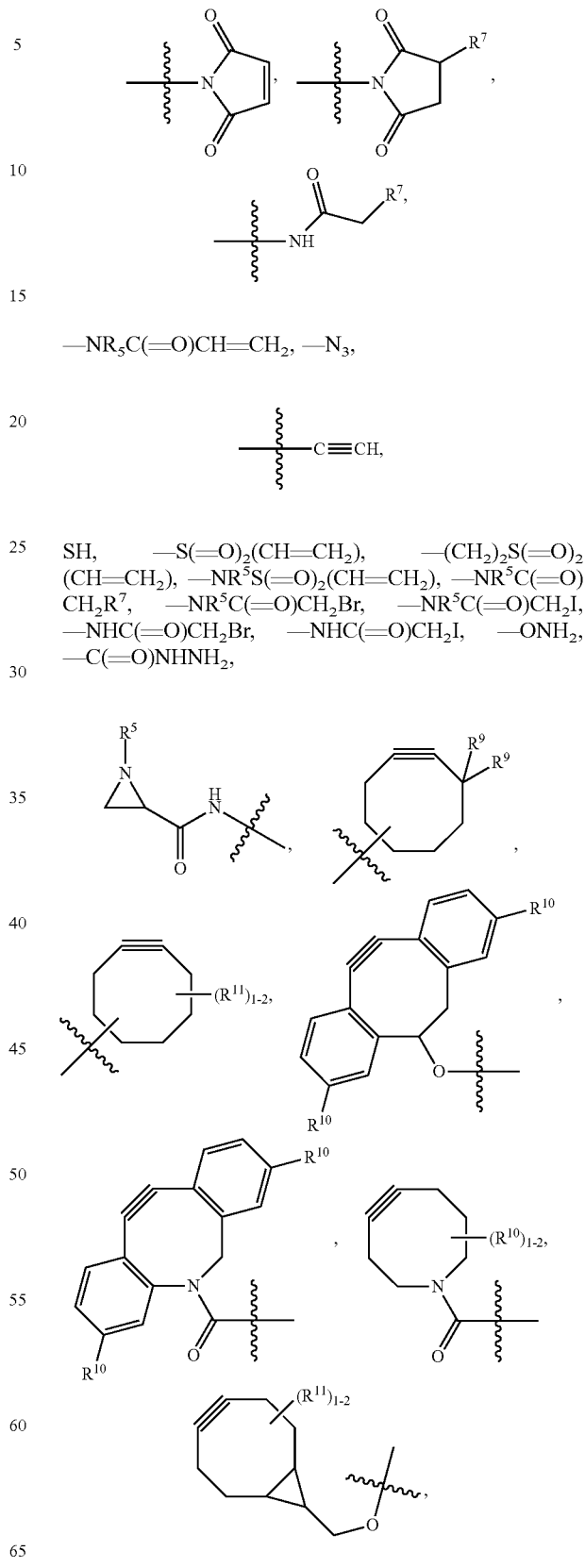
—$NR_5 C(=O)CH=CH_2$, —$N_3$,
SH, —$S(=O)_2(CH=CH_2)$, —$(CH_2)_2 S(=O)_2 (CH=CH_2)$, —$NR^5 S(=O)_2(CH=CH_2)$, —$NR^5 C(=O) CH_2 R^7$, —$NR^5 C(=O)CH_2 Br$, —$NR^5 C(=O)CH_2 I$, —$NHC(=O)CH_2 Br$, —$NHC(=O)CH_2 I$, —$ONH_2$, —$C(=O)NHNH_2$,
—$CO_2 H$, —$NH_2$, —$NC(=O)$, —$NC(=S)$,

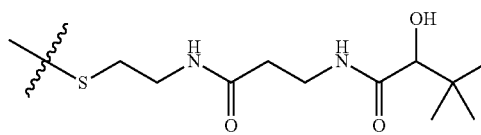

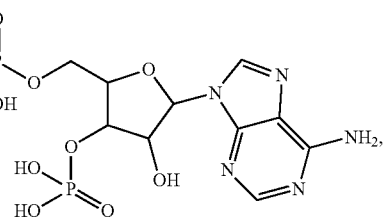

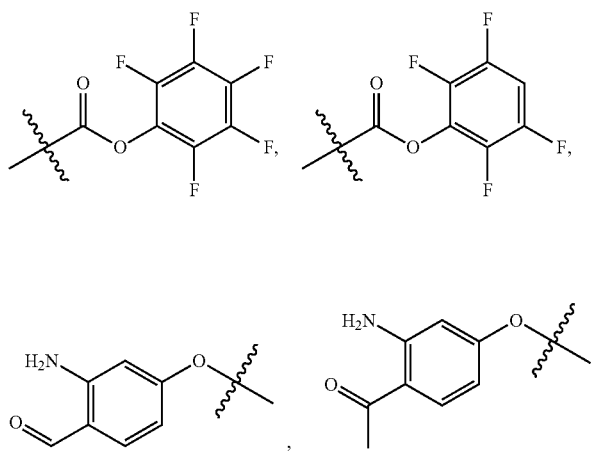

each $R^5$ is independently selected from H and $C_1$-$C_6$alkyl;
$R^6$ is $R^7$ is —S($CH_2$)$_n$$CHR^8$NHC(=O)$R^5$ or
$R^8$ is $R^5$ or —C(=O)O$R^5$;

each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —N($CH_3$)$_2$, —CN, —$NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments the cytotoxic cyclic peptides having the structure of Formula (A), are cytotoxic cyclic peptides having the structure of Formula (I):

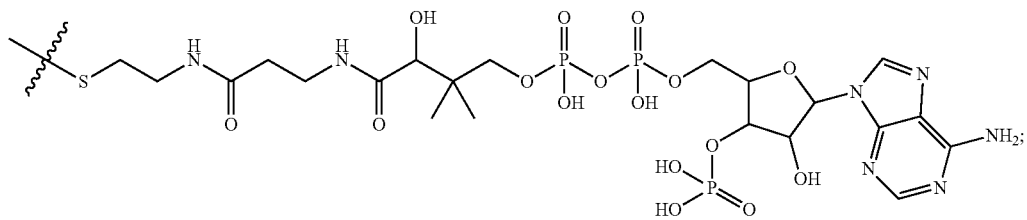 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]

Formula (I)

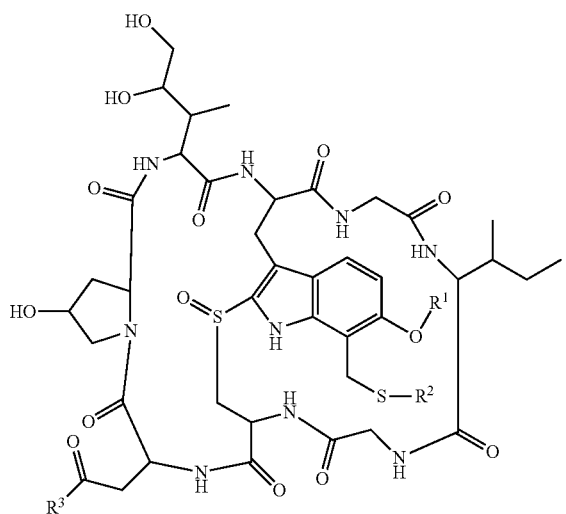

wherein:
R$^1$ is H or —CH$_3$; R$^2$ is -L$_1$L$_2$R$^4$, -L$_3$R$^6$ or —(CH$_2$)$_m$X$_3$(CH$_2$)$_m$R$^4$; R$^3$ is —NH$_2$ or —OH;
L$_1$ is —(CH$_2$)$_m$NR$^5$C(=O)—,

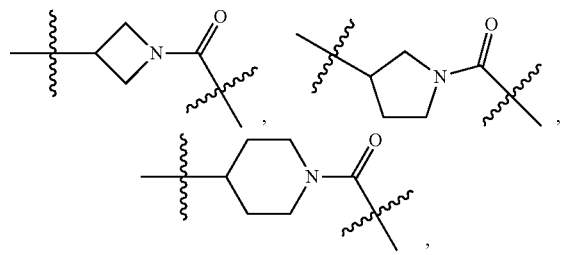

—(CH$_2$)$_m$X$_3$(CH$_2$)$_m$—, —(CH$_2$)$_m$NR$^5$—,

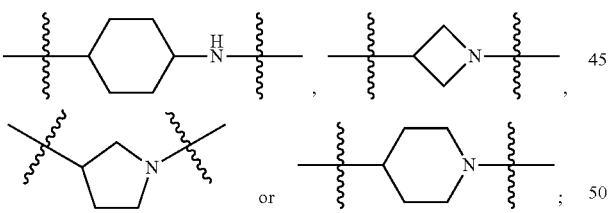

or ;

L$_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$—, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$(O(CH$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$— or —(CH$_2$)$_m$X$_3$(CH$_2$)$_m$NR$^5$C(=O)—, wherein:

X$_1$ is

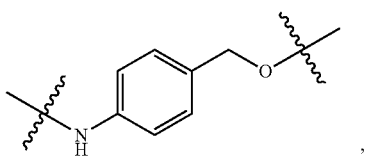

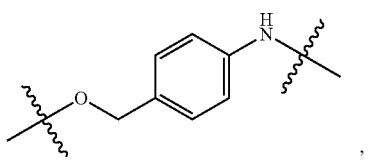

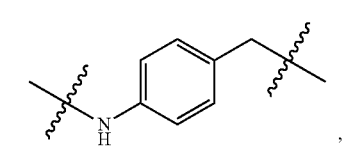

325
-continued
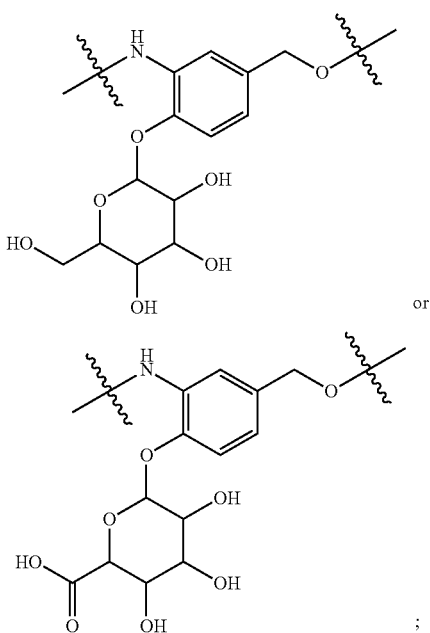
or
$X_2$ is
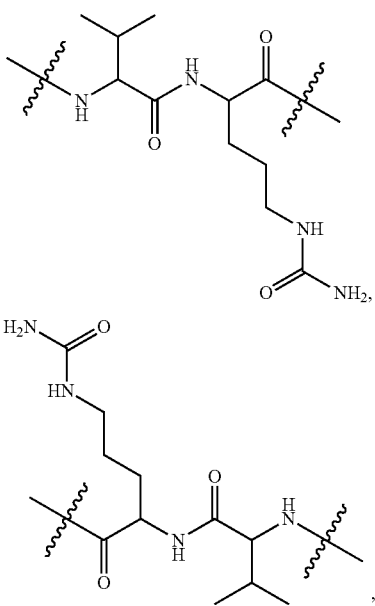
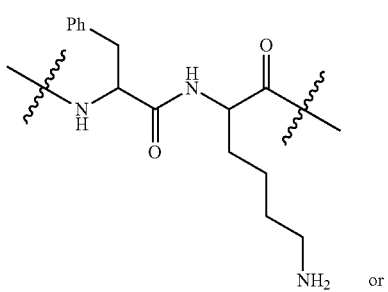
or
326
-continued
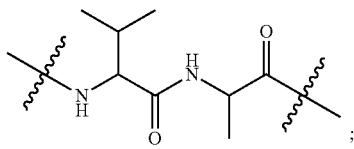
$X_3$ is
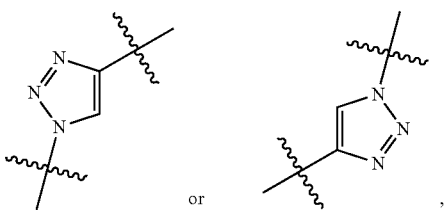 [SMILES: *c1cn(*)nn1 ; *c1cn(*)nn1]
or
and $X_4$ is
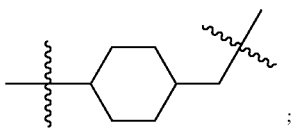
$L_3$ is $-(CH_2)_m NR^5 C(=O)-$;
$R_4$ is
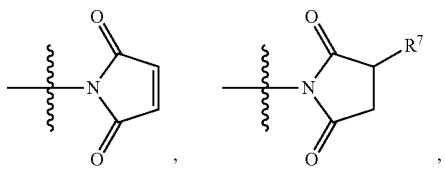
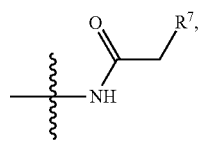
$-NR_5C(=O)CH=CH_2$, $-N_3$,
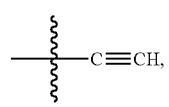
SH, $-S(=O)_2(CH=CH_2)$, $-(CH_2)_2S(=O)_2$ $(CH=CH_2)$, $-NR^5S(=O)_2(CH=CH_2)$, $-NR^5C(=O)$ $CH_2R^7$, $-NR^5C(=O)CH_2Br$, $-NR^5C(=O)CH_2I$, $-NHC(=O)CH_2Br$, $-NHC(=O)CH_2I$, $-ONH_2$, $-C(=O)NHNH_2$,

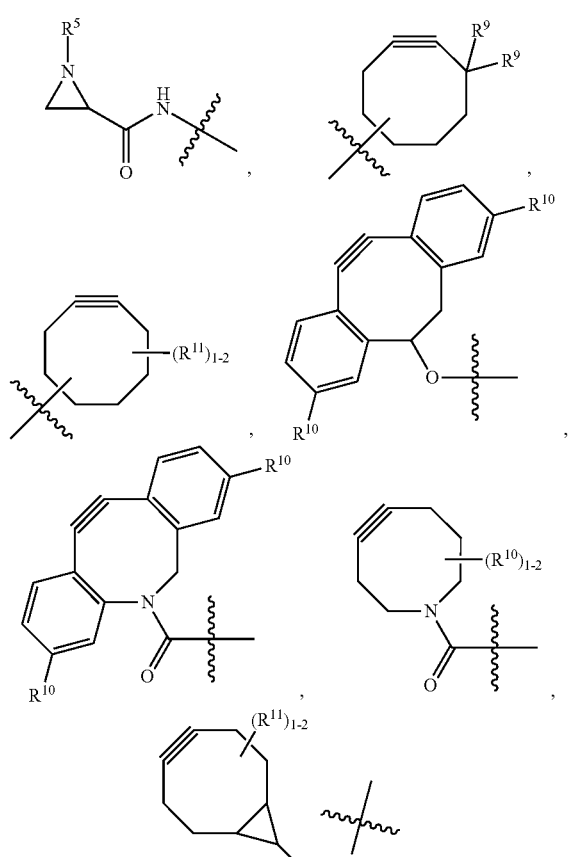
each R[5] is independently selected from H and $C_1$-$C_6$alkyl;
R[6] is
—$CO_2H$, —$NH_2$, —NC(=O), —NC(=S),
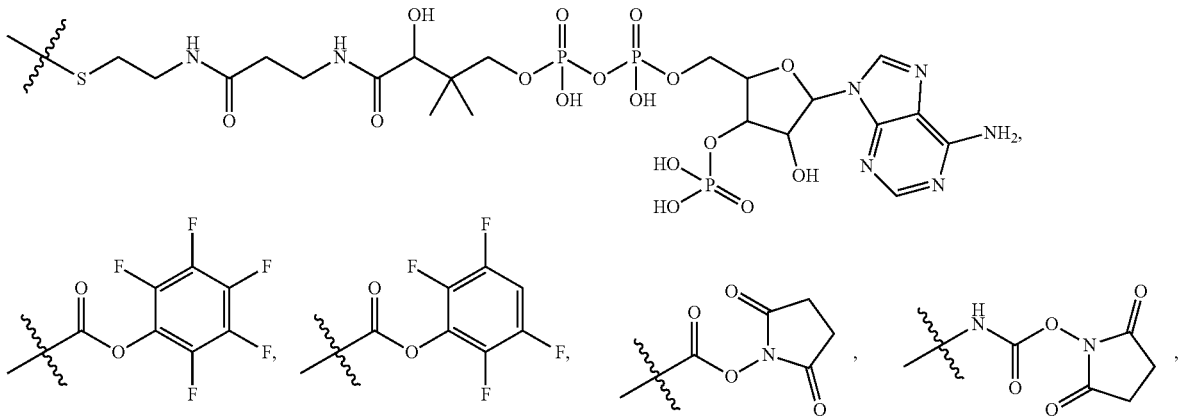
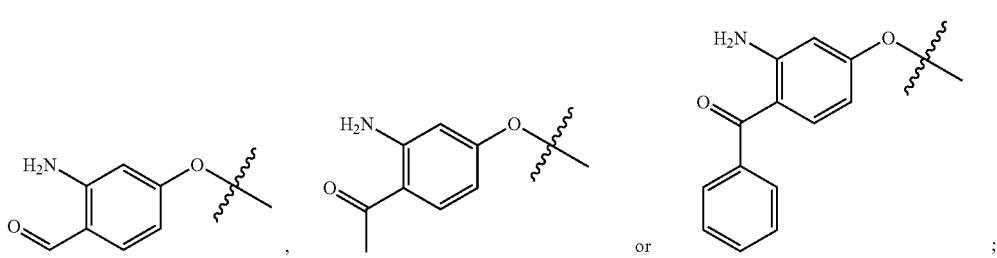

$R^7$ is —S(CH$_2$)$_n$CHR$^8$NHC(=O)R$^5$ or

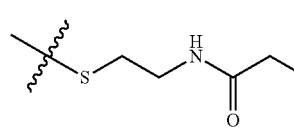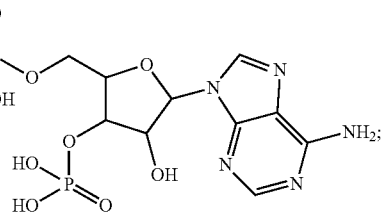

$R^8$ is $R^5$ or —C(=O)OR$^5$;
each $R^9$ is independently selected from H, C$_1$-C$_6$alkyl, F, Cl, and —OH;
each $R^{10}$ is independently selected from H, C$_1$-C$_6$alkyl, F, Cl, —NH$_2$, —OCH$_3$, —OCH$_2$CH$_3$, —N(CH$_3$)$_2$, —CN, —NO$_2$ and —OH;
each $R^{11}$ is independently selected from H, C$_{1-6}$alkyl, fluoro, benzyloxy substituted with —C(=O)OH, benzyl substituted with —C(=O)OH, C$_{1-4}$alkoxy substituted with —C(=O)OH and C$_{1-4}$alkyl substituted with —C(=O)OH;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.

In other embodiments the cytotoxic cyclic peptides having the structure of Formula (A), are cytotoxic cyclic peptides having the structure of Formula (I):

Formula (I)

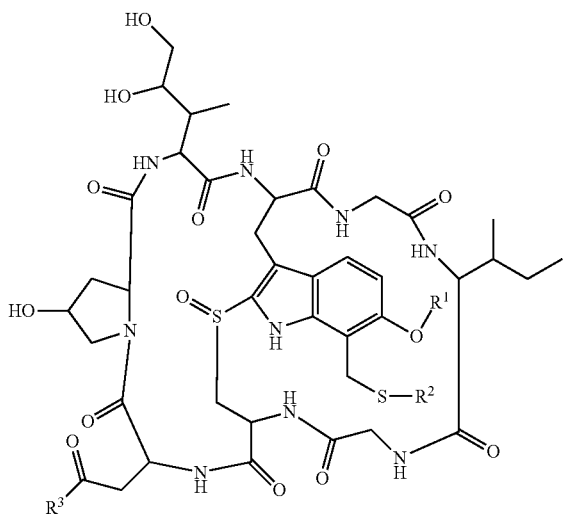

wherein:
$R^1$ is H or —CH$_3$; $R^2$ is -L$_1$L$_2$R$^4$, -L$_3$R$^6$ or —(CH$_2$)$_m$X$_3$(CH$_2$)$_m$R$^4$; $R^3$ is —NH$_2$ or —OH;
L$_1$ is —(CH$_2$)$_m$NR$^5$C(=O)—,

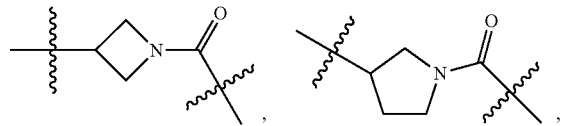

-continued

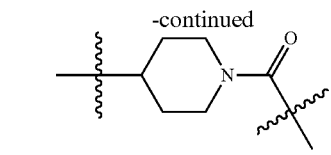

—(CH$_2$)$_m$X$_3$(CH$_2$)$_m$—, —(CH$_2$)$_m$NR$^5$—,

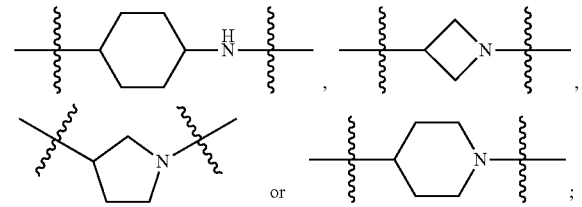

L$_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$—, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$(O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O

—(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$(O(CH$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$—, —(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$— or —(CH$_2$)$_m$X$_3$(CH$_2$)$_m$NR$^5$C(=O)—, wherein:

X$_1$ is

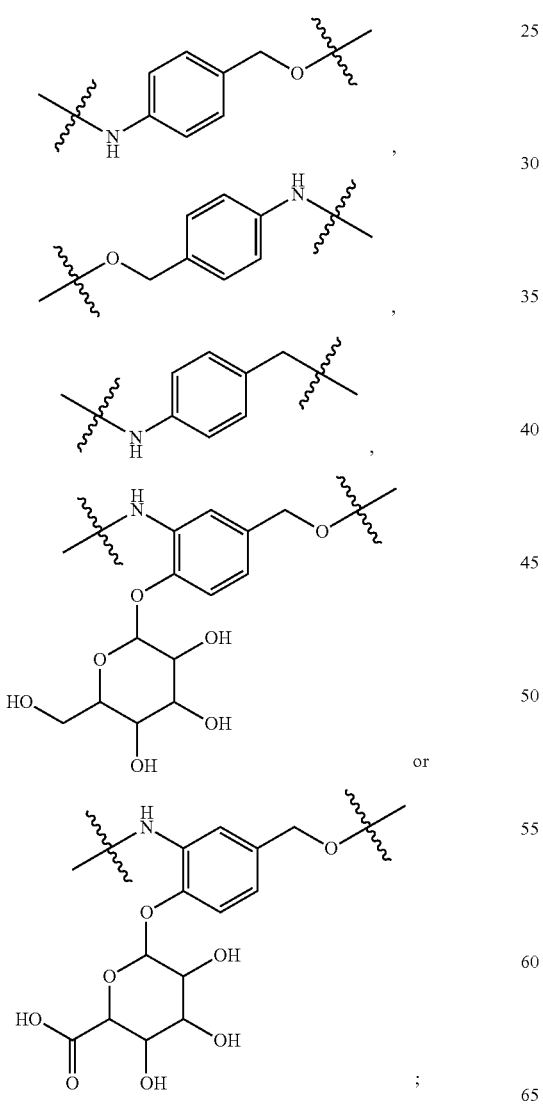

;

X$_2$ is

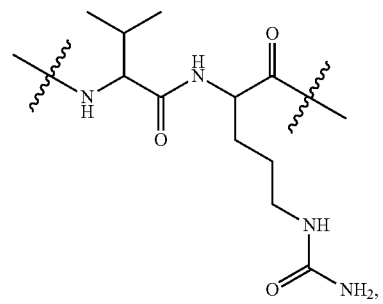

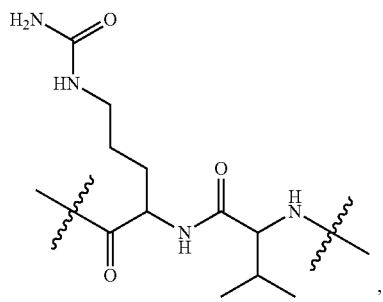

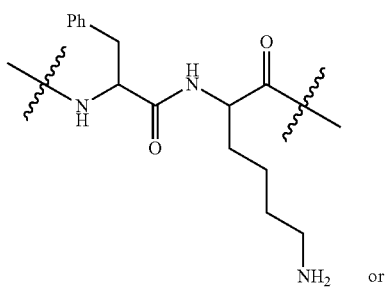

;

X$_3$ is

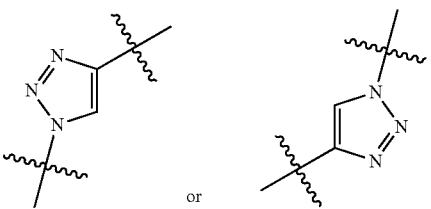 [SMILES: *c1cn(*)nn1 ; *c1cn(*)nn1]

or and X$_4$ is

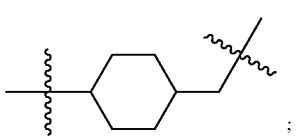

;

333
$L_3$ is $-(CH_2)_m NR^5C(=O)-$;
$R^4$ is
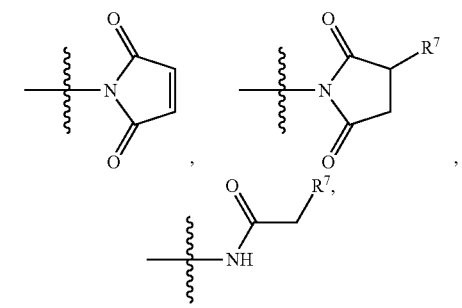
$-NR_5C(=O)CH=CH_2$, $-N_3$,
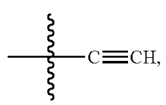
SH, $-S(=O)_2(CH=CH_2)$, $-NR^5S(=O)_2(CH=CH_2)$, $-NR^5C(=O)CH_2R^7$, $-NR^5C(=O)CH_2Br$, $-NR^5C(=O)CH_2I$, $-NHC(=O)CH_2Br$, $-NHC(=O)CH_2I$, $-ONH_2$, $-C(=O)NHNH_2$,
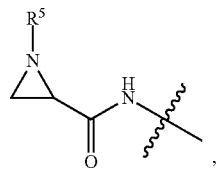 , 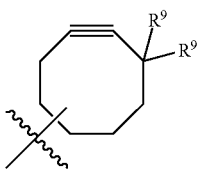 ,
334
-continued
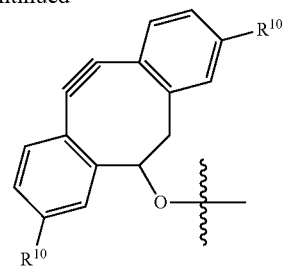
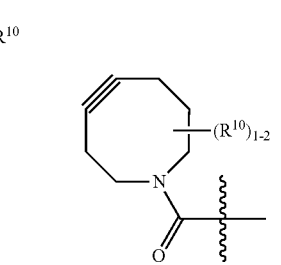
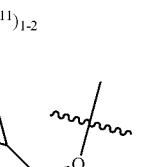
$-CO_2H$, $-NH_2$, $-NCO$, $-NCS$,
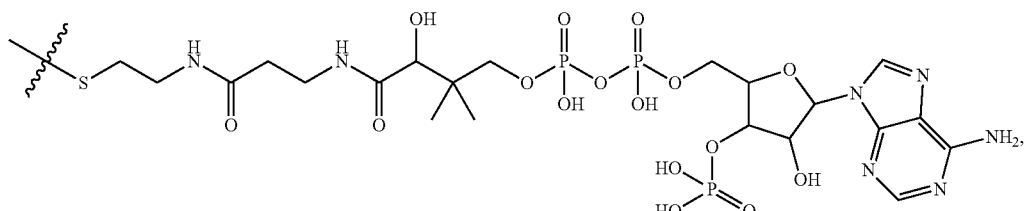
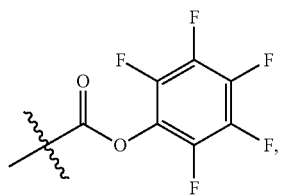 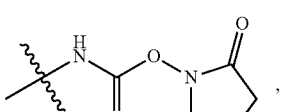 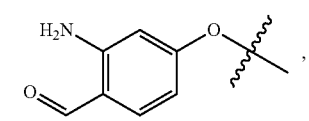
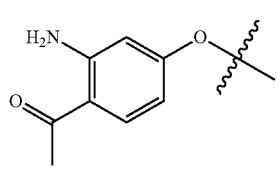 or 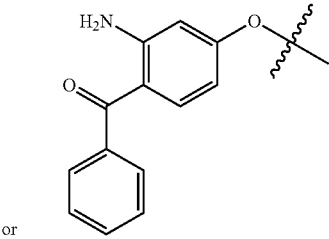 ;

each $R^5$ is independently selected from H and $C_1$-$C_6$alkyl;
$R^6$ is

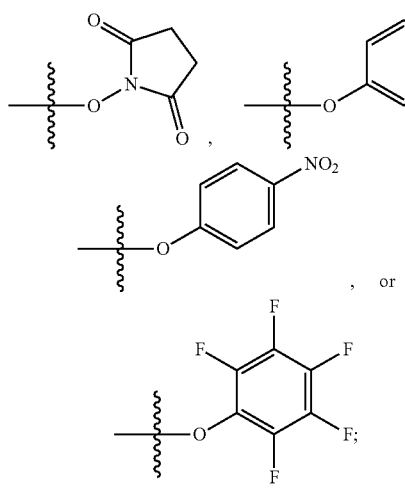

, or $R^7$ is —S(CH$_2$)$_n$CHR$^8$NHC(=O)R$^5$ or

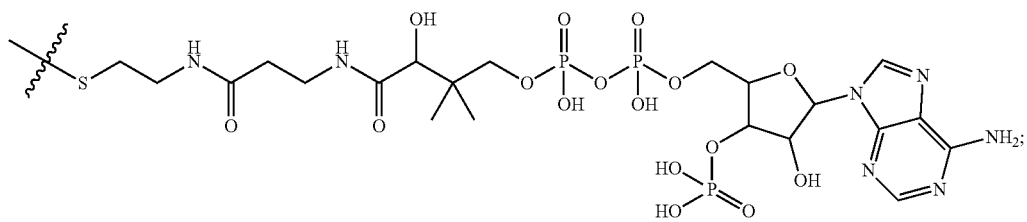 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]

$R^8$ is $R^5$ or —C(=O)OR$^5$;

each $R^9$ is independently selected from H, $C_1$-$C_6$alkyl, F, Cl, and —OH;

each $R^{10}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments the cytotoxic cyclic peptides having the structure of Formula (I), are cytotoxic cyclic peptides having the structure of Formula (Ia):

Formula (Ia)

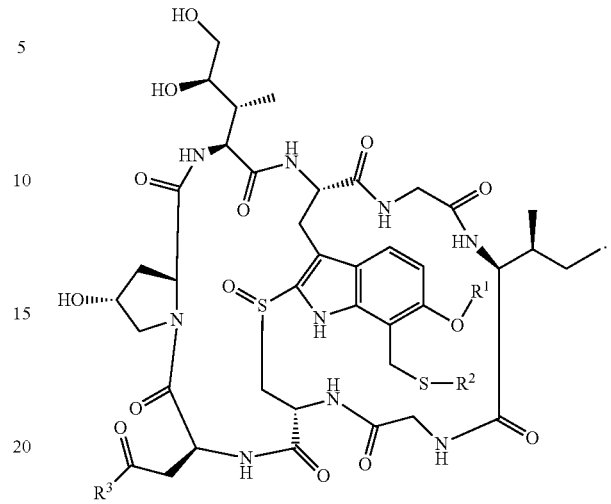

Synthetic Methods

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (see e.g., Houben-Weyl 4th Ed. 1952, *Methods of Organic Synthesis*, Thieme, Volume 21). Further, the compounds of the present invention can be produced by organic synthesis methods known to one of ordinary skill in the art in view of the following examples.

Illustrative examples of synthetic approaches to the compound of Formula (I) and Formula (Ia) are provided in the following general Scheme 1 and Scheme 2.

In Scheme 1, a Thiol-Mannich reaction is used to couple a protected amine to the 7 position of the indole of an Amanitin (α or β) via formation of a methylene linked thio ether. Following deprotection of the amine, an R$^2$ group is coupled to the amine via the formation of an amide bond.

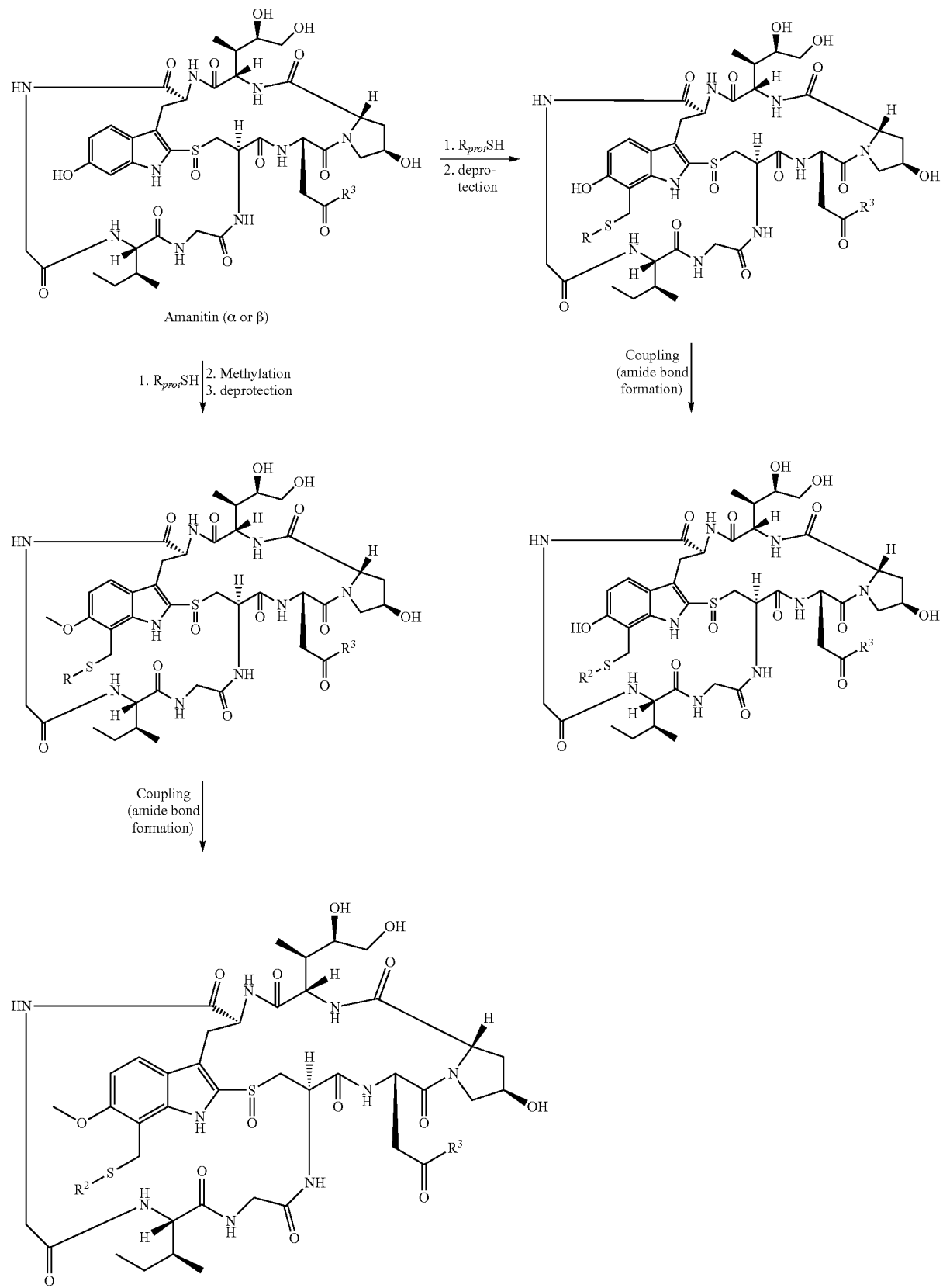

where: $R_{prot}$ is a protected amine including, but not limited to, $-(CH_2)_m NH\text{-Prot}$,

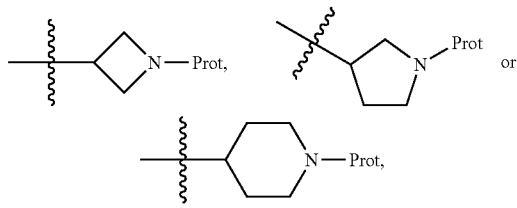

where Prot is an amine protecting group including, but not limited to, $-C(=O)OC(CH_3)_3$ (i.e. Boc). R is an amine including, but not limited to, $-(CH_2)_m NH_2$,

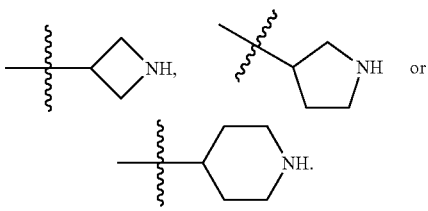

$R^2$ is $-L_1L_2R^4$ or $-L_3R^6$. $L_1$, $L_2$, $R^4$ and $R^6$ are as defined herein.

In Scheme 2, a Thiol-Mannich reaction is used to couple a reactive group (Rx) to the 7 position of the indole of an Amanitin (α or β) via formation of a methylene linked thio ether. Then an $R^4$ group is linked to the thio ether via formation of chemical moiety (Rz) formed by the reaction Rx with a second reaction group Ry.

Scheme 2

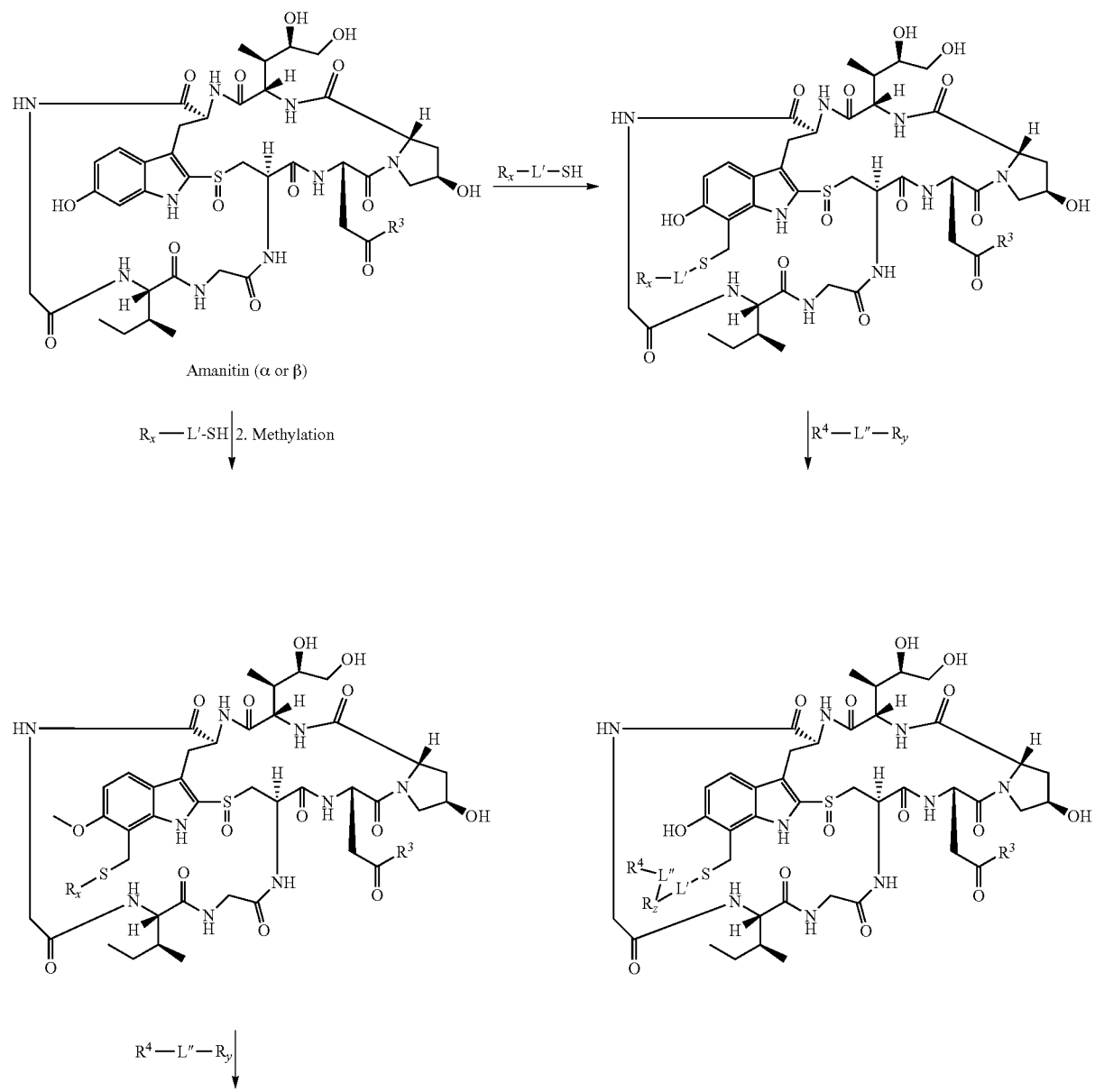

-continued

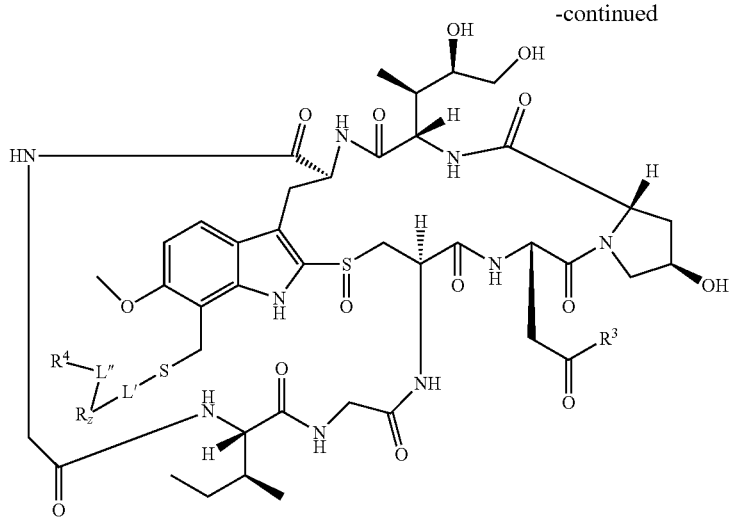

where: Rx is Reactive Group 1 (RG$_1$) or Reactive Group 2 (RG$_2$) as shown in Table 1 and Ry is Reactive Group 1 (RG$_1$) or Reactive Group 2 (RG$_2$) as shown in Table 1. Rz is the resulting chemical moiety, as shown in Table 1, formed from the reaction of Reactive Group 1 (RG1) or Reactive Group 2 (RG2). L' and L" are a bond or a linker component, such as those described herein for L$_2$. R$^4$ is as defined herein.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The following examples are intended to illustrate the invention and are not to be construed as being limitations thereon. Temperatures are given in degrees Celsius. Room temperature (rt) is 20 to 21° C. If not mentioned otherwise, all evaporations are performed under reduced pressure, typically between about 1 mm Hg and 100 mm Hg (=1-133 mbar). Abbreviations used are those conventional in the art. All reactions were carried out under nitrogen using commercial grade anhydrous solvents without any further distillation. Reagents were used as commercial grade without further purification. Thin layer chromatography was carried out using TLC silica gel plates. Column chromatography was carried out using an ISCO Combiflash Rf system, using flash grade prepacked Redisep® columns.

Preparative HPLC was performed on Waters Autopurification system using the following conditions: Column Sunfire C18 30×100 mm, 5ρ, gradient elution with CH$_3$CN in water+0.05% TFA-CH$_3$CN at 30 ml/min.

After chromatography purification fractions containing desired product of appropreate purity were combined and concentrated to obtain desired products.

Analytical Methods

Unless otherwise indicated, the following HPLC and HPLC/MS methods were used in the preparation of Intermediates and Examples.

LC/MS analysis was performed on an Agilent 1200 sl/6140 system.

Column: Waters Acquity HSS T3 C18, 50×2.0, 1.8 um

Mobile Phase: A) H$_2$O+0.05% TFA; B: acetonitrile+ 0.035% TFA

Pump Method:

| Time | A % | B % | Flow (mL/min) |
| --- | --- | --- | --- |
| 0 | 90 | 10 | 0.9 |
| 1.35 | 0 | 100 | 0.9 |
| 1.36 | 0 | 100 | 0.9 |
| 1.95 | 0 | 100 | 0.9 |
| 1.96 | 90 | 10 | 0.9 |
| 2.0 | 90 | 10 | 0.9 |

Detection: UV Diode Array at 190 nm-400 nm
MS Scan: 200-1350 amu
ELSD: 60° C.
MS Parameters:

| Polarity | Positive |
| --- | --- |
| Drying Gas | 12 |
| Nebulizer Pressure | 50 |
| Drying Gas Temperature | 350 |
| Capillary Voltage | 3000 |

Synthetic Procedure for Intermediates

Synthesis of 6-(6-(2,5-dioxo-2,5-dihydro-1H-pyrrol-1-yl)hexanamido)hexanoic Acid (i-1)

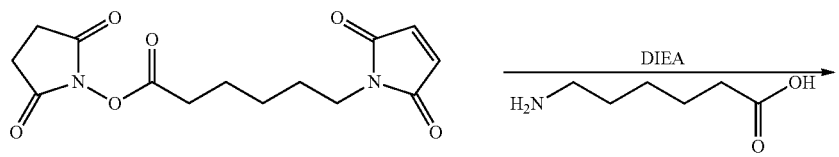

-continued

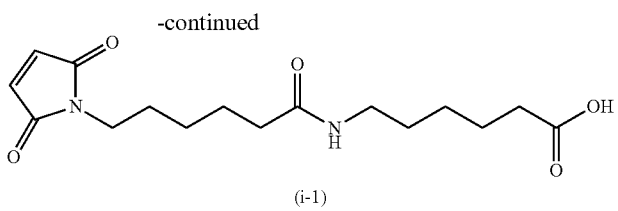

(i-1)

DIEA (N,N-diisopropylethylamine, 85 μL, 0.49 mmol) and 6-aminohexanoic acid (47 mg, 0.36 mmol) were added to a solution of 6-maleimidohexanoic acid N-hydroxysuccinimide ester (0.32 mmol) in DMF (5 mL) in a 40 mL vial and the reaction mixture was stirred at rt for 4 h. The reaction mixture was then purified by HPLC and lyophilized to give 6-(6-(2,5-dioxo-2,5-dihydro-1H-pyrrol-1-yl)hexanamido)hexanoic acid (i-1). MS (M+1)=325, 1H-NMR (CDCl3, 400 MHz) δ 6.69 (s, 2H), 5.67 (s, 1H), 3.51 (t, 2H, J=7.2 Hz), 3.26 (dd, 2H, J=6.8 and 12.8 Hz), 2.36 (t, 2H, 7.2 Hz), 2.17 (t, 2H, 7.2 Hz), 1.61 (m, 6H) 1.52 (m, 2H), 1.30 (m, 4H).

Synthesis of 6-(4-((2,5-dioxo-2,5-dihydro-1H-pyrrol-1-yl)methyl)cyclohexanecarboxamido) hexanoic Acid (i-2)

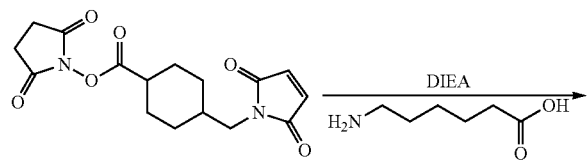

(i-2)

DIEA (78 μL, 0.50 mmol) and 6-aminohexanoic acid (44 mg, 0.33 mmol) were added to a solution of succinimidyl-4-(N-maleimidomethyl)cyclohexane-1-carboxylate (0.30 mmol) in DMF (5 mL) in a 40 mL vial, and the reaction mixture was stirred at rt for 4 h. The reaction mixture was then purified by HPLC and lyophilized to give 76-(4-((2,5-dioxo-2,5-dihydro-1H-pyrrol-1-yl)methyl)cyclohexanecarboxamido)hexanoic acid (i-2). MS (M+1)=351, 1H-NMR (MeOD, 400 MHz) δ 7.79 (bs, 1H), 6.76 (s, 2H), 3.29 (d, 2H, J=4.4 Hz), 3.10 (m, 2H), 2.24 (t, 2H, J=7.2 Hz), 2.07 (m, 4H), 1.56 (m, 3H) 1.43 (m, 3H), 1.33 (m, 3H), 0.97 (m, 2H).

Synthesis of 6-(4-((2,5-dioxo-2,5-dihydro-1H-pyrrol-1-yl)methyl)cyclohexanecarboxamido) hexanoic Acid (i-3)

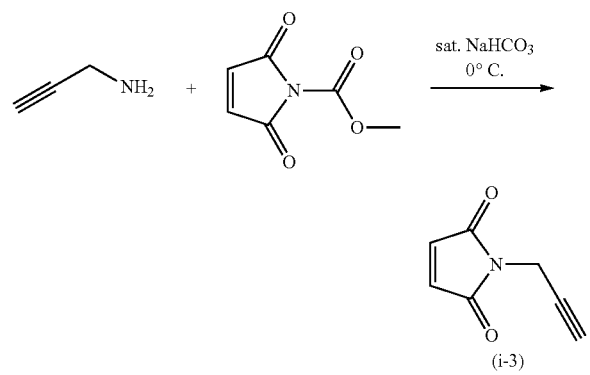

(i-3)

Using a 40 mL vial, a solution of prop-2-yn-1-amine (500 mg, 9.08 mmol) in 15 mL of sat. aqueous NaHCO3 was cooled to 0° C. with ice bath and then methyl 2,5-dioxo-2,5-dihydro-1H-pyrrole-1-carboxylate (1.27 g, 8.17 mmol) was added. The reaction mixture was then stirred at the same temperature for 4 h and then extracted with 50 mL of CH2Cl2 three times. The combined organic layers were dried over Na2SO4, concentrated, purified by ISCO (24 g, silica gel) and concentrated to give 1-(prop-2-yn-1-yl)-1H-pyrrole-2,5-dione (i-3). 1H-NMR (CDCl3, 400 MHz) δ 6.76 (s, 2H), 4.29 (d, 2H, J=2.8 Hz), 2.21 (t, 1H, J=2.8 Hz).

Synthesis of 1-(6-aminohexyl)-1H-pyrrole-2,5-dione (i-4)

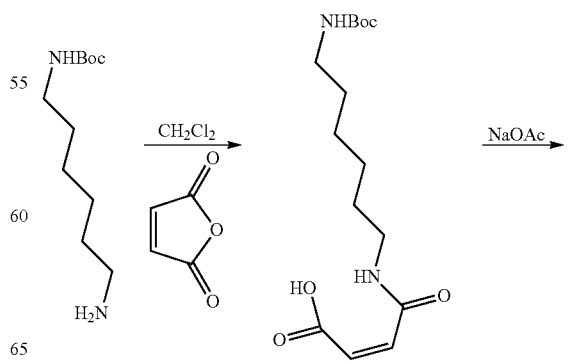

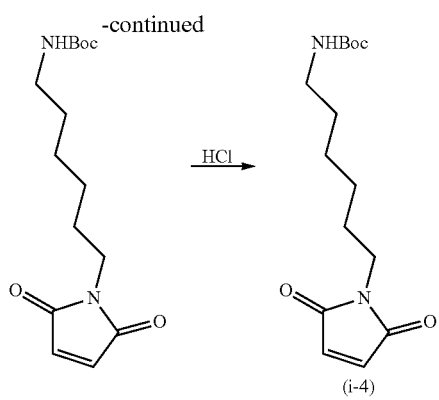

(i-4)

Step 1: Maleic anhydride (249 mg, 2.54 mmol) was added to a solution of tert-butyl (6-aminohexyl)carbamate (500 mg, 2.31 mmol) in anhydrous $CH_2Cl_2$ (10 mL) and the reaction mixture was stirred at rt for 6 h and then concentrated to give (Z)-4-((6-((tert-butoxycarbonyl)amino)hexyl) amino)-4-oxobut-2-enoic acid, which was used in the next reaction without further purification. MS (m+1)=315.2, HPLC Peak RT=1.011 min.

Step 2: Sodium acetate (29 mg, 0.35 mmol) was added to a solution of (Z)-4-((6-((tert-butoxycarbonyl)amino)hexyl) amino)-4-oxobut-2-enoic acid (100 mg, 0.311 mmol) in acetic anhydride (10 mL). The reaction mixture was stirred at 140° C. for 6 h, cooled to rt and then poured into ice water (50 mL). The reaction mixture was extracted with 100 mL of $CH_2Cl_2$ and the organic layer was dried over $Na_2SO_4$, filtered and concentrated. The residue was purified by ISCO on a silica gel (hexanes/ethyl acetate=90/10 to 50/50 v/v) to give tert-butyl (6-(2,5-dioxo-2,5-dihydro-1H-pyrrol-1-yl) hexyl)carbamate. 1H-NMR (CDCl3, 400 MHz) δ 6.68 (s, 2H), 4.51 (bs, 1H), 3.50 (t, 2H, J=7.2 Hz), 3.08 (s, 2H), 1.71 (bs, 1H), 1.52 (m, 2H), 1.44 (m, 2H), 1.43 (s, 9H), 1.31 (m, 4H).

Step 3: A solution of tert-butyl (6-(2,5-dioxo-2,5-dihydro-1H-pyrrol-1-yl)hexyl)carbamate (30 mg, 0.14 mmol) in 3M HCl in MeOH (5 mL) was concentrated in a vacuo This process was repeated three times to give 1-(6-aminohexyl)-1H-pyrrole-2,5-dione (i-4). MS (m+1)=196.8, HPLC Peak RT=0.488 min, 1H-NMR (MeOD-d4, 400 MHz) δ 6.72 (s, 2H), 3.41 (t, 2H, J=6.8 Hz), 3.22 (m, 2H), 2.82 (t, 2H, J=7.6 Hz), 1.53 (m, 4H), 1.33 (m, 4H).

Synthesis of 4-nitrophenyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate
(i-6)

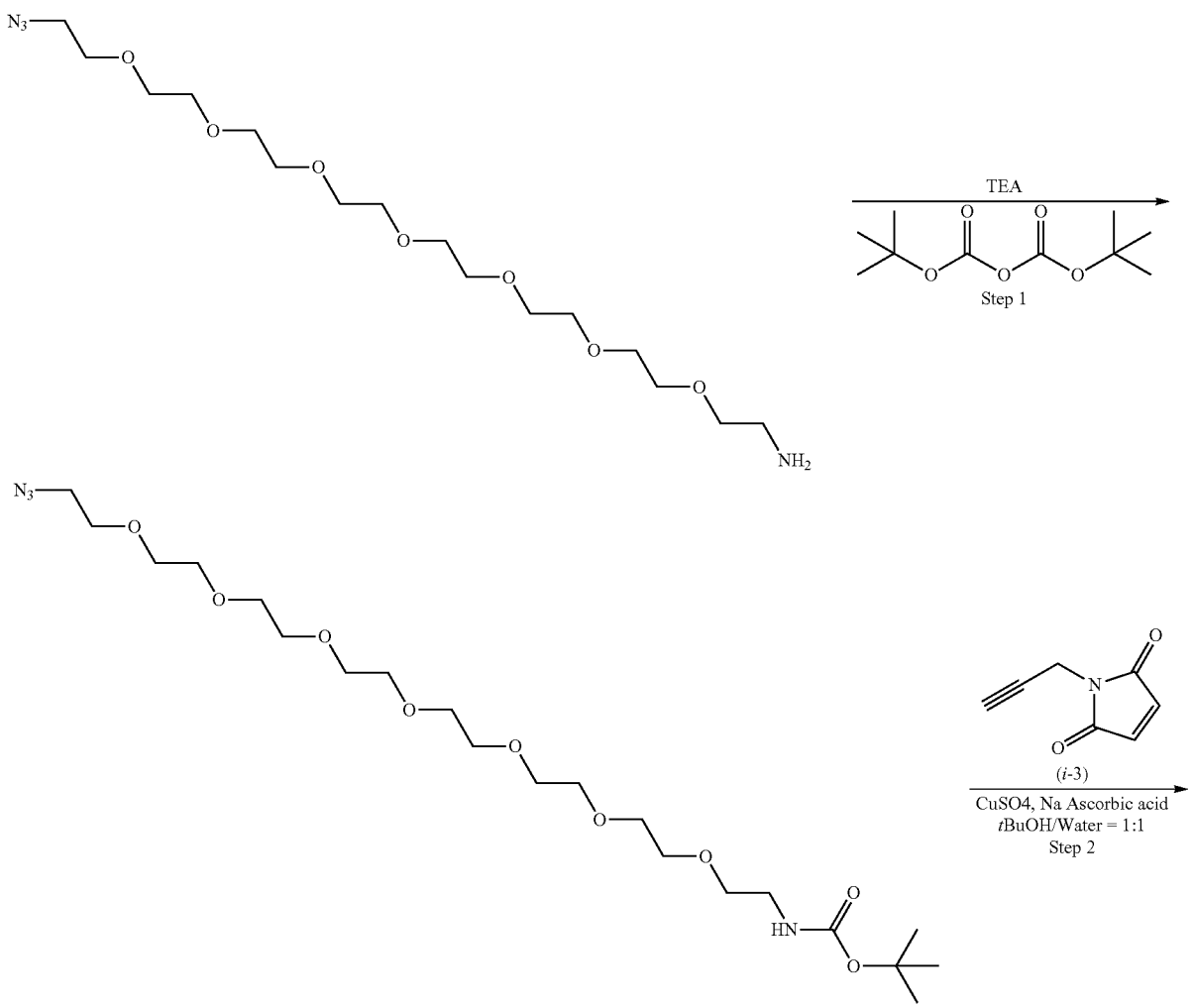

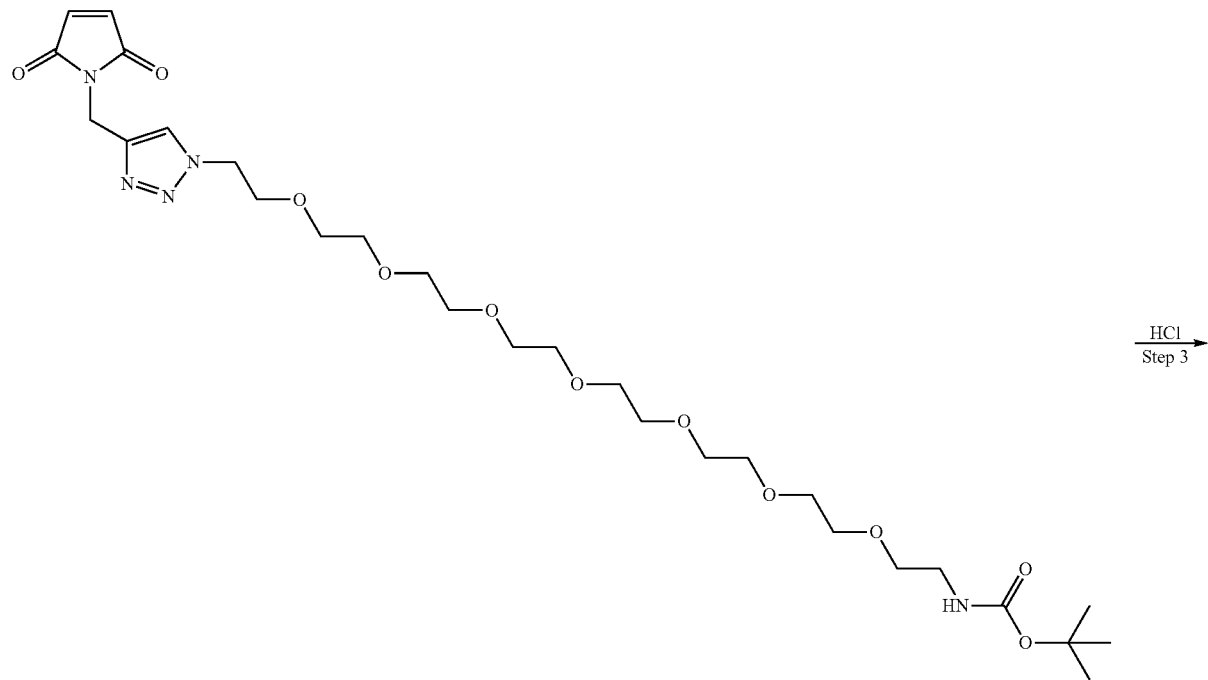
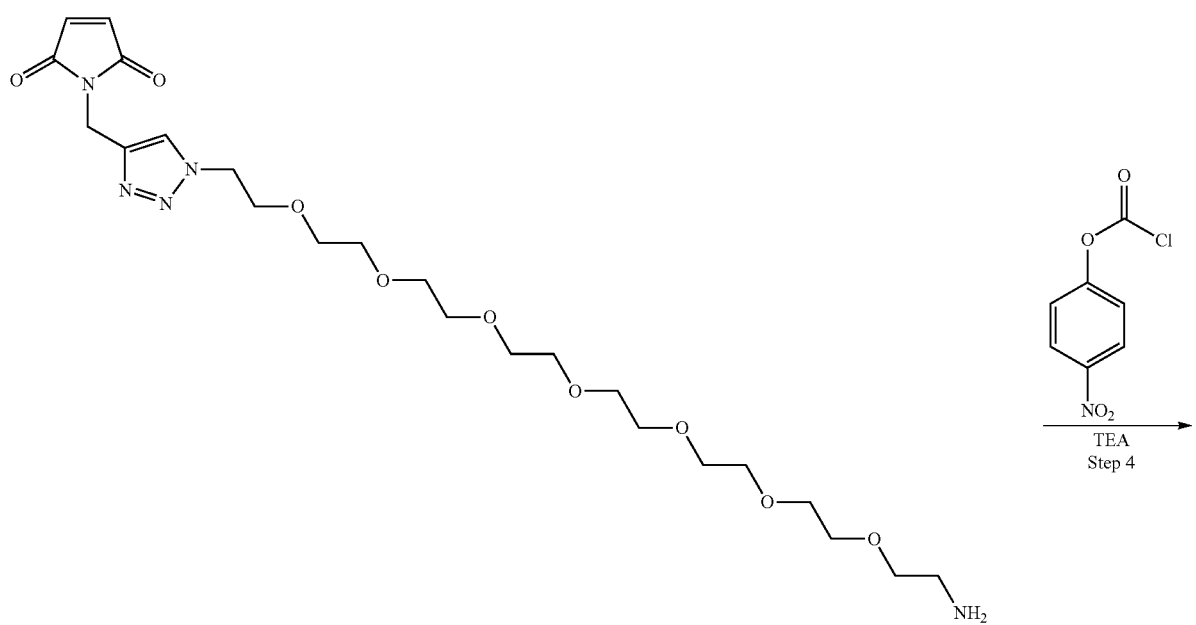

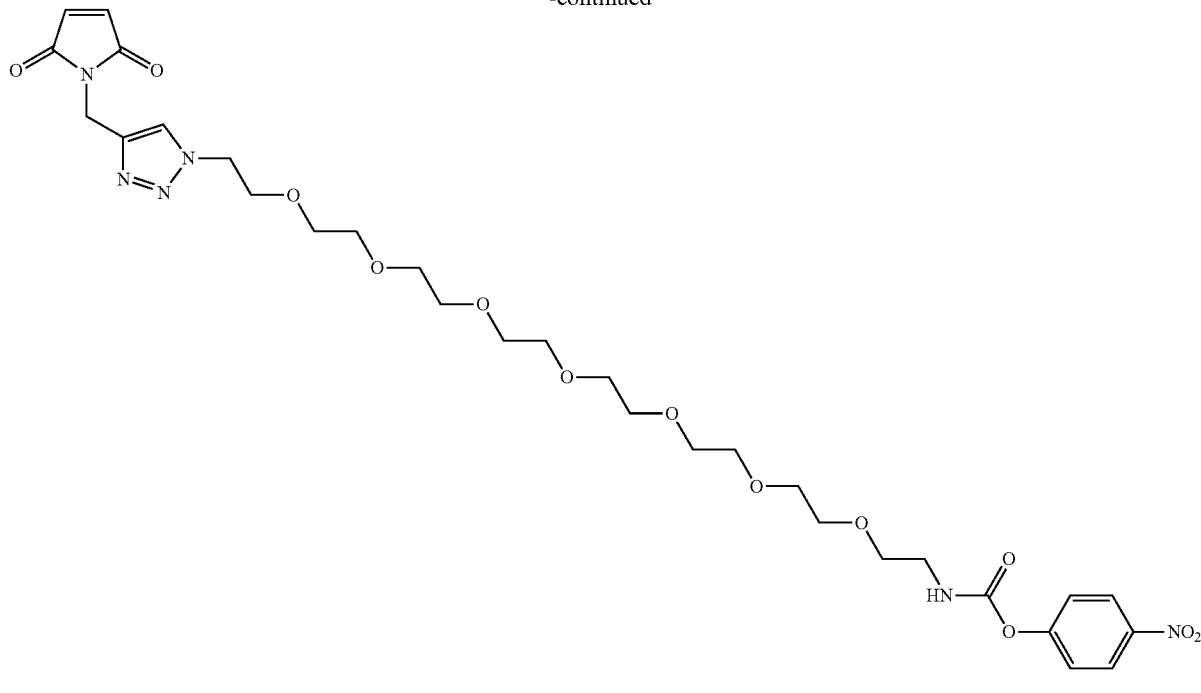

(i-6)

Step 1: Synthesis of tert-butyl (23-azido-3,6,9,12,15,18,21-heptaoxatricosyl)carbamate Triethylamine (0.044 mL, 0.32 mmol) and di-tert-butyl dicarbonate (31 mg, 0.14 mmol) were added to a solution of 23-azido-3,6,9,12,15,18,21-heptaoxatricosan-1-amine (50 mg, 0.13 mmol) in $CH_2Cl_2$ (5 mL) and the reaction mixture was stirred at rt for 1 h. The reaction mixture was then concentrated in vacuo and the residue was purified using 15.5 g of RP-C18 ISCO and then lyophilized to give tert-butyl (23-azido-3,6,9,12,15,18,21-heptaoxatricosyl)carbamate. 1H-NMR (MeOD-d4, 400 MHz) δ 3.61 (m, 24H), 3.48 (t, 2H, J=5.6 Hz), 3.34 (t, 2H, J=4.8 Hz), 3.19 (t, 2H, J=5.6 Hz), 1.41 (s, 9H).

Step 2: Synthesis of tert-butyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate A solution of tert-butyl (23-azido-3,6,9,12,15,18,21-heptaoxatricosyl)carbamate (61 mg, 0.12 mmol) and 1-(prop-2-yn-1-yl)-1H-pyrrole-2,5-dione (i-3) (34 mg, 0.25 mmol) in t-butanol (3 mL) was flushed with $N_2$ gas five times and then L-ascorbic acid sodium salt (24 mg, 0.12 mmol in 1.5 mL of $H_2O$) and $CuSO_4$ (3.9 mg, 0.025 mmol in 1.5 mL water) were added. The reaction mixture was again flushed with $N_2$ gas five times and then stirred at rt for 4 h. The reaction mixture was then purified by HPLC and lyophilized to give tert-butyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate. MS (m+2/2)=630.4, HPLC Peak RT=0.968 min, 1H-NMR (MeOD-d4, 400 MHz) δ 7.93 (s, 1H), 6.83 (s, 2H), 4.23 (s, 2H), 4.51 (t, 2H, J=4.8 Hz), 3.83 (t, 2H, J=5.2 Hz), 3.55 (m, 24H), 3.46 (t, 2H, J=5.6 Hz), 3.17 (t, 2H, J=5.6 Hz), 1.39 (s, 9H).

Step 3: Synthesis of 1-((1-(23-amino-3,6,9,12,15,18,21-heptaoxatricosyl)-1H-1,2,3-triazol-4-yl)methyl)-1H-pyrrole-2,5-dione A solution of tert-butyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate (54 mg, 0.086 mmol) in 3M HCl in MeOH (5 mL) was concentrated in vacuo, and the process was repeated three times to give 1-((1-(23-amino-3,6,9,12,15,18,21-heptaoxatricosyl)-1H-1,2,3-triazol-4-yl)methyl)-1H-pyrrole-2,5-dione. MS (m+2/2)=530.3, HPLC Peak RT=0.653 min, 1H-NMR (MeOD-d4, 400 MHz) δ 8.17 (s, 1H), 6.80 (s, 2H), 4.74 (s, 2H), 4.57 (t, 2H, J=5.2 Hz), 3.81 (t, 2H, J=5.2 Hz), 3.62 (t, 2H, J=5.2 Hz), 3.53 (m, 24H), 3.02 (t, 2H, J=4.8 Hz).

Step 4: Synthesis of 4-nitrophenyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate (i-6)

4-Nitrophenyl carbonochloridate (20 mg, 0.095 mmol) and triethylamine (0.033 mL, 0.24 mmol) were added to a solution of 1-((1-(23-amino-3,6,9,12,15,18,21-heptaoxatricosyl)-1H-1,2,3-triazol-4-yl)methyl)-1H-pyrrole-2,5-dione (49 mg, 0.086 mmol) in $CH_2Cl_2$ (10 mL) and the reaction mixture was stirred at rt for 2 h. The reaction mixture was then concentrated in vacuo, purified by 15.5 g of RP-C18 ISCO and then lyophilized to give 4-nitrophenyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate (i-6). MS (m+2/2)=695.3, HPLC Peak RT=1.000 min, 1H-NMR (MeOD-d4, 400 MHz) δ 8.22 (d, 2H, J=9.2 Hz), 7.92 (s, 1H), 7.33 (d, 2H, J=9.2 Hz), 6.81 (s, 2H), 4.72 (s, 2H), 4.49 (t, 2H, J=4.8 Hz), 3.81 (t, 2H, J=5.2 Hz), 3.55 (m, 26H), 3.34 (t, 2H, J=5.6 Hz).

Synthesis of tert-butyl (4-mercaptobutyl)carbamate (i-7)

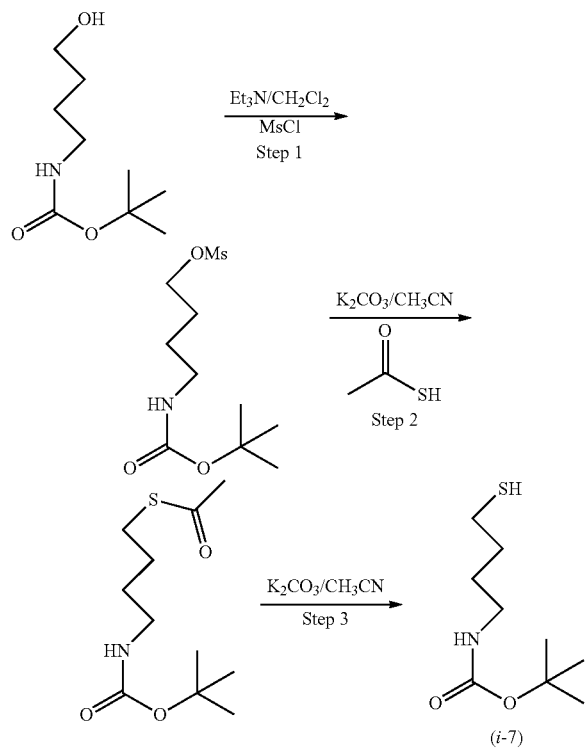

Step 1: Synthesis of 4-((tert-butoxycarbonyl)amino)butyl methanesulfonate

A solution of tert-butyl (4-hydroxybutyl)carbamate (500 mg, 2.64 mmol) and triethylamine (0.442 mL, 3.17 mmol) in CH$_2$Cl$_2$ (100 mL) was cooled to 0° C. with ice-bath and then methanesulfonyl chloride (0.224 mL, 2.91 mmol) was added over 10 min. The reaction mixture was then stirred at rt for 24 h and then washed with water (100 mL×2), dried over Na$_2$SO$_4$ and filtered. The filtrate was concentrated in vacuo and purified by ISCO (40 g of silica gel, EtOAc: hexanes=1:5 to 1:1) to give 4-((tert-butoxycarbonyl)amino) butyl methanesulfonate. 1H-NMR (CDCl3, 400 MHz) δ 4.56 (bs, 1H), 4.25 (t, 2H, J=6.4 Hz), 3.17 (d, 2H, J=6.4 Hz), 3.01 (s, 3H), 1.78 (m, 2H), 1.61 (m, 2H), 1.44 (s, 9H)

Step 2: Synthesis of S-(4-((tert-butoxycarbonyl)amino)butyl) ethanethioate

Thioacetic acid (0.216 mL, 3.07 mmol) and potassium carbonate (636 mg, 4.60 mmol) were added to a solution of 4-((tert-butoxycarbonyl)amino)butyl methanesulfonate (410 mg, 1.53 mmol) in CH$_3$CN (20 mL) and the reaction mixture was stirred at rt for 24 h. The reaction mixture was then filtered over a celite pad and concentrated. The residue was dissolved in 100 mL of EtOAc, washed with brine (100 mL×2), dried over Na$_2$SO$_4$, filtered and concentrated. The residue was purified by ISCO (24 g of silica gel EtOAc: hexanes=1:20 to 1:5) and concentrated to give S-(4-((tert-butoxycarbonyl)amino)butyl) ethanethioate. 1H-NMR (CDCl3, 400 MHz) δ 3.12 (t, 2H, J=6.8 Hz), 2.87 (t, 2H, J=7.2 Hz), 2.32 (s, 3H), 1.56 (m, 4H), 1.44 (s, 9H)

Step 3: Synthesis of tert-butyl (4-mercaptobutyl)carbamate (i-7)

Potassium carbonate (21 mg, 0.15 mmol) was added to a solution of S-(4-((tert-butoxycarbonyl)amino)butyl) ethanethioate (370 mg, 1.49 mmol) in MeOH (20 mL) and the reaction mixture was stirred at room temperature for 3 h. The reaction mixture was then concentrated and the residue dissolved in 100 mL of EtOAc, washed with brine (100 mL×2), dried over Na$_2$SO$_4$, filtered and concentrated. The residue was purified by ISCO (24 g of silica gel, EtOAc: hexanes=1:20 to 1:10) and concentrated to give tert-butyl (4-mercaptobutyl)carbamate (i-7). 1H-NMR (CDCl3, 400 MHz) δ 3.14 (m, 2H), 2.68 (t, 1H, J=7.2 Hz), 2.54 (dd, 2H, J=14.8 and 6.8 Hz) 1.61 (m, 4H), 1.44 (s, 9H), 1.36 (t, 1H, J=7.6 Hz).

Synthesis of 4-azidobutane-1-thiol (i-8)

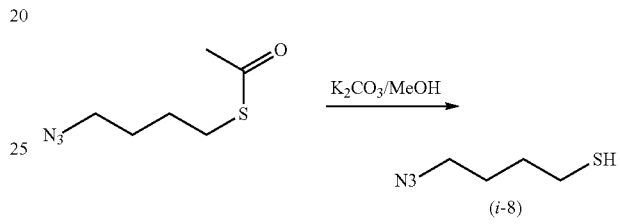

Using a 40 mL vial, potassium carbonate (7 mg, 0.06 mmol) was added to S-(4-azidobutyl) ethanethioate (100 mg, 0.577 mmol) in MeOH (20 mL) and the reaction mixture was stirred at rt for 1 h. The reaction mixture was then filtered over celite pad and concentrated. The residue was dissolved in EtOAc (100 mL), washed with 0.1N HCl solution (50 mL) and brine (50 mL), dried over Na$_2$SO4, filtered and concentrated. The residue was purified by ISCO purification on 24 g of silica gel and concentrated to give 4-azidobutane-1-thiol (i-8). 1H-NMR (CDCl3, 400 MHz) δ 3.31 (m, 2H), 2.55 (m, 2H), 1.71 (m, 4H), 1.53 (s, 2H), 1.36 (t, J=8.0 Hz, 1H).

Synthesis of (R)-2,4-dihydroxy-3,3-dimethyl-N-(3-oxo-3-((3-oxobutyl)amino)propyl) butanamide (i-9)

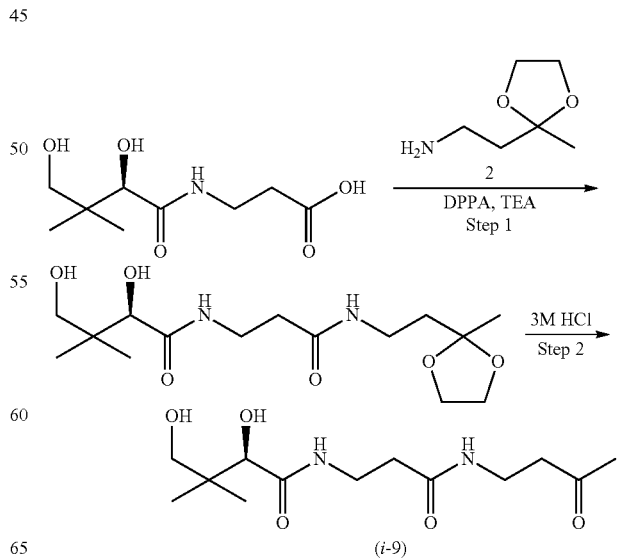

Step 1: Synthesis of (R)-2,4-dihydroxy-3,3-dimethyl-N-(3-((2-(2-methyl-1,3-dioxolan-2-yl)ethyl)amino)-3-oxopropyl)butanamide Panthotheic acid hemicalcium salt (100 mg, 0.390 mmol) was dissolved in CH$_3$CN (10 mL) and exchanged to panthotheic acid using sulfuric acid resin. Panthotheic acid (10 mg, 0.046 mmol) was dissolved in DMF (2 mL) and diphenylphosphoryl azide (20 μL, 0.091 mmol) and 2-(2-methyl-1,3-dioxolan-2-yl)ethanamine (7 mg, 0.005 mmol) were added. The reaction mixture was cooled to 0° C. and triethylamine (16 μL, 0.114 mmol) was added. The reaction mixture was stirred at 0° C. for 10 min, and then stirred at rt for 24 h. EtOAc (50 mL) was added and washed with 0.1N HCl solution (20 mL), 0.1N NaOH solution (20 mL), brine (20 mL), dried over Na$_2$SO$_4$ and filtered. The filtrate was concentrated in vacuo and the residue was purified by HPLC and lyophilized to give (R)-2,4-dihydroxy-3,3-dimethyl-N-(3-((2-(2-methyl-1,3-dioxolan-2-yl)ethyl)amino)-3-oxopropyl)butanamide. MS (m+1)=333.2, HPLC Peak RT=0.512 min

Step 2: Synthesis of Compound 4

(R)-2,4-dihydroxy-3,3-dimethyl-N-(3-((2-(2-methyl-1,3-dioxolan-2-yl)ethyl)amino)-3-oxopropyl)butanamide (6 mg, 0.018 mmol) was dissolved in THF (2 mL) and 3N HCl solution (1 mL) and stirred at rt for 4 h. After cooling to 0° C., the reaction mixture was neutralized with 1N NaOH solution and concentrated half volume in vacuo. The reaction mixture was purified by ISCO RP-C18 and lyophilized to give (R)-2,4-dihydroxy-3,3-dimethyl-N-(3-oxo-3-((3-Oxobutyl)amino)propyl) butanamide (i-9). MS (m+1) =289.2, HPLC Peak RT=0.362 min, 1H-NMR (MeOD, 400 MHz) δ 3.83 (s, 1H), 3.37~4.45 (m, 3H), 3.34 (d, 2H, J=7.2 Hz), 3.32 (d, 1H, J=3.2 Hz), 2.65 (t, 2H, J=6.4 Hz), 2.34 (t, 2H, J=6.8 Hz), 2.10 (s, 3H), 0.87 (s, 6H).

Synthetic Procedure for Non-Linked Amatoxins

Example 1: Synthesis of Compound (1)—6'O-methyl-7'C-((2-(2-(maleimido)ethanecarboxamido)ethylthio)methyl)-α-Amanitin

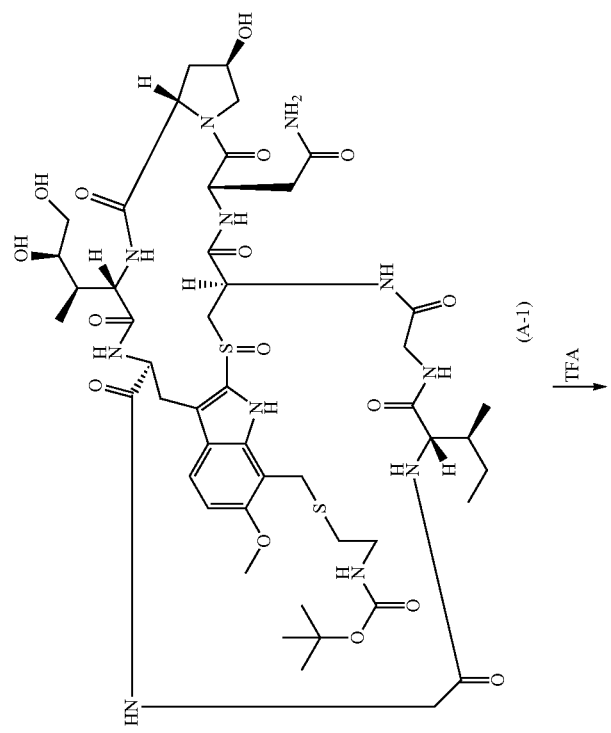
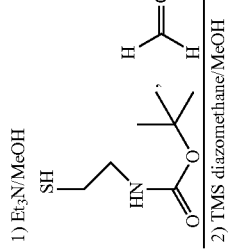
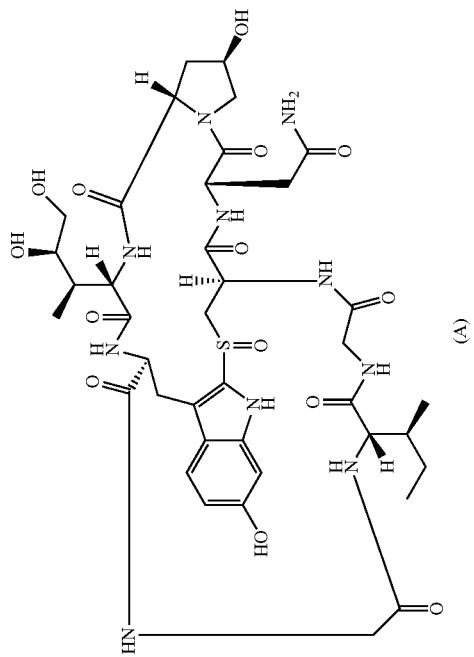

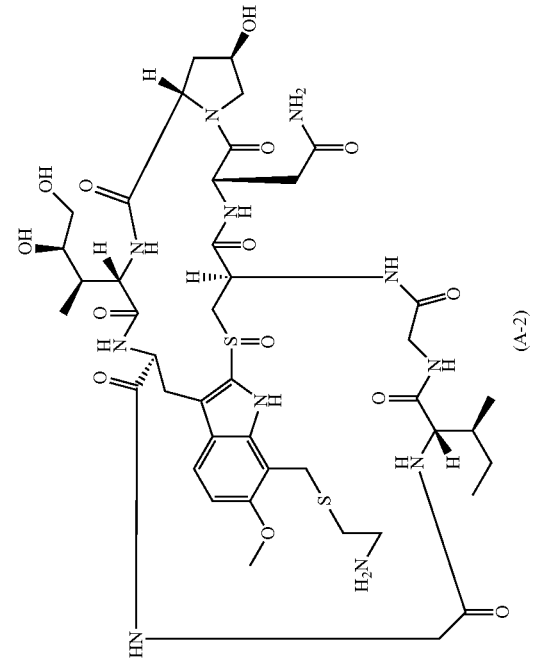
(A-2)
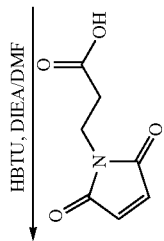
HBTU, DIEA/DMF
-continued
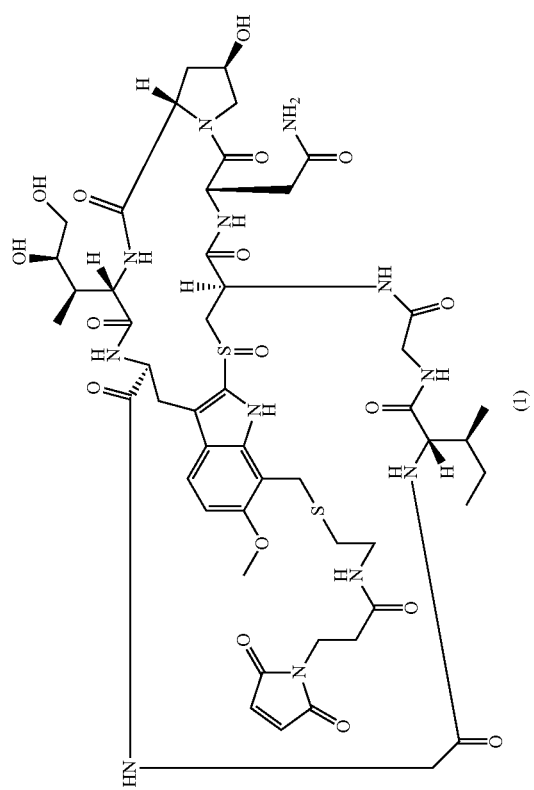
(1)

Step 1: Synthesis of Compound (A-1)

Formaldehyde (0.013 mL, 0.44 mmol) and tert-butyl (2-mercaptoethyl)carbamate (39 mg, 0.22 mmol) were added to a solution of α-Amanitin (A) (20 mg, 0.022 mmol) in MeOH (5 mL) and triethylamine (0.607 mL, 4.35 mmol) in a 40 mL vial, and the reaction mixture was stirred at 40° C. for 3 days. After concentration in vacuo, the residue was dissolved in 2 mL of MeOH and 218 μL of 2 M of trimethylsilyl diazomethane in diethyl ether was added and the mixture was stirred for 2 h at rt. Then another 218 μL of 2 M of trimethylsilyl diazomethane in diethyl ether was added and stirred at rt for 2 h. The reaction mixture was purified by HPLC and lyophilized to give the desired compound (A-1). MS (m+1-boc)=1022.4. HPLC Peak RT=0.924 min. 1H-NMR (MeOD, 400 MHz) δ 8.84 (dd, 1H, J=5.6 and 6.8 Hz), 8.58 (s, 1H), 8.47 (s, 1H), 8.46 (d, 1H, J=10.0 Hz), 8.35 (bs, 1H), 8.16 (d, 1H, J=8.8 Hz), 8.01 (d, 1H, J=9.6 Hz), 7.92 (d, 1H, J=8.8 Hz), 7.69 (bs, 1H), 7.64 (d, 1H, J=9.2 Hz), 6.92 (d, 1H, J=8.8 Hz), 5.27 (m, 1H), 5.13 (m, 1H), 4.74 (bs, 1H), 4.61 (dd, 1H, J=5.2 and 9.6 Hz), 4.50 (m, 2H), 4.30 (dd, 1H, J=8.8 and 18.4 Hz), 4.12 (dd, 1H, J=7.6 and 17.6 Hz), 4.06 (d, 1H, J=13.2 Hz), 3.95 (d, 1H, J=13.2 Hz), 3.91 (bs, 1H), 3.86 (s, 3H), 3.69 (m, 2H), 3.65 (m, 2H), 3.47~3.67 (m, 6H), 3.35~3.43 (m, 3H), 3.22 (m, 3H), 3.08 (m, 1H), 3.04 (d, 1H, J=3.6 Hz), 2.92 (dd, 1H, J=12.0 and 14.8 Hz), 2.46 (t, 2H, J=7.2 Hz), 2.39 (m, 2H), 2.00 (m, 1H), 1.59 (m, 2H), 1.38 (s, 9H), 1.15 (m, 2H), 0.94 (d, 3H, J=7.2 Hz), 0.85 (m, 6H).

Step 2: Synthesis of Compound (A-2)

TFA (1 mL) was added to 7.5 mg of compound (A-1) in a 40 mL vial and the resulting solution was allowed to stand at rt for 1 min and then concentrated under vacuum to give the desired compound (A-2), which was used without further purification. MS (m+1)=1022.4. HPLC Peak RT=0.601 min. 1H-NMR (MeOD, 400 MHz) δ 8.94 (t, 1H, J=6.8 Hz), 8.64 (s, 1H), 8.52 (s, 1H), 8.51 (d, 1H, J=15.2 Hz), 8.22 (d, 1H, J=8.8 Hz), 8.03 (d, 1H, J=8.8 Hz), 7.99 (d, 1H, J=8.8 Hz), 7.72 (d, 1H, J=8.8 Hz), 7.00 (d, 1H, J=8.8 Hz), 5.30 (m, 1H), 5.18 (m, 1H), 4.93 (bs, 1H), 4.78 (bs, 1H), 4.66 (dd, 1H, J=5.6 and 9.6 Hz), 4.54 (m, 2H), 4.36 (dd, 1H, J=8.8 and 18.0 Hz), 4.16 (m, 2H), 4.11 (s, 2H), 3.98 (m, 2H), 3.92 (s, 3H), 3.71 (m, 4H), 3.39~3.62 (m, 10H), 3.13 (m, 3H), 2.97 (dd, 1H, J=11.6 and 14.4 Hz), 2.66 (t, 2H, J=7.2 Hz), 2.45 (m, 2H), 2.05 (m, 1H), 1.63 (m, 2H), 1.23 (m, 2H), 0.99 (d, 3H, J=6.8 Hz), 0.89 (m, 6H).

Step 3: Synthesis of Compound (1)

Compound (A-2) (4 mg, 0.004 mmol) in DMF (1 mL) was added to a 40 mL vial, to which 1 mg of 3-maleimidopropionic acid (6 μmol), 1 mg of HBTU (0.003 mmol) and 2 μL of DIEA (0.01 mmol) were added. The reaction mixture was then stirred at rt for 1 h and then purified by HPLC and lyophillized to give the desired compound (1). MS (m+2/2)=587.3, HPLC Peak RT=0.711 min, 1H-NMR (MeOD, 400 MHz) δ 10.78 (s, 1H), 8.83 (dd, 1H, J=5.6 and 7.2 Hz), 8.59 (s, 1H), 8.47 (s, 1H), 8.46 (d, 1H, J=6.0 Hz), 8.34 (bs, 1H), 8.16 (d, 1H, J=8.4 Hz), 8.01 (d, 1H, J=9.6 Hz), 7.92 (d, 1H, J=8.8 Hz), 7.68 (bs, 1H), 7.64 (d, 1H, J=8.8 Hz), 6.92 (d, 1H, J=9.2 Hz), 6.70 (s, 2H), 5.25 (m, 1H), 5.13 (m, 1H), 4.74 (bs, 1H), 4.62 (dd, 1H, J=5.2 and 9.6 Hz), 4.50 (m, 2H), 4.30 (dd, 1H, J=8.8 and 18.4 Hz), 4.12 (m, 1H), 4.09 (d, 1H, J=12.8 Hz), 3.95 (d, 1H, J=12.8 Hz), 3.91 (m, 1H), 3.86 (s, 3H), 3.69 (m, 6H), 3.35~3.55 (m, 8H), 3.08 (m, 1H), 2.92 (dd, 1H, J=12.0 and 14.8 Hz), 2.39 (m, 6H), 2.00 (m, 1H), 1.59 (m, 2H), 1.13 (m, 2H), 0.94 (d, 3H, J=6.8 Hz), 0.85 (m, 6H).

Example 2: Synthesis of Compound (2)—6'O-methyl-7'C-((2-(3-(maleimido)propanecarboxamido)ethylthio)methyl)-α-Amanitin

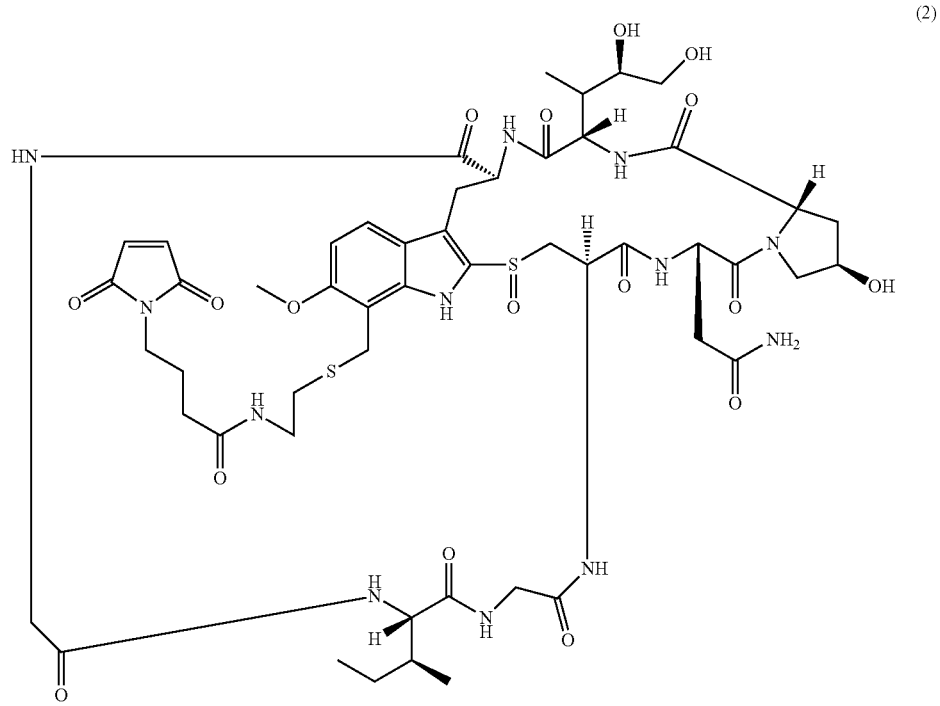 [SMILES: CC[C@H](C)[C@@H]1NC(=O)CNC(=O)[C@@H]2Cc3c([nH]c4c(CSCCNC(=O)CCCN5C(=O)C=CC5=O)c(OC)ccc34)S(=O)C[C@H](NC(=O)CNC1=O)C(=O)N[C@@H](CC(N)=O)C(=O)N1C[C@H](O)C[C@H]1C(=O)N[C@@H](C(C)[C@@H](O)CO)C(=O)N2]

(2)

Compound (2) was prepared using the method described for compound (1) except 4-maleimidobutyric acid was used instead of 3-maleimidopropionic acid. MS (m+2/2)=594.4, HPLC Peak RT=0.744 min, 1H-NMR (MeOD, 400 MHz) δ 10.85 (s, 1H), 8.89 (dd, 1H, J=6.4 and 7.2 Hz), 8.64 (s, 1H), 8.52 (s, 1H), 8.50 (d, 1H, J=10.0 Hz), 8.40 (bs, 1H), 8.20 (d, 1H, J=8.8 Hz), 8.06 (d, 1H, J=9.6 Hz), 7.97 (d, 1H, J=8.8 Hz), 7.72 (bs, 1H), 7.68 (d, 1H, J=8.8 Hz), 6.98 (d, 1H, J=9.2 Hz), 6.80 (s, 2H), 5.31 (m, 1H), 5.17 (m, 1H), 4.79 (bs, 1H), 4.66 (dd, 1H, J=5.2 and 9.6 Hz), 4.55 (m, 2H), 4.35 (dd, 1H, J=8.8 and 18.4 Hz), 4.16 (m, 1H), 4.09 (d, 1H, J=13.2 Hz), 4.01 (d, 1H, J=13.2 Hz), 3.96 (m, 1H), 3.91 (s, 3H), 3.71 (m, 4H), 3.39~3.56 (m, 10H), 3.13 (m, 1H), 2.96 (dd, 1H, J=12.0 and 15.2 Hz), 2.48 (m, 4H), 2.15 (m, 2H), 2.03 (m, 1H), 1.85 (m, 2H), 1.61 (m, 2H), 1.20 (m, 1H), 0.98 (d, 3H, J=6.8 Hz), 0.89 (m, 6H).

Example 3: Synthesis of Compound (3)—6'O-methyl-7'C-((2-(4-(maleimido)butanecarboxamido)ethylthio)methyl)-α-Amanitin

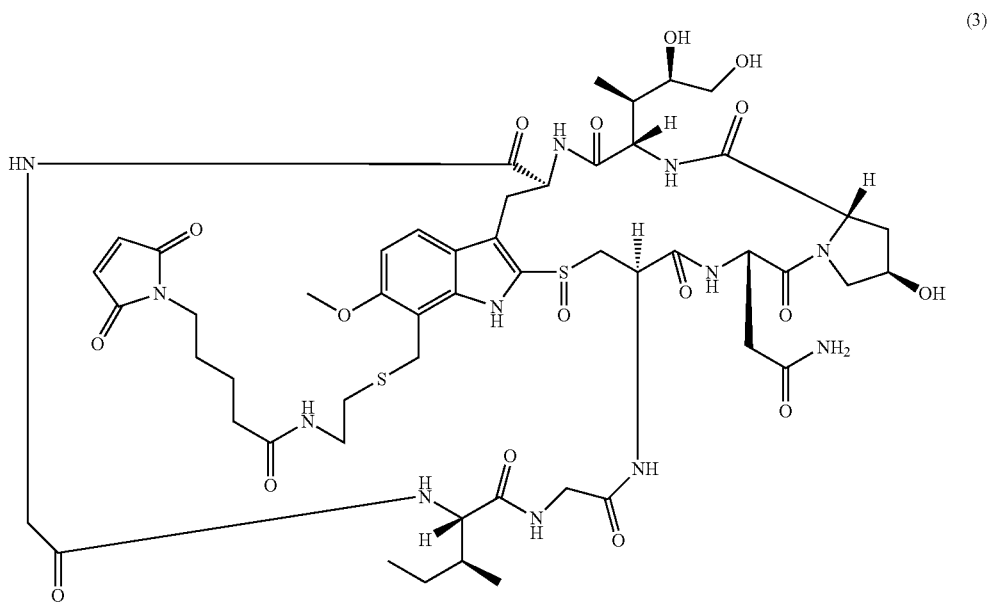 [SMILES: CC[C@H](C)[C@@H]1NC(=O)CNC(=O)[C@@H]2Cc3c([nH]c4c(CSCCNC(=O)CCCCN5C(=O)C=CC5=O)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(3)

Compound (3) was prepared using the method described for compound (1) except 5-maleimidopentanoic acid was used instead of 3-maleimidopropionic acid. MS (m+2/2)=601.3, HPLC Peak RT=0.702 min, 1H-NMR (MeOD, 400 MHz) δ 10.80 (s, 1H), 8.84 (dd, 1H, J=5.6 and 6.4 Hz), 8.60 (s, 1H), 8.47 (s, 1H), 8.46 (d, 1H, J=10.4 Hz), 8.16 (d, 1H, J=8.8 Hz), 8.01 (d, 1H, J=9.6 Hz), 7.92 (d, 1H, J=8.8 Hz), 7.64 (d, 1H, J=9.2 Hz), 6.92 (d, 1H, J=8.8 Hz), 6.72 (s, 2H), 5.27 (m, 1H), 5.14 (m, 1H), 4.75 (bs, 1H), 4.62 (dd, 1H, J=5.6 and 9.6 Hz), 4.51 (m, 2H), 4.30 (dd, 1H, J=8.8 and 18.4 Hz), 4.11 (m, 1H), 4.06 (d, 1H, J=13.2 Hz), 3.96 (d, 1H, J=13.2 Hz), 3.91 (m, 1H), 3.86 (s, 3H), 3.70 (m, 4H), 3.39~3.56 (m, 8H), 3.20 (m, 2H), 3.07 (m, 1H), 2.95 (m, 1H), 2.49 (m, 2H), 2.40 (m, 2H), 2.15 (m, 2H), 2.00 (m, 1H), 1.60 (m, 1H), 1.53 (m, 4H), 1.32 (m, 2H), 1.15 (m, 1H), 0.93 (d, 3H, J=7.2 Hz), 0.86 (m, 6H).

Example 4: Synthesis of Compound (4)—6'O-methyl-7'C-((2-(5-(maleimido)pentanecarboxamido)ethylthio)methyl)-α-Amanitin

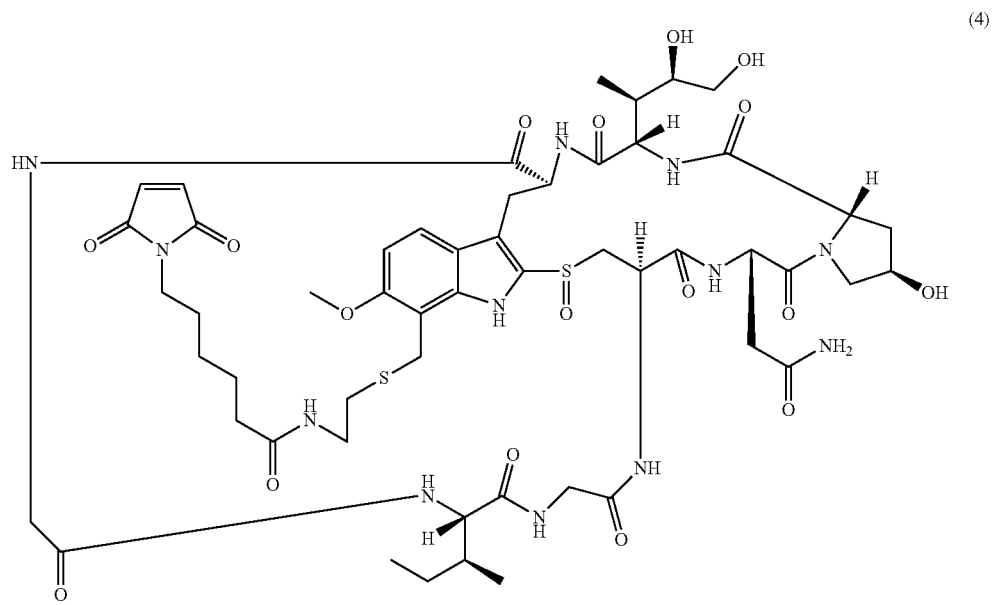 [SMILES: CC[C@H](C)[C@@H]1NC(=O)CNC(=O)[C@@H]2Cc3c([nH]c4c(CSCCNC(=O)CCCCCN5C(=O)C=CC5=O)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(4)

Compound (4) was prepared using the method described for compound (1) except 6-maleimidohexanoic acid was used instead of 3-maleimidopropionic acid. MS (m+1) =1216.3, HPLC Peak RT=0.798 min, 1H-NMR (MeOD, 400 MHz) δ 8.59 (s, 1H), 8.49 (d, 1H, J=10.0 Hz), 8.34 (s, 1H), 8.16 (d, 1H, J=8.8 Hz), 8.01 (d, 1H, J=9.6 Hz), 7.92 (d, 1H, J=8.8 Hz), 7.91 (s, 1H), 7.64 (d, 1H, J=8.8 Hz), 6.93 (d, 1H, J=9.2 Hz), 6.70 (s, 2H), 5.27 (m, 1H), 5.13 (m, 1H), 4.74 (bs, 1H), 4.61 (dd, 1H, J=5.6 and 9.6 Hz), 4.51 (m, 2H), 4.30 (dd, 1H, J=8.8 and 18.4 Hz), 4.11 (m, 4H), 3.91 (m, 2H), 3.86 (s, 3H), 3.40~3.80 (m, 18H), 3.08 (m, 1H), 2.92 (m, 1H), 2.49 (m, 2H), 2.40 (m, 2H), 2.12 (m, 2H), 2.00 (m, 1H), 1.56 (m, 8H), 1.25 (m, 4H), 0.93 (d, 3H, J=7.2 Hz), 0.86 (m, 6H).

Example 5: Synthesis of Compound (5)—6'O-methyl-7'C-(2-((4-((maleimido)methyl)cyclohexanecarboxamido)ethylthio)methyl)-α-Amanitin

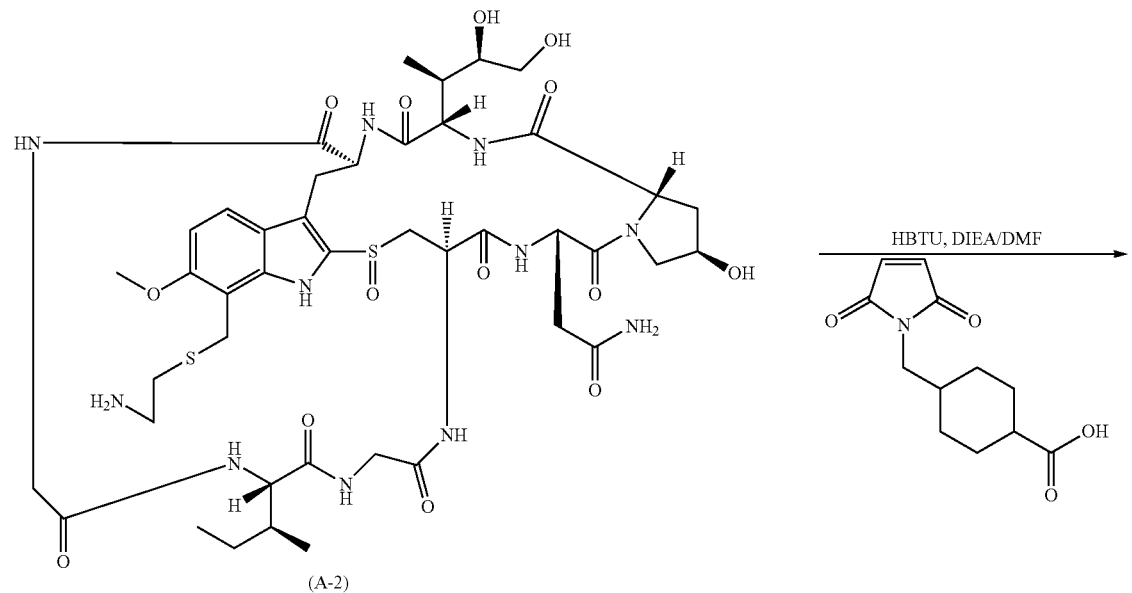

(A-2)

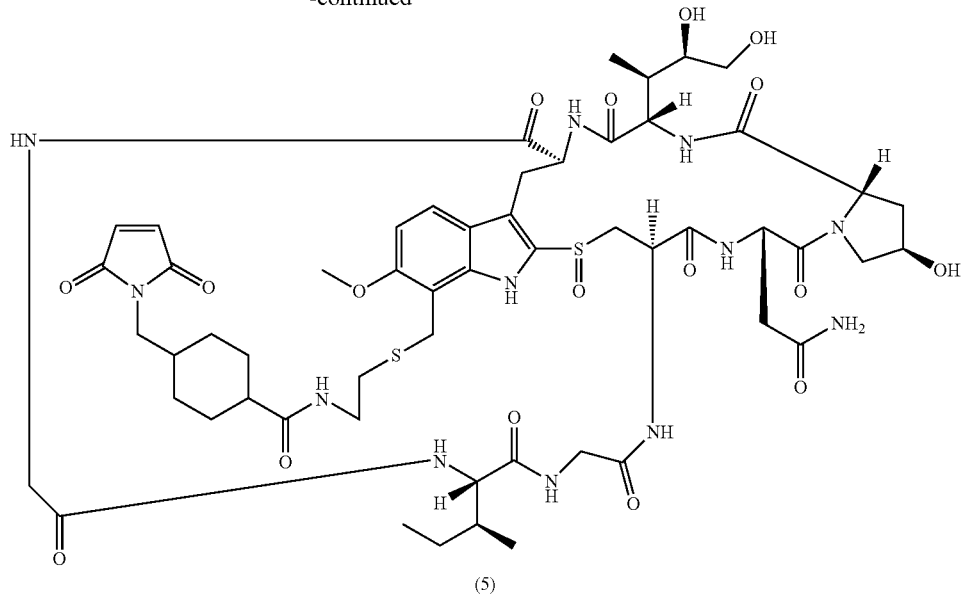

Compound (5) was prepared from compound (A-2) using the method described for the preparation of compound (1), except 4-((2,5-dioxo-2,5-dihydro-1H-pyrrol-1-yl)methyl)cyclohexanecarboxylic acid was used instead of 3-maleimidopropionic acid. MS (m+2/2)=621.4, HPLC Peak RT=0.832 min, 1H-NMR (MeOD, 400 MHz) δ 10.87 (s, 1H), 8.89 (t, 1H, J=5.6 Hz), 8.64 (s, 1H), 8.52 (s, 1H), 8.50 (d, 1H, J=10.4 Hz), 8.20 (d, 1H, J=8.8 Hz), 8.06 (d, 1H, J=9.6 Hz), 7.98 (d, 1H, J=8.8 Hz), 7.94 (s, 1H), 7.68 (d, 1H, J=8.8 Hz), 6.96 (d, 1H, J=8.8 Hz), 6.81 (s, 2H), 5.30 (m, 1H), 5.18 (m, 1H), 4.79 (bs, 1H), 4.66 (dd, 1H, J=5.6 and 9.6 Hz), 4.54 (m, 2H), 4.35 (dd, 1H, J=8.8 and 18.0 Hz), 4.16 (m, 1H), 4.10 (d, 1H, J=13.2 Hz), 3.99 (d, 1H, J=13.2 Hz), 3.96 (m, 1H), 3.89 (s, 3H), 3.39~3.75 (m, 14H), 3.13 (m, 1H), 2.97 (m, 1H), 2.53 (m, 2H), 2.45 (m, 2H), 2.07 (m, 2H), 1.60~1.80 (m, 8H), 1.38 (m, 2H), 1.20 (m, 2H), 1.05 (m, 1H), 0.98 (d, 3H, J=6.8 Hz), 0.86 (m, 6H).

Example 6: Synthesis of Compound (6)—6'O-methyl-7'C-((2-(5-(5-(maleimido)pentanecarboxamido)pentanecarboxamido)ethylthio)methyl)-α-Amanitin

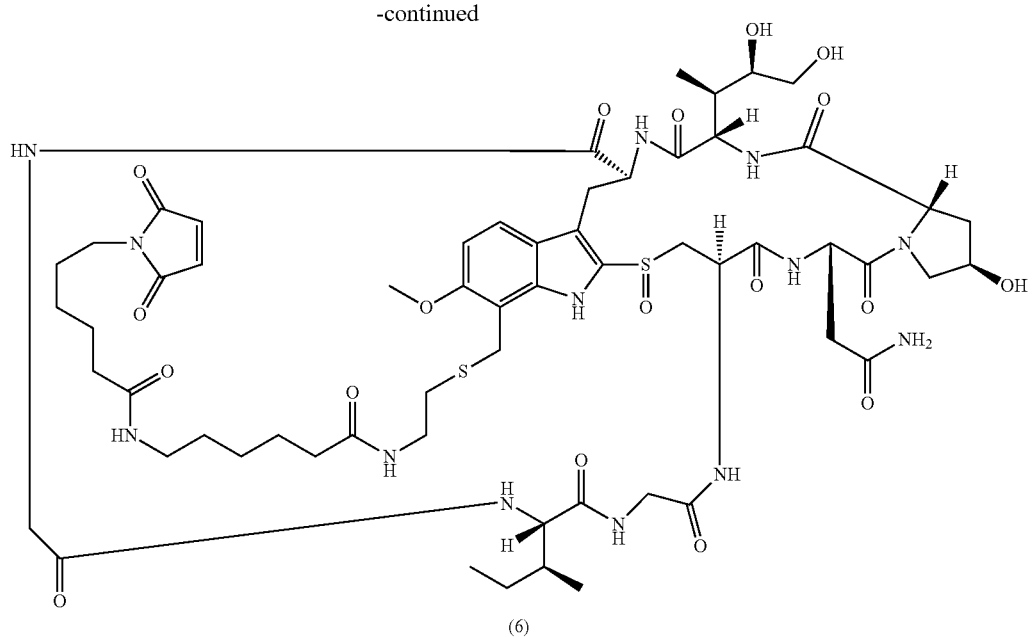

(6)

To a solution of compound (A-2) (3 mg, 3 μmol) and DIEA (1.2 μl, 7 μmol) in DMF (1 mL) in a 40 mL vial was added 6-(6-(2,5-dioxo-2,5-dihydro-1H-pyrrol-1-yl)hexanamido)hexanoic acid (i-1) (0.9 mg, 3 μmol) and HBTU (0.7 mg, 2 μmol), and the reaction mixture was stirred at rt for 30 min and then purified by HPLC and lyophilized to give Compound (6). MS (m+2/2)=664.9, HPLC Peak RT=0.828 min. 1H-NMR (MeOD, 400 MHz) δ 10.81 (s, 1H), 8.83 (dd, 1H, J=5.6 and 6.8 Hz), 8.59 (s, 1H), 8.48 (s, 1H), 8.47 (d, 1H, J=5.2 Hz), 8.35 (s, 1H), 8.16 (d, 1H, J=8.8 Hz), 8.01 (d, 1H, J=9.6 Hz), 7.93 (d, 1H, J=8.8 Hz), 7.69 (s, 1H), 7.63 (d, 1H, J=8.8 Hz), 6.92 (d, 1H, J=9.2 Hz), 6.73 (s, 2H), 5.27 (m, 1H), 5.13 (m, 1H), 4.74 (bs, 1H), 4.62 (dd, 1H, J=5.6 and 9.6 Hz), 4.50 (m, 2H), 4.30 (dd, 1H, J=8.8 and 18.4 Hz), 4.14 (m, 1H), 4.07 (d, 1H, J=13.2 Hz), 3.96 (d, 1H, J=13.2 Hz), 3.92 (m, 1H), 3.86 (s, 3H), 3.10~3.75 (m, 16H), 3.09 (m, 4H), 2.94 (m, 1H), 2.50 (m, 2H), 2.39 (m, 2H), 2.08 (m, 4H), 2.00 (m, 1H), 1.40~1.60 (m, 12H), 1.10~1.40 (m, 8H), 0.94 (d, 3H, J=7.2 Hz), 0.86 (m, 6H).

Example 7: Synthesis of Compound (7)—6'O-methyl-7'C-((2-(6-(4-((maleimido)methyl)cyclohexanecarboxamido)hexanecarboxamido)ethylthio)methyl)-α-Amanitin

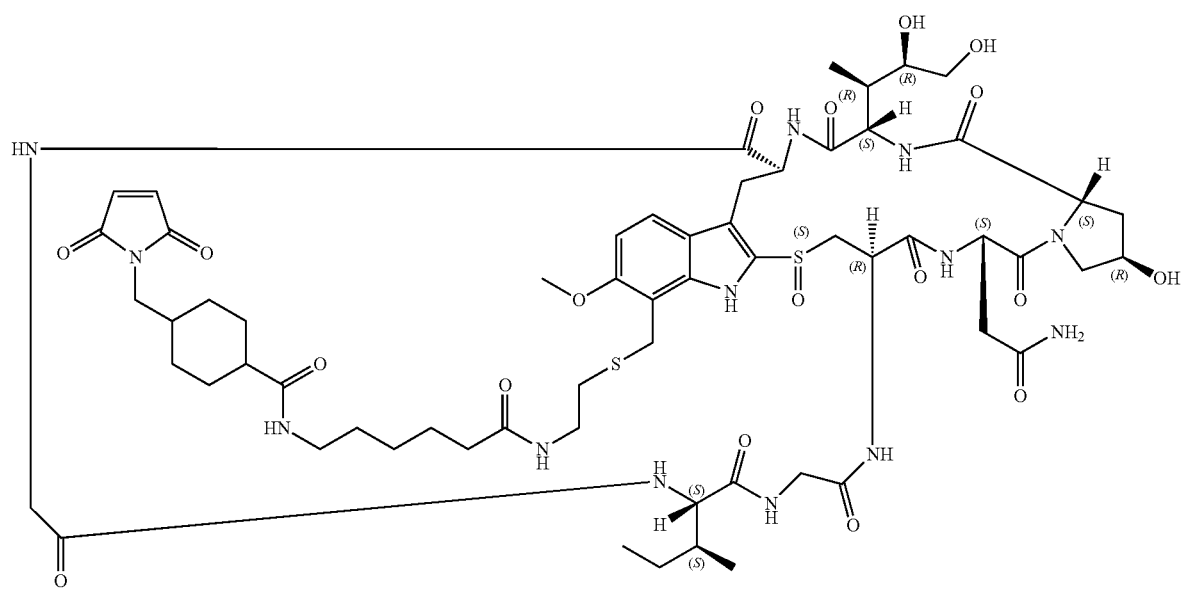

(7)

Compound (7) was prepared from compound (A-2) using the method described for the preparation of compound (6), except 6-(4-((2,5-dioxo-2,5-dihydro-1H-pyrrol-1-yl)methyl)cyclohexanecarboxamido)hexanoic acid (i-2) was used instead of 6-(6-(2,5-dioxo-2,5-dihydro-1H-pyrrol-1-yl)hexanamido)hexanoic acid (i-1). MS (m+2/2)=678.0, HPLC Peak RT=0.843 min, 1H-NMR (MeOD, 400 MHz) δ 10.81 (s, 1H), 8.85 (d, 1H, J=4.8 and 6.4 Hz), 8.59 (d, 1H, J=2.0 Hz), 8.49 (s, 1H), 8.47 (d, 1H, J=6.4 Hz), 8.34 (s, 1H), 8.16 (d, 1H, J=8.0 Hz), 8.02 (d, 1H, J=9.6 Hz), 7.93 (d, 1H, J=8.8 Hz), 7.73 (m, 1H), 7.69 (s, 1H), 7.65 (d, 1H, J=8.8 Hz), 6.93 (d, 1H, J=9.2 Hz), 6.74 (s, 2H), 5.27 (m, 1H), 5.13 (m, 1H), 4.74 (bs, 1H), 4.62 (dd, 1H, J=5.6 and 9.6 Hz), 4.50 (m, 2H), 4.30 (dd, 1H, J=8.8 and 18.0 Hz), 4.14 (m, 1H), 4.07 (d, 1H, J=13.6 Hz), 3.97 (d, 1H, J=12.8 Hz), 3.92 (m, 1H), 3.86 (s, 3H), 3.39~3.75 (m, 14H), 3.07 (m, 4H), 2.93 (m, 1H), 2.51 (m, 2H), 2.40 (m, 2H), 2.13 (m, 2H), 2.00 (m, 2H), 1.50~1.70 (m, 8H), 1.20~1.42 (m, 8H), 1.15 (m, 2H), 0.93 (d, 3H, J=6.8 Hz), 0.83 (m, 6H).

Example 8: Synthesis of Compound (8)—6'O-methyl-7'C-((2-(14-(maleimido)-3,6,9,12-tetraoxa-tetradecancarboxamido)ethylthio)methyl)-α-Amanitin

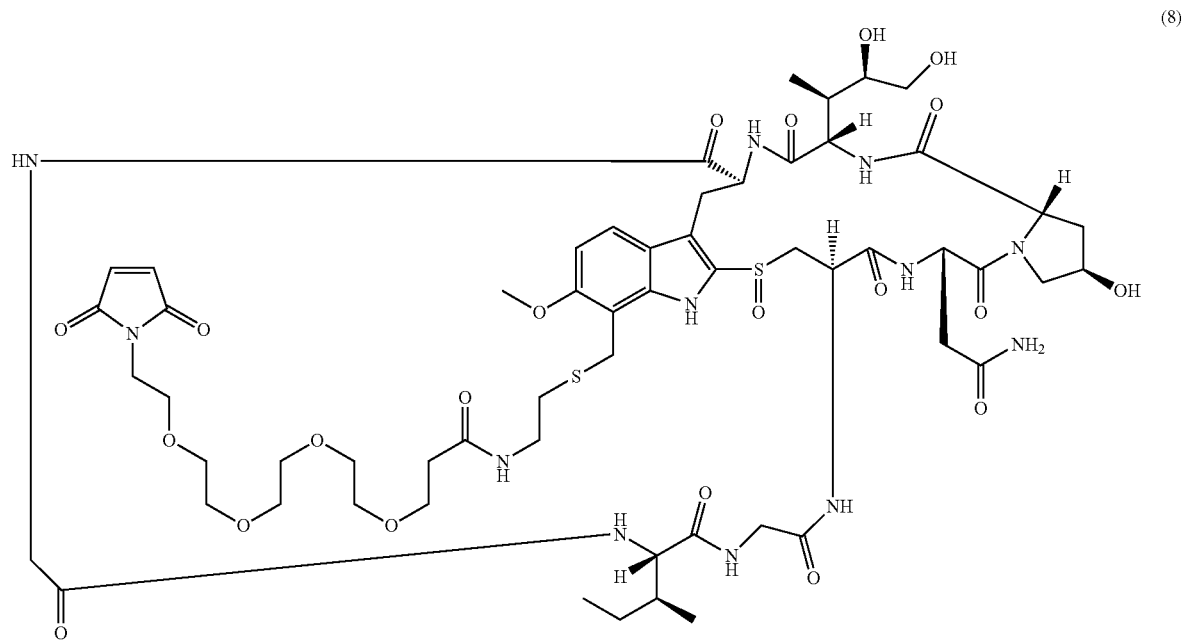 [SMILES: CC[C@H](C)[C@@H]1NC(=O)CNC(=O)[C@@H]2Cc3c([nH]c4c(CSCCNC(=O)CCOCCOCCOCCOCCN5C(=O)C=CC5=O)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(8)

Compound (8) was prepared from Compound (A-2) using the method described for the preparation of Compound (6), except 1-(2,5-dioxo-2,5-dihydro-1H-pyrrol-1-yl)-3,6,9,12-tetraoxapentadecan-15-oic acid was used instead of 6-(6-(2,5-dioxo-2,5-dihydro-1H-pyrrol-1-yl)hexanamido)hexanoic acid (i-1). MS (m+2/2)=683.4, HPLC Peak RT=0.785 min, 1H-NMR (MeOD, 400 MHz) δ 10.78 (s, 1H), 8.83 (t, 1H, J=6.0 Hz), 8.59 (d, 1H, J=2.0 Hz), 8.47 (d, 1H, J=10.4 Hz), 8.46 (s, 1H), 8.34 (s, 1H), 8.15 (d, 1H, J=8.0 Hz), 8.01 (d, 1H, J=9.6 Hz), 7.93 (d, 1H, J=8.8 Hz), 7.69 (s, 1H), 7.66 (d, 1H, J=8.8 Hz), 6.93 (d, 1H, J=9.2 Hz), 6.74 (s, 2H), 5.26 (m, 1H), 5.15 (m, 1H), 4.75 (bs, 1H), 4.61 (dd, 1H, J=6.0 and 9.6 Hz), 4.50 (m, 2H), 4.28 (dd, 1H, J=9.2 and 18.8 Hz), 4.11 (m, 1H), 4.08 (d, 1H, J=13.6 Hz), 3.97 (d, 1H, J=12.8 Hz), 3.92 (m, 1H), 3.86 (s, 3H), 3.60~3.75 (m, 10H), 3.45~3.55 (m, 20H), 3.35~3.45 (m, 5H), 3.09 (m, 1H), 2.89 (m, 1H), 2.54 (m, 2H), 2.48 (m, 4H), 2.00 (m, 1H), 1.60 (m, 2H), 1.26 (s, 1H), 1.11 (m, 1H), 0.93 (d, 3H, J=7.2 Hz), 0.85 (m, 6H).

Example 9: Synthesis of Compound (9)—6'O-methyl-7'C-((2-(14-((4-maleimido)methyl-1H-1,2,3-triazol-1-yl)-3,6,9,12-tetraoxatetradecancarboxamido)ethylthio)methyl)-α-Amanitin
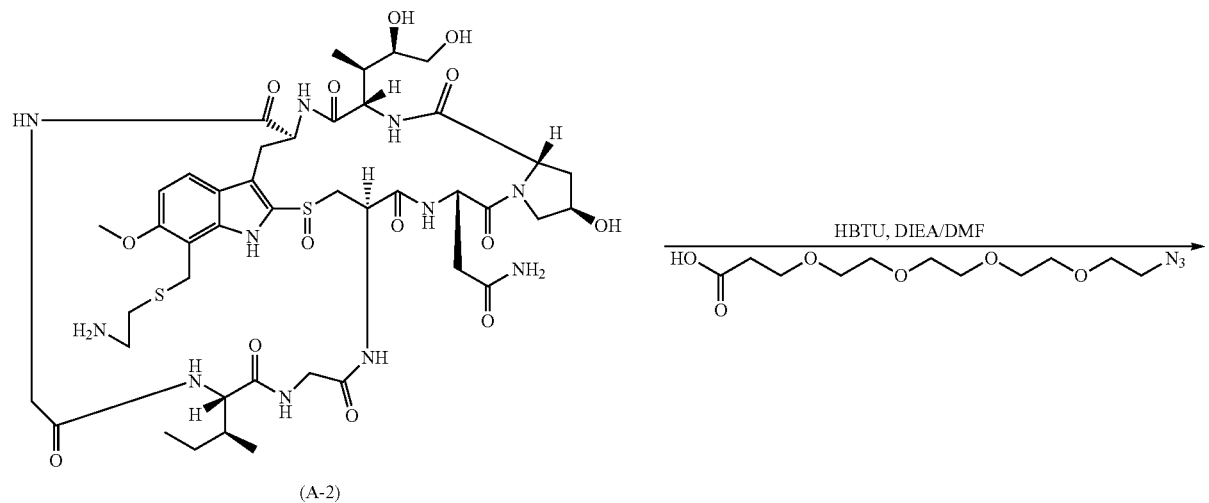
(A-2)
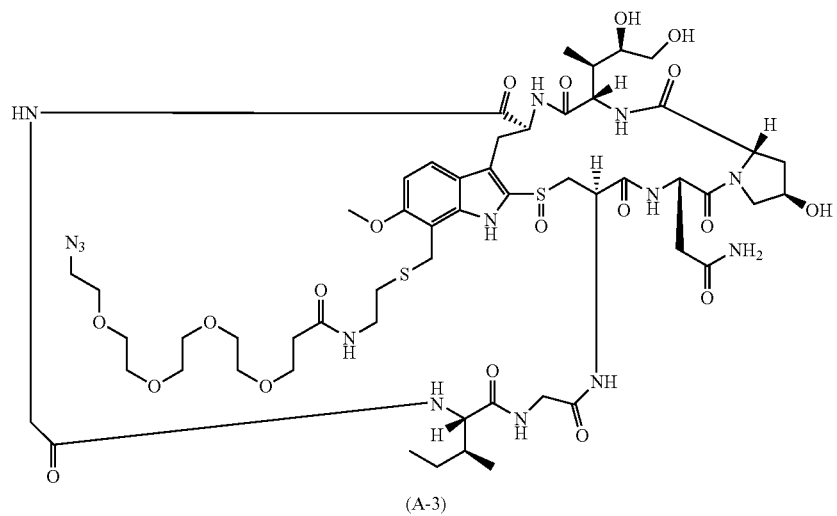

-continued

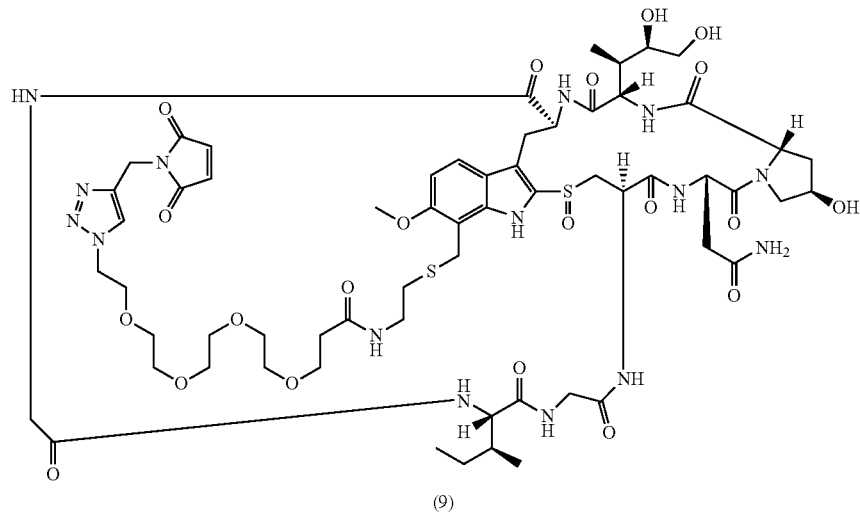

(9)

Step 1: 1-Azido-3,6,9,12-tetraoxapentadecan-15-oic acid (1.0 mg, 4 μmol) and HBTU (0.9 mg, 2 μmol) were added to a solution of compound (A-2) (4 mg, 4 μmol) and DIEA (1.6 μl, 9 μmol) in DMF (1 mL). The reaction mixture was then stirred at rt for 30 min and then purified by HPLC and lyophilized to give the desired product (A-3). MS (m+2/2) =648.4, HPLC Peak RT=0.822 min, 1H-NMR (MeOD, 400 MHz) δ 10.80 (s, 1H), 8.83 (m, 1H), 8.59 (d, 1H, J=2.0 Hz), 8.47 (H), 8.34 (s, 1H), 8.59 (d, 1H, J=8.0 Hz), 8.01 (d, 1H, J=9.6 Hz), 7.93 (d, 1H, J=9.2 Hz), 7.68 (s, 1H), 7.64 (d, 1H, J=8.8 Hz), 6.93 (d, 1H, J=9.2 Hz), 5.28 (m, 1H), 5.12 (m, 1H), 4.74 (m, 1H), 4.60 (dd, 1H, J=5.6 and 9.6 Hz), 4.51 (m, 2H), 4.30 (dd, 1H, J=9.2 and 18.8 Hz), 4.14 (m, 1H), 4.09 (d, 1H, J=10.4 Hz), 3.98 (d, 1H, J=12.8 Hz), 3.92 (m, 1H), 3.86 (s, 3H), 3.65~3.75 (m, 6H), 3.50~3.65 (m, 24H), 3.40~3.50 (m, 5H), 3.30~3.40 (m, 6H), 3.06 (m, 1H), 2.95 (m, 1H), 2.54 (m, 2H), 2.53 (m, 2H), 2.40 (m, 4H), 2.00 (m, 1H), 1.56 (m, 2H), 1.10~1.30 (m, 3H), 0.95 (d, 3H, J=6.8 Hz), 0.85 (m, 6H).

Step 2: Compound (A-3) (3.5 mg, 3 μmol) and compound (i-3) (0.7 mg, 5 μmol) were add to t-butanol (0.5 mL) and the reaction mixture was flushed with N$_2$ gas five times. L-Ascorbic acid sodium salt (0.54 mg, 3 μmol), CuSO$_4$ (0.09 mg, 0.5 μmol) and 0.5 mL of H$_2$O were then added and the reaction mixture was flushed with N$_2$ gas five times and stirred at rt for 4 h. The reaction mixture was then purified by HPLC and lyophilized to give Compound (9). MS (m+2/2)=715.9, HPLC Peak RT=0.771 min, 1H-NMR (MeOD, 400 MHz) δ 10.78 (s, 1H), 8.83 (m, 1H), 8.59 (d, 1H, J=2.0 Hz), 8.47 (d, 1H, J=9.2 Hz), 8.45 (s, 1H), 8.34 (s, 1H), 8.14 (d, 1H, J=8.4 Hz), 8.01 (d, 1H, J=9.6 Hz), 7.93 (d, 1H, J=8.4 Hz), 7.87 (s, 1H), 7.63 (d, 1H, J=8.8 Hz), 6.92 (d, 1H, J=8.8 Hz), 6.78 (s, 2H), 5.26 (m, 1H), 5.12 (m, 1H), 4.74 (bs, 1H), 4.69 (s, 2H), 4.61 (dd, 1H, J=5.6 and 9.6 Hz), 4.51 (m, 2H), 4.44 (t, 1H, J=4.8 Hz), 4.29 (dd, 1H, J=8.4 and 18.0 Hz), 4.10 (m, 1H), 4.09 (d, 1H, J=12.8 Hz), 3.97 (d, 1H, J=13.2 Hz), 3.92 (m, 1H), 3.85 (s, 3H), 3.75 (t, 2H, J=4.8 Hz), 3.59~3.73 (m, 8H), 3.42~3.53 (m, 24H), 3.30~3.41 (m, 6H), 3.06 (m, 1H), 2.92 (dd, 1H, J=12.0 and 14.8 Hz), 2.51 (m, 2H), 2.40 (m, 4H), 1.99 (m, 1H), 1.58 (m, 2H), 1.10~1.30 (m, 3H), 0.93 (d, 3H, J=7.2 Hz), 0.85 (m, 6H).

Example 10: Synthesis of Compound (10)—6'O-methyl-7'C-(2-((2,5-dioxopyrrolidin-1-yl)oxycarbonylamino)ethylthiomethyl)-α-Amanitin
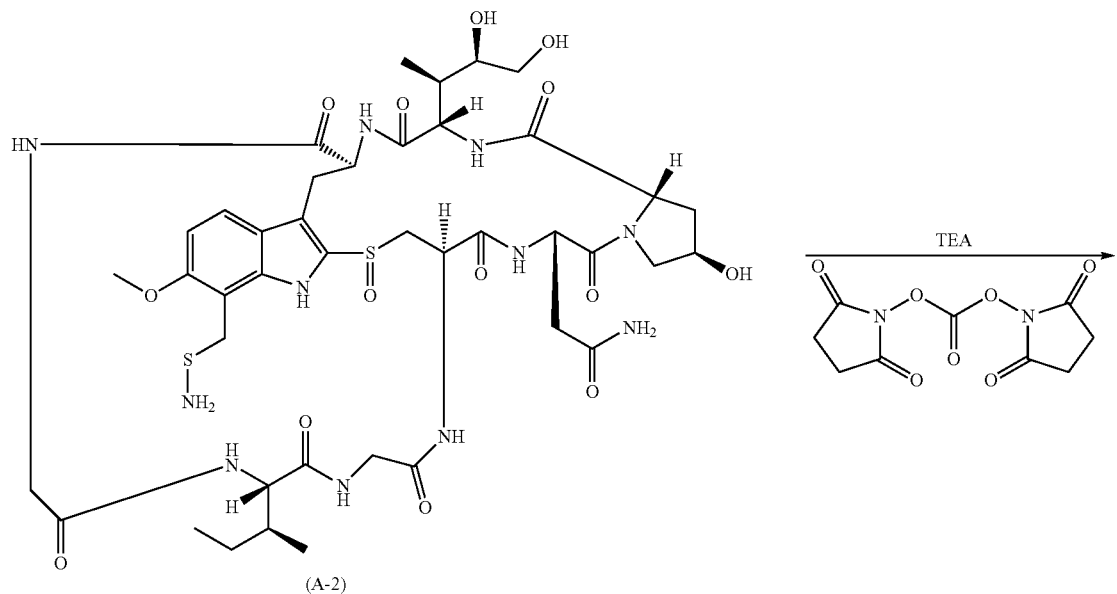

(A-2)

(10)

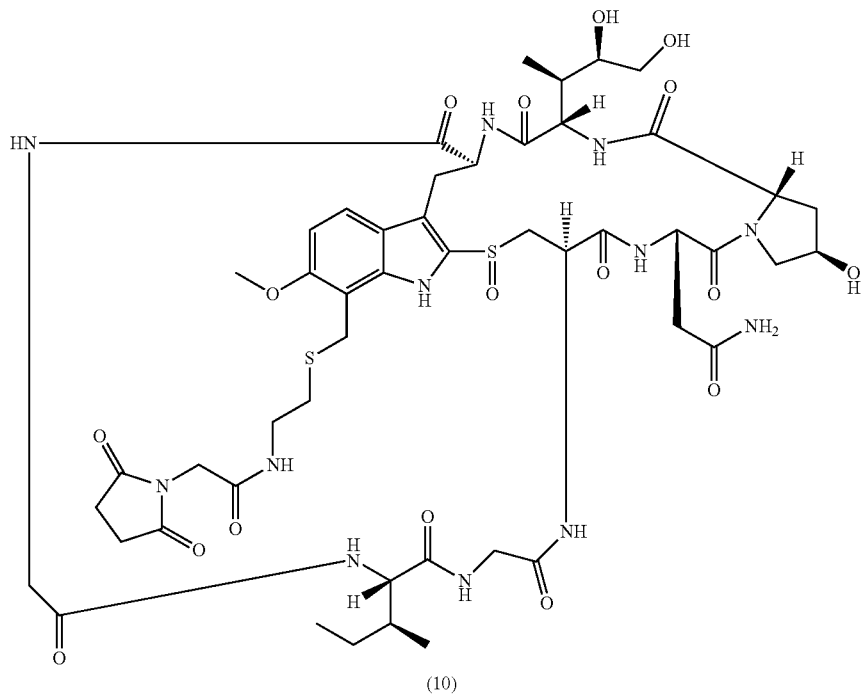

Using a 3 mL vial, 15 μL of a solution containing 26.8 mg of bis(2,5-dioxopyrrolidin-1-yl) carbonate and 29 μL of triethylamine in 1 mL of DMF was added to a solution of compound (A-2) (1.5 mg, 1 μmol) in DMF (0.06 mL). The reaction mixture was then stirred at rt for 30 min to give compound (10), which was then used without purification for attachment to an antibody. MS (m+1)=1163.3, HPLC Peak RT=0.739 min.

Example 11: Synthesis of Compound (11)—6'-O-methyl-7'-C-((2-(3-(6-(maleimido)hexyl)ureido)ethylthio)methyl)-α-Amanitin

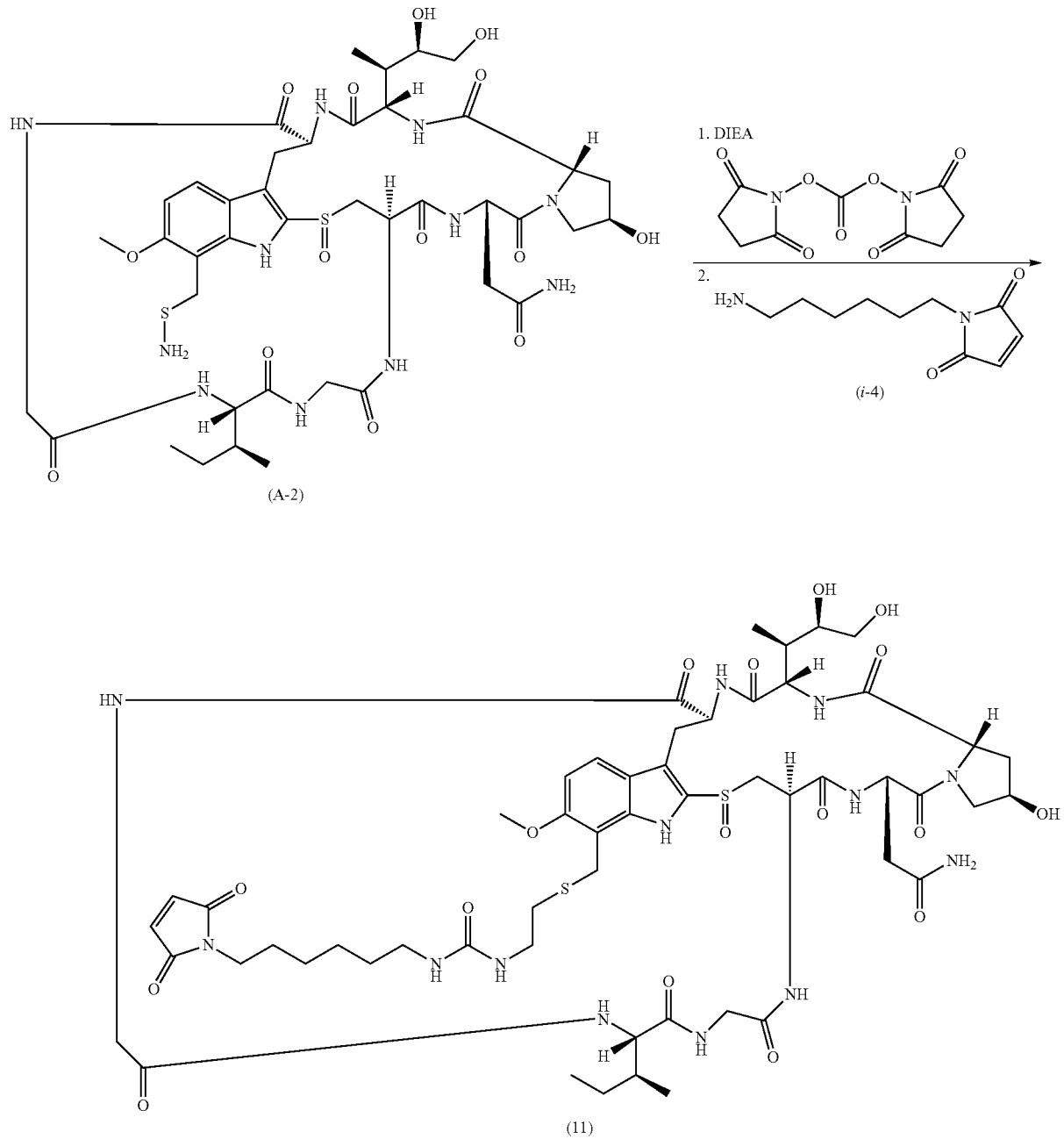

DIEA (3 μL, 0.02 mmol) and bis(2,5-dioxopyrrolidin-1-yl) carbonate (1 mg, 4 mol) were added to a solution of Compound (A-2) (4.4 mg, 4 μmol) in DMF (500 μL) and the reaction mixture was allowed to stand at rt for 30 min before the addition of compound (i-4) (1.8 mg, 8 μmol). The reaction mixture was then stirred overnight at rt and then purified by HPLC and lyophilized to give compound (11). MS (m+1)=1244.4, HPLC Peak RT=0.873 min, 1H-NMR (MeOD-d4, 400 MHz) δ 8.84 (m, 1H), 8.59 (d, 1H, J=2.0 Hz), 8.48 (d, 1H, J=5.6 Hz), 8.45 (s, 1H), 8.35 (s, 1H), 8.15 (d, 1H, J=7.6 Hz), 8.01 (d, 1H, J=9.6 Hz), 7.92 (d, 1H, J=8.8 Hz), 7.68 (s, 1H), 7.62 (d, 1H, J=9.2 Hz), 6.91 (d, 1H, J=9.2 Hz), 6.74 (s, 2H), 5.25 (m, 1H), 5.13 (m, 1H), 4.75 (bs, 1H), 4.69 (s, 2H), 4.61 (dd, 1H, J=4.8 and 9.6 Hz), 4.51 (m, 2H), 4.28 (dd, 1H, J=8.8 and 18.4 Hz), 4.10 (m, 1H), 4.06 (d, 1H, J=12.8 Hz), 3.98 (d, 1H, J=13.2 Hz), 3.92 (m, 1H), 3.86 (s, 3H), 3.55~3.65 (m, 7H), 3.42~3.53 (m, 16H), 3.31~3.41 (m, 5H), 3.08 (m, 1H), 3.03 (m, 2H), 2.92 (m, 1H), 2.29~2.53 (m, 4H), 2.00 (m, 2H), 1.50~1.65 (m, 4H), 1.35~1.50 (m, 6H), 1.05~1.20 (m, 20H), 0.93 (d, 3H, J=6.8 Hz), 0.85 (m, 6H).

Example 12: Synthesis of Compound (12) 6'-O-methyl-7'C-(MC-Val-Cit-PABC-(2-aminoethyl)thio-methyl-)-α-Amanitin (A-2)

(12)
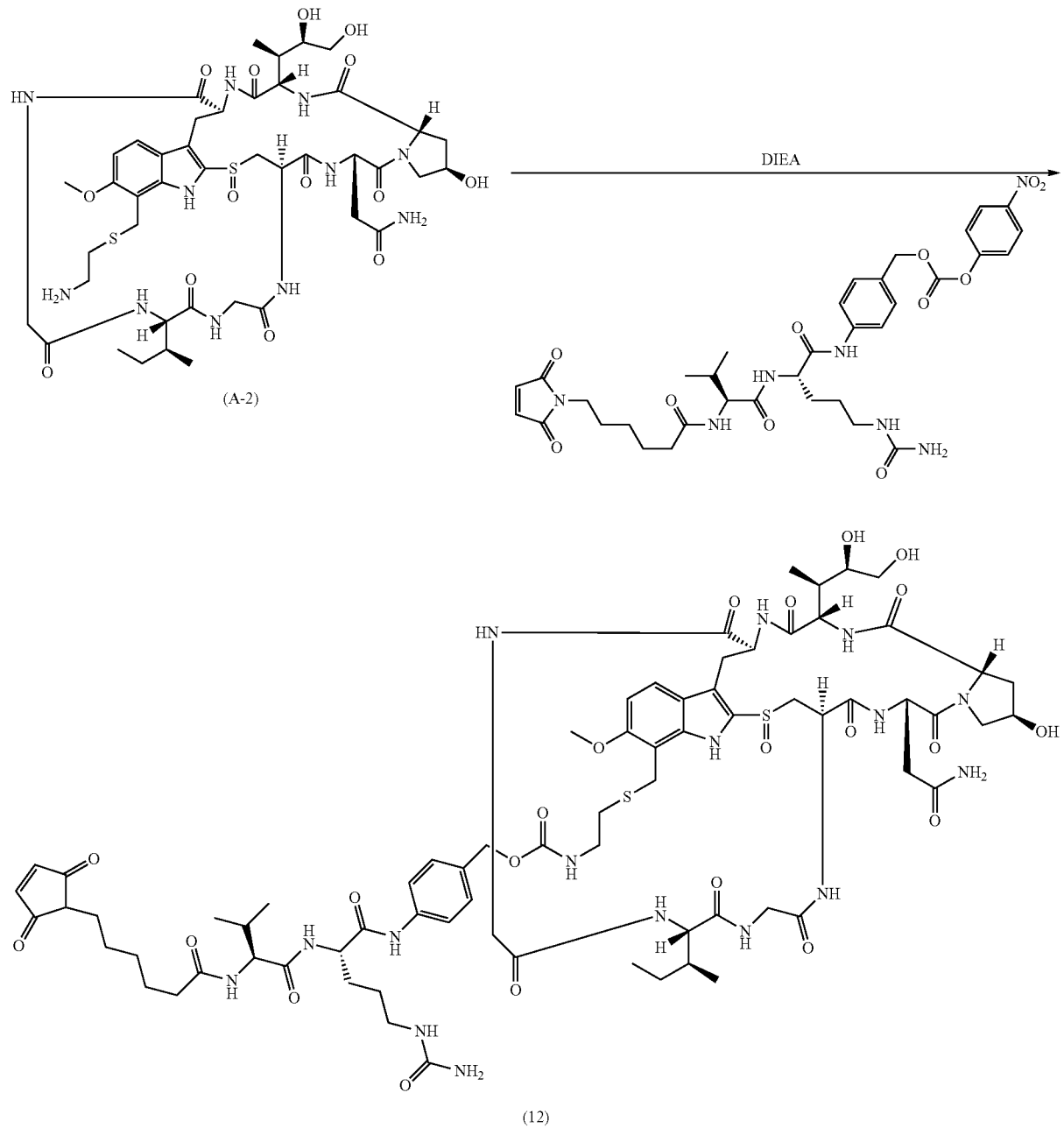
DIEA (1 μL, 7 μmol) and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (i-5) (2.2 mg, 3 mol) were added to a solution of compound (A-2) (3 mg, 3 μmol) in DMF (1 mL) and the reaction mixture was stirred at rt for 2 h. The mixture was then purified by HPLC and lyophilized to give compound (12). MS (m+2/2)=811.0, HPLC Peak RT=0.871 min, 1H-NMR (MeOD-d4, 400 MHz) δ 10.72 (s, 1H), 9.68 (s, 1H), 8.84 (m, 1H), 8.60 (d, 1H, J=1.2 Hz), 8.48 (m, 1H), 8.34 (s, 1H), 8.17 (m, 2H), 8.02 (d, 1H, J=9.6 Hz), 7.96 (d, 1H, J=8.4 Hz), 7.94 (d, 1H, J=7.6 Hz), 7.68 (s, 1H), 7.64 (d, 1H, J=8.8 Hz), 7.42 (d, 2H, J=8.0 Hz), 7.25 (d, 2H, J=8.8 Hz), 6.89 (d, 2H, J=8.8 Hz), 6.74 (s, 2H), 5.28 (m, 1H), 5.13 (m, 1H), 5.00 (d, 2H, J=5.2 Hz), 4.74 bs, 1H), 4.69 (s, 2H), 4.61 (dd, 1H, J=5.6 and 9.6 Hz), 4.50 (m, 3H), 4.31 (dd, 1H, J=8.4 and 18.4 Hz), 4.10 (m, 2H), 3.99 (d, 1H, J=12.8 Hz), 3.92 (m, 2H), 3.79 (s, 3H), 3.60~3.75 (m, 4H), 3.35~3.60 (m, 17H), 3.07 (m, 3H), 2.93 (m, 1H), 2.52 (m, 1H), 2.40 (m, 2H), 2.22 (t, 2H, J=7.2 Hz), 1.90~2.10 (m, 2H), 1.85 (m, 1H), 1.69 (m, 1H), 1.54 (m, 9H), 1.27 (m, 4H), 1.15 (m, 2H), 0.94 (m, 10H), 0.85 (m, 6H).

Example 13: Synthesis of Compound (13)—6'O-methyl-7'C-((2-(3-(23-((4-maleimido)methyl-1H-1,2,3-triazol-1-yl)-3,6,9,12,15,18,21-heptaoxatricosyl)ureido)ethylthio)methyl)-α-Amanitin

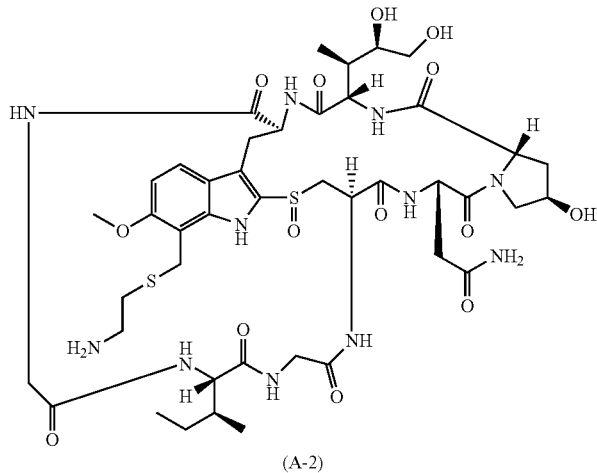

(A-2)

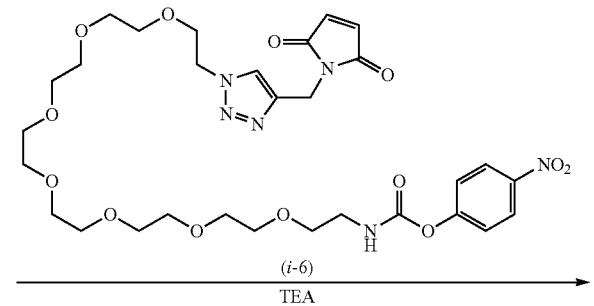

(i-6)

TEA

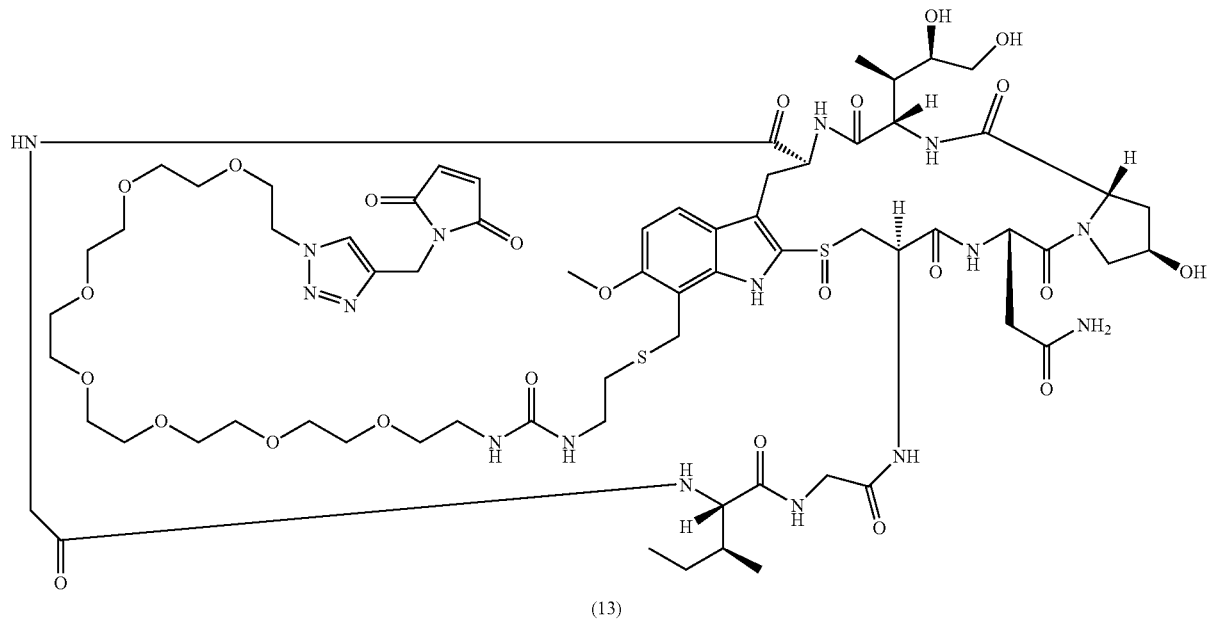

(13)

Triethylamine (3 μL, 18 μmol) was added to a solution of compound (A-2) (7.5 mg, 7 μmol) and 4-nitrophenyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate (i-6) (5.0 mg, 7 μmol) in DMF (1 mL) and the reaction mixture was stirred at rt for 2 h, purified by HPLC and lyophilized to give compound (13). MS (m+2/2)=789.5, HPLC Peak RT=0.799 min, 1H-NMR (MeOD-d4, 400 MHz) δ 8.83 (m, 1H), 8.59 (d, 1H, J=2.0 Hz), 8.48 (d, 1H, J=5.2 Hz), 8.45 (s, 1H), 8.14 (d, 1H, J=8.8 Hz), 8.08 (d, 1H, J=9.2 Hz), 8.01 (d, 1H, J=9.6 Hz), 7.92 (d, 1H, J=8.8 Hz), 7.90 (s, 1H), 7.63 (d, 1H, J=8.8 Hz), 6.92 (d, 1H, J=8.8 Hz), 6.84 (d, 1H, J=9.2 Hz), 6.80 (s, 2H), 5.26 (m, 1H), 5.13 (m, 1H), 4.75 (bs, 1H), 4.71 (s, 2H), 4.62 (dd, 1H, J=5.2 and 9.6 Hz), 4.44~4.52 (m, 4H), 4.29 (dd, 1H, J=8.8 and 18.4 Hz), 4.10 (m, 1H), 4.08 (d, 1H, J=13.2 Hz), 3.96 (d, 1H, J=13.2 Hz), 3.92 (m, 1H), 3.86 (s, 3H), 33.79 (t, 2H, J=5.2 Hz), 3.60~3.75 (m, 4H), 3.45~3.60 (m, 35H), 3.37 (dd, 2H, J=7.6 and 14.4 Hz), 3.22 (m, 1H), 3.04~3.09 (m, 1H), 2.92 (dd, 1H, J=12.0 and 15.2 Hz), 2.35~2.53 (m, 4H), 2.00 (m, 2H), 1.50~1.65 (m, 2H), 1.1 (m, 1H), 0.94 (d, 3H, J=7.2 Hz), 0.85 (m, 6H).

Example 14: Synthesis of Compound (14)—6'O-methyl-7'C-((2-(4-(maleimido)ethanecarboxamido)butylthio)methyl)

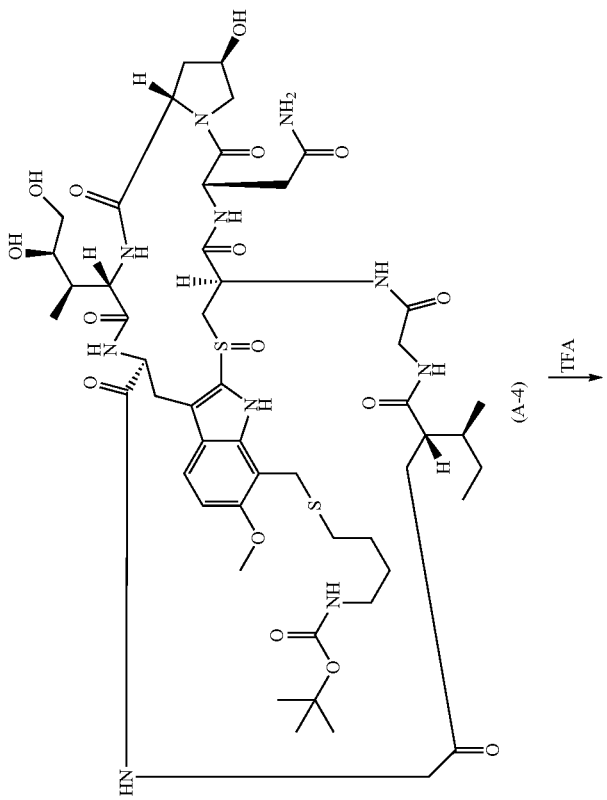
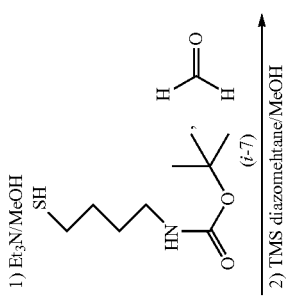
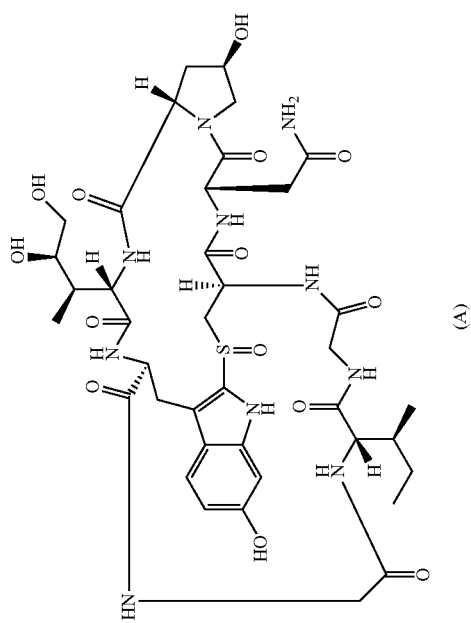

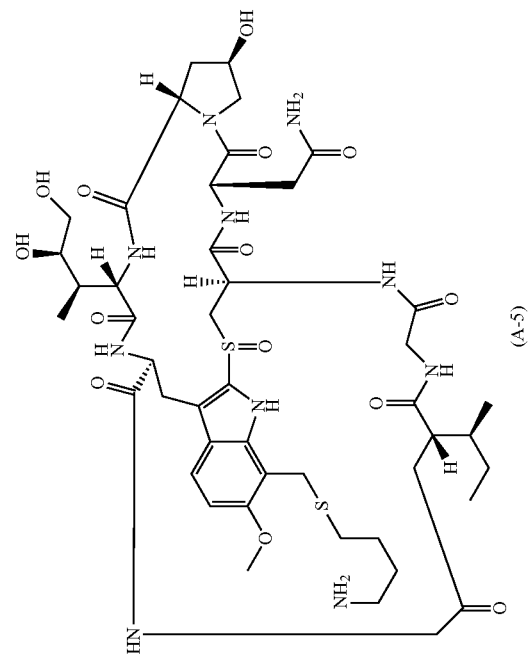
(A-5)
HBTU, DIEA/DMF
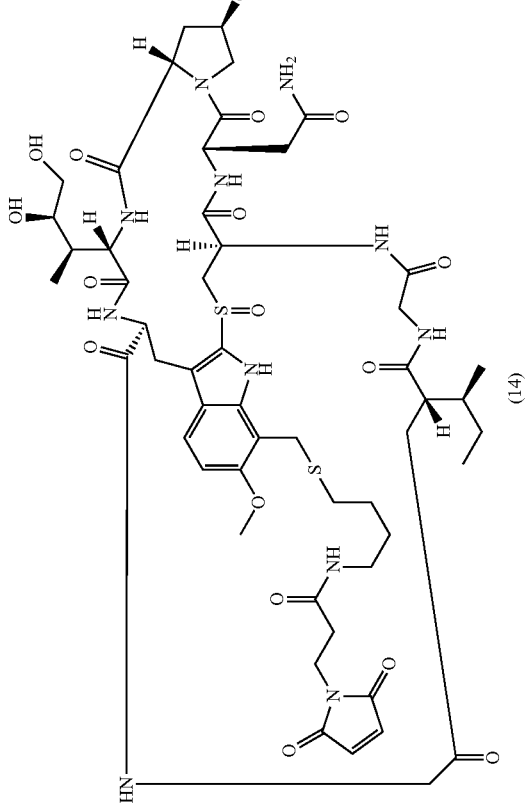
(14)

Step 1: Synthesis of Compound (A-4)

Formaldehyde (0.027 mL, 0.33 mmol) and tert-butyl (4-mercaptobutyl)carbamate (i-7) (34 mg, 0.16 mmol) were added to a solution of α-Amanitin (A) (15 mg, 0.016 mmol) in MeOH (5 mL) and triethylamine (0.46 mL, 3.26 mmol) in a 40 mL vial, and the reaction mixture was stirred at 40° C. for 3 days. After concentration in vacuo, the residue was dissolved in 2 mL of MeOH and 408 μL of 2M of trimethylsilyl diazomethane in diethyl ether was added and the mixture was stirred for 2 h at rt. Then another 408 μL of 2M of trimethylsilyl diazomethane in diethyl ether was added and stirred at rt for 2 h. The reaction mixture was purified by HPLC and lyophilized to give the desired compound (A-4). MS (m+2-boc/2)=525.8, HPLC Peak RT=0.936 min, 1H-NMR (MeOD-d4, 400 MHz) δ 10.78 (s, 1H), 8.84 (m, 1H), 8.59 (d, 1H, J=2.4 Hz), 8.48 (s, 1H), 8.46 (d, 1H, J=14.4 Hz), 8.35 (s, 1H), 8.15 (d, 1H, J=8.8 Hz), 8.01 (d, 1H, J=10.0 Hz), 7.92 (d, 1H, J=8.8 Hz), 7.69 (s, 1H), 7.63 (d, 1H, J=8.8 Hz), 6.92 (d, 1H, J=8.8 Hz), 5.28 (m, 1H), 5.13 (m, 1H), 4.73 (bs, 1H), 4.61 (dd, 1H, J=5.6 and 8.4 Hz), 4.51 (m, 2H), 4.30 (dd, 1H, J=8.8 and 18.4 Hz), 4.12 (m, 1H), 4.04 (d, 1H, J=13.2 Hz), 3.94 (d, 1H, J=13.2 Hz), 3.92 (m, 1H), 3.86 (s, 3H), 3.35~3.75 (m, 14H), 3.05 (m, 1H), 2.92 (m, 3H), 2.49 (m, 4H), 2.00 (m, 1H), 1.39~1.65 (m, 8H), 1.37 (s, 9H), 1.15 (m, 1H), 0.93 (d, 3H, J=7.2 Hz), 0.84 (m, 6H).

Step 2: Synthesis of Compound (A-5)

TFA (1 mL) was added to 8 mg of compound (A-4) in a 40 mL vial and the resulting solution was allowed to stand at rt for 2 min and then concentrated under vacuum to give the desired compound (A-5), which was used without further purification. MS (m+1)=1050.4, HPLC Peak RT=0.635 min, 1H-NMR (MeOD-d4, 400 MHz) δ 8.87 (m, 1H), 8.58 (d, 1H, J=2.4 Hz), 8.48 (d, 1H, J=10.4 Hz), 8.44 (d, 1H, J=1.6 Hz), 8.16 (d, 1H, J=8.4 Hz), 7.97 (d, 1H, J=9.6 Hz), 7.94 (d, 1H, J=9.2 Hz), 7.62 (d, 1H, J=8.8 Hz), 6.92 (d, 1H, J=9.2 Hz), 5.25 (m, 1H), 5.13 (m, 1H), 4.73 (m, 1H), 4.60 (dd, 1H, J=5.6 and 9.2 Hz), 4.49 (m, 2H), 4.28 (dd, 1H, J=8.8 and 18.4 Hz), 4.12 (m, 1H), 4.04 (d, 1H, J=13.2 Hz), 3.99 (s, 2H), 3.92 (m, 1H), 3.86 (s, 3H), 3.83 (s, 1H), 3.60~3.72 (m, 4H), 3.30~3.60 (m, 10H), 3.00~3.20 (m, 2H), 2.90 (m, 1H), 2.76 (m, 2H), 2.00 (m, 1H), 1.50~1.75 (m, 7H), 1.16 (d, 1H, J=5.6 Hz), 1.24 (d, 2H, J=7.6 Hz), 1.15 (m, 1H), 0.94 (d, 3H, J=6.8 Hz), 0.85 (m, 6H).

Step 3: Synthesis of Compound (14)

Compound (A-5) (4 mg, 4 μmol) in DMF (1 mL) was added to a 40 mL vial, to which 1 mg of HBTU (3 μmol), 1 mg of 3-maleimidopropionic acid (4 μmol) and 0.002 mL of diisopropylethylamine (10 μmol) were added. The reaction mixture was then stirred at rt for 1 h and then purified by HPLC and lyophillized to give the desired compound (14). MS (m+2/2)=601.4, HPLC Peak RT=0.764 min, 1H-NMR (MeOD-d4, 400 MHz) δ 10.76 (s, 1H), 8.84 (m, 1H), 8.59 (d, 1H, J=2.0 Hz), 8.49 (s, 1H), 8.47 (d, 1H, J=10.0 Hz), 8.15 (d, 1H, J=8.4 Hz), 8.01 (d, 1H, J=9.6 Hz), 7.91 (d, 1H, J=8.8 Hz), 7.63 (d, 1H, J=8.8 Hz), 6.92 (d, 1H, J=9.2 Hz), 6.73 (s, 2H), 5.27 (m, 1H), 5.13 (m, 1H), 4.74 (m, 1H), 4.62 (dd, 1H, J=5.2 and 9.6 Hz), 4.49 (m, 2H), 4.30 (dd, 1H, J=9.2 and 18.4 Hz), 4.12 (m, 1H), 4.02 (d, 1H, J=13.2 Hz), 3.94 (d, 1H, J=13.2 Hz), 3.92 (m, 1H), 3.85 (s, 3H), 3.35'3.72 (m, 12H), 3.05 (m, 3H), 2.91 (dd, 1H, J=12.0 and 14.8 Hz), 2.41 (m, 4H), 2.10 (t, 2H, J=7.2 Hz), 2.00 (m, 1H), 1.40~1.65 (m, 10H), 1.10~1.28 (m, 3H), 0.94 (d, 3H, J=7.2 Hz), 0.85 (m, 6H).

Example 15: Synthesis of Compound (15)—6'O-methyl-7'C-((4-(5-(maleimido)pentanecarboxamido)butylthio)methyl)-α-Amanitin

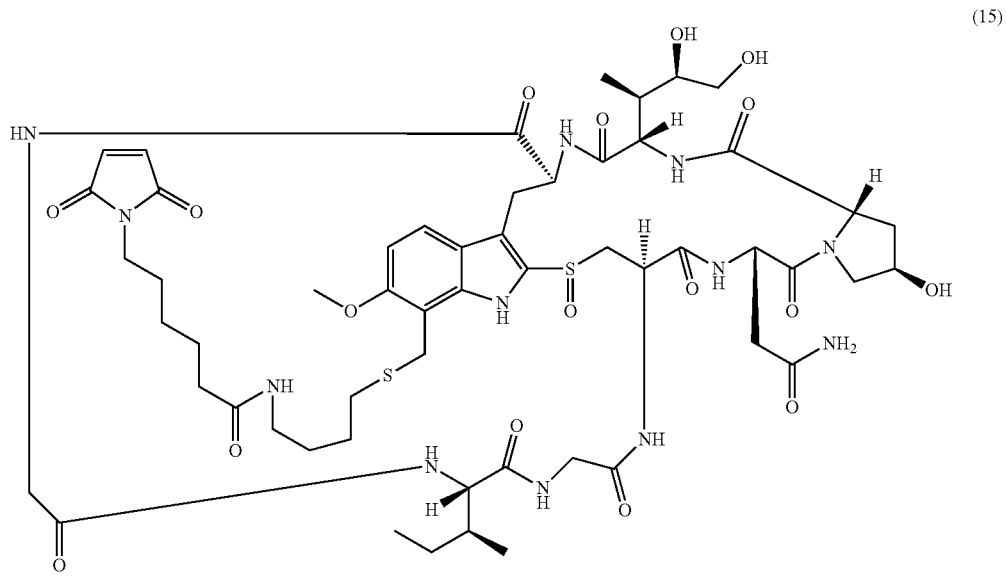 [SMILES: CC[C@H](C)[C@@H]1NC(=O)CNC(=O)[C@@H]2Cc3c([nH]c4c(CSCCCCNC(=O)CCCCCN5C(=O)C=CC5=O)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(15)

Compound (15) was prepared using the method described for compound (14) except 6-maleimidohexanoic acid was used instead of 3-maleimidopropionic acid. MS (m+2/2) =622.4, HPLC Peak RT=0.854 min, 1H-NMR (MeOD-d4, 400 MHz) δ 10.76 (s, 1H), 8.84 (m, 1H), 8.59 (d, 1H, J=2.0 Hz), 8.49 (s, 1H), 8.47 (d, 1H, J=4.8 Hz), 8.15 (d, 1H, J=8.8 Hz), 8.01 (d, 1H, J=9.6 Hz), 7.92 (d, 1H, J=8.8 Hz), 7.64 (d, 1H, J=8.8 Hz), 6.92 (d, 1H, J=8.8 Hz), 6.73 (s, 2H), 5.27 (m, 1H), 5.13 (m, 1H), 4.74 (m, 1H), 4.61 (dd, 1H, J=4.8 and 9.6 Hz), 4.49 (m, 2H), 4.30 (dd, 1H, J=9.2 and 18.8 Hz), 4.12 (m, 1H), 4.02 (d, 1H, J=13.2 Hz), 3.95 (d, 1H, J=13.2 Hz), 3.92 (m, 1H), 3.86 (s, 3H), 3.35~3.75 (m, 15H), 3.08 (m, 1H), 3.00 (t, 2H, J=6.4 Hz), 2.92 (dd, 1H, J=12.0 and 14.8 Hz), 2.38 (m, 6H), 2.00 (m, 1H), 1.33~1.68 (m, 6H), 1.14 (m, 1H), 0.94 (d, 3H, J=7.2 Hz), 0.85 (m, 6H).

Example 16: Synthesis of Compound (16)—6'O-methyl-7'C-(4-((2,5-dioxopyrrolidin-1-yl)oxycarbonylamino)butylthiomethyl)-α-Amanitin

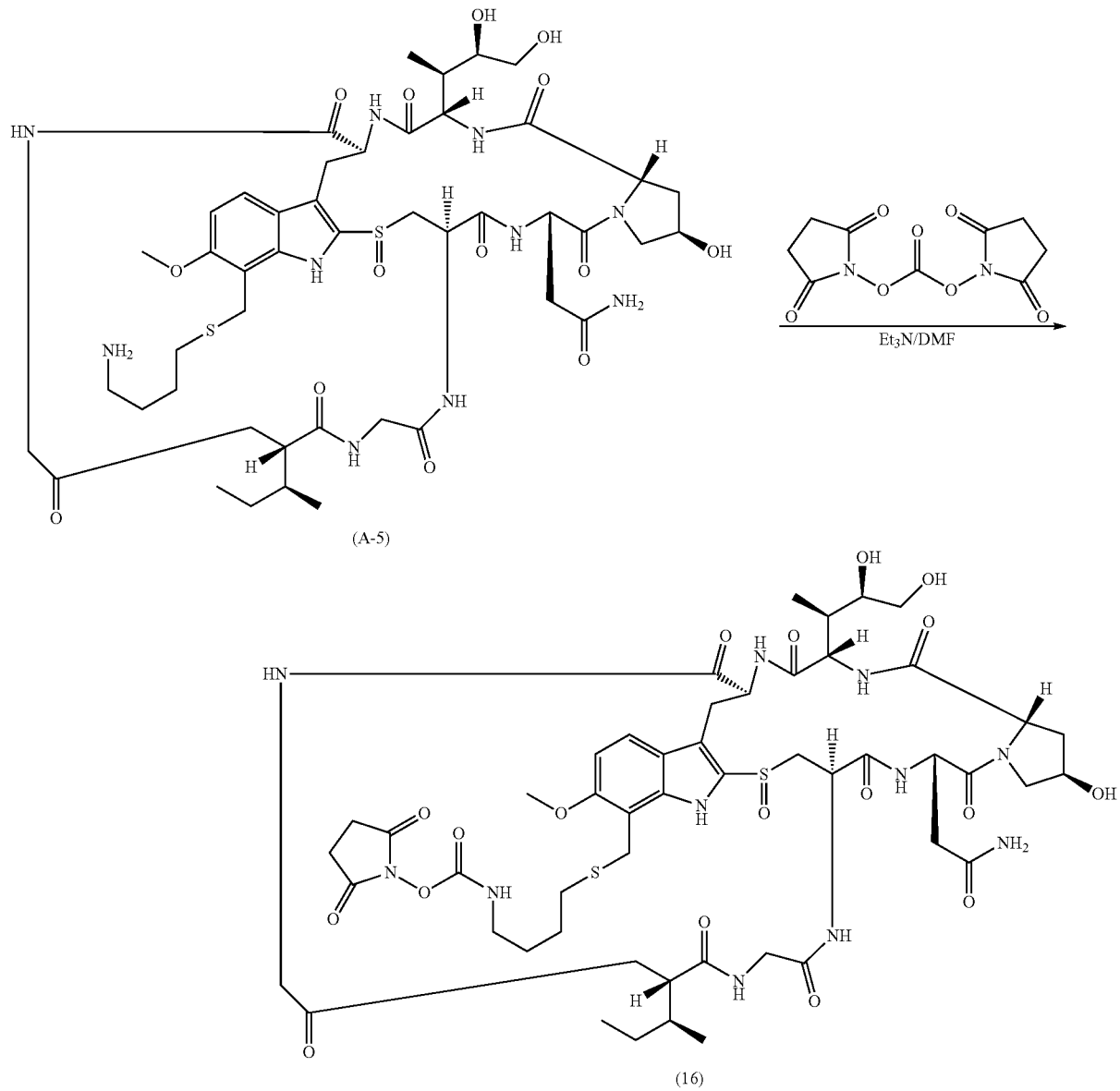

Using a 3 mL vial, 0.27 mg of N,N'-disuccinimidyl carbonate (1 μmol) and 0.3 μL of diisopropylethylamine (2 μmol) were added to 1.0 mg of compound (A-5) (1 μmol) in DMF (0.05 mL) and the reaction mixture stirred at rt for 30 min to give compound (16), which was then used without purification for attachment to an antibody. MS (m+1) =1191.4, HPLC Peak RT=0.779 min.

Example 17: Synthesis of Compound (17)—6'O-methyl-7'C-((4-(4-((maleimido)methyl)cyclohexan-ecarboxamido)butylthio)methyl)-α-Amanitin

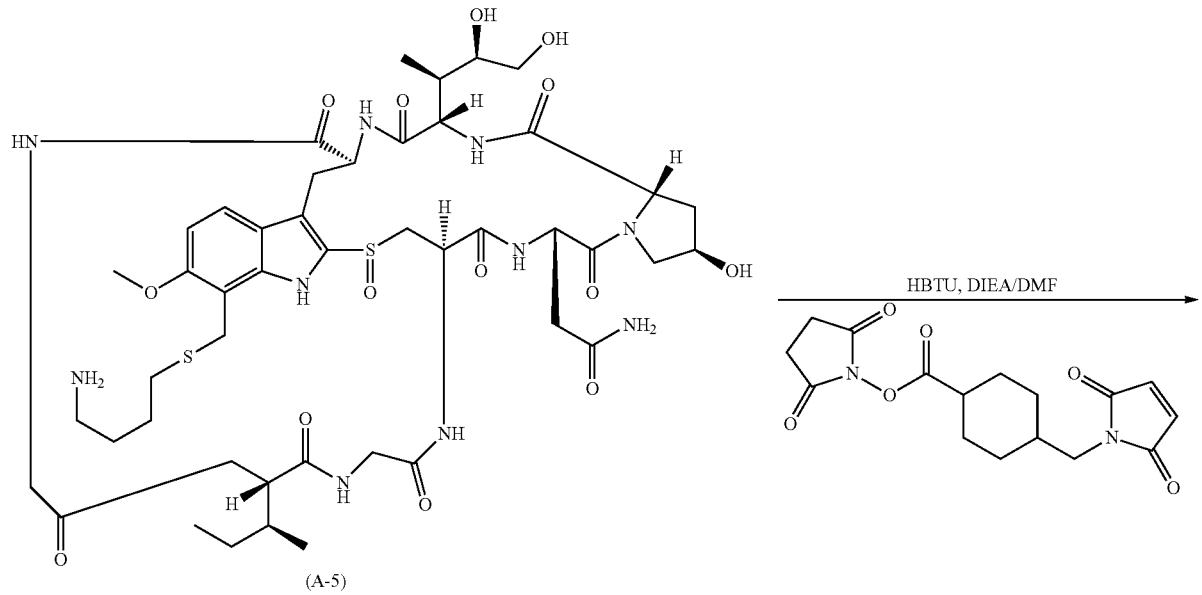

(A-5)

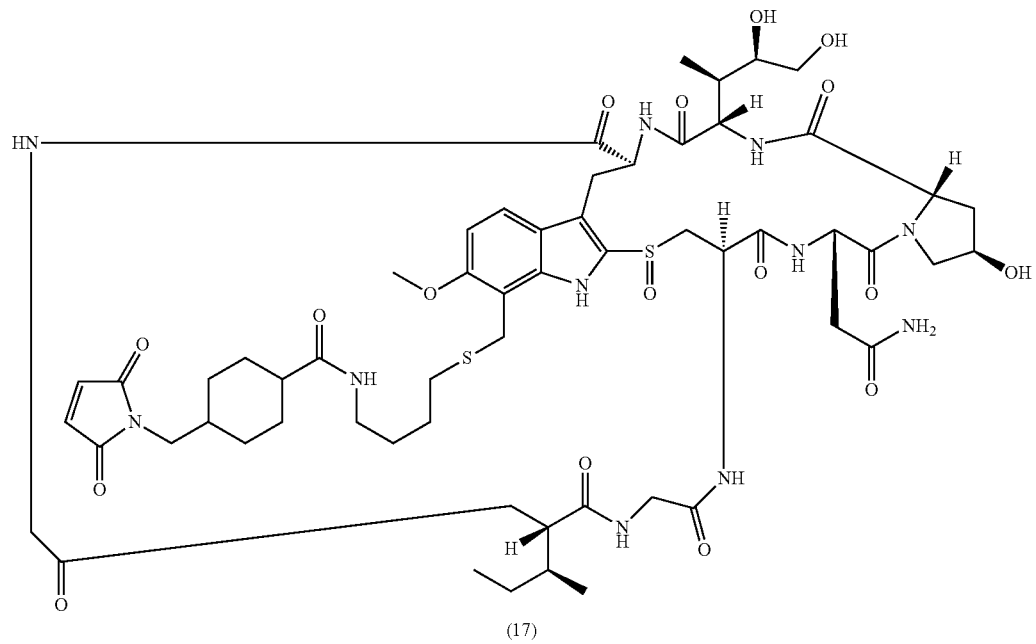

(17)

Using a 3 mL vial, 1 μL of diisopropylethylamine (6 μmol) and 1.0 mg of succinimidyl-4-(N-maleimidomethyl)cyclohexane-1-carboxylate (3 μmol) were added to 3.0 mg of compound (A-5) (3 μmol) in DMF (1 mL) and the reaction mixture was stirred at rt for 30 min. The reaction mixture was purified by HPLC and lyophilized to give compound (17). MS (m+2/2)=635.4, HPLC Peak RT=0.898 min, 1H-NMR (MeOD-d4, 400 MHz) δ 10.78 (s, 1H), 8.84 (m, 1H), 8.59 (d, 1H, J=2.0 Hz), 8.48 (s, 1H), 8.47 (d, 1H, J=10.0 Hz), 8.34 (s, 1H), 8.15 (d, 1H, J=8.4 Hz), 8.01 (d, 1H, J=10.0 Hz), 7.92 (d, 1H, J=8.8 Hz), 7.69 (s, 1H), 7.62 (d, 1H, J=8.8 Hz), 6.91 (d, 1H, J=9.2 Hz), 6.76 (s, 2H), 5.27 (m, 1H), 5.13 (m, 1H), 4.75 (m, 1H), 4.62 (dd, 1H, J=5.2 and 9.6 Hz), 4.49 (m, 2H), 4.30 (dd, 1H, J=8.8 and 18.4 Hz), 4.11 (m, 1H), 4.02 (d, 1H, J=13.2 Hz), 3.94 (d, 1H, J=13.2 Hz), 3.92 (m, 1H), 3.85 (s, 3H), 3.35~3.75 (m, 15H), 3.05 (m, 3H), 3.00 (t, 2H, J=6.4 Hz), 2.92 (dd, 1H, J=12.0 and 14.8 Hz), 2.39 (m, 4H), 2.02 (m, 2H), 2.00 (s, 1H), 1.10'1.75 (m, 18H), 1.10 (m, 1H), 0.94 (d, 3H, J=6.8 Hz), 0.85 (m, 6H).

Example 18: Synthesis of Compound (18)—6'O-methyl-7'C-((4-(3-(6-(maleimido)hexyl)ureido)butylthio)methyl)-α-Amanitin

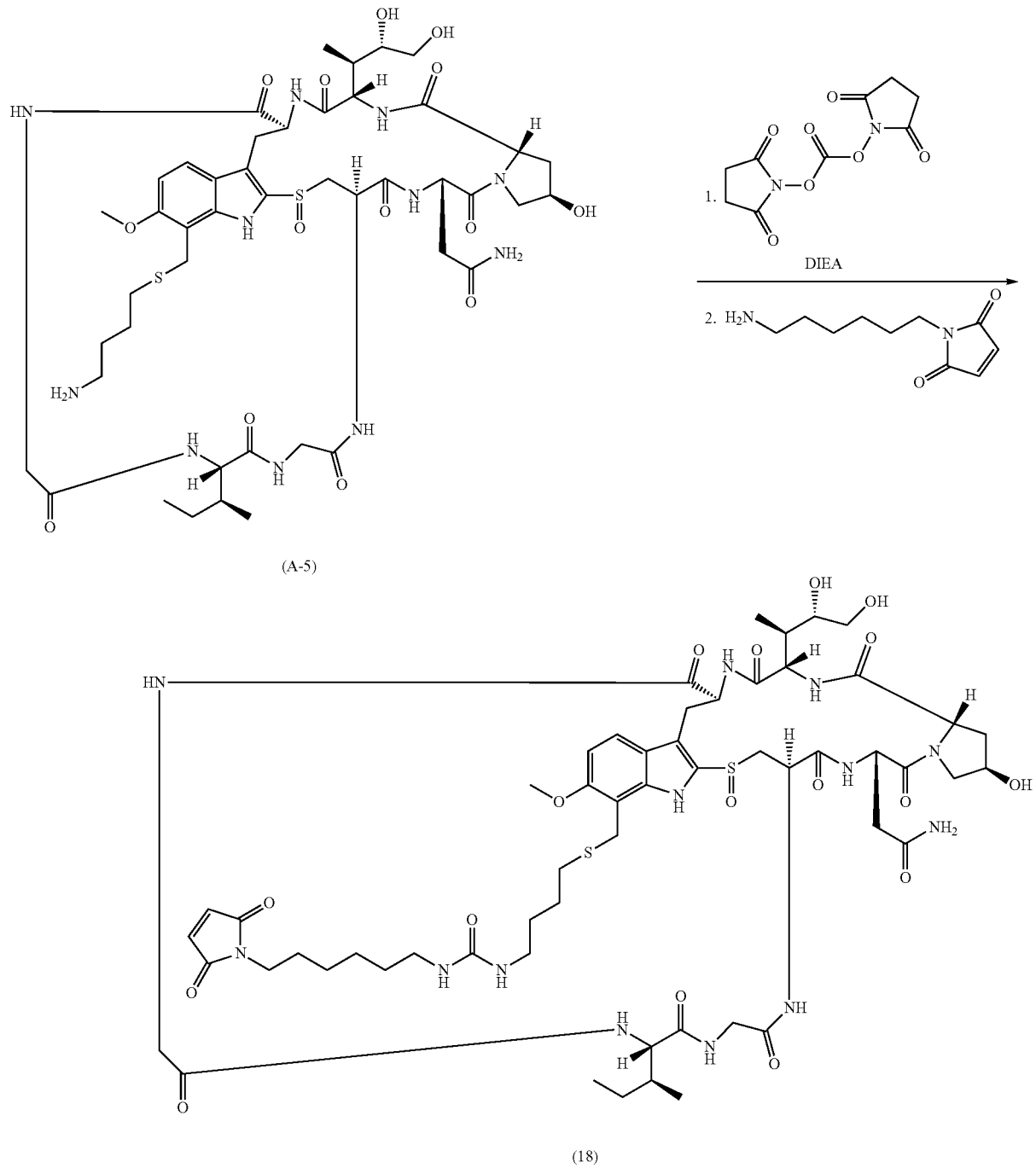

DIEA (3.0 μL, 19 μmol) and N,N'-disuccinimidyl carbonate (1.0 mg, 4 μmol) were added to 4.5 mg of Compound (A-5) (4 μmol) in DMF (0.5 mL) and the reaction mixture was allowed to stand at rt for 30 min, then 1-(6-aminohexyl)-1H-pyrrole-2,5-dione (1.8 mg, 8 μmol) was added, and the mixture was stirred overnight at rt. The reaction mixture was then purified by HPLC and lyophilized to give Compound (18). MS (m+1)=1273.4, HPLC Peak RT=0.864 min, 1H-NMR (MeOD-d4, 400 MHz) δ 10.75 (s, 1H), 8.85 (m, 1H), 8.59 (d, 1H, J=2.0 Hz), 8.49 (s, 1H), 8.47 (d, 1H, J=10.0 Hz), 8.34 (s, 1H), 8.16 (d, 1H, J=8.8 Hz), 8.01 (d, 1H, J=9.6 Hz), 7.92 (d, 1H, J=8.4 Hz), 7.68 (s, 1H), 7.62 (d, 1H, J=9.2 Hz), 6.92 (d, 1H, J=8.8 Hz), 6.73 (s, 2H), 5.28 (m, 1H), 5.11 (m, 1H), 4.74 (m, 1H), 4.62 (dd, 1H, J=4.8 and 9.6 Hz), 4.49 (m, 2H), 4.30 (dd, 1H, J=8.4 and 18.0 Hz), 4.12 (m, 1H), 3.90~4.05 (m, 3H), 3.85 (s, 3H), 3.35~3.75 (m, 27H), 2.85~3.10 (m, 8H), 2.39 (m, 4H), 2.02 (m, 2H), 1.10~1.75 (m, 32H), 0.94 (d, 3H, J=7.2 Hz), 0.85 (m, 6H).

Example 19: Synthesis of Compound (19)—6'O-methyl-7'C-((4-(5-(5-(maleimido)pentanecarboxamido)pentanecarboxamido)butylthio)methyl)-α-Amanitin
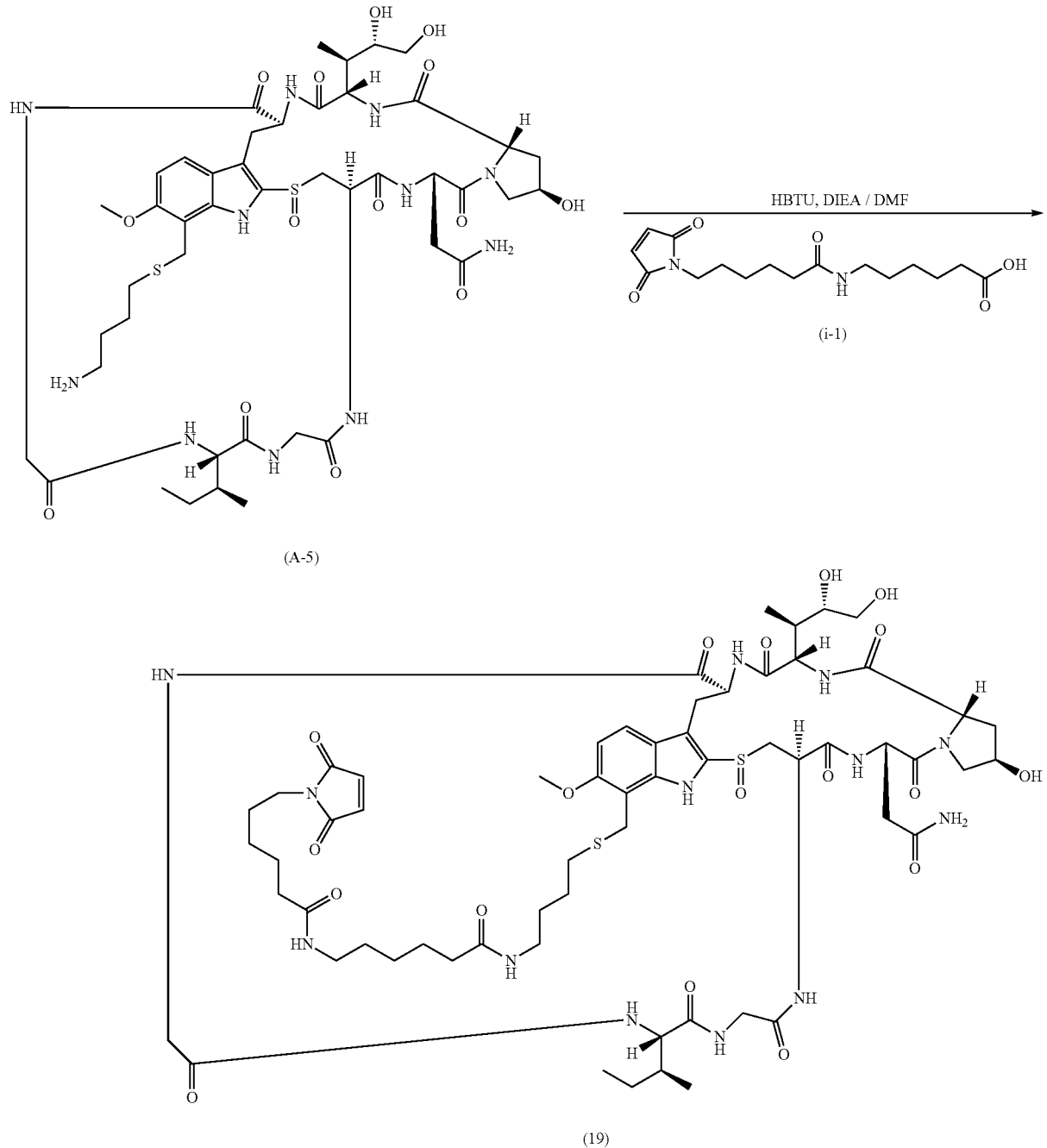

(A-5) (i-1)

(19)

Compound 6-(6-(2,5-dioxo-2,5-dihydro-1H-pyrrol-1-yl)hexanamido)hexanoic acid (i-1) (1.0 mg, 3 μmol) and HBTU (0.7 mg, 2 μmol) were added to compound (A-5) (3 mg, 3 μmol) and DIEA (1 μl, 6 μmol) in DMF (1 mL) and the reaction mixture was stirred at rt for 30 min. The reaction mixture was purified by HPLC and lyophilized to give compound (19). MS (m+2/2)=679.0, HPLC Peak RT=0.827 min, 1H-NMR (MeOD-d4, 400 MHz) δ 10.78 (s, 1H), 8.85 (m, 1H), 8.59 (d, 1H, J=2.0 Hz), 8.49 (s, 1H), 8.47 (d, 1H, J=10.4 Hz), 8.15 (d, 1H, J=8.4 Hz), 8.01 (d, 1H, J=9.6 Hz), 7.92 (d, 1H, J=8.4 Hz), 7.63 (d, 1H, J=8.8 Hz), 6.92 (d, 1H, J=9.2 Hz), 6.73 (s, 2H), 5.28 (m, 1H), 5.13 (m, 1H), 4.75 (m, 1H), 4.62 (dd, 1H, J=5.6 and 9.6 Hz), 4.49 (m, 2H), 4.30 (dd, 1H, J=8.4 and 18.8 Hz), 4.10 (m, 1H), 4.03 (d, 1H, J=13.2 Hz), 3.94 (d, 1H, J=13.2 Hz), 3.93 (m, 1H), 3.85 (s, 3H), 3.35~3.75 (m, 15H), 2.75~3.05 (m, 10H), 2.41 (m, 4H), 2.10 (m, 4H), 2.00 (m, 1H), 1.10~1.65 (m, 22H), 0.94 (d, 3H, J=7.2 Hz), 0.85 (m, 6H).

Example 20: Synthesis of Compound (20)—6'O-methyl-7'C-((4-(5-(4-((maleimido)methyl)cyclohexanecarboxamido)pentanecarboxamido)butylthio)methyl)-α-Amanitin
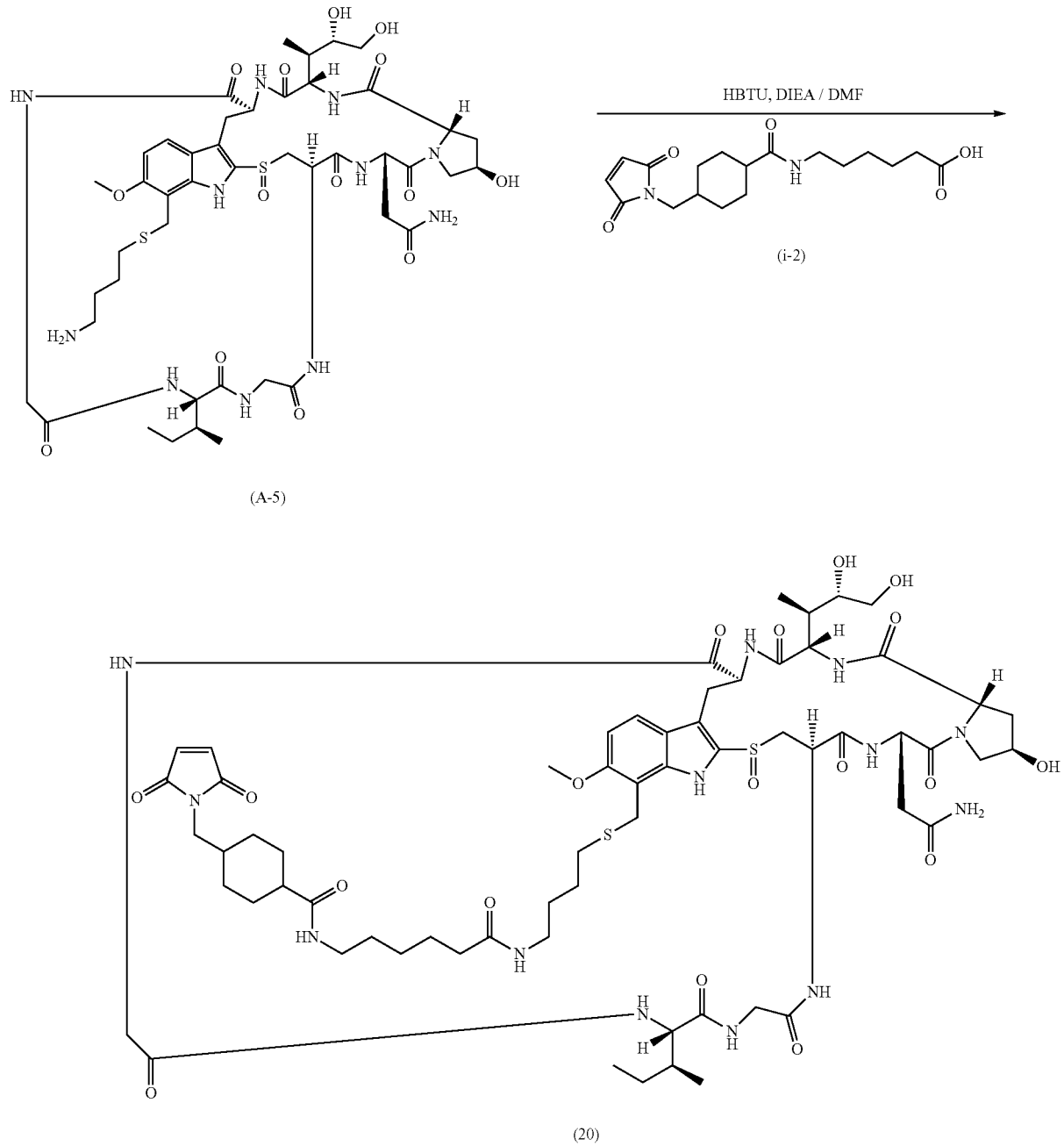 [SMILES: CC[C@H](C)[C@@H]1NC(=O)CNC(=O)[C@@H]2Cc3c([nH]c4c(CSCCCCN)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@H](O)CO)C(=O)N2 ; O=C(O)CCCCCNC(=O)C1CCC(CN2C(=O)C=CC2=O)CC1 ; "(A-5)" ; CC[C@H](C)[C@@H]1NC(=O)CNC(=O)[C@@H]2Cc3c([nH]c4c(CSCCCCNC(=O)CCCCCNC(=O)C5CCC(CN6C(=O)C=CC6=O)CC5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@H](O)CO)C(=O)N2]

(A-5)

(i-2)

(20)

Compound (20) was prepared using the method described in Example 19, except 6-(4-((2,5-dioxo-2,5-dihydro-1H-pyrrol-1-yl)methyl)cyclohexanecarboxamido)hexanoic acid (i-2) was used in place of 6-(6-(2,5-dioxo-2,5-dihydro-1H-pyrrol-1-yl)hexanamido)hexanoic acid (i-1). MS (m+2/2) =692.0, HPLC Peak RT=0.850 min, 1H-NMR (MeOD-d4, 400 MHz) δ 10.77 (s, 1H), 8.85 (m, 1H), 8.59 (d, 1H, J=2.0 Hz), 8.49 (s, 1H), 8.47 (d, 1H, J=10.4 Hz), 8.15 (d, 1H, J=8.8 Hz), 8.01 (d, 1H, J=9.6 Hz), 7.93 (s, 1H), 7.92 (d, 1H, J=8.4 Hz), 7.63 (d, 1H, J=8.8 Hz), 6.92 (d, 1H, J=9.2 Hz), 6.74 (s, 2H), 5.28 (m, 1H), 5.13 (m, 1H), 4.75 (m, 1H), 4.62 (dd, 1H, J=4.8 and 9.6 Hz), 4.49 (m, 2H), 4.30 (dd, 1H, J=8.4 and 18.4 Hz), 4.10 (m, 1H), 4.03 (d, 1H, J=13.2 Hz), 3.95 (d, 1H, J=13.2 Hz), 3.93 (m, 1H), 3.85 (s, 3H), 3.35~3.75 (m, 15H), 3.07 (m, 7H), 2.38 (m, 4H), 1.95~2.15 (m, 4H), 2.00 (m, 1H), 1.10~1.75 (m, 28H), 0.94 (d, 3H, J=6.8 Hz), 0.85 (m, 6H).

Example 21: Synthesis of Compound (21)—6'O-methyl-7'C-((4-(14-(maleimido)-3,6,9,12-tetraoxa-tetradecancarboxamido)butylthio)methyl)-α-Amanitin

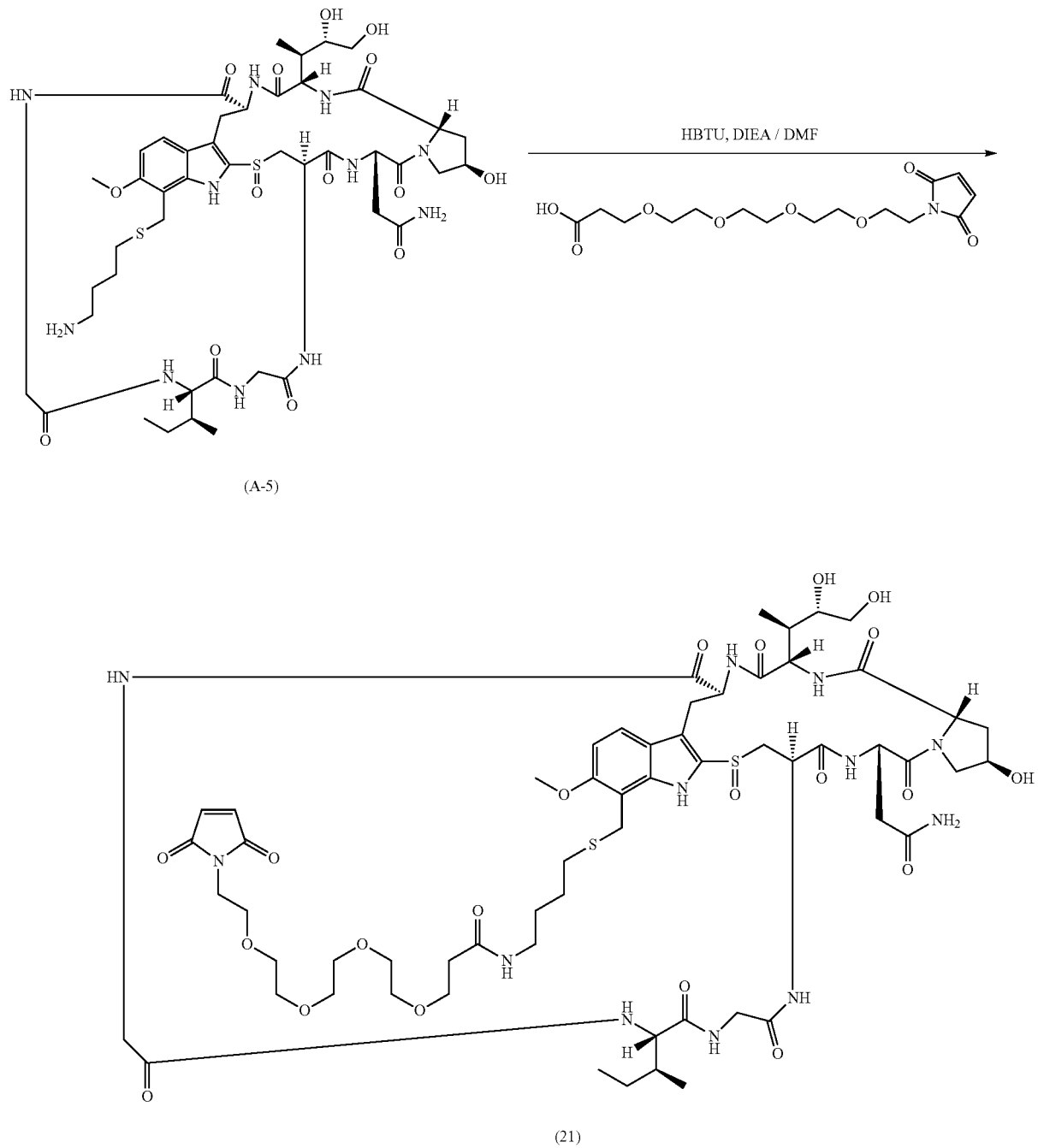

Compound (21) was prepared using the method described in Example 19, except 1-(2,5-dioxo-2,5-dihydro-1H-pyrrol-1-yl)-3,6,9,12-tetraoxapentadecan-15-oic acid was used in place of 6-(6-(2,5-dioxo-2,5-dihydro-1H-pyrrol-1-yl)hexanamido)hexanoic acid (i-1). MS (m+2/2)=689.4, HPLC Peak RT=0.793 min, 1H-NMR (MeOD-d4, 400 MHz) δ 10.75 (s, 1H), 8.85 (m, 1H), 8.59 (d, 1H, J=1.6 Hz), 8.48 (s, 1H), 8.47 (d, 1H, J=4.8 Hz), 8.15 (d, 1H, J=8.0 Hz), 8.01 (d, 1H, J=9.6 Hz), 7.93 (d, 1H, J=8.8 Hz), 7.64 (d, 1H, J=8.8 Hz), 6.92 (d, 1H, J=9.2 Hz), 6.74 (s, 2H), 5.28 (m, 1H), 5.13 (m, 1H), 4.75 (m, 1H), 4.62 (dd, 1H, J=4.8 and 9.6 Hz), 4.49 (m, 2H), 4.30 (dd, 1H, J=8.4 and 18.4 Hz), 4.10 (m, 1H), 4.03 (d, 1H, J=13.2 Hz), 3.93 (d, 1H, J=13.2 Hz), 3.92 (m, 1H), 3.85 (s, 3H), 3.35~3.75 (m, 36H), 3.07 (m, 4H), 2.91 (m, 1H), 2.38 (m, 6H), 2.00 (m, 1H), 1.10'1.60 (m, 8H), 0.94 (d, 3H, J=7.2 Hz), 0.85 (m, 6H).

Example 22: Synthesis of Compound (A-6)—6'O-methyl-7'C-((4-(14-azido-3,6,9,12-tetraoxatetradecancarboxamido)butylthio)methyl)-α-Amanitin and Compound (22)—6'O-methyl-7'C-((4-(14-((4-maleimido)methyl-1H-1,2,3-triazol-1-yl)-3,6,9,12-tetraoxatetradecancarboxamido)butylthio)methyl)-α-Amanitin

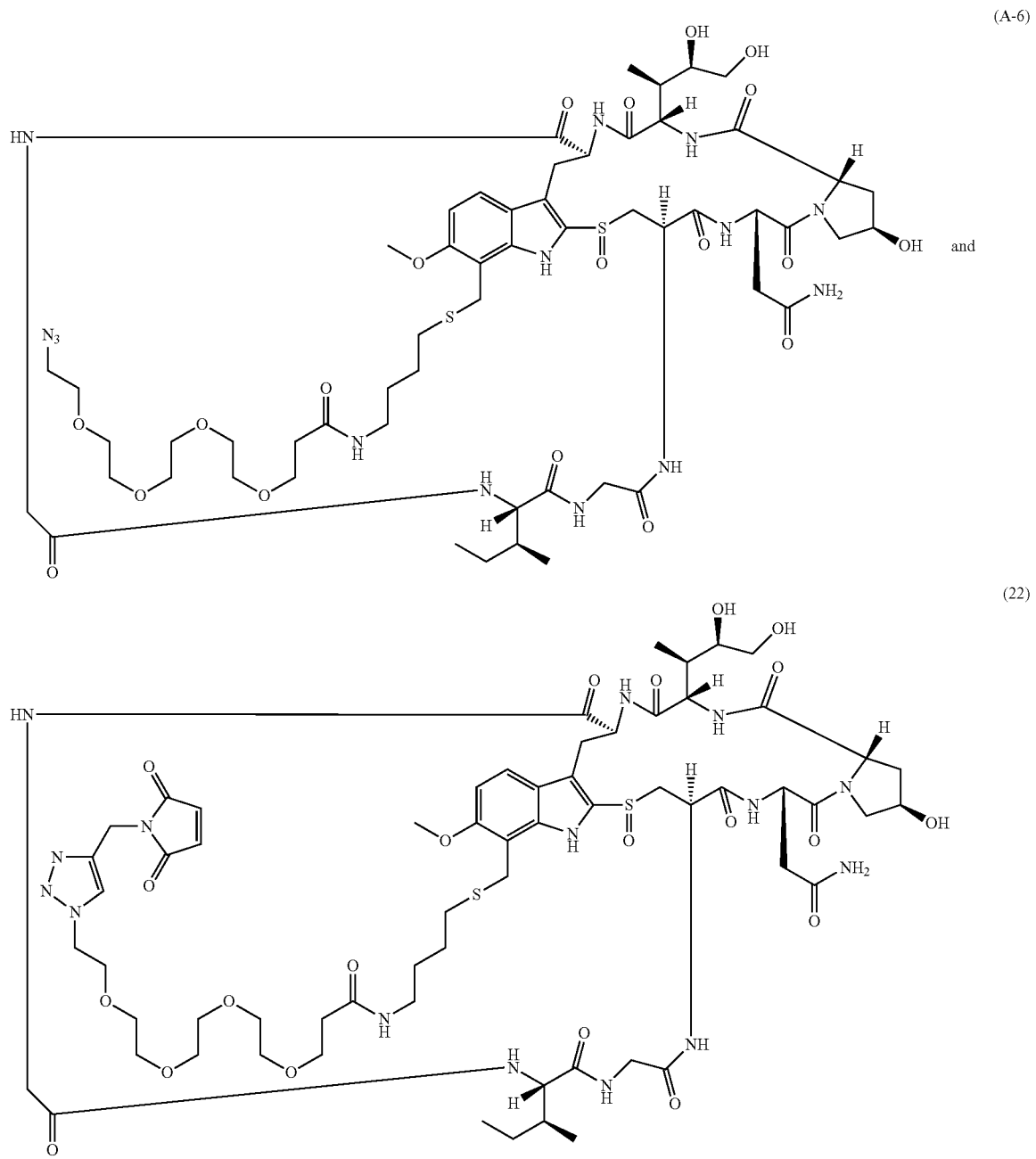

Compound (A-6) was prepared using the method described in Example 9, except Compound (A-5) was used in place of Compound (A-2). MS (m+2/2)=662.4, HPLC Peak RT=0.875 min, 1H-NMR (MeOD-d4, 400 MHz) δ 10.77 (s, 1H), 8.84 (m, 1H), 8.59 (d, 1H, J=1.6 Hz), 8.48 (s, 1H), 8.46 (d, 1H, J=7.2 Hz), 8.15 (d, 1H, J=8.0 Hz), 8.01 (d, 1H, J=9.6 Hz), 7.92 (d, 1H, J=8.8 Hz), 7.64 (d, 1H, J=8.8 Hz), 6.92 (d, 1H, J=9.2 Hz), 5.28 (m, 1H), 5.13 (m, 1H), 4.74 (m, 1H), 4.62 (dd, 1H, J=5.2 and 9.6 Hz), 4.49 (m, 2H), 4.30 (dd, 1H, J=9.2 and 18.4 Hz), 4.12 (m, 1H), 4.04 (d, 1H, J=13.2 Hz), 3.94 (d, 1H, J=13.2 Hz), 3.92 (m, 1H), 3.85 (s, 3H), 3.30~3.75 (m, 34H), 3.08 (m, 4H), 2.92 (m, 1H), 2.37 (m, 6H), 2.00 (m, 1H), 1.40~1.60 (m, 6H), 1.15 (m, 1H), 0.94 (d, 3H, J=6.8 Hz), 0.85 (m, 6H).

Compound (22) was prepared using the method described in Example 9, except Compound (A-6) was used in place of Compound (A-4). MS (m+2/2)=730.0, HPLC Peak RT=0.787 min, 1H-NMR (MeOD-d4, 400 MHz) δ 10.75 (s, 1H), 8.84 (m, 1H), 8.61 (d, 1H, J=2.0 Hz), 8.49 (d, 1H, J=9.2 Hz), 8.48 (s, 1H), 8.16 (d, 1H, J=9.0 Hz), 8.02 (d, 1H, J=9.6 Hz), 7.94 (d, 1H, J=9.0 Hz), 7.90 (s, 1H), 7.64 (d, 1H, J=9.0 Hz), 6.93 (d, 1H, J=9.0 Hz), 6.80 (s, 2H), 5.28 (m, 1H), 5.13 (m, 1H), 4.77 (m, 1H), 4.71 (s, 2H), 4.64 (dd, 1H, J=5.4 and 9.6 Hz), 4.52 (m, 2H), 4.48 (t, 2H, J=4.8 Hz), 4.30 (dd, 1H, J=8.4 and 18.6 Hz), 4.15 (m, 1H), 4.06 (d, 1H, J=13.2 Hz), 3.96 (d, 1H, J=13.2 Hz), 3.92 (m, 1H), 3.87 (s, 3H), 3.79 (t, 2H, J=5.4 Hz), 3.4~3.75 (m, 32H), 3.08 (m, 4H), 2.93 (m, 1H), 2.37 (m, 6H), 2.02 (m, 1H), 1.42~1.52 (m, 6H), 1.18 (m, 1H), 0.96 (d, 3H, J=7.2 Hz), 0.85 (m, 6H).

Example 23: Synthesis of Compound (23)—6′O-methyl-7′C-((4-(3-(23-((4-maleimido)methyl-1H-1,2,3-triazol-1-yl)-3,6,9,12,15,18,21-heptaoxatricosyl)ureido)butylthio)methyl)-α-Amanitin

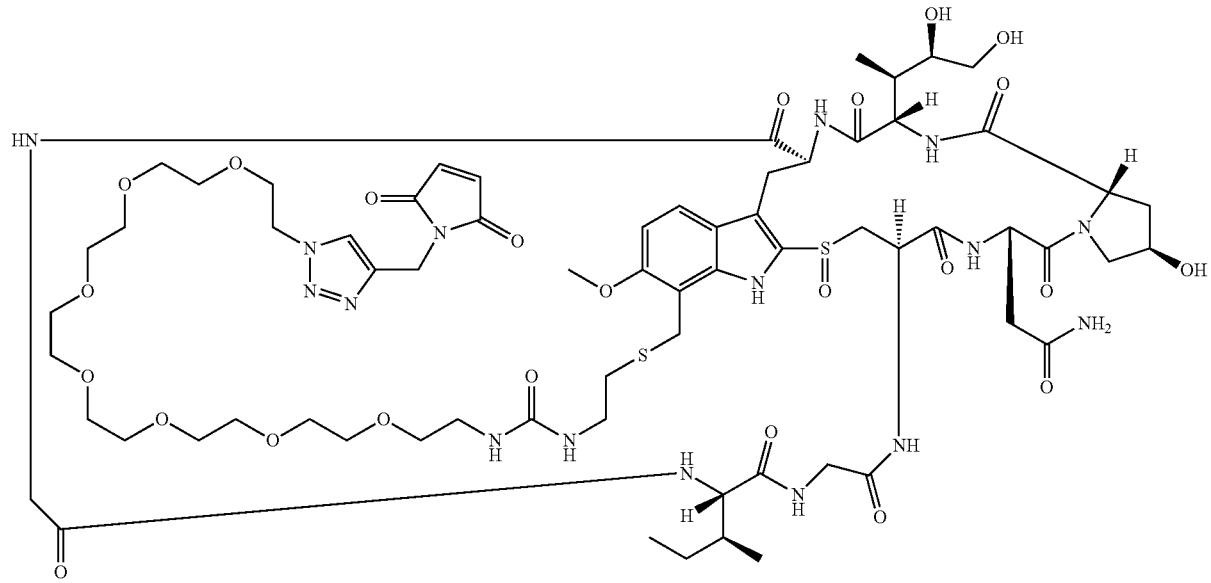

(23)

Compound (23) was prepared using the method described in Example 13, except Compound (A-5) was used in place of Compound (A-2). MS (m+2/2)=803.5, HPLC Peak RT=0.834 min, 1H-NMR (MeOD-d4, 400 MHz) δ 10.76 (s, 1H), 8.84 (m, 1H), 8.59 (d, 1H, J=2.0 Hz), 8.49 (s, 1H), 8.47 (d, 1H, J=8.0 Hz), 8.15 (d, 1H, J=8.4 Hz), 8.01 (d, 1H, J=9.6 Hz), 7.92 (d, 1H, J=8.8 Hz), 7.90 (s, 1H), 7.63 (d, 1H, J=8.8 Hz), 6.92 (d, 1H, J=9.2 Hz), 6.79 (s, 2H), 5.28 (m, 1H), 5.13 (m, 1H), 4.74 (m, 1H), 4.71 (s, 2H), 4.62 (dd, 1H, J=5.2 and 9.6 Hz), 4.49 (m, 4H), 4.30 (dd, 1H, J=8.8 and 18.4 Hz), 4.14 (m, 1H), 4.04 (d, 1H, J=13.2 Hz), 3.94 (d, 1H, J=13.2 Hz), 3.92 (m, 1H), 3.85 (s, 3H), 3.80 (t, 2H, J=4.8 Hz), 3.35~3.75 (m, 38H), 2.90~3.10 (m, 4H), 2.92 (m, 1H), 2.40 (m, 4H), 2.01 (m, 1H), 1.38~1.65 (m, 6H), 1.15 (m, 1H), 0.94 (d, 3H, J=6.8 Hz), 0.85 (m, 6H).

Example 24: Synthesis of Compound (24)—7'C-((2-(5-(maleimido)pentanecarboxamido)ethylthio)methyl)-α-Amanitin
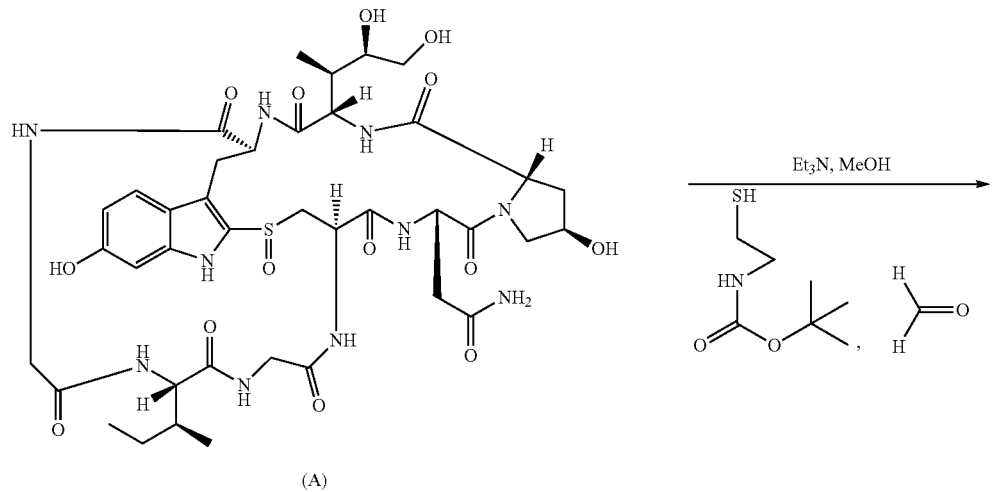
(A)
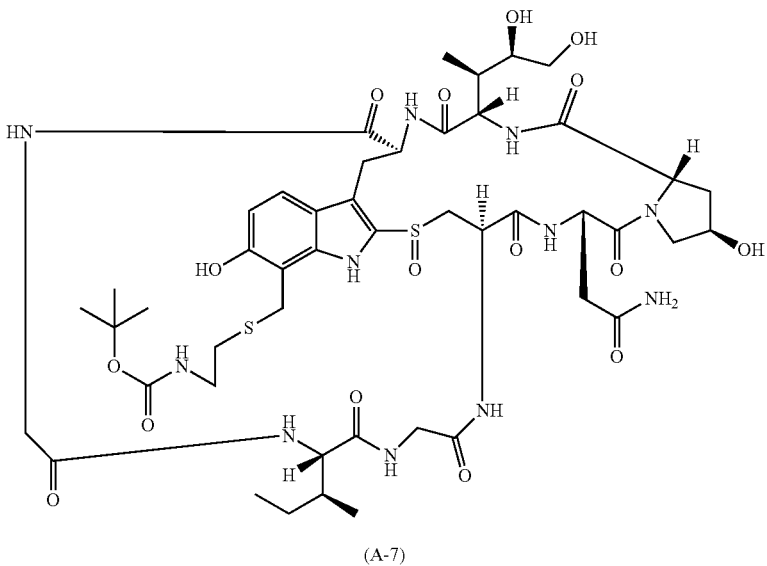
(A-7)
↓ TFA

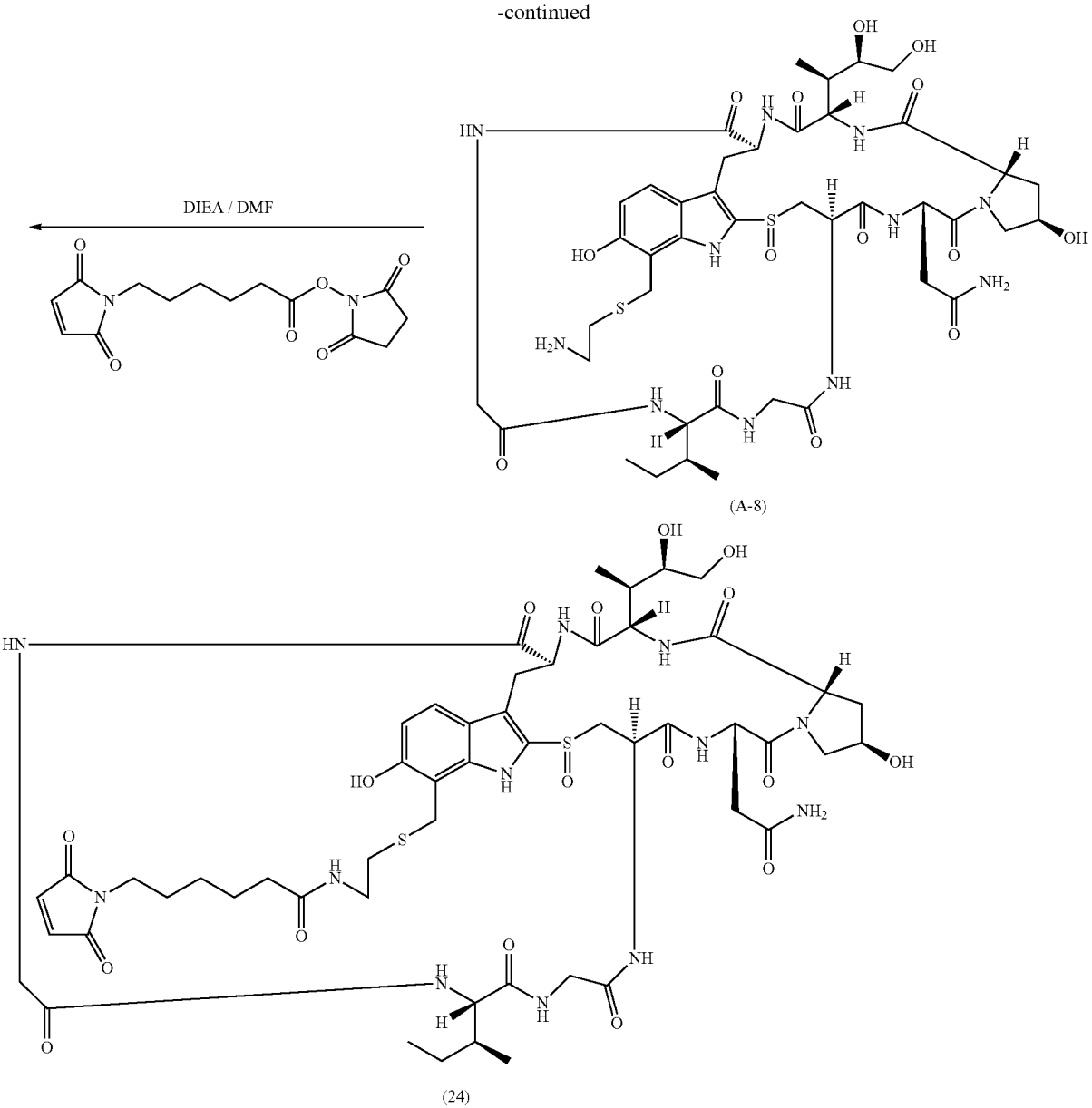

(A-8)

(24)

Step 1: Synthesis of Compound (A-7)

Formaldehyde (0.017 mL, 0.22 mmol) and tert-butyl (2-mercaptoethyl)carbamate (10 mg, 0.054 mmol) were added to a solution of α-Amanitin (A) (10 mg, 0.011 mmol) in MeOH (5 mL) and triethylamine (1.0 mL, 7.2 mmol) in a 40 mL vial, and the reaction mixture was stirred at 40° C. for 3 days. After concentration in vacuo, the reaction mixture was purified by HPLC and lyophilized to give Compound (A-7). MS (m+1)=1109.4., HPLC Peak RT=0.808 min, 1H-NMR (MeOD, 400 MHz) δ 10.77 (s, 1H), 8.89 (m, 1H), 8.63 (d, 1H, J=2.0 Hz), 8.51 (m, 2H), 8.40 (s, 1H), 8.20 (d, 1H, J=8.4 Hz), 8.06 (d, 1H, J=9.6 Hz), 7.96 (d, 1H, J=8.8 Hz), 7.74 (s, 1H), 7.53 (d, 1H, J=8.4 Hz), 6.74 (d, 1H, J=8.8 Hz), 5.31 (m, 1H), 5.17 (m, 1H), 4.79 (bs, 1H), 4.65 (dd, 1H, J=5.2 and 9.6 Hz), 4.55 (m, 2H), 4.35 (dd, 1H, J=8.8 and 18.4 Hz), 4.17 (m, 1H), 4.11 (d, 1H, J=13.2 Hz), 3.99 (d, 1H, J=13.2 Hz), 3.96 (m, 1H), 3.40~3.75 (m, 14H), 3.10~3.25 (m, 3H), 2.96 (dd, 1H, J=12.0 and 14.8 Hz), 2.57 (t, 2H, J=6.8 Hz), 2.45 (m, 2H), 2.05 (m, 1H), 1.64 (m, 2H), 1.43 (s, 9H), 1.20 (m, 2H), 0.98 (d, 3H, J=7.2 Hz), 0.90 (m, 6H).

Step 2: Synthesis of Compound (A-8)

TFA (1 mL) was added to 4 mg of compound (A-7) in a 40 mL vial and the resulting solution was allowed to stand at rt for 1 min and then concentrated under vacuum to give the desired Compound (A-8), which was used without further purification. MS (m+1)=1009.2, HPLC Peak RT=0.492 min, 1H-NMR (MeOD, 400 MHz) δ 8.89 (m, 1H), 8.58 (d, 1H, J=2.0 Hz), 8.47 (m, 2H), 8.17 (d, 1H, J=8.4 Hz), 7.99 (d, 1H, J=9.6 Hz), 7.93 (d, 1H, J=8.8 Hz), 7.51 (d, 1H, J=8.8 Hz), 6.70 (d, 1H, J=8.8 Hz), 5.24 (m, 1H), 5.13 (m, 1H), 4.74 (bs, 1H), 4.60 (dd, 1H, J=5.6 and 9.6 Hz), 4.50 (m, 2H), 4.31 (dd, 1H, J=9.2 and 18.0 Hz), 4.17 (m, 1H), 4.11 (dd, 1H, J=7.6 and 17.6 Hz), 4.05 (s, 2H), 3.92 (d, 1H, J=3.6 and 11.2 Hz), 3.35~3.75 (m, 9H), 3.00~3.25 (m, 5H), 2.91 (dd, 1H, J=12.0 and 14.8 Hz), 2.65 (t, 2H, J=6.8 Hz), 2.40 (m, 2H), 2.00 (m, 1H), 1.56 (m, 2H), 1.17 (m, 2H), 0.98 (d, 3H, J=7.2 Hz), 0.90 (m, 6H).

Step 3: Synthesis of Compound (24)

Compound (A-8) (3 mg, 3 μmol) in DMF (1 mL) was added to a 40 mL vial, to which N-succinimidyl 6-maleimidohexanoate (1 mg, 3 μmol) and DIEA (1 μL, 6 μmol) were added. The reaction mixture was then stirred at rt for 1 h and then purified by HPLC and lyophillized to give the desired Compound (24). MS (m+2/2)=601.4, HPLC Peak RT=0.742 min, 1H-NMR (MeOD, 400 MHz) δ 10.70 (s, 1H), 8.84 (m, 1H), 8.58 (d, 1H, J=2.0 Hz), 8.47 (m, 2H), 8.45 (d, 1H, J=10.4 Hz), 8.34 (s, 1H), 8.15 (d, 1H, J=8.8 Hz), 8.01 (d, 1H, J=9.6 Hz), 7.90 (d, 1H, J=9.2 Hz), 7.68 (s, 1H), 7.49 (d, 1H, J=8.4 Hz), 6.70 (m, 2H), 5.24 (m, 1H), 5.12 (m, 1H), 4.74 (bs, 1H), 4.60 (dd, 1H, J=5.2 and 9.6 Hz), 4.50 (m, 2H), 4.31 (dd, 1H, J=9.2 and 17.6 Hz), 4.12 (m, 1H), 4.07 (d, 1H, J=13.2 Hz), 3.96 (d, 1H, J=13.2 Hz), 3.91 (m, 1H), 3.35~3.75 (m, 20H), 3.17 (m, 1H), 3.08 (m, 2H), 2.96 (m, 1H), 2.52 (t, 2H, J=7.2 Hz), 2.39 (m, 2H), 2.15 (t, 2H, J=6.8 Hz), 2.00 (m, 1H), 1.50~1.65 (m, 6H), 1.10~1.35 (m, 8H), 0.94 (d, 3H, J=6.8 Hz), 0.85 (m, 6H).

Example 25: Synthesis of Compound (25)—6'O-methyl-7'C-((1-(3-(maleimido)propanoyl)-azetidin-3-thio)methyl)-α-Amanitin

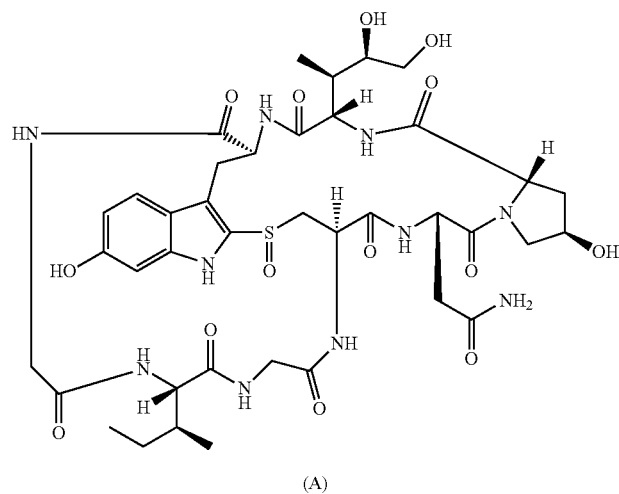

(A)

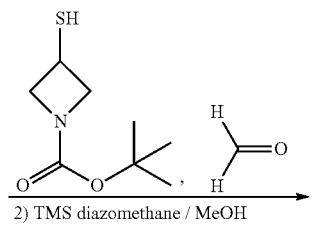

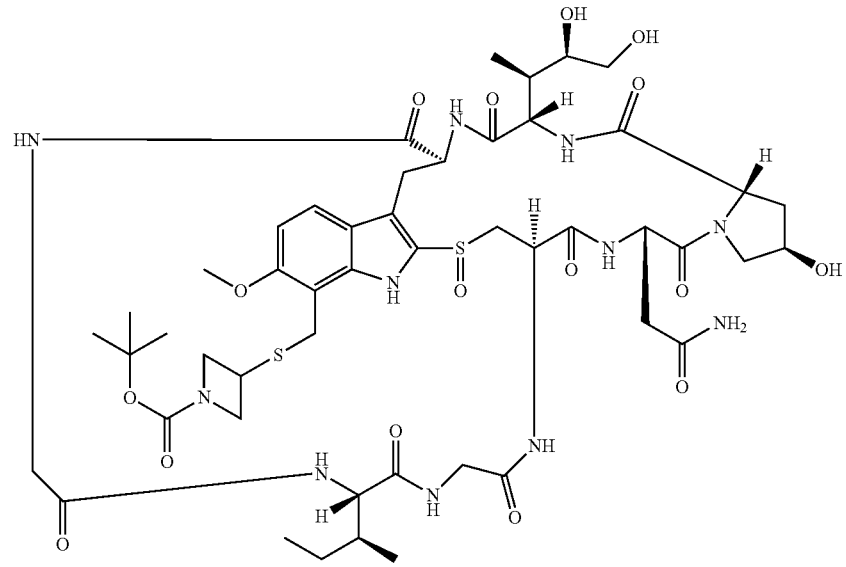

(A-9)

↓ TFA

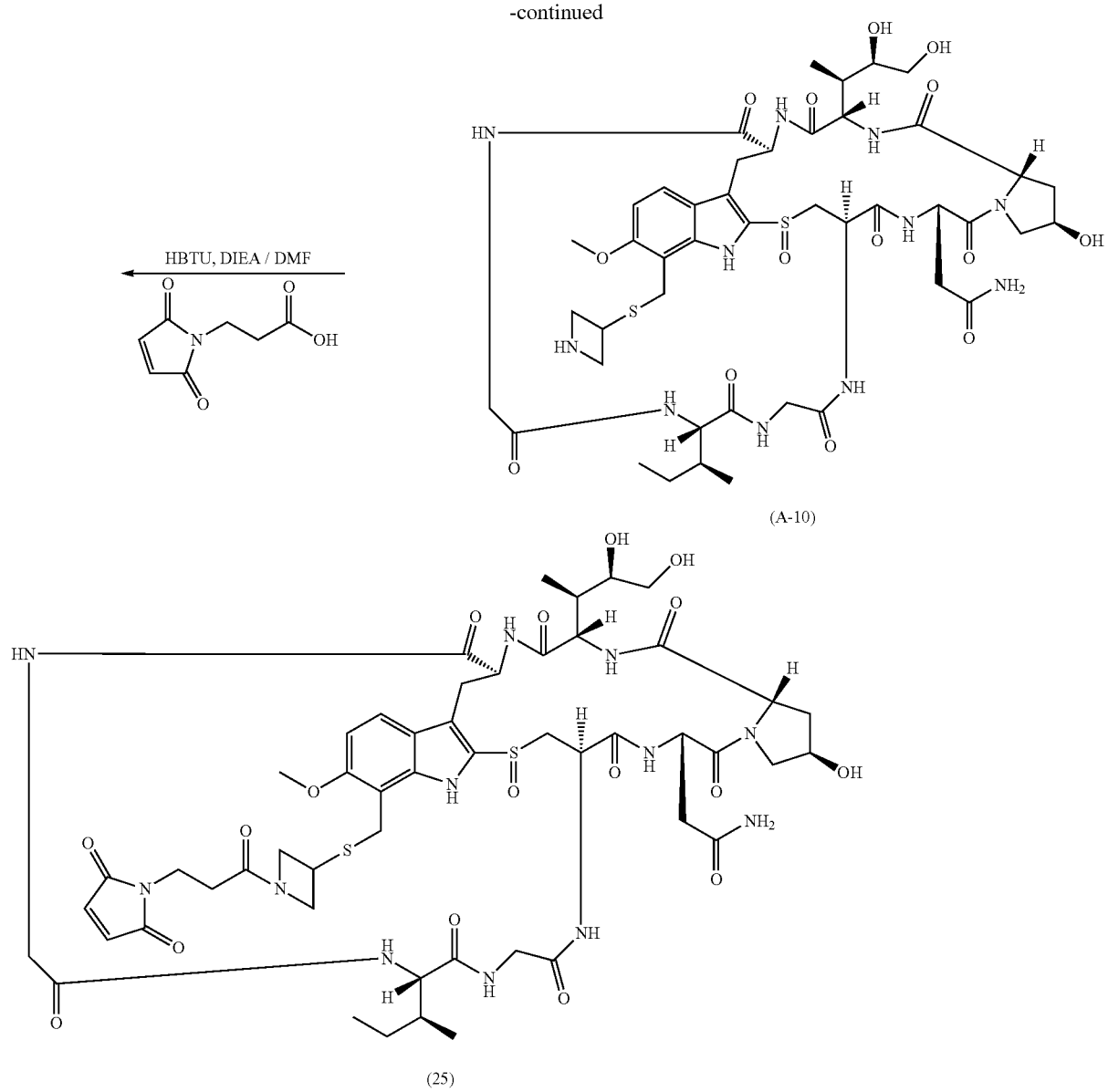

Step 1: Synthesis of Compound (A-9)

Formaldehyde (0.017 mL, 0.22 mmol) and tert-butyl 3-mercaptoazetidine-1-carboxylate (4.1 mg, 0.022 mmol) were added to a solution of α-Amanitin (A) (10 mg, 0.011 mmol) in MeOH (2 mL) and triethylamine (1.0 mL, 7.17 mmol) in a 40 mL vial, and the reaction mixture was stirred at rt for 5 days. After concentration in vacuo, the residue was dissolved in 2 mL of MeOH, and 54 μL of 2M of trimethylsilyl diazomethane in diethyl ether was added, and the mixture was stirred for 2 h at rt. Another 54 μL of 2M of trimethylsilyl diazomethane in diethyl ether was added and the mixture was stirred at rt for another 2 h. The reaction mixture was then purified by HPLC and lyophilized to give Compound (A-9). MS (m+2-boc/2)=517.8, HPLC Peak RT=1.054 min, 1H-NMR (MeOD, 400 MHz) δ 10.95 (s, 1H), 8.85 (m, 1H), 8.59 (d, 1H, J=2.0 Hz), 8.47 (s, 1H), 8.45 (d, 1H, J=10.4 Hz), 8.35 (s, 1H), 8.15 (d, 1H, J=8.4 Hz), 8.01 (d, 1H, J=9.6 Hz), 7.93 (d, 1H, J=9.2 Hz), 7.69 (s, 1H), 7.65 (d, 1H, J=8.4 Hz), 6.92 (d, 1H, J=8.8 Hz), 5.25 (m, 1H), 5.13 (m, 1H), 4.74 (bs, 1H), 4.61 (dd, 1H, J=5.2 and 9.6 Hz), 4.50 (m, 2H), 4.31 (dd, 1H, J=8.8 and 18.0 Hz), 4.14 (m, 1H), 4.09 (d, 1H, J=13.2 Hz), 3.97 (d, 1H, J=13.2 Hz), 3.92 (m, 1H), 3.87 (s, 3H), 3.35~3.75 (m, 17H), 3.08 (m, 2H), 2.92 (dd, 1H, J=12.0 and 14.8 Hz), 2.40 (m, 2H), 2.00 (m, 1H), 1.58 (m, 2H), 1.35 (s, 9H), 1.16 (m, 1H), 0.94 (d, 3H, J=6.8 Hz), 0.85 (m, 6H).

Step 2: Synthesis of Compound (A-10)

TFA (1 mL) was added to 4 mg of compound (A-9) in a 40 mL vial and the resulting solution was allowed to stand at rt for 1 min and then concentrated under vacuum to give the desired compound (A-10), which was used without further purification. MS (m+1)=1034.4, HPLC Peak RT=0.595 min, 1H-NMR (MeOD, 400 MHz) δ 8.64 (s, 1H), 8.54 (d, 1H, J=10.0 Hz), 8.49 (s, 1H), 8.21 (d, 1H, J=8.4 Hz), 8.04 (d, 1H, J=9.6 Hz), 8.02 (d, 1H, J=8.8 Hz), 7.72 (d, 1H, J=8.8 Hz), 7.00 (d, 1H, J=8.8 Hz), 5.29 (m, 1H), 5.19 (m, 1H), 4.78 (bs, 1H), 4.66 (m, 1H), 4.56 (m, 2H), 4.33 (m, 1H), 4.05~4.20 (m, 5H), 3.85~4.00 (m, 3H), 3.94 (s, 3H), 3.40~3.78 (m, 16H), 3.13 (m, 1H), 2.97 (m, 1H), 2.42 (m, 2H), 2.06 (m, 1H), 1.64 (m, 2H), 1.31 (m, 1H), 1.20 (m, 1H), 0.99 (d, 3H, J=7.2 Hz), 0.89 (m, 6H).

Step 3: Synthesis of Compound (25)

Compound (A-10) (3 mg, 3 μmol) in DMF (1 mL) was added to a 40 mL vial, to which 3-maleimidopropionic acid (0.5 mg, 43 μmol), HBTU (0.7 mg, 4 μmol) and DIEA (1 μL, 06 μmol) were added. The reaction mixture was then stirred at rt for 30 min and then purified by HPLC and lyophillized to give the desired Compound (25). MS (m+2/2)=593.3, HPLC Peak RT=0.731 min, 1H-NMR (MeOD, 400 MHz) δ 10.96 (s, 1H), 8.85 (bs, 1H), 8.60 (d, 1H, J=2.0 Hz), 8.45 (m, 2H), 8.35 (s, 1H), 8.14 (d, 1H, J=8.4 Hz), 8.01 (d, 1H, J=9.6 Hz), 7.91 (d, 1H, J=9.2 Hz), 7.68 (s, 1H), 7.66 (d, 1H, J=8.8 Hz), 6.93 (d, 1H, J=9.2 Hz), 6.74 (s, 2H), 6.72 (s, 1H), 5.27 (m, 1H), 5.13 (m, 1H), 4.75 (bs, 1H), 4.62 (d, 1H, J=5.2 and 9.6 Hz), 4.50 (m, 2H), 3.90~4.33 (m, 7H), 3.88 (s, 3H), 3.35~3.70 (m, 18H), 3.08 (m, 1H), 2.92 (m, 1H), 2.40 (m, 2H), 2.27 (m, 2H), 2.00 (m, 1H), 1.61 (m, 2H), 1.17 (m, 1H), 0.94 (d, 3H, J=6.8 Hz), 0.84 (m, 6H).

Example 26: Synthesis of Compound (26)—6'O-methyl-7'C-((1-(6-(maleimido)hexanoyl)-azetidin-3-thio)methyl)-α-Amanitin

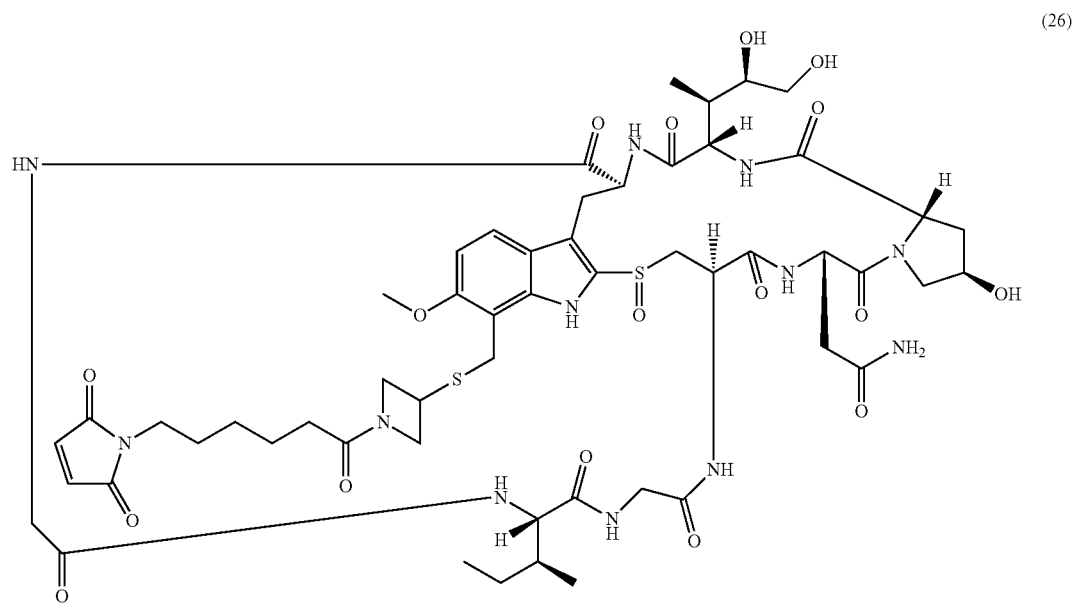 [SMILES: CC[C@H](C)[C@@H]1NC(=O)CNC(=O)[C@@H]2Cc3c([nH]c4c(CSC5CN(C(=O)CCCCCN6C(=O)C=CC6=O)C5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(26)

Compound (26) was prepared using the method described in Example 25 for Compound (25), except 6-maleimidohexanoic acid was used in place of 3-maleimidopropionic acid. MS (m+1)=1128.4, HPLC Peak RT=0.829 min, 1H-NMR (MeOD, 400 MHz) δ 10.95 (s, 1H), 8.84 (bs, 1H), 8.60 (s, 1H), 8.46 (m, 2H), 8.14 (d, 1H, J=8.4 Hz), 8.00 (dd, 1H, J=2.0 and 10.0 Hz), 7.91 (d, 1H, J=8.8 Hz), 7.68 (s, 1H), 7.66 (d, 1H, J=8.8 Hz), 6.94 (d, 1H, J=9.2 Hz), 6.75 (s, 2H), 5.26 (m, 1H), 5.13 (m, 1H), 4.75 (bs, 1H), 4.62 (d, 1H, J=5.2 and 9.6 Hz), 4.50 (m, 2H), 4.20~4.33 (m, 2H), 3.90~4.15 (m, 5H), 3.89 (s, 3H), 3.30~3.75 (m, 18H), 3.21 (m, 1H), 3.08 (m, 1H), 2.91 (dd, 1H, J=12.0 and 14.8 Hz), 2.40 (m, 2H), 2.00 (m, 3H), 1.45~1.65 (m, 6H), 1.18 (m, 3H), 0.94 (d, 3H, J=7.2 Hz), 0.84 (m, 6H).

Example 27: Synthesis of Compound (27))—6'O-methyl-7'C-((1-(3-(maleimido)propanoyl)-piperidine-4-thio)methyl)-α-Amanitin, Compound (A-11))—6'O-methyl-7'C-((tert-butoxycarbonyl-piperidine-4-thio)methyl)-α-Amanitin and Compound (A-12)—6'O-methyl-7'C-((piperidine-4-thio)methyl)-α-Amanitin
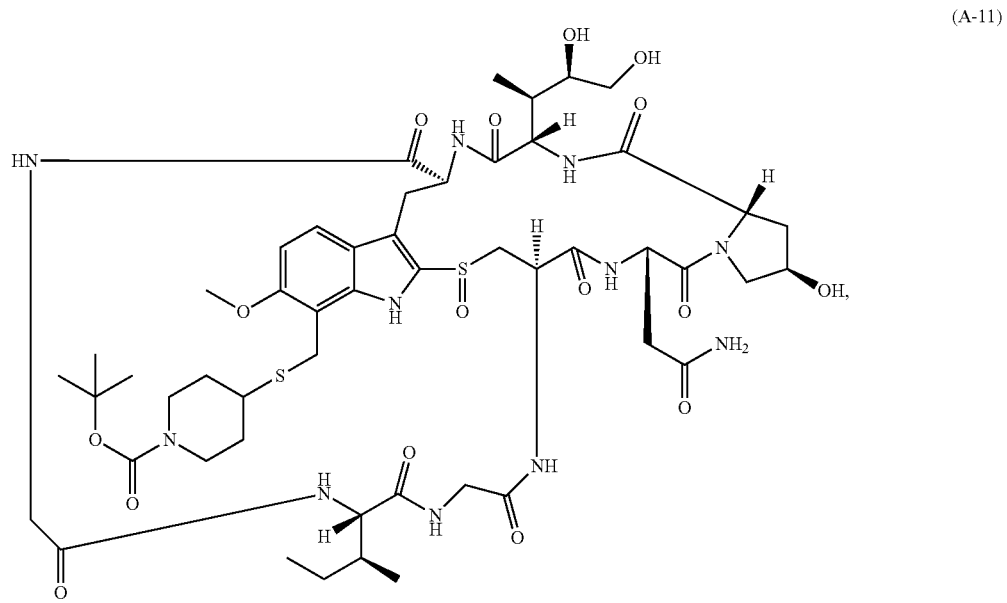
(A-11)
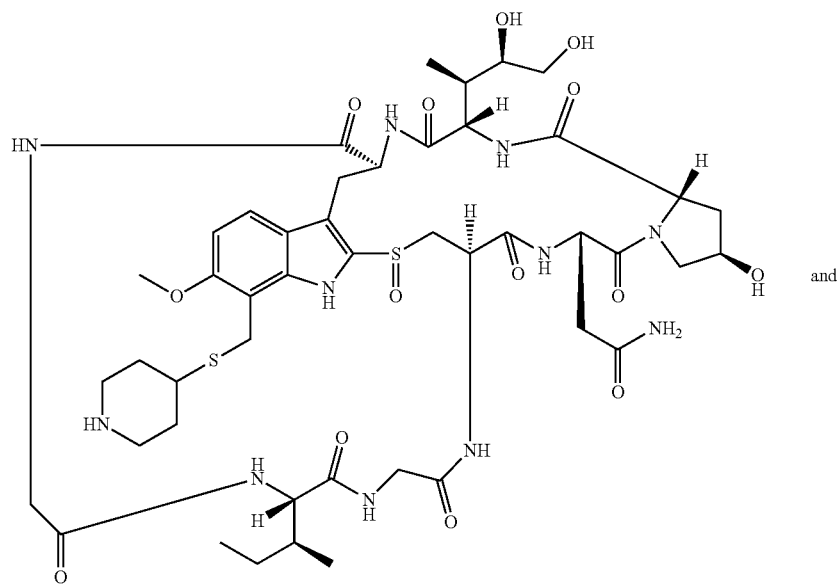
(A-12)
and

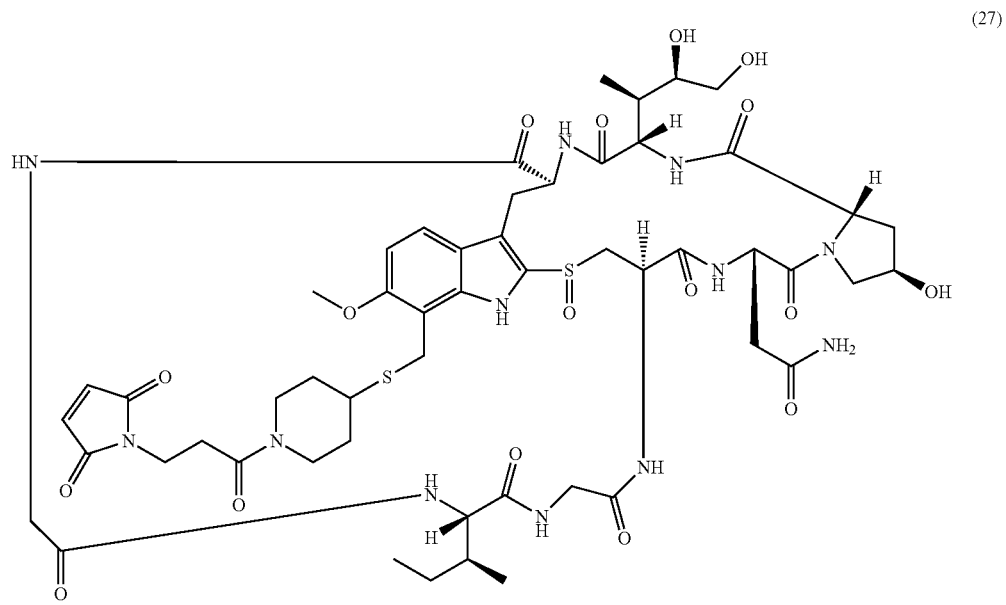

(27)

Compound (A-11) was prepared using the method described in Example 25 for Compound (A-9), except tert-butyl 3-mercaptopiperidine-1-carboxylate was used in place of tert-butyl 3-mercaptoazetidine-1-carboxylate. MS (m+2/2-boc)=531.7, HPLC Peak RT=1.158 min, 1H-NMR (MeOD, 400 MHz) δ 8.60 (s, 1H), 8.46 (d, 1H, J=10.4 Hz), 8.16 (d, 1H, J=8.8 Hz), 8.00 (d, 1H, J=9.6 Hz), 7.92 (d, 1H, J=8.8 Hz), 7.64 (d, 1H, J=8.8 Hz), 6.92 (d, 1H, J=9.2 Hz), 5.28 (m, 1H), 5.13 (m, 1H), 4.74 (bs, 1H), 4.62 (d, 1H, J=5.2 and 9.6 Hz), 4.57 (bs, 1H), 4.50 (m, 2H), 4.31 (dd, 1H, J=9.2 and 18.4 Hz), 4.13 (d, 1H, J=17.6 Hz), 4.11 (d, 1H, J=13.2 Hz), 3.97 (d, 1H, J=13.2 Hz), 3.89 (m, 1H), 3.86 (s, 3H), 3.82 (m, 1H), 3.35~3.75 (m, 19H), 3.08 (m, 1H), 2.81 (m, 1H), 2.40 (m, 1H), 2.00 (m, 1H), 1.86 (m, 1H), 1.57 (m, 2H), 1.39 (s, 9H), 1.33 (m, 2H), 1.15 (m, 1H), 0.94 (d, 3H, J=6.8 Hz), 0.84 (m, 6H).

Compound (A-12) was prepared using the method described in Example 25 for Compound (A-10), except Compound (A-11) was used in place of compound (A-9). MS (m+1)=1063.4, HPLC Peak RT=0.610 min, 1H-NMR (MeOD, 400 MHz) δ 8.64 (s, 1H), 8.53 (d, 1H, J=10.0 Hz), 8.48 (d, 1H, J=2.4 Hz), 8.20 (d, 1H, J=8.4 Hz), 8.05 (d, 1H, J=8.8 Hz), 8.02 (d, 1H, J=8.0 Hz), 7.70 (d, 1H, J=8.8 Hz), 6.99 (d, 1H, J=9.2 Hz), 5.28 (m, 1H), 5.17 (m, 1H), 4.79 (bs, 1H), 4.65 (m, 1H), 4.56 (bs, 1H), 4.50 (m, 2H), 4.36 (m, 1H), 4.19 (d, 1H, J=2.4 Hz), 4.15 (d, 1H, J=6.4 Hz), 4.08 (d, 1H, J=13.2 Hz), 3.98 (m, 1H), 3.96 (m, 1H), 3.92 (s, 3H), 3.40~3.75 (m, 15H), 3.10 (m, 1H), 2.91 (m, 4H), 2.45 (m, 2H), 2.17 (m, 1H), 2.02 (m, 2H), 1.65 (m, 2H), 1.15'1.35 (m, 4H), 0.98 (d, 3H, J=7.2 Hz), 0.90 (m, 6H).

Compound (27) was prepared using the method described in Example 25 for Compound (25), except Compound (A-12) was used in place of Compound (A-10). MS (m+2/2)=607.5, HPLC Peak RT=0.772 min, 1H-NMR (MeOD, 400 MHz) δ 10.80 (s, 1H), 8.84 (bs, 1H), 8.59 (s, 1H), 8.46 (m, 2H), 8.35 (s, 1H), 8.15 (d, 1H, J=8.8 Hz), 8.00 (d, 1H, J=10.0 Hz), 7.92 (d, 1H, J=8.8 Hz), 7.69 (s, 1H), 7.64 (d, 1H, J=8.8 Hz), 6.93 (d, 1H, J=8.8 Hz), 6.76 (s, 2H), 5.28 (m, 1H), 5.13 (m, 1H), 4.74 (bs, 1H), 4.60 (dd, 1H, J=5.2 and 9.6 Hz), 4.50 (m, 2H), 4.32 (m, 1H), 4.07~4.15 (m, 3H), 3.90~4.03 (m, 2H), 3.87 (s, 3H), 3.30~3.75 (m, 15H), 3.09 (m, 2H), 2.92 (m, 1H), 2.77 (m, 2H), 2.63 (m, 2H), 2.40 (m, 2H), 1.80~2.05 (m, 3H), 1.10~1.65 (m, 6H), 0.94 (d, 3H, J=7.2 Hz), 0.85 (m, 6H).

Example 28: Synthesis of Compound (28)—6'O-methyl-7'C-((1-(6-(maleimido)hexanoyl)-piperidine-4-thio)methyl)-α-Amanitin

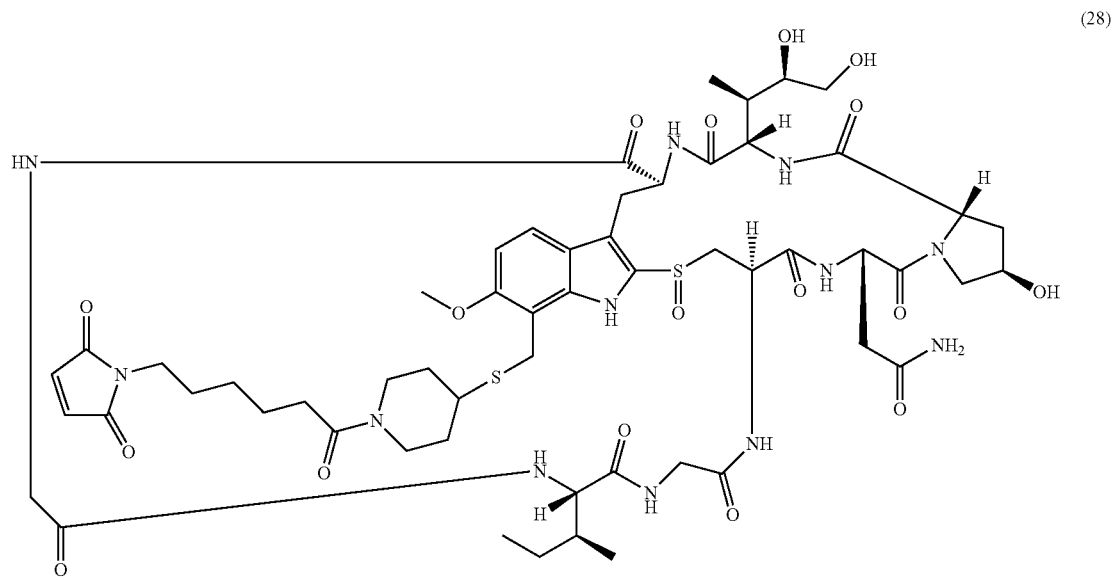 [SMILES: CC[C@H](C)[C@@H]1NC(=O)CNC(=O)[C@@H]2Cc3c([nH]c4c(CSC5CCN(C(=O)CCCCCN6C(=O)C=CC6=O)CC5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(28)

Compound (28) was prepared using the method described in Example 25 for Compound (25), except Compound (A-12) was used in place of Compound (A-10) and 6-maleimidohexanoic acid was used in place of 3-maleimidopropionic acid. MS (m+2/2)=628.3, HPLC Peak RT=0.864 min, 1H-NMR (MeOD, 400 MHz) δ 10.80 (s, 1H), 8.85 (bs, 1H), 8.59 (s, 1H), 8.46 (s, 1H), 8.44 (d, 1H, J=8.6 Hz), 8.15 (d, 1H, J=8.8 Hz), 8.00 (d, 1H, J=9.6 Hz), 7.92 (dd, 1H, J=1.6 and 9.2 Hz), 7.64 (d, 1H, J=8.8 Hz), 6.93 (d, 1H, J=8.8 Hz), 6.75 (s, 2H), 5.27 (m, 1H), 5.13 (m, 1H), 4.75 (bs, 1H), 4.61 (dd, 1H, J=5.2 and 9.6 Hz), 4.51 (m, 2H), 4.30 (m, 1H), 4.10~4.20 (m, 3H), 3.90~4.01 (m, 2H), 3.87 (s, 3H), 3.80 (m, 1H), 3.35~3.75 (m, 18H), 3.08 (m, 2H), 2.92 (m, 1H), 2.28~2.45 (m, 2H), 1.80~2.05 (m, 3H), 1.10~1.65 (m, 12H), 0.94 (d, 3H, J=12.4 Hz), 0.85 (m, 6H).

Example 29: Synthesis of Compound (29)—6'O-methyl-7'C—((N-(4-((maleimido)methyl)cyclohexanecarbonyl)piperidine-4-thio)methyl)-α-Amanitin

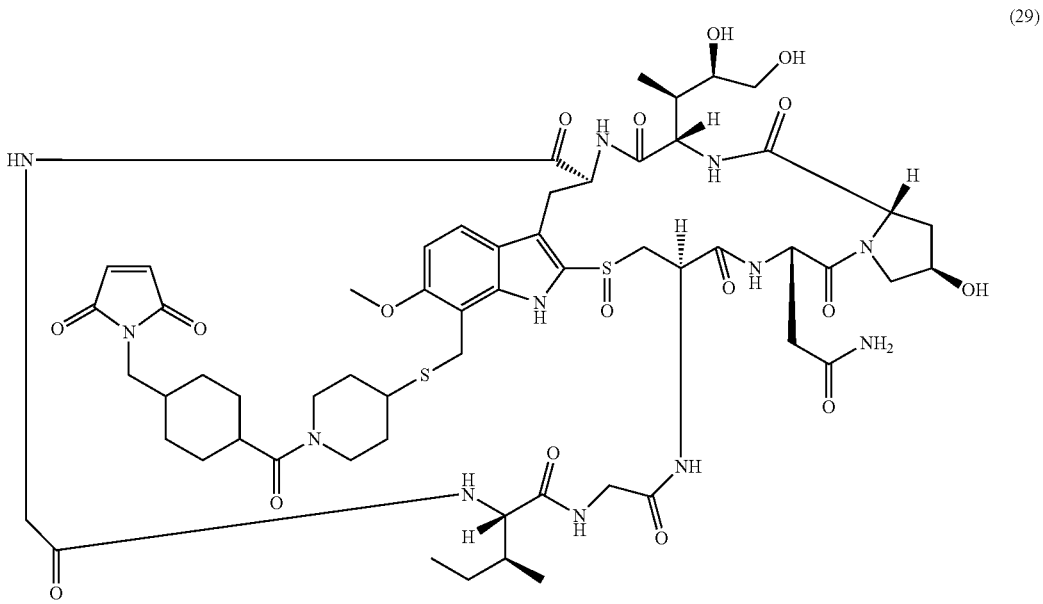 [SMILES: CC[C@H](C)[C@@H]1NC(=O)CNC(=O)[C@@H]2Cc3c([nH]c4c(CSC5CCN(C(=O)C6CCC(CN7C(=O)C=CC7=O)CC6)CC5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(29)

Compound (29) was prepared using the method described in Example 17 for Compound (17), except Compound (A-12) was used in place of Compound (A-5). MS (m+2/2)=641.5, HPLC Peak RT=0.860 min, 1H-NMR (MeOD, 400 MHz) δ 10.80 (s, 1H), 8.85 (m, 1H), 8.59 (s, 1H), 8.47 (s, 1H), 8.44 (d, 1H, J=8.4 Hz), 8.35 (s, 1H), 8.15 (d, 1H, J=8.4 Hz), 8.00 (d, 1H, J=9.6 Hz), 7.92 (dd, 1H, J=2.4 and 8.8 Hz), 7.69 (s, 1H), 7.64 (d, 1H, J=8.8 Hz), 6.93 (d, 1H, J=9.2 Hz), 6.75 (s, 2H), 5.27 (m, 1H), 5.13 (m, 1H), 4.75 (bs, 1H), 4.61 (dd, 1H, J=5.2 and 9.6 Hz), 4.51 (m, 2H), 4.30 (m, 1H), 4.10~4.20 (m, 3H), 3.90~4.01 (m, 2H), 3.86 (s, 3H), 3.35~3.75 (m, 13H), 3.08 (m, 2H), 2.92 (m, 1H), 2.77 (m, 2H), 2.35~2.55 (m, 3H), 1.80~2.05 (m, 3H), 1.00~1.65 (m, 18H), 0.94 (d, 3H, J=7.2 Hz), 0.85 (m, 6H).

Example 30: Synthesis of Compound (30)—6'O-methyl-7'C-((1-(6-(6-(maleimido)hexanamido)hexanoyl)-piperidine-4-thio)methyl)-α-Amanitin

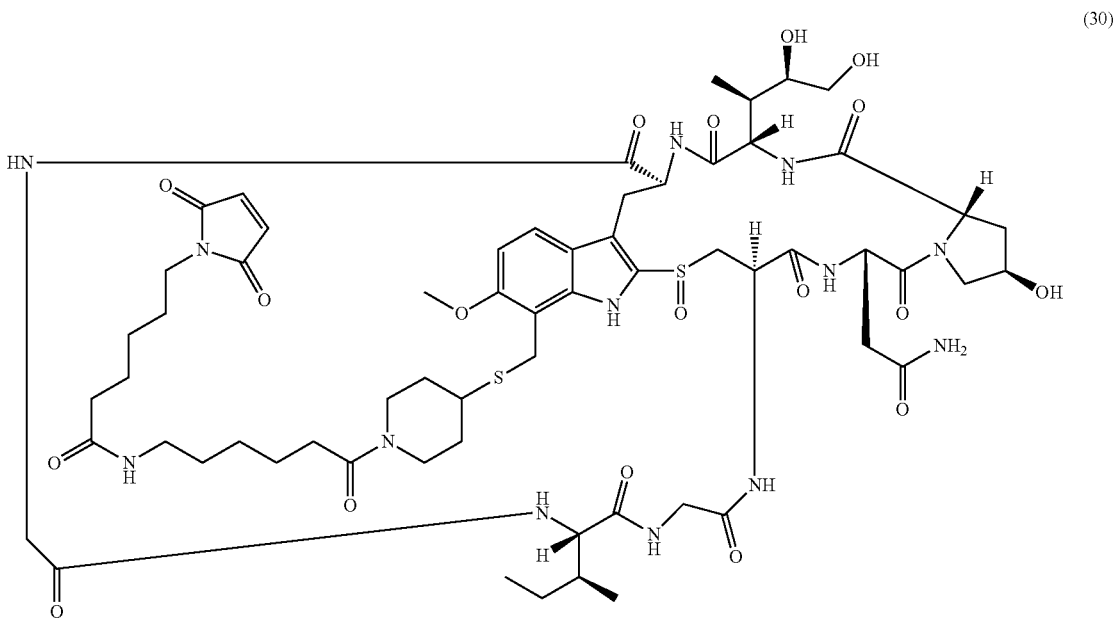 [SMILES: CC[C@H](C)[C@@H]1NC(=O)CNC(=O)[C@@H]2Cc3c([nH]c4c(CSC5CCN(C(=O)CCCCCNC(=O)CCCCCN6C(=O)C=CC6=O)CC5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(30)

Compound (30) was prepared using the method described in Example 19 for Compound (19), except Compound (A-12) was used in place of Compound (A-5). MS (m+2/2)=685.1, HPLC Peak RT=0.872 min, 1H-NMR (MeOD, 400 MHz) δ 10.80 (s, 1H), 8.84 (m, 1H), 8.59 (s, 1H), 8.47 (s, 1H), 8.44 (d, 1H, J=8.8 Hz), 8.35 (s, 1H), 8.15 (d, 1H, J=8.4 Hz), 8.00 (d, 1H, J=10.0 Hz), 7.92 (d, 1H, J=8.8 Hz), 7.68 (s, 1H), 7.64 (d, 1H, J=8.8 Hz), 6.93 (d, 1H, J=8.8 Hz), 6.74 (s, 2H), 5.27 (m, 1H), 5.13 (m, 1H), 4.75 (bs, 1H), 4.61 (dd, 1H, J=5.2 and 9.6 Hz), 4.51 (m, 2H), 4.30 (m, 1H), 4.08~4.20 (m, 3H), 3.90~4.01 (m, 2H), 3.86 (s, 3H), 3.35~3.75 (m, 15H), 3.08 (m, 4H), 2.92 (m, 1H), 2.80 (m, 2H), 2.30~2.45 (m, 4H), 2.11 (t, 2H, J=7.2 Hz), 1.80~2.05 (m, 3H), 1.00~1.65 (m, 19H), 0.94 (d, 3H, J=7.2 Hz), 0.85 (m, 6H).

Example 31: Synthesis of Compound (31)—6'O-methyl-7'C-((1-(6-(4-((maleimido)methyl)cyclo-hexanecarboxamido)hexanoyl)-piperidine-4-thio)methyl)-α-Amanitin

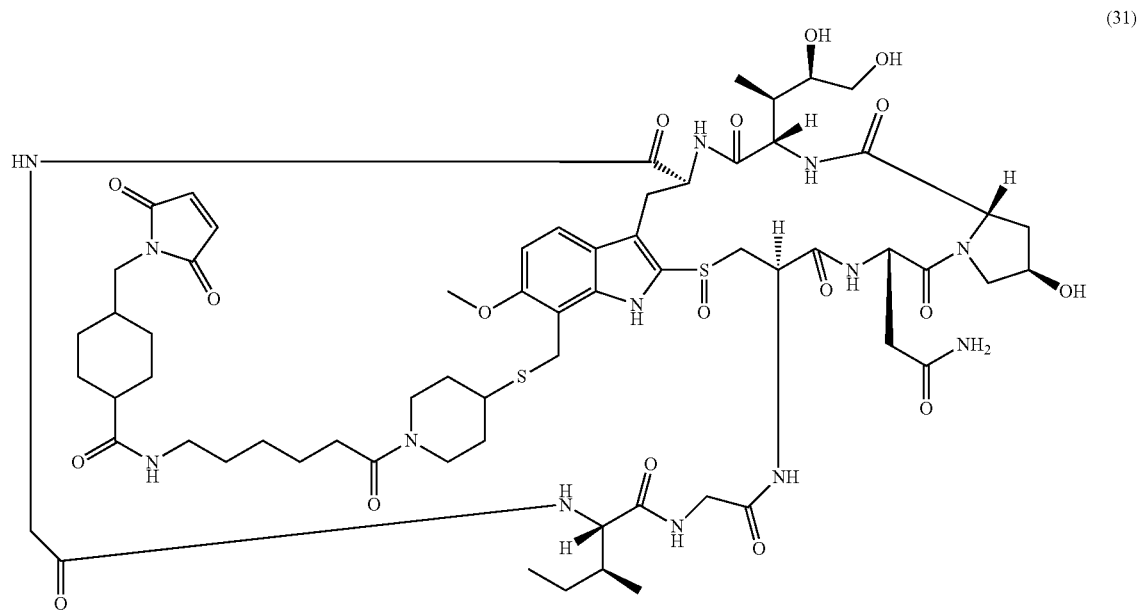 [SMILES: CC[C@H](C)[C@@H]1NC(=O)CNC(=O)[C@@H]2Cc3c([nH]c4c(CSC5CCN(C(=O)CCCCCNC(=O)C6CCC(CN7C(=O)C=CC7=O)CC6)CC5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(31)

Compound (31) was prepared using the method described in Example 20 for Compound (20), Compound (A-12) was used in place of compound (A-5). MS (m+2/2)=698.0, HPLC Peak RT=0.889 min, 1H-NMR (MeOD, 400 MHz) δ 10.79 (s, 1H), 8.84 (m, 1H), 8.59 (s, 1H), 8.47 (s, 1H), 8.45 (d, 1H, J=8.8 Hz), 8.35 (s, 1H), 8.16 (d, 1H, J=8.4 Hz), 8.00 (d, 1H, J=9.6 Hz), 7.92 (d, 1H, J=8.4 Hz), 7.68 (s, 1H), 7.65 (d, 1H, J=8.8 Hz), 6.93 (d, 1H, J=8.8 Hz), 6.75 (s, 2H), 5.27 (m, 1H), 5.13 (m, 1H), 4.75 (bs, 1H), 4.61 (dd, 1H, J=5.2 and 9.6 Hz), 4.51 (m, 2H), 4.30 (m, 1H), 4.08~4.22 (m, 3H), 3.90~4.01 (m, 2H), 3.87 (s, 3H), 3.81 (m, 1H), 3.35~3.75 (m, 14H), 3.08 (m, 4H), 2.92 (m, 1H), 2.80 (m, 2H), 2.30~2.45 (m, 4H), 1.80~2.05 (m, 4H), 1.10~1.80 (m, 16H), 1.00 (m, 1H), 0.94 (d, 3H, J=7.2 Hz), 0.85 (m, 6H).

Example 32: Synthesis of Compound (32)—6'O-methyl-7'C-((1-(15-(maleimido)-4,7,10,13-tetraoxa-pentadecanoyl)-piperidine-4-thio)methyl)-α-Amanitin

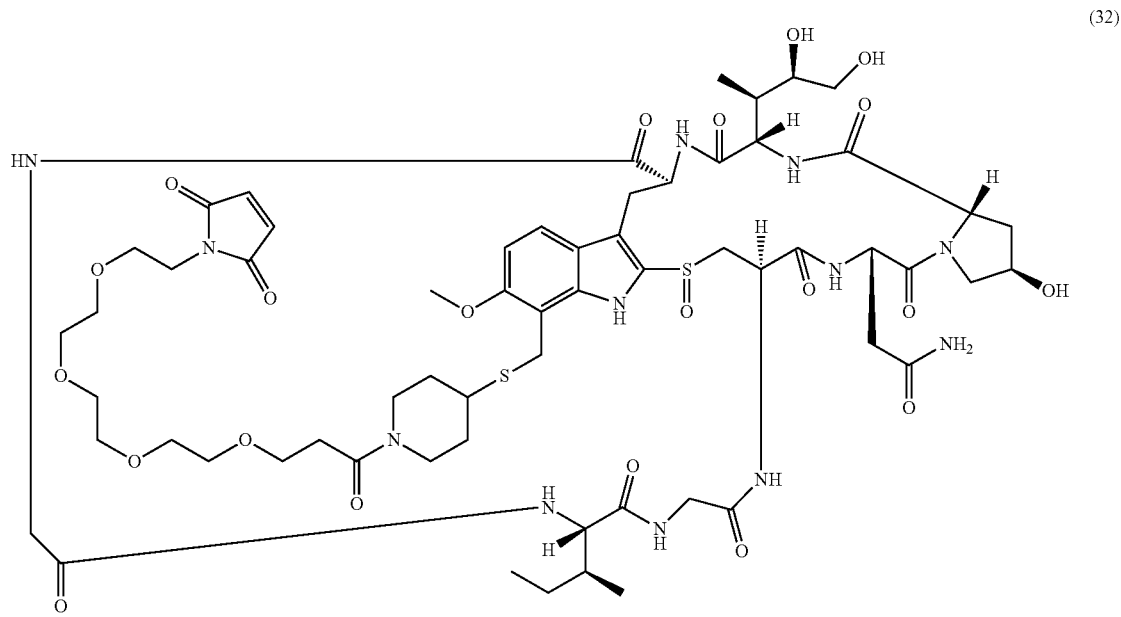 [SMILES: CC[C@H](C)[C@@H]1NC(=O)CNC(=O)[C@@H]2Cc3c([nH]c4c(CSC5CCN(C(=O)CCOCCOCCOCCOCCN6C(=O)C=CC6=O)CC5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(32)

Compound (32) was prepared using the method described in Example 21 for Compound (21), Except Compound (A-12) was used in place of Compound (A-5). MS (m+2/2)=695.5, HPLC Peak RT=0.822 min, 1H-NMR (MeOD, 400 MHz) δ 10.78 (s, 1H), 8.84 (m, 1H), 8.59 (d, 1H, J=1.6 Hz), 8.48 (s, 1H), 8.46 (d, 1H, J=8.8 Hz), 8.15 (d, 1H, J=8.0 Hz), 8.00 (d, 1H, J=9.6 Hz), 7.92 (d, 1H, J=8.8 Hz), 7.63 (d, 1H, J=9.2 Hz), 6.93 (d, 1H, J=8.8 Hz), 6.75 (s, 2H), 5.27 (m, 1H), 5.13 (m, 1H), 4.75 (bs, 1H), 4.61 (dd, 1H, J=5.2 and 9.6 Hz), 4.51 (m, 2H), 4.30 (m, 1H), 4.08 (m, 1H), 4.04 (d, 1H, J=13.2 Hz), 3.90~3.95 (m, 2H), 3.86 (s, 3H), 3.35~3.75 (m, 36H), 3.10 (m, 4H), 2.93 (m, 1H), 2.37 (m, 6H), 2.00 (m, 1H), 1.10'1.60 (m, 8H), 0.94 (d, 3H, J=7.2 Hz), 0.85 (m, 6H).

Example 33: Synthesis of Compound (33)—6'O-methyl-7'C—(R)—(N-(3-(maleimido)propanoyl) pyrrolidine-3-thio)methyl -α-Amanitin, Compound (A-13)—6'O-methyl-7'C—(R)—(N-(tert-butylcarbonyl)pyrrolidine-3-thio)methyl-α-Amanitin and Compound (A-14)—6'O-methyl-7'C—(R)-(pyrrolidine-3-thio)methyl-α-Amanitin

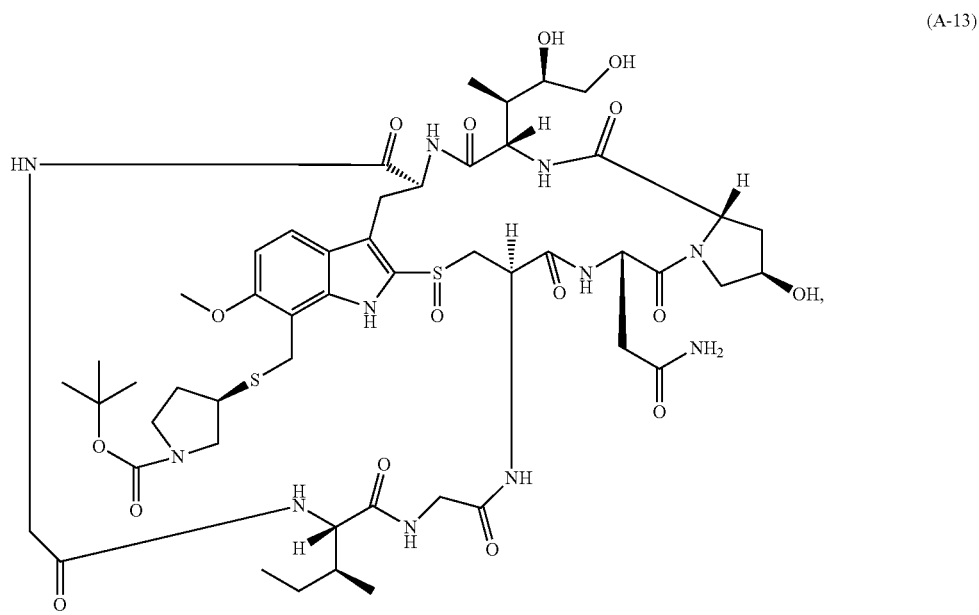

(A-13)

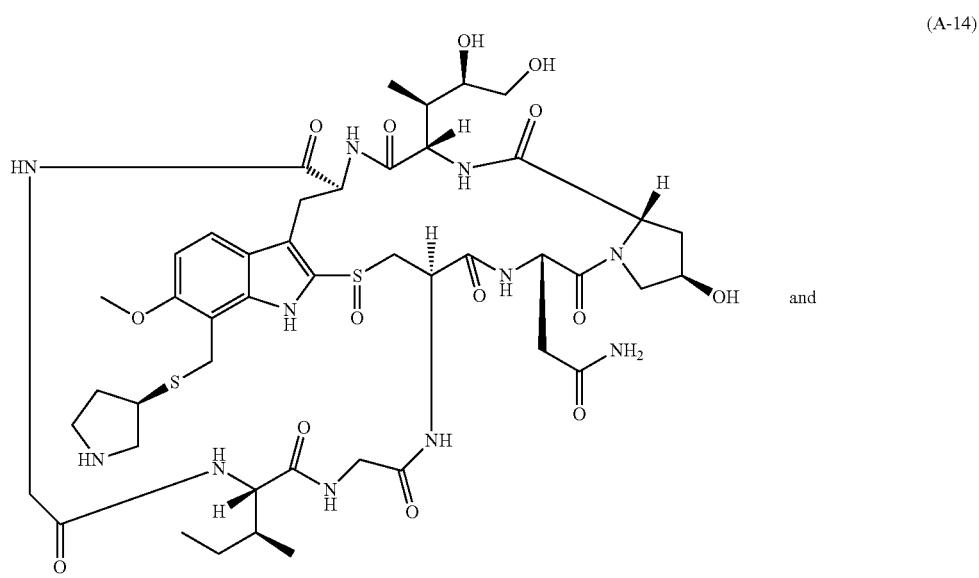

(A-14) and

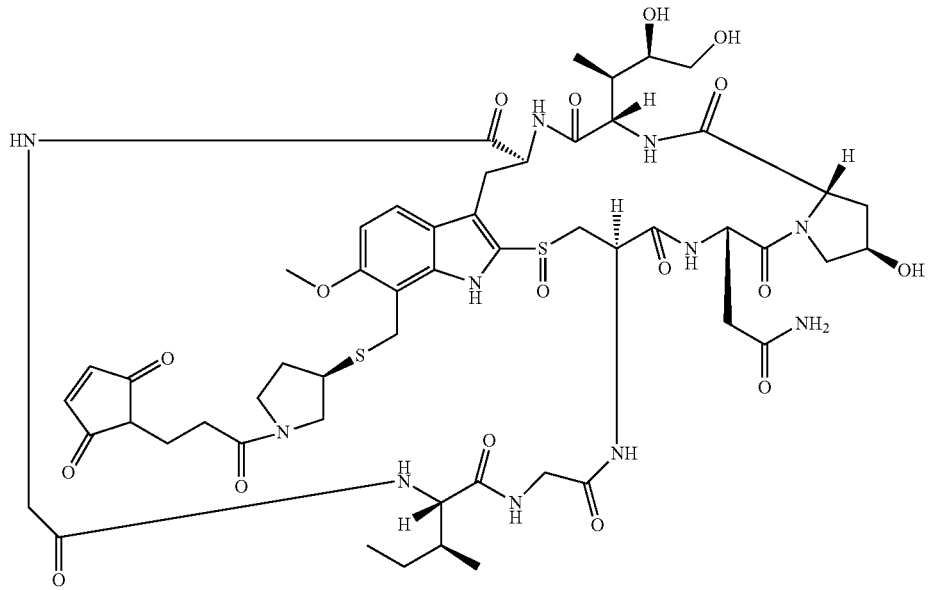

(33)

Compound (A-13) was prepared using the method described in Example 25 for Compound (A-9), except (R)-tert-butyl 3-mercaptopyrrolidine-1-carboxylate was used in place of tert-butyl 3-mercaptoazetidine-1-carboxylate. MS (m+1-boc)=1049.4, HPLC Peak RT=0.940 min, 1H-NMR (MeOD, 400 MHz) δ 10.88 (s, 1H), 8.84 (m, 1H), 8.59 (d, 1H, J=1.6 Hz), 8.48 (s, 1H), 8.46 (d, 1H, J=10.4 Hz), 8.15 (d, 1H, J=8.8 Hz), 8.00 (d, 1H, J=9.6 Hz), 7.92 (d, 1H, J=8.8 Hz), 7.64 (d, 1H, J=8.8 Hz), 6.92 (d, 1H, J=9.2 Hz), 5.27 (m, 1H), 5.13 (m, 1H), 4.75 (bs, 1H), 4.61 (m, 1H), 4.57 (bs, 1H), 4.51 (m, 2H), 4.30 (dd, 1H, J=8.8 and 14.4 Hz), 4.12 (d, 1H, J=17.6 Hz), 4.10 (d, 1H, J=13.2 Hz), 3.97 (d, 1H, J=13.2 Hz), 3.90 (m, 1H), 3.86 (s, 3H), 3.81 (m, 1H), 3.35~3.75 (m, 18H), 3.08 (m, 1H), 2.82 (m, 1H), 2.00 (m, 1H), 1.87 (m, 2H), 1.57 (m, 2H), 1.39 (s, 9H), 1.33 (m, 1H), 1.15 (m, 1H), 0.94 (d, 3H, J=7.2 Hz), 0.85 (m, 6H).

Compound (A-14) was prepared using the method described in Example 25 for Compound (A-10), except Compound (A-13) was used in place of Compound (A-9). MS (m+1)=1048.4 HPLC Peak RT=0.612 min, 1H-NMR (MeOD, 400 MHz) δ 10.89 (s, 1H), 8.88 (m, 1H), 8.57 (d, 1H, J=2.0 Hz), 8.46 (d, 1H, J=10.4 Hz), 8.43 (d, 1H, J=3.2 Hz), 8.15 (d, 1H, J=8.4 Hz), 7.98 (d, 1H, J=9.2 Hz), 7.93 (d, 1H, J=8.0 Hz), 7.66 (d, 1H, J=9.2 Hz), 6.93 (d, 1H, J=8.8 Hz), 5.23 (m, 1H), 5.13 (m, 1H), 4.72 (bs, 1H), 4.59 (dd, 1H, J=5.6 and 9.6 Hz), 4.50 (m, 2H), 4.30 (dd, 1H, J=8.8 and 14.0 Hz), 4.10 (m, 3H), 3.91 (m, 1H), 3.86 (s, 3H), 3.81 (m, 1H), 3.35~3.75 (m, 14H), 3.15 (m, 2H), 3.03 (m, 1H), 2.91 (m, 1H), 2.37 (m, 2H), 2.14 (m, 1H), 2.00 (m, 1H), 1.80 (m, 1H), 1.57 (m, 2H), 1.23 (m, 1H), 1.14 (m, 1H), 0.93 (d, 3H, J=7.2 Hz), 0.85 (m, 6H).

Compound (33) was prepared using the method described in Example 25 for Compound (25), except Compound (A-14) was used in place of Compound (A-10). MS (m+2/2)=600.3, HPLC Peak RT=0.749 min, 1H-NMR (MeOD, 400 MHz) δ 10.89 (s, 1H), 8.85 (m, 1H), 8.58 (m, 1H), 8.47 (m, 2H), 8.12 (dd, 1H, J=8.4 and 20.0 Hz), 8.00 (d, 1H, J=9.2 Hz), 7.89 (dd, 1H, J=8.8 and 18.4 Hz), 7.64 (t, 1H, J=8.8 Hz), 6.93 (dd, 1H, J=2.4 and 8.8 Hz), 6.77 (s, 1H), 6.75 (s, 1H), 5.26 (m, 1H), 5.13 (m, 1H), 4.74 (bs, 1H), 4.63 (m, 1H), 4.50 (m, 2H), 4.27 (m, 1H), 4.10 (m, 3H), 3.96 (m, 1H), 3.88 and 3.86 (s, 3H), 3.35~3.75 (m, 16H), 3.04 (m, 1H), 2.93 (m, 1H), 2.59 (m, 1H), 2.42 (m, 3H), 1.95~2.15 (m, 2H), 1.52~1.80 (m, 3H), 1.14 (m, 1H), 0.93 (d, 3H, J=7.2 Hz), 0.85 (m, 6H).

Example 34: Synthesis of Compound (34)—6'O-methyl-7'C—(R)—(N-(6-(maleimido)hexanoyl)pyrrolidine-3-thio)methyl -α-Amanitin
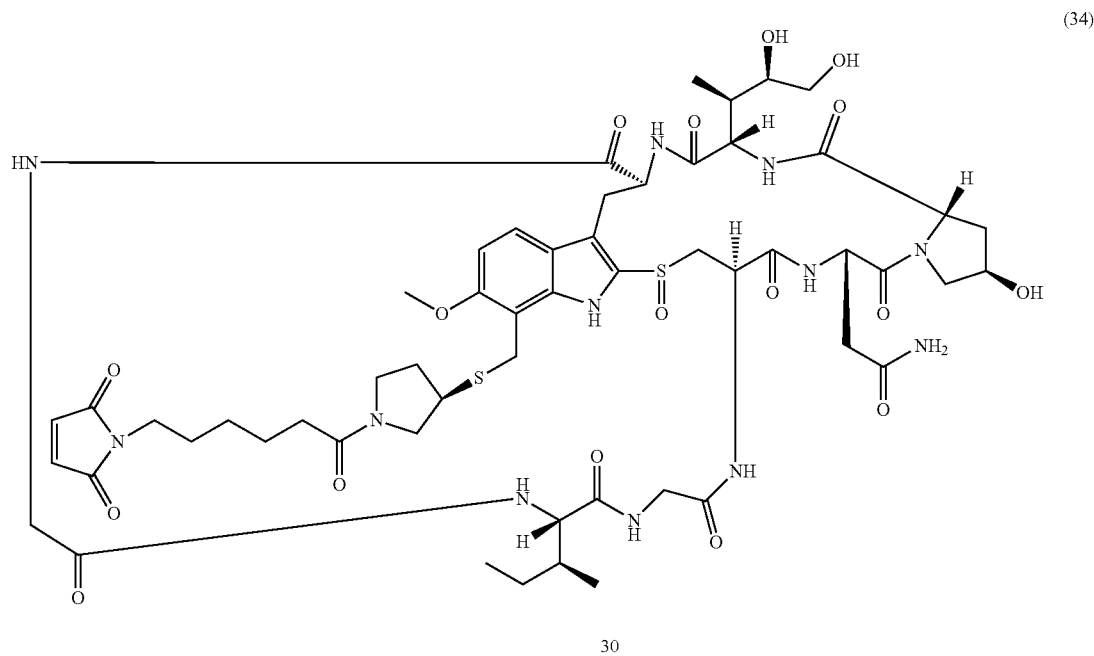
(34)
Compound (34) was prepared using the method described in Example 25 for Compound (25), except Compound (A-14) was

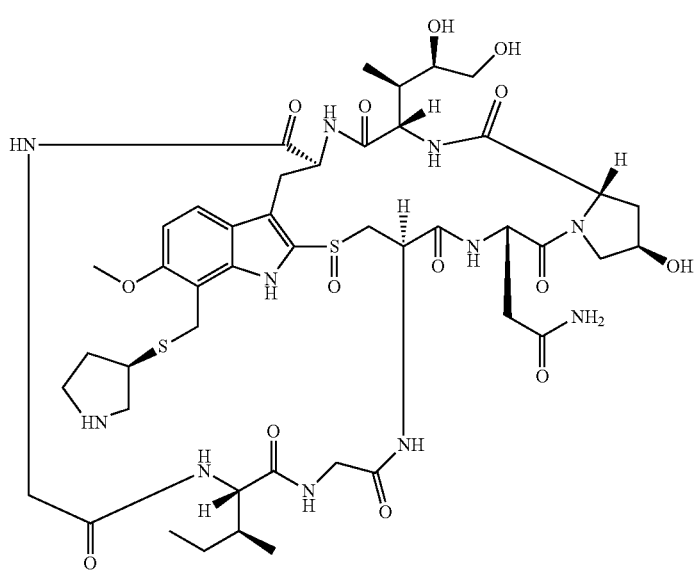

(A-16)

and

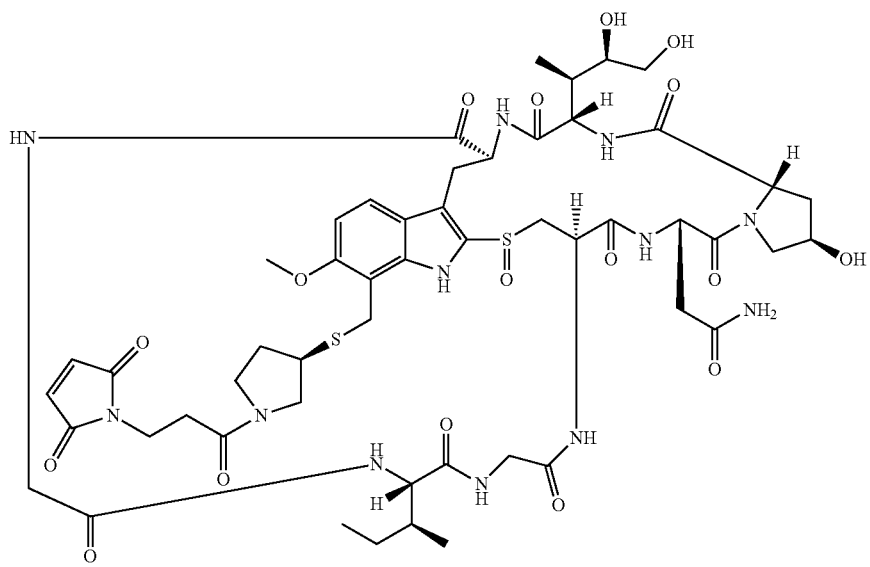

(35)

Compound (A-15) was prepared using the method described in Example 25 for Compound (A-9), except (S)-tert-butyl 3-mercaptopyrrolidine-1-carboxylate was used in place of tert-butyl 3-mercaptoazetidine-1-carboxylate. MS (m+1-boc)=1048.4, HPLC Peak RT=0.935 min, 1H-NMR (MeOD, 400 MHz) δ 10.89 (s, 1H), 8.85 (m, 1H), 8.59 (s, 1H), 8.48 (s, 1H), 8.46 (d, 1H, J=10.0 Hz), 8.16 (d, 1H, J=8.4 Hz), 8.01 (d, 1H, J=9.6 Hz), 7.93 (d, 1H, J=8.8 Hz), 7.65 (d, 1H, J=9.2 Hz), 6.93 (d, 1H, J=8.8 Hz), 5.27 (m, 1H), 5.13 (m, 1H), 4.74 (bs, 1H), 4.61 (dd, 1H, J=5.2 and 9.6 Hz), 4.51 (m, 2H), 4.30 (m, 1H), 3.90~4.15 (m, 3H), 3.86 (s, 3H), 3.35~3.75 (m, 14H), 3.24 (m, 1H), 3.05 (m, 1H), 2.93 (dd, 1H, J=14.0 and 14.8 Hz), 2.40 (m, 2H), 1.95~2.15 (m, 2H), 1.77 (m, 1H), 1.58 (m, 2H), 1.40 and 1.39 (s, 9H), 1.13 (m, 1H), 0.94 (d, 3H, J=7.2 Hz), 0.85 (m, 6H).

Compound (A-16) was prepared using the method described in Example 25 for Compound (A-10), except Compound (A-15) was used in place of Compound (A-9). MS (m+1)=1048.4, HPLC Peak RT=0.608 min, 1H-NMR (MeOD, 400 MHz) δ 10.90 (s, 1H), 8.87 (m, 1H), 8.58 (d, 1H, J=2.0 Hz), 8.48 (s, 1H), 8.45 (d, 1H, J=5.2 Hz), 8.16 (d, 1H, J=8.4 Hz), 7.97 (d, 1H, J=10.0 Hz), 7.94 (d, 1H, J=10.0 Hz), 7.66 (d, 1H, J=9.2 Hz), 6.93 (d, 1H, J=9.2 Hz), 5.24 (m, 1H), 5.12 (m, 1H), 4.73 (bs, 1H), 4.59 (dd, 1H, J=5.6 and 9.6 Hz), 4.49 (m, 2H), 4.30 (q, 1H, J=9.2 Hz), 4.09 (m, 3H), 3.91 (m, 2H), 3.86 (s, 3H), 3.35~3.75 (m, 14H), 3.05 (m, 1H), 2.91 (dd, 1H, J=13.2 and 14.8 Hz), 2.40 (m, 2H), 2.22 (m, 1H), 1.99 (m, 1H), 1.86 (m, 1H), 1.57 (m, 2H), 1.10~1.25 (m, 2H), 0.93 (d, 3H, J=7.2 Hz), 0.85 (m, 6H).

Compound (35) was prepared using the method described in Example 25 for Compound (25), except Compound (A-16) was used in place of Compound (A-10). MS (m+2/2)=600.4, HPLC Peak RT=0.747 min 1H-NMR (MeOD, 400 MHz) δ 10.88 (s, 1H), 8.84 (m, 1H), 8.58 (dd, 1H, J=2.0 and 6.8 Hz), 8.48 (m, 1H), 8.14 (dd, 1H, J=8.8 and 20.0 Hz), 8.01 (dd, 1H, J=2.4 and 10.0 Hz), 7.92 (dd, 1H, J=8.8 and 18.0 Hz), 7.64 (dd, 1H, J=8.8 and 12.0 Hz), 6.92 (dd, 1H, J=1.6 and 9.2 Hz), 6.80 and 6.74 (s, 2H), 5.24 (m, 1H), 5.12 (m, 1H), 4.74 (bs, 1H), 4.62 (m, 1H), 4.50 (m, 2H), 4.20~4.35 (m, 1H), 4.00~4.20 (m, 3H), 3.95 (m, 1H), 3.87 and 3.88 (s, 3H), 3.35~3.75 (m, 14H), 3.04 (m, 2H), 2.90 (m, 1H), 2.54 (m, 1H), 2.30~2.45 (m, 3H), 1.95~2.20 (m, 2H), 1.59 (m, 2H), 1.13 (m, 1H), 0.94 (d, 3H, J=7.2 Hz), 0.85 (m, 6H).

Example 36: Synthesis of Compound (36)—6'O-methyl-7'C—(S)—(N-(6-(maleimido)hexanoyl)pyrrolidine-3-thio)methyl -α-Amanitin

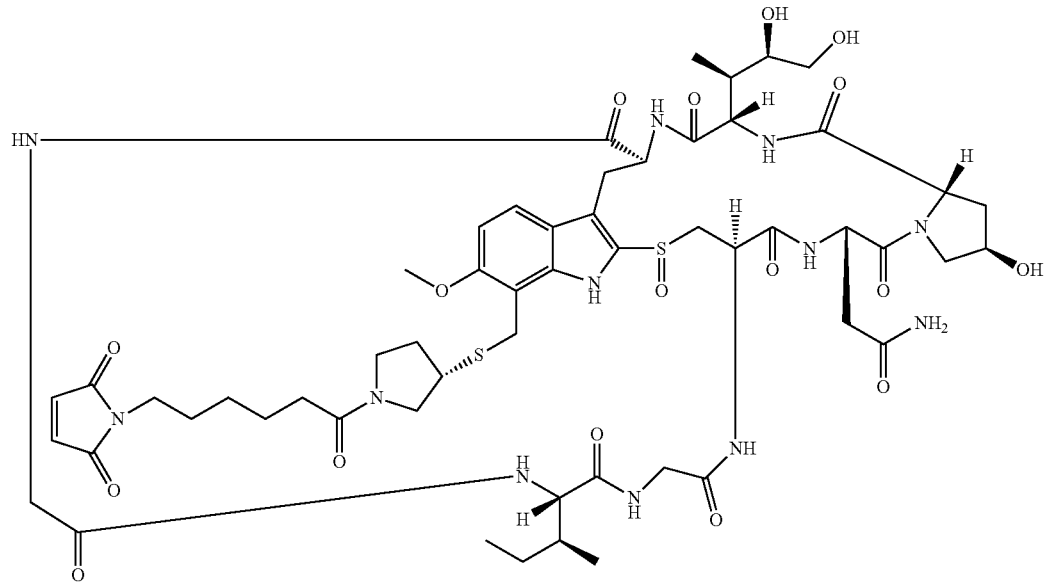

(36)

Compound (36) was prepared using the method described in Example 25 for Compound (25), except Compound (A-16) was used in place of Compound (A-10) and 6-maleimidohexanoic acid was used in place of 3-maleimidopropionic acid. MS (m+2/2)=621.4, HPLC Peak RT=0.834 min, 1H-NMR (MeOD, 400 MHz) δ 10.90 and 10.88 (s, 1H), 8.84 (m, 1H), 8.59 (d, 1H, J=2.0 Hz), 8.47 (s, 1H), 8.46 (d, 1H, J=8.8 Hz), 8.34 (s, 1H), 8.15 (dd, 1H, J=8.8 and 9.2 Hz), 8.01 (d, 1H, J=9.6 Hz), 7.94 (d, 1H, J=8.4 Hz), 7.66 (dd, 1H, J=4.0 and 8.8 Hz), 6.94 (dd, 1H, J=4.4 and 9.2 Hz), 6.77 and 6.74 (s, 2H), 5.26 (m, 1H), 5.12 (m, 1H), 4.74 (bs, 1H), 4.61 (dd, 1H, J=5.6 and 9.6 Hz), 4.50 (m, 2H), 4.30 (m, 1H), 3.98~4.20 (m, 3H), 3.82 (m, 1H), 3.88 and 3.86 (s, 3H), 3.35~3.75 (m, 16H), 3.15 (m, 1H), 3.08 (m, 1H), 2.93 (m, 1H), 2.40 (m, 2H), 1.70~2.20 (m, 6H), 1.45~1.65 (m, 6H), 1.25 (m, 2H), 1.13 (m, 1H), 0.94 (d, 3H, J=7.2 Hz), 0.85 (m, 6H).

Example 37: Synthesis of Compound (37)—6'O-methyl-7'C—(N-(6-(maleimido)hexanoyl)pyrrolidine-3-thio)methyl -α-Amanitin, Compound (A-17)—6'O-methyl-7'C—(N-(tert-butylcarbonyl)pyrrolidine-3-thio)methyl-α-Amanitin and Compound (A-18)—6'O-methyl-7'C-(pyrrolidine-3-thio)methyl-α-Amanitin

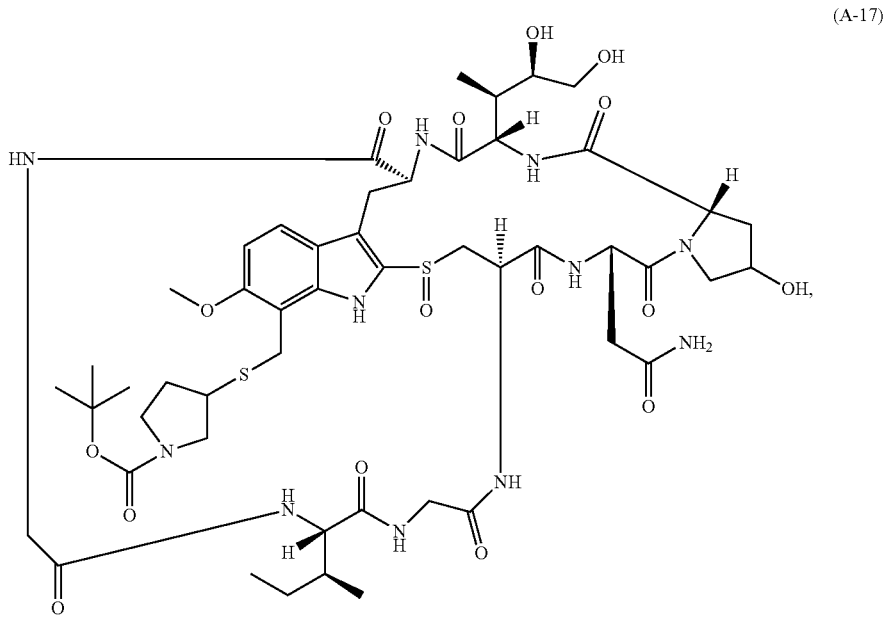

(A-17)

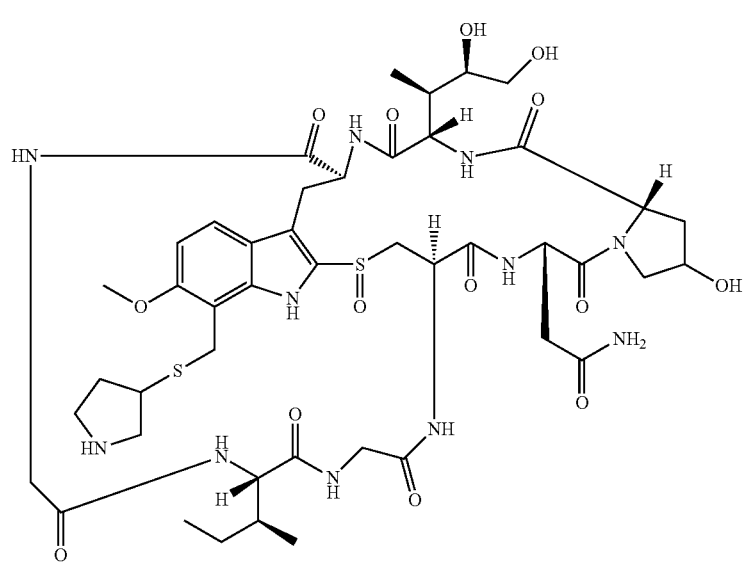

(A-18)

and

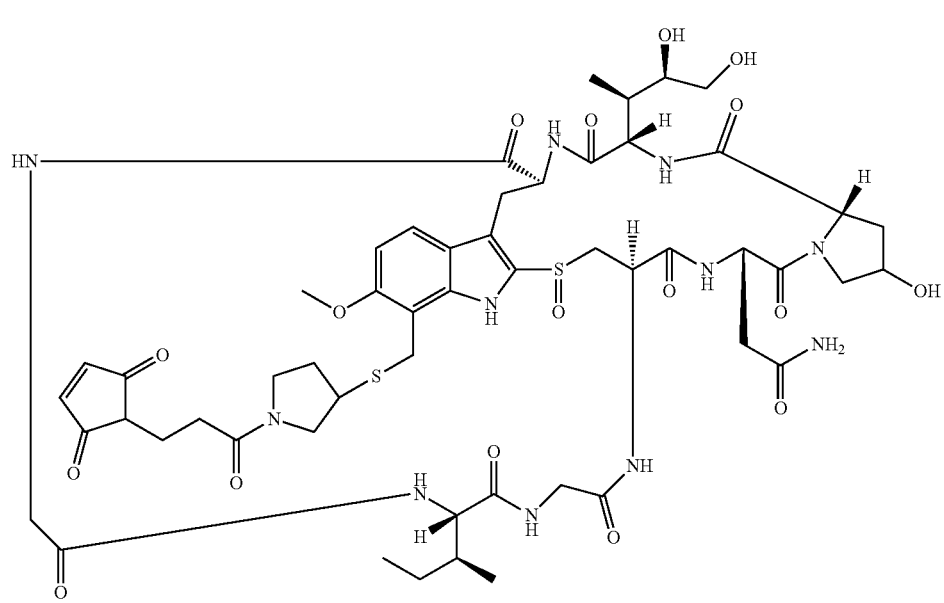

(37)

Compound (A-17) was prepared using the method described in Example 25 for Compound (A-9), except tert-butyl 3-mercaptopyrrolidine-1-carboxylate was used in place of tert-butyl 3-mercaptoazetidine-1-carboxylate. MS (m+1-boc)=1048.4, HPLC Peak RT=0.930 min, 1H-NMR (MeOD, 400 MHz) δ 10.88 (s, 1H), 8.84 (m, 1H), 8.59 (s, 1H), 8.48 (s, 1H), 8.46 (d, 1H, J=10.4 Hz), 8.34 (s, 1H), 8.16 (d, 1H, J=8.4 Hz), 8.01 (d, 1H, J=9.6 Hz), 7.93 (d, 1H, J=9.6 Hz), 7.68 (s, 1H), 7.65 (d, 1H, J=8.8 Hz), 7.32 (m, 3H), 7.12~7.20 (m, 4H), 6.93 (d, 1H, J=8.8 Hz), 5.26 (m, 1H), 5.13 (m, 1H), 4.74 (bs, 1H), 4.61 (dd, 1H, J=5.2 and 9.6 Hz), 4.50 (m, 2H), 4.30 (m, 1H), 3.92~4.15 (m, 2H), 4.00 (m, 1H), 3.91 (m, 1H), 3.87 (s, 3H), 3.35~3.75 (m, 18H), 3.15 (m, 1H), 3.08 (m, 1H), 2.91 (m, 1H), 2.42 (m, 2H), 1.95~2.10 (m, 2H), 1.76 (m, 1H), 1.53 (m, 2H), 1.38 (s, 9H), 1.19 (m, 2H), 0.94 (d, 3H, J=7.2 Hz), 0.85 (m, 6H).

Compound (A-18) was prepared using the method described in Example 25 for Compound (A-10), except Compound (A-17) was used in place of compound (A-9). MS (m+2/2)=525.3, HPLC Peak RT=0.621 min.

Compound (37) was prepared using the method described in Example 25 for Compound (25), except Compound (A-18) was used in place of Compound (A-10) and 6-maleimidohexanoic acid was used in place of 3-maleimidopropionic acid. MS (m+2/2)=600.4, HPLC Peak RT=0.797 min, 1H-NMR (MeOD, 400 MHz) δ 10.73 (s, 1H), 8.73 (m, 1H), 8.56 (s, 1H), 8.43 (d, 1H, J=10.4 Hz), 8.36 (s, 1H), 8.23 (s, 1H), 8.07 (m, 1H), 7.96 (d, 1H, J=9.6 Hz), 7.84 (m, 1H), 7.65 (t, 1H, J=8.8 Hz), 7.55 (m, 1H), 6.93 (dd, 1H, J=2.4 and 8.8 Hz), 6.79, 6.77 and 6.73 (s, 2H), 5.26 (m, 1H), 5.13 (m, 1H), 4.74 (bs, 1H), 3.92~4.15 (m, 3H), 3.88 and 3.87 (s, 3H), 3.35~3.75 (m, 18H), 3.08 (m, 2H), 2.90 (m, 1H), 2.55 (m, 1H), 2.40 (m, 3H), 2.00 (m, 1H), 1.58 (m, 2H), 0.94 (d, 3H, J=7.2 Hz), 0.85 (m, 6H).

Example 38: Synthesis of Compound (38)—6'O-methyl-7'C-(((4-(4-maleimido)methyl-1H-1,2,3-triazol-1-yl)butylthio)methyl)-α-Amanitin and Compound (A-19)—6'O-methyl-7'C-((4-azidobutyl-thio)methyl)-α-Amanitin
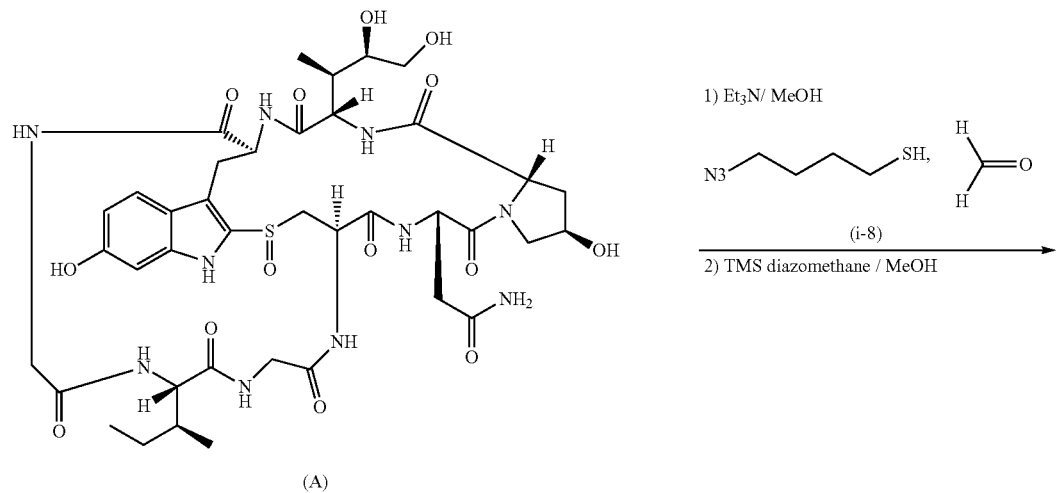
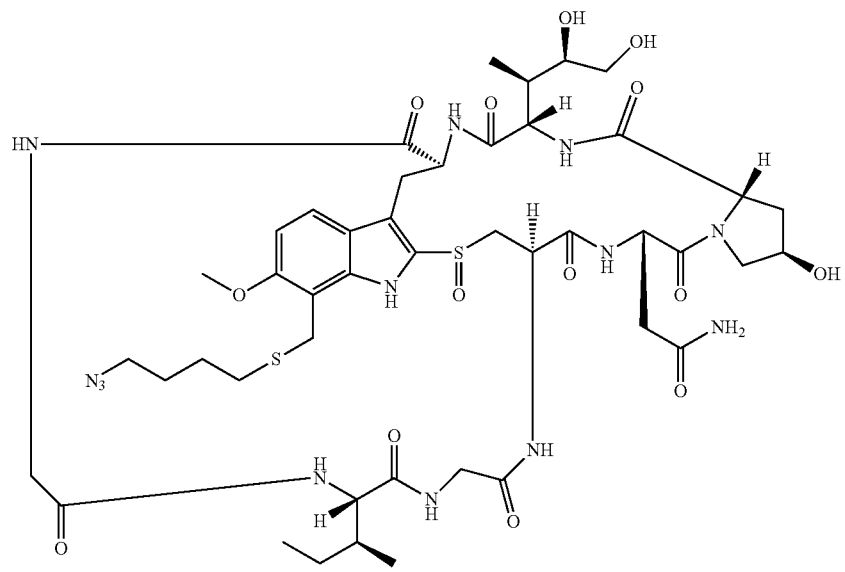
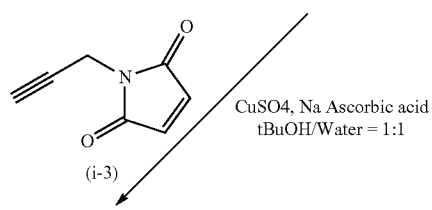

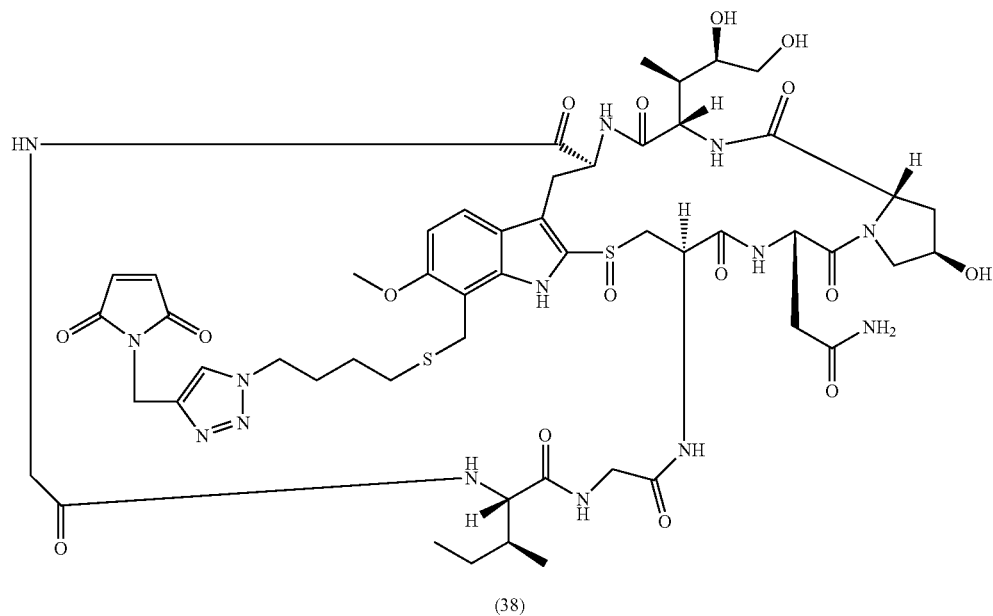 [SMILES: CC[C@H](C)[C@@H]1NC(=O)CNC(=O)[C@@H]2Cc3c([nH]c4c(CSCCCCn5cc(CN6C(=O)C=CC6=O)nn5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(38)

Step 1: Synthesis of Compound (A-19)

Formaldehyde (0.017 mL, 0.22 mmol) and 4-azidobutane-1-thiol (i-8) (14.3 mg, 0.11 mmol) were added to a solution of α-Amanitin (A) (10 mg, 0.011 mmol) in MeOH (2 mL) and triethylamine (0.3 mL, 2.2 mmol) in a 40 mL vial, and the reaction mixture was stirred at 40° C. for 3 days. After concentration in vacuo, the residue was dissolved in 2 mL of MeOH and 0.27 mL of 2M of trimethylsilyl diazomethane in diethyl ether was added and the mixture was stirred for 2 h at rt. The reaction mixture was then purified by HPLC and lyophilized to give Compound (A-19). MS (m+1)=1076.4, HPLC Peak RT=0.902 min, 1H-NMR (MeOD, 400 MHz) δ 10.78 (s, 1H), 8.86 (m, 1H), 8.59 (d, 1H, J=2.0 Hz), 8.48 (s, 1H), 8.46 (d, 1H, J=8.8 Hz), 8.15 (d, 1H, J=8.4 Hz), 8.00 (d, 1H, J=9.6 Hz), 7.92 (d, 1H, J=8.8 Hz), 7.64 (d, 1H, J=8.8 Hz), 6.92 (d, 1H, J=9.2 Hz), 5.28 (m, 1H), 5.13 (m, 1H), 4.75 (bs, 1H), 4.62 (dd, 1H, J=5.2 and 9.4 Hz), 4.50 (m, 2H), 4.31 (dd, 1H, J=8.8 and 18.4 Hz), 3.90~4.20 (m, 4H), 3.86 (s, 3H), 3.35~3.75 (m, 16H), 3.17 (m, 2H), 3.08 (m, 1H), 2.92 (dd, 1H, J=12.0 and 15.2 Hz), 2.38 (m, 4H), 2.01 (m, 1H), 1.56 (m, 4H), 1.17 (m, 2H), 0.94 (d, 3H, J=7.2 Hz), 0.85 (m, 6H).

Step 2: Compound (A-19) (3.0 mg, 3 μmol) and Compound (i-3) (0.8 mg, 6 μmol) were add to t-butanol (0.5 mL) and the reaction mixture was flushed with $N_2$ gas five times. L-Ascorbic acid sodium salt (0.6 mg, 3 μmol), $CuSO_4$ (0.1 mg, 0.6 μmol) and 0.5 mL of $H_2O$ were then added and the reaction mixture was flushed with $N_2$ gas five times and stirred at rt for 4 h. The reaction mixture was then purified by HPLC and lyophilized to give Compound (38). MS (m+2/2)=606.4, HPLC Peak RT=0.796 min, 1H-NMR (MeOD, 400 MHz) δ 10.76 (s, 1H), 8.84 (m, 1H), 8.59 (d, 1H, J=2.0 Hz), 8.47 (d, 1H, J=8.8 Hz), 8.46 (s, 1H), 8.14 (d, 1H, J=8.4 Hz), 8.01 (d, 1H, J=10.0 Hz), 7.92 (d, 1H, J=8.8 Hz), 7.81 (s, 1H), 7.63 (d, 1H, J=8.8 Hz), 6.90 (d, 1H, J=8.8 Hz), 6.78 (s, 2H), 5.28 (m, 1H), 5.13 (m, 1H), 4.74 (bs, 1H), 4.71 (s, 2H), 4.62 (dd, 1H, J=5.2 and 9.4 Hz), 4.50 (m, 2H), 4.10~4.30 (m, 4H), 3.98 (d, 1H, J=13.2 Hz), 3.93 (m, 1H), 3.88 (d, 1H, J=13.2 Hz), 3.81 (s, 3H), 3.35~3.75 (m, 16H), 3.08 (m, 1H), 2.92 (dd, 1H, J=12.0 and 15.2 Hz), 2.35 (m, 4H), 2.01 (m, 1H), 1.86 (m, 2H), 1.55 (m, 2H), 1.42 (m, 2H), 1.12 (m, 1H), 0.94 (d, 3H, J=7.2 Hz), 0.85 (m, 6H).

Example 39: Synthesis of Compound (39)—6'O-methyl-7'C-((6-(aminoxy)hexaneamido)-ethylthiomethyl)-α-Amanitin and Compound (A-20)

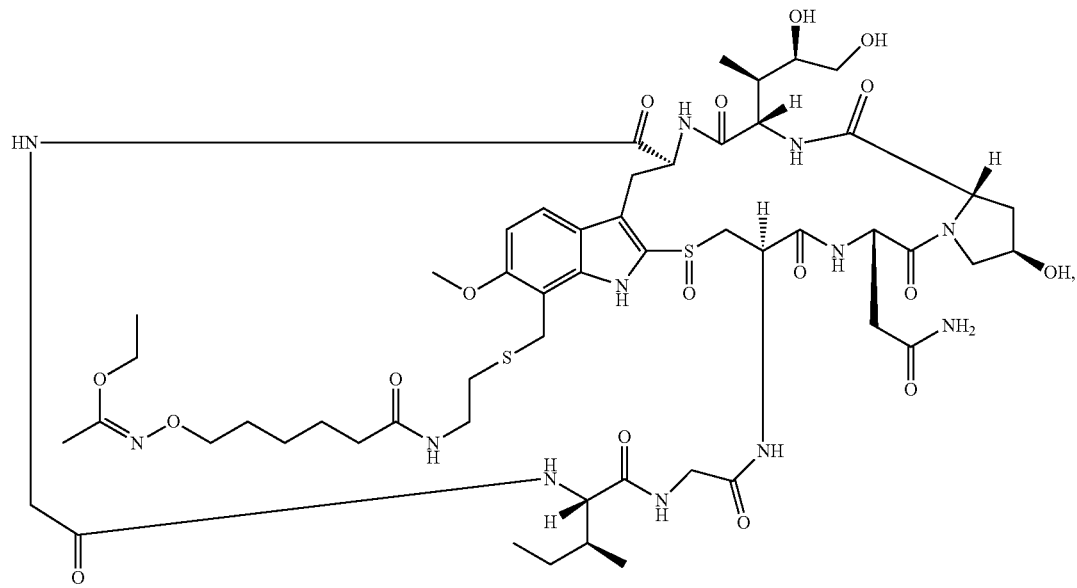

(A-20)

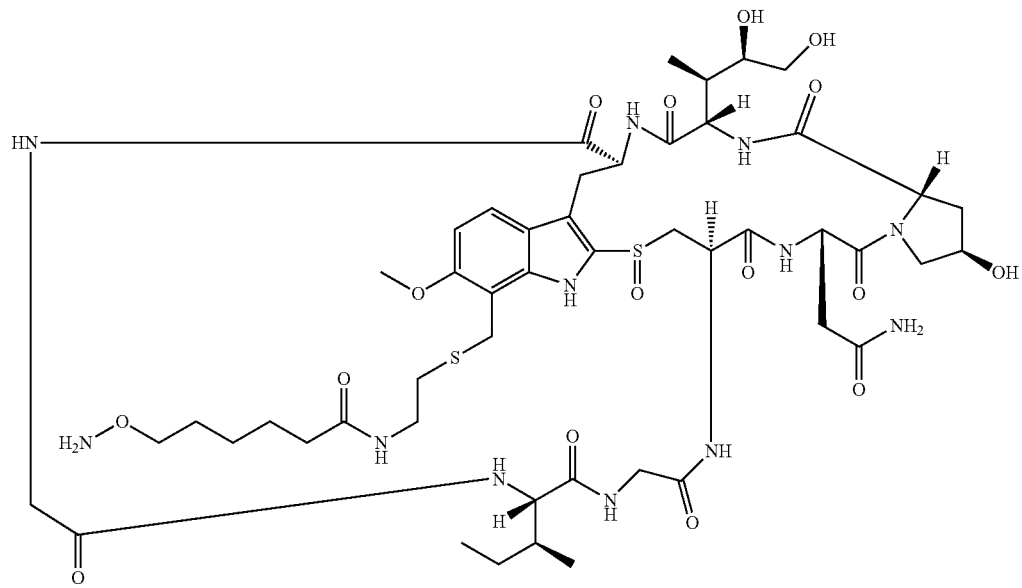

(39)

Synthesis of Compound (A-20)

(A-2) (5.0 mg, 4.5 mmol) in DMF (1 mL) were combined in a 3 mL vial to give a clean solution. (E)-6-(((1-Ethoxyethylidene)amino)oxy)hexanoate lithium salt (1.2 mg, 5.4 μmol), HATU (1.3 mg, 3.4 μmol) and DIEA (3.0 μL, 12 μmol) were added. The reaction mixture was stirred at rt for 1 h, and then the reaction mixture was purified by HPLC to give compound (A-20). MS (m+2/2)=611.4. HPLC Peak RT=0.945 min. 1H-NMR (MeOD, 400 MHz) δ 10.84 (bs, 1H), 8.87 (m, 1H), 8.61 (s, 1H), 8.50 (d, 1H, J=9.6 Hz), 8.48 (d, 1H, J=10.2 Hz), 8.35 (bs, 1H), 8.17 (m, 1H), 8.02 (t, 1H, J=10.2 Hz), 7.95 (dd, 1H, J=4.2 and 9.0 Hz), 7.69 (bs, 1H), 7.67 (dd, 1H, J=3.0 and 8.4 Hz), 6.96 (dd, 1H, J=3.0 and 8.4 Hz), 5.28 (m, 1H), 5.15 (m, 1H), 4.77 (bs, 1H), 4.64 (dd, 1H, J=5.4 and 9.6 Hz), 4.52 (m, 2H), 4.32 (dd, 1H, J=8.4 and 18.0 Hz), 4.05~4.16 (m, 2H), 3.95~4.15 (m, 5H), 3.88 (s, 3H), 3.83 (t, 1H, J=6.0 Hz), 3.35~3.75 (m, 17H), 3.09 (m, 1H), 2.95 (dd, 1H, J=12.0 and 15.0 Hz), 2.55 (m, 2H), 2.40 (m, 2H), 2.15 (m, 2H), 2.00 (m, 1H), 1.55~1.70 (m, 7H), 1.40 (m, 2H), 1.20 (m, 2H), 0.96 (d, 3H, J=6.6 Hz), 0.87 (m, 6H).

Synthesis of Compound (39)

Compound (A-20) (2.9 mg, 2.3 mmol) in TFA (1 mL) were combined to give a clean solution. H₂O (100 μL) was added to the reaction mixture and concentrated in vacuo.

The reaction mixture was purified by RP-C18 ISCO and to give 1.0 mg of the desired compound (39). MS (m+1) =1151.4, HPLC Peak RT=0.634 min, 1H-NMR (MeOD, 400 MHz) δ 8.87 (m, 1H), 8.61 (d, 1H, J=1.8 Hz), 8.50 (d, 1H, J=14.4 Hz), 8.49 (s, 1H), 8.34 (s, 1H), 8.19 (d, 1H, J=8.4 Hz), 8.01 (d, 1H, J=9.6 Hz), 7.95 (d, 1H, J=9.0 Hz), 7.69 (bs, 1H), 7.67 (d, 1H, J=8.4 Hz), 6.95 (d, 1H, J=9.0 Hz), 5.30 (m, 1H), 5.15 (m, 1H), 4.76 (bs, 1H), 4.64 (dd, 1H, J=5.4 and 9.6 Hz), 4.52 (m, 2H), 4.32 (dd, 1H, J=8.4 and 18.0 Hz), 4.16 (m, 2H), 4.09 (d, 1H, J=13.2 Hz), 4.02 (d, 1H, J=13.2 Hz), 3.97 (t, 2H, J=6.6 Hz), 3.95 (dd, 1H, J=13.2 Hz), 3.88 (s, 3H), 3.35~3.75 (m, 16H), 3.15 (m, 1H), 3.10 (m, 1H), 2.95 (d, 1H, J=12.0 and 15.0 Hz), 2.55 (m, 2H), 2.40 (m, 3H), 2.20 (m, 2H), 2.01 (m, 1H), 1.55~1.70 (m, 7H), 1.39 (m, 2H), 1.17 (m, 1H), 0.97 (d, 3H, J=7.2 Hz), 0.86 (m, 6H).

Example 40: Synthesis of Compound (40)—6'O-methyl-7'C-((1-(6-(aminooxy)hexanoyl)-piperidine-4-thio)methyl)-α-Amanitin

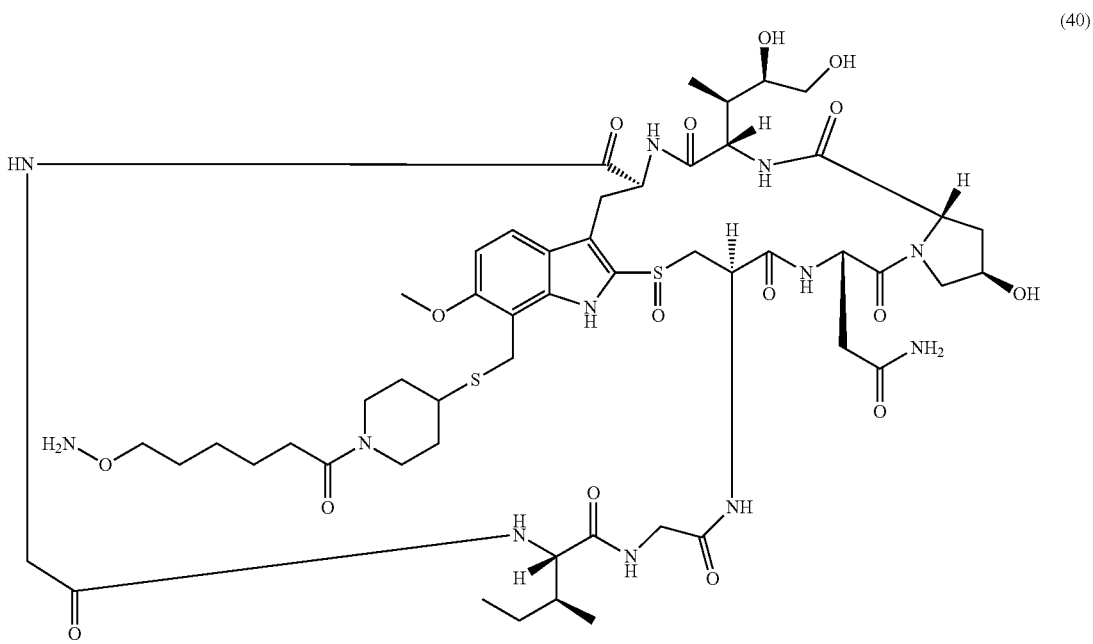 [SMILES: CC[C@H](C)[C@@H]1NC(=O)CNC(=O)[C@@H]2Cc3c([nH]c4c(CSC5CCN(C(=O)CCCCCON)CC5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(40)

Compound (40) was prepared using the method described for compound (39), except Compound (A-12) was used in place of Compound (A-2). MS (m+1)=1192.2, HPLC Peak RT=0.696 min, 1H-NMR (MeOD, 400 MHz) δ 8.87 (m, 1H), 8.62 (s, 1H), 8.50 (m, 1H), 8.36 (s, 1H), 8.19 (d, 1H, J=9.0 Hz), 8.02 (d, 1H, J=9.0 Hz), 7.96 (dd, 1H, J=2.5 and 9.0 Hz), 7.69 (bs, 1H), 7.68 (d, 1H, J=8.5 Hz), 6.95 (d, 1H, J=9.0 Hz), 5.31 (m, 1H), 5.15 (m, 1H), 4.78 (bs, 1H), 4.64 (dd, 1H, J=5.5 and 9.5 Hz), 4.54 (m, 2H), 4.34 (m, 1H), 4.24 (m, 1H), 4.15 (m, 2H), 4.05 (d, 1H, J=9.5 Hz), 3.95 (m, 2H), 3.90 (s, 3H), 3.84 (m, 2H), 3.40~3.75 (m, 15H), 3.08~3.18 (m, 2H), 2.95 (m, 1H), 2.85 (m, 2H), 2.30~2.50 (m, 6H), 1.90~2.00 (m, 2H), 1.55~1.65 (m, 12H), 1.45 (m, 6H), 1.18 (m, 1H), 0.97 (d, 3H, J=7.0 Hz), 0.86 (m, 6H)

Example 41: Synthesis of Compound (41)—6'O-methyl-7'C-((6-(aminoxy)hexaneamido)-butylthiomethyl)-α-Amanitin

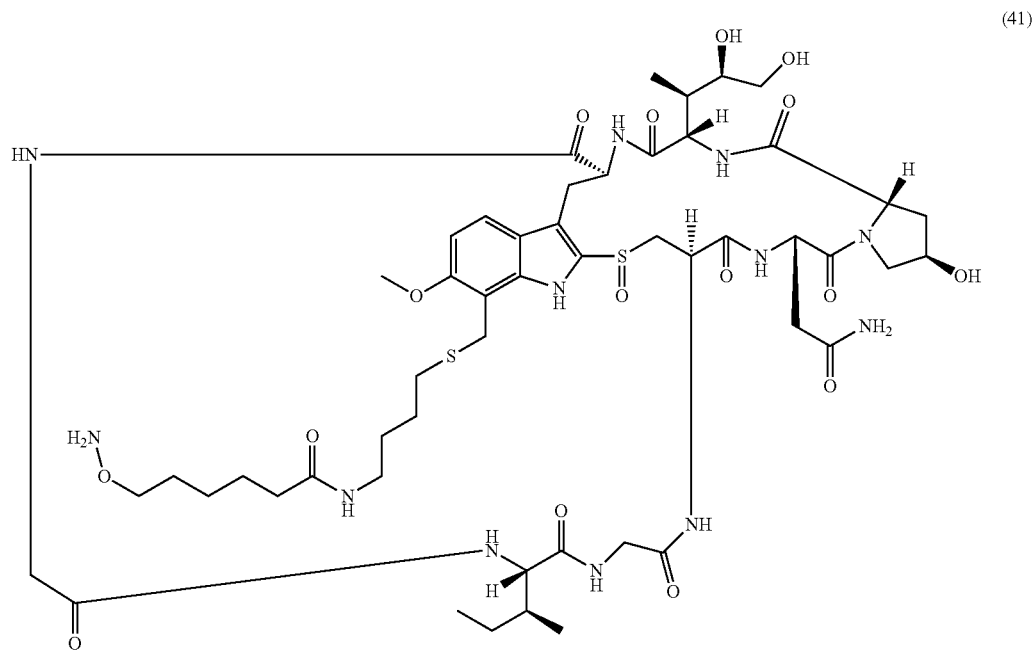 [SMILES: CC[C@H](C)[C@@H]1NC(=O)CNC(=O)[C@@H]2Cc3c([nH]c4c(CSCCCCNC(=O)CCCCCON)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(41)

Compound (41) was prepared using the method described for compound (39), except Compound (A-5) was used in place of Compound (A-2). MS (m+1)=1180.4, HPLC Peak RT=0.699 min, 1H-NMR (MeOD, 400 MHz) δ 8.87 (m, 1H), 8.61 (s, 1H), 8.50 (s, 1H), 8.49 (d, 1H, J=6.6 Hz), 8.35 (s, 1H), 8.19 (d, 1H, J=8.4 Hz), 8.02 (d, 1H, J=9.6 Hz), 7.96 (d, 1H, J=9.0 Hz), 7.68 (bs, 1H), 7.66 (d, 1H, J=9.0 Hz), 6.94 (d, 1H, J=9.0 Hz), 5.31 (m, 1H), 5.15 (m, 1H), 4.78 (bs, 1H), 4.64 (dd, 1H, J=5.4 and 9.6 Hz), 4.54 (m, 2H), 4.32 (dd, 1H, J=9.0 and 18.6 Hz), 4.24 (m, 1H), 4.15 (m, 1H), 4.04 (d, 1H, J=13.2 Hz), 3.95~4.00 (m, 4H), 3.88 (s, 3H), 3.35~3.75 (m, 14H), 3.16 (m, 1H), 3.10 (m, 4H), 2.95 (m, 1H), 2.45 (m, 4H), 2.15 (m, 2H), 2.00 (m, 1H), 1.55~1.70 (m, 9H), 1.45~1.50 (m, 6H), 1.18 (m, 1H), 0.96 (d, 3H, J=6.6 Hz), 0.87 (m, 6H).

Example 42: Synthesis of Compound (42)—NHS Ester of 6'O-methyl-7'C-((2-(3-(carboxy)propanecarboxamido)ethylthio)methyl)-α-Amanitin

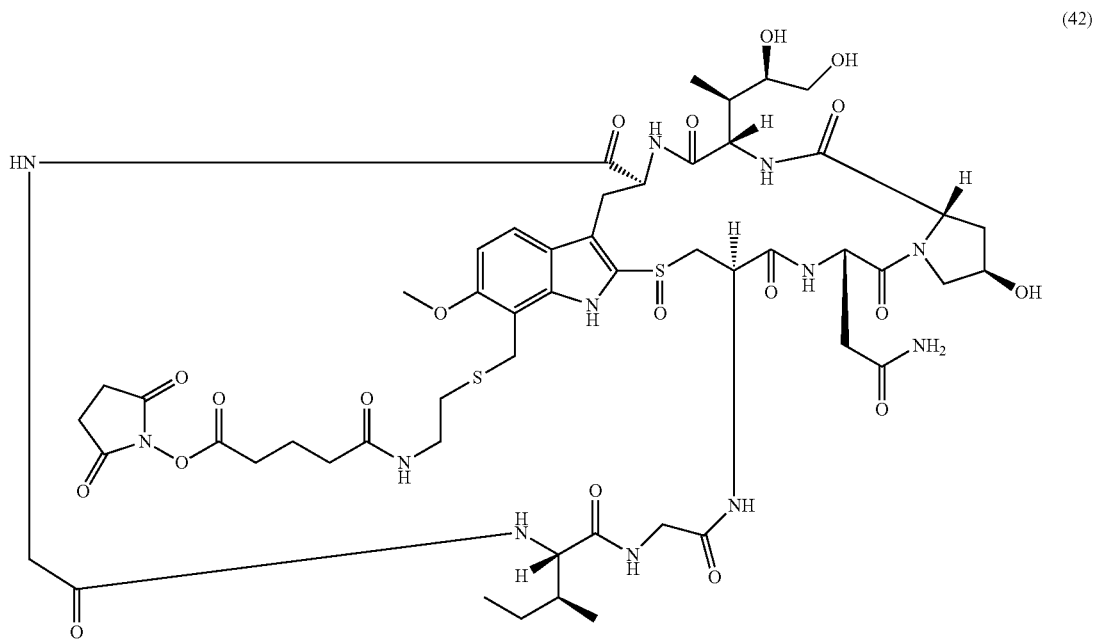 [SMILES: CC[C@H](C)[C@@H]1NC(=O)CNC(=O)[C@@H]2Cc3c([nH]c4c(CSCCNC(=O)CCCC(=O)ON5C(=O)CCC5=O)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(42)

(A-2) (5 mg, 5 µmol) and DMF (1 mL) were combined in a 40 mL vial to give a clean solution. Bis(2,5-dioxopyrrolidin-1-yl) glutarate (2 mg, 5 µmol) and DIEA (4 µL, 20 µmol) were added. After the reaction mixture was stirred at rt for 2 h, the reaction mixture was purified by HPLC to give NHS ester of 6'O-methyl-7'C-((2-(3-(carboxy)propanecarboxamido)ethylthio)methyl)-α-Amanitin (42). MS (m+1)=1234.4, HPLC Peak RT=0.750 min, 1H-NMR (MeOD, 400 MHz) δ 10.79 (s, 1H), 8.46 (m, 1H), 8.60 (s, 1H), 8.48 (s, 1H), 8.46 (d, 1H, J=5.6 Hz), 8.34 (bs, 1H), 8.16 (d, 1H, J=8.4 Hz), 8.01 (d, 1H, J=9.6 Hz), 7.93 (d, 1H, J=9.2 Hz), 7.67 (bs, 1H), 7.64 (d, 1H, J=9.2 Hz), 6.92 (d, 1H, J=9.2 Hz), 5.27 (m, 1H), 5.14 (m, 1H), 4.74 (bs, 1H), 4.61 (dd, 1H, J=5.2 and 9.6 Hz), 4.51 (m, 2H), 4.30 (dd, 1H, J=8.4 and 18.0 Hz), 4.12 (dd, 1H, J=7.6 and 17.2 Hz), 4.07 (d, 1H, J=12.8 Hz), 3.98 (d, 1H, J=12.8 Hz), 3.90 (m, 1H), 3.86 (s, 3H), 3.35~3.75 (m, 13H), 3.05 (m, 1H), 2.92 (dd, 1H, J=11.6 and 15.2 Hz), 2.78 (s, 4H), 2.65 (t, 2H, J=7.2 Hz), 2.61 (s, 1H), 2.50 (m, 2H), 2.40 (m, 2H), 2.25 (m, 2H), 1.90~2.05 (m, 3H), 1.60 (m, 2H), 1.15 (m, 1H), 0.94 (d, 3H, J=7.2 Hz), 0.87 (m, 6H)

Example 43: Synthesis of Compound (43)—NHS Ester of 6'O-methyl-7'C-((4-(3-(carboxy)propanecarboxamido)butylthio)methyl)-α-Amanitin

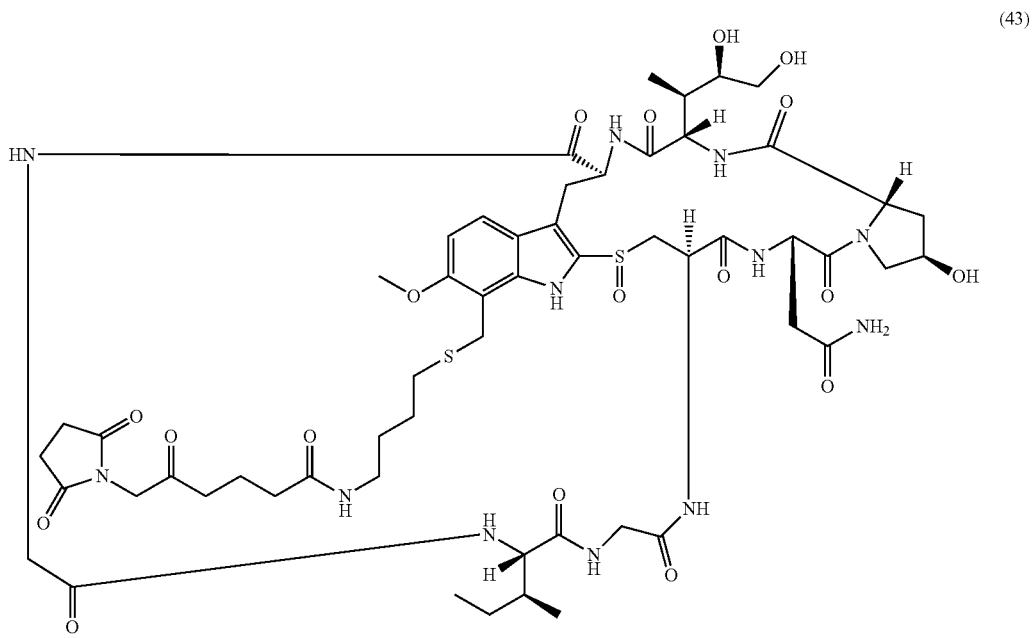 [SMILES: CC[C@H](C)[C@@H]1NC(=O)CNC(=O)[C@@H]2Cc3c([nH]c4c(CSCCCCNC(=O)CCCC(=O)CN5C(=O)CCC5=O)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(43)

Compound (43) was prepared using the method described for Compound (42), except (A-5) was used in place of (A-2). MS (m+1)=1261.3, HPLC Peak RT=0.791 min, 1H-NMR (MeOD, 400 MHz) δ 10.75 (s, 1H), 8.85 (m, 1H), 8.60 (s, 1H), 8.48 (s, 1H), 8.46 (d, 1H, J=4.8 Hz), 8.34 (bs, 1H), 8.15 (d, 1H, J=8.4 Hz), 8.01 (d, 1H, J=9.6 Hz), 7.93 (d, 1H, J=8.4 Hz), 7.69 (bs, 1H), 7.64 (d, 1H, J=8.8 Hz), 6.92 (d, 1H, J=9.2 Hz), 5.27 (m, 1H), 5.14 (m, 1H), 4.75 (bs, 1H), 4.61 (dd, 1H, J=5.6 and 9.6 Hz), 4.51 (m, 2H), 4.30 (dd, 1H, J=9.2 and 18.4 Hz), 4.12 (dd, 1H, J=7.6 and 17.6 Hz), 4.02 (d, 1H, J=13.2 Hz), 3.95 (d, 1H, J=13.2 Hz), 3.91 (m, 1H), 3.85 (s, 3H), 3.35~3.75 (m, 16H), 3.08 (m, 2H), 2.94 (m, 1H), 2.76 (s, 4H), 2.63 (t, 2H, J=11.6 Hz), 2.41 (m, 4H), 2.25 (t, 2H, J=7.2 Hz), 1.92~2.04 (m, 3H), 1.40~1.60 (m, 6H), 1.16 (m, 1H), 0.94 (d, 3H, J=7.2 Hz), 0.87 (m, 6H)

Example 44: Synthesis of Compound (44)—NHS Ester of 6'O-methyl-7'C-((1-(4-(carboxy)butanoyl)-piperidine-4-thio)methyl)-α-Amanitin

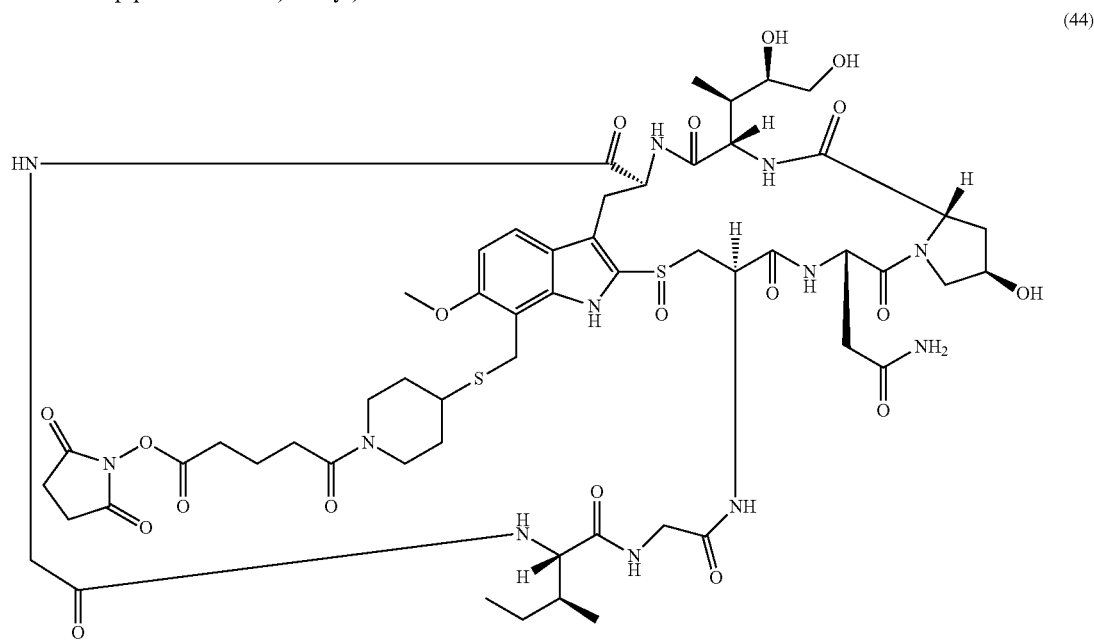

(44)

Compound (44) was prepared using the method described for Compound (42), except (A-12) was used in place of (A-2). MS (m+1)=1274.3, HPLC Peak RT=0.795 min, 1H-NMR (MeOD, 400 MHz) δ 10.81 (s, 1H), 8.85 (m, 1H), 8.59 (s, 1H), 8.47 (s, 1H), 8.46 (d, 1H, J=5.2 Hz), 8.35 (bs, 1H), 8.16 (d, 1H, J=8.4 Hz), 8.01 (d, 1H, J=9.6 Hz), 7.93 (d, 1H, J=8.4 Hz), 7.69 (bs, 1H), 7.65 (d, 1H, J=9.2 Hz), 6.93 (d, 1H, J=9.2 Hz), 5.27 (m, 1H), 5.14 (m, 1H), 4.71 (bs, 1H), 4.61 (dd, 1H, J=5.2 and 10.0 Hz), 4.51 (m, 2H), 4.30 (m, 1H), 4.09~4.18 (m, 2H), 3.90~4.02 (m, 2H), 3.87 (s, 3H), 3.35~3.75 (m, 14H), 3.08 (m, 2H), 2.92 (m, 1H), 2.79 (s, 4H), 2.67 (t, 2H, J=6.8 Hz), 2.48 (m, 2H), 2.35~2.45 (m, 2H), 1.69 (m, 4H), 1.55 (m, 1H), 1.25~1.45 (m, 2H), 1.14 (m, 1H), 0.94 (d, 3H, J=7.2 Hz), 0.85 (m, 6H).

Example 45: Synthesis of Compound (A-21)—6'O-methyl-7'C-((1-(14-azido-3,6,9,12-tetraoxatetradecancarbonyl)-piperidine-4-thio)methyl)-α-Amanitin and Compound (45) 6'O-methyl-7'C-((1-(14-((4-maleimido)methyl-1H-1,2,3-triazol-1-yl)-3,6,9,12-tetraoxatetradecancarbonyl)-piperidine-4-thio)methyl)-α-Amanitin

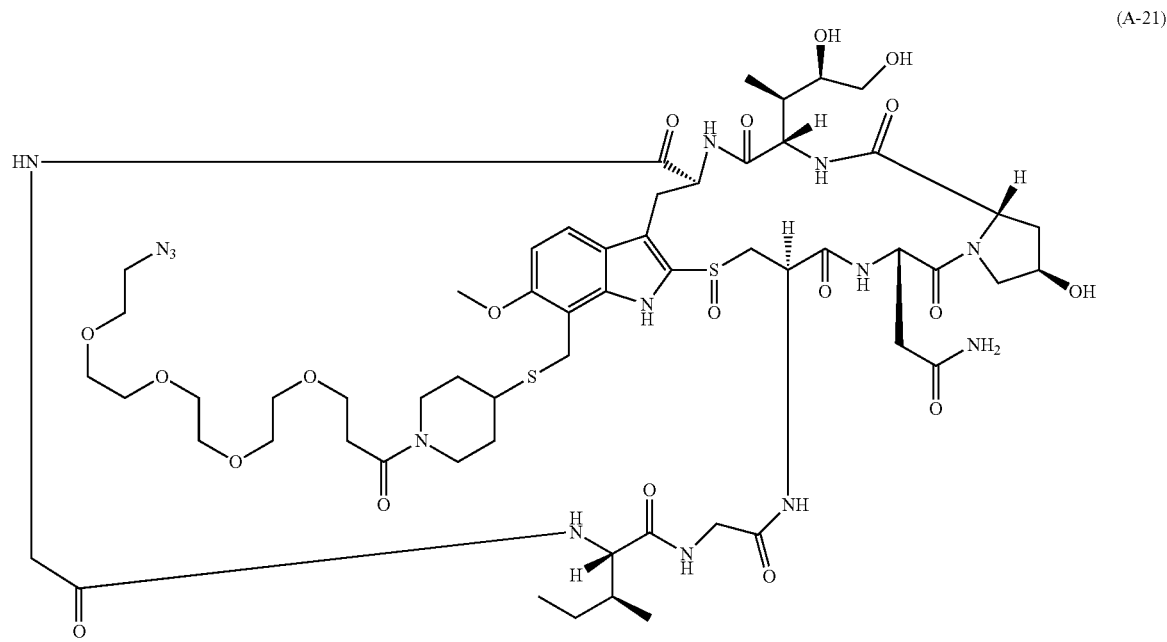

(A-21)

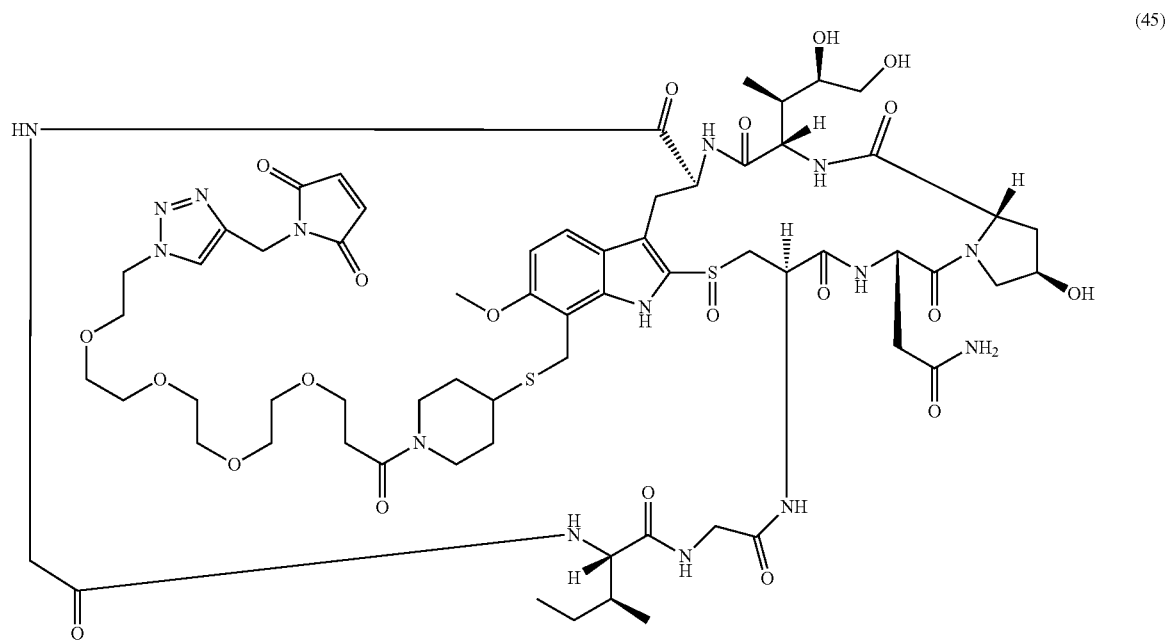

(45)

Compound (A-21) was prepared using the method described in Example 9, except Compound (A-12) was used in place of Compound (A-2) MS (m+2/2)=668.4, HPLC Peak RT=0.904 min, 1H-NMR (MeOD, 400 MHz) δ 10.80 (s, 1H), 8.84 (m, 1H), 8.59 (d, 1H, J=2.0 Hz), 8.48 (s, 1H), 8.45 (d, 1H, J=2.0 Hz), 8.35 (s, 1H), 8.15 (d, 1H, J=8.4 Hz), 8.00 (d, 1H, J=9.6 Hz), 7.92 (d, 1H, J=8.8 Hz), 7.68 (s, 1H), 7.64 (d, 1H, J=9.2 Hz), 6.93 (d, 1H, J=8.8 Hz), 5.27 (m, 1H), 5.13 (m, 1H), 4.75 (bs, 1H), 4.61 (dd, 1H, J=5.6 and 9.6 Hz), 4.51 (m, 2H), 4.30 (m, 1H), 4.10~4.25 (m, 3H), 3.98 (d, 1H, J=13.2 Hz), 3.90~3.95 (m, 3H), 3.86 (s, 3H), 3.30~3.75 (m, 36H), 2.80~3.20 (m, 4H), 2.60 (m, 2H), 2.37 (m, 6H), 2.00 (m, 3H), 1.57 (m, 2H), 1.10~1.45 (m, 4H), 0.94 (d, 3H, J=7.2 Hz), 0.85 (m, 6H).

Compound (45) was prepared using the method described in Example 9, except Compound (A-21) was used in place of Compound (A-3). MS (m+2/2)=736.0, HPLC Peak RT=0.782 min, 1H-NMR (MeOD-d4, 400 MHz) δ 10.78 (s, 1H), 8.84 (m, 1H), 8.59 (d, 1H, J=2.0 Hz), 8.46 (d, 1H, J=10.0 Hz), 8.45 (s, 1H), 8.15 (d, 1H, J=8.4 Hz), 8.01 (d, 1H, J=9.6 Hz), 7.92 (d, 1H, J=8.8 Hz), 7.88 (d, 1H, J=4.8 Hz), 7.63 (d, 1H, J=8.4 Hz), 6.92 (d, 1H, J=8.4 Hz), 6.79 (s, 2H), 5.27 (m, 1H), 5.13 (m, 1H), 4.75 (m, 1H), 4.69 (d, 2H, J=2.8 Hz), 4.62 (dd, 1H, J=5.2 and 9.6 Hz), 4.51 (m, 2H), 4.48 (m, 2H), 4.28 (m, 1H), 4.15 (m, 3H), 3.96 (m, 2H), 3.92 (m, 1H), 3.86 (s, 3H), 3.77 (m, 2H), 3.40~3.75 (m, 32H), 3.09 (m, 1H), 2.91 (m, 1H), 2.80 (m, 1H), 2.63 (m, 1H), 2.52 (m, 1H), 2.40 (m, 2H), 2.00 (m, 3H), 1.10~1.62 (m, 6H), 0.94 (d, 3H, J=7.2 Hz), 0.85 (m, 6H).

Example 46: Synthesis of Compound (46)—Tetrafluorophenyl ester of 6'O-methyl-7'C-((4-(3-(carboxy)propanecarboxamido)butylthio)methyl)-α-Amanitin

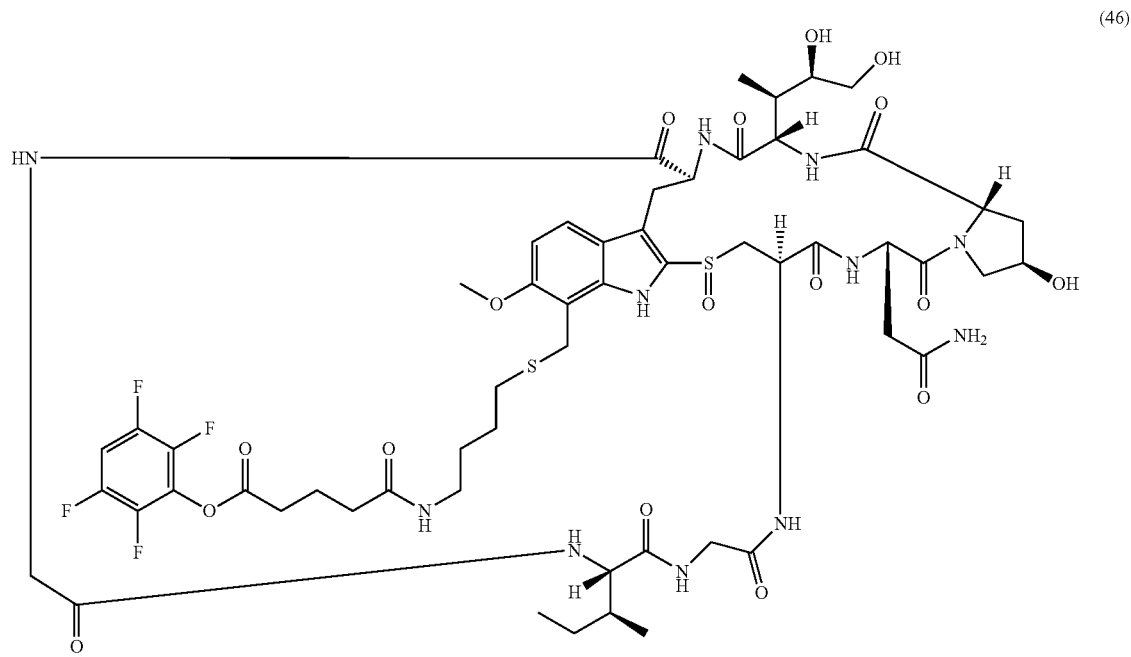 [SMILES: CC[C@H](C)[C@@H]1NC(=O)CNC(=O)[C@@H]2Cc3c([nH]c4c(CSCCCCNC(=O)CCCC(=O)Oc5c(F)c(F)cc(F)c5F)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

Compound (46) was prepared using the method described for Compound (43), except bis(2,3,5,6-tetrafluorophenyl) glutarate (i-10) was used in place of bis(2,5-dioxopyrrolidin-1-yl) glutarate. MS (m+1)=1313.3, HPLC Peak RT=0.996 min, 1H-NMR (MeOD, 400 MHz) δ 10.78 (s, 1H), 8.85 (m, 1H), 8.59 (s, 1H), 8.49 (s, 1H), 8.47 (d, 1H, J=10.0 Hz), 8.35 (bs, 1H), 8.15 (d, 1H, J=8.0 Hz), 8.01 (d, 1H, J=9.6 Hz), 7.93 (d, 1H, J=8.8 Hz), 7.69 (bs, 1H), 7.63 (d, 1H, J=8.8 Hz), 7.36 (m, 1H), 6.92 (d, 1H, J=8.8 Hz), 5.27 (m, 1H), 5.14 (m, 1H), 4.75 (bs, 1H), 4.61 (dd, 1H, J=5.2 and 9.6 Hz), 4.51 (m, 2H), 4.30 (dd, 1H, J=8.4 and 18.0 Hz), 4.12 (m, 1H), 4.00 (d, 1H, J=13.2 Hz), 3.95 (d, 1H, J=13.2 Hz), 3.91 (m, 1H), 3.85 (s, 3H), 3.34~3.70 (m, 9H), 3.08 (m, 4H), 2.91 (m, 1H), 2.73 (t, 2H, J=14.4 Hz), 1.98 (t, 2H, J=7.6 Hz), 1.92~2.04 (m, 1H), 1.40~1.60 (m, 6H), 1.16 (m, 1H), 0.94 (d, 3H, J=6.8 Hz), 0.87 (m, 6H).

Example 47: Synthesis of Compound (47)—7'C-((4-(3-(23-((4-maleimido)methyl-1H-1,2,3-triazol-1-yl)-3,6,9,12,15,18,21-heptaoxatricosyl)ureido)butylthio)methyl)-α-Amanitin

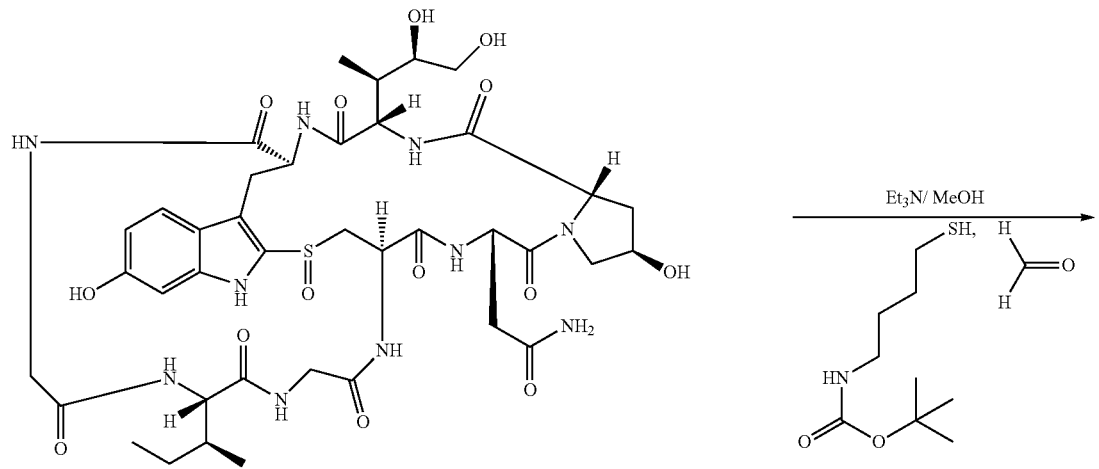

(A)

-continued
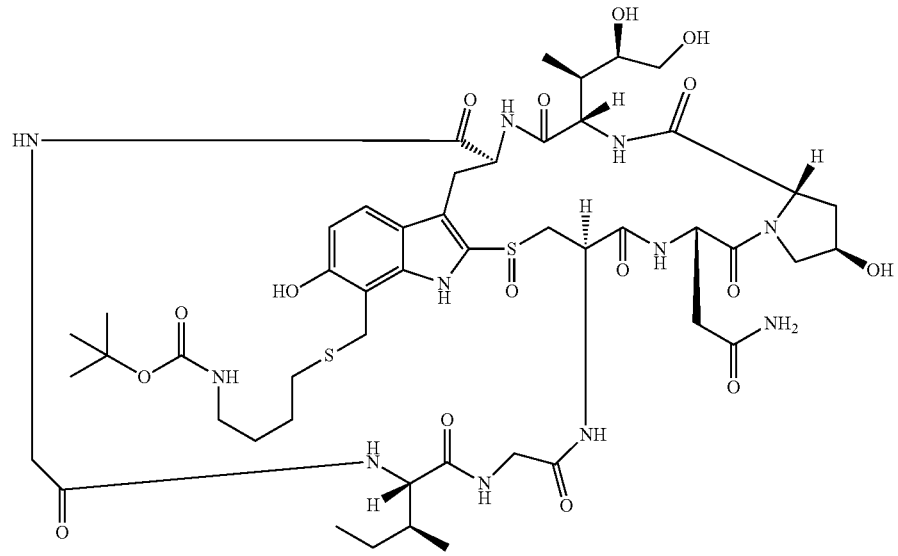
(A-22)
↓TFA
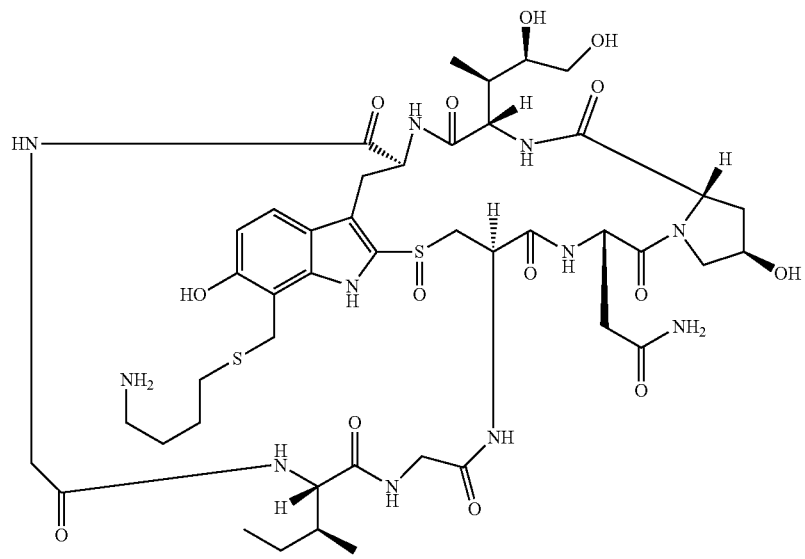
(A-23)

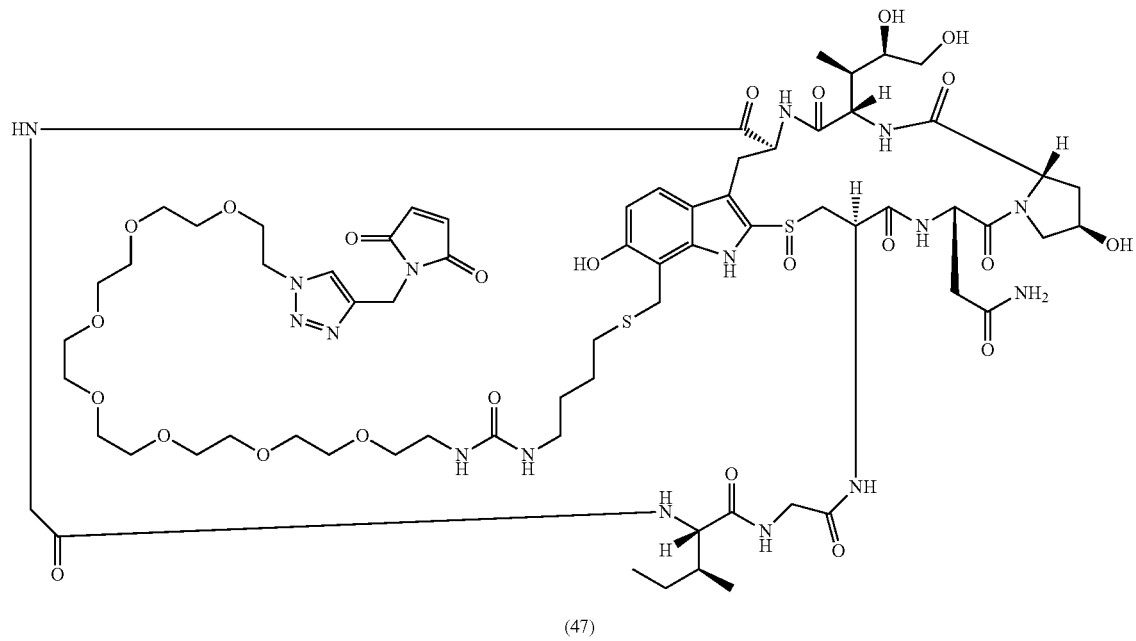 [SMILES: CC[C@H](C)[C@@H]1NC(=O)CNC(=O)[C@@H]2Cc3c([nH]c4c(CSCCCCNC(=O)NCCOCCOCCOCCOCCOCCOCCOCCn5cc(CN6C(=O)C=CC6=O)nn5)c(O)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(47)

Step 1: Compound (A-22) was prepared using the method described in Example 24, except (4-mercaptobutyl)carbamate was used in place of (2-mercaptoethyl)carbamate. MS (m+1)=1136.4., HPLC Peak RT=0.873 min, 1H-NMR (MeOD, 600 MHz) δ 10.66 (s, 1H), 8.85 (m, 1H), 8.60 (d, 1H, J=2.4 Hz), 8.49 (m, 1H), 8.47 (d, 1H, J=10.8 Hz), 8.35 (s, 1H), 8.16 (d, 1H, J=8.4 Hz), 8.03 (d, 1H, J=9.6 Hz), 7.92 (d, 1H, J=9.0 Hz), 7.69 (s, 1H), 7.49 (d, 1H, J=9.0 Hz), 6.70 (d, 1H, J=9.0 Hz), 5.28 (m, 1H), 5.14 (m, 1H), 4.77 (bs, 1H), 4.63 (dd, 1H, J=5.4 and 9.6 Hz), 4.53 (m, 2H), 4.31 (dd, 1H, J=8.4 and 17.4 Hz), 4.17 (m, 1H), 4.15 (dd, 1H, J=7.8 and 17.4 Hz), 4.05 (d, 1H, J=13.2 Hz), 3.94 (m, 2H), 3.40~3.74 (m, 18H), 3.08~3.23 (m, 3H), 2.95 (m, 3H), 2.38~2.46 (m, 4H), 2.02 (t, 1H, J=15.6 Hz), 1.42~1.64 (m, 8H), 1.40 (s, 9H), 1.29 (m, 1H), 1.16 (m, 1H), 0.96 (d, 3H, J=7.2 Hz), 0.88 (m, 6H).

Step 2: Compound (A-23) was prepared using the method described in Example 24, except A-22 was used in place of A-7. MS (m+1)=1036.4, HPLC Peak RT=0.564 min.

Step 3: Compound (47) was prepared using the method described in Example 23, except Compound (A-23) was used in place of Compound (A-2). MS (m+2/2)=796.5, HPLC Peak RT=0.791 min, 1H-NMR (MeOD-d4, 500 MHz) δ 8.84 (m, 1H), 8.63 (d, 1H, J=2.5 Hz), 8.50 (m, 2H), 8.18 (d, 1H, J=8.0 Hz), 8.06 (d, 1H, J=9.5 Hz), 7.95 (t, 2H, J=4.5 Hz), 7.52 (d, 1H, J=8.5 Hz), 6.85 (s, 2H), 6.73 (d, 1H, J=8.5 Hz), 5.29 (m, 1H), 5.15 (m, 1H), 4.80 (m, 1H), 4.76 (s, 2H), 4.67 (dd, 1H, J=5.0 and 9.5 Hz), 4.56 (m, 2H), 4.52 (t, 2H, J=5.0 Hz), 4.34 (dd, 1H, J=9.0 and 13.0 Hz), 4.18 (dd, 1H, J=8.0 and 17.5 Hz), 4.08 (d, 1H, J=13.5 Hz), 3.98 (m, 2H), 3.85 (t, 2H, J=5.0 Hz), 3.48~3.79 (m, 39H), 3.39 (m, 1H), 3.21~3.30 (m, 3H), 3.04~3.13 (m, 3H), 2.96 (m, 1H), 2.45 (m, 4H), 2.06 (m, 1H), 1.52~1.70 (m, 4H), 1.47 (m, 2H), 1.22 (m, 1H), 0.99 (d, 3H, J=7.0 Hz), 0.91 (m, 6H).

Example 48: Synthesis of Compound (48)—7′C-((4-(14-(maleimido)-3,6,9,12-tetraoxatetradecancarboxamido)butylthio)methyl)-α-Amanitin

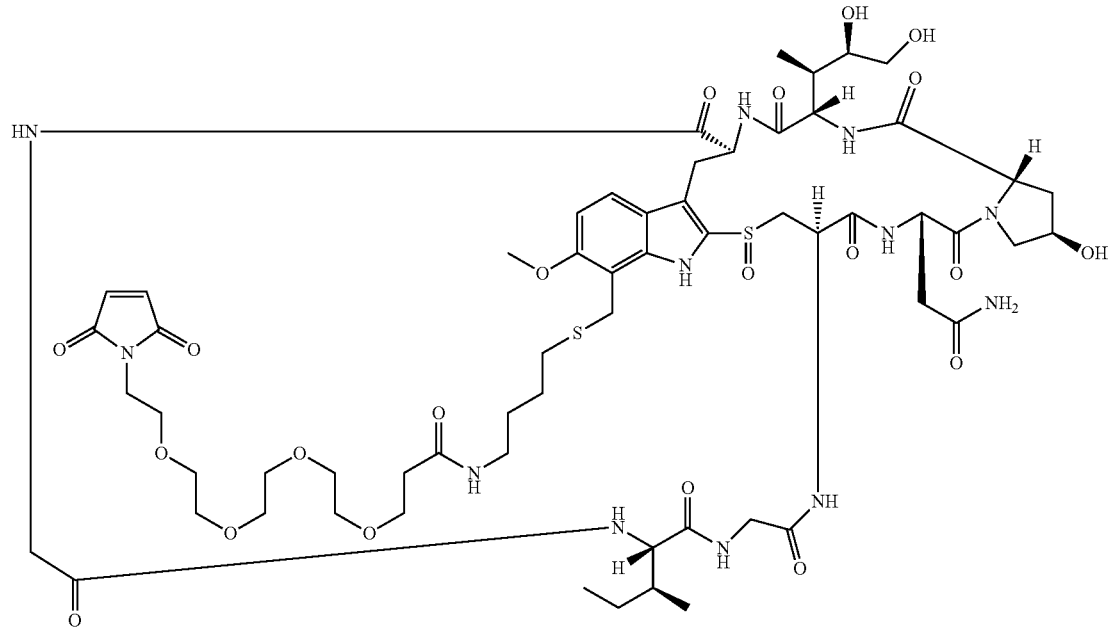

(48)

Compound (48) was prepared using the method described in Example 21, except Compound (A-23) was used in place of Compound (A-5). MS (m+2/2)=682.4, HPLC Peak RT=0.777 min, 1H-NMR (MeOD-d4, 400 MHz) δ 10.63 (s, 1H), 8.84 (m, 1H), 8.59 (d, 1H, J=2.0 Hz), 8.47 (s, 1H), 8.46 (d, 1H, J=4.8 Hz), 8.15 (d, 1H, J=8.4 Hz), 8.01 (d, 1H, J=10.0 Hz), 7.90 (d, 1H, J=8.8 Hz), 7.47 (d, 1H, J=8.8 Hz), 6.75 (s, 2H), 6.68 (d, 1H, J=8.8 Hz), 5.26 (m, 1H), 5.11 (m, 1H), 4.75 (m, 1H), 4.61 (dd, 1H, J=5.2 and 9.6 Hz), 4.51 (m, 2H), 4.29 (dd, 1H, J=8.8 and 18.0 Hz), 4.11 (m, 1H), 4.04 (d, 1H, J=13.2 Hz), 3.92 (m, 3H), 3.35~3.75 (m, 36H), 3.07 (m, 4H), 2.91 (m, 1H), 2.38 (m, 6H), 2.31 (t, 1H, J=8.0 Hz), 2.00 (m, 2H), 1.44~1.64 (m, 6H), 1.15 (m, 1H), 0.93 (d, 3H, J=6.8 Hz), 0.85 (m, 6H)

Example 49: Synthesis of Compound (49)—6′O-methyl-7′C-((4-(26-(maleimido)-3,6,9,12,15,18,21,24-octaoxahexacosancarboxamido)butylthio)methyl)-α-Amanitin

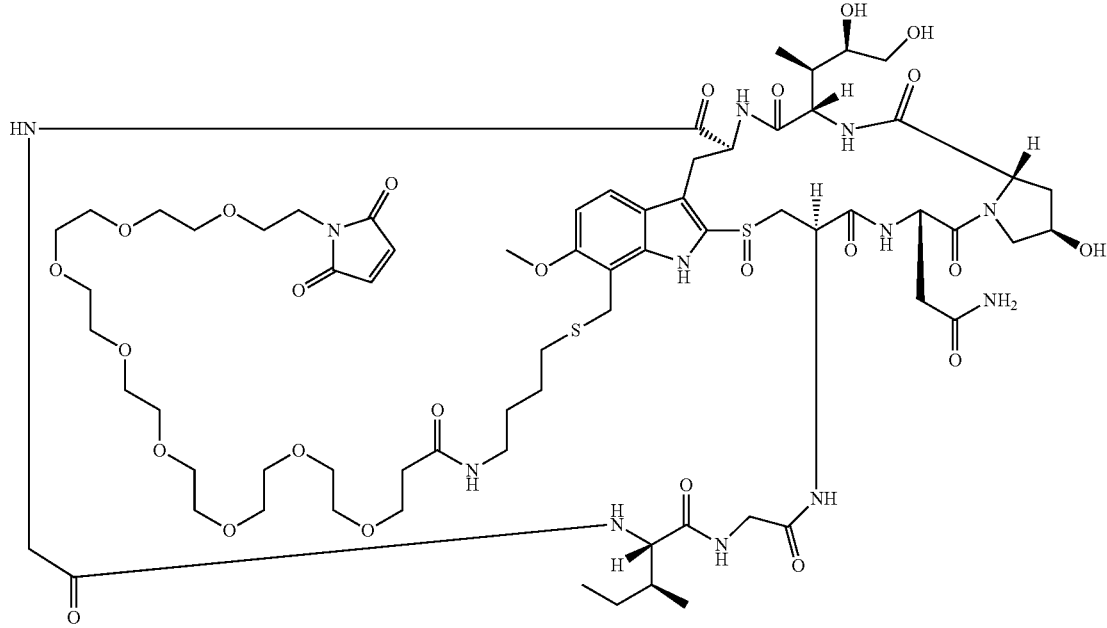

(49)

Compound (49) was prepared using the method described in Example 19, except 1-(2,5-dioxo-2,5-dihydro-1H-pyrrol-1-yl)-3,6,9,12,15,18,21,24-octaoxaheptacosan-27-oic acid was used in place of 6-(6-(2,5-dioxo-2,5-dihydro-1H-pyrrol-1-yl)hexanamido)hexanoic acid (i-1). MS (m+2/2)=777.5, HPLC Peak RT=0.871 min, 1H-NMR (MeOD-d4, 500 MHz) δ 10.75 (s, 1H), 8.85 (m, 1H), 8.63 (s, 1H), 8.52 (d, 1H, J=10.0 Hz), 8.48 (d, 1H, J=3.5 Hz), 8.19 (d, 1H, J=8.5 Hz), 8.05 (d, 1H, J=9.5 Hz), 7.96 (d, 1H, J=9.0 Hz), 7.69 (d, 1H, J=9.0 Hz), 6.98 (d, 1H, J=9.0 Hz), 6.82 (s, 2H), 5.33 (m, 1H), 5.19 (m, 1H), 4.79 (bs, 1H), 4.67 (dd, 1H, J=5.0 and 9.5 Hz), 4.59 (m, 2H), 4.35 (dd, 1H, J=8.5 and 18.0 Hz), 4.18 (m, 1H), 4.09 (d, 1H, J=13.5 Hz), 3.99 (d, 1H, J=13.0 Hz), 3.96 (m, 1H), 3.91 (s, 3H), 3.40~3.78 (m, 50H), 3.27 (d, 1H, J=13.5 Hz), 3.13 (m, 3H), 2.97 (dd, 1H, J=12.0 and 15.0 Hz), 2.48 (m, 6H), 2.06 (m, 1H), 1.50~1.69 (m, 6H), 1.19 (m, 1H), 0.99 (d, 3H, J=7.0 Hz), 0.91 (m, 6H).

Example 50: Synthesis of Compound (50)—6'O-methyl-7'C-((4-(3-(2-(2-(2-(2-((4-maleimido)methyl-1H-1,2,3-triazol-1-yl)-ethoxy)ethoxy)ethoxy)ethyl)ureido)butylthio)methyl)-α-Amanitin

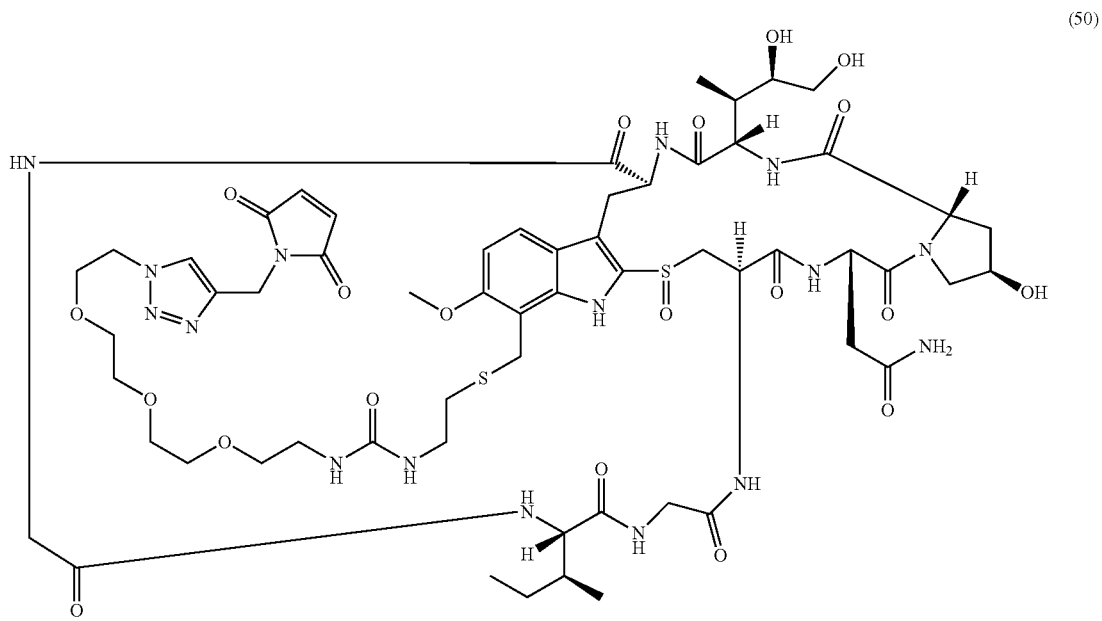 [SMILES: CC[C@H](C)[C@@H]1NC(=O)CNC(=O)[C@@H]2Cc3c([nH]c4c(CSCCNC(=O)NCCOCCOCCOCCn5cc(CN6C(=O)C=CC6=O)nn5)c(OC)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(50)

Compound (50) was prepared using the method described in Example 23, except Compound (i-11) was used in place of Compound (i-6). MS (m+2/2)=715.4, HPLC Peak RT=0.790 min, 1H-NMR (MeOD-d4, 500 MHz) δ 10.76 (s, 1H), 8.87 (m, 1H), 8.64 (d, 1H, J=2.5 Hz), 8.52 (d, 1H, J=14.5 Hz), 8.51 (s, 1H), 8.19 (d, 1H, J=8.5 Hz), 8.05 (d, 1H, J=10.0 Hz), 7.98 (s, 1H), 7.96 (d, 1H, J=8.5 Hz), 7.92 (s, 1H), 7.68 (d, 1H, J=8.5 Hz), 6.96 (d, 1H, J=9.0 Hz), 6.84 (s, 2H), 5.33 (m, 1H), 5.18 (m, 1H), 4.75 (s, 2H), 4.67 (dd, 1H, J=5.0 and 9.5 Hz), 4.57 (m, 2H), 4.51 (t, 2H, J=5.0 Hz), 4.33 (dd, 1H, J=8.5 and 18.5 Hz), 4.18 (m, 1H), 4.08 (d, 1H, J=13.5 Hz), 3.99 (d, 1H, J=13.5 Hz), 3.97 (m, 1H), 3.90 (s, 3H), 3.84 (t, 2H, J=5.0 Hz), 3.40~3.75 (m, 25H), 2.90~3.19 (m, 5H), 2.44 (m, 4H), 2.06 (m, 1H), 1.43~1.68 (m, 6H), 1.20 (m, 1H), 0.99 (d, 3H, J=7.0 Hz), 0.91 (m, 6H).

Example 51: Synthesis of Compound (51)—6'O-methyl-7'C-((1-(26-(maleimido)-3,6,9,12,15,18,21,24-octaoxahexacosancarboxamido)-piperidine-4-thio)methyl)-α-Amanitin

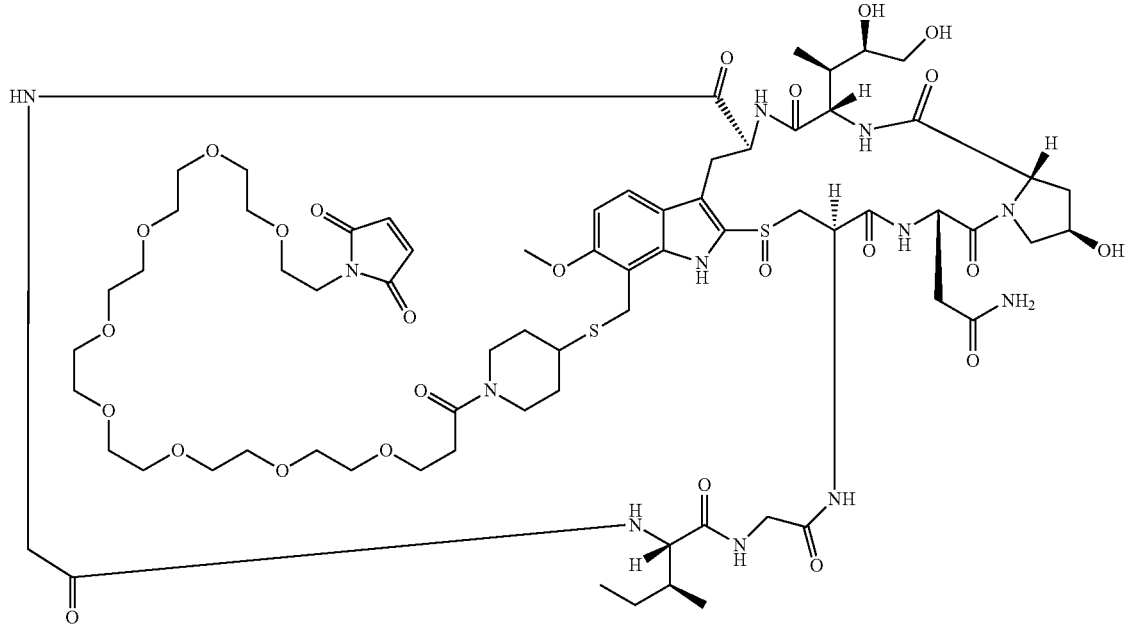

(51)

Compound (51) was prepared using the method described in Example 51, except Compound (A-12) was used in place of Compound (A-5). MS (m+2/2)=783.5, HPLC Peak RT=0.865 min, 1H-NMR (MeOD-d4, 500 MHz) δ 10.77 (s, 1H), 8.86 (m, 1H), 8.63 (s, 1H), 8.52 (d, 1H, J=10.0 Hz), 8.46 (m, 1H), 8.36 (s, 1H), 8.19 (d, 1H, J=9.0 Hz), 8.04 (d, 1H, J=9.5 Hz), 7.97 (d, 1H, J=9.0 Hz), 7.69 (d, 1H, J=9.0 Hz), 6.98 (d, 1H, J=9.0 Hz), 6.83 (s, 2H), 5.33 (m, 1H), 5.19 (m, 1H), 4.80 (bs, 1H), 4.67 (dd, 1H, J=5.5 and 10.0 Hz), 4.55 (m, 2H), 4.35 (m, 1H), 4.25 (m, 1H), 4.18 (m, 2H), 4.04 (d, 1H, J=13.5 Hz), 3.99 (d, 1H, J=13.0 Hz), 3.97 (m, 1H), 3.92 (s, 3H), 3.40~3.78 (m, 50H), 3.13 (m, 3H), 2.97 (dd, 1H, J=11.5 and 15.0 Hz), 2.86 (m, 2H), 2.71 (m, 1H), 2.60 (m, 1H), 2.45 (m, 2H), 1.91~2.08 (m, 3H), 1.17~1.68 (m, 6H), 0.99 (d, 3H, J=7.0 Hz), 0.91 (m, 6H).

Example 52: Synthesis of Compound (52)—Perfluorophenyl ester of 6'O-methyl-7'C-((4-((23-carboxy) 3,6,9,12,15,18,21-heptaoxatricosancarboxamido)butylthio)methyl)-α-Amanitin

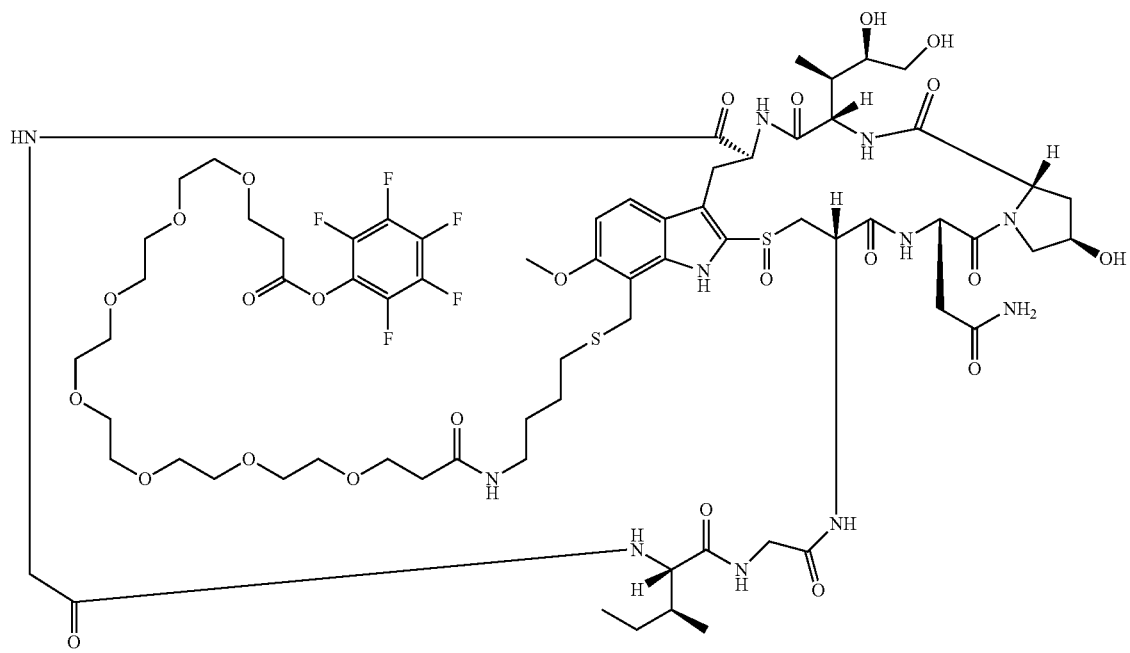

(52)

Compound (52) was prepared using the method described for Compound (43), except bis(perfluorophenyl) 4,7,10,13,16,19,22-heptaoxapentacosane-1,25-dioate was used in place of bis(2,5-dioxopyrrolidin-1-yl) glutarate. MS (m+2/2)=812.9, HPLC Peak RT=1.066 min, 1H-NMR (MeOD, 500 MHz) δ 10.76 (s, 1H), 8.84 (m, 1H), 8.59 (d, 1H, J=2.0 Hz), 8.47 (m, 2H), 8.34 (bs, 1H), 8.15 (d, 1H, J=11.0 Hz), 8.00 (d, 1H, J=12.0 Hz), 7.92 (d, 1H, J=11.0 Hz), 7.68 (bs, 1H), 7.63 (d, 1H, J=11.0 Hz), 6.92 (d, 1H, J=11.5 Hz), 5.27 (m, 1H), 5.14 (m, 1H), 4.75 (bs, 1H), 4.62 (dd, 1H, J=6.5 and 12.0 Hz), 4.51 (m, 2H), 4.30 (dd, 1H, J=11.0 and 22.5 Hz), 4.12 (m, 1H), 4.04 (d, 1H, J=16.5 Hz), 3.94 (d, 1H, J=16.5 Hz), 3.92 (m, 1H), 3.86 (s, 3H), 3.80 (m, 5H), 3.34~3.70 (m, 54H), 3.08 (m, 4H), 2.95 (m, 5H), 2.39 (m, 7H), 2.01 (m, 1H), 1.42~1.68 (m, 6H), 1.15 (m, 1H), 0.94 (d, 3H, J=8.5 Hz), 0.85 (m, 6H)

Example 53: Synthesis of Compound (53)—Tetrafluorophenyl ester of 6'O-methyl-7'C-((4-(14-carboxy-3,6,9,12-tetraoxatetradecancarboxamido)butylthio)methyl)-α-Amanitin

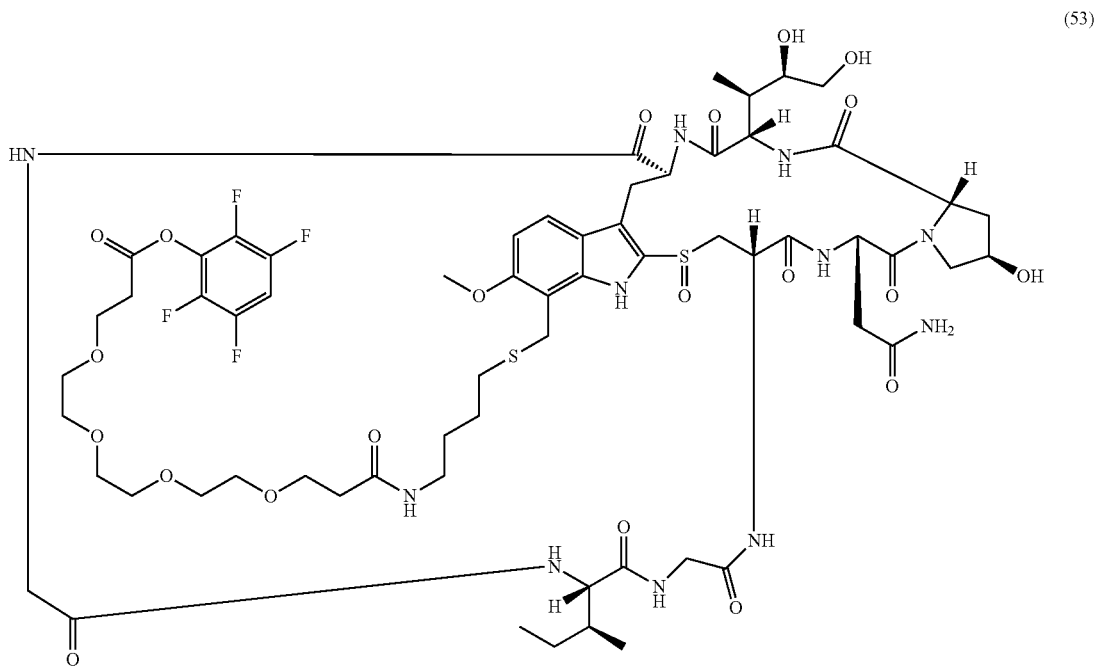 [SMILES: CC[C@H](C)[C@@H]1NC(=O)CNC(=O)[C@@H]2Cc3c([nH]c4c(CSCCCCNC(=O)CCOCCOCCOCCOCCC(=O)Oc5c(F)c(F)cc(F)c5F)c(OC)ccc34)S(=O)C[C@@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

(53)

Compound (53) was prepared using the method described for Compound (43), except bis(2,3,4,6-tetrafluorophenyl) 4,7,10,13-tetraoxahexadecane-1,16-dioate was used in place of bis(2,5-dioxopyrrolidin-1-yl) glutarate. MS (m+2/2)=737.9, HPLC Peak RT=1.012 min, 1H-NMR (MeOD, 500 MHz) δ 10.76 (s, 1H), 8.84 (m, 1H), 8.59 (d, 1H, J=2.5 Hz), 8.47 (m, 2H), 8.34 (bs, 1H), 8.15 (d, 1H, J=11.0 Hz), 8.00 (d, 1H, J=12.5 Hz), 7.92 (d, 1H, J=11.0 Hz), 7.67 (bs, 1H), 7.63 (d, 1H, J=11.0 Hz), 7.37 (m, 1H), 6.92 (d, 1H, J=11.0 Hz), 5.27 (m, 1H), 5.14 (m, 1H), 4.75 (bs, 1H), 4.62 (dd, 1H, J=6.5 and 12.0 Hz), 4.51 (m, 2H), 4.30 (dd, 1H, J=11.0 and 23.0 Hz), 4.12 (m, 1H), 4.02 (d, 1H, J=16.5 Hz), 3.93 (d, 1H, J=16.5 Hz), 3.92 (m, 1H), 3.85 (s, 3H), 3.80 (m, 3H), 3.35~3.73 (m, 36H), 3.08 (m, 4H), 2.95 (m, 5H), 2.37 (m, 7H), 2.01 (m, 1H), 1.43~1.68 (m, 6H), 1.15 (m, 1H), 0.94 (d, 3H, J=9.0 Hz), 0.85 (m, 6H)

Example 54: Synthesis of Compound (54)—6'O-methyl-7'C-((4-(26-(3-(maleimido)propanamido)-3,6,9,12,15,18,21,24-octaoxahexacosancarboxamido)butylthio)methyl)-α-Amanitin
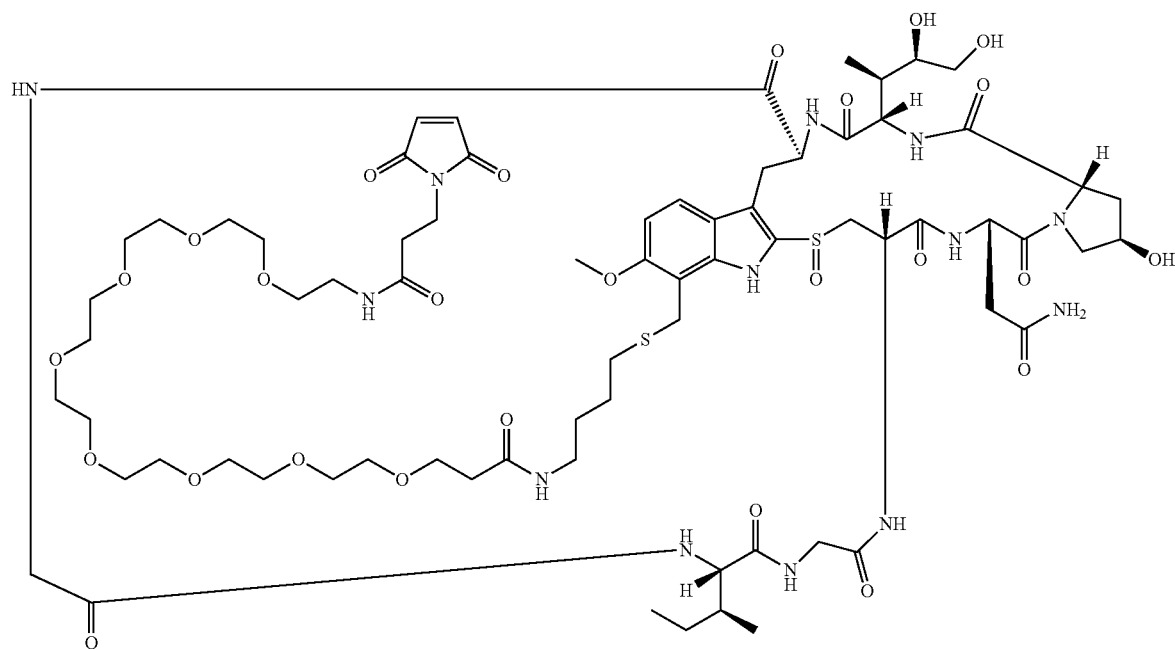
(54)

Compound (A-5) (6 mg, 5 μmol) and DMSO (2 mL) was in a 40 mL vial to give a clean solution. 2,3,5,6-tetrafluorophenyl 1-(2,5-dioxo-2,5-dihydro-1H-pyrrol-1-yl)-3-oxo-7,10,13,16,19,22,25,28-octaoxa-4-azahentriacontan-31-oate (3 mg, 5 μmol) and triethylamine (2 μL, 13 μmol) were added. The reaction mixture was stirred at rt for 30 min, and then purified by HPLC to give Compound (54). MS (m+2/2)=813.0, HPLC Peak RT=0.835 min, 1H-NMR (MeOD, 500 MHz) δ 10.75 (s, 1H), 8.86 (m, 1H), 8.63 (d, 1H, J=2.0 Hz), 8.52 (d, 1H, J=10.5 Hz), 8.49 (d, 1H, J=3.5 Hz), 8.36 (bs, 1H), 8.19 (d, 1H, J=8.5 Hz), 8.05 (d, 1H, J=9.5 Hz), 7.96 (d, 1H, J=9.0 Hz), 7.69 (bs, 1H), 7.68 (d, 1H, J=9.0 Hz), 6.98 (d, 1H, J=9.0 Hz), 6.81 (s, 1H), 5.32 (m, 1H), 5.19 (m, 1H), 4.80 (bs, 1H), 4.67 (dd, 1H, J=5.5 and 10.0 Hz), 4.56 (m, 2H), 4.35 (dd, 1H, J=9.0 and 18.0 Hz), 4.18 (dd, 1H, J=8.0 and 17.5 Hz), 4.10 (d, 1H, J=13.5 Hz), 3.99 (d, 1H, J=13.0 Hz), 3.97 (m, 1H), 3.91 (s, 3H), 3.77 (t, 1H, J=7.0 Hz), 3.72 (t, 1H, J=6.0 Hz), 3.40~3.65 (m, 38H), 3.14 (m, 3H), 2.97 (dd, 1H, J=12.0 and 14.5 Hz), 2.46 (m, 8H), 2.06 (m, 1H), 1.50~1.69 (m, 6H), 1.23 (m, 1H), 0.99 (d, 3H, J=7.0 Hz), 0.90 (m, 6H)

Example 55: Synthesis of Compound (55)—Perfluorophenyl ester of 6'O-methyl-7'C-(1-((23-carboxy-3,6,9,12,15,18,21-heptaoxatricosancarbonyl)-piperidine-4-thio)methyl)-α-Amanitin
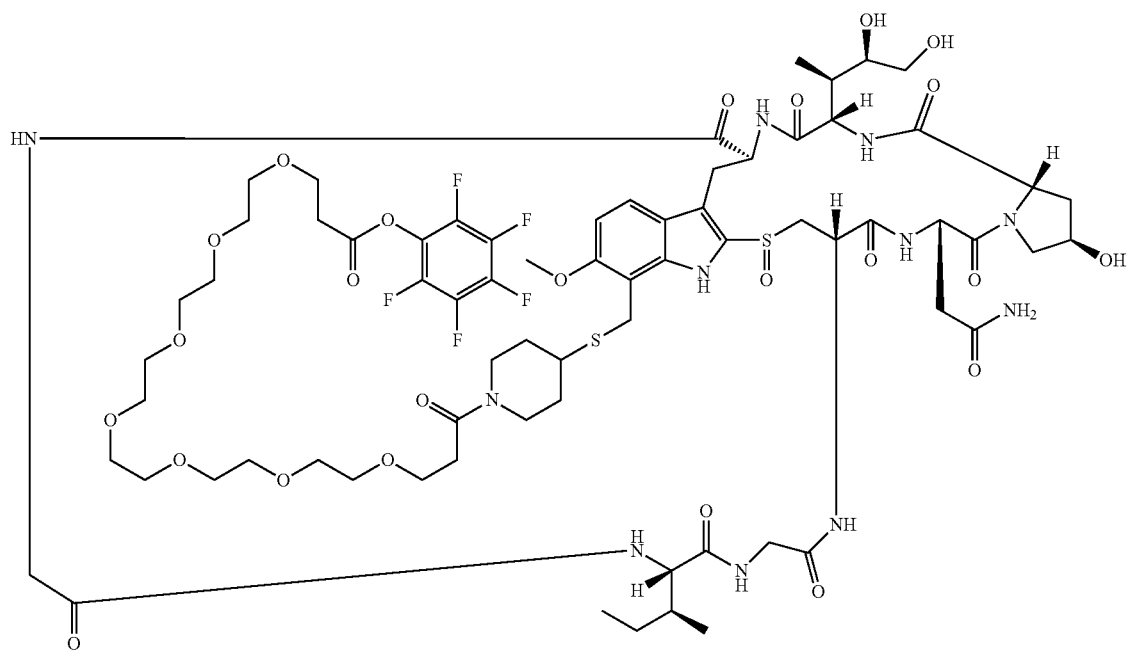
(55)

Compound (55) was prepared using the method described for Example 52, except Compound (A-12) was used in place of Compound (A-5). MS (m+2/2)=819.4, HPLC Peak RT=1.074 min, 1H-NMR (MeOD, 500 MHz) δ 10.78 (s, 1H), 8.85 (m, 1H), 8.63 (d, 1H, J=2.0 Hz), 8.51 (m, 2H), 8.36 (bs, 1H), 8.20 (d, 1H, J=8.0 Hz), 7.98 (bs, 1H), 7.96 (d, 1H, J=9.0 Hz), 7.70 (d, 1H, J=9.0 Hz), 6.98 (d, 1H, J=9.0 Hz), 5.32 (m, 1H), 5.18 (m, 1H), 4.79 (bs, 1H), 4.67 (dd, 1H, J=5.0 and 9.5 Hz), 4.56 (m, 2H), 4.35 (m, 1H), 4.25 (m, 1H), 4.15 (m, 2H), 4.04 (d, 1H, J=13.5 Hz), 3.96 (m, 1H), 3.91 (s, 3H), 3.87 (t, 2H, J=6.0 Hz), 3.40~3.77 (m, 43H), 3.14 (m, 2H), 2.99 (m, 3H), 2.86 (m, 2H), 2.69 (m, 1H), 2.62 (m, 1H), 2.45 (m, 2H), 2.04 (m, 2H), 1.92 (m, 1H), 1.17~1.68 (m, 6H), 0.99 (d, 3H, J=7.0 Hz), 0.90 (m, 6H).

Synthetic Procedure for Coenzyme A Analogues

Example 56: 3-Buten-2-one Adduct of Coenzyme A (CoA-1)

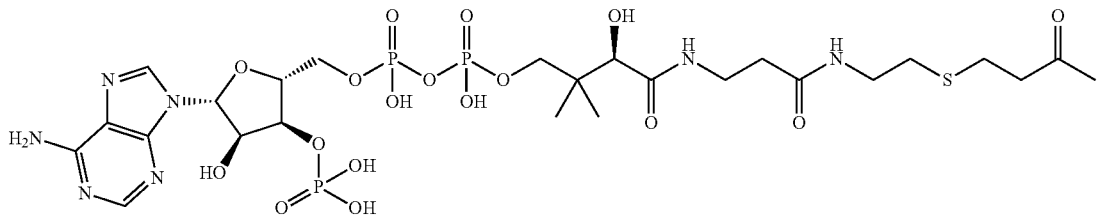

CoA-1

Coenzyme A trilithium salt (259 mg, Sigma, assay >93%) was dissolved in 2.0 mL of phosphate buffer with EDTA (100 mM phosphate, 5 mM EDTA, pH7.5). To The reaction mixture was added 3-buten-2-one (29.0 µL, Aldrich, 99%), and the reaction mixture was let stand at 20° C. for 75 min. The whole reaction mixture was loaded onto an ISCO C18 Aq Gold 15.5 g column which was pre-equilibrated with 100% H$_2$O. The desired product was eluted at 100% H$_2$O. The fractions containing the pure desired product were combined and lyophilized, affording compound CoA-1 as a crystalline solid. MS (ESI+) m/z 838.2 (M+1). H-NMR (400 MHz, D$_2$O) δ 8.525 (s, 1H), 8.235 (s, 1H), 6.140 (d, 1H, J=7.2 Hz), 4.746 (m, 1H), 4.546 (bs, 1H), 4.195 (bs, 1H), 3.979 (s, 1H), 3.786 (dd, 1H, J=4.8, 9.6 Hz), 3.510 (dd, 1H, J=4.8, 9.6 Hz), 3.429 (t, 2H, J=6.6 Hz), 3.294S (t, 2H, J=6.6 Hz), 2.812 (t, 2H, J=6.8 Hz), 2.676 (t, 2H, J=6.8 Hz), 2.604 (t, 2H, J=6.8 Hz), 2.420 (t, 2H, J=6.6 Hz), 2.168 (s, 3H), 0.842 (s, 3H), 0.711 (s, 3H) (note: some peaks which overlap with D$_2$O are not reported).

Example 57: Coenzyme A Analogue (CoA-i-9)

Compound i-9 was converted into the ketone-functionalized CoA analogue CoA-i-9 by reacting 5 mM of Compound i-9 with 25 mM of ATP in the presence of 10 µM *Staphylococcus aureus* CoAA, 25 µM *Escherichia coli* CoAD, and 20 µM *Escherichia coli* CoAE for 16 h at 37° C. in 50 mM HEPES buffer (pH 8.0) containing 20 MgCl$_2$. After removing small amounts of precipitate by centrifugation, soluble enzyme was separated by ultrafiltration through an Amicon Ultra centrifugal filter with 10 kDa cutoff. Enzymatic conversion of Compound i-9 into the CoA analogue CoA-i-9 was verified by LC-MS analysis after reaction of a small fraction of the ultrafiltrate with two-fold molar excess of a hydrophobic aminooxy molecule. The oxime ligation occurred for 3 h at 37° C. in 100 mM citrate-phosphate buffer (pH 3.0), and the reaction mixture was separated on a reverse-phase Acquity UPLC HSS T3 column (100 Å, 2.1 mm×50 mm, Waters) using a 1.35 min-gradient elution from 10 to 100% acetonitrile in water containing 0.05% TFA at a flow rate of 0.9 mL/min. Mass spectral analysis revealed the presence of the desired oxime adduct thereby confirming conversion of Compound i-9 by all three CoA biosynthetic enzymes into CoA analogue CoA-i-9.

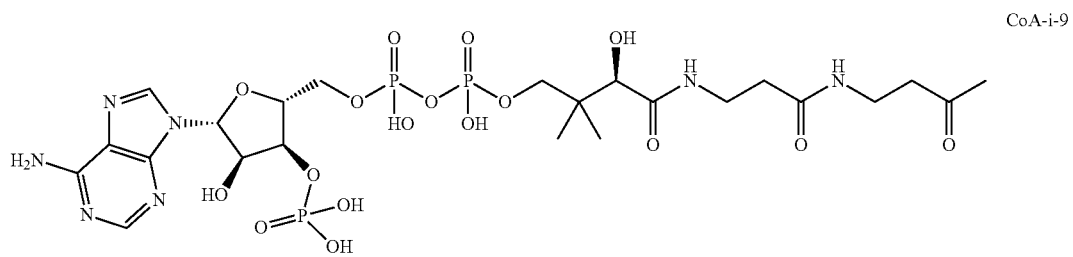 [SMILES: CC(=O)CCNC(=O)CCNC(=O)[C@H](O)C(C)(C)COP(=O)(O)OP(=O)(O)OC[C@H]1O[C@@H](n2cnc3c(N)ncnc32)[C@H](O)[C@@H]1OP(=O)(O)O]

CoA-i-9

Synthetic Procedure Comparative Peptide

Synthesis of (S)-2-((2R,3R)-3-((S)-1-((3R,4S,5S)-4-((S)-2-((S)-2-(6-(2,5-dioxo-2,5-dihydro-1H-pyrrol-1-yl)-N-methylhexanamido)-3-methylbutanamido)-N,3-dimethylbutanamido)-3-methoxy-5-methylheptanoyl)pyrrolidin-2-yl)-3-methoxy-2-methylpropanamido)-3-phenylpropanoic Acid (MC-MMAF)

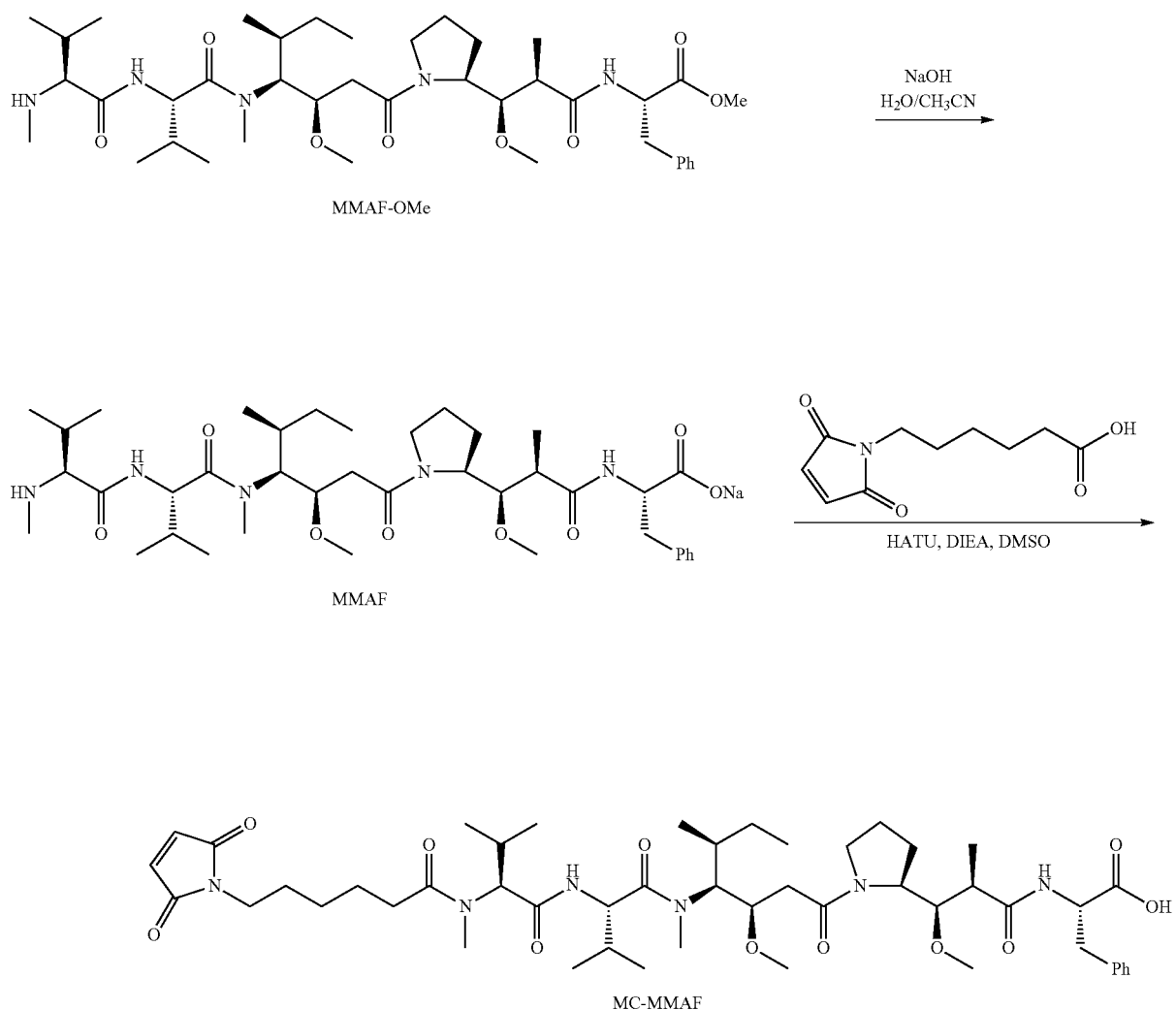

MMAF-OMe (135 mg, Concortis Biosystems) was dissolved in CH$_3$CN (10 mL). To the resulting clear solution was added 5 mL water, followed by 0.375 mL of 1N aq NaOH (certified, Fisher Scientific). The reaction mixture was stirred magnetically at 21° C. for 18 h, at which time LCMS analysis indicated a complete reaction. The reaction mixture was lyophilized, affording MMAF sodium salt. LCMS retention time 0.911 min. MS (ESI+) m/z 732.5 (M+1). The whole MMAF sodium salt thus obtained in previous reaction was dissolved in 10 mL DMSO. In a separate reaction vessel, EMCA (95 mg) was treated with HATU (165 mg) and DIEA (0.126 mL) in 3.0 mL DMSO at 21° C. for 25 min. The whole reaction mixture of the activated ester was added to the solution of MMAF sodium salt, and the reaction mixture was stirred at 21° C. for 3 h. The reaction mixture was partitioned between 40 mL of EtOAc and 20 mL of 5% aq citric acid. The organic layer was separated, and the aqueous layer was extracted with 20 mL of EtOAc. The combined organic layers was washed with 10 mL saturated aq NaCl, dryed over anhydrous MgSO4, filtered and concentrated. The residue was purified on an ISCO CombiFlash instrument using an ISCO C18 gold 15.5 g column. The desired material was eluted with 50% CH$_3$CN in H$_2$O, affording the desired compound as white solid. LCMS retention time 1.392 minutes. MS (ESI+) m/z 925.6 (M+1).

Synthesis of α-amnitin-6'-(-6-aminohexyl-6-hydroxysuccinimidyl Carbonate) (REF-AMAN)

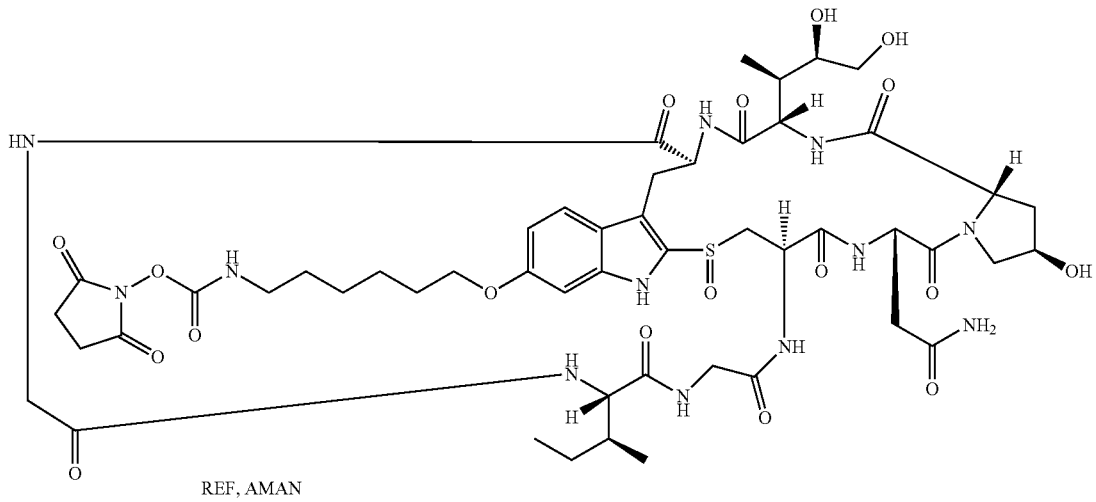 [SMILES: CC[C@H](C)[C@@H]1NC(=O)CNC(=O)[C@@H]2Cc3c([nH]c4cc(OCCCCCCNC(=O)ON5C(=O)CCC5=O)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

REF, AMAN

The reference Aminitin (REF. AMAN) was synthesized as described in US2013/0259880 A1.

Antigen-Binding Moieties

The antigen-binding moiety (Ab) in Formula (II) or Formula (IIa) can be any moiety that selectively binds to a targeted cell type. In some aspects, Ab is an antibody or antibody fragment (e.g. antigen binding fragment of an antibody) that specifically binds to an antigen predominantly or preferentially found on the surface of cancer cells, e.g., a tumor-associated antigen. In some aspects, Ab is an antibody or antibody fragment (e.g., antigen binding fragment) that specifically binds to a cell surface receptor protein or other cell surface molecules, a cell survival regulatory factor, a cell proliferation regulatory factor, a molecules associated with (for e.g., known or suspected to contribute functionally to) tissue development or differentiation, a lymphokine, a cytokine, a molecule involved in cell cycle regulation, a molecule involved in vasculogenesis or a molecule associated with (for e.g., known or suspected to contribute functionally to) angiogenesis. A tumor-associated antigen may be a cluster differentiation factor (i.e., a CD protein). In some aspects of the invention, the antigen binding moiety of the invention specifically binds to one antigen. In some aspects of the invention, the antigen binding moiety of the invention specifically binds to two or more antigens described herein, for example, the antigen binding moiety of the invention is a bispecific or multispecific antibody or antigen binding fragment thereof.

Exemplary antibodies or antigen binding fragments include but are not limited to anti-estrogen receptor antibody, anti-progesterone receptor antibody, anti-p53 antibody, anti-HER-2 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

The antigen binding moiety of the antibody-drug conjugates (ADC) of Formula (II) or Formula (IIa) specifically binds to a receptor encoded by an ErbB gene. The antigen binding moiety may bind specifically to an ErbB receptor selected from EGFR, HER2, HER3 and HER4. The antigen binding moiety may be an antibody that will specifically bind to the extracellular domain (ECD) of the HER2 receptor and inhibit the growth of tumor cells which overexpress HER2 receptor. The antibody may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

Antigen-binding moieties in Formula (II) or Formula (IIa) include, but are not limited to, antibodies or antibody fragments (e.g., antigen binding fragments) against cell surface receptors and tumor-associated antigens. Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies and antibody fragments (e.g., antigen binding fragment) useful for the immunoconjugates of the invention include modified or engineered antibodies, such as an antibody modified to introduce a cysteine residue (Junutula J R, Raab H, Clark S, Bhakta S, Leipold D D, Weir S, Chen Y, Simpson M, Tsai S P, Dennis M S, Lu Y et al.: Nat Biotechnol 2008, 26:925-932), or other reactive amino acid, including Pcl, pyrrolysine, and non-natural amino acids, in place of at least one amino acid of the native sequence, thus providing a reactive site on the antibody or antigen binding fragment for conjugation to a cytotoxic peptide of Formula (I) or subformulae thereof. For example, the antibodies or antibody fragments can be modified to incorporate Pcl or pyrrolysine (W. Ou et al. (2011) PNAS 108 (26), 10437-10442) or unnatural amino acids (J. Y. Axup, K. M. Bajjuri, M. Ritland, B. M. Hutchins, C. H. Kim, S. A. Kazane, R. Halder, J. S. Forsyth, A. F. Santidrian, K. Stafin, Y. Lu et al. Proc Natl Acad Sci USA, 109 (2012), pp. 16101-16106; for review, see C. C. Liu and P. G. Schultz (2010) Annu Rev Biochem 79, 413-444; C. H. Kim, J. Y. Axup, P. G. Schultz (2013) Curr Opin Chem Biol. 17, 412-419) as sites for conjugation to a drug. Similarly, peptide tags for enzymatic conjugation methods can be introduced into an antibody (Strop P. et al. Chem Biol. 2013, 20(2):161-7; Rabuka D., Curr Opin Chem Biol. 2010 December; 14(6):790-6; Rabuka D, et al., Nat Protoc. 2012, 7(6):1052-67). One other example is the use of 4'-phosphopantetheinyl transferases (PPTase) for the conjugation of Co-enzyme A analogs to peptide tags such as S6, A1 and ybbR tags (Site-Specific Labeling Methods and Molecules Produced Thereby, WO20130184514). Methods for conjugating such modified or engineered antibodies with payloads or linker-payload combinations are known in the art.

Antigen-binding moieties (e.g., antibodies and antigen binding fragments) useful in the invention may also have other modifications or be conjugated to other moieties, such as but not limited to polyethylene glycol tags, albumin, and other fusion polypeptide.

The antibodies used in the examples herein have the heavy chain and light chain sequences listed in Table 3. Some of these antibodies were engineered to contain cysteine residues or PPTase enzyme tags for site-specific conjugation with cytotoxic cyclic peptides of the invention. The examples herein illustrate that these engineered antibodies are suitable antibody for use in the immunoconjugates of Formula (II) or Formula (IIa). In addition, non-engineered antibodies can also be used for the preparation of the immunoconjugates of Formula (II) or Formula (IIa) through traditional methods (Carter P J, Senter P D, Antibody-drug conjugates for cancer therapy, Cancer J. 2008, 14(3):154-69; J. E. Stefano, M. Busch, L. Hou, A. Park, and D. A. Gianolio, p. 145-171, and M.-P. Brun and L. Gauzy-Lazo, p. 173-187 in Antibody-Drug Conjugate, Methods in Molecular Biology, Vol. 1045, Editor L. Ducry, Humana Press, 2013).

TABLE 3

Amino acid sequences of example antibodies

SEQ ID NO: 1 (anti-Her2 heavy chain wild-type; CDR sequences underlined)
EVQLVESGGGLVQPGGSLRLSCAAS<u>GFNIKDTYIH</u>WVRQAPGKGLEWVA<u>R TABLE 3-continued Amino acid sequences of example antibodies <u>IYPTNGYTRYADSVKG</u>RFTISADTSKNTAYLQMNSLRAEDTAVYYCSR<u>WG
GDGFYAMDY</u>WGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK SEQ ID NO: 2 (anti-Her2 light chain wild-type; CDR sequences underlined)
DIQMTQSPSSLSASVGDRVTITC<u>RASQDVNTAVA</u>WYQQKPGKAPKLLIY<u>S
ASFLYS</u>GVPSRFSGSRSGTDFTLTISSLQPEDFATYYC<u>QQHYTTPPT</u>FGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC SEQ ID NO: 3 (constant region of the heavy chain wild-type of anti-Her2)
SASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNHYTQKSLSLSPGK SEQ ID NO: 4 (constant region of the light chain wild-type of anti-Her2)
KRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVT
KSFNRGEC SEQ ID NO: 5 (constant region of the mutant light chain of anti-Her2-LC-S159C)
KRTVAAPSVFIFPPSDEQLKSGTASVVCLLNNFYPREAKVQWKVDNALQS
GN<u>C</u>QESVTEQDSKDSTYSLSSTLTLSKADYEKHKVYACEVTHQGLSSPVT
KSFNRGEC SEQ ID NO: 6 (constant region of the mutant heavy chain of HC-E388-DSLEFIASKLA-N389 in anti-Her2)
SASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPE<b>DSLEFIASKLA</b>NNYKTTPPVLDSDGSFF
LYSKLTVDKSRWQQGNVFSCSVMHEALHNHYTQKSLSLSPGK SEQ ID NO: 7 (ybbR tag)
DSLEFIASKLA SEQ ID NO: 8 (signal sequence)
MKTFILLLWVLLLWVIFLLPGATA SEQ ID NO: 9 (Full length sequence of the mutant heavy chain of anti-Her2-HC-E152C-S375C, CDR sequences underlined)
EVQLVESGGGLVQPGGSLRLSCAAS<u>GFNIKDTYIH</u>WVRQAPGKGLEWVA<u>R
IYPTNGYTRYADSVKG</u>RFTISADTSKNTAYLQMNSLRAEDTAVYYCSR<u>WG
GDGFYAMDY</u>WGQGTLVTVSSASTKGPSVFPLAPSSKSTSGGTAALGCLVK
DYFP<u>C</u>PVTVSWNSGALTSGVHTFPAVLQSSGLYSLSSVVTVPSSSLGTQT
YICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSREEMTKNQVSLTCLVKGFYP<u>C</u>DIAVEWESNGQPENNYKTTPPV
LDSDGSFFLYSKLTVDKSRWQQGNVFSCSVMHEALHNHYTQKSLSLSPGK SEQ ID NO:1 and SEQ ID NO:2 are the full length amino acid sequence of wild-type anti-Her2 antibody heavy chain (HC) and light chain (LC), respectively. SEQ ID NO:3, and SEQ ID NO:4 are the amino acid sequences of the constant regions for the HC and LC, respectively of anti-Her2 antibody. SEQ ID NO:5 is the amino acid sequence of the LC constant region of anti-Her2-LC-S159C and SEQ ID NO:6 is the amino acid sequence of the constant region of the mutant heavy chain for anti-Her2-HC-E388-DSLE-FIASKLA-N389 antibody wherein the ybbR tag is inserted after the HC residue Glu388. SEQ ID NO:7 is the amino acid sequence of the ybbR tag. SEQ ID NO:8 is the signal peptide used. Mutant Cys residue and the inserted sequence tag of ybbR are shown in bold and are underlined in the sequences of corresponding mutant chains. CDR sequences are underlined in SEQ ID NO:1 and SEQ ID NO:2. SEQ ID NO:9 is the full length amino acid sequence of the heavy chain double cysteine mutant HC-E152C and HC-S375C of anti-Her2.

Antibody Production

The antibodies and antibody fragments (e.g., antigen binding fragments) of the invention can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementary determining regions as described herein.

The polynucleotide sequences can be produced by de novo solid-phase DNA synthesis or by PCR mutagenesis of an existing sequence (e.g., sequences as described in the examples below) encoding an antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR PROTOCOLS: A GUIDE TO METHODS AND APPLICATIONS, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the antibodies or antibody fragments described above. Various expression vectors can be employed to express the polynucleotides encoding the antibody chains or binding fragments of the invention. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the polynucleotides and polypeptides in mammalian (e.g., human) cells include pThioHis A, B & C, pcDNA3.1/His, pEBVHis A, B & C (Life Tech., San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an antibody chain or fragment of the invention. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an antibody chain or fragment of the invention. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted antibody sequences. More often, the inserted antibody sequences are linked to a signal sequences before inclusion in the vector. Vectors to be used to receive sequences encoding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the antibody chains of the invention can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters may be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express the antibodies or antibody fragments of the invention. Insect cells in combination with baculovirus vectors can also be used.

In one aspect, mammalian host cells are used to express and produce the antibodies and antibody fragments of the present invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen et al., *Immunol. Rev.* 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, *Cell* 88:223, 1997), agent-enhanced uptake of DNA, and ex vivo transduction. For long-term, high-yield production of recombinant proteins, stable expression will often be desired. For example, cell lines which stably express antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Example 58: Cloning of Anti-Her2 Cys and Ybbr Tagged Mutant Antibodies for Conjugation Studies DNA oligonucleotides encoding variable regions of heavy and light chains of an anti-Her2 antibody (Carter P, Presta L, Gorman C M, Ridgway J B, Henner D, Wong W L, Rowland A M, Kotts C, Carver M E, Shepard H M. (1992) Proc. Natl. Acad. Sci. USA, 89, 4285-4289, Humanization of an anti-p185her2 antibody for human Cancer therapy) were chemically synthesized and cloned into two mammalian expression vectors, pOG-HC and pOG-LC that contain the constant regions of human IgG1 and human kappa light chain, resulting in two wild-type constructs, pOG-anti-Her2 antibody HC and pOG-anti-Her2 antibody LC, respectively.

The amino acid sequences of the constant regions are shown in Table 3 with the mutated Cys in bold and underlined.

In these vectors, the expression of antibody heavy and light chain in mammalian cells is driven by a CMV promoter. The vectors encode a synthetic 24 amino acid signal sequence, MKTFILLLWVLLLWVIFLLPGATA (SEQ ID NO:8), at the N-terminal of heavy chain and light chain to guide their secretion from mammalian cells. The signal sequence has been validated to be efficient in directing protein secretion in hundreds of mammalian proteins in 293 Freestyle™ cells (Gonzalez R, Jennings L L, Knuth M, Orth A P, Klock H E, Ou W, Feuerhelm J, Hull M V, Koesema E, Wang Y, Zhang J, Wu C, Cho C Y, Su A I, Batalov S, Chen H, Johnson K, Laffitte B, Nguyen D G, Snyder E Y, Schultz P G, Harris J L, Lesley S A. (2010) Proc Natl Acad Sci USA. 107:3552-7). Oligonucleotide directed mutagenesis was employed to prepare mutant constructs of anti-Her2 antibodies listed in Table 3. The sense and anti-sense primers (Table 5) that correspond to mutation sites in the constant regions of human IgG heavy chain and human kappa light chain were chemically synthesized. PCR reactions were performed using PfuUltra II Fusion HS DNA Polymerase (Stratagene) with pOG-anti-Her2 antibody HC and pOG-anti-Her2 antibody LC as the templates. The PCR products were confirmed on agarose gels, and treated with DPN I followed by transformation in DH5a cells (Klock et al., (2009) *Methods Mol Biol.* 498:91-103).

The sequences of wild-type and the Cys mutant constructs were confirmed by DNA sequencing. The full-length amino acid sequence of wild-type anti-Her2 antibody heavy chain is shown as SEQ ID NO:1 and that of light chain is shown as SEQ ID NO:2 (Table 3). The amino acid sequence of the LC-S159C mutant constructs of anti-Her2 antibody is shown in Table 3 with the Cys mutation site in bold and underlined (SEQ ID NO:5). Amino acid residues in human IgG1 heavy chain and human kappa light chain are numbered according to the Eu numbering system (Edelman et al, (1969) *Proc Natl Acad Sci US A,* 63:78-85). The anti-Her-HC-E152C-S375C double Cys mutant was cloned similarly. The anti-Her2-LC-S159C and anti-Her-HC-E152C-S375C antibodies were further cloned into vectors containing antibiotic selection markers for selection of stably transfected cell clones in media containing corresponding antibiotics.

The DNA sequence encoding a ybbR tag (DSLEFIASKLA, SEQ ID NO:7) for PPTase-mediated conjugation was incorporated into the human IgG1 heavy chain using standard molecular biology techniques and confirmed by DNA sequencing. Table 4 lists the oligonucleotide sequences (SEQ ID NO:12 and SEQ ID NO:13) used for PCR amplification of the plasmid pOG-anti-Her2 antibody HC, resulting in the expression vector of the anti-Her2 heavy chain of the HC-E388-DSLEFIASKLA-N389 antibody. Table 3 shows the amino acid sequence of the heavy chain constant region of HC-E388-DSLEFIASKLA-N389 (SEQ ID NO:6). The ybbR tag (highlighted in bold and underlined) is inserted after residue Glu388 according to the Eu numbering system (Edelman et al, (1969) *Proc Natl Acad Sci USA,* 63:78-85).

The anti-Her2 HC-E388-DSLEFIASKLA-N389 antibody was further cloned into vectors that are suitable for the selection of cell lines stably expressing this ybbR-tagged antibody.

TABLE 4

```
DNA sequences of mutation primers used to
   clone Cys mutant and ybbR-tagged antibodies.

LC-S159C    SenseAGCGGCAACTGTCAGGAGAGC  SEQ ID NO: 10
            GTCACCGAGCAGGACAGCAA
            Anti-CTCTCCTGACAGTTGCCGCTC  SEQ ID NO: 11
            senseTGCAGGGCGTTGTCCACCT
HC-E388-    SenseCTGGAGTTCATCGCCAGCAAG  SEQ ID NO: 12
DSLEFIASK   CTGGCCAACAACTACAAGACC
LA-N389     ACACCTCCAG
            Anti-CTTGCTGGCGATGAACTCCAG  SEQ ID NO: 13
            senseGCTGTCCTCGGGCTGGCCGTT
            GCTC
```

Example 59: Preparation of Antibodies

Antibodies were expressed in 293 Freestyle™ cells by co-transfecting heavy chain and light chain plasmids using transient transfection method as described previously (Meissner, et al., *Biotechnol Bioeng.* 75:197-203 (2001)). The DNA plasmids used in co-transfection were prepared using Qiagen plasmid preparation kit according to manufacturer's protocol. 293 Freestyle™ cells were cultured in suspension in Freestyle™ expression media (Invitrogen) at 37° C. under 5% $CO_2$. On the day before transfection, cells were split to $0.7 \times 10^6$ cells/mL into fresh media. On the day of transfection, the cell density typically reached $1.5 \times 10^6$ cells/mL. The cells were transfected with a mixture of heavy chain and light chain plasmids at the ratio of 1:1 using the PEI method (Meissner et al., 2001 supra). The transfected cells were further cultured for five days. The media from the culture was harvested by centrifugation of the culture at 2000×g for 20 min and filtered through 0.2 micrometer filters. The expressed antibodies were purified from the filtered media using Protein A-Sepharose™ (GE Healthcare Life Sciences). IgG antibodies were eluted from the Protein A-Sepharose™ column using a pH 3.0 elution buffer. Eluted IgG solutions were immediately neutralized with 1 M Tris-HCl (pH 8.0) followed by a buffer exchange to PBS.

Expression constructs for anti-Her2-LC-S159C, anti-Her2-HC-E152C-S375C and anti-Her2-HC-E388-DSLEFIASKLA-N389 antibodies were also transfected into CHO cells. Following standard protocols, cells stably expressing anti-Her2-LC-S159C, anti-Her2-HC-E152C-S375C and anti-Her2-HC-E388-DSLEFIASKLA-N389 were then selected using antibiotics. All anti-Her2 antibody constructs expressed in the selected CHO cell clones were purified by Protein A-Sepharose chromatography as described above.

Immunoconjugates

Immunoconjugates of the invention that comprise such cytotoxic cyclic peptides of the invention, and subformulae thereof, as a payload (drug) include conjugates of Formula (B):

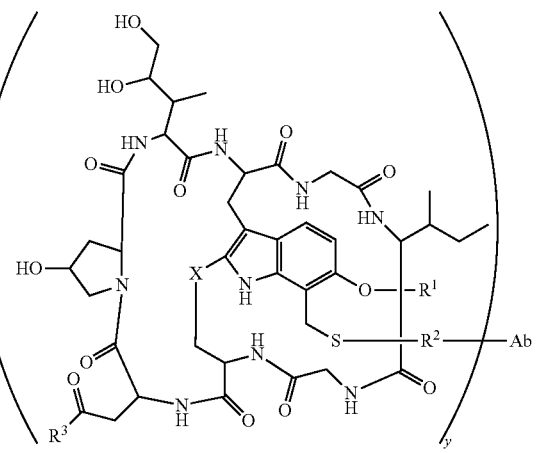

Formula (B)

wherein:
X is S(=O), S(=O)$_2$ or S;
Ab represents an antigen binding moiety;
y is an integer from 1 to 16;
$R^1$ is H or —$CH_3$; $R^3$ is —$NH_2$ or —OH; $R^{20}$ is -$L_1L_2R^{40}$, -$L_3R^{60}$ or —$(CH_2)_mX_3(CH_2)_mR^{40}$;
$L_1$ is —$(CH_2)_mNR^5C(=O)$—

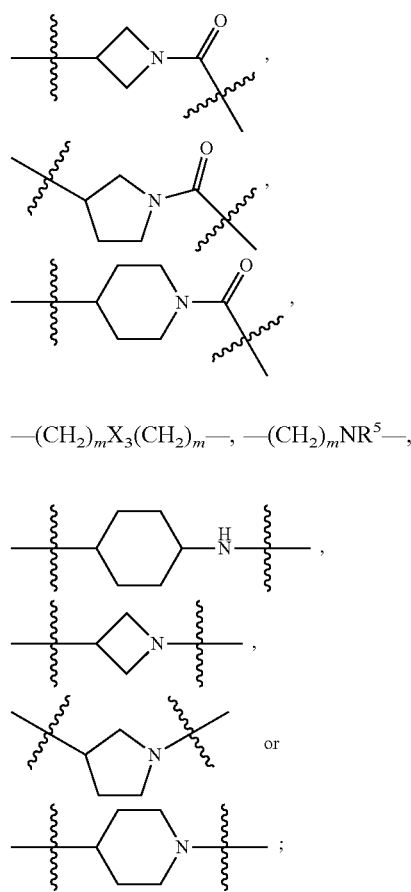

—$(CH_2)_mX_3(CH_2)_m$—, —$(CH_2)_mNR^5$—, $L_2$ is —$(CH_2)_m$—, —$NR^5(CH_2)_m$—, —$(CH_2)_mNR^5C$ (=O)$(CH_2)_m$—, —$X_4$—, —$(CH_2)_mNR^5C(=O)X_4$,

—(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$ X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$(O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$ C(=O)NR$^5$(CH$_2$)$_m$C(=O)NR$^5$(CH$_2$)$_m$—, —(CH$_2$)$_m$ NR$^5$C(=O)(CH$_2$)$_m$NR$^5$C(=O)(CH$_2$)$_m$—, —(CH$_2$)$_m$ X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$ C(R$^5$)$_2$NR$^5$—, —(CH$_2$)$_m$C(=O)NR$^5$(CH$_2$)$_m$ NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O) (CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$ (CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$ (O(H$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$—, or —(CH$_2$)$_m$X$_3$(CH$_2$)$_m$NR$^5$C(=O)—, wherein:

X$_1$ is

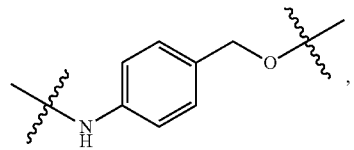

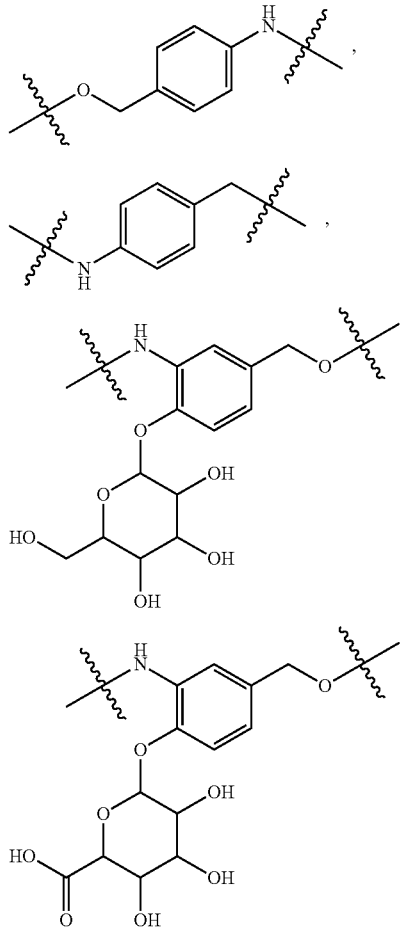

or

X$_2$ is

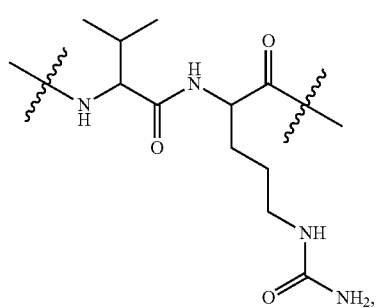

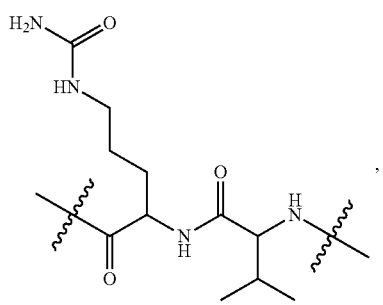

-continued
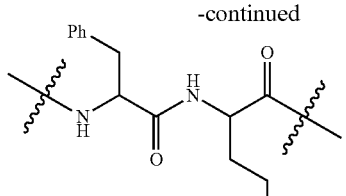
or
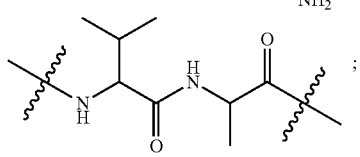
X₃ is
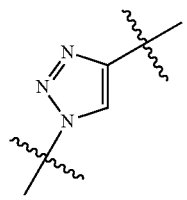 or 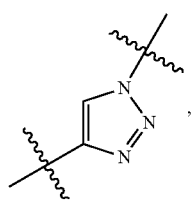
and X₄ is
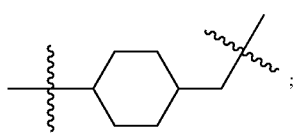 [SMILES: *CC1CCC(*)CC1]
L₃ is —(CH₂)$_m$NR⁵C(=O)—;
R⁴⁰ is
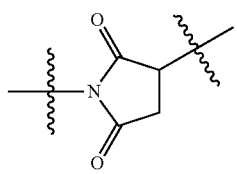, 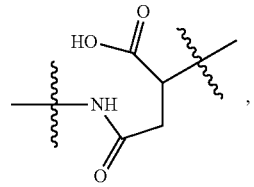,
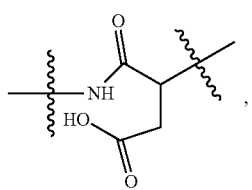,
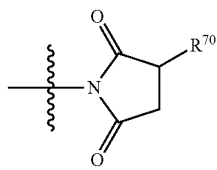, 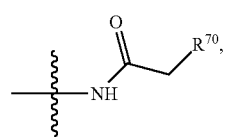
—NR⁵C(=O)CH₂—, —NHC(=O)CH₂—,
—S(=O)₂CH₂CH₂—, —(CH₂)₂S(=O)₂CH₂CH₂—,
—NR⁵S(=O)₂CH₂CH₂, —NR⁵C(=O)CH₂CH₂—,
—NH—, —C(=O)—, —NHC(=O)—,
—CH₂NHCH₂CH₂—, —NHCH₂CH₂—, —S—,
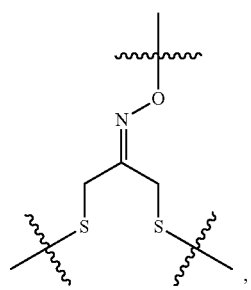, 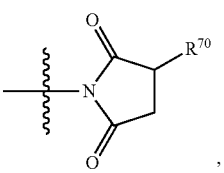, 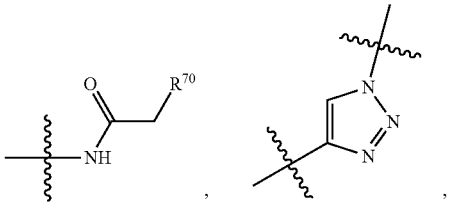,
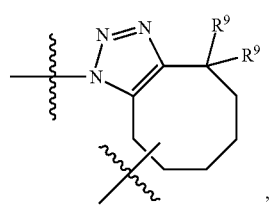, 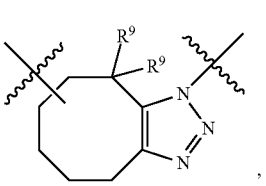, 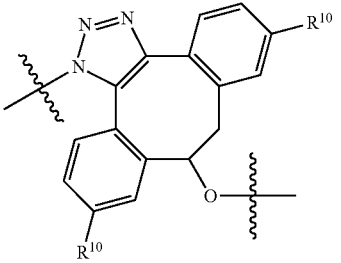, 489
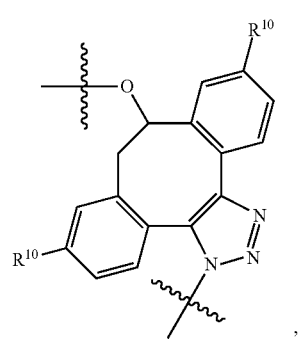, 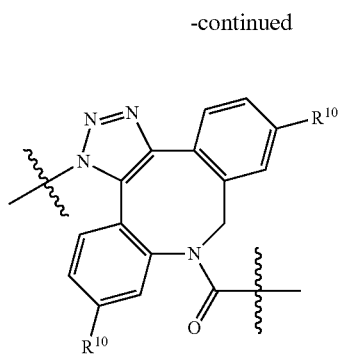, 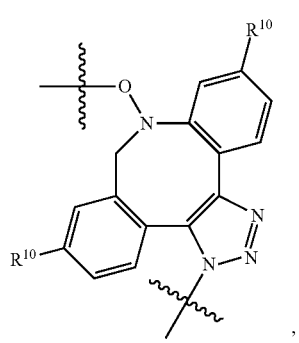,
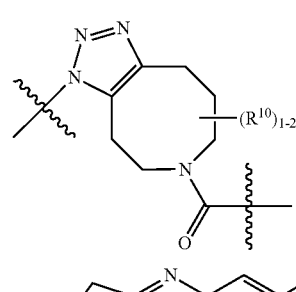, 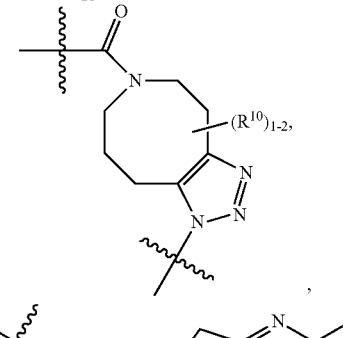, 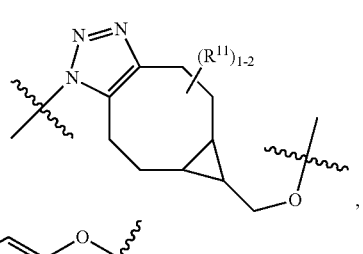,
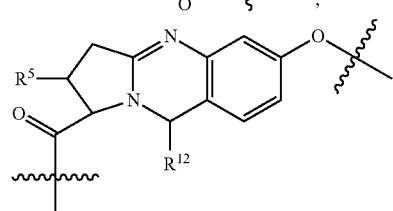, 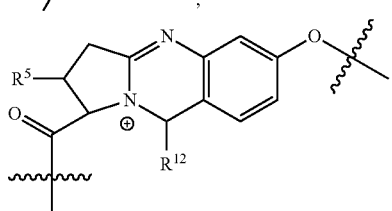,
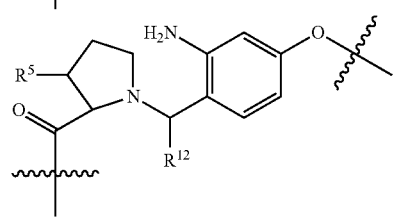, 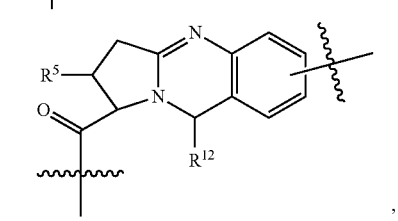,
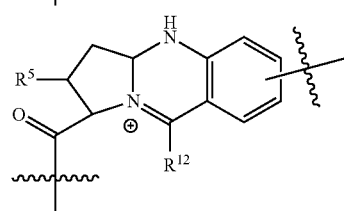, 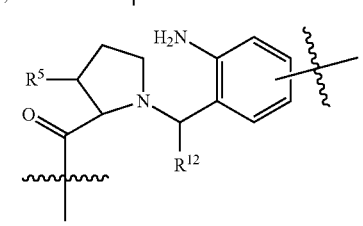 or
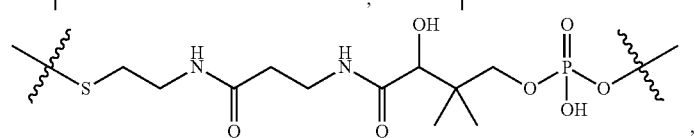,
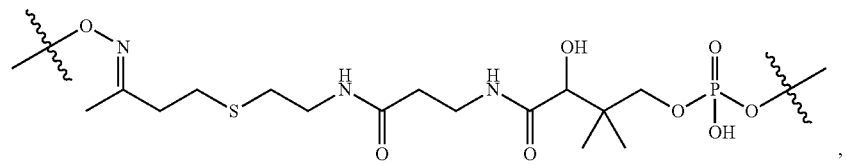,
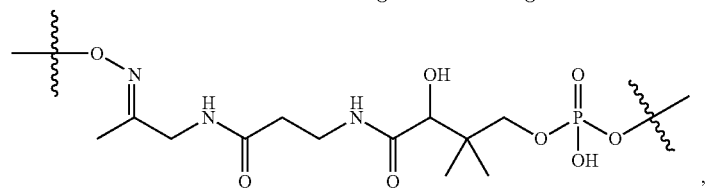, -continued

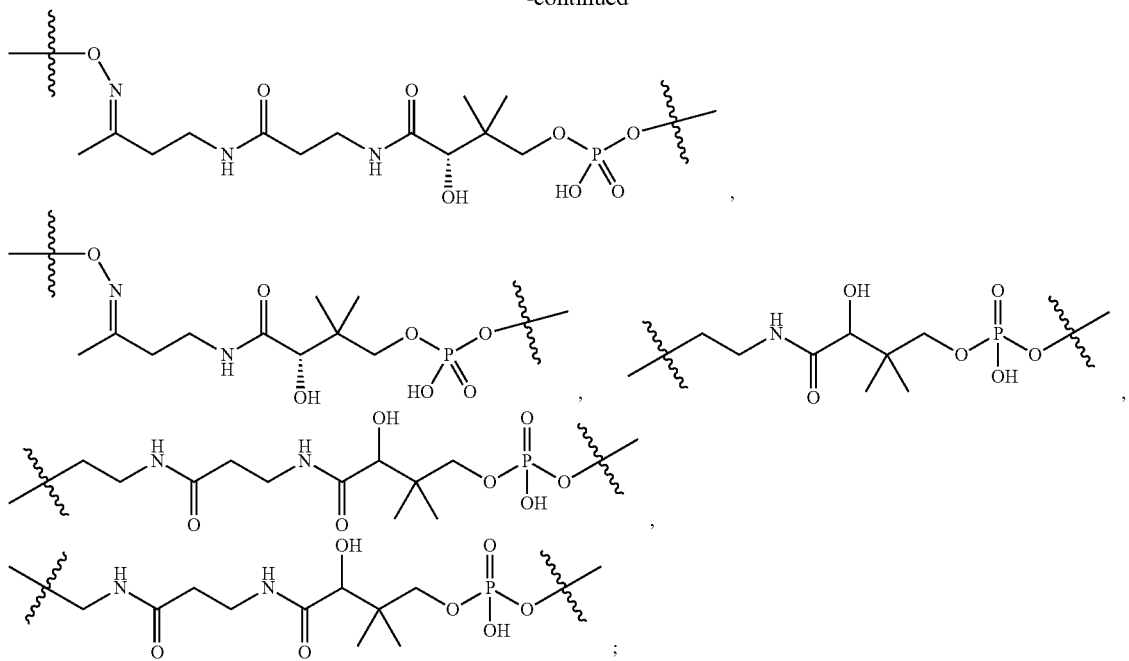

each $R^5$ is independently selected from H and $C_1$-$C_6$alkyl;
$R^{60}$ is —NH—;
$R^{70}$ is

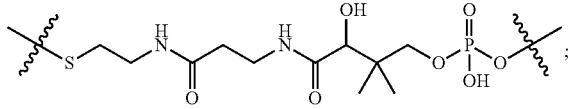 [SMILES: *OP(=O)(O)OCC(C)(C)C(O)C(=O)NCCC(=O)NCCS*]

$R^8$ is H, $C_1$-$C_6$alkyl or —C(=O)OR$^5$;

each $R^9$ is independently selected from H, $C_1$-$C_6$alkyl, F, Cl, and —OH;

each $R^{10}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{12}$ is independently selected from H, —CH$_3$ and phenyl;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments the immunoconjugates of the invention having the structure of Formula (B) include immunoconjugates of Formula (II):

Formula (II)

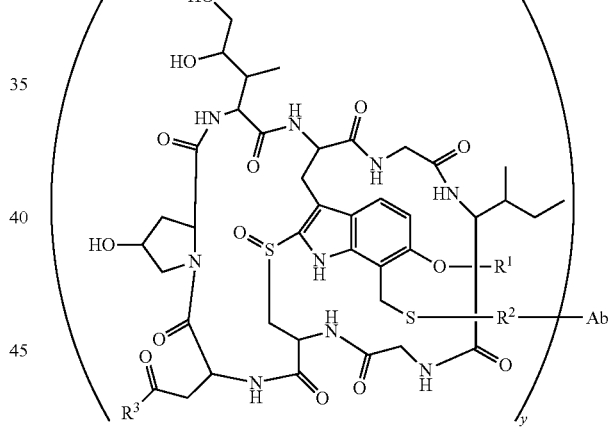

wherein:
Ab represents an antigen binding moiety;
y is an integer from 1 to 16;
$R^1$ is H or —CH$_3$; $R^3$ is —NH$_2$ or —OH; $R^{20}$ is -L$_1$L$_2$R$^{40}$, -L$_3$R$^{60}$ or —(CH$_2$)$_m$X$_3$(CH$_2$)$_m$R$^{40}$;
$L_1$ is —(CH$_2$)$_m$NR$^5$C(=O)—,

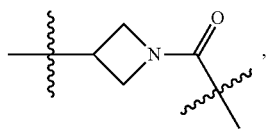

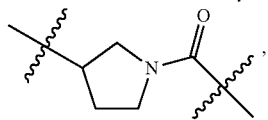

-continued

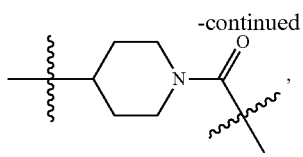

—(CH$_2$)$_m$X$_3$(CH$_2$)$_m$—, —(CH$_2$)$_m$NR$^5$—,

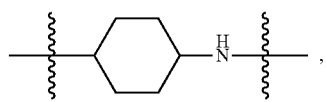

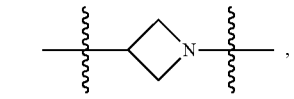

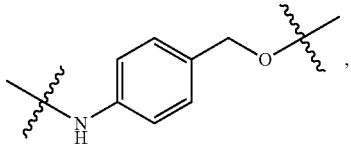

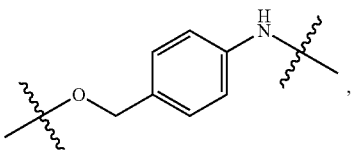

;

L$_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$X$_3$(CH$_2$)$_m$—, —(CH$_2$)$_m$C(=O)NR$^5$(CH$_2$)$_m$NR$^5$C(=O)(CH$_2$)$_m$—, —(CH$_2$)$_m$C(=O)—, —(CH$_2$)$_m$NR$^5$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)NR$^5$C(=O)(CH$_2$)$_m$—, —(CH$_2$)$_m$C(=O)NR$^5$(CH$_2$)$_m$(O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$ C(R$^5$)$_2$NR$^5$—, —(CH$_2$)$_m$C(=O)NR$^5$(CH$_2$)$_m$ NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O) (CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$ (CH$_2$)$_m$—, —(CH$_2$)$_m$X$_3$(CH$_2$)$_m$C(R$^5$)$_2$NR$^5$—, —C(R$^5$)$_2$ (CH$_2$)$_m$OC(=O)NR$^5$(CH$_2$)$_m$—, —(CH$_2$)$_m$NR$^5$C(=O)O(H$_2$)$_m$C(R$^5$)$_2$NR$^5$—, —(CH$_2$)$_m$X$_3$ (CH$_2$)$_m$ NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$ (CH$_2$)$_m$ (O(H$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$—, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$—, or —(CH$_2$)$_m$X$_3$(CH$_2$)$_m$NR$^5$C(=O)—, wherein:

X$_1$ is

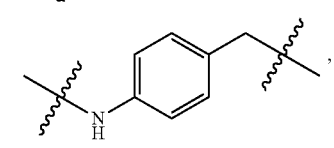

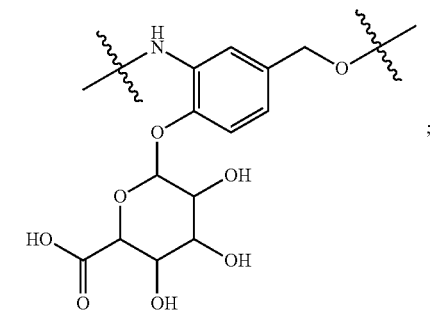

X₂ is
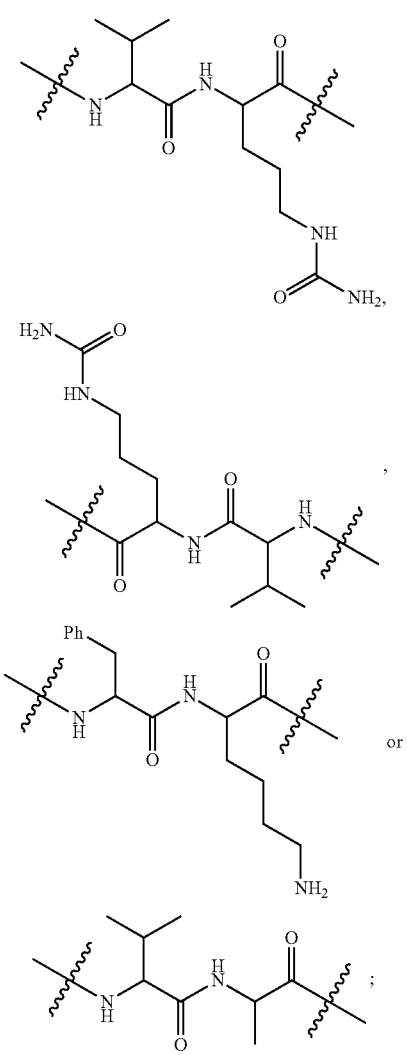
X₃ is
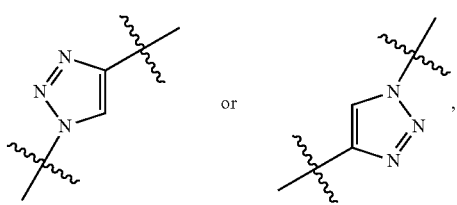 [SMILES: *c1cn(*)nn1 ; *c1cn(*)nn1]
and X₄ is
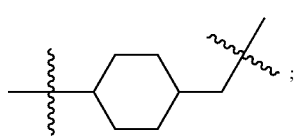
L₃ is —(CH₂)ₘNR⁵C(=O)—;
R⁴⁰ is
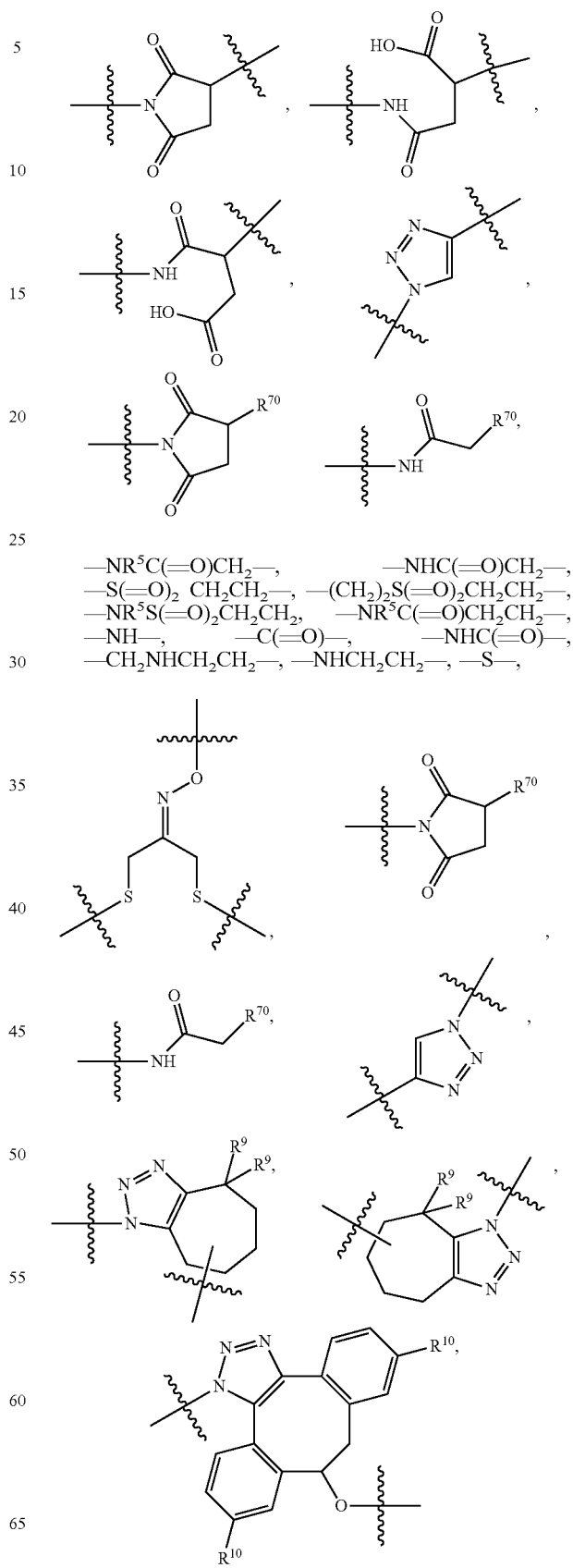
—NR⁵C(=O)CH₂—, —NHC(=O)CH₂—,
—S(=O)₂ CH₂CH₂—, —(CH₂)₂S(=O)₂CH₂CH₂—,
—NR⁵S(=O)₂CH₂CH₂—, —NR⁵C(=O)CH₂CH₂—,
—NH—, —C(=O)—, —NHC(=O)—,
—CH₂NHCH₂CH₂—, —NHCH₂CH₂—, —S—, 497
-continued
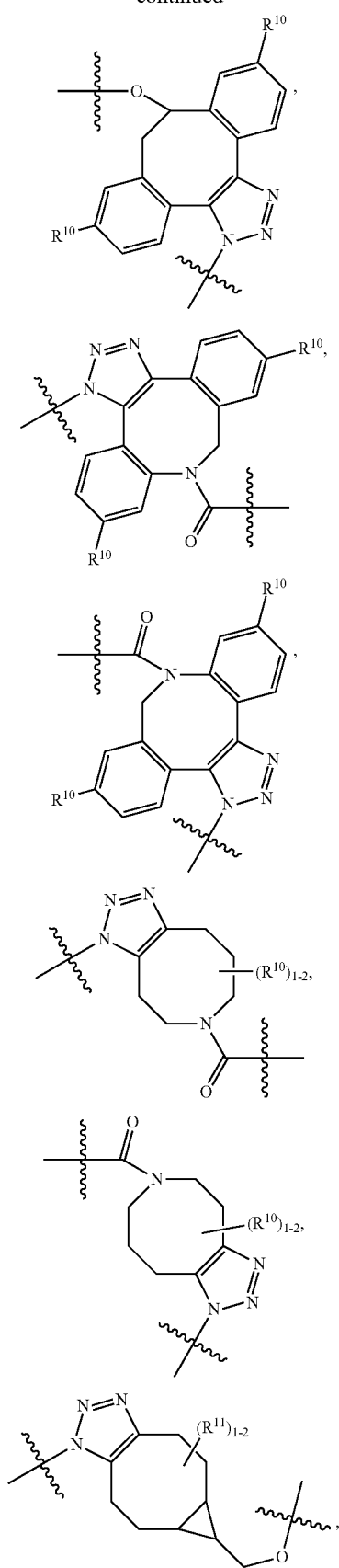
498
-continued
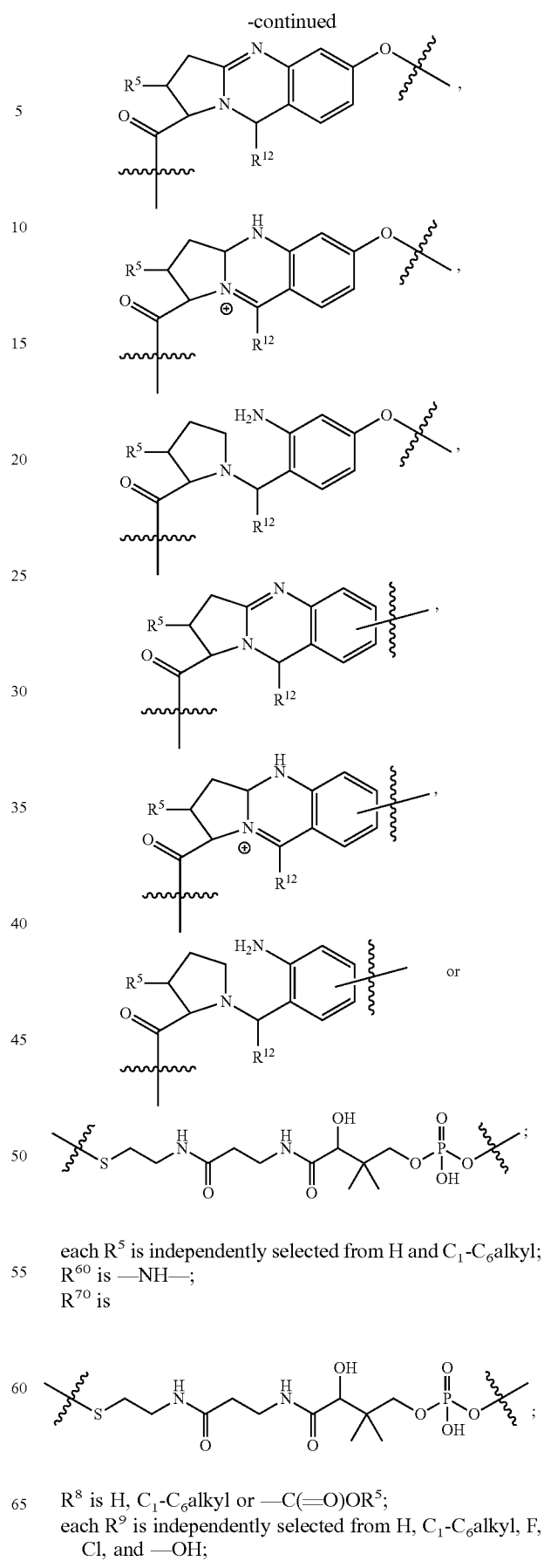
each $R^5$ is independently selected from H and $C_1$-$C_6$alkyl;
$R^{60}$ is —NH—;
$R^{70}$ is
$R^8$ is H, $C_1$-$C_6$alkyl or —C(=O)OR$^5$;
each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{12}$ is independently selected from H, —$CH_3$ and phenyl;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

Immunoconjugates of the invention that comprise such cytotoxic cyclic peptides of Formula (I), and subformulae thereof, as a payload (drug) include conjugates of Formula (II):

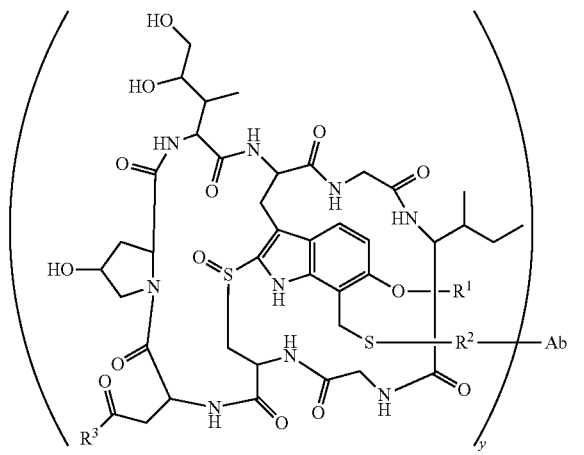

Formula (II)

wherein:
Ab represents an antigen binding moiety;
$R^1$ is H or —$CH_3$;
$R^3$ is —$NH_2$ or —OH;
$R^{20}$ is -$L_1L_2R^{40}$, -$L_3R^{60}$ or —$(CH_2)_mX_3(CH_2)_mR^{40}$;
$L_1$ is —$(CH_2)_mNR^5C(=O)$—,

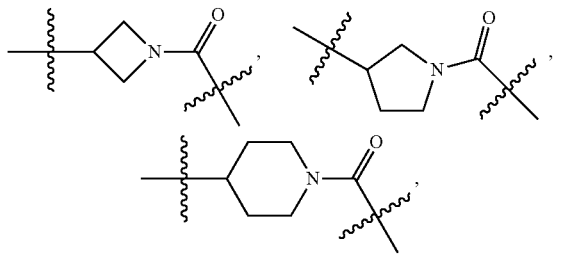

$(CH_2)_mX_3(CH_2)_m$—, —$(CH_2)_mNR^5$—,

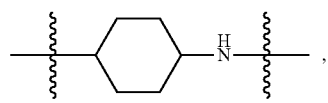

, $L_2$ is —$(CH_2)_m$—, —$NR^5(CH_2)_m$—, —$(CH_2)_mNR^5C(=O)(CH_2)_m$—, —$X_4$—, —$(CH_2)_mNR^5C(=O)X_4$, —$(CH_2)_mNR^5C(=O)$—, —$((CH_2)_mO)_n(CH_2)_m$—, —$((CH_2)_mO)_n(CH_2)_mX_3(CH_2)_m$—, —$NR^5((CH_2)_mO)_nX_3(CH_2)_m$—, —$X_1X_2C(=O)(CH_2)_m$—, —$(CH_2)_m(OCH_2)_m)_n$—, —$(CH_2)_mNR^5(CH_2)_m$—, —$(CH_2)_mNR^5C(=O)(CH_2)_mX_3(CH_2)_m$—, —$(CH_2)_mC(=O)NR^5(CH_2)_mNR^5C(=O)(CH_2)_m$—, —$(CH_2)_mC(=O)$—, —$(CH_2)_mNR^5(CH_2)_mC(=O)X_2X_1C(=O)$—, —$(CH_2)_mX_3(CH_2)_mC(=O)X_2X_1C(=O)$—, —$(CH_2)_mC(=O)NR^5(CH_2)_m$—, —$(CH_2)_mC(=O)NR^5(CH_2)_mX_3(CH_2)_m$—, —$(CH_2)_mX_3(CH_2)_mNR^5C(=O)(CH_2)_m$—, —$(CH_2)_mX_3(CH_2)_mC(=O)NR^5(CH_2)_m$—, —$(CH_2)_mO)_n(CH_2)_mNR^5C(=O)(CH_2)_m$—, —$(CH_2)_mC(=O)NR^5(CH_2)_m(O(CH_2)_m)_n$—, —$(CH_2)_m(OCH_2)_m)_nC(=O)$—, —$(CH_2)_mNR^5(CH_2)_mC(=O)$—, —$(CH_2)_mC(=O)NR^5(CH_2)_mNR^5C(=O)$—, —$(CH_2)_m(O(CH_2)_m)_nX_3(CH_2)_m$—, —$(CH_2)_mX_3((CH_2)_mO)_n(CH_2)_m$—, —$(CH_2)_mX_3(CH_2)_mC(=O)$—, —$(CH_2)_mC(=O)NR^5(CH_2)_mO)_n(CH_2)_mX_3(CH_2)_m$—, —$(CH_2)_mX_3(CH_2)_m(OCH_2)_m)_nNR^5C(=O)(CH_2)_m$—, —$(CH_2)_mX_3(CH_2)_m(OH_2)_m)_nC(=O)$—, —$(CH_2)_mX_3(CH_2)_m(O(CH_2)_m)_n$—, —$(CH_2)_mC(=O)NR^5(CH_2)_mC(=O)$—, —$(CH_2)_mC(=O)NR^5(CH_2)_m(O(CH_2)_m)_nC(=O)$—, —$((CH_2)_mO)_n(CH_2)_mNR^5C(=O)(CH_2)_m$—, —$(CH_2)_mC(=O)NR^5(CH_2)_mC(=O)NR^5(CH_2)_m$—, —$(CH_2)_mNR^5C(=O)(CH_2)_mNR^5C(=O)(CH_2)_m$—, —$(CH_2)_mX_3(CH_2)_mC(=O)NR^5$—, —$(CH_2)_mC(=O)NR^5$—, —$(CH_2)_mX_3$—, —$C(R^5)_2(CH_2)_m$—, —$(CH_2)_mC(R^5)_2NR^5$—, —$(CH_2)_mC(=O)NR^5(CH_2)_mNR^5$—, —$(CH_2)_mC(=O)NR^5(CH_2)_mNR^5C(=O)NR^5$—, —$(CH_2)_mC(=O)X_2X_1C(=O)$—, —$C(R^5)_2(CH_2)_mNR^5C(=O)(CH_2)_m$—, —$(CH_2)_mC(=O)NR^5(CH_2)_mC(R^5)_2NR^5$—, —$C(R^5)_2(CH_2)_mX_3(CH_2)_m$—, —$(CH_2)_mX_3(CH_2)_mC(R^5)_2NR^5$—, —$C(R^5)_2(CH_2)_mOC(=O)NR^5(CH_2)_m$—, —$(CH_2)_mNR^5C(=O)O(H_2)_mC(R^5)_2NR^5$—, —$(CH_2)_mX_3(CH_2)_mNR^5$—, —$(CH_2)_mX_3(CH_2)_m(O(CH_2)_m)_nNR^5$—, —$(CH_2)_mNR^5$—, —$(CH_2)_mC(=O)NR^5(CH_2)_m(O(H_2)_m)_nNR^5$—, —$(CH_2)_m(O(CH_2)_m)_nNR^5$—, —$(CH_2CH_2O)_n(CH_2)_m$—, —$(CH_2)_m(OCH_2CH_2)_n$—, —$(CH_2)_mO(CH_2)_m$—, —$(CH_2)_mS(=O)_2$—, —$(CH_2)_mC(=O)NR^5(CH_2)_mS(=O)_2$—, —$(CH_2)_mX_3(CH_2)_mS(=O)_2$—, —$(CH_2)_mX_2X_1C(=O)$—, —$(CH_2)_m(O(CH_2)_m)_nC(=O)X_2X_1C(=O)$—, —$(CH_2)_m(O(CH_2)_m)_nX_2X_1C(=O)$—, —$(CH_2)_mX_3(CH_2)_mX_2X_1C(=O)$—, —$(CH_2)_mX_3(CH_2)_m(O(CH_2)_m)_nX_2X_1C(=O)$—, —$(CH_2)_mX_3(CH_2)_mC(=O)NR^5(CH_2)_mNR^5C(=O)$—, —$(CH_2)_mX_3(CH_2)_mC(=O)NR^5(CH_2)_mC(=O)$—, —$(CH_2)_mX_3(CH_2)_mC(=O)NR^5(CH_2)_m(O(CH_2)_m)C(=O)$—, —$(CH_2)_mC(=O)X_2X_1C(=O)NR^5(CH_2)_m$—, —$(CH_2)_mX_3(O(CH_2)_m)C(=O)$—, —$(CH_2)_mNR^5C(=O)((CH_2)_mO)_n(CH_2)_m$—, —$(CH_2)_m(O$ $(CH_2)_mC(=O)NR^5(CH_2)_m-$, $-(CH_2)_mNR^5C(=O)NR^5(CH_2)_m-$, or $-(CH_2)_mX_3(CH_2)_mNR^5C(=O)-$,
wherein:
$X_1$ is
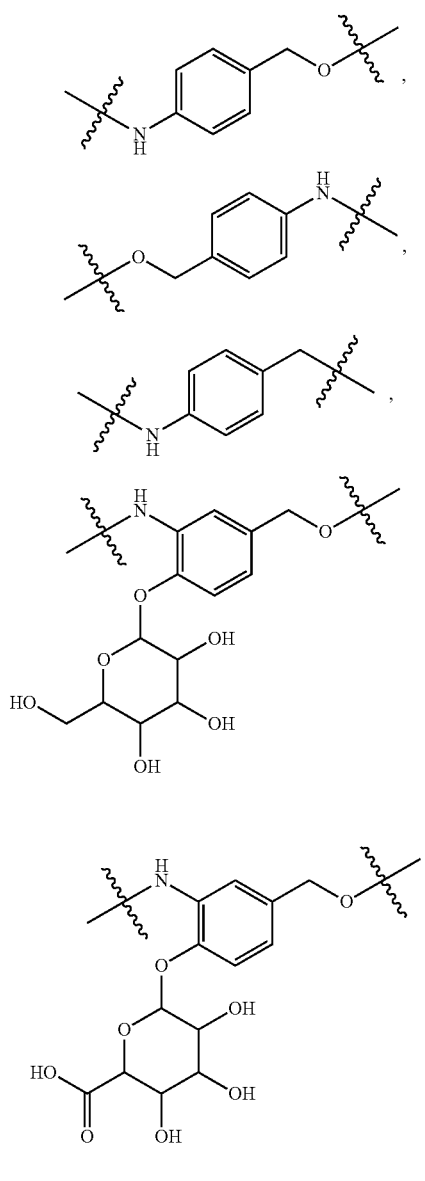
$X_2$ is
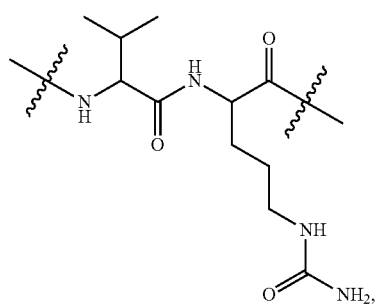
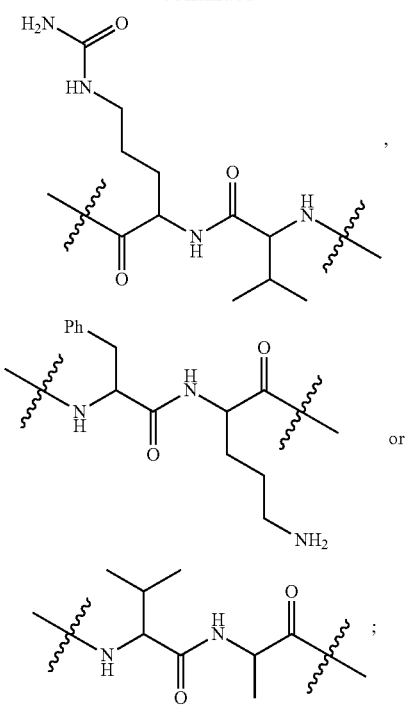
$X_3$ is
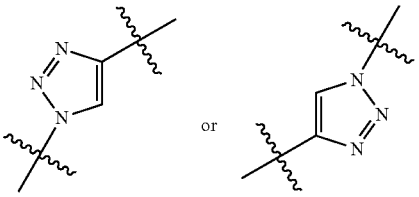
and
$X_4$ is
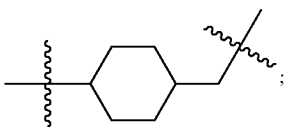 [SMILES: *CC1CCC(*)CC1]
$L_3$ is $-(CH_2)_mNR^5C(=O)-$;
$R^{40}$ is
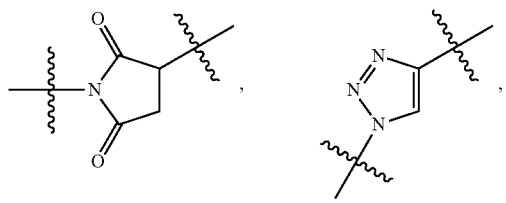

503
-continued
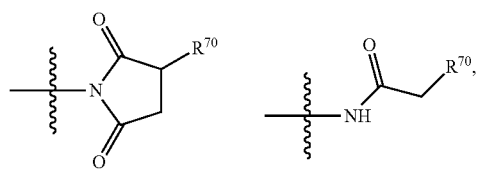
—NR⁵C(=O)CH₂—,         —NHC(=O)CH₂—,
—S(=O)₂   CH₂CH₂—,     —NR⁵S(=O)₂CH₂CH₂,
—NR⁵C(=O)CH₂CH₂—,      —CH₂NHCH₂CH₂—,
—NHCH₂CH₂—, —S—,
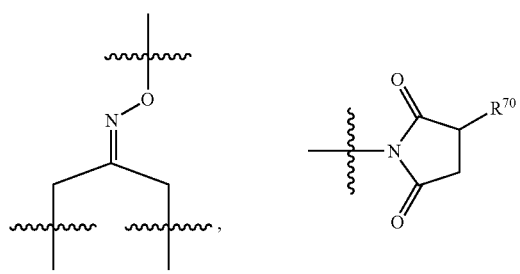
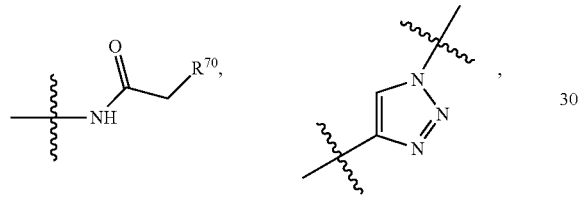
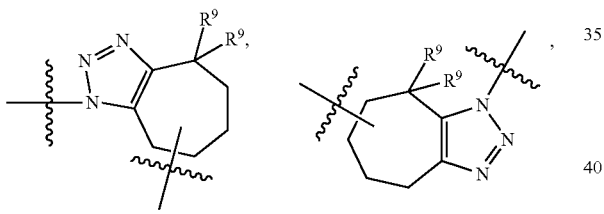
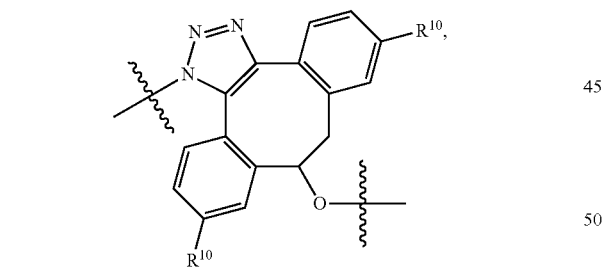
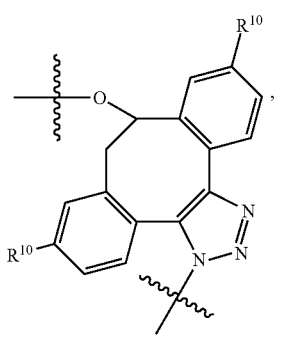
504
-continued
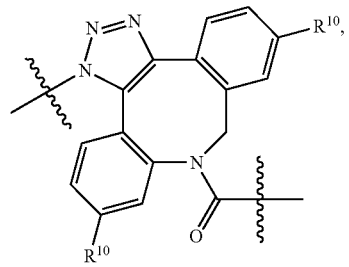
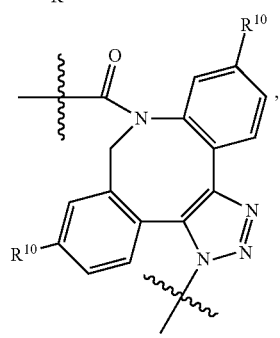
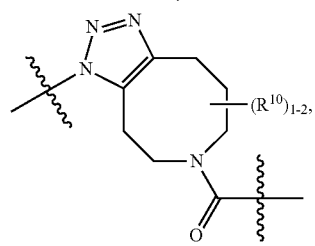
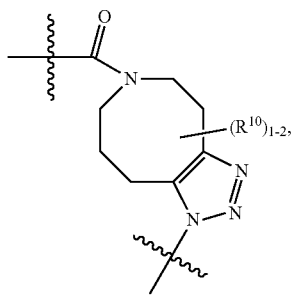
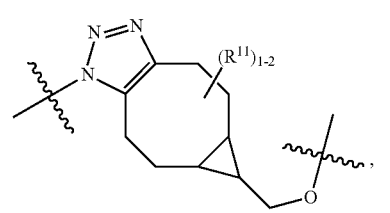
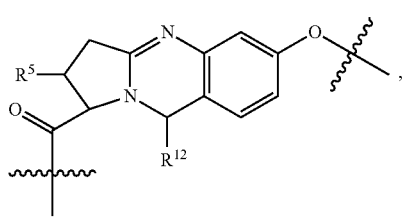

-continued

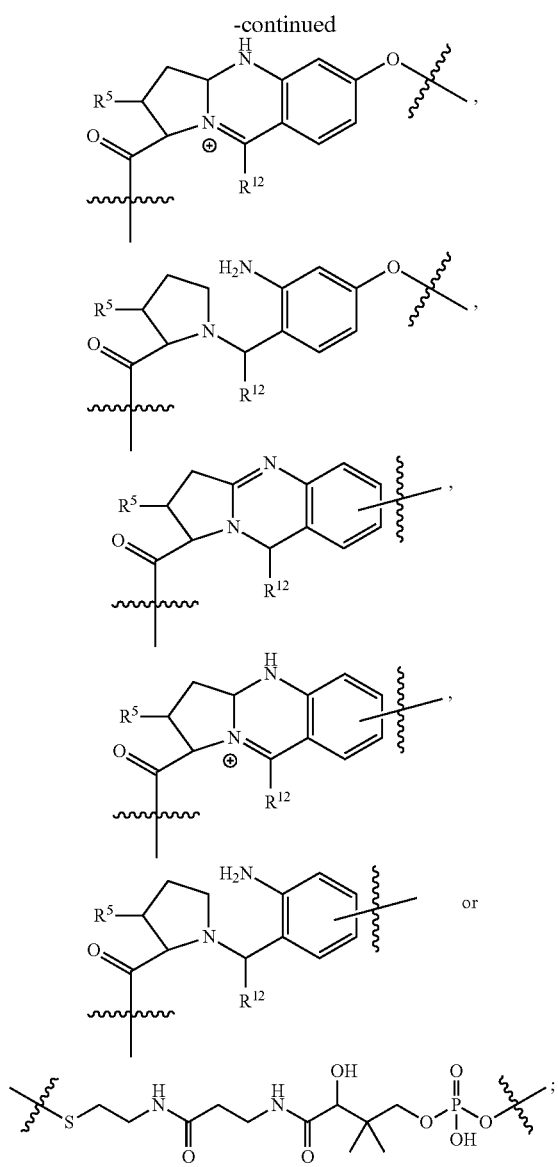

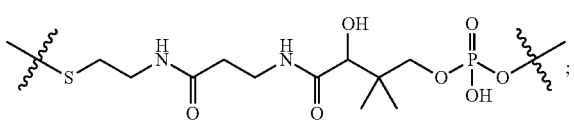 [SMILES: *OP(=O)(O)OCC(C)(C)C(O)C(=O)NCCC(=O)NCCS*]

each $R^5$ is independently selected from H and $C_1$-$C_6$alkyl;
$R^{60}$ is a bond or —NH—;
$R^{70}$ is $R^8$ is H, $C_1$-$C_6$alkyl or —C(=O)O$R^5$;
each $R^9$ is independently selected from H, $C_1$-$C_6$alkyl, F, Cl, and —OH;
each $R^{10}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{12}$ is independently selected from H, —CH$_3$ and phenyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.

In certain embodiments of the immunoconjugates having the structure of Formula (II), are immunoconjugates having the structure of Formula (IIa):

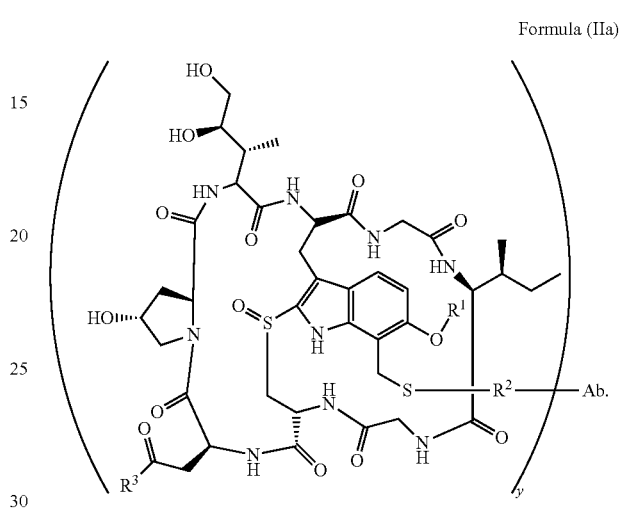

Formula (IIa)

In the immunoconjugates of Formula (II) or Formula (IIa), unless otherwise described, Ab can be any antigen binding moiety, and is preferably an antigen or antigen fragment that recognizes a cell surface marker such as those described herein that is characteristic of a targeted cell, such as a cancer cell. In addition, in the immunoconjugates of Formula (II) or Formula (IIa), unless otherwise described, Ab can be any antigen binding moiety, typically one that recognizes an antigen characteristic of cells to be targeted for pharmaceutical intervention, such as cancer cells. Many suitable antigens are well known in the art; specific ones of special interest are described herein. Typically, Ab is an antibody, which may be isolated or constructed, and may be natural or modified (engineered), or an antibody fragment that retains antigen binding activity similar to the antibody.

The invention provides immunoconjugates comprising one or more cytotoxic cyclic peptides linked to an antigen-binding moiety, such as an antibody or antibody fragment. Preferred immunoconjugates of the invention are those of Formula (II) or Formula (IIa) as described herein.

Examples of immunoconjugates of Formula (II) or Formula (IIa) are given in Tables 6-8 and Examples 51 to 53. However, immunoconjugates of Formula (II) or Formula (IIa) can also include variations thereof having another antigen binding moiety instead of anti-Her2 antibody, particularly such conjugates where anti-Her2 antibody is replaced by an antibody selected from the following list: anti-estrogen receptor antibody, anti-progesterone receptor antibody, anti-p53 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti- CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

In the most preferred embodiments, an immunoconjugate of Formula (II) or Formula (IIa) comprises Ab, an antibody or antibody fragment having antigen-binding activity, where the linker -$L_1L_2R^{40}$ or the linker —$(CH_2)_mX_3(CH_2)_mR^{40}$ is attached to Ab at a cysteine sulfur atom of Ab. In such embodiments the $R^{40}$ of linkers -$L_1L_2R^{40}$ and —$(CH_2)_mX_3(CH_2)_mR^{40}$ is

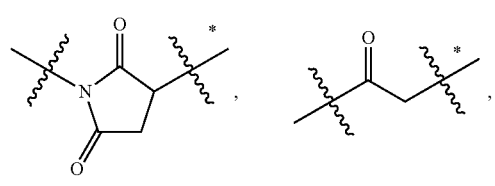

and the * indicates the pont of attachment to the cysteine sulfur atom. The resulting linkage formed by reaction with a cysteine residue of the antigen binding moiety include is

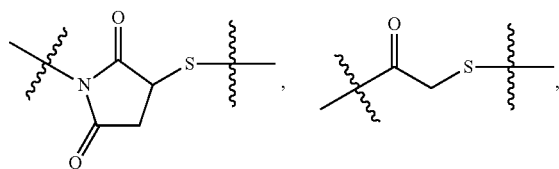

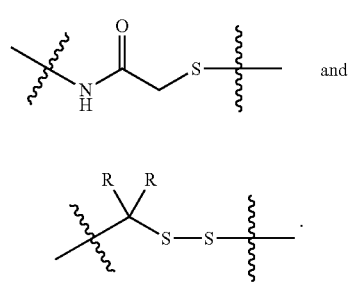

In other preferred embodiments, an immunoconjugate of Formula (II) or Formula (IIa) comprises Ab, an antibody or antibody fragment having antigen-binding activity, where the linker -$L_1L_2R^{40}$ or the linker —$(CH_2)_mX_3(CH_2)_mR^{40}$ is attached to Ab via a bridged disulfide in Ab. In such embodiments the $R^{40}$ of linkers -$L_1L_2R^{40}$ and —$(CH_2)_mX_3(CH_2)_mR^{40}$ is

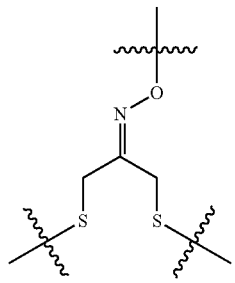

which is formed upon reaction of

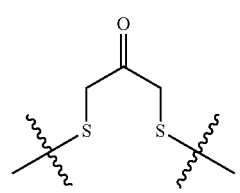 [SMILES: *SCC(=O)CS*]

and a compound of Formula (I) or Formula (Ia) which contains an hydroxylamine. The

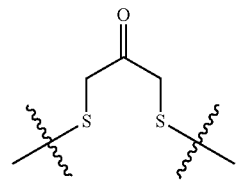 [SMILES: *SCC(=O)CS*]

group is formed from the bridged disulfide in Ab.

Other reactive groups used for reaction with a cysteine sulfur group and the resulting group formed are given in Table 1.

In other embodiments, an immunoconjugate of Formula (II) or Formula (IIa) comprises Ab, an antibody or antibody fragment having antigen-binding activity, where the linker -$L_1L_2R^{40}$, -$L_3R^{60}$ or —$(CH_2)_mX_3(CH_2)_mR^{40}$ is attached to Ab at a free —$NH_2$ of a lysine residue.

In some embodiments, an immunoconjugate of Formula (II) or Formula (IIa) comprises Ab, an antibody or antibody fragment Ab having antigen-binding activity, where the linker -$L_1L_2R^{40}$ or the linker —$(CH_2)_mX_3(CH_2)_mR^{40}$ is attached to Ab at a Pcl or Pyl group engineered into Ab. See e.g., Ou, et al., *PNAS* 108(26), 10437-42 (2011). In such embodiments the $R^{40}$ of linkers -$L_1L_2R^{40}$ and —$(CH_2)_mX_3(CH_2)_mR^{40}$ is

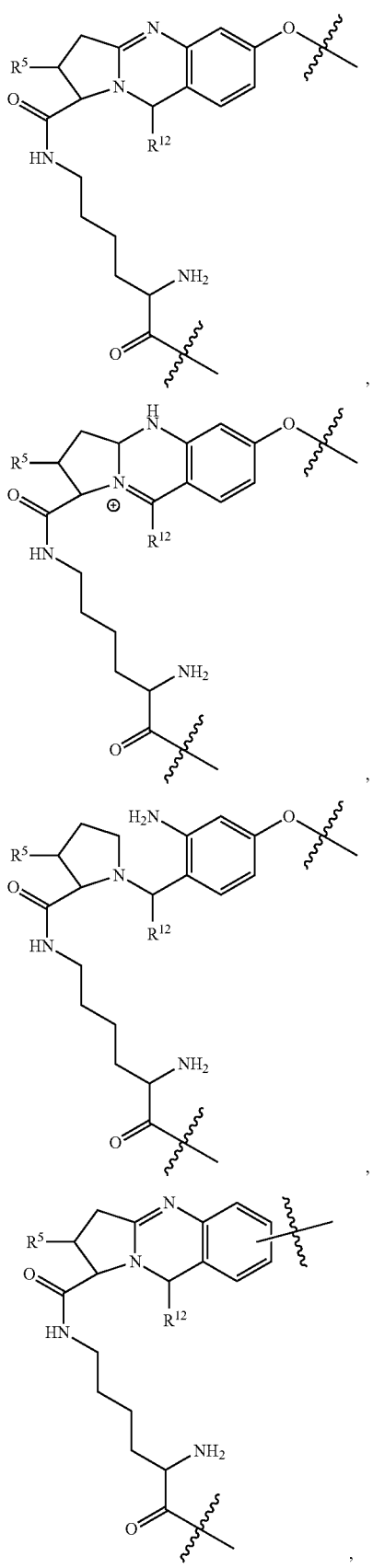

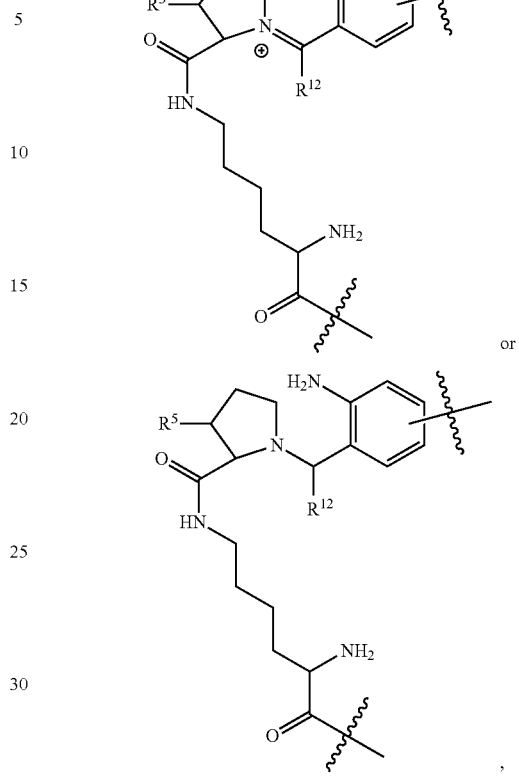

wherein $R^5$ is H or Me, and $R^{12}$ is H, Me or phenyl, for linking, where the

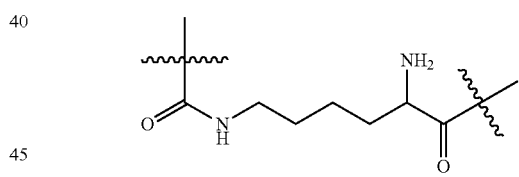

group shown is the lysine portion of a Pcl or Pyl in the engineered antibody.

In some embodiments, an immunoconjugate of Formula (II) or Formula (IIa) comprises Ab, an antibody or antibody fragment Ab having antigen-binding activity, where the linker -$L_1L_2R^{40}$ or the linker —$(CH_2)_mX_3(CH_2)_mR^{40}$ is attached to Ab at a serine residue in an S6, ybbR or A1 peptide engineered into Ab. In such embodiments the $R^{40}$ of linkers -$L_1L_2R^{40}$ and —$(CH_2)_mX_3(CH_2)_mR^{40}$ is

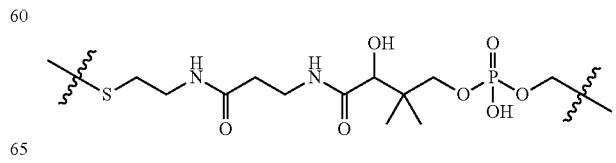

or
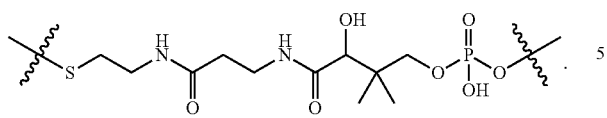
By way of example, one general reaction scheme for the formation of immunoconjugates of Formula (II) is shown in Scheme 3 below:
Scheme 3
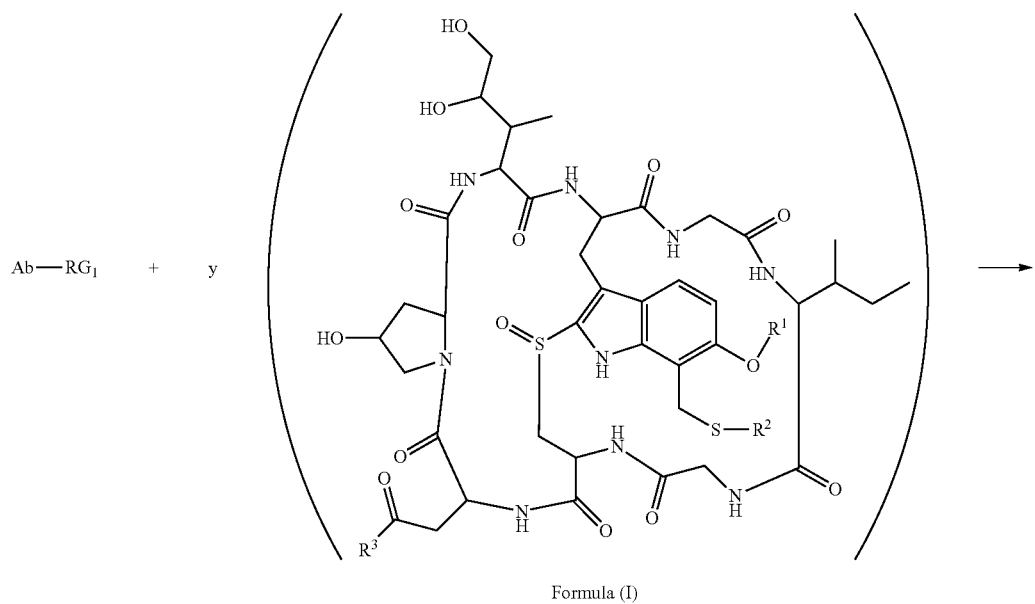
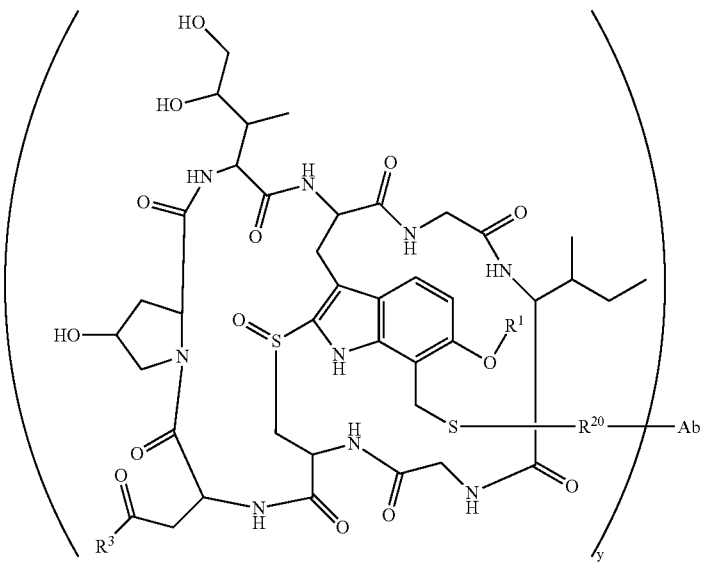

where $RG_1$ is a reactive group 1 from Table 1 and $R^2$ is -$L_1L_2R^4$, -$L_3R^6$ or —$(CH_2)_mX_3(CH_2)_mR^4$, where $R^4$ is as defined herein or is a reactive group 2 from Table 1. The reaction product is $R^{20}$ as defined herein or is the product as seen in Table 1. $R^1$, $R^3$, and Ab are as defined herein.

Another general reaction scheme for the formation of immunoconjugates of Formula (II) is shown in Scheme 4 below:

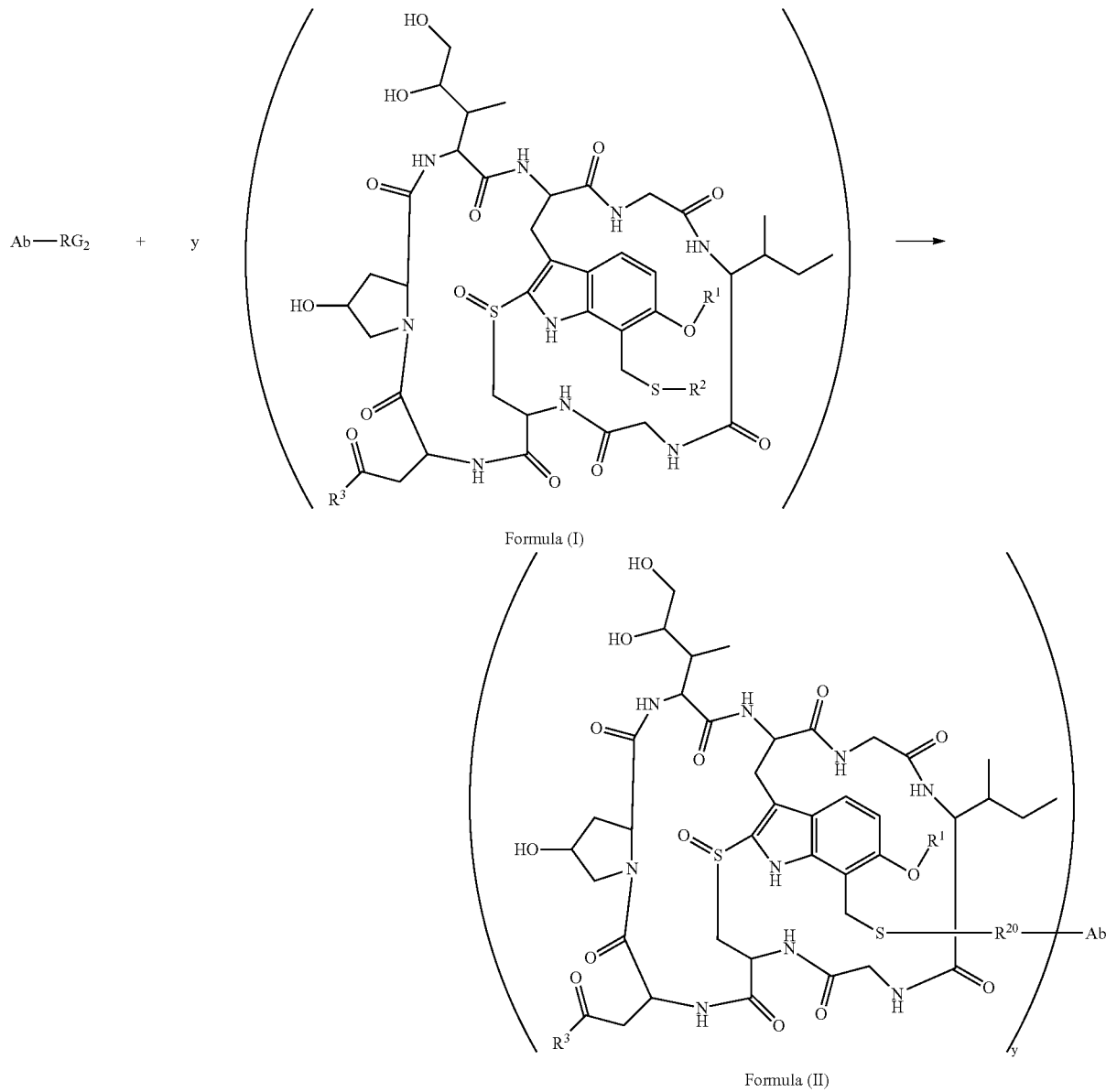

Scheme 4 where $RG_2$ is a reactive group 2 from Table 1 and $R^2$ is -$L_1L_2R^4$, -$L_3R^6$ or —$(CH_2)_mX_3(CH_2)_mR^4$, where $R^4$ is as defined herein or is a reactive group 1 from Table 1. The reaction product is $R^{20}$ as defined herein or is the product as seen in Table 1. $R^1$, $R^3$, and Ab are as defined herein.

In another aspect, the present invention provides a pharmaceutical composition comprising an immunoconjugate of Formula (II) or Formula (IIa) of the present invention and at least one pharmaceutically acceptable carrier. The pharmaceutical composition can be formulated for particular routes of administration such as intravenous administration, parenteral administration, and the like.

The immunoconjugates of the invention are typically formulated as solutions or suspensions in aqueous buffer and/or isotonic aqueous solution. They are typically administered parenterally, either by injection or by infusion. Methods for their formulation and administration are similar to those for formulation and administration of other biologicbased pharmaceuticals such as antibody therapeutics, and are known to those of skill in the art.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The immunoconjugates comprising a compound of formula (I), as demonstrated herein, exhibit substantial activity on targeted cells in vitro and on tumors in vivo, as demonstrated by potent growth inhibition of xenograft tumors representing different human cancers. Thus the immunoconjugates of Formula (II) or Formula (IIa) of the invention, comprising a payload of Formula (I), and subformulae thereof, linked to an antigen binding moiety such as an antibody, are also useful to treat cancers, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

An embodiment of the invention provides conjugation of a compound of Formula (I) or Formula (Ia) to an antigen binding moiety and thereby forming an immunoconjugate of Formula (II) or Formula (IIa), as described herein.

The immunoconjugates of Formula (II) or Formula (IIa) of the invention, which comprise a compound of Formula (I) or Formula (Ia), are particularly useful for treating cancers known in the art to be inhibited by toxins which inhibit RNA polymerase, and those tumor types demonstrated herein to be susceptible to inhibition by the compounds and conjugates of the invention. Suitable indications for treatment include, but are not limited to, gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma. The immunoconjugates of the invention comprising a compound of Formula (I), or subformulae thereof, are particularly useful in therapy. In a further embodiment, the therapy is for a disease which may be treated by anti-mitotic toxins. In another embodiment, the compounds of the invention are useful to treat cancers, including but not limited to gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The methods typically comprise administering an effective amount of an immunoconjugate of Formula (II) or Formula (IIa) of the invention as described herein or a pharmaceutical composition comprising such immunoconjugates to a subject in need of such treatment. The immunoconjugate may be administered by any suitable method such as those described herein, and the administration may be repeated at intervals selected by a treating physician.

Thus, as a further embodiment, the present invention provides the use of a immunoconjugate of Formula (II) or Formula (IIa) for the manufacture of a medicament. In a further embodiment, the medicament is for treatment of a disease which may be treated by the inhibition of RNA polymerase. In another embodiment, the disease is selected from gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The pharmaceutical composition or combination of the present invention can be in unit dosage of about 1-1000 mg of active ingredient(s) for a subject of about 50-100 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-12}$ molar concentrations. A therapeutically effective amount in vivo may range depending on the route of administration, between about 0.1-500 mg/kg, or between about 1-100 mg/kg.

An immunoconjugate of Formula (II) or Formula (IIa), of the present invention may be administered either simultaneously with, or before or after, one or more therapeutic co-agent(s). An immunoconjugate of Formula (II) or Formula (IIa), of the present invention may be administered separately, by the same or different route of administration, or together in the same pharmaceutical composition as the co-agent(s).

In one embodiment, the invention provides a product comprising immunoconjugate of Formula (II) or Formula (IIa), and at least one other therapeutic co-agent as a combined preparation for simultaneous, separate or sequential use in therapy. In one embodiment, the therapy is the treatment of a disease or condition such as cancer with an anti-mitotic toxin. Products provided as a combined preparation include a composition comprising an immunoconjugate of Formula (II) or Formula (IIa), and the other therapeutic co-agent(s) together in the same pharmaceutical composition, or the immunoconjugate of Formula (II) or Formula (IIa), and the other therapeutic co-agent(s) in separate form, e.g. in the form of a kit.

In one embodiment, the invention provides a pharmaceutical composition comprising an immunoconjugate of Formula (II) or Formula (IIa), and another therapeutic co-agent (s). Optionally, the pharmaceutical composition may comprise a pharmaceutically acceptable carrier, as described above.

Suitable co-agents for use with the immunoconjugates of the invention include other anti-cancer agents, anti-allergic agents, anti-nausea agents (or anti-emetics), pain relievers, anti-inflammatory agents, cytoprotective agents, and combinations thereof.

Specific co-agents considered for use in combination with the compounds and conjugates disclosed herein include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one embodiment, the invention provides a kit comprising two or more separate pharmaceutical compositions, at least one of which contains an immunoconjugate of Formula (II) or Formula (IIa). In one embodiment, the kit comprises means for separately retaining said compositions, such as a container, divided bottle, or divided foil packet In the combination therapies of the invention, the immunoconjugate of Formula (II) or Formula (IIa) of the invention and the other therapeutic co-agent may be manufactured and/or formulated by the same or different manufacturers. Moreover, the immunoconjugate of Formula (II) or Formula (IIa) of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The invention also provides an immunoconjugate of Formula (II) or Formula (IIa), for use in a method of treating a disease or condition with a cytotoxic peptide. The invention also provides an immunoconjugate of Formula (II) or Formula (IIa) for use in a method of treating a disease or condition with a cytotoxic peptide, wherein the immunoconjugate of Formula (II) or Formula (IIa) is prepared for administration with another therapeutic agent. The invention also provides an immunoconjugate of Formula (II) or Formula (IIa) for use in a method of treating a disease or condition with cytotoxic peptide, wherein the immunoconjugate of Formula (II) or Formula (IIa), is administered to the a subject in need of such treatment. The invention also provides another therapeutic co-agent for use in a method of treating a disease or condition with a cytotoxic peptide, wherein the other therapeutic co-agent is prepared for administration with an immunoconjugate of Formula (II) or Formula (IIa). The invention also provides an immunoconjugate of Formula (II) or Formula (IIa) for use in a method of treating a disease or condition with an toxin which inhibits RNA Polymerase, wherein the immunoconjugate of Formula (II) or Formula (IIa), is administered with another therapeutic co-agent.

The invention also provides the use of an immunoconjugate of Formula (II) or Formula (IIa), for treating a disease or condition with a cytotoxic peptide, wherein the patient has previously (e.g. within 24 h) been treated with another therapeutic agent. The invention also provides the use of another therapeutic agent for treating a disease or condition with an anti-mitotic toxin, wherein the patient has previously (e.g. within 24 h) been treated with an immunoconjugate of Formula (II) or Formula (IIa).

The invention also provides an immunoconjugate of Formula (II) or Formula (IIa) for use in a method of treating a disease or condition with a toxin which inhibits RNA polymerase, wherein the immunoconjugate of Formula (II) or Formula (IIa), is administered to the a subject in need of such treatment. The invention also provides an immunoconjugate of Formula (II) or Formula (IIa), for use in a method of treating a disease or condition with a toxin which inhibits RNA polymerase. The invention also provides an immunoconjugate of Formula (II) or Formula (IIa) for use in a method of treating a disease or condition with a toxin which inhibits RNA polymerase, wherein the immunoconjugate of Formula (II) or Formula (IIa) is prepared for administration with another therapeutic agent. The invention also provides another therapeutic co-agent for use in a method of treating a disease or condition with a toxin which inhibits RNA polymerase, wherein the other therapeutic co-agent is prepared for administration with an immunoconjugate of Formula (II) or Formula (IIa). The invention also provides an immunoconjugate of Formula (II) or Formula (IIa) for use in a method of treating a disease or condition with a toxin which inhibits RNA polymerase, wherein the immunoconjugate of Formula (II) or Formula (IIa) is administered with another therapeutic co-agent. The invention also provides another therapeutic co-agent for use in a method of treating a disease or condition with a toxin which inhibits RNA polymerase, wherein the other therapeutic co-agent is administered with an immunoconjugate of Formula (II) or Formula (IIa).

The invention also provides the use of an i immunoconjugate of Formula (II) or Formula (IIa), for treating a disease or condition with a toxin which inhibits RNA polymerase, wherein the patient has previously (e.g. within 24 h) been treated with another therapeutic agent. The invention also provides the use of another therapeutic agent for treating a disease or condition with an anti-mitotic toxin, wherein the patient has previously (e.g. within 24 h) been treated with an immunoconjugate of Formula (II) or Formula (IIa).

Conjugation of Linker-Payload (L-P) with an Antigen Binding Moiety

Example 60: Preparation of Antibody Drug Conjugates Using Engineered Cys Mutant Antibodies Numerous methods for conjugating linker-payloads to antigen binding moieties are known in the art (reviewed in for example: Antibody-Drug Conjugate, Methods in Molecular Biology, Vol. 1045, Editor L. Ducry, Humana Press (2013)). In this example, compounds described in the invention comprising a linker were conjugated to cysteine residues engineered into an antibody as described in Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925-932. As way of example, conjugation of the cytotoxic peptides of the invention is illustrated for only a small set of Cys antibody mutants but it is anticipated that the cytotoxic peptides can be conjugated to most if not all possible Cys antibody mutants.

Because engineered Cys in antibodies expressed in mammalian cells are modified by adducts (disulfides) such as glutathione (GSH) and/or cysteine during their biosynthesis (Chen et al. 2009), the modified Cys in the product as initially expressed is unreactive to thiol reactive reagents such as maleimido or bromo- or iodo-acetamide groups. To conjugate the engineered cysteine after expression, the glutathione or cysteine adducts need to be removed by reducing these disulfides, which generally entails reducing also the native disulfides in the expressed antibody. This can be accomplished by first exposing the antibody to a reducing agent such as dithiothreitol (DTT) followed by a procedure that allows for the re-oxidation of all native disulfide bonds of the antibody to restore and/or stabilize the functional antibody structure. Accordingly, in order to reduce all native disulfide bonds and the disulfide bound between the cysteine or GSH adducts of the engineered cysteine residue, freshly prepared DTT was added to Cys engineered antibodies to a final concentration of 10 mM. Anti-Her2-LC-S159C and anti-Her2-HC-E152C-S375C are used as examples of Cys engineered antibodies that can be used with the cytotoxic peptides of the invention. After incubation with DTT at 37° C. for 1 h, the mixtures were dialyzed at 4° C. against PBS for three days with daily buffer exchange to remove DTT and re-oxidize the native disulfide bonds. An alternative method is to remove the reducing reagents through a desalting column such as Sephadex G-25 after the protein is reduced. 1 mM oxidized ascorbate (dehydro-ascorbic acid) is added to the desalted samples and the re-oxidation incubations are carried out for 20 h. Both methods produce similar results. However, attempts to follow the re-oxidation protocols previously described in the literature using $CuSO_4$ resulted in protein precipitation (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925). All examples herein use the dialysis protocol described above. Reoxidation restores intra-chain disulfides, while the dialysis removes cysteines and glutathiones initially connected to the engineered cysteine(s) of the antibody.

After re-oxidation, the antibody was conjugated with cytotoxic peptides comprises a linker and a reactive moiety. By way of example, cytotoxic peptides having a linked maleimide moiety (10 molar equivalents relative to the antibody) were added to re-oxidized anti-Her2 Cys engineered antibodies in PBS buffer (pH 7.2). The incubations were carried out for 1 h. The conjugation process was monitored by reverse-phase HPLC, which is able to separate conjugated antibodies from unconjugated ones. The conjugation reaction mixtures were analyzed on a PRLP-S column (4000 Å, 50 mm×2.1 mm, Agilent) heated to 80° C. and elution from the column was carried out by a linear gradient of 30-60% acetonitrile in water containing 0.1% TFA at a flow rate of 1.5 mL/min. Antibody elution from the column was monitored at 280 nm, 309 nm and 215 nm.

Conjugation efficiency of various cytotoxic peptides having a linked maleimide to anti-Her2 Cys engineered antibodies varied depending on the solubility of the cytotoxic peptides used but most reactions resulted in more than 80% conjugate (Table 5). To evaluate the aggregation state, the resulting ADCs were analyzed by size exclusion chromatography (Agilent Bio SEC3, 300 Å, 7.8×150 mm) at a flow rate of 1 mL/min in PBS. The most ADC preparations contained more than 95% monomeric material. All ADC preparations contained less than 8% dimeric and oligomeric material (Table 5).

The conjugates were also characterized in terms of average loading of a cytotoxic peptide to the antibody binding moiety, generally referred to as drug to antibody ratio (DAR). The DAR value is extrapolated from LC-MS analysis. LC/MS allows quantitation of the average number of molecules of payload (drug) attached to an antibody in an ADC. For LC-MS analysis, ADCs are typically reduced and deglycosylated. LC separates heavy chain (HC) and light chain (LC) of the reduced antibody according to the number of linker-payload groups per chain. Mass spectral data enables identification of the component species in the mixture, e.g., LC, LC+1 drug, LC+2 drugs, HC, HC+1 drug, HC+2 drugs, etc. From the average loading on the LC and HC chains, the average DAR can be calculated for an ADC. The DAR for a given conjugate represents the average number of drug (payload) molecules attached to a typical antibody containing two light chains and two heavy chains. Table 5 lists DAR values obtained by MS for ADCs of two Cys-engineered anti-Her2 antibodies.

The maleimide-activated linker-payloads of the invention can also be used in conjugation reactions with partially reduced non-engineered antibodies. In this case, attachment occurs at the native cysteines of an antibody.

A single Cys mutation site engineered in the light chain of anti-Her2 results in up to two payload molecules conjugated to each antibody molecule producing a DAR 2 ADC. To increase the number of payloads per antibody, antibody constructs containing four Cys mutations per antibody molecule were produced by introducing two Cys mutations at two sites in the heavy chain of anti-Her2, resulting in a DAR of 4. As way of example, anti-Her2-HC-E152C-S375C antibody was conjugated to compounds 23, 47, 49 and 50. Selected properties of these double mutant ADCs are shown in Table 5.

While the immunoconjugates of Formula (II) disclosed in Tables 6 were obtained by conjugating anti-Her2 Cys mutant antibodies with certain cytotoxic cyclic peptides of Formula (I) having a linked maleimide moiety, other linker-payload combinations of the invention have also been used as exemplified by the immunoconjugates disclosed in Tables 7 and 8. In addition, conjugation to non-engineered antibodies is also possible, in particular at cysteine or lysine residues using methods know in the art.

All example ADCs were tested for in vitro cell killing potency as described in Example 64. Pharmacokinetic studies (Example 65) were preformed for selected immunoconjugates of the invention.

Table 5. Properties of Various Anti-Her2-LC-S159C and Anti-Her2-HC-E152C-S375C ADCs

TABLE 5

Properties of various anti-Her2-LC-S159C and anti-Her2-LC-E152C-S375C ADCs

| ADC[a] | Conjugation efficiency[b] (%) | Oligomer[c] (%) | DAR[d] |
|---|---|---|---|
| anti-Her2-LC-S159C-24 | 93 | 6 | 1.9 |
| anti-Her2-LC-S159C-3 | 96 | 5 | 1.9 |
| anti-Her2-LC-S159C-26 | 98 | 2 | 2.0 |
| anti-Her2-LC-S159C-28 | 99 | 2 | 2.0 |
| anti-Her2-LC-S159C-1 | 98 | 2 | 2.0 |
| anti-Her2-LC-S159C-2 | 99 | 2 | 2.0 |
| anti-Her2-LC-S159C-5 | 99 | 3 | 2.0 |
| anti-Her2-LC-S159C-34 | 98 | 3 | 2.0 |
| anti-Her2-LC-S159C-36 | 99 | 3 | 2.0 |
| anti-Her2-LC-S159C-33 | 97 | 3 | 1.9 |
| anti-Her2-LC-S159C-35 | 97 | 3 | 1.9 |
| anti-Her2-LC-S159C-38 | 97 | 3 | 1.9 |
| anti-Her2-LC-S159C-25 | 98 | 3 | 2.0 |
| anti-Her2-LC-S159C-27 | 98 | 3 | 2.0 |
| anti-Her2-LC-S159C-15 | 87 | 4 | 1.7 |
| anti-Her2-LC-S159C-14 | 86 | 4 | 1.7 |
| anti-Her2-LC-S159C-37 | 84 | 4 | 1.7 |
| anti-Her2-LC-S159C-6 | 94 | 4 | 1.9 |
| anti-Her2-LC-S159C-7 | 83 | 5 | 1.7 |
| anti-Her2-LC-S159C-8 | 93 | 4 | 1.9 |
| anti-Her2-LC-S159C-12 | 82 | 6 | 1.6 |
| anti-Her2-LC-S159C-9 | 80 | 8 | 1.6 |
| anti-Her2-LC-S159C-30 | 88 | 8 | 1.8 |
| anti-Her2-LC-S159C-31 | 90 | 7 | 1.8 |
| anti-Her2-LC-S159C-32 | 85 | 8 | 1.7 |
| anti-Her2-LC-S159C-29 | 95 | 3 | 1.9 |
| anti-Her2-LC-S159C-19 | 93 | 4 | 1.9 |
| anti-Her2-LC-S159C-20 | 93 | 4 | 1.9 |
| anti-Her2-LC-S159C-21 | 93 | 4 | 1.9 |
| anti-Her2-LC-S159C-45 | 95 | 4 | 1.9 |
| anti-Her2-LC-S159C-11 | 80 | 6 | 1.6 |
| anti-Her2-LC-S159C-18 | 95 | 4 | 1.9 |
| anti-Her2-LC-S159C-17 | 97 | 4 | 1.9 |
| anti-Her2-LC-S159C-22 | 96 | 4 | 1.9 |
| anti-Her2-LC-S159C-23 | 80 | 5 | 1.6 |
| anti-Her2-LC-S159C-13 | 80 | 6 | 1.6 |
| anti-Her2-LC-S159C-3 | 95 | 3 | 1.9 |
| anti-Her2-HC-E152C-S375C-23 | 95 | 1 | 3.8 |
| anti-Her2-HC-E152C-S375C-47 | 90 | 1 | 3.6 |
| anti-Her2-HC-E152C-S375C-49 | 90 | 1 | 3.6 |
| anti-Her2-HC-E152C-S375C-50 | 90 | 1 | 3.6 |

[a]Name consists of a description of the Cys engineered antibody and a description of the compound used in the chemical conjugation step.
[b]Conjugation efficiency was measured by MS and describes the percentage of antibody converted to ADC.
[c]Aggregation was measured by analytical size exclusion chromatography. Percent oligomer includes dimeric and oligomeric species.
[d]Drug-to-antibody ratio according to MS.

Example 61: Preparation of Antibody Drug Conjugates Using Lysine Reactive Cytotoxic Compounds Cytotoxic drugs of the invention can also be conjugated to native lysine residues of antibodies. This can be accomplished, for example, by reacting a cytotoxic drug linked to a NHS ester group with antibodies under neutral pH in PBS buffer devoid of free amines. The NHS ester group in the drugs readily reacts with lysine residues in antibodies (Basle E, Joubert N, Pucheault M. Chem Biol. 2010, 17:213-227. Protein chemical modification on endogenous amino acids). In one example, anti-Her2 was reacted with reference amatoxin compound REF. AMAN and compound 16 at the molar compound to antibody ratio of 20:1. The resulting ADCs anti-Her2-REF. AMAN and anti-Her2-16 had an average DAR range from 1.7-4 (Table 6). Selected properties of anti-Her2 ADCs are listed in Table 6.

Table 6. Properties of Various ADCs Prepared with Non-Engineered Antibodies

TABLE 6

Properties of various ADCs prepared with non-engineered antibodies

| Name of ADC[a] | DAR[b] | Oligomer (%)[c] |
|---|---|---|
| Anti-Her2-REF. AMAN | 4 | 6.1 |
| Anti-Her2-16 | 1.7 | 1.0 |

[a]Name consists of a description of the mutated antibody and a description of the compound used in the chemical conjugation step.
[b]Drug-to-antibody ratio according to MS.
[c]Aggregation was measured by analytical size exclusion chromatography. Percent oligomer includes dimeric and oligomeric species

Example 62: Preparation of Antibody-Drug Conjugates Through Enzymatic Conjugation of ybbR-Tagged Antibodies Enzymatic and chemoenzymatic conjugation of cytotoxic payloads to monoclonal antibodies enables the efficient preparation of homogeneous ADCs. The methodology is based on highly specific enzymatic recognition of peptidic sequences that are engineered at distinct antibody sites. Using this approach, site-specific payload attachment has been achieved through catalysis by various enzymes such as transglutaminase, formylglycine generating enzyme, and sortase (Strop P, Liu S H, Dorywalska M, Delaria K, Dushin R G, Tran T T, Ho W H, Farias S, Casas M G, Abdiche Y, Zhou D, Chandrasekaran R, Samain C, Loo C, Rossi A, Rickert M, Krimm S, Wong T, Chin S M, Yu J, Dilley J, Chaparro-Riggers J, Filzen G F, O'Donnell C J, Wang F, Myers J S, Pons J, Shelton D L, Rajpal A. (2013) Chem Biol. 20:161-167; Drake P M, Albers A E, Baker J, Banas S, Barfield R M, Bhat A S, de Hart G W, Garofalo A W, Holder P, Jones L C, Kudirka R, McFarland J, Zmolek W, Rabuka D. (2014) Bioconjug Chem. 25:1331-1341; Paterson B M, Alt K, Jeffery C M, Price R I, Jagdale S, Rigby S, Williams C C, Peter K, Hagemeyer C E, Donnelly P S. (2014) Angew Chem Int Ed Engl. 53:6115-6119). In this example, cytotoxins are chemoenzymatically conjugated to an embedded 11-mer ybbR peptide sequence (DSLEFIASKLA (SEQ ID NO:7)) via phosphopantetheinyl transferase (PPTase) catalyzed posttranslational modification (Zhou Z, Cironi P, Lin A J, Xu Y, Hrvatin S, Golan D E, Silver P A, Walsh C T, Yin J. (2007) ACS Chem Biol. 2:337-346). As way of example, site-specific payload conjugation is demonstrated for an engineered IgG with the ybbR recognition motif incorporated into the CH3 domain. This approach is expandable to numerous conjugation sites within the antibody constant regions of heavy and light chains and to other PPTase tag and enzyme combinations.

The bioorthogonality of PPTase catalysis allows antibody labeling with coenzyme A (CoA) analogues to be performed in complex mixtures such as cell culture medium. As provided herein a CoA analogue containing a ketone group (CoA-1, see Example 56) was enzymatically conjugated to an antibody and the ketone group of the activated antibody was chemically reacted with an aminooxy-functionalized compound of Formula (I). The small size of the ketone moiety makes this two-step chemoenzymatic conjugation process preferable over direct antibody modification with bulky payload-CoA conjugates that are likely to impair the catalytic efficiency of PPTase enzymes (Sieber S A, Walsh C T, Marahiel M A. (2003) J Am Chem Soc. 125:10862-10866).

In order to attach the ketone functionality to an engineered peptide sequence, 2.5 µM of an anti-Her2 antibody containing a ybbR tag inserted between heavy chain residues E388 and N389 (anti-Her2-HC-E388-DSLEFIASKLA-N389) was reacted with 30 µM of keto-CoA analogue CoA-1 in the presence of 1.5 µM *Bacillus subtilis* Sfp PPTase (see Example 63 below). The enzymatic reaction was incubated for approximately 16 h at 23° C. in 75 mM Tris buffer (pH 8.0) that was supplemented with 12.5 mM $MgCl_2$ and 20 mM NaCl. Next, enzyme and excess keto-CoA analogue CoA-1 were removed by binding the antibody to protein A affinity medium (MabSelect SuRe, GE Healthcare) followed by extensive washing with PBS supplemented with 1% Triton X-100 and 1 M NaCl. After additional washing steps with PBS, elution was carried out with acidic IgG Elution Buffer (Thermo Scientific). The antibody eluate was neutralized with 1 M Tris buffer (pH 8.0) and buffer-exchanged into PBS using PD-10 desalting columns (GE Healthcare). Mass spectrometric analysis of the deglycosylated heavy chain revealed near quantitative conversion to the desired ketone-functionalized species.

In another aspect of this two step labelling approach, a modified CoA analogue was prepared chemoenzymatically using the CoA biosynthetic enzymes CoAA, CoAD, and CoAE (Worthington A S, Burkart M D (2006) Org Biomol Chem. 4:44-46). Adopting this approach, a ketone-functionalized CoA analogue for the preparation of ADCs was prepared from the corresponding pantothenate precursor molecule (Compound i-9). In this approach the ultrafiltrate from Example 57 was used without further purification, and the CoA analogue CoA-i-9 was used in the conjugation reaction with anti-Her2-HC-E388-DSLEFIASKLA-N389, at a final concentration of about 30 µM of CoA analogue CoA-i-9. Antibody labeling and subsequent affinity purification were conducted in the exactly same manner as described above for keto-CoA analogue CoA-1. Covalent attachment of the ketone moiety to the ybbR-tagged antibody was confirmed by mass spectrometric analysis following sample treatment with PNGase F and TCEP.

Following enzymatic attachment of keto-CoA analogues, CoA-1 or CoA-i-9, the resulting antibody construct were conjugated with compounds of Formula (I) comprising an aminooxy group. Oxime ligations were performed with 67 µM (10 mg/mL) of a ketone-functionalized antibody and 10- to 20-fold molar excess (667-1333 µM) of the compound of Formula (I) comprising an aminooxy group in 100 mM sodium acetate buffer at pH 4.0. The bioorthogonal reaction was allowed to proceed for about 16 h at 37° C., then excess compound of Formula (I) and small amounts of aggregate were removed by preparative size-exclusion chromatography on a HiLoad 26/600 Superdex 200 column (GE Healthcare) in PBS at a flowrate of 2.5 mL/min. The drug loading of the oxime-linked ADCs was determined by mass spectrometry on a 6520 Accurate-Mass Quadrupole Time-of-Flight (Q-TOF) LC/MS system (Agilent Technologies). Prior to mass spectrometric analysis, the oxime-linked ADCs were treated with PNGase F to remove the N-linked glycan on the antibody. Next, in order to separate unlabeled light chain from enzymatically labeled heavy chain comprising the ybbR recognition sequence, all interchain disulfide bonds were reduced in the presence of 16 mM TCEP. After acquiring deconvoluted mass spectra of the deglycosylated and reduced ADC samples, drug-to-antibody ratios (DARs) were calculated from the peak intensities of labeled and unlabeled heavy chain. The resulting DARs of the ybbR-tagged anti-Her2 ADCs containing oxime-linked cytotoxic peptides are summarized in Table 7. Conjugation efficiencies of at least 85% were obtained at 7.5- to 10-fold molar excess of aminooxy-functionalized peptide over engineered ybbR peptide, resulting in site-specific ADCs with DARs of 1.7 or higher. The conjugation efficiency dropped to 60% when the molar excess of cytotoxic peptide was decreased to 5-fold, resulting in DARs of approximately 1.2 (Table 7). The quaternary structure of all oxime-linked ADCs was assessed by analytical size-exclusion chromatography on an Agilent Bio SEC-3 column (300 Å, 7.8×150 mm) at a flow rate of 1.0 mL/min in PBS. All ADC preparations consisted of predominantly monomeric material and contained less than 0.5% of oligomeric material as summarized in Table 7.

Table 7. Properties of Various Chemoenzymatically Labeled Anti-Her2 ADCs Containing an Engineered ybbR Tag

TABLE 7

Properties of various chemoenzymatically labeled anti-Her2 ADCs containing an engineered ybbR tag

| ADC name$^a$ | Conjugation efficiency (%)$^b$ | Oligomer (%)$^c$ | DAR$^d$ |
|---|---|---|---|
| anti-Her2-HC-E388-DS-ppan-CoA-1-40-LEFIASKLA-N389 | 88 | 0.1 | 1.8 |
| anti-Her2-HC-E388-DS-ppan-CoA-1-39-LEFIASKLA-N389 | 85 | 0.2 | 1.7 |
| anti-Her2-HC-E388-DS-ppan- | 60 | 0.1 | 1.2 |

TABLE 7-continued

Properties of various chemoenzymatically labeled anti-Her2 ADCs containing an engineered ybbR tag

| ADC name[a] | Conjugation efficiency (%)[b] | Oligomer (%)[c] | DAR[d] |
|---|---|---|---|
| CoA-1-41-LEFIASKLA-N389 anti-Her2-HC-E388-DS-ppan-CoA-i-9-40-LEFIASKLA-N389 | 90 | 0.1 | 1.8 |
| anti-Her2-HC-E388-DS-ppan-CoA-i-9-39-LEFIASKLA-N389 | 87 | 0.1 | 1.7 |
| anti-Her2-HC-E388-DS-ppan-CoA-i-9-41-LEFIASKLA-N389 | 60 | 0.2 | 1.2 |

[a]Name represents part of the HC that contains the ybbR tag with the attached cytotoxic peptide, the paired wildtype chain is not listed.
[b]Conjugation efficiency was measured by MS and describes the percentage of antibody converted to ADC.
[c]Aggregation was measured by analytical size exclusion chromatography. Percent oligomer includes dimeric, oligomeric, and aggregate species.
[d]Drug-to-antibody ratio (DAR) according to MS.

Example 63: Production of Sfp 4'-Phosphopantetheinyl Transferase (PPTase)

The *Bacillus subtilis* Sfp PPTase was cloned into the pET22b expression vector using the PIPE method (see Klock et al., Proteins 71:982-994 (2008)). To allow cleavage of the C-terminal His$_6$ tag, a TEV (tobacco etch virus) protease recognition site was inserted downstream of the Sfp coding sequence. All primers used for cloning and the Sfp protein sequence are listed in the Table 8 below.

TABLE 8

Primers used for cloning of Sfp enzyme

| Sequence name | Sequence | SEQ ID NO |
|---|---|---|
| B. subtilis Sfp pET22b | GAAGGAGATATACATATGAAAATT TATGGGATTTACATGGATCGC | SEQ ID NO: 14 |
| | GTGGTGGTGGTGGTGGTGCAGCAA TTCTTCATAGGAGACCATCG | SEQ ID NO: 15 |
| pET22b | CACCACCACCACCACCACTGAG | SEQ ID NO: 16 |
| | CATATGTATATCTCCTTCTTAAAG TTAAACAAAATTATTTC | SEQ ID NO: 17 |
| TEV into B. subtilis Sfp pET22b | GAGAACCTGTACTTCCAAGGCCA CCACCACCACCACCACTGAG | SEQ ID NO: 18 |
| | GCCTTGGAAGTACAGGTTCTCCA GCAATTCTTCATAGGAGACCATCG | SEQ ID NO: 19 |
| Bacillus subtilis Sfp PPTase with C-terminal TEV cleavage site and His6 tag | MKIYGIYMDRPLSQEENERFMSF ISPEKREKCRRFYHKEDAHRTLL GDVLVRSVISRQYQLDKSDIRFS TQEYGKPCIPDLPDAHFNISHSG RWVICAFDSQPIGIDIEKTKPIS LEIAKRFFSKTEYSDLLAKDKDE QTDYFYHLWSMKESFIKQEGKGL SLPLDSFSVRLHQDGQVSIELPD SHSPCYIKTYEVDPGYKMAVCAA HPDFPEDITMVSYEELLENLYFQG HHHHHH | SEQ ID NO: 20 |

Protein expression and purification were performed according to Yin et al. (see Nat. Protoc. 1:280-285 (2006)) with some modifications. First, a 4 mL LB starter culture (containing 200 μg/mL ampicillin) was inoculated from a glycerol stock of *Escherichia coli* BL21 (DE3) cells harboring the pET22b/sfp expression plasmid. The culture was grown to saturation by overnight incubation at 37° C. at 279 rpm. The next day, 1 mL of the starter culture was used to inoculate 1 L of TB medium (containing 200 μg/mL ampicillin), which was agitated at 230 rpm and maintained at 37° C. After reaching an optical density of 0.5 at 600 nm, the culture was induced by the addition of IPTG to a final concentration of 1 mM and the temperature was reduced to 30° C. The culture was shaken for another 12-16 hours and the bacterial cells were harvested by centrifugation (15 min at 3724×g). Prior to use, the cell pellets were stored at −20° C.

To initiate protein purification, the frozen pellets (2×16 g) were thawed for approximately 15 minutes on ice and re-suspended in a buffer containing 20 mM Tris/HCl (pH 8), 0.5 M NaCl, 5 mM imidazole, and 2 U/mL DNase I (3 mL of buffer per g wet weight of cells). Cell lysis was induced by sonication for 2 min, with intervals of 1 sec on and 1 sec off. In order to remove insoluble cell debris, the resulting lysate was centrifuged at 39,410×g for 20 min at 4° C. The His$_6$-tagged Sfp enzyme was then captured by the addition of 6 mL of 50% Ni-NTA agarose slurry (Qiagen) to the cleared lysate. After shaking for 1 hour at 4° C., the resin-lysate mixture was poured into three disposable columns (Bio-Rad). The settled resin was washed with 50 column volumes of 50 mM Tris/HCl (pH 8), 300 mM NaCl, 20 mM imidazole and eluted with 6 column volumes of 50 mM Tris/HCl (pH 8), 300 mM NaCl, 250 mM imidazole. After elution, the Sfp enzyme was exchanged into TEV cleavage buffer containing 50 mM Tris/HCl (pH 8) and 50 mM NaCl. His$_6$ tag removal was carried out by digestion with about 8% (w/w) TEV protease at 23° C. for 2 hours and then at 4° C. for 16 hours. The TEV-digested Sfp enzyme was then reloaded onto three Ni-NTA columns (ca. 1 mL bed volume per column) equilibrated with PBS. The cleaved enzyme was collected from the column flow-through and from a washing step involving 5 column volumes of 50 mM Tris/HCl (pH 8), 300 mM NaCl, and 20 mM imidazole. Purified Sfp enzyme was then dialyzed against 10 mM Tris/HCl (pH 7.4), 1 mM EDTA, 10% glycerol using Slide-A-Lyzer Dialysis Cassettes (Pierce) with a 2.0 kDa cut-off. After passing the dialysate through a 0.22 μm-filter, the yield of Sfp was quantified by ultraviolet spectroscopy at 280 nm (ND-1000 UV-Vis Spectrophotometer, NanoDrop Technologies, Wilmington, Del.) using a molar extinction coefficient of 28620 $M^{-1}$ $cm^{-1}$. 68 mg of TEV-cleaved Sfp enzyme was obtained per liter culture. Next, Sfp was concentrated to 137 μM using Amicon Ultra-15 Centrifugal Filter Units (Millipore) with a 10 kDa cut-off. The purity of Sfp was assessed by SDS-PAGE, and His$_6$ tag removal was verified by LC-MS. According to analytical size-exclusion chromatography, TEV-cleaved Sfp PPTase is 87% monomeric. Finally, the concentrated enzyme was aliquoted, flash-frozen in liquid nitrogen, and stored at −80° C.

Example 64: Cell Proliferation Assays to Measure In Vitro Cell Killing Potency of ADCs Cells that naturally express target antigens or cell lines engineered to express target antigens are frequently used to assay the activity and potency of ADCs. For evaluation of the cell killing potency of anti-Her2 antibody ADCs in vitro, two engineered cell lines, MDA-MB231 clone 16 and clone 40, and four endogenous cell lines, NCI-N87, SK-BR-3, JimT-1 and HCC1954 cells were employed (Clinchy B, Gazdar A, Rabinovsky R, Yefenof E, Gordon B, Vitetta E S. Breast Cancer Res Treat. (2000) 61:217-228). MDA-MB231 clone 16 cells stably express high copy numbers (~5×10$^5$ copies/cell) of recombinant human Her2 on the cell surface while clone 40 expresses human Her2 at low levels (~5×10$^3$ copies/cell). High levels of Her2 are endogenously expressed in HCC1954 (~5×10$^5$ copies/cell), SKBR-3 (5.4× 10$^5$ copies/cell) and NCI-N87 (2.7×10$^5$ copies/cell) cell lines while JimT-1 cells express human Her2 at a medium level (~8×10$^4$ copies/cell). An ADC should kill cells in an antigen-dependent manner, meaning that only cells that express sufficient antigen in the cell surface but not cells lacking the antigen will be killed. To measure antigen-dependent cell killing, cell proliferation assays were conducted with Cell-Titer-Glo™ (Promega) five days after different cell types were incubated with various concentrations of ADCs (Riss et al., (2004) Assay Drug Dev. Technol. 2:51-62). In some studies, the cell based assays are high throughput and conducted on an automated system (Melnick et al., (2006) Proc Natl Acad Sci USA. 103:3153-3158).

Anti-Her2 amanitin ADCs prepared with compounds of Formula (I) disclosed in the invention and conjugated site-specifically to anti-Her2 Cys engineered antibodies and ybbR-tagged anti-Her2 antibodies (see Table 5 and Table 7) were assayed in the aforementioned six cell lines to evaluate their cytotoxicity (FIG. 1 and FIG. 2). The majority of ADCs specifically killed MDA-MB231-16, HCC1954, NCI-87, and SK-BR-3, the four cell lines with high levels of Her2 expression (FIG. 1 B to C, FIG. 2 D to F, Table 9), but not MDA-MB231-40 and A375 cells that express a low level of Her2 (FIG. 1 A FIG. 2 B to E, Table 9). IC$_{50}$ values of the majority of anti-Her2 Cys mutant ADCs in MDA-MB231-16 and HCC1954 cell assays ranged from 40 pM to 200 pM (Table 9). With the exception of anti-Her2-HC-E388-DS-ppan-CoA-i-9-40-LEFIASKLA-N389, IC$_{50}$ values of all ybbR-tagged anti-Her2 ADCs in NCI-87 and SK-BR-3 cell assays were lower than 200 pM. In JimT-1 cells, anti-Her2-LC-S159C ADCs (DAR2) with payloads compound 21, compound 45, compound 32, compound 23, compound 13, compound 11, compound 18, compound 17, compound 22, and compound 39 showed a weak cytotoxic potency (Table 9, FIG. 1 D and FIG. 2A) while majority of the ADCs did not exhibit cytotoxicity in JimT-1 cells. However, anti-Her2-HC-E152C-S375C ADCs (DAR4) with compounds 23, compound 47, compound 49 and compound 50 showed potent cytotoxicity towards JimT-1 cells with IC$_{50}$ values between 0.04 nM to 0.08 nM (Table 9). ADCs with payload compound 16 conjugated to lysine residues of anti-Her2 was also prepared as described in Example 61. Anti-Her2-16 showed good cytotoxic potency in all three Her2 positive cell lines (Table 9; FIG. 1 B to D). The potency of ADCs containing compound 16 is similar to that of ADCs prepared with a reference amatoxin, REF. AMAN (US 2013/0259880). An ADC with MC-MMAF, an auristatin, conjugated to anti-Her2-LC-S159C was prepared as a second reference ADC for all the aforementioned cell proliferation assays. Anti-Her2-LC-S159C-MMAF showed cytotoxicity towards MDA-MB231-16, HCC1954 and JimT-1 but not to MDA231-40 cells (Table 9).

Table 9. ADC Potency in In Vitro Cell Killing Assay: IC$_{50}$ of Anti-Her2 ADCs in MDA-MB231 Clone 40, MDA-MB231 Clone 16, HCC1954, JimT-1, NCI-87, and SK-BR-3 Cell Proliferation Assays

TABLE 9

ADC potency in in vitro cell killing assay: IC$_{50}$ of anti-Her2 ADCs in MDA-MB231 clone 40, MDA-MD231 clone 16, HCC1954, JimT-1, NCI-87, and SK-BR-3 cell proliferation assays

| ADC name[a] | IC$_{50}$ (nM)[b] | | | | | |
|---|---|---|---|---|---|---|
| | MDA-MB-231-40 | HCC1954 | JimT-1 | MDA-MB-231-16 | NCI-N87 | SK-BR-3 |
| anti-Her2-LC-S159C-MMAF | >67 | 0.09 | 0.37 | 0.35 | ND | ND |
| anti-Her2-LC-S159C-4 | >67 | 0.10 | >67 | 0.18 | ND | ND |
| anti-Her2-LC-S159C-24 | >67 | 0.99 | >67 | 45 | ND | ND |
| anti-Her2-LC-S159C-3 | >67 | 0.06 | >67 | 0.07 | ND | ND |
| anti-Her2-LC-S159C-26 | >67 | 0.04 | >67 | 0.08 | ND | ND |
| anti-Her2-LC-S159C-2 | >67 | 0.07 | >67 | 0.10 | ND | ND |
| anti-Her2-LC-S159C-5 | >67 | 0.07 | >67 | 0.07 | ND | ND |
| anti-Her2-LC-S159C-28 | >67 | 0.08 | >67 | 0.12 | ND | ND |
| anti-Her2-LC-S159C-1 | >67 | 0.05 | >67 | 0.08 | ND | ND |
| anti-Her2-LC-S159C-34 | >67 | 0.12 | >67 | 0.25 | ND | ND |
| anti-Her2-LC-S159C-36 | >67 | 0.08 | 23 | 0.11 | ND | ND |
| anti-Her2-LC-S159C-33 | >67 | 0.10 | 52 | 0.25 | ND | ND |
| anti-Her2-LC-S159C-35 | >67 | 0.38 | >67 | 1.03 | ND | ND |
| anti-Her2-LC-S159C-38 | >67 | 0.07 | 52 | 0.10 | ND | ND |
| anti-Her2-LC-S159C-25 | >67 | 0.41 | >67 | 0.85 | ND | ND |
| anti-Her2-LC-S159C-27 | >67 | 0.11 | >67 | 0.22 | ND | ND |
| anti-Her2-LC-S159C-15 | >67 | 0.10 | >67 | 0.14 | ND | ND |
| anti-Her2-LC-S159C-14 | >67 | 0.08 | >67 | 0.09 | ND | ND |
| anti-Her2-LC-S159C-37 | >67 | 0.37 | >67 | 0.78 | ND | ND |
| anti-Her2-LC-S159C-6 | >67 | 0.07 | 47 | 0.07 | ND | ND |
| anti-Her2-LC-S159C-7 | >67 | 0.07 | 47 | 0.07 | ND | ND |
| anti-Her2-LC-S159C-8 | >67 | 0.07 | 52 | 0.08 | ND | ND |
| anti-Her2-LC-S159C-12 | >67 | 0.74 | >67 | 0.90 | ND | ND |
| anti-Her2-LC-S159C-9 | >67 | 0.13 | >67 | 22.51 | ND | ND |
| anti-Her2-LC-S159C-30 | >67 | 0.12 | >67 | 0.20 | ND | ND |
| anti-Her2-LC-S159C-31 | >67 | 0.08 | >67 | 0.12 | ND | ND |
| anti-Her2-LC-S159C-32 | >67 | 0.08 | >67 | 0.11 | ND | ND |
| anti-Her2-LC-S159C-29 | >67 | 0.09 | >67 | 0.17 | ND | ND |
| anti-Her2-LC-S159C-19 | >67 | 0.07 | >67 | 0.08 | ND | ND |
| anti-Her2-LC-S159C-20 | >67 | 0.08 | >67 | 0.10 | ND | ND |

TABLE 9-continued

ADC potency in in vitro cell killing assay: $IC_{50}$ of anti-Her2 ADCs in MDA-MB231 clone 40, MDA-MD231 clone 16, HCC1954, JimT-1, NCI-87, and SK-BR-3 cell proliferation assays

| | $IC_{50}$ (nM)[b] | | | | | |
|---|---|---|---|---|---|---|
| ADC name[a] | MDA-MB-231-40 | HCC1954 | JimT-1 | MDA-MB-231-16 | NCI-N87 | SK-BR-3 |
| anti-Her2-LC-S159C-21 | >67 | 0.06 | 45 | 0.07 | ND | ND |
| anti-Her2-LC-S159C-45 | >67 | 0.06 | >67 | 0.07 | ND | ND |
| anti-Her2-LC-S159C-11 | >67 | 0.06 | >67 | 0.06 | ND | ND |
| anti-Her2-LC-S159C-18 | >67 | 0.03 | >67 | 0.04 | ND | ND |
| anti-Her2-LC-S159C-17 | >67 | 0.06 | 0.42 | 0.06 | ND | ND |
| anti-Her2-LC-S159C-22 | >67 | 0.03 | 0.22 | 0.05 | ND | ND |
| anti-Her2-LC-S159C-23 | >67 | 0.09 | >67 | 0.14 | ND | ND |
| anti-Her2-LC-S159C-13 | >67 | 0.08 | >67 | 0.10 | ND | ND |
| anti-Her2-16 | >67 | 0.17 | 0.59 | 0.30 | ND | ND |
| anti-Her2-REF.AMAN | >67 | 0.09 | 0.32 | 0.12 | ND | ND |
| anti-Her2-HC-E388-DS-ppan-CoA-1-40-LEFIASKLA-N389 | ND | 0.10 | >67 | ND | 0.15 | 0.16 |
| anti-Her2-HC-E388-DS-ppan-CoA-1-39-LEFIASKLA-N389 | ND | 0.13 | >67 | ND | 0.14 | 0.14 |
| anti-Her2-HC-E388-DS-ppan-CoA-1-41-LEFIASKLA-N389 | ND | 0.15 | >67 | ND | 0.18 | 0.15 |
| anti-Her2-HC-E388-DS-ppan-CoA-I-9-40-LEFIASKLA-N389 | ND | 1.74 | >67 | ND | 1.1 | 0.57 |
| anti-Her2-HC-E388-DS-ppan-CoA-i-9-39-LEFIASKLA-N389 | ND | 0.08 | >67 | ND | 0.06 | 0.09 |
| anti-Her2-HC-E388-DS-ppan-CoA-i-9-41-LEFIASKLA-N389 | ND | 0.18 | >67 | ND | 0.16 | 0.17 |
| anti-Her2-HC-E152C-S375C-23 | ND | 0.03 | 0.04 | ND | 0.03 | 0.03 |
| anti-Her2-HC-E152C-S375C-47 | ND | 0.08 | 0.08 | ND | 0.06 | 0.05 |
| anti-Her2-HC-E152C-S375C-49 | ND | 0.06 | 0.06 | ND | 0.05 | 0.05 |
| anti-Her2-HC-E152C-S375C-50 | ND | 0.08 | 0.08 | ND | 0.07 | 0.06 |

[a]Name consists of a description of the mutated antibody and a description of the compound(s) used in the chemical conjugation step.
[b]The highest concentration used in the assay was 67 nM. $IC_{50}$ values of 67 nM indicate inactivity of the ADC in the assay.
ND: Not determined Example 65: ADC Pharmacokinetic Study It has been demonstrated that a long serum half-life is critical for high in vivo efficacy of ADCs (Hamblett, et al., "Effects of drug loading on the antitumor activity of a monoclonal antibody drug conjugate," *Clin Cancer Res.*, 10:7063-7070 (2004); Alley et al., *Bioconjug Chem.* 19:759-765 (2008)). Attaching a hydrophobic drug payload to an antibody could affect the properties of an antibody, and this may lead to a fast clearance of the ADCs in vivo (Hamblett et al., 2004) and poor in vivo efficacy. To evaluate the effects of conjugation of various compounds of Formula (I) on clearance of the ADCs in vivo, pharmacokinetic studies in non-tumor bearing mice were carried out. ELISA assays for the detection of immunoconjugates were developed on a Gyros™ platform using an anti-hIgG antibody to capture human IgG molecules from the plasma and a second anti-human IgG antibody.

Figure 3:
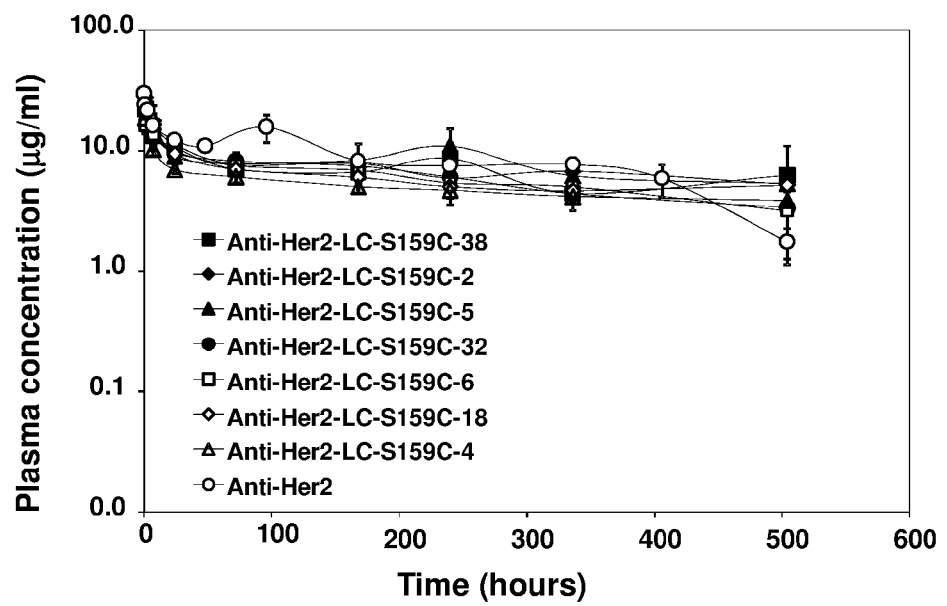
FIG. 3. Pharmacokinetic studies of anti-Her2 antibodies conjugated through engineered Cys residues using anti-hIgG assay.

Examples of PK studies are shown in FIG. 3. Three mice per group were administered with a single dose of the indicated ADCs. Seven anti-Her2 Cys mutant ADCs, anti-Her2-LC-S159C-38, anti-Her2-LC-S159C-2, anti-Her2-LC-S159C-5, anti-Her2-LC-S159C-32, anti-Her2-LC-S159C-6, anti-Her2-LC-S159C-18, and anti-Her2-LC-S159C-4, were intravenously injected into mice at 1 mg/kg. Plasma samples were collected over the course of three weeks and assayed by ELISAs to determine plasma concentration of hIgG. As shown in FIG. 3 all seven Cys-conjugated anti-Her2 ADCs containing a compound of Formula (I) exhibited excellent PK properties resembling those of wild-type un-conjugated antibody, indicating that conjugation of compounds of Formula (I) to anti-Her2 antibody did not change the PK properties of the antibody.

To determine the retention of drug payloads in ADCs after three weeks in mouse circulation, the ADCs were affinity-purified from mouse serum collected through terminal bleeding and the drug payloads attached to ADCs were analyzed by MS analysis. In this process, typically, 200 µl of plasma was diluted with an equal amount of PBS containing 10 mM EDTA. To the dilution, 10 µl of affinity resin (IgG Select Sepharose 6 Fast flow; GE Healthcare 17-0969-01; 50% slurry) is added. Resin binding was performed for 1 hr at room temperature applying mild agitation to avoid resin settling. The resin was filtered off and washed two times with 200 µl of PBS. To deglycosylate the antibody, 10 µl of PNGase F (1 mg/mL, ½×TBS pH 7.4, 2.5 mM EDTA, 50% Glycerol) diluted with 10 µl of PBS was added to the resin and incubated for 2-3 hrs at 37° C. PNGase F was then removed by washing the affinity resin 2 times with 200 µl PBS. The sample was then repeatedly (2×) eluted from the affinity resin by adding 20 µl of 1% formic acid and filtering off the resin. The combined eluate was diluted with 20 µl of 6 M guanidine hydrochloride and 5 µl of reduction buffer (0.66 M TCEP, 3.3 M ammonium acetate, pH 5). To effectively reduce the antibody, samples were incubated for at least 30 min at room temperature before analysis. LCMS was performed with an Agilent Technologies 6550-iFunnel QTOF MS/Agilent 1260 HPLC system. Standard reversed-phase chromatography was used for sample desalting (Column: PLRP-S 8 µm, 2.1×50 mm, 1000 Å) and separation (flow rate=0.5 ml/min; temp.=80° C.; buffer A) 0.1% formic acid; buffer B) 0.1% formic acid in acetonitrile; elution using linear gradient from 20%-B to 60%-B in 6 min). Agilent Qualitative Analysis was used for processing of the spectral record and spectral deconvolution. For analysis the spectral record was summed over the elution time interval covering elution of all relevant species. Sum spectra were charge-state deconvoluted and images of the deconvoluted spectra recorded. Peak intensity values were extracted for assignable species. DAR state and fragment species assignments were made based on calculated mass values from sequence and the expected mass shifts on conjugation with drug molecules. The average DAR was calculated as the DAR state weighted average of the relative peak heights across a distribution. Average antibody DAR was calculated as the sum of 2 average light chain DARs and 2 average heavy chain DARs.

The average DAR in purified ADCs after three weeks in mouse circulation was compared to the DAR in the original ADC preparations. Payload retention was calculated from the ratio of the two DARs (DAR of ADC isolated from mouse plasma/DAR of original ADC preparation), and represent the percentage of payloads remained in ADC after three weeks in mouse circulation. As shown in Table 10, payload retention ranged from 0% to 88%.

Table 10. Payload Retention on ADCs Recovered from Mice after 3 Weeks

TABLE 10

Payload retention on ADCs recovered from mice after 3 weeks

| ADC name[a] | Payload retention (%)[b] |
|---|---|
| anti-Her2-LC-S159C-3 | 42 |
| anti-Her2-LC-S159C-38 | 88 |
| anti-Her2-LC-S159C-2 | 65 |
| anti-Her2-LC-S159C-32 | 54 |
| anti-Her2-LC-S159C-18 | 43 |
| anti-Her2-LC-S159C-6 | 36 |
| anti-Her2-LC-S159C-5 | 38 |
| anti-Her2-HC-E388-DS-ppan-CoA-1-40-LEFIASKLA-N389 | 0 |
| anti-Her2-HC-E388-DS-ppan-CoA-1-39-LEFIASKLA-N389 | 43 |
| anti-Her2-HC-E388-DS-ppan-CoA-1-41-LEFIASKLA-N389 | 41 |
| anti-Her2-HC-E388-DS-ppan-CoA-i-9-40-LEFIASKLA-N389 | 12 |
| anti-Her2-HC-E388-DS-ppan-CoA-i-9-39-LEFIASKLA-N389 | 43 |
| anti-Her2-HC-E388-DS-ppan-CoA-i-9-41-LEFIASKLA-N389 | 44 |

[a]Name consists of a description of the mutated antibody and a description of the compound(s) used in the chemical conjugation step.
[b]Payload retention % = (DAR of ADCs isolated from mouse plasma after three weeks injection/DAR of ADC preparation) %

Example 66: Cellular Activity of Anti-HER2 Amanitin ADCs with DAR 4 in an In Vitro Cytotoxicity Assay The cellular activity of a series of anti-HER2 amanitin ADCs in a panel of cancer cell lines was evaluated. This panel comprised three cancer cell lines featuring endogenous expression of HER2 (MDA-MB-453, JimT-1 and NCI-N87), the HER2-negative cell line MDA-MB-231, as well as an engineered clone of MDA-MB-231 featuring exogenous overexpression of HER2, here forth called MDA-MB-231-HER2(+). Four anti-HER2 amanitin ADCs with DAR4 were generated as described in Example 60: anti-HER2-HC-E152C-S375C-23, anti-HER2-HC-E152C-S375C-47, anti-HER2-HC-E152C-S375C-49 and anti-HER2-HC-E152C-S375C-50.

The cell lines were acquired and cultured as follows: MDA-MB-453 (ATCC; RPMI-1640 (Lonza 12-702F)+10% FBS), JIMT1 (DSMZ (Deutsche Sammlung von Mikroorganismen und Zellkulturen; DMEM (Lonza 12-604)+10% FBS)); NCI-N87 (ATCC; RPMI-1640 (Lonza 12-702F)+10% FBS) and MDA-MB-231 (ATCC; RPMI-1640 (Lonza 12-702F)+10% FBS). All cell culture was performed at 37° C. in a humidified incubator. To generate the MDA-MB-231-HER2(+) cell line featuring exogenous Her2-overexpression, MDA-MB-231 breast cancer cells were stably transduced with a lentiviral construct (pLenti 6.3 (Invitrogen); driven by a cytomegalovirus enhancer-promoter) encoding a mutant form of the Her2 antigen (NM_004448; codon K753M), lacking kinase activity and therefore non-oncogenic but still recognized by the anti-Her2 antibody. A HER2-overexpressing line, MDA-MB-231-HER2(+), was isolated by fluorescence-activated cell sorting and selection with blasticidin. MDA-MB-231-HER2(+) and parental MDA-MB-231-HER2(−) cultures were maintained by passage in RPMI-1640 growth medium, supplemented with 10% (v/v) fetal bovine serum.

In Vitro Cytotoxicity Assay:

Cells in culture were trypsinized, counted and diluted in medium to a concentration of $1 \times 10^5$ cells/ml. 1000 cells/well were transferred to 384-well plates (Corning Costar#3707, Corning, Tewksbury, Mass.). ADC stock solutions were prepared in 1.4 ml Matrix tubes (Thermo, #3790, Rockford, Ill.). A 20-point, 1:3 serial dilution was prepared in a 384-well deep-well plate (Brandtech Scientific Inc #701355, Essex, Conn.) and 25 µl were transferred per assay plate (triplicates) to yield a highest starting concentration of the ADC of 33 nM. For controls, wells with cells only (=100% viability control) were prepared. Plates were incubated for 120 h at 37° C. and 5% CO2. Cellular activity of the ADCs was determined using CellTiter-Glo® reagent (Promega #G7571, Madison, Wis.) according to the manufacturer's instructions. Viability was normalized to the cells-only control, the data were plotted using Tibco Spotfire (Tibco Software Inc, Palo Alto, Calif.) and inflection point ($IC_{50}$) and Amax were derived from exporting the curve fit parameters of a logistical regression fit of the data.

Treatment of the cells with the anti-HER2 amanitin ADCs resulted in target-dependent cellular cytotoxicity (Table 11) as evidenced by activity at sub-nanomolar concentrations in HER2-positive cell lines, but not in the HER2-negative wild-type MDA-MB-231 cell line.

Table 11. Anti-HER2 Amanitin DAR 4 ADC Potency in In Vitro Cell Killing Assay

TABLE 11

Anti-HER2 amanitin DAR 4 ADC potency in in vitro cell killing assay

| ADC Name[a] | MDA-MB-231 HER2(+) | MDA-MB-231 HER2(−) | MDA-MB-453 | JimT-1 | NCI-N87 |
|---|---|---|---|---|---|
| | Inflection point: $IC_{50}$ (nM) | | | | |
| anti-Her2-HC-E152C-S375C-23 | 1.74E−04 | >33 | 2.14E−05 | 1.38E−03 | 2.54E−05 |
| anti-Her2-HC-E152C-S375C-47 | 2.05E−03 | >33 | 2.05E−05 | 2.77E−03 | 3.37E−04 |
| anti-Her2-HC-E152C-S375C-49 | 1.12E−04 | >33 | 2.28E−06 | 3.29E−04 | 1.44E−06 |
| anti-Her2-HC-E152C-S375C-50 | 3.58E−04 | >33 | 1.35E−05 | 1.65E−03 | n/a |
| | Amax % inhibition | | | | |
| anti-Her2-HC-E152C-S375C-23 | 93 | 7 | 88 | 72 | 90 |
| anti-Her2-HC-E152C-S375C-47 | 91 | 10 | 89 | 52 | 92 |
| anti-Her2-HC-E152C-S375C-49 | 93 | 32 | 87 | 81 | 92 |
| anti-Her2-HC-E152C-S375C-50 | 95 | 37 | 91 | 77 | 93 |

[a]Name consists of a description of the mutated antibody and a description of the compound(s) used in the chemical conjugation step.

In addition to the evaluation of the cellular activity of a series of anti-HER2 amanitin ADCs in a panel of cancer cell lines, the cellular activity of anti-HER2 amanitin ADCs was also evaluated in an in vitro colony formation assay using the MDA-MB-231-HER2(+) and NCI-N87 cells lines. Specifically, cells from both cell lines were either untreated or were treated with a dilution series of anti-HER2-HC-E152C-S375C-23, anti-HER2-HC-E152C-S375C-47, anti-HER2-HC-E152C-S375C-49 or anti-HER2-HC-E152C-S375C-50. The HER2 amanitin ADCs showed a concentration-dependent inhibition of colony formation, with anti-HER2-HC-E152C-S375C-23, anti-HER2-HC-E152C-S375C-49 showing the most potent inhibition across the two cell lines and anti-HER2-HC-E152C-S375C-47 showing slightly weaker activity compared to the other ADCs tested.

In Vitro Colony Formation Assay:

Cells in culture were trypsinized, counted and plated into 12-well plates (Corning, #CLS3513, Corning, Tewksbury, Mass.) at 5000 cells per well. Following incubation of cells overnight, the ADCs were diluted into cell culture media to yield 10 Ox concentration stocks for final concentrations of 1 nM, 0.01 nM, $1 \times 10-4$ nM and $1 \times 10^{-6}$ nM. 100 µl of the dilutions were added to each well followed by addition of 900 µl cell culture media. Following incubation of the plates for 8 days, cells were fixed and stained for 30 minutes at room temperature using a solution of crystal violet/formaldehyde (0.4% crystal violet dissolved in milliQwater and 25% methanol, formaldehyde added once completely resuspended-to yield final concentration of 4%; all Sigma, St Louis, Mo.). Plates were then washed twice using tap water, drained and scanned on a LiCor Odyssey imaging system (LiCor, Lincoln, Nebr.) using scan intensity 1 in the 700 nm channel at 169 µm resolution, lowest quality and 3.0 mm focus offset. The images were exported using LiCor ImageStudio software.

Example 67: Cellular Activity of Anti-HER2 Amanitin ADCs in an In Vitro Pharmacodynamic Assay Measuring Inhibition of RNA Transcription Alpha-amanitin is a potent and specific inhibitor of RNA polymerase II (Science. 1970 Oct. 23; 170(3956):447-9.) and treatment of cells with alpha-amanitin results in inhibition of RNA polymerase II-dependent transcription. To evaluate the activity of anti-HER2 amanitin ADCs to inhibit RNA polymerase II, a microscopy-based in vitro assay was developed to measure nascent RNA transcripts following amanitin ADC treatment. Specifically, MDA-MB-231-HER2(+) cells were treated with a dilution series of anti-HER2-HC-E152C-S375C-23, anti-HER2-HC-E152C-S375C-47, anti-HER2-HC-E152C-S375C-49 or anti-HER2-HC-E152C-S375C-50 ADCs.

In Vitro Pharmacodynamics Assay to Measure Inhibition of Nascent RNA Transcription:

Cells in culture were trypsinized, counted and plated into a 96-well cell bind plate (Corning#354640 (Biocoat Plates), Corning, Tewksbury, Mass.) at 40,000 cells per well. ADC stock solutions were prepared as 10× stocks in 1.4 ml Matrix tubes (Thermo, #3790, Rockford, Ill.) and serially diluted 1:10 across 6 concentration points. Cells were treated with the ADCs and incubated for 24 h at 37 degrees Celsius. Following this incubation cells were stained using the Click-iT® RNA Alexa Fluor® 488 HCS Assay (Molecular Probes#C10327, Lot#1698441; Thermo Scientific, Rockford, Ill.; PNAS (2008) 105:15779-84) according to the manufacturer's instructions. Briefly, following 24 h treatment of cells with the ADCs, cells were incubated for 2 hours with 5-ethynyl uridine (EU) at 1 mM final concentration. Following this step all incubations were done protected from light. After EU incubation cells were fixed, permeabilized and incubated with the Click-IT reaction cocktail for 30 minutes at room temperature. Cells were then washed and stained using HCS Nuclear Mask Blue reagent for 15 minutes at room temperature, washed twice in PBS and kept in PBS onward. The plates were scanned on an InCell2000 imager (GE Healtcare Life Sciences, Marlborough, Mass.). Nine images per well were acquired using 10× magnification and data were analyzed using the InCell Developer Toolbox software. The number of positive objects was determined using object based segmentation in the DAPI channel to count all nuclei. The FITC channel was used to quantify both number of objects and intensity corresponding to the RNA signal in treated versus non-treated cells. The mean object RNA intensity data were plotted using Tibco Spotfire (Tibco Software Inc, Palo Alto, Calif.) and $IC_{50}$ and maximal inhibition were derived from exporting the curve fit parameters of a logistical regression fit of the data.

Consistent with the cellular activity as read out by the in vitro cytotoxicity and colony formation assays, a concentration-dependent inhibition of nascent RNA transcript production following ADC treatment was observed. The $IC_{50}$ and max % RNA inhibition obtained are given in Table 12.

Table 12. Anti-HER2 Amanitin ADC Cellular Activity Summary: RNA Transcription Assay

TABLE 12

Anti-HER2 amanitin ADC cellular activity summary: RNA transcription assay

| ADC Name[a] | $IC_{50}$ (nM) | max % RNA inhibition relative to untreated |
|---|---|---|
| anti-Her2-HC-E152C-S375C-23 | 0.012 | 18 |
| anti-Her2-HC-E152C-S375C-47 | 0.055 | 17 |
| anti-Her2-HC-E152C-S375C-49 | 0.0096 | 22 |
| anti-Her2-HC-E152C-S375C-50 | 0.0039 | 13 |
| Untreated | — | — |

[a]Name consists of a description of the mutated antibody and a description of the compound(s) used in the chemical conjugation step.

Example 68: Dose-Dependent In Vivo Efficacy of Anti-HER2-Cys-mAb-Amanitin ADCs Against the N87 HER2-Positive Gastric Model in Mice Xenograft models of human cancer have played an important role in the screening and evaluation of new antibody drug candidates (ADCs) in an in vivo setting. The NCI-N87 gastric model expresses approximately 250,000 Her2 receptors on the surface of each cell. Given the high expression of the Her2 receptor in this model, this is an ideal setting to assess in vivo efficacy of anti-Her2 antibodies in both in vitro and in vivo assays. Therefore, the N87 xenograft model was use to assess the in vivo efficacy of anti-HER2-HC-E152C-S375C-23 in a dose-dependent manner.

Materials and Methods

For N87 gastric carcinoma xenograft mouse model, female nu/nu mice at 6-8 weeks of age (purchased from Charles River Laboratories) were used for implantation. N87 cells (obtained from ATCC, Catalog#CRL-5822) were grown in sterile conditions in a 37° C. incubator with 5% $CO_2$ for two weeks. Cells were grown in RPMI medium with 10% fetal bovine serum. Cells were passaged every 3-4 days with 0.05% Trypsin/EDTA. On the day of implantation, N87 cells were lifted (passage ×4) and re-suspended in RPMI1640 serum-free media at a concentration of $1×10^6$ cells and 50% matrigel/100 µl.

N87 cells were implanted with a subcutaneous injection into the lower flank using a 28 gauge needle (100 µl injection volume). After implant, tumors were measured by caliper and mice weighed two times per week once tumors were palpable. Tumors then were measured twice a week in two dimensions. Caliper measurements were calculated using $(L×W^2)/2$. Mice were fed with normal diet and housed in SPF animal facility in accordance with the Guide for Care and Use of Laboratory Animals and regulations of the Institutional Animal Care and Use Committee.

When xenograft tumors reached about 200 $mm^3$, mice were administered by intravenous route 2.5-10 mg/kg of ADC (anti-HER2-HC-E152C-S375C-23). Isotype control antibody-23 was generated by expressing an antibody against a target not found in rodents and conjugating through similar methods described for anti-HER2 antibodies. Tumors were measured twice a week. Average tumor volumes were plotted using Prism 5 (GraphPad) software and stastical analysis was performed using SigmaPlot 12.0. An endpoint for efficacy studies was achieved when tumor size reached a volume approximately 1500 $mm^3$. Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

Results

Figure 4:
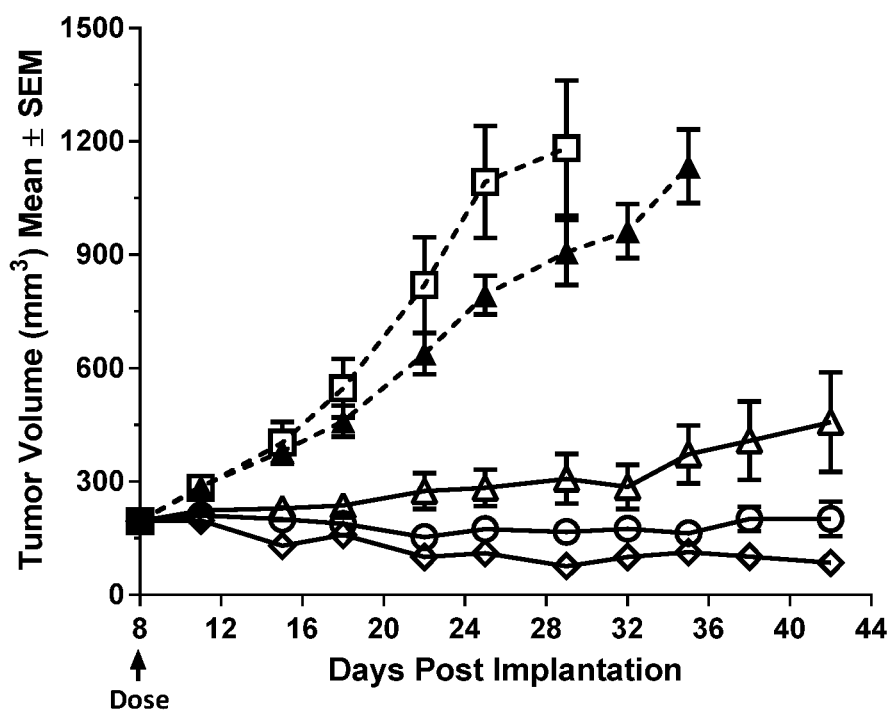
FIG. 4. Efficacy of anti-Her2-HC-E152C-S375C-23 in the NCI-N87 gastric model. Open Squares: Vehicle; Filled Triangle: Isotype control; Open Triangle: 2.5 mg/kg anti-Her2-HC-E152C-S375C-23; Open Circles: 5 mg/kg anti-Her2-HC-E152C-S375C-23 and Open Diamonds: 10 mg/kg anti-Her2-HC-E152C-S375C-23.

Female nude mice were implanted subcutaneously with $5×10^6$ N87 cells in a suspension containing 50% Matrigel™ (BD Biosciences) in Hank's balanced salt solution. The total injection volume containing cells in suspension was 200 µl. When tumors averaged ~200 mm3, mice were randomized according to tumor volume into treatment groups (n=5/group) and dosed with a single IV administration of either anti-HER2-HC-E152C-S375C-23 (2.5, 5, 10 mg/kg), non-specific isotype control antibody-23 (10 mg/kg) or vehicle control (PBS). Doses were adjusted to individual mouse body weights and the IV dose volume was 10 ml/kg. The mean tumor volumes in the 2.5-10 mg/kg anti-HER2-HC-E152C-S375C-23 treated groups were significantly different from the isotype control group and the vehicle group on day 29 (One way ANOVA; Ranks/Tukey's test, p≤0.05). % ΔT/ΔC or regression (denoted by negative values) at day 29 for the groups treated with anti-HER2-HC-E152C-S375C-23 were as follows: 11.4% (2.5 mg/kg), −14.8% (5 mg/kg), −59.4% (10.0 mg/kg). No significant body weight loss was observed in any group. Tumor regression was observed following the single dose of anti-HER2-HC-E152C-S375C-23 in the 5 and 10 mg/kg groups, with sustained durable responses lasting for days for 23 and 35 days respectively (FIG. 4).

Example 69: In Vitro Stability

A thio-Mannich reaction was used to attach the linkers to the 7' position of the amatoxin indole in the compounds and immunoconjugates of the invention. The stability of this drug-linker attachment was measured by monitoring the Drug-to-Antibody Ratio (DAR) as a function of time. Briefly, 200 ul of anti-Her2-LC-S159C-24 in PBS (0.8 mg/ml) was incubated at 37° C. Aliquots of 20 uL were drawn at 0, 2, 5, 8, 20, 48, 96, and 192 hours of incubation and stored at −80° C. until further analysis.

The conjugation state of the antibody light chain (LC) was assessed after disulfide reduction by LCMS. For that purpose time point aliquots were diluted 3 fold by addition of one sample volume of 6M Guanidinium Hydrochloride in 100 mM Na Formate pH 4, and another sample volume of a 2:1 mixture of 1 M Tris(2-carboxyethyl)phosphine hydrochloride and 10M ammonium acetate. The reduced samples were desalted and analyzed by reversed-phase liquid chromatography mass spectrometry using an Agilent 1260 UHPLC coupled to an Agilent 6550 mass spectrometer. Analysis was performed with an Agilent PLRP-S 8 μm, 2.1×50 mm, 1000 Å column at 60° C. A linear gradient from 20% B (Buffer B=0.1% Formic Acid in Acetonitrile, Buffer A=0.1% Formic Acid in water) to 60% B in 6 min at a flow rate of 0.5 ml/min was used for elution into the mass spectrometer.

Chromatogram extraction, spectrum averaging over analyte peaks, and charge-state deconvolution was performed using the instrument manufacturer's software (Agilent MassHunter). Peak assignments were made based on theoretically calculated masses for free light chain (LC), conjugated LC, and cleaved LC species and the DAR was calculated as the DAR state weighted (weight of 0 for free LC and cleaved LC species; weight of 1 for conjugated LC species) average over the distribution of species using peak intensity values. The calculated experimental DAR values are plotted as a function of incubation time together with predicted values on the basis of fitting the data to a first-order exponential decay model in A=Ao*exp(−k*t), where A is the predicted DAR value, Ao is the predicted DAR at the zero time point, k is the first order decay constant, and t is the incubation time. Fitting was performed in Microsoft Excel using the Solver Add-in. The first order decay constant was transformed into a half-life value $t_{1/2}$ using the relation $t_{1/2}=\ln(2)/k$.

The in vitro stability of thio-mannich attachment was found to be significantly improved in comparison to the typical Mannich reaction (WO2014043403). This improved stability is illustrated in Table 12, where the $t_{1/2}$ (hours) for the release of free drug or drug-linker from an ADC are shown.

TABLE 12

| | | $t\ \frac{1}{2}$ (hours) |
|---|---|---|
| 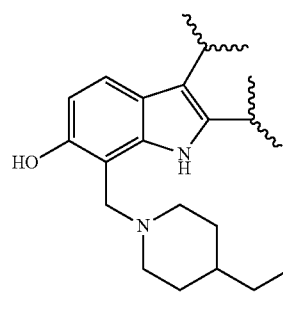 alfa-Amanitin | WO2014043403 Example 27 Herceptin Conjugate | 41 |
| 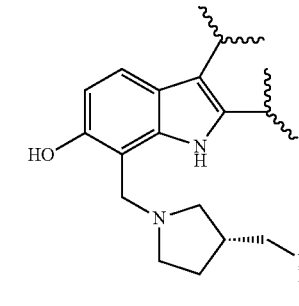 alfa-Amanitin | WO2014043403 Example 30 Herceptin Conjugate | 290 |
| 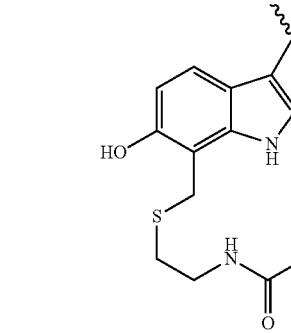 alfa-Amanitin | Compound (24) antiHer2 S159C Conjugate | 660 |

We claim:

1. A compound or stereoisomer thereof having the structure of Formula (I)

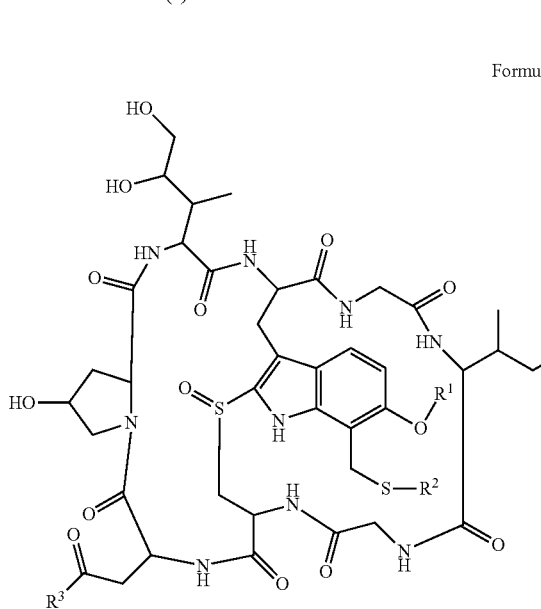

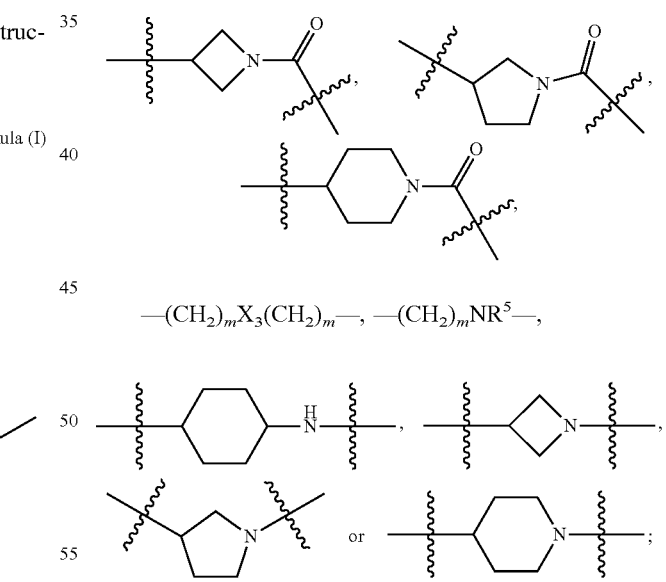

wherein:

$R^1$ is H or —$CH_3$;

$R^2$ is -$L_1L_2R^4$, -$L_3R^6$ or —$(CH_2)_mX_3(CH_2)_mR^4$;

$R^3$ is —$NH_2$ or —OH;

$L_1$ is —$(CH_2)_mNR^5C(=O)$—, $L_2$ is —$(CH_2)_m$—, —$NR^5(CH_2)_m$—, —$(CH_2)_mNR^5C(=O)(CH_2)_m$—, —$X_4$, —$(CH_2)_mNR^5C(=O)X_4$, —$(CH_2)_mNR^5C(=O)$—, —$((CH_2)_mO)_n(CH_2)_m$—, —$((CH_2)_mO)_n(CH_2)_mX_3(CH_2)_m$—, —$NR^5((CH_2)_mO)_nX_3(CH_2)_m$—, —$NR^5((CH_2)_mO)_n(CH_2)_mX_3(CH_2)_m$—, —$X_1X_2C(=O)(CH_2)_m$—, —$(CH_2)_m(O(CH_2)_m)_n$—, —$(CH_2)_mNR^5C(CH_2)_m$—, —$(CH_2)_mNR^5C(=O)(CH_2)_m X_3(CH_2)_m$—, —$(CH_2)_mC(=O)NR^5(CH_2)_m NR^5C(=O)(CH_2)_m$—, —$(CH_2)_mC(=O)$—, —$(CH_2)_m NR^5(CH_2)_mC(=O)X_2X_1C(=O)$—, —$(CH_2)_mX_3$

—(CH$_2$)$_m$C(=O)X$_2$X$_1$C(=O)—, —(CH$_2$)$_m$C(=O)NR$^5$(CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$X$_3$(CH$_2$)$_m$C(=O)NR$^5$(CH$_2$)$_m$—, —(CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$(O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$C(R$^5$)$_2$NR$^5$—, —(CH$_2$)$_m$C(=O)NR$^5$(CH$_2$)$_m$NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —(CH$_2$)$_m$C(=O)NR$^5$(CH$_2$)$_m$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$(CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$(O(CH$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)$_m$C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$— or —(CH$_2$)$_m$X$_3$(CH$_2$)$_m$NR$^5$C(=O)—, wherein:

X$_1$ is

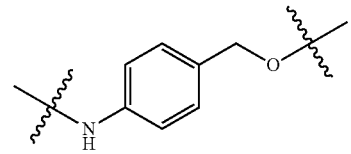

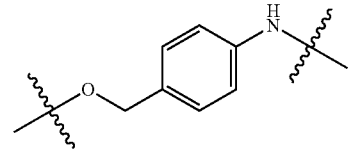

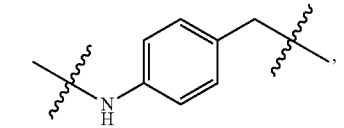

-continued

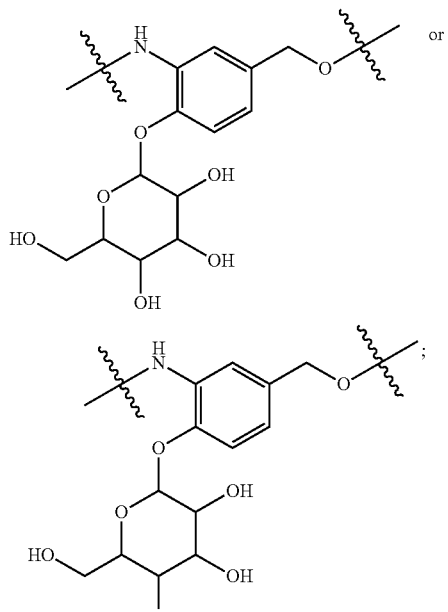

X$_2$ is

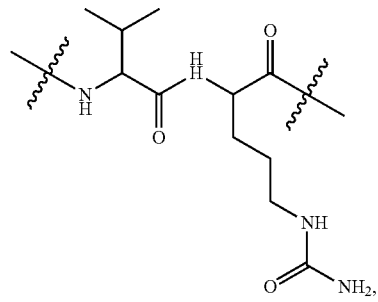

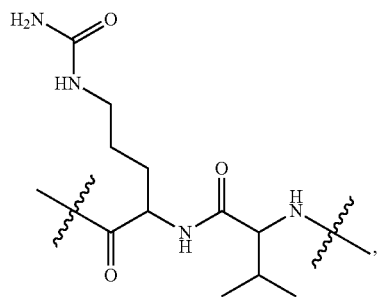

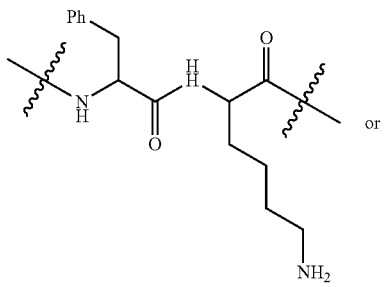

559
-continued
$X_3$ is
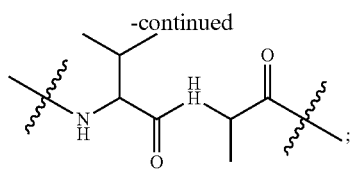
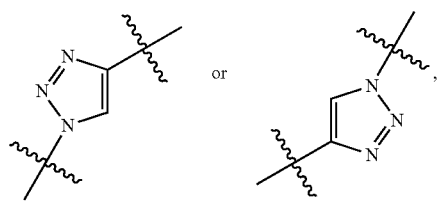 [SMILES: *c1cn(*)nn1 ; *c1cn(*)nn1]
and
$X_4$ is
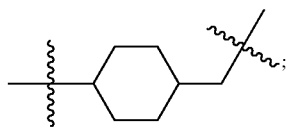 [SMILES: *CC1CCC(*)CC1]
$L_3$ is $-(CH_2)_m NR^5 C(=O)-$;
$R^4$ is
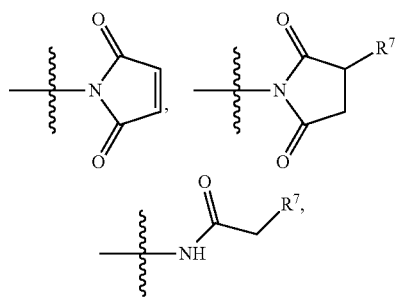
$-NR_5C(=O)CH=CH_2$, $-N_3$,
560
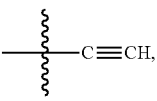
$-SH$, $-S(=O)_2(CH=CH_2)$, $-NR^5S(=O)_2(CH=CH_2)$, $-NR^5C(=O)CH_2R^7$, $-NR^5C(=O)CH_2Br$, $-NR^5C(=O)CH_2I$, $-NHC(=O)CH_2Br$, $-NHC(=O)CH_2I$, $-ONH_2$, $-C(=O)NHNH_2$,
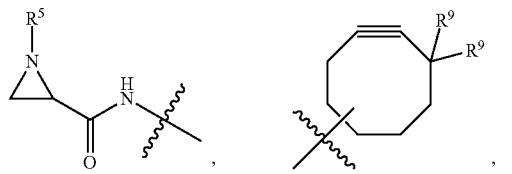
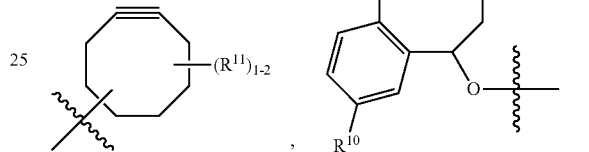
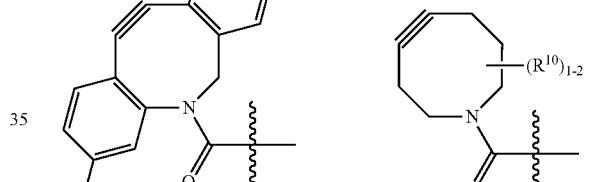
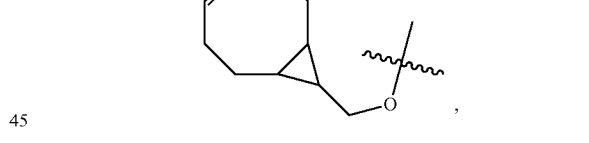
$-CO_2H$, $-NH_2$, $-NCO$, $-NCS$,
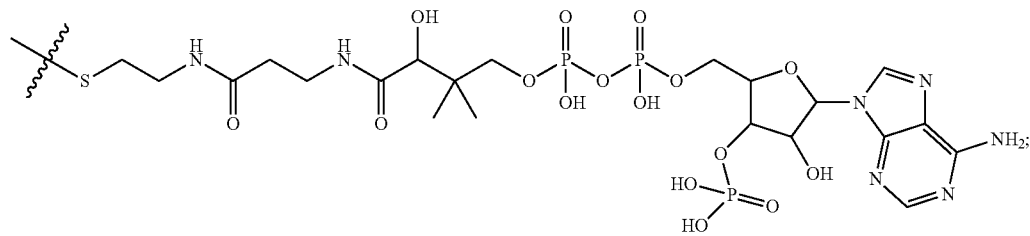
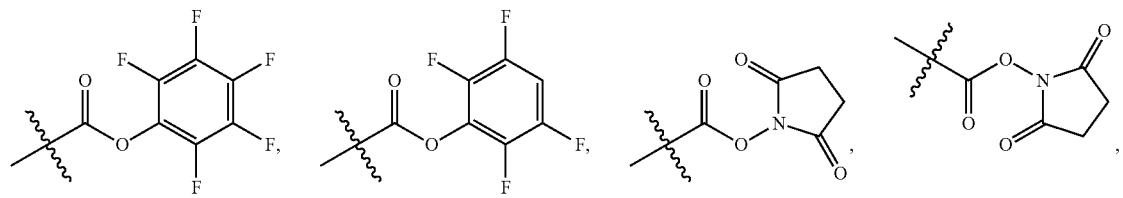

-continued

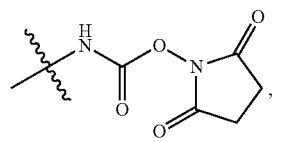, 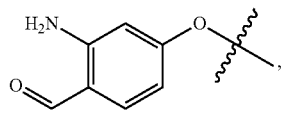, 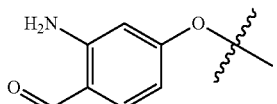 or

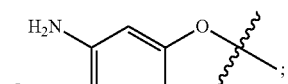;

each R⁵ is independently selected from H and $C_1$-$C_6$alkyl;
R⁶ is

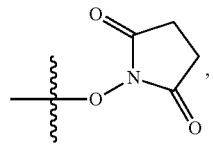, 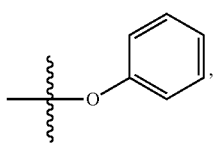,

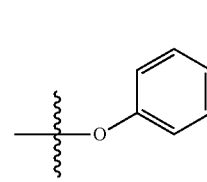, or 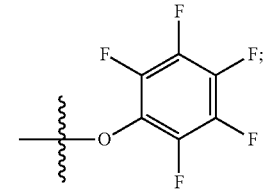;

R⁷ is —S(CH₂)ₙCHR⁸NHC(=O)R⁵ or

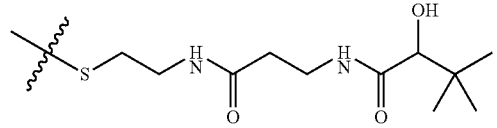

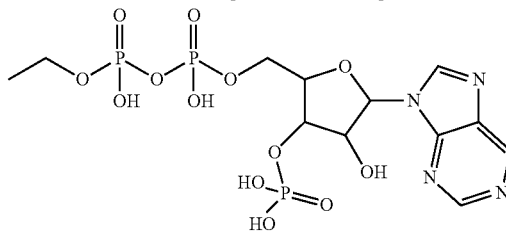

R⁸ is R⁵ or —C(=O)OR⁵;
each R⁹ is independently selected from H, $C_1$-$C_6$alkyl, F, Cl, and —OH;
each R¹⁰ is independently selected from H, $C_1$-$C_6$alkyl, F, Cl, —NH₂, —OCH₃, —OCH₂CH₃, —N(CH₃)₂, —CN, —NO₂ and —OH;
each R¹¹ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, 4, 5, 6, 7, 8, 9 and 10;

each n is independently selected from 1, 2, 3, 4, 5, 6, 7, 8, 9, 10, 11, 12, 13 and 14;
or a pharmaceutically acceptable salt thereof.

2. The compound of claim 1, wherein the compound is a compound having the structure of Formula (Ia):

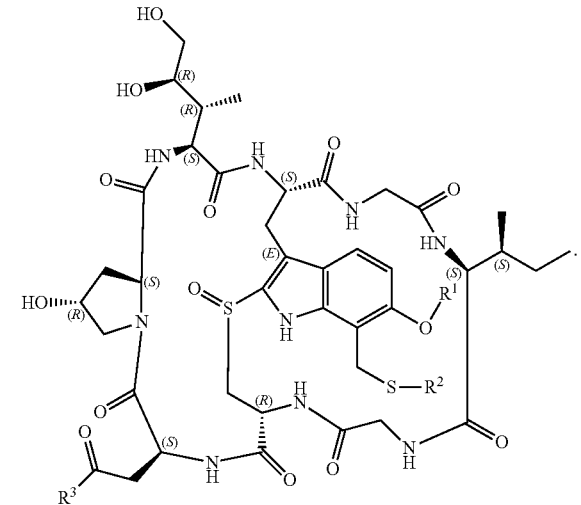

Formula (Ia)

3. The compound of claim 1, wherein:
R¹ is H or —CH₃;
R² is -L₁L₂R⁴, -L₃R⁶ or —(CH₂)ₘX₃(CH₂)ₘR⁴;
R³ is —NH₂ or —OH;
L₁ is —(CH₂)ₘNR⁵C(=O)—,

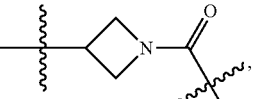, 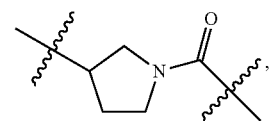,

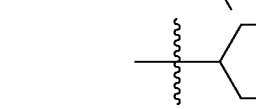

or —(CH₂)ₘX₃(CH₂)ₘ—;

$L_2$ is —$(CH_2)_m$—, —$NR^5(CH_2)_m$—, —$(CH_2)_mNR^5C(=O)(CH_2)_m$—, —$X_4$—, —$(CH_2)_mNR^5C(=O)X_4$—, —$(CH_2)_mNR^5C(=O)$—, —$((CH_2)_mO)_n(CH_2)_m$—, —$((CH_2)_mO)_n(CH_2)_mX_3(CH_2)_m$—, —$NR^5((CH_2)_mO)_n X_3(CH_2)_m$—, —$NR^5((CH_2)_mO)_n(CH_2)_mX_3(CH_2)_m$— or —$X_1X_2C(=O)(CH_2)_m$—,
wherein:
$X_1$ is

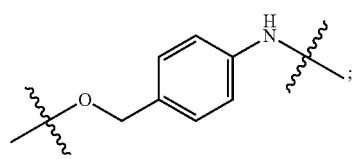 [SMILES: *Nc1ccc(CO*)cc1]

$X_2$ is

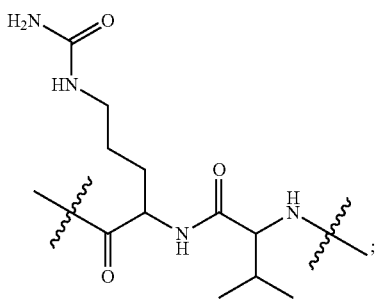 [SMILES: *NC(C(=O)NC(CCCNC(N)=O)C(*)=O)C(C)C]

$X_3$ is

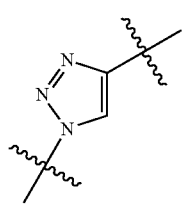 [SMILES: *c1cn(*)nn1]

and
$X_4$ is

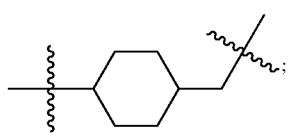 [SMILES: *CC1CCC(*)CC1]

$L_3$ is —$(CH_2)_mNR^5C(=O)$—;
$R^4$ is

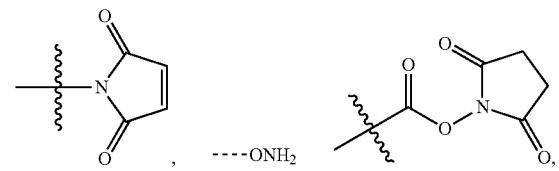

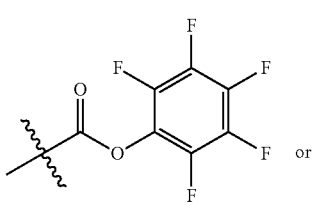 or

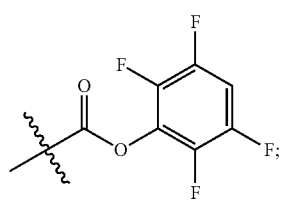;

each $R^5$ is independently selected from H and $C_1$-$C_6$alkyl;
$R^6$ is

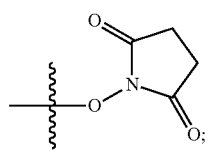;

each m is independently selected from 1, 2, 3, 4, 5, 6, 7, 8, 9 and 10,
and
each n is independently selected from 1, 2, 3, 4, 5, 6, 7, 8, 9, 10, 11, 12, 13 and 14.

4. The compound of claim 1, wherein $R^2$ is

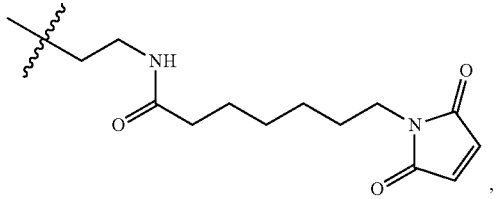 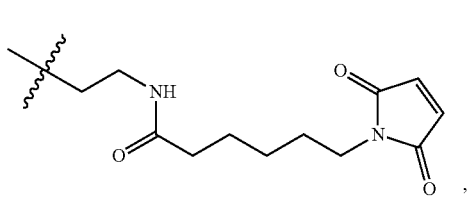

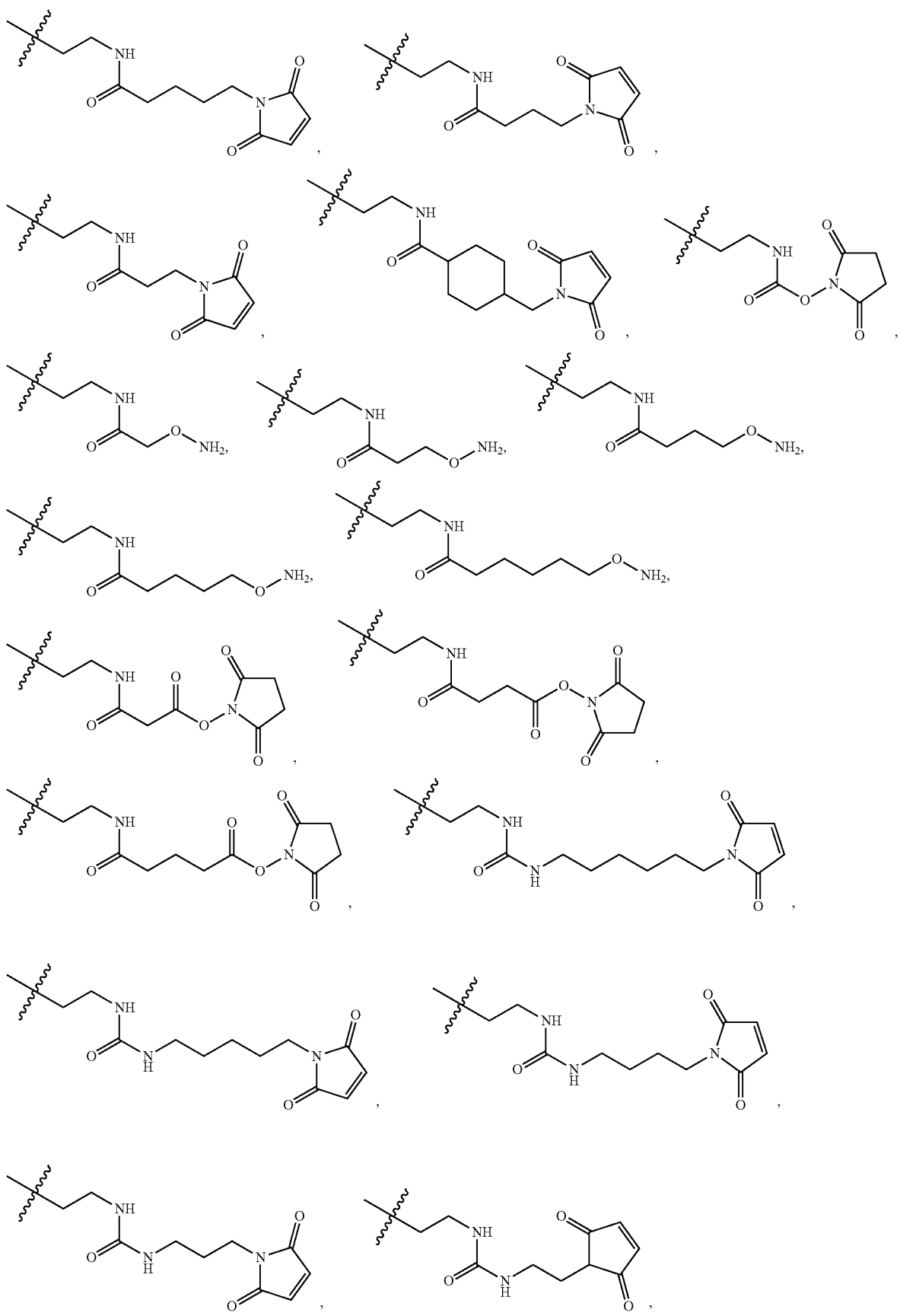

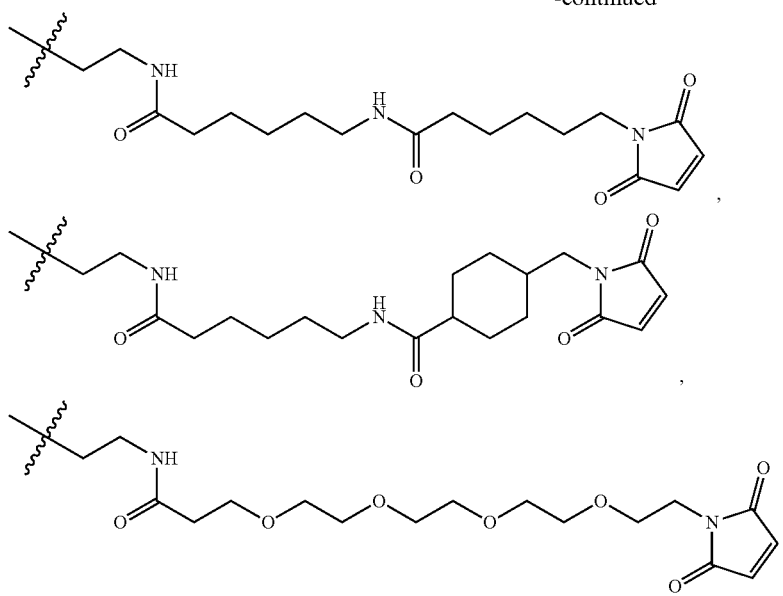
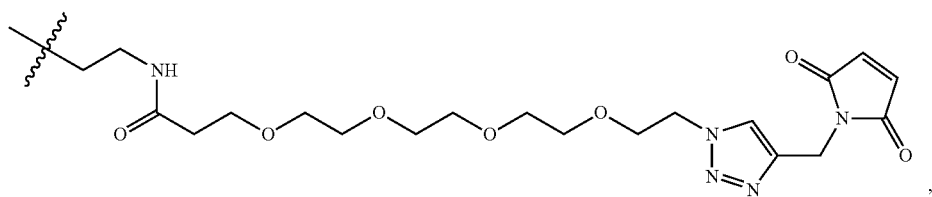
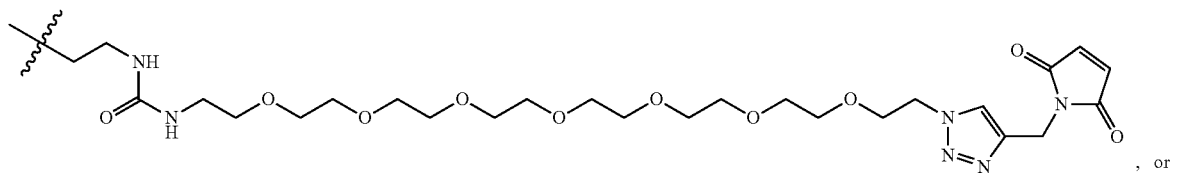
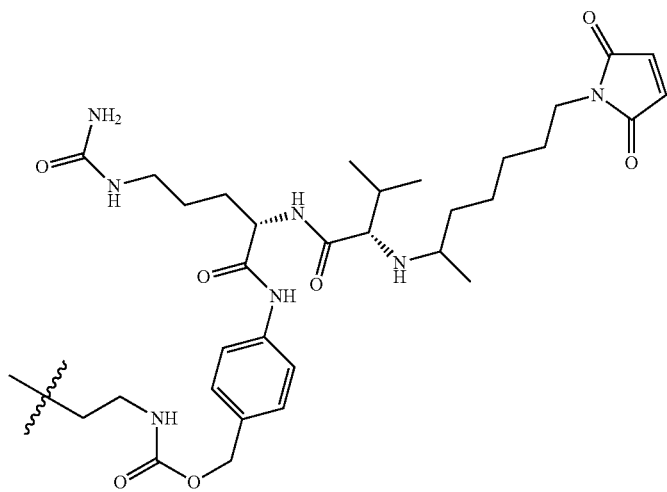

5. The compound of claim 1, wherein R² is
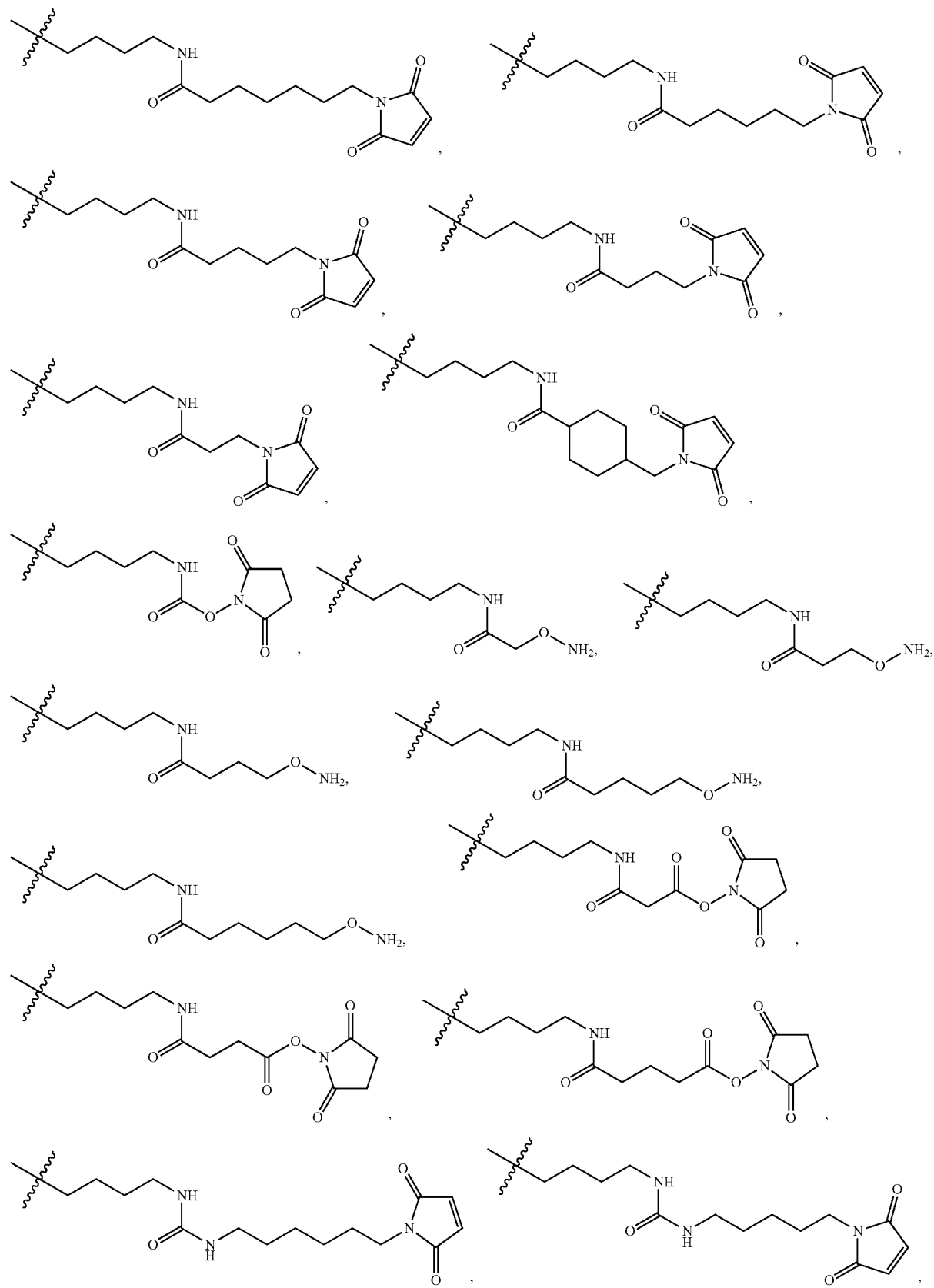

571                                              572
-continued
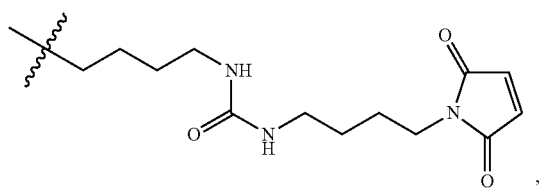 , 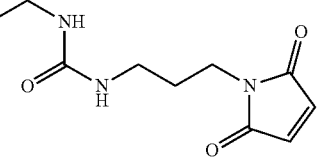 ,
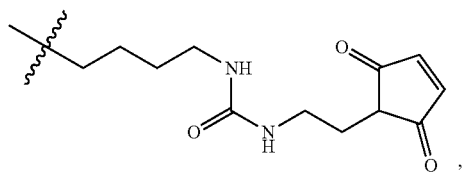 ,
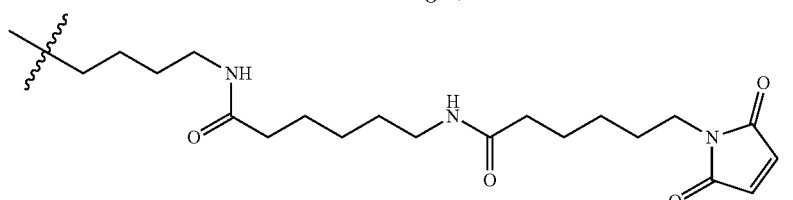 ,
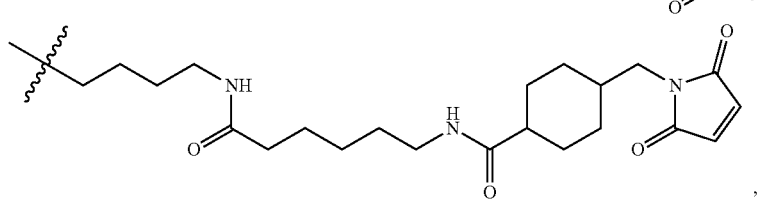 ,
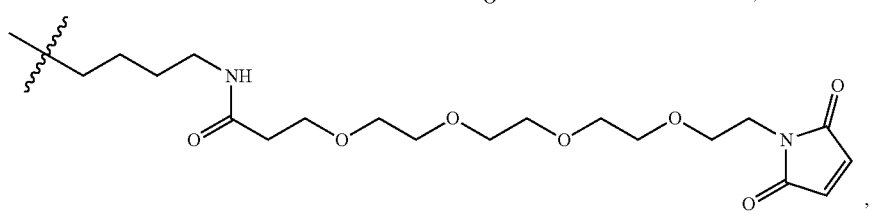 ,
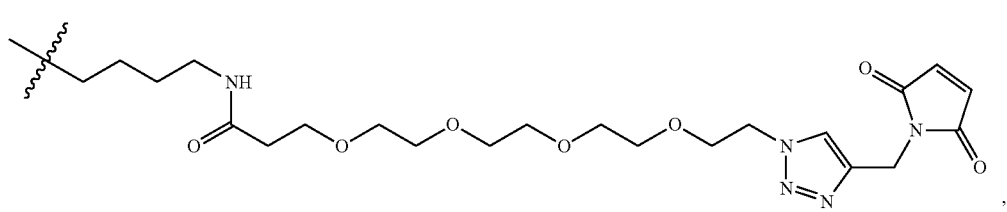 ,
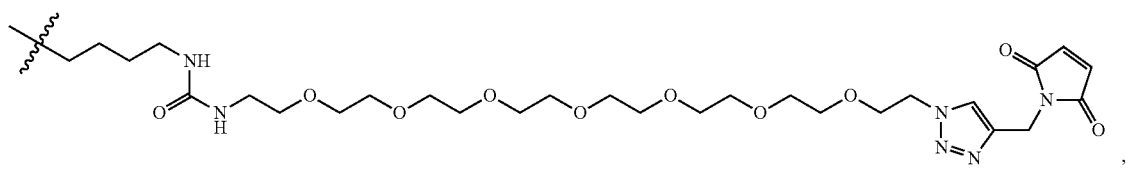 ,
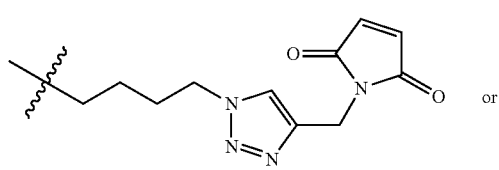 or -continued
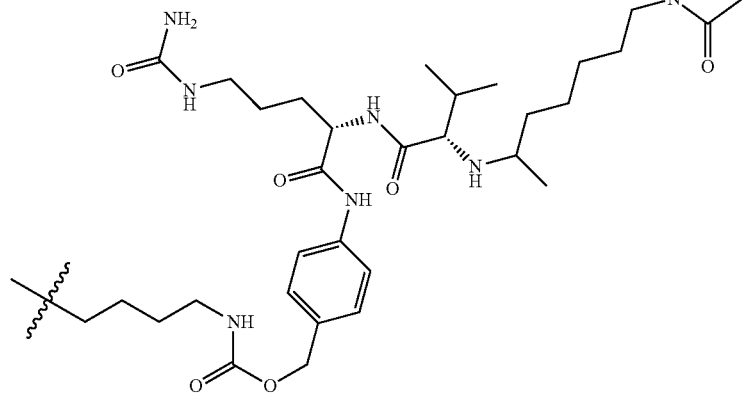
6. The compound of claim 1, wherein $R^2$ is
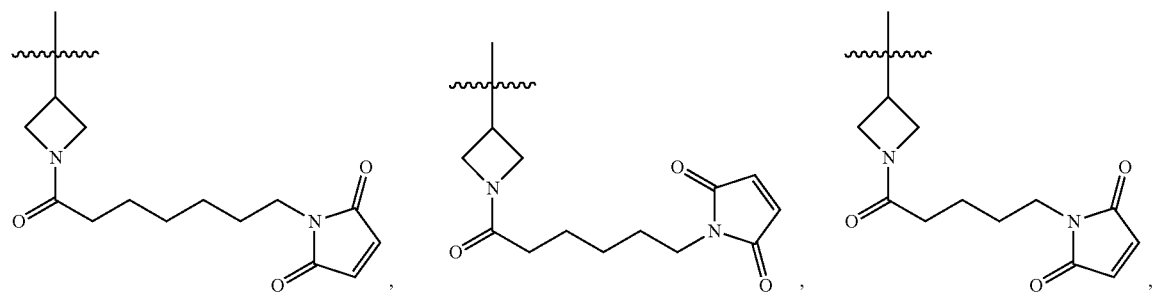
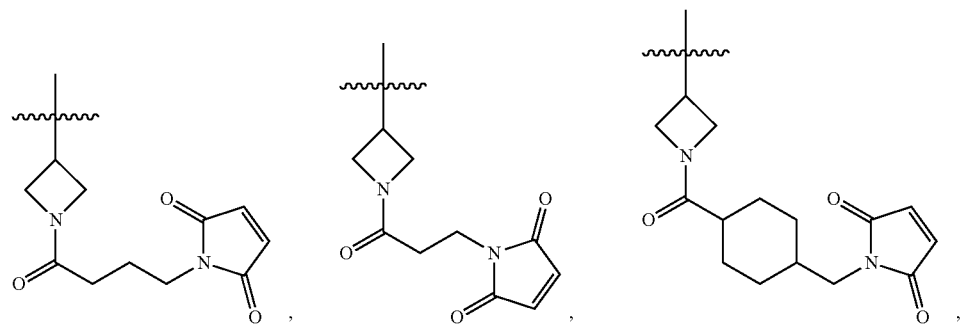
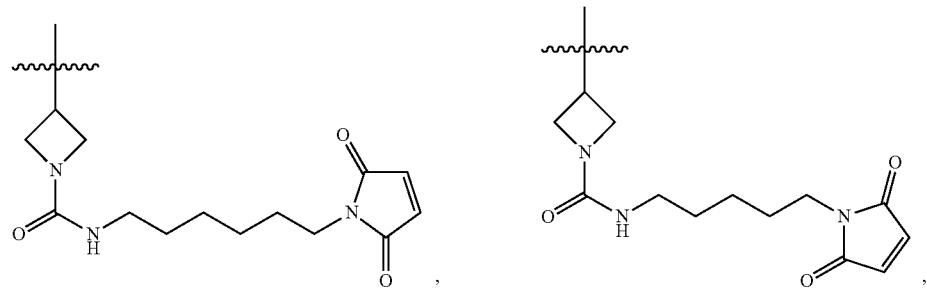

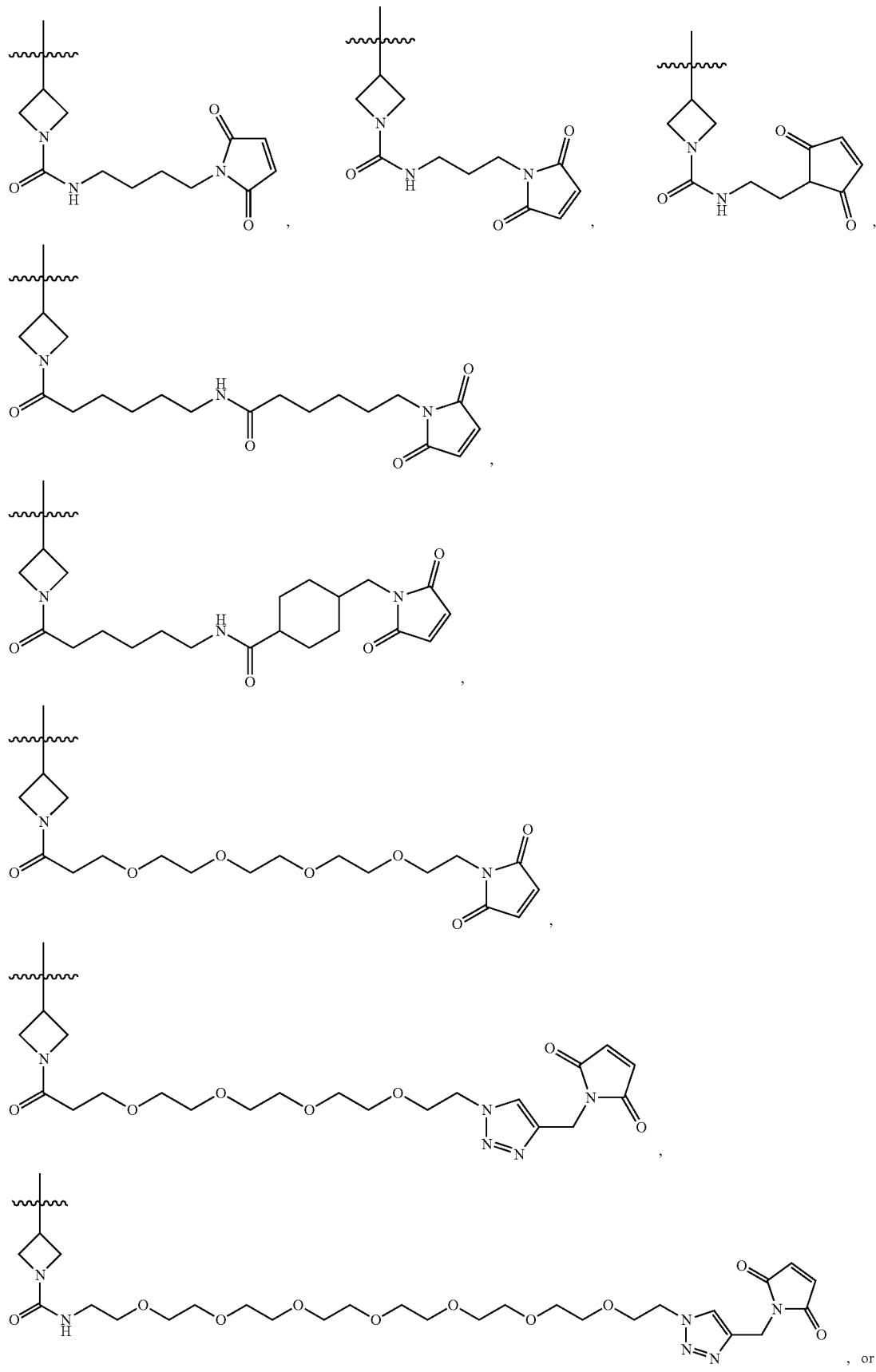

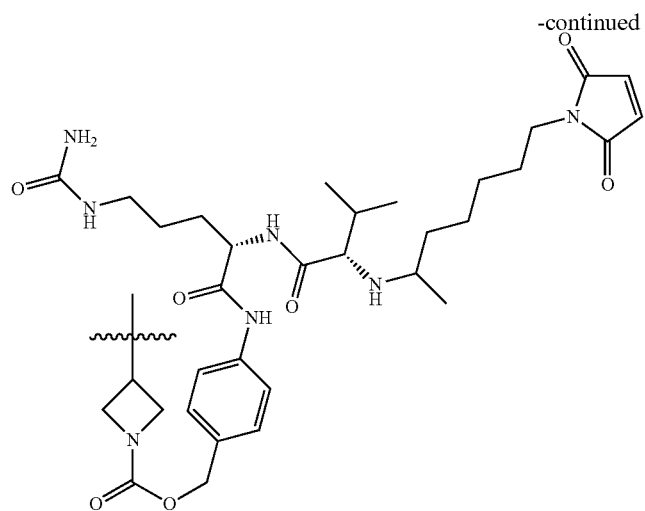
7. The compound of claim 1, wherein $R^2$ is
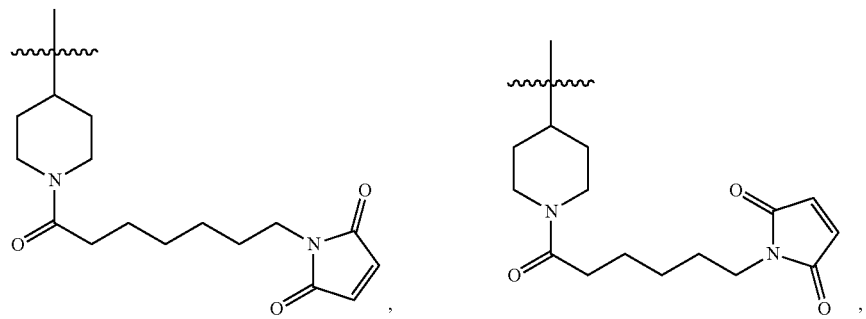
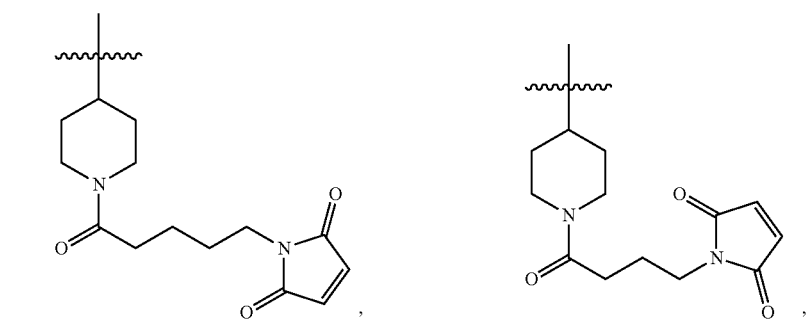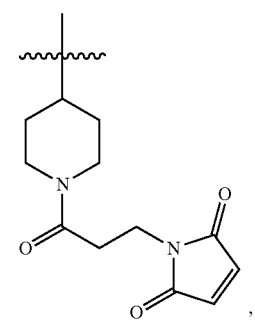
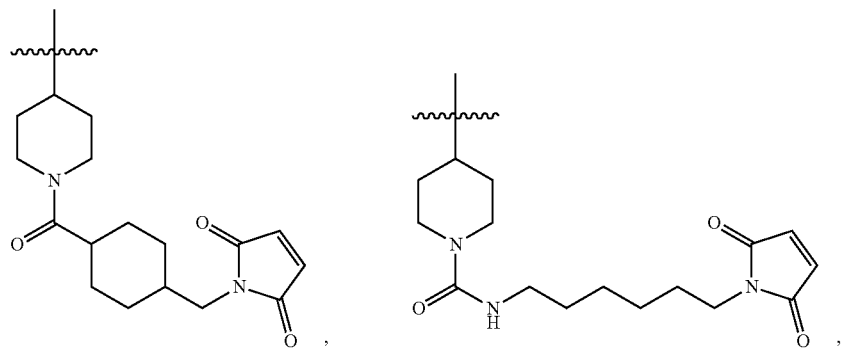

-continued
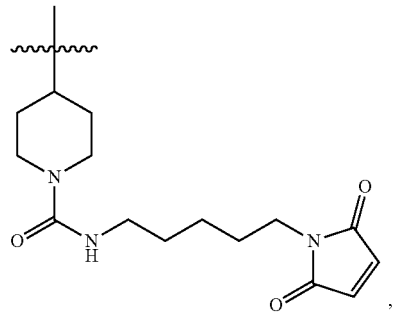 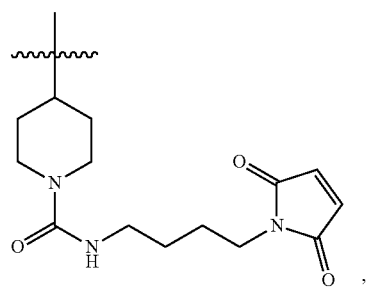
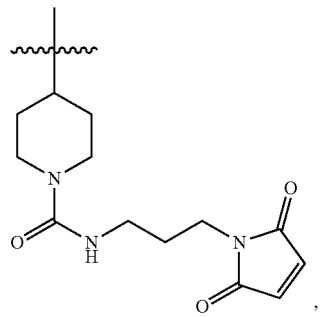 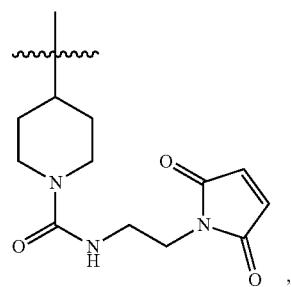 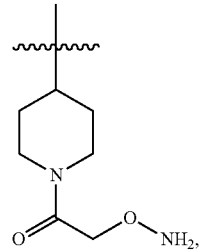 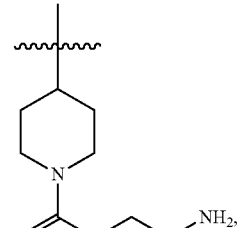
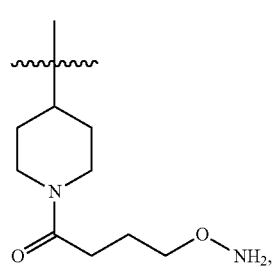 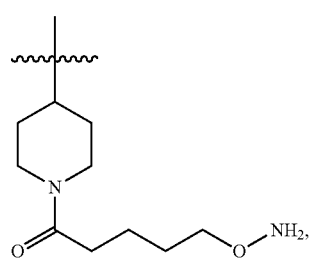 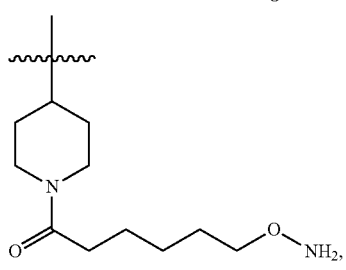
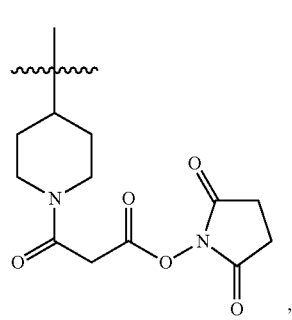 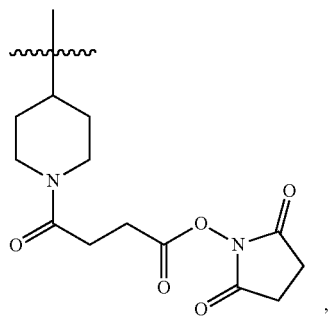 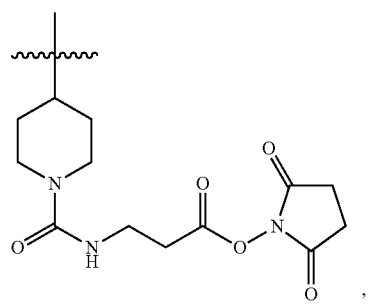
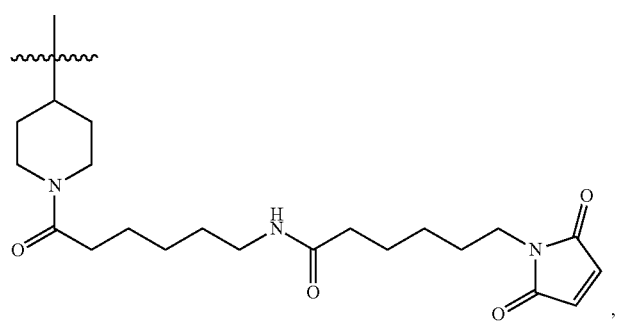

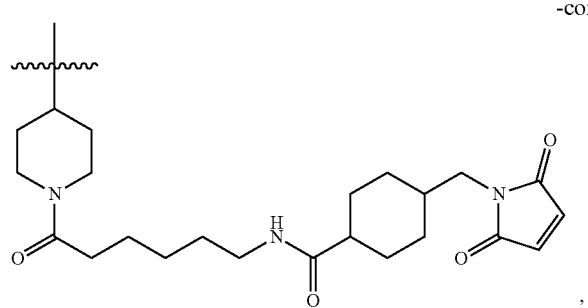
,
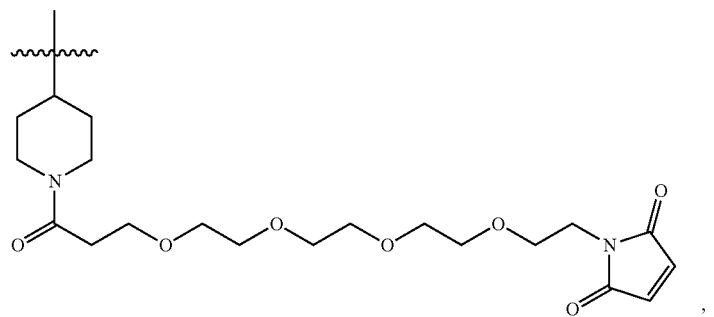
,
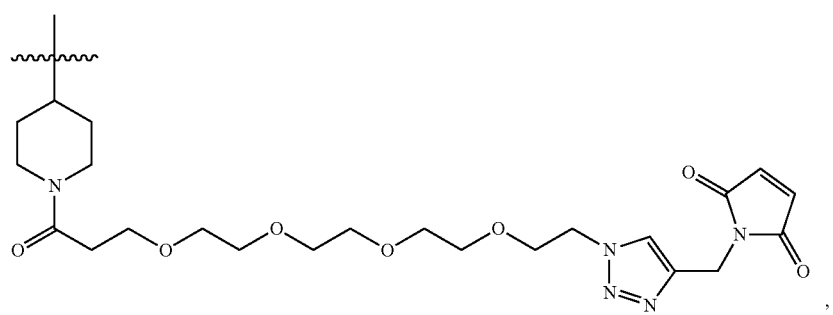
,
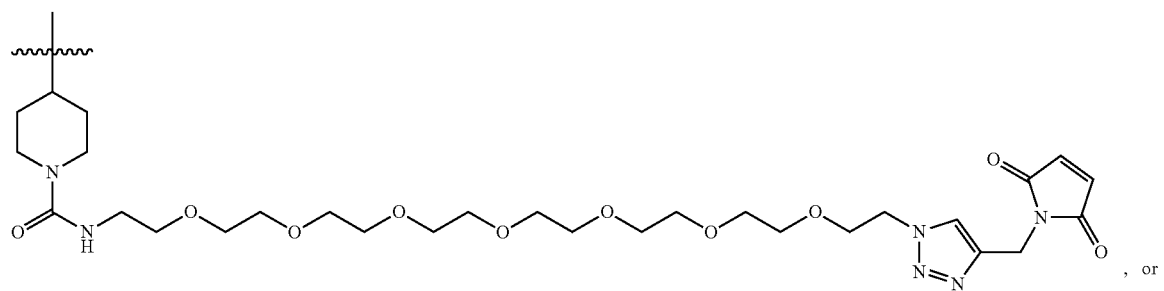
, or

-continued
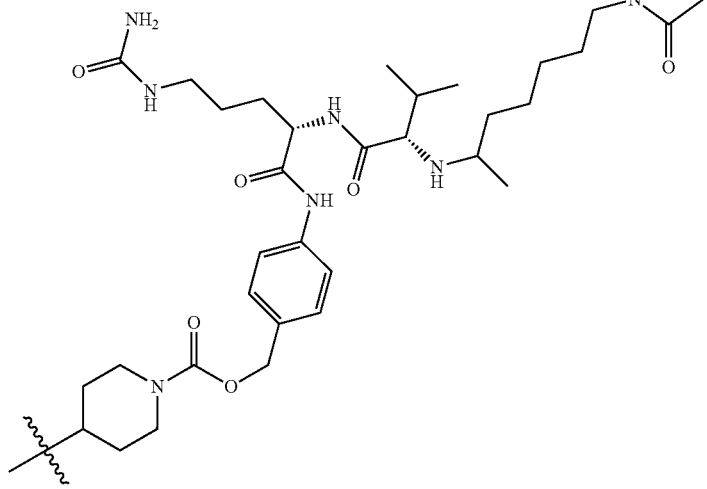
8. The compound of claim 1, wherein $R^2$ is
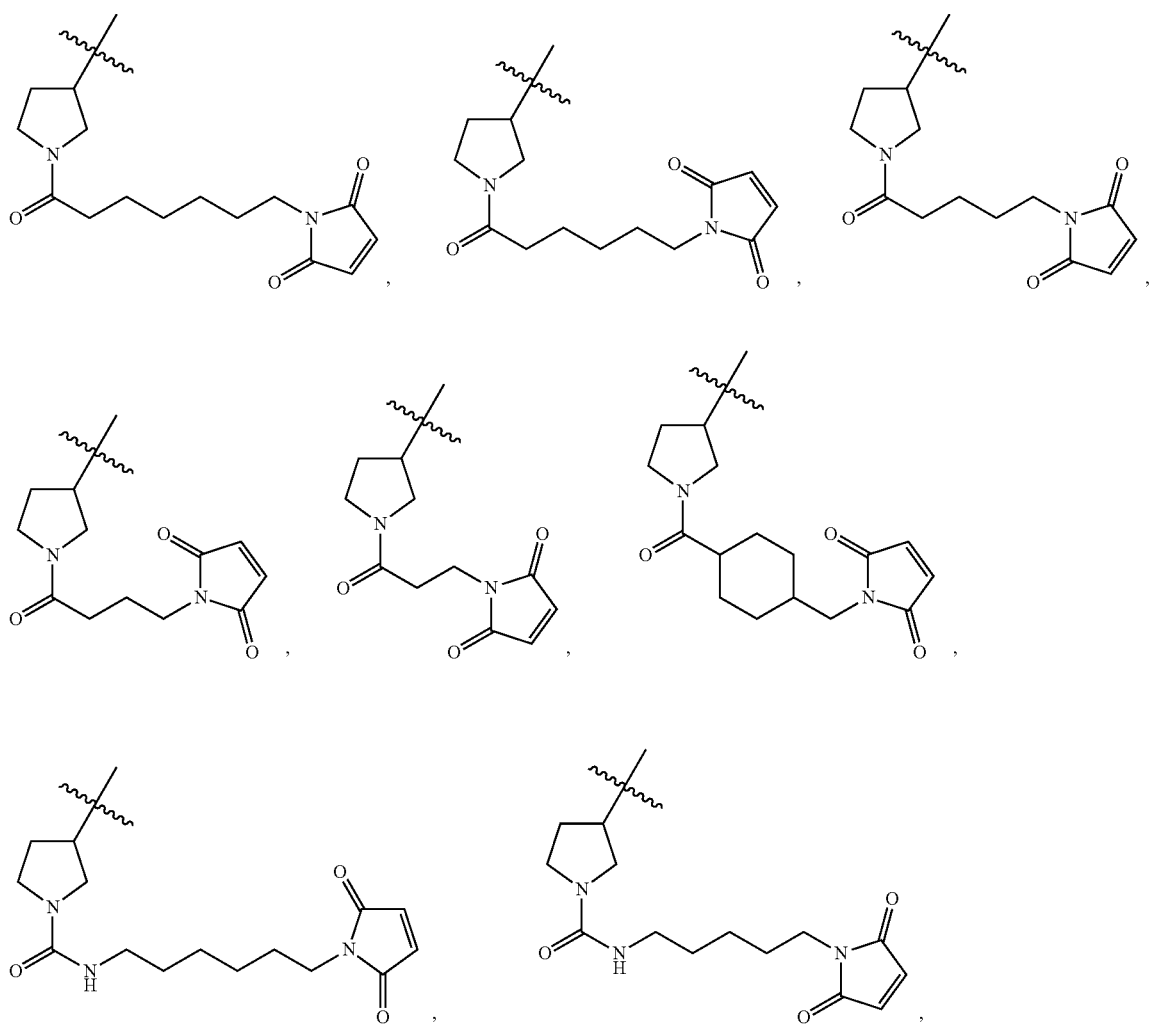

-continued
585
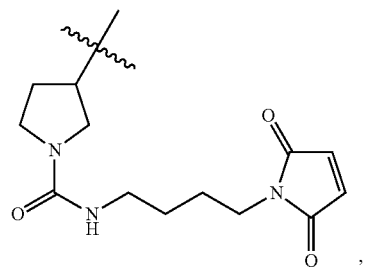 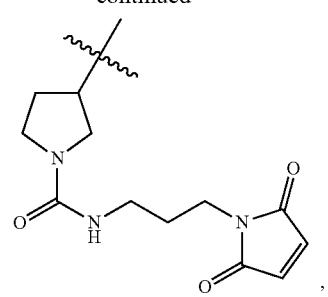 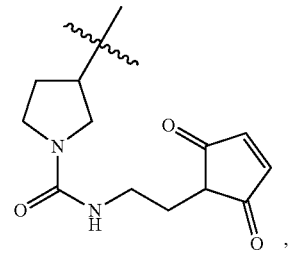
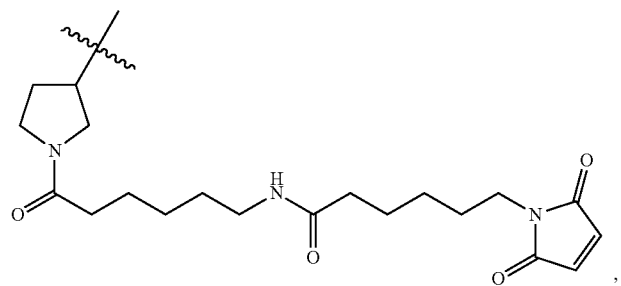
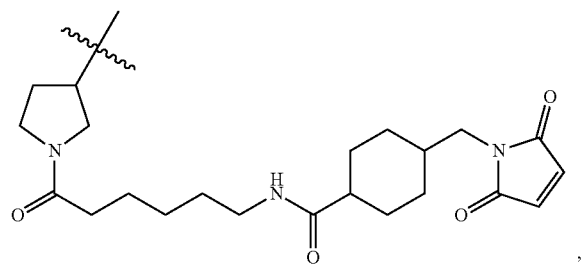
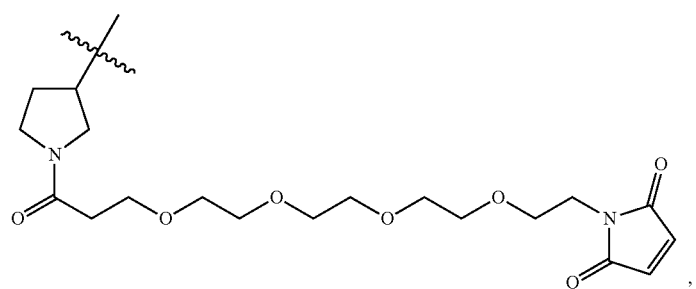
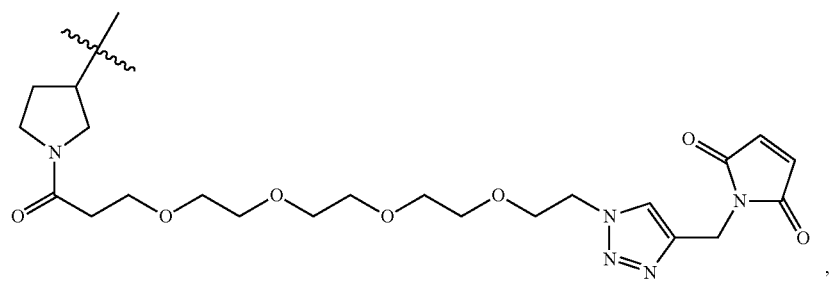
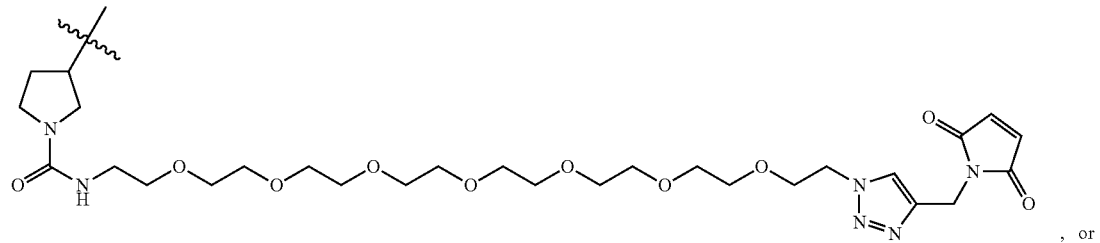, or
586

-continued
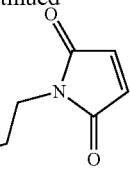
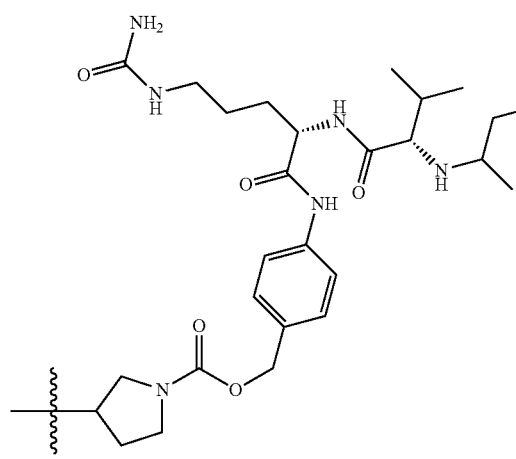
9. The compound of claim 1, wherein $R^2$ is
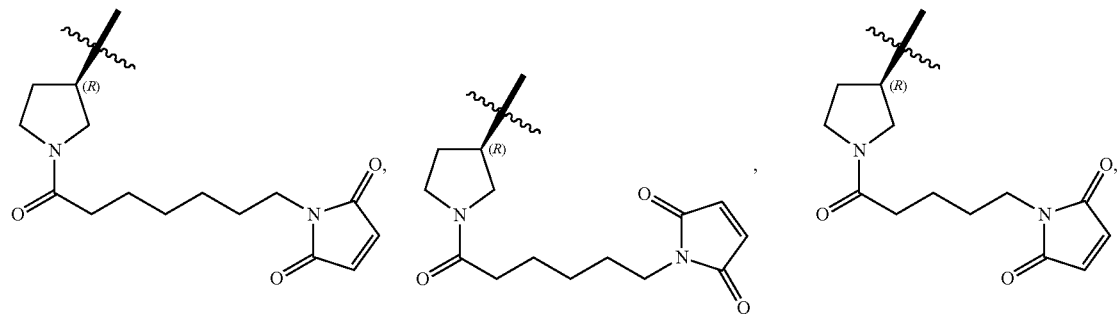
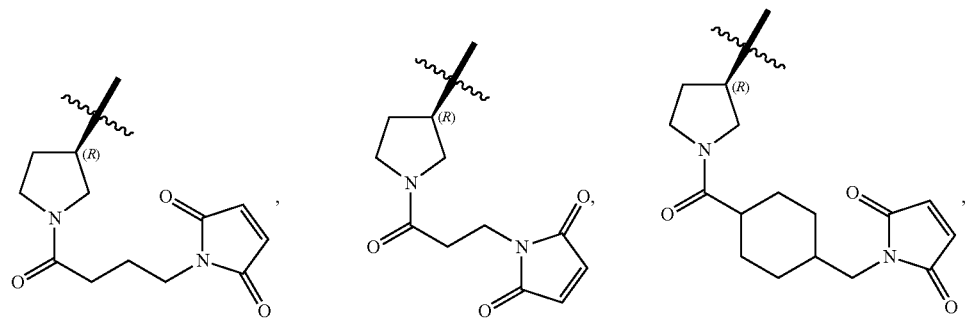
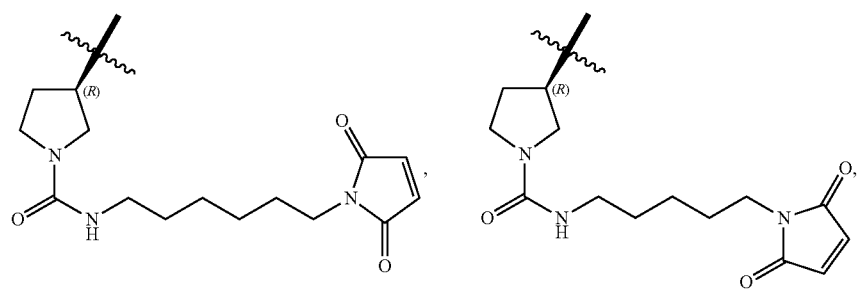

589 590
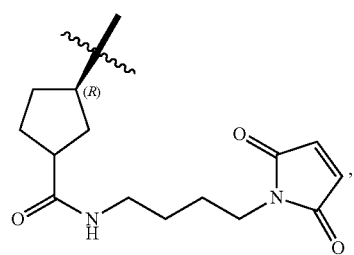 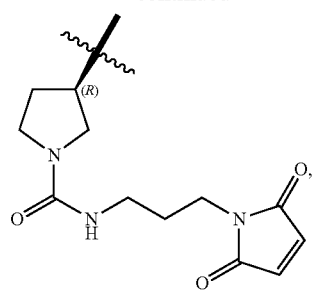 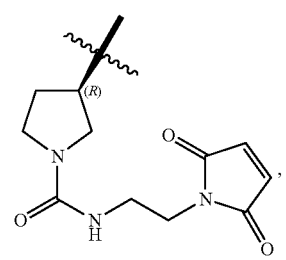
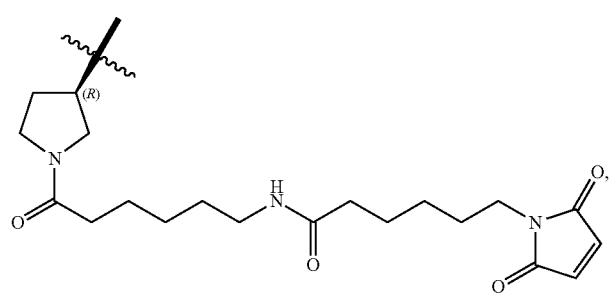
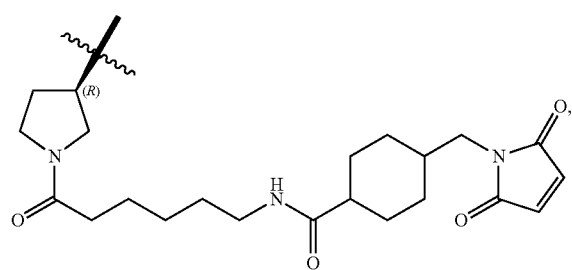
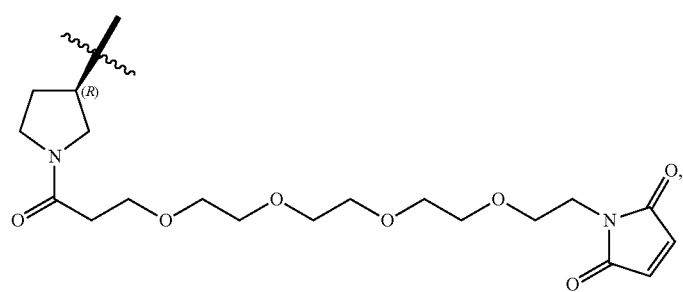
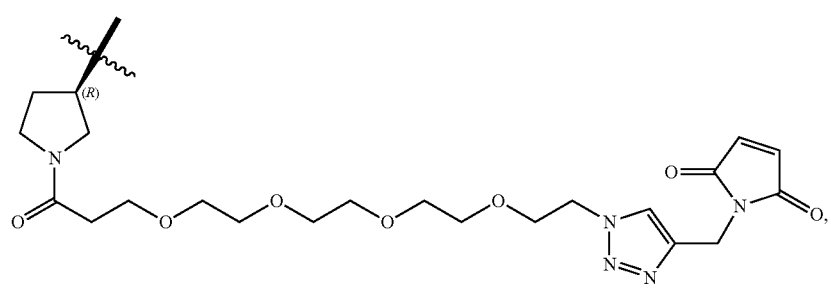
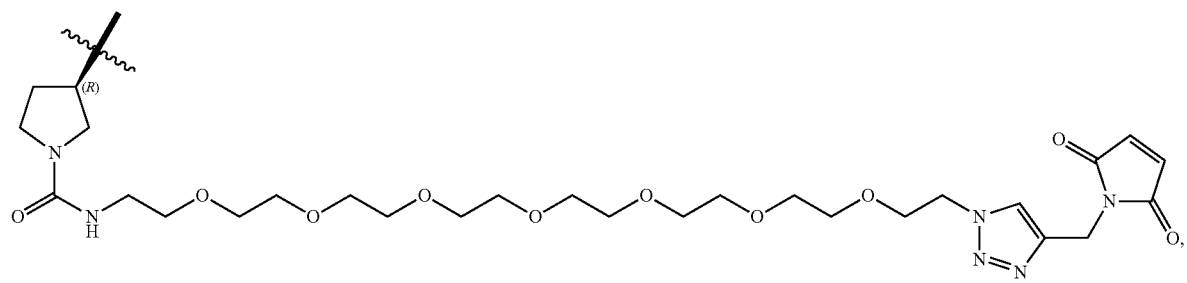

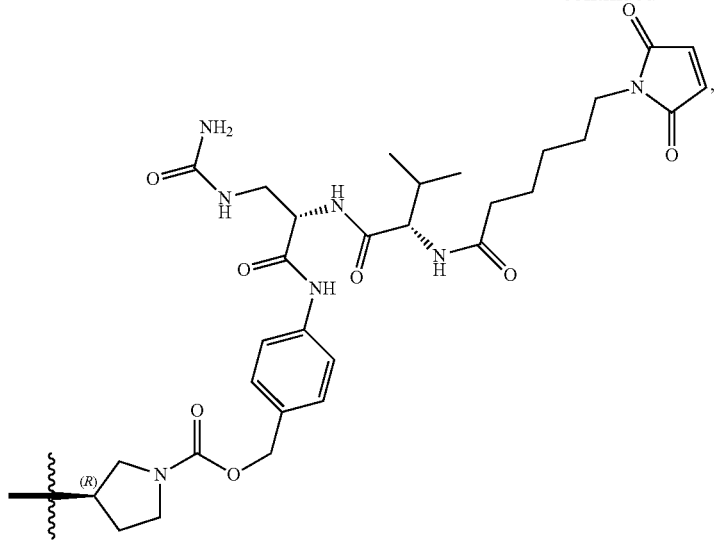
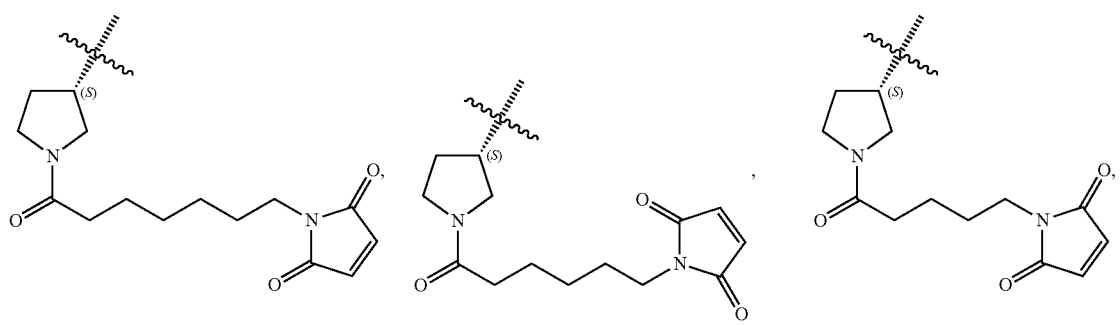
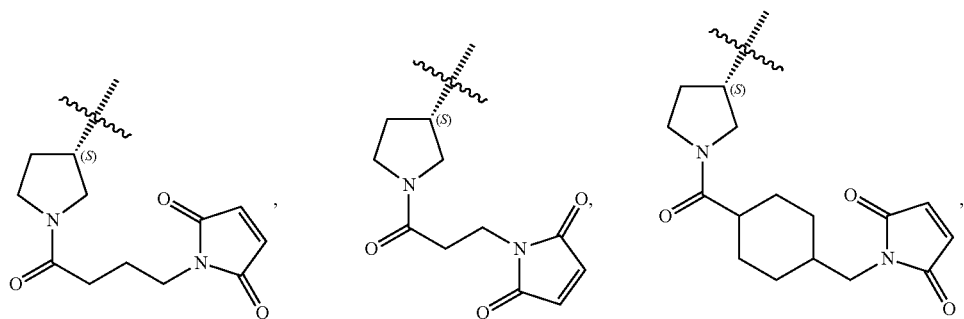
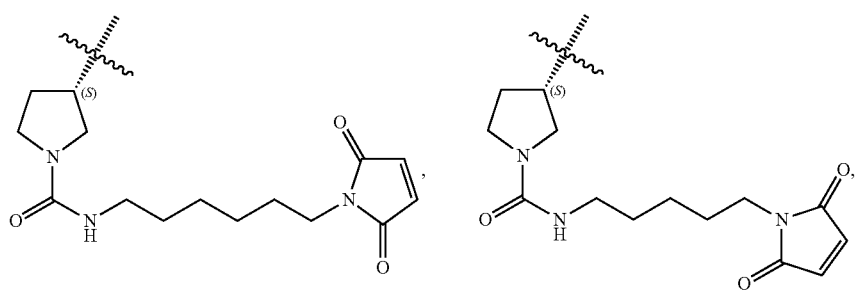

593 594
-continued
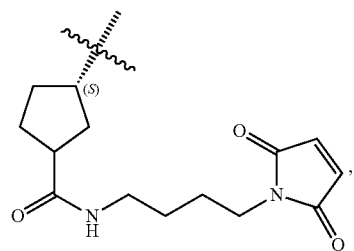
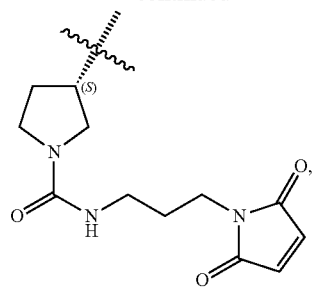
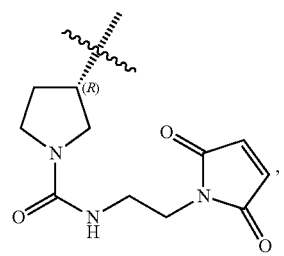
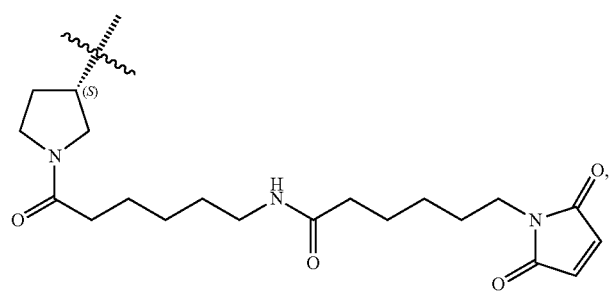
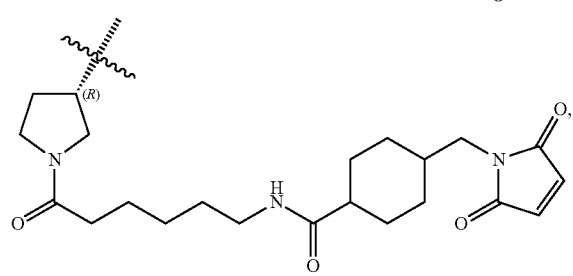
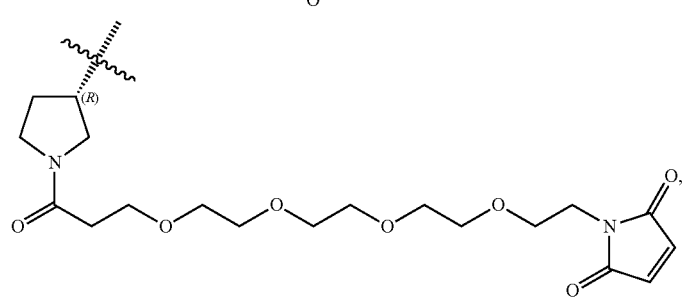
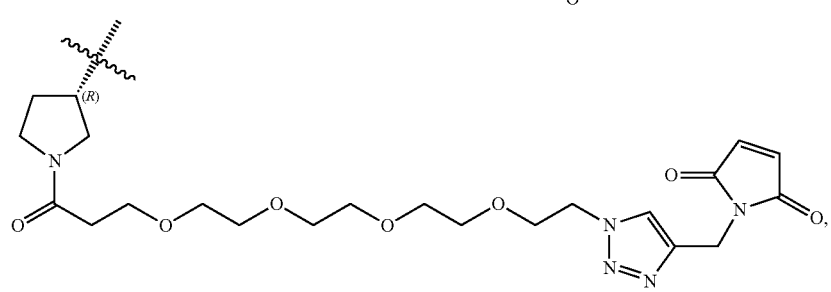
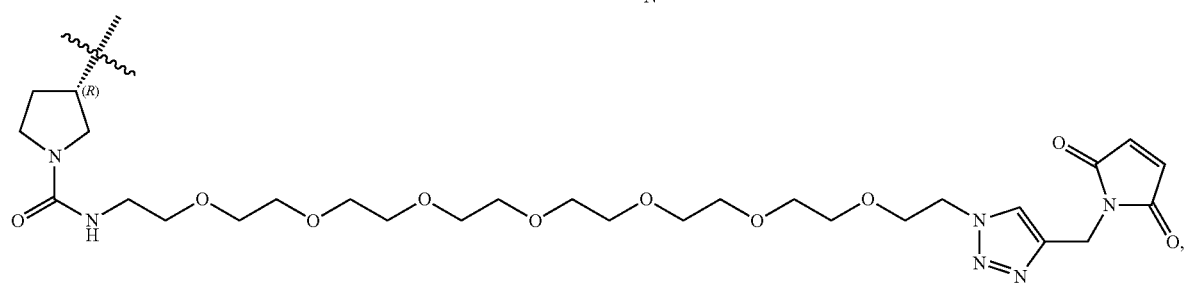

or
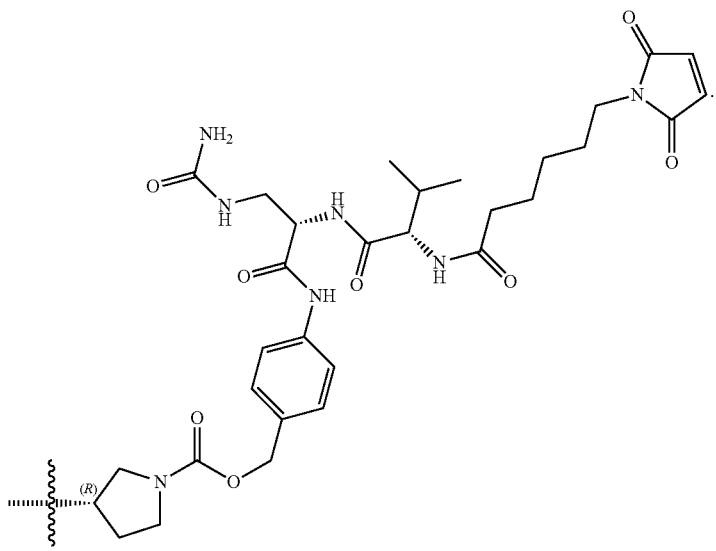
10. The compound of claim 1, wherein $R^2$ is
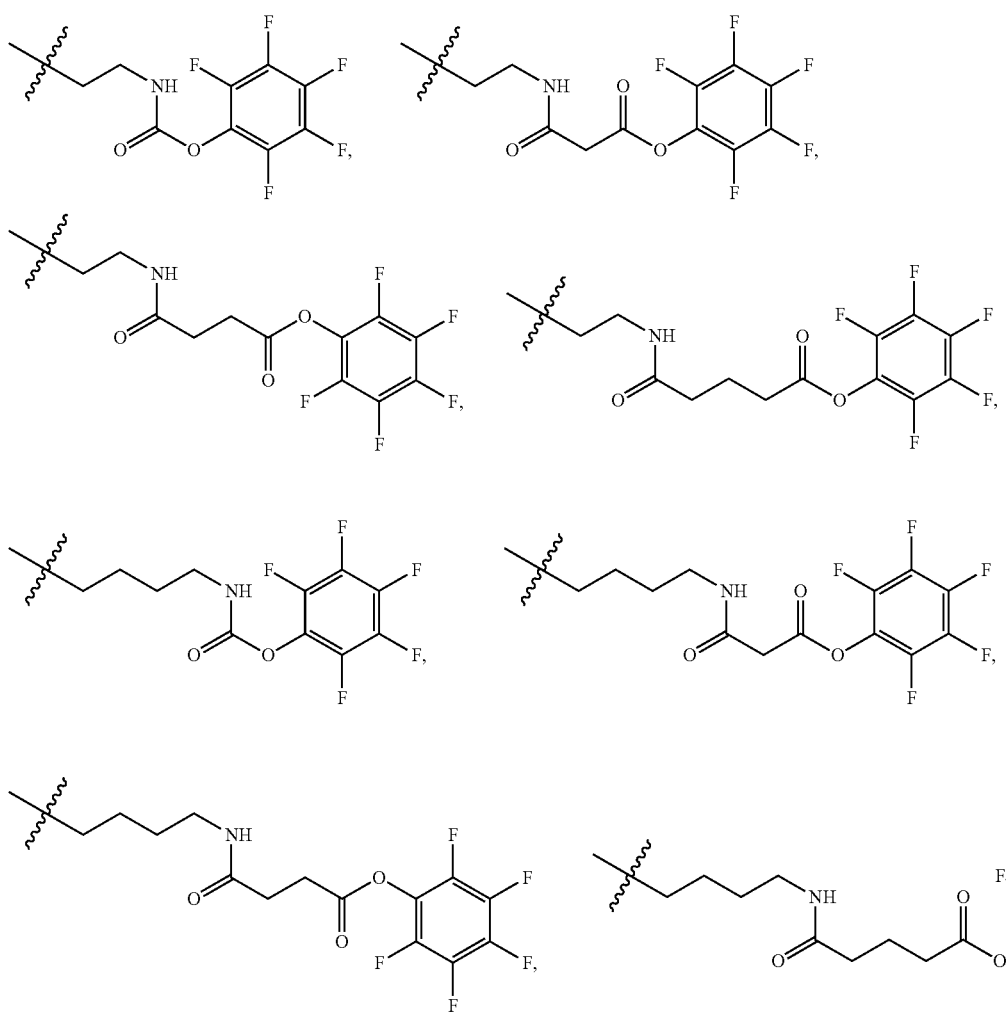

597
-continued
598
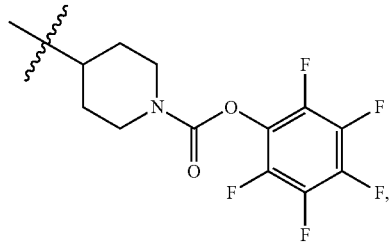
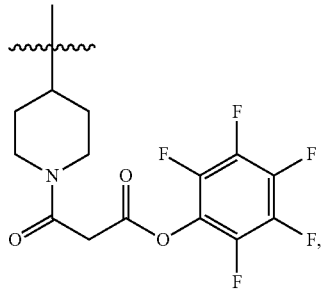
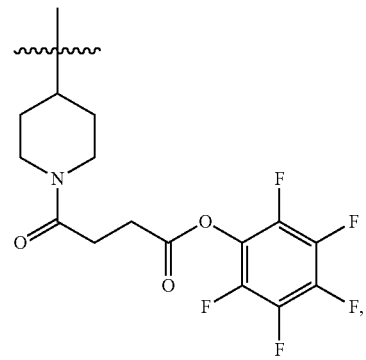
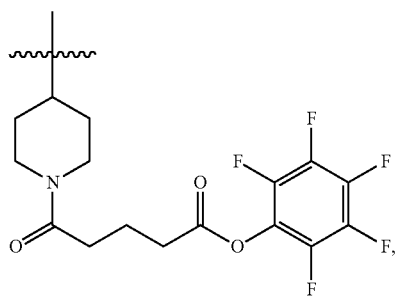
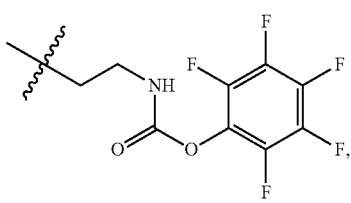
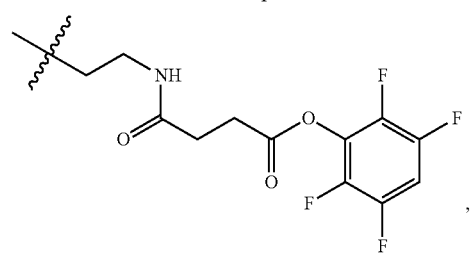
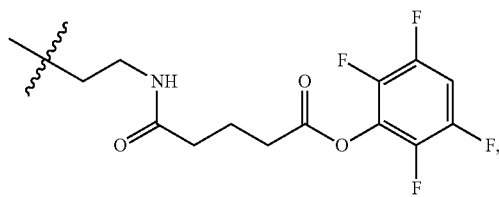
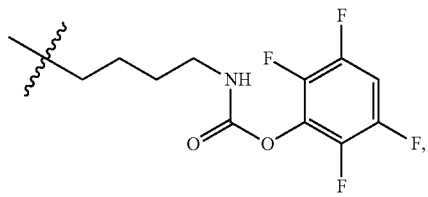
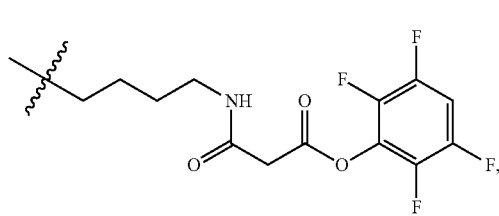
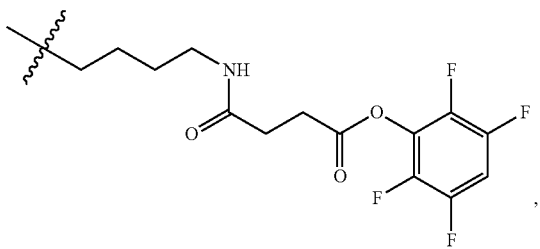
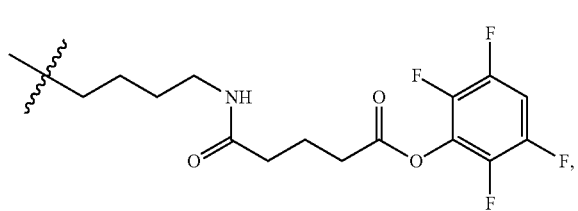
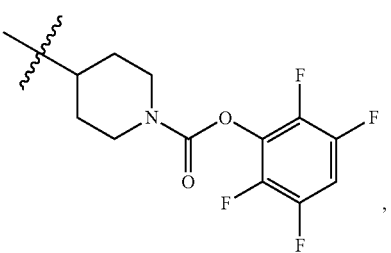

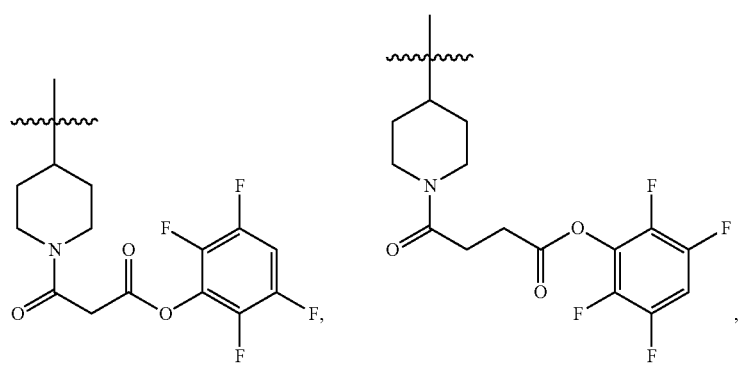
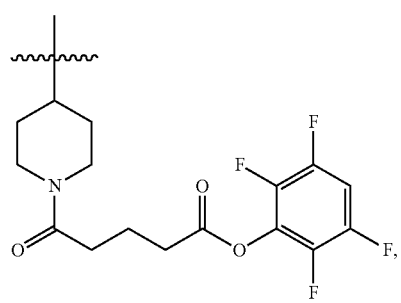
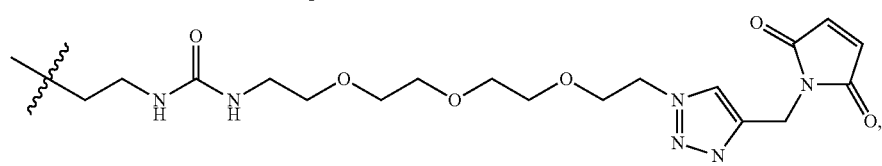
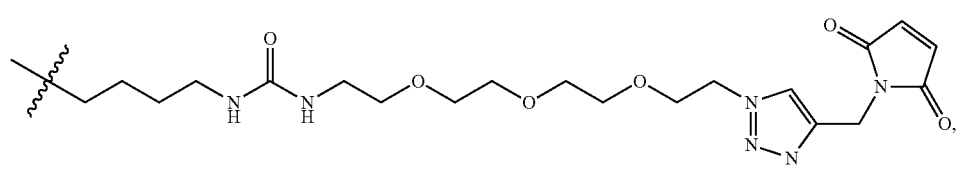
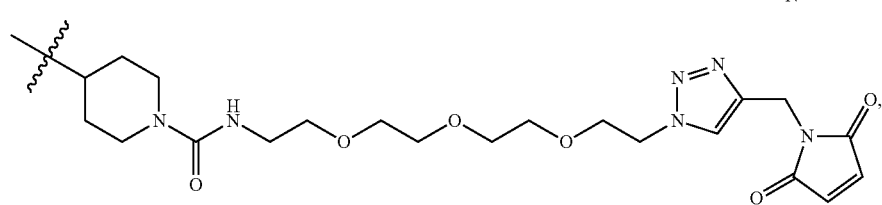
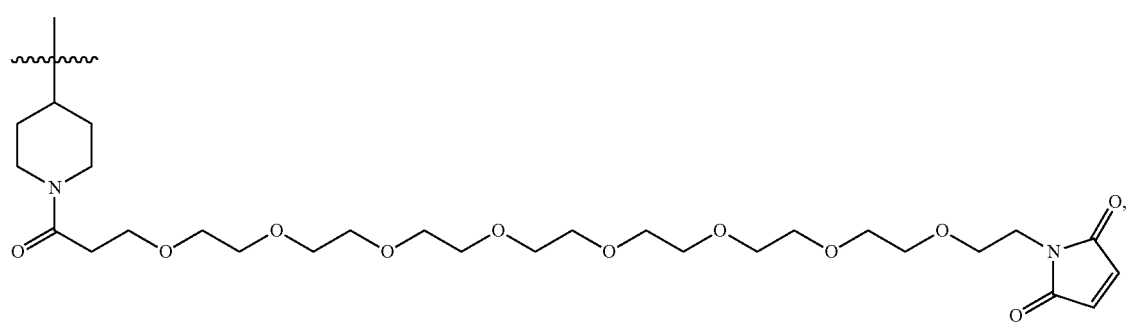
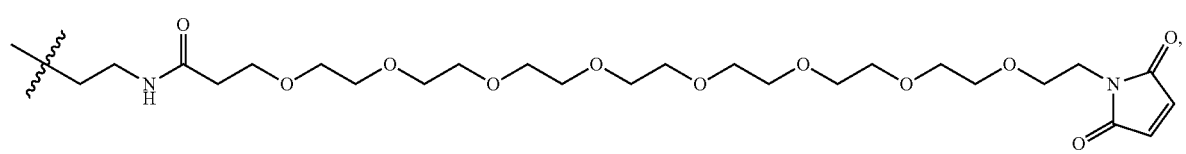

-continued
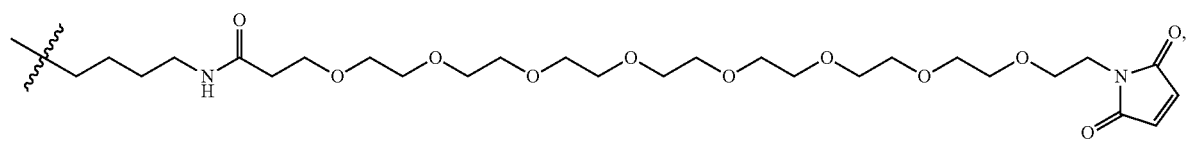
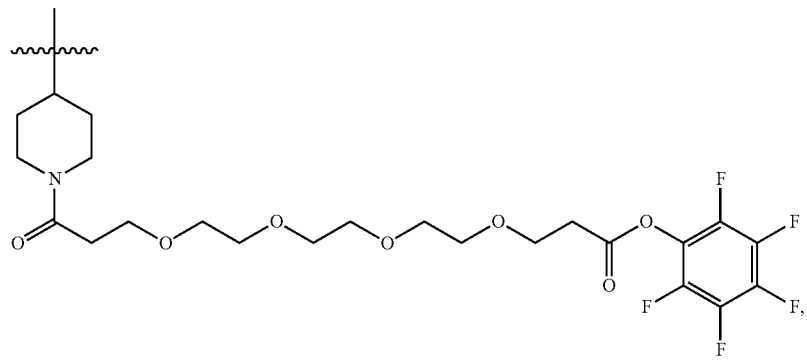
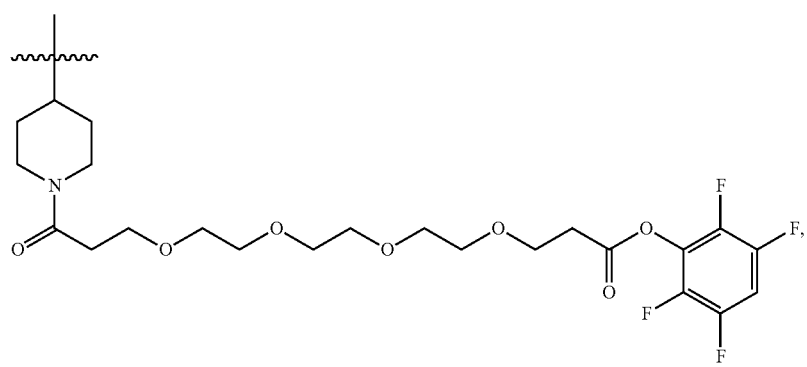
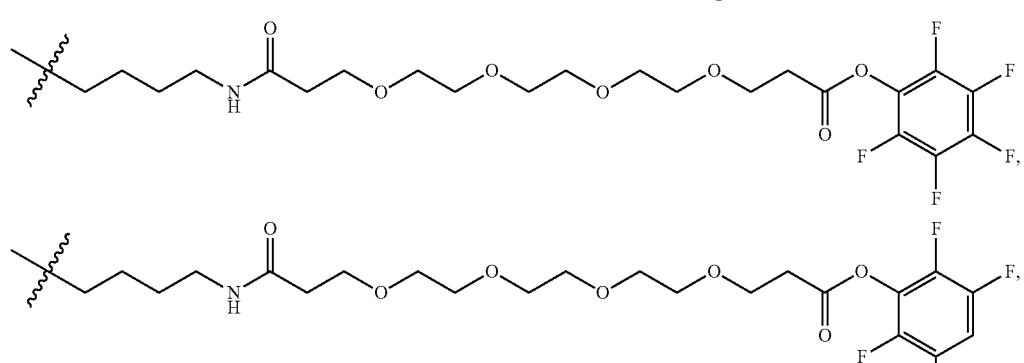
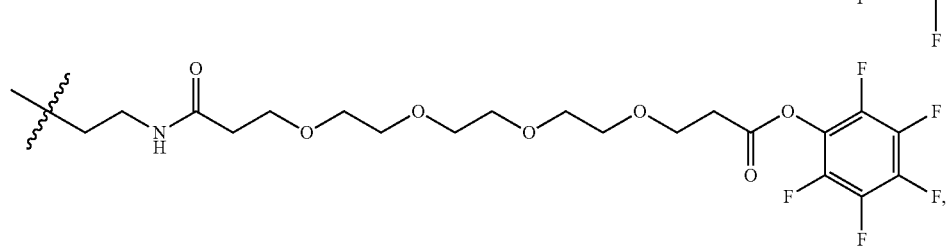
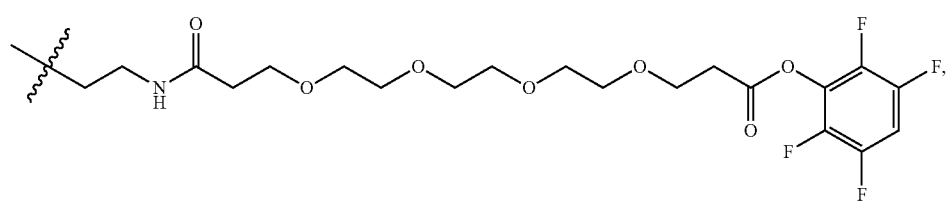

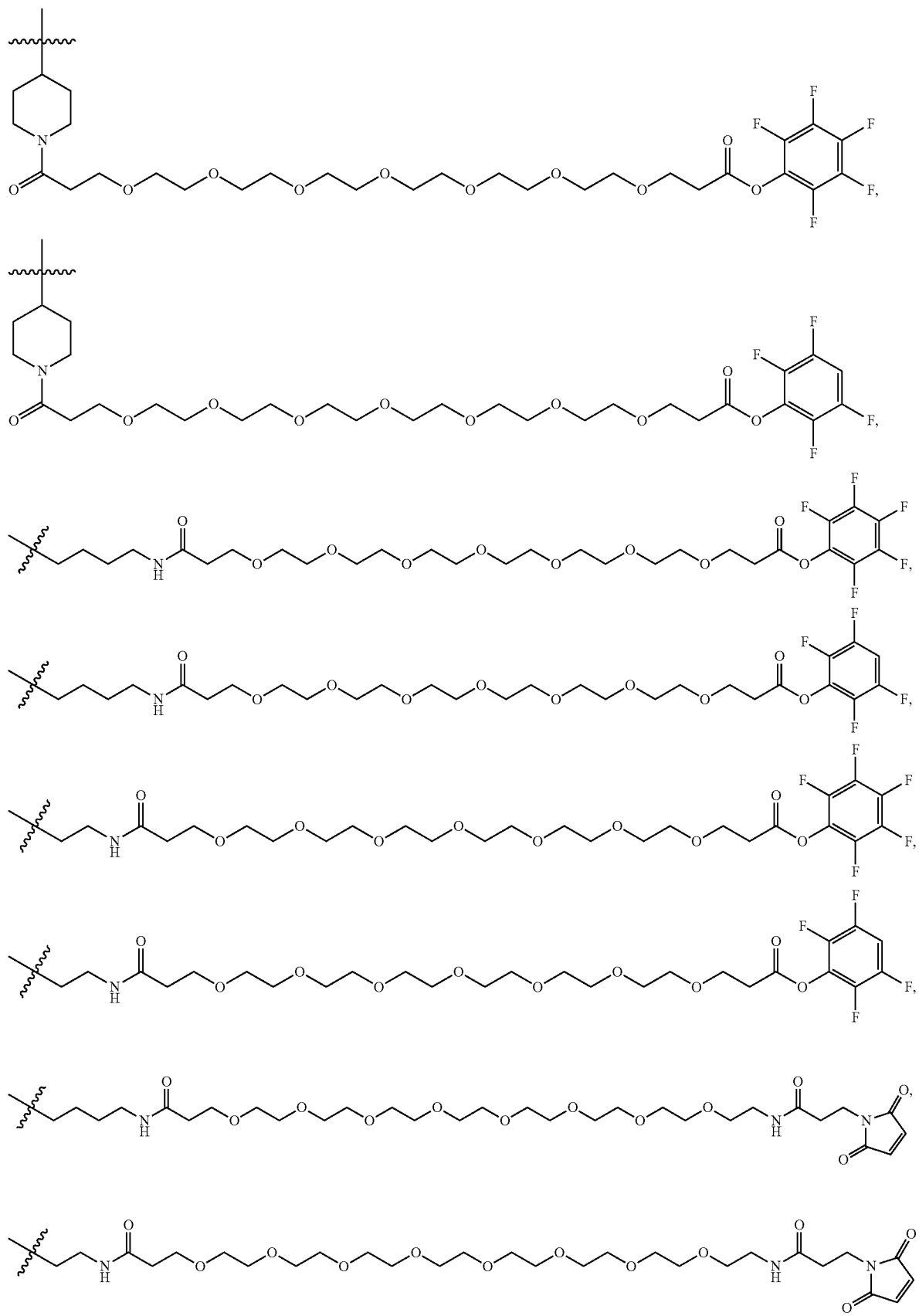

or

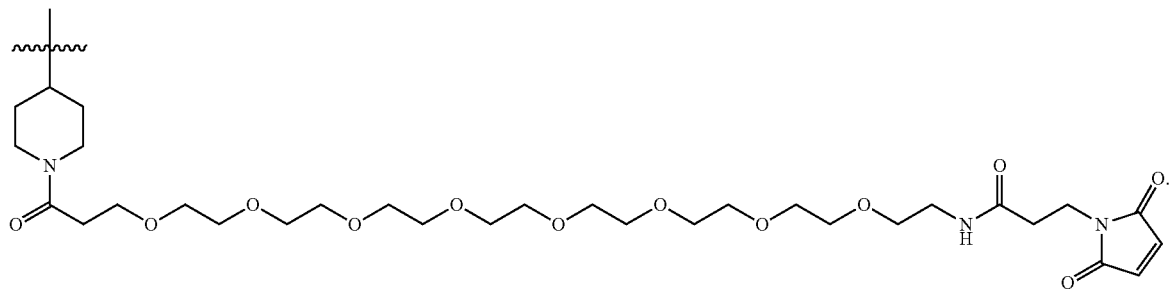

11. The compound of claim 1 selected from:
6'O-methyl-7'C-((2-(2-(maleimido)ethanecarboxamido)ethylthio)methyl)-α-Amanitin;
6'O-methyl-7'C-((2-(3-(maleimido)propanecarboxamido)ethylthio)methyl)-α-Amanitin;
6'O-methyl-7'C-((2-(4-(maleimido)butanecarboxamido)ethylthio)methyl)-α-Amanitin;
6'O-methyl-7'C-((2-(5-(maleimido)pentanecarboxamido)ethylthio)methyl)-α-Amanitin;
6'O-methyl-7'C-(2-((4-((maleimido)methyl)cyclohexanecarboxamido)ethylthio)methyl)-α-Amanitin;
6'O-methyl-7'C-((2-(5-(5-(maleimido)pentanecarboxamido)pentanecarboxamido)ethylthio)methyl)-α-Amanitin;
6'O-methyl-7'C-((2-(6-(4-((maleimido)methyl)cyclohexanecarboxamido)hexanecarboxamido)ethylthio)methyl)-α-Amanitin;
6'O-methyl-7'C-((2-(14-(maleimido)-3,6,9,12-tetraoxatetradecancarboxamido)ethylthio)methyl)-α-Amanitin;
6'O-methyl-7'C-((2-(14-((4-maleimido)methyl-1H-1,2,3-triazol-1-yl)-3,6,9,12-tetraoxatetradecancarboxamido)ethylthio)methyl)-α-Amanitin;
6'O-methyl-7'C-(2-((2,5-dioxopyrrolidin-1-yl)oxycarbonylamino)ethylthiomethyl)-α-Amanitin;
6'-O-methyl-7'-C-((2-(3-(6-(maleimido)hexyl) ureido)ethylthio)methyl) -α-Amanitin;
6'-O-methyl-7'C-(MC-Val-Cit-PABC-(2-aminoethyl)thiomethyl-)-α-Amanitin;
6'O-methyl-7'C-((2-(3-(23-((4-maleimido)methyl-1H-1,2,3-triazol-1-yl)-3,6,9,12,15,18,21-heptaoxatricosyl)ureido)ethylthio)methyl)-α-Amanitin;
6'O-methyl-7'C-((2-(4-(maleimido)ethanecarboxamido)butylthio)methyl)-α-Amanitin;
6'O-methyl-7'C-((4-(5-(maleimido)pentanecarboxamido)butylthio)methyl)-α-Amanitin;
6'O-methyl-7'C-(4-((2,5-dioxopyrrolidin-1-yl)oxycarbonylamino)butylthiomethyl)-α-Amanitin;
6'O-methyl-7'C-((4-(4-((maleimido)methyl)cyclohexanecarboxamido)butylthio)methyl)-α-Amanitin;
6'O-methyl-7'C-((4-(3-(6-(maleimido) hexyl)ureido)butylthio)methyl)-α-Amanitin;
6'O-methyl-7'C-((4-(5-(5-(maleimido)pentanecarboxamido)pentanecarboxamido)butylthio)methyl)-α-Amanitin;
6'O-methyl-7'C-((4-(5-(4-((maleimido)methyl)cyclohexanecarboxamido)pentanecarboxamido)butylthio)methyl)-α-Amanitin;
6'O-methyl-7'C-((4-(14-(maleimido)-3,6,9,12-tetraoxatetradecancarboxamido)butylthio)methyl)-α-Amanitin;
6'O-methyl-7'C-((4-(14-((4-maleimido)methyl-1H-1,2,3-triazol-1-yl)-3,6,9,12-tetraoxatetradecancarboxamido)butylthio)methyl)-α-Amanitin;
6'O-methyl-7'C-((4-(3-(23-((4-maleimido)methyl-1H-1,2,3-triazol-1-yl)-3,6,9,12,15,18,21-heptaoxatricosyl)ureido)butylthio)methyl)-α-Amanitin;
7'C-((2-(5-(maleimido)pentanecarboxamido)ethylthio)methyl) -α-Amanitin;
6'O-methyl-7'C-((1-(3-(maleimido)propanoyl)-azetidin-3-thio)methyl)-α-Amanitin;
6'O-methyl-7'C-((1-(6-(maleimido)hexanoyl)-azetidin-3-thio)methyl)-α-Amanitin;
6'O-methyl-7'C-((1-(3-(maleimido)propanoyl)-piperidine-4-thio)methyl)-α-Amanitin;
6'O-methyl-7'C-((1-(6-(maleimido)hexanoyl)-piperidine-4-thio)methyl)-α-Amanitin;
6'O-methyl-7'C—((N-(4-((maleimido)methyl)cyclohexanecarbonyl)piperidine-4-thio)methyl)-α-Amanitin;
6'O-methyl-7'C-((1-(6-(6-(maleimido) hexanamido)hexanoyl)-piperidine-4-thio)methyl)-α-Amanitin;
6'O-methyl-7'C-((1-(6-(4-((maleimido)methyl)cyclohexanecarboxamido)hexanoyl)-piperidine-4-thio)methyl)-α-Amanitin;
6'O-methyl-7'C-((1-(15-(maleimido)-4,7,10,13-tetraoxapentadecanoyl)-piperidine-4-thio)methyl)-α-Amanitin;
6'O-methyl-7'C—(R)—(N-(3-(maleimido)propanoyl)pyrrolidine-3-thio)methyl -α-Amanitin;
6'O-methyl-7'C—(R)—(N-(6-(maleimido)hexanoyl)pyrrolidine-3-thio)methyl -α-Amanitin;
6'O-methyl-7'C—(S)—(N-(3-(maleimido)propanoyl)pyrrolidine-3-thio)methyl -α-Amanitin;
6'O-methyl-7'C—(S)—(N-(6-(maleimido)hexanoyl)pyrrolidine-3-thio)methyl -α-Amanitin;
6'O-methyl-7'C—(N-(6-(maleimido)hexanoyl)pyrrolidine-3-thio)methyl -α-Amanitin;
6'O-methyl-7'C-(((4-(4-maleimido)methyl-1H-1,2,3-triazol-1-yl)butylthio)methyl)-α-Amanitin;
6'O-methyl-7'C-((6-(aminoxy)hexaneamido)-ethylthiomethyl)-☐-Amanitin;
6'O-methyl-7'C-((1-(6-(aminooxy) hexanoyl)-piperidine-4-thio)methyl)-α-Amanitin;
6'O-methyl-7'C-((6-(aminoxy)hexaneamido)-butylthiomethyl)-☐-Amanitin;
NHS ester of 6'O-methyl-7'C-((2-(3-(carboxy)propanecarboxamido)ethylthio)methyl)-α-Amanitin;
NHS ester of 6'O-methyl-7'C-((4-(3-(carboxy)propanecarboxamido)butylthio)methyl)-α-Amanitin;
NHS ester of 6'O-methyl-7'C-((1-(4-(carboxy)butanoyl)-piperidine-4-thio)methyl)-α-Amanitin, and 6'O-methyl-7'C-((1-(14-((4-maleimido)methyl-1H-1,2,3-triazol-1-yl)-3,6,9,12-tetraoxatetradecancarbonyl)-piperidine-4-thio)methyl)-α-Amanitin.

12. The compound of claim 1 selected from:

Tetrafluorophenyl ester of 6'O-methyl-7'C-((4-(3-(carboxy)propanecarboxamido)butylthio)methyl)-α-Amanitin;

7'C-((4-(3-(23-((4-maleimido)methyl-1H-1,2,3-triazol-1-yl)-3,6,9,12,15,18,21-heptaoxatricosyl)ureido)butylthio)methyl)-α-Amanitin;

7'C-((4-(14-(maleimido)-3,6,9,12-tetraoxatetradecancarboxamido)butylthio)methyl)-α-Amanitin;

6'O-methyl-7'C-((4-(26-(maleimido)-3,6,9,12,15,18,21,24-octaoxahexacosancarboxamido)butylthio)methyl)-α-Amanitin;

6'O-methyl-7'C-((4-(3-(2-(2-(2-(2-((4-maleimido)methyl-1H-1,2,3-triazol-1-yl)-ethoxy)ethoxy)ethoxy)ethyl) ureido)butylthio)methyl) -α-Amanitin;

6'O-methyl-7'C-((1-(26-(maleimido)-3,6,9,12,15,18,21,24-octaoxahexacosancarboxamido)-piperidine-4-thio)methyl)-α-Amanitin;

Perfluorophenyl ester of 6'O-methyl-7'C-((4-((23-carboxy) 3,6,9,12,15,18,21-heptaoxatricosancarboxamido)butylthio)methyl)-α-Amanitin;

Tetrafluorophenyl ester of 6'O-methyl-7'C-((4-(14-carboxy-3,6,9,12-tetraoxatetradecancarboxamido)butylthio)methyl)-α-Amanitin;

6'O-methyl-7'C-((4-(26-(3-(maleimido)propanamido)-3,6,9,12,15,18,21,24-octaoxahexacosancarboxamido)butylthio)methyl)-α-Amanitin; and Perfluorophenyl ester of 6'O-methyl-7'C-(1-((23-carboxy-3,6,9,12,15,18,21-heptaoxatricosancarbonyl)-piperidine-4-thio)methyl)-α-Amanitin.

13. An immunoconjugate of Formula (II):

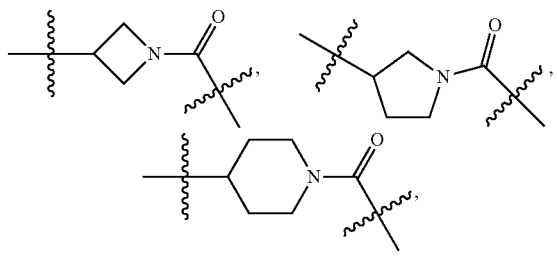

—(CH$_2$)$_m$X$_3$(CH$_2$)$_m$—, —(CH$_2$)$_m$NR$^5$—,

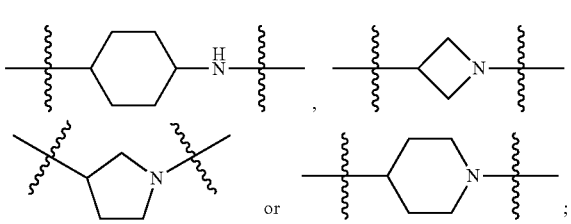

L$_2$ is —(CH$_2$)$_m$—, —NR$^5$(CH$_2$)$_m$—, —(CH$_2$)$_m$NR$^5$C(=O)(CH$_2$)$_m$—, —X$_4$—, —(CH$_2$)$_m$NR$^5$C(=O)X$_4$, —(CH$_2$)$_m$NR$^5$C(=O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^5$((CH$_2$)$_m$O)$_n$X$_3$(CH$_2$)$_m$—, —NR$^5$((CH$_2$)$_m$O)$_n$(CH$_2$)$_m$X$_3$(CH$_2$)$_m$—, —X$_1$X$_2$C(=O)(CH$_2$)$_m$—, —(CH$_2$)$_m$(O(CH$_2$)$_m$)$_n$—, —(CH$_2$)$_m$NR$^5$(CH$_2$)$_m$—, —(CH$_2$)$_m$NR$^5$C(=O)(CH$_2$)$_m$ X$_3$(CH$_2$)$_m$—, —(CH$_2$)$_m$C(=O)NR$^5$(CH$_2$)$_m$ NR$^5$C(=O)(CH$_2$)$_m$—, —(CH$_2$)$_m$C(=O)—, —(CH$_2$)$_m$ NR$^5$(CH$_2$)$_m$C(=O)X$_2$X$_1$C(=O)—, —(CH$_2$)$_m$X$_3$

Formula (II)

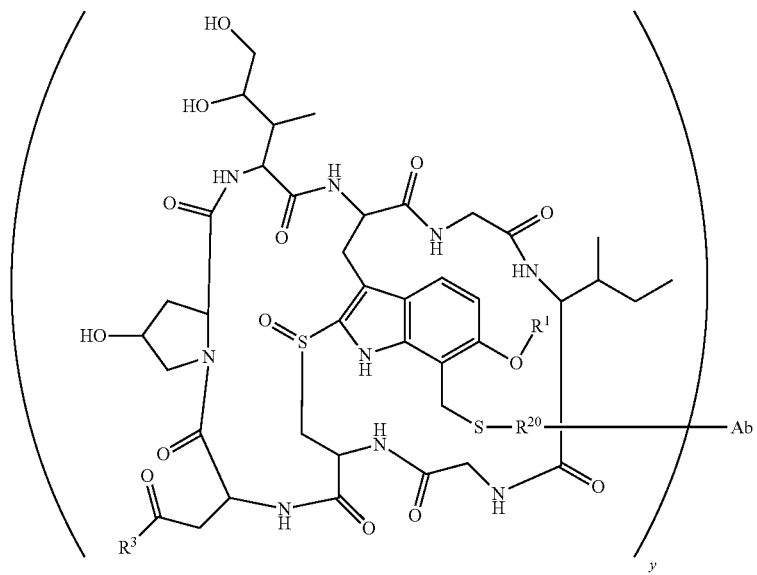

wherein:
Ab represents an antigen binding moiety;
y is an integer from 1 to 16;
R$^1$ is H or —CH$_3$;
R$^3$ is —NH$_2$ or —OH;
R$^{20}$ is -L$_1$L$_2$R$^{40}$, -L$_3$R$^{60}$ or —(CH$_2$)$_m$X$_3$(CH$_2$)$_m$R$^{40}$;
L$_1$ is —(CH$_2$)$_m$NR$^5$C(=O)—, (CH$_2$)$_m$C(=O)X$_2$X$_1$C(=O)—, —(CH$_2$)$_m$C(=O)NR$^5$ (CH$_2$)$_m$—, —(CH$_2$)$_m$C(=O)NR$^5$(CH$_2$)$_m$X$_3$(CH$_2$)$_m$—, —(CH$_2$)$_m$X$_3$(CH$_2$)$_m$NR$^5$C(=O)(CH$_2$)$_m$—, —(CH$_2$)$_m$ X$_3$(CH$_2$)$_m$C(=O)NR$^5$(CH$_2$)$_m$—, —(CH$_2$)$_m$O)$_n$(CH$_2$)$_m$ NR$^5$C(=O)(CH$_2$)$_m$—, —(CH$_2$)$_m$C(=O)NR$^5$(CH$_2$)$_m$ (O(CH$_2$)$_m$)$_n$—, —(CH$_2$)$_m$(O(CH$_2$)$_m$)$_n$C(=O)—, —(CH$_2$)$_m$NR$^5$(CH$_2$)$_m$C(=O)—, —(CH$_2$)$_m$C(=O)

NR$^5$(CH$_2$)$_m$NR$^5$C(=O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —(CH$_2$)$_m$C(=O)NR$^5$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^5$C(=O)(CH$_2$)$_m$—, —(CH$_2$)$_m$X$_3$(CH$_2$)$_m$(O(CH$_2$)$_m$)$_n$C(=O)—, —(CH$_2$)$_m$X$_3$(CH$_2$)$_m$(O(CH$_2$)$_m$)$_n$—, —(CH$_2$)$_m$C(=O)NR$^5$(CH$_2$)$_m$C(=O)—, —(CH$_2$)$_m$C(=O)NR$^5$(CH$_2$)$_m$(O(CH$_2$)$_m$)$_n$C(=O)—, —((CH$_2$)$_m$O)$_n$(CH$_2$)$_m$NR$^5$C(=O)(CH$_2$)$_m$—, —(CH$_2$)$_m$ C(=O)NR$^5$(CH$_2$)$_m$C(=O)NR$^5$(CH$_2$)$_m$—, —(CH$_2$)$_m$NR$^5$C(=O)(CH$_2$)$_m$NR$^5$C(=O)(CH$_2$)$_m$—, —(CH$_2$)$_m$X$_3$(CH$_2$)$_m$C(=O)NR$^5$—, —(CH$_2$)$_m$C(=O)NR$^5$—, —(CH$_2$)$_m$X$_3$—, —C(R$^5$)$_2$(CH$_2$)$_m$—, —(CH$_2$)$_m$ C(R$^5$)$_2$NR$^5$—, —(CH$_2$)$_m$C(=O)NR$^5$(CH$_2$)$_m$ NR$^5$—, —(CH$_2$)$_m$C(=O)NR$^5$(CH$_2$)$_m$NR$^5$C(=O)NR$^5$—, —(CH$_2$)$_m$C(=O)X$_2$X$_1$C(=O)—, —C(R$^5$)$_2$(CH$_2$)$_m$NR$^5$C(=O)(CH$_2$)$_m$—, —(CH$_2$)$_m$C(=O)NR$^5$(CH$_2$)$_m$C(R$^5$)$_2$NR$^5$—, —C(R$^5$)$_2$(CH$_2$)$_m$X$_3$(CH$_2$)$_m$—, —(CH$_2$)$_m$X$_3$(CH$_2$)$_m$C(R$^5$)$_2$NR$^5$—, —C(R$^5$)$_2$ (CH$_2$)$_m$OC(=O)NR$^5$(CH$_2$)$_m$—, —(CH$_2$)$_m$NR$^5$C(=O)O(CH$_2$)$_m$C(R$^5$)$_2$NR$^5$—, —(CH$_2$)$_m$X$_3$(CH$_2$)$_m$NR$^5$—, —(CH$_2$)$_m$X$_3$(CH$_2$)$_m$(O(CH$_2$)$_m$)$_n$NR$^5$—, —(CH$_2$)$_m$NR$^5$—, —(CH$_2$)$_m$C(=O)NR$^5$(CH$_2$)$_m$ (O(CH$_2$)$_m$)$_n$NR$^5$—, —(CH$_2$)$_m$(O(CH$_2$)$_m$)$_n$NR$^5$—, —(CH$_2$CH$_2$O)$_n$(CH$_2$)$_m$—, —(CH$_2$)$_m$(OCH$_2$CH$_2$)$_n$, —(CH$_2$)$_m$O(CH$_2$)$_m$—, —(CH$_2$)$_m$S(=O)$_2$—, —(CH$_2$)$_m$C(=O)NR$^5$(CH$_2$)$_m$S(=O)$_2$—, —(CH$_2$)$_m$X$_3$(CH$_2$)$_m$S(=O)$_2$—, —(CH$_2$)$_m$X$_2$X$_1$C(=O)—, —(CH$_2$)$_m$(O(CH$_2$)$_m$)$_n$C(=O)X$_2$X$_1$C(=O)—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^5$(CH$_2$)$_m$NR$^5$C(=O)—, —(CH$_2$)$_m$X$_3$(CH$_2$)C(=O)NR$^5$(CH$_2$)$_m$C(=O)—, —(CH$_2$)$_m$X$_3$(CH$_2$)$_m$C(=O)NR$^5$(CH$_2$)$_m$(O(CH$_2$)$_m$)$_n$C(=O)—, —(CH$_2$)$_m$C(=O)X$_2$X$_1$C(=O)NR$^5$(CH$_2$)$_m$—, —(CH$_2$)$_m$X$_3$(O(CH$_2$)$_m$)$_n$C(=O)—, —(CH$_2$)$_m$NR$^5$C(=O)((CH$_2$)$_m$O)$_n$(CH$_2$)$_m$—, —(CH$_2$)$_m$(O(CH$_2$)$_m$)$_n$C(=O)NR$^5$(CH$_2$)$_m$—, —(CH$_2$)$_m$NR$^5$C(=O)NR$^5$(CH$_2$)$_m$—, or —(CH$_2$)$_m$X$_3$(CH$_2$)$_m$NR$^5$C(=O)—,
wherein:

X$_1$ is

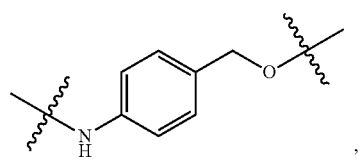,

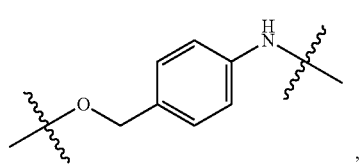,

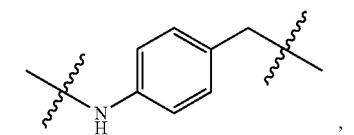,

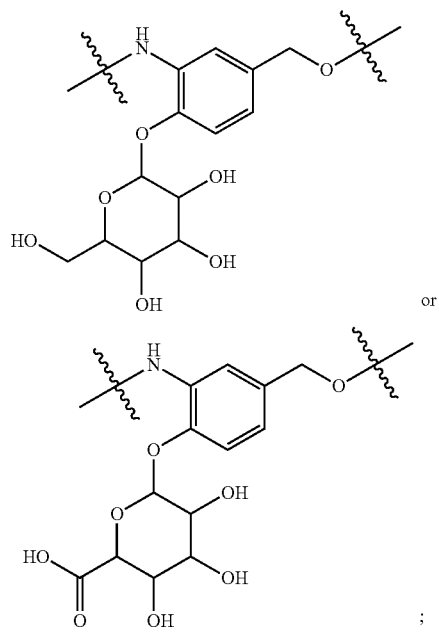

X$_2$ is

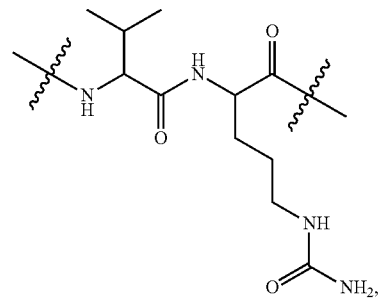,

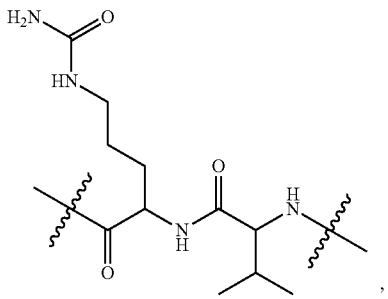,

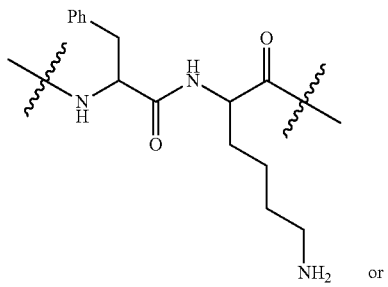 or

-continued
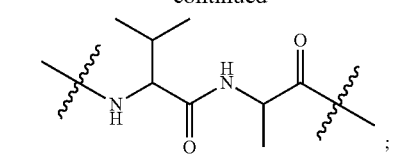
X₃ is
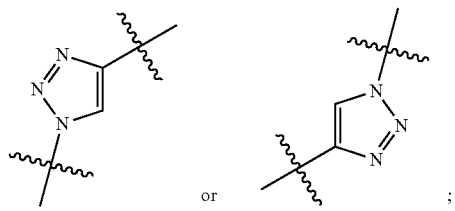 [SMILES: *c1cn(*)nn1 ; *c1cn(*)nn1]
or
X₄ is
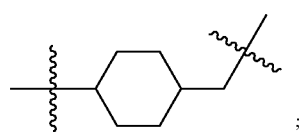 [SMILES: *CC1CCC(*)CC1]
L₃ is —(CH₂)ₘNR⁵C(=O)—;
R⁴⁰ is
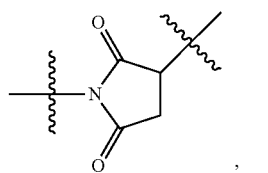 , 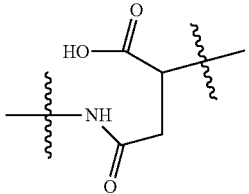 ,
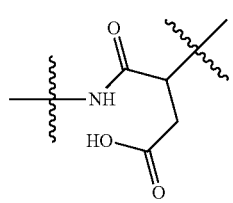 , 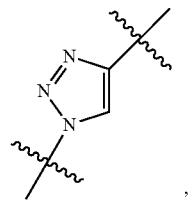 ,
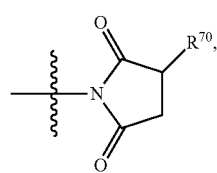 , 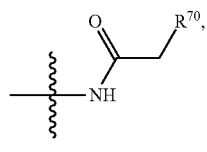 ,
—NR⁵C(=O)CH₂—, —NHC(=O)CH₂—,
—S(=O)₂CH₂CH₂—, —NR⁵S(=O)₂CH₂CH₂—,
—NR⁵C(=O)CH₂CH₂—, —CH₂NHCH₂CH₂—,
—NHCH₂CH₂—, —NH—, —C(=O)—, —NHC(=O)—, —NHC(=S)—, —S—,
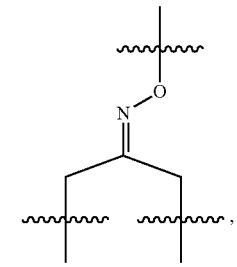
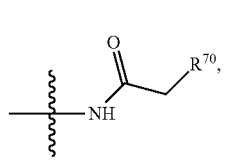
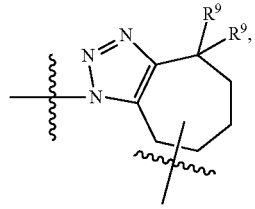
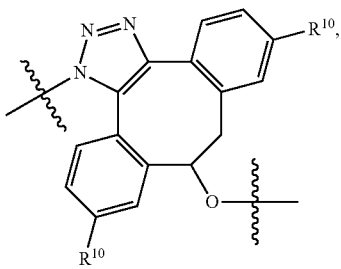
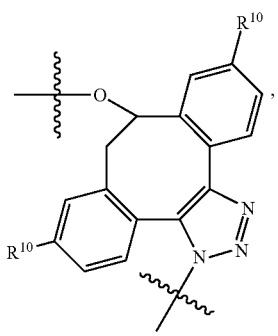
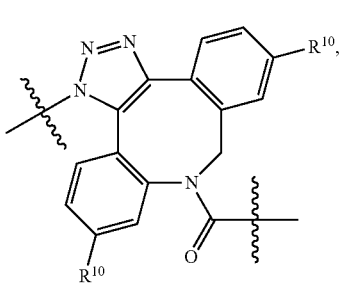

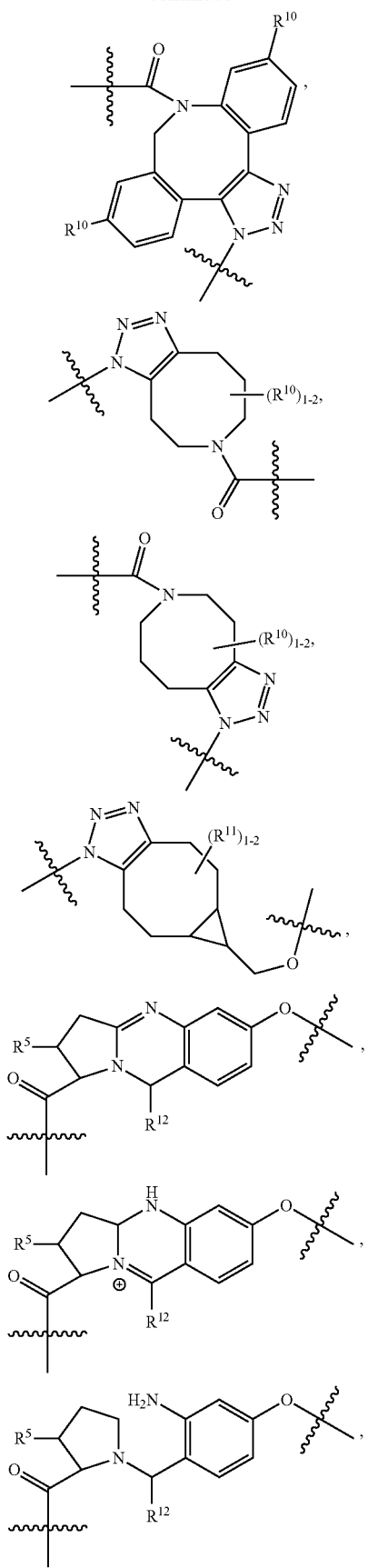

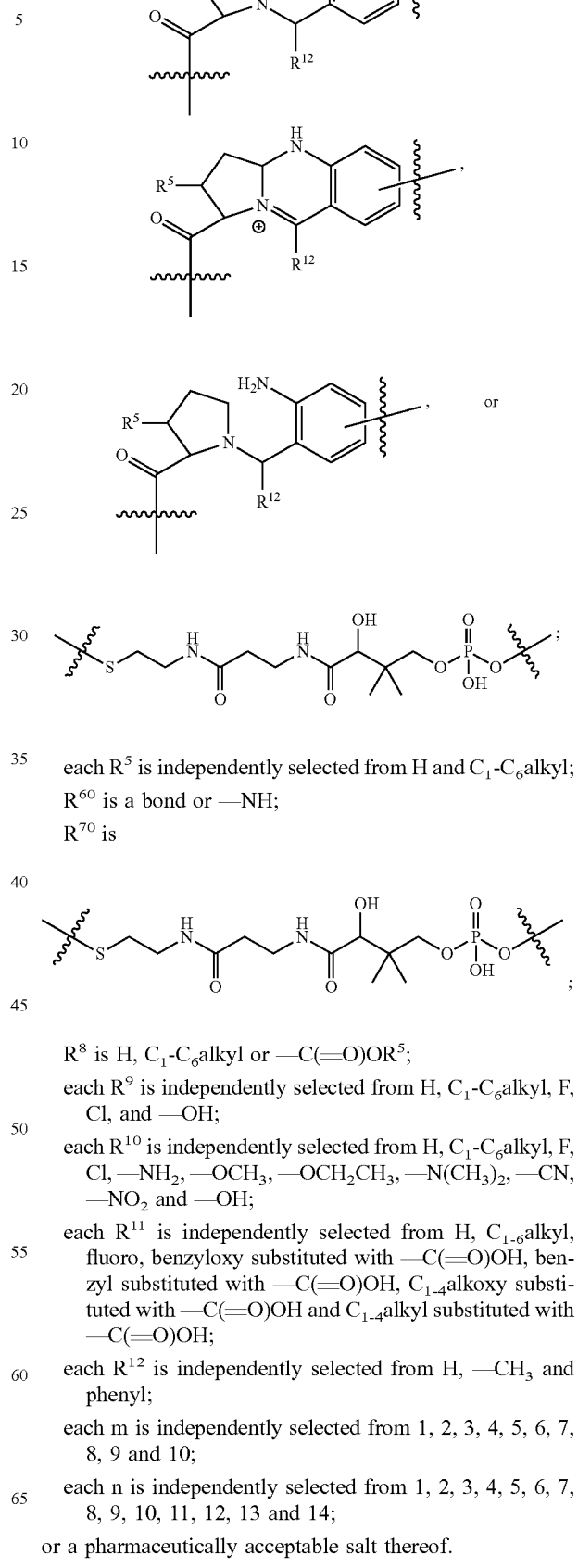

each $R^5$ is independently selected from H and $C_1$-$C_6$alkyl;
$R^{60}$ is a bond or —NH;
$R^{70}$ is $R^8$ is H, $C_1$-$C_6$alkyl or —C(=O)$OR^5$;
each $R^9$ is independently selected from H, $C_1$-$C_6$alkyl, F, Cl, and —OH;
each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each $R^{12}$ is independently selected from H, —$CH_3$ and phenyl;
each m is independently selected from 1, 2, 3, 4, 5, 6, 7, 8, 9 and 10;
each n is independently selected from 1, 2, 3, 4, 5, 6, 7, 8, 9, 10, 11, 12, 13 and 14;
or a pharmaceutically acceptable salt thereof.

14. The immunoconjugate of claim 13 having the structure of Formula (IIa):

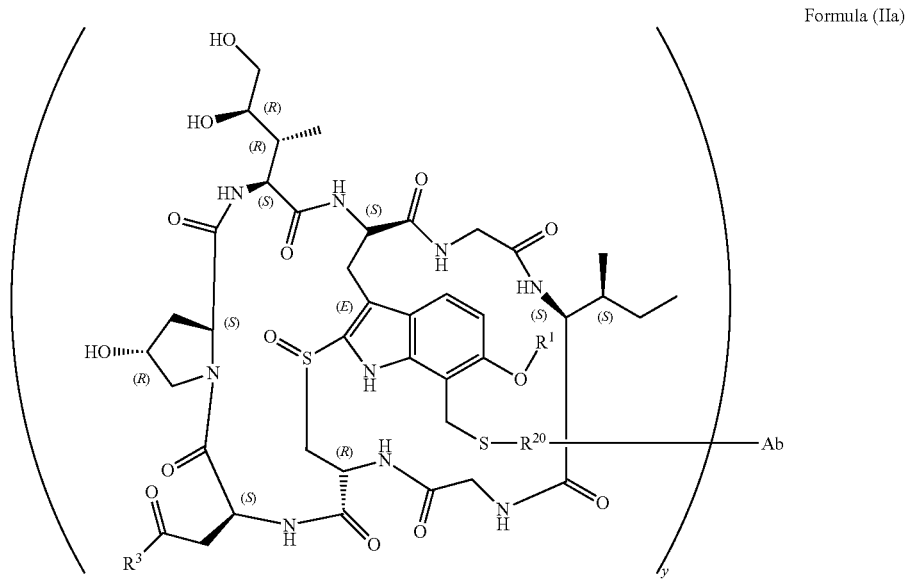

Formula (IIa)

15. The immunoconjugate of claim 13, wherein:
Ab represents an antigen binding moiety;
y is an integer from 1 to 16;
$R^1$ is H or —$CH_3$;
$R^{20}$ is -$L_1L_2R^{40}$, -$L_3R^{60}$ or —$(CH_2)_mX_3(CH_2)_mR^{40}$;
$R^3$ is —$NH_2$ or —OH;
$L_1$ is —$(CH_2)_mNR^5C(=O)$—,

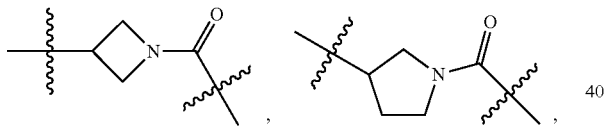

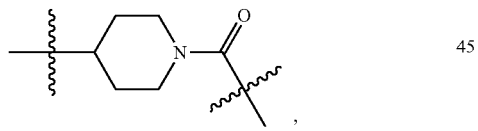

or —$(CH_2)_mX_3(CH_2)_m$—;
$L_2$ is —$(CH_2)_m$—, —$NR^5(CH_2)_m$—, —$(CH_2)_mNR^5C(=O)(CH_2)_m$—, —$X_4$—, —$(CH_2)_mNR^5C(=O)X_4$, —$(CH_2)_mNR^5C(=O)$—, —$((CH_2)_mO)_n(CH_2)_m$—, —$((CH_2)_mO)_n(CH_2)_mX_3(CH_2)_m$—, —$NR^5((CH_2)_mO)_nX_3(CH_2)_m$—, —$NR^5((CH_2)_mO)_n(CH_2)_mX_3(CH_2)_m$— or —$X_1X_2C(=O)(CH_2)_m$—,
wherein:
$X_1$ is

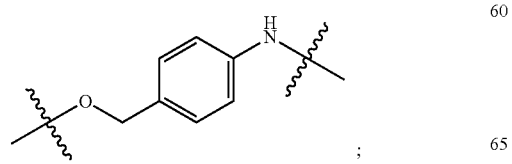

$X_2$ is

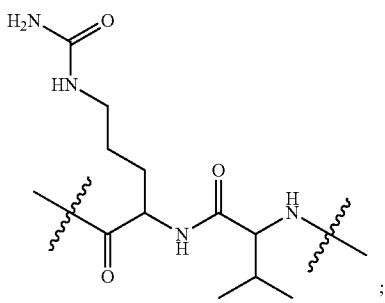 [SMILES: *NC(C(=O)NC(CCCNC(N)=O)C(*)=O)C(C)C]

$X_3$ is

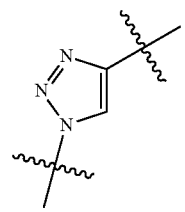 [SMILES: *c1cn(*)nn1]

and
$X_4$ is

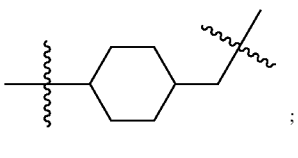 [SMILES: *CC1CCC(*)CC1]

$L_3$ is —$(CH_2)_mNR^5C(=O)$—;

$R^{40}$ is
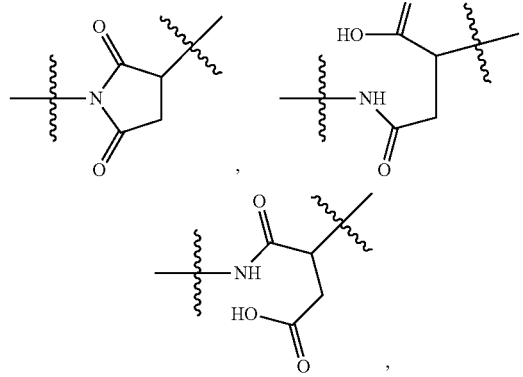
—NH—, —C(=O)—, —NHC(=O)— or
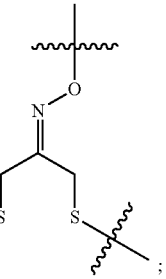;
each $R^5$ is independently selected from H and $C_1$-$C_6$alkyl;
$R^{60}$ is —NH—;
each m is independently selected from 1, 2, 3, 4, 5, 6, 7, 8, 9 and 10,
and
each n is independently selected from 1, 2, 3, 4, 5, 6, 7, 8, 9, 10, 11, 12, 13 and 14.
16. The immunoconjugate of claim 13, wherein $R^{20}$ is
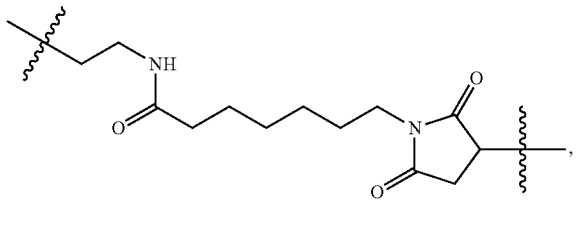
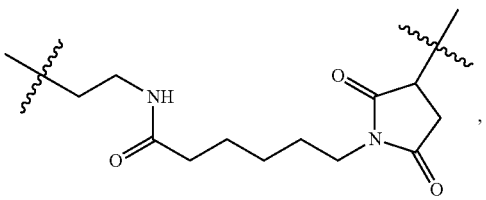
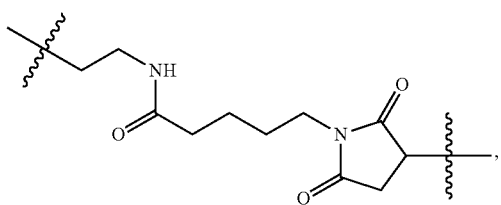
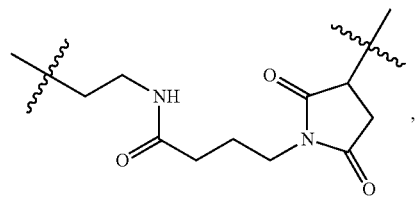
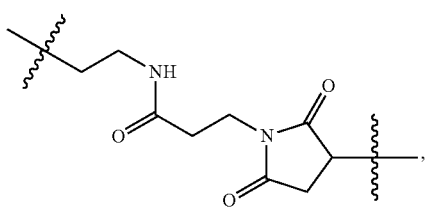
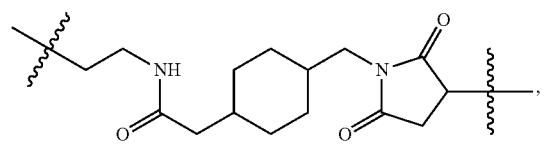
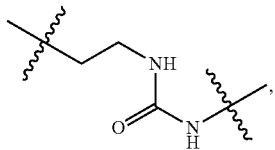
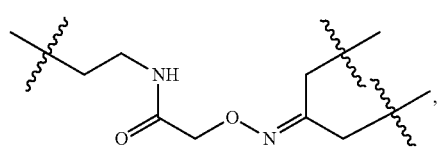
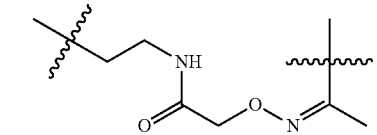
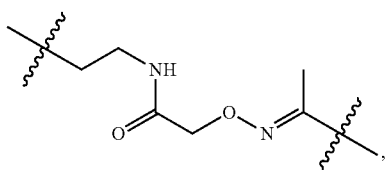
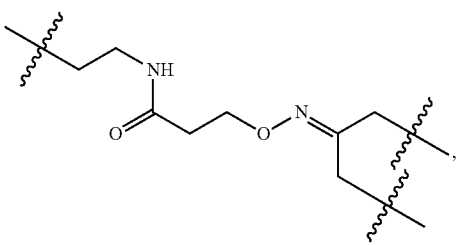

-continued
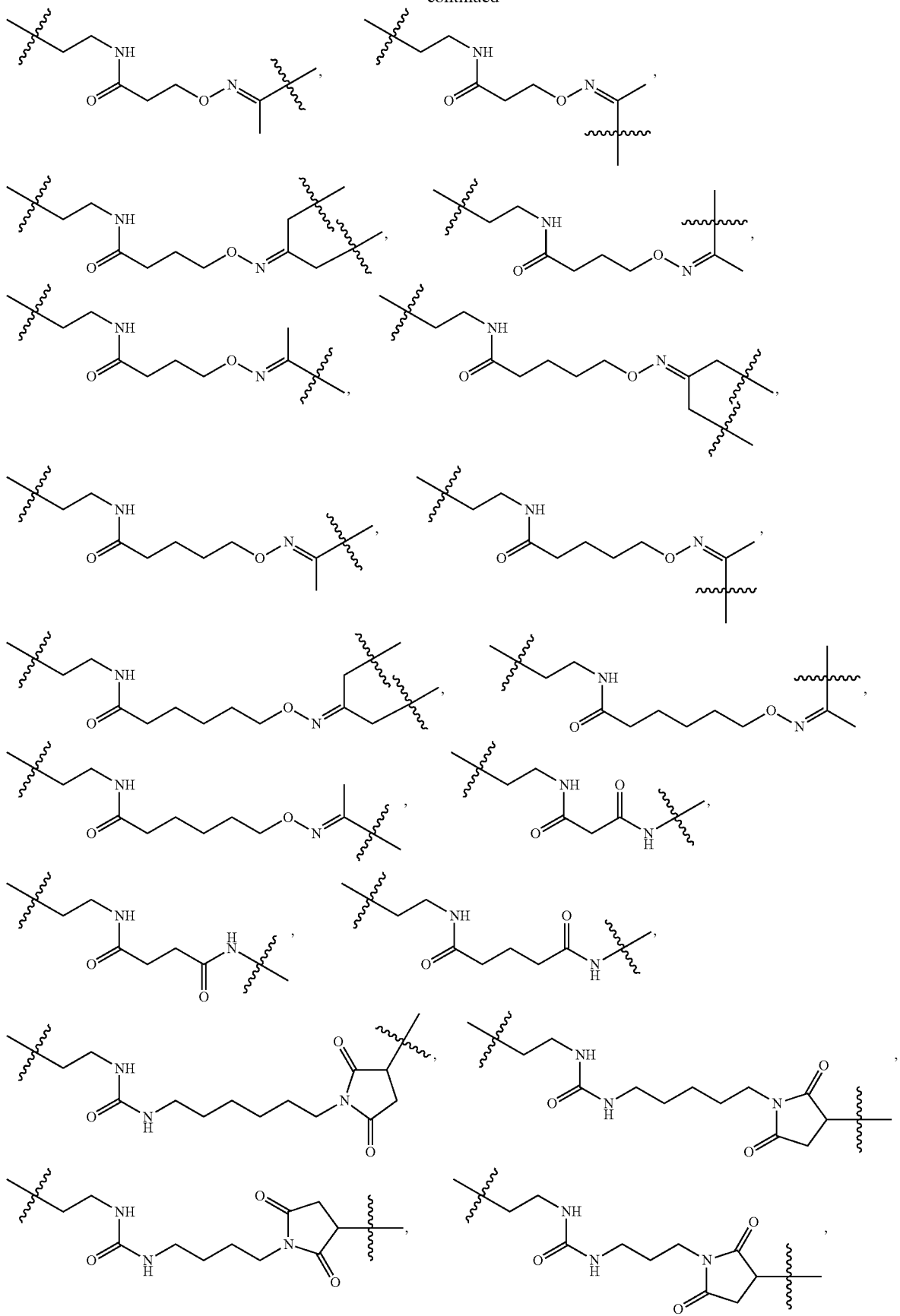

-continued
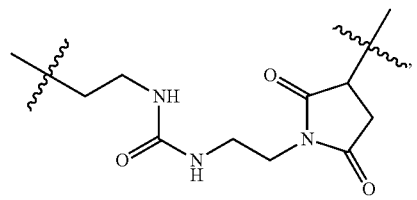
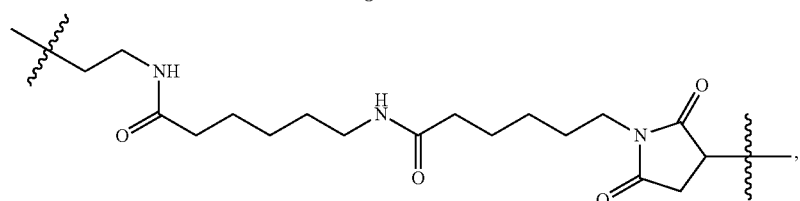
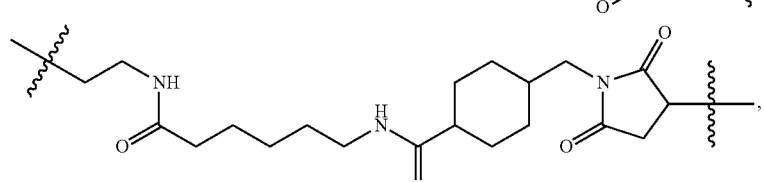
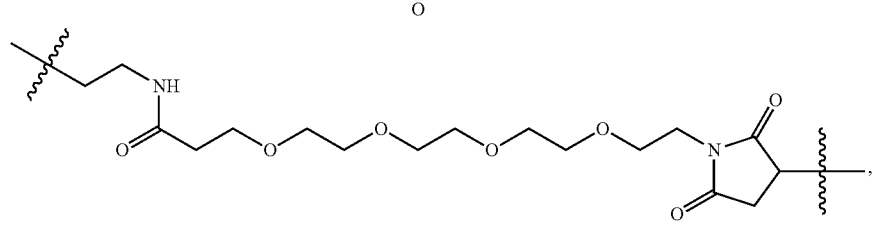
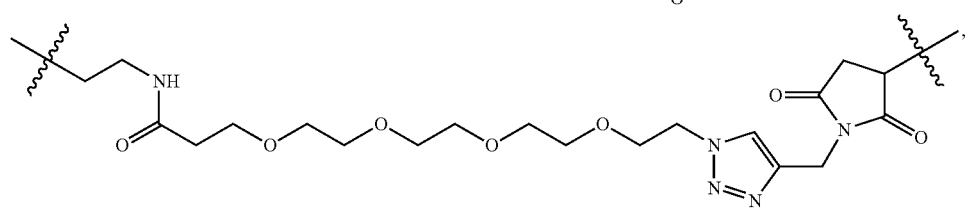
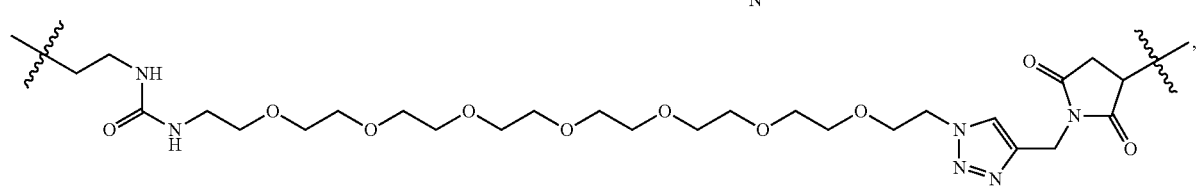
or
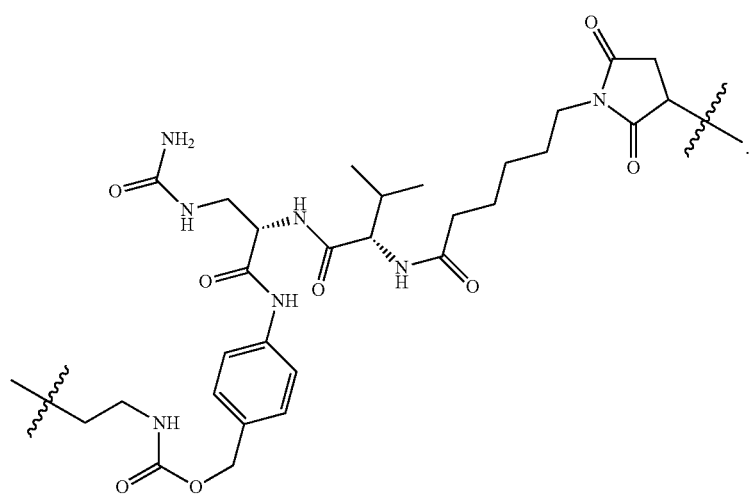

17. The immunoconjugate of claim 13, wherein $R^{20}$ is
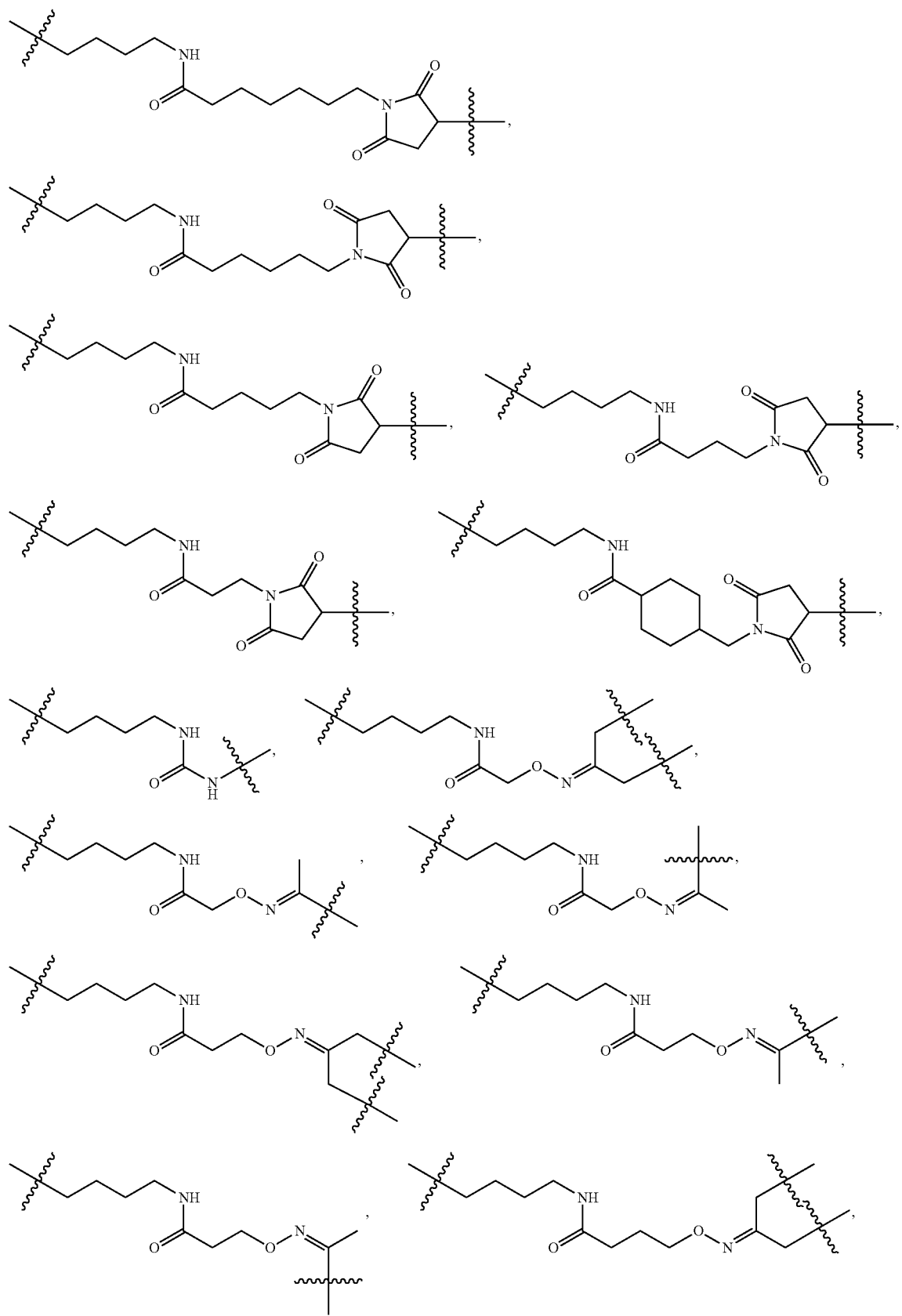

625
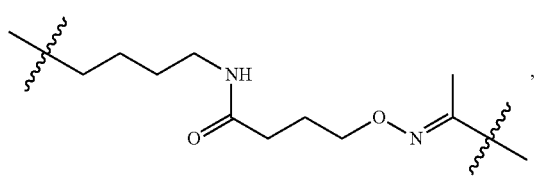
626
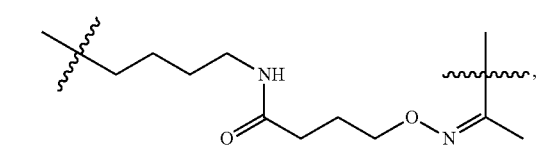
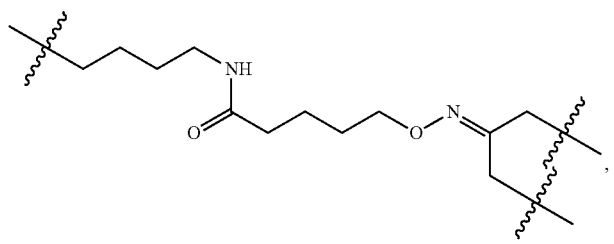
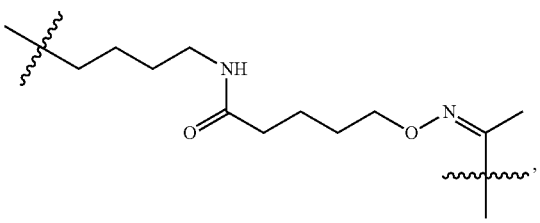
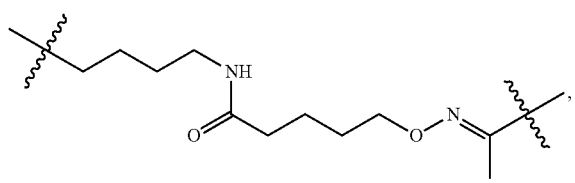
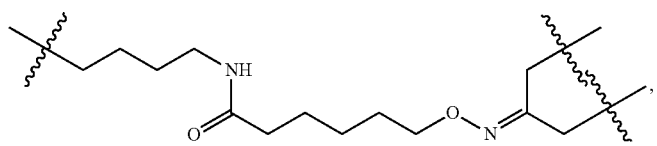
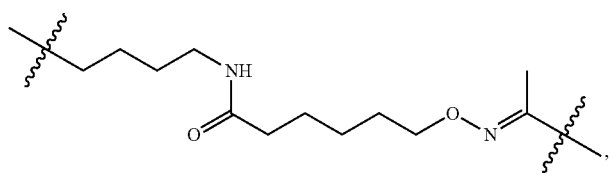
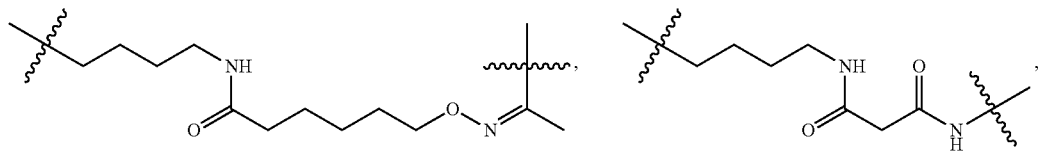
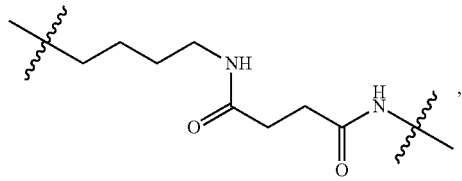
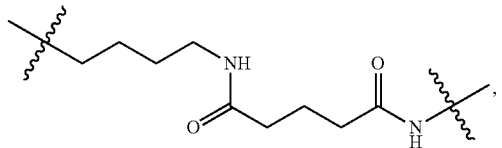
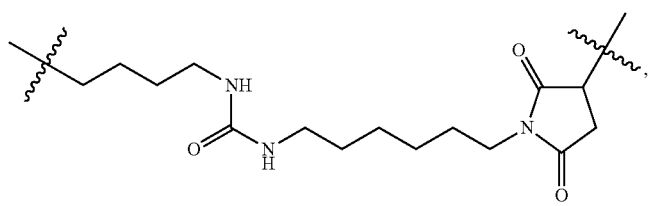
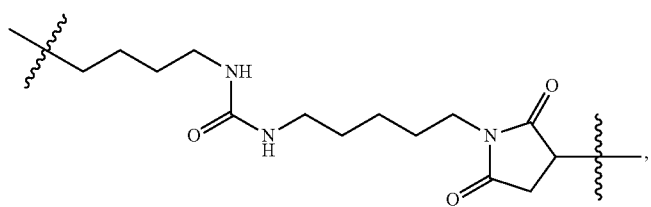

-continued
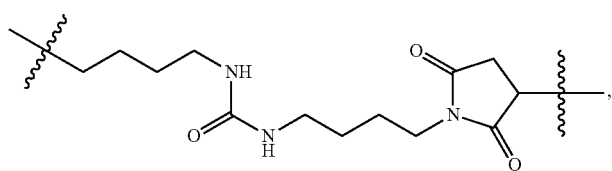
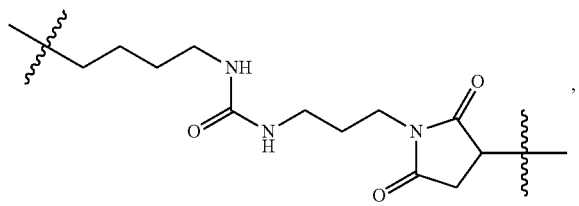
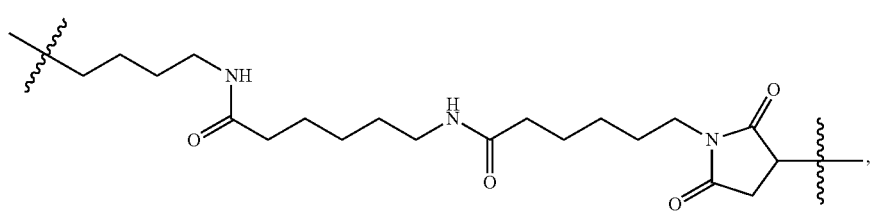
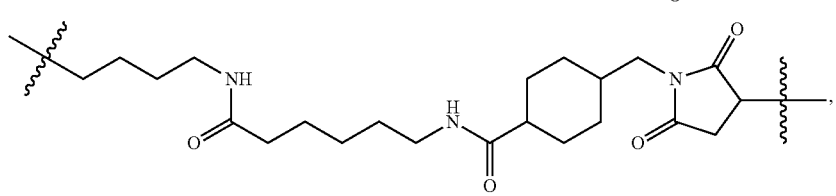
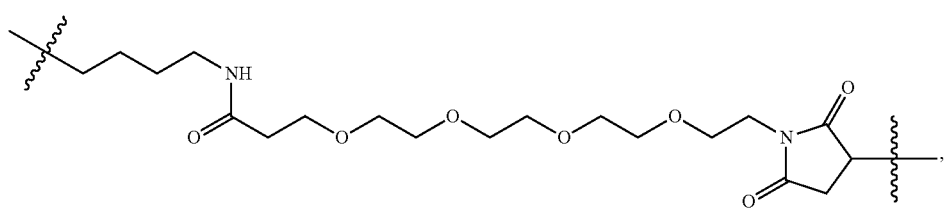
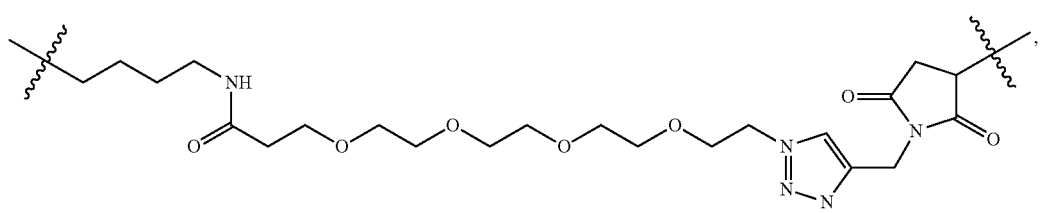
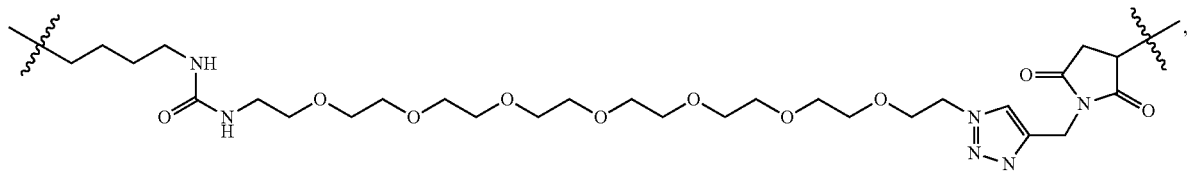
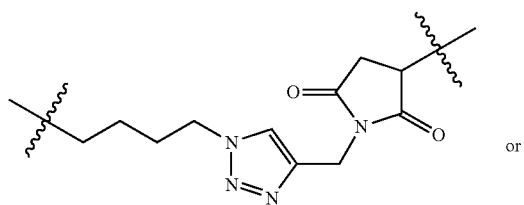 or -continued
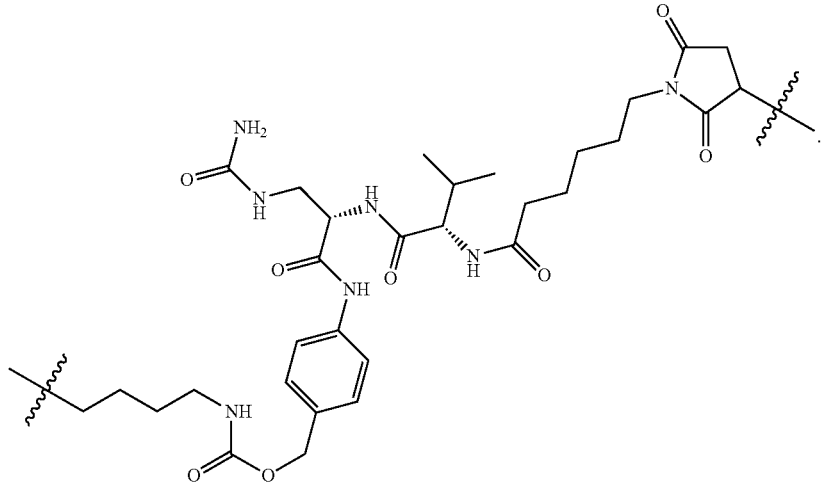
18. The immunoconjugate of claim 13, wherein $R^{20}$ is
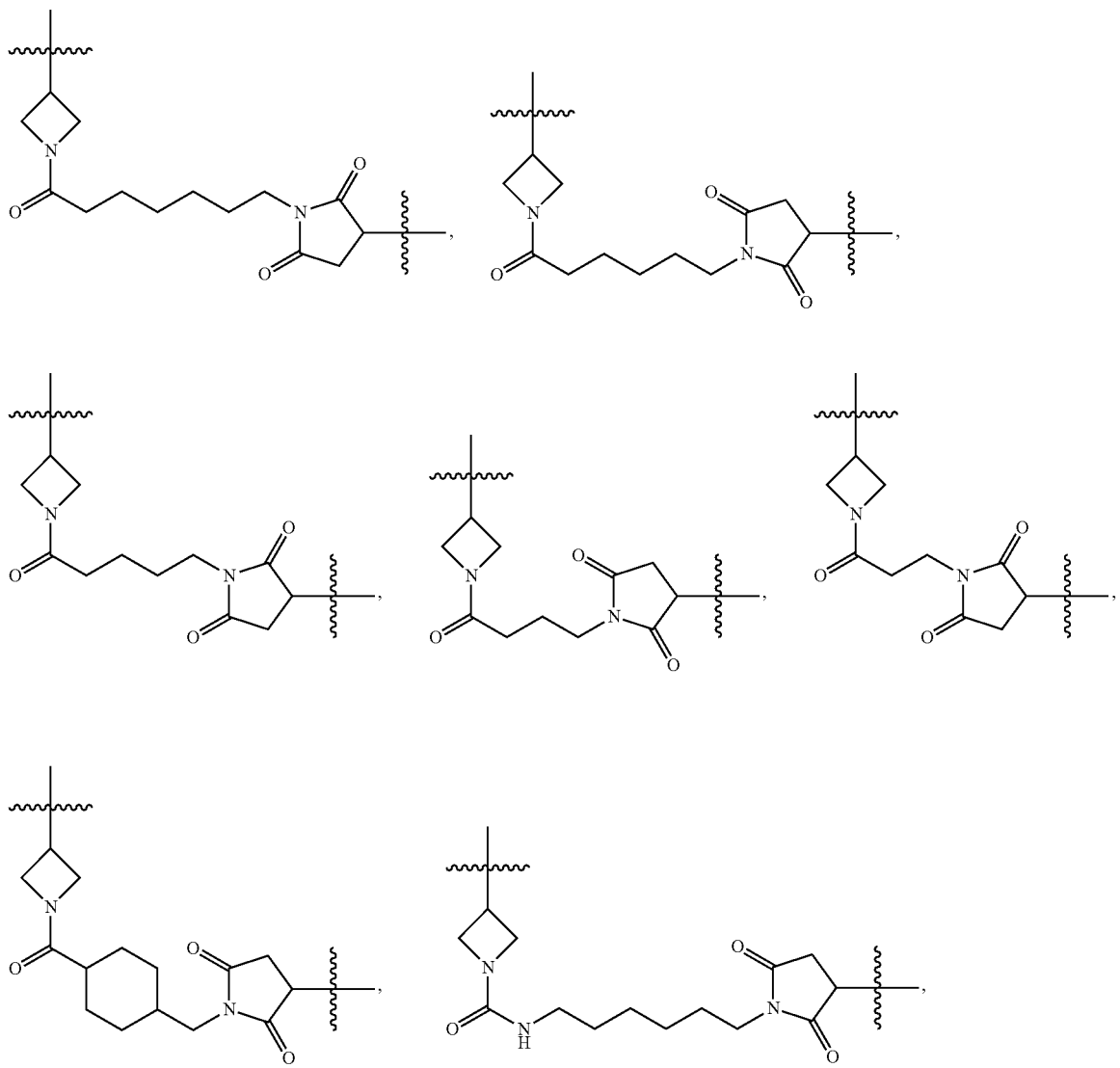

-continued
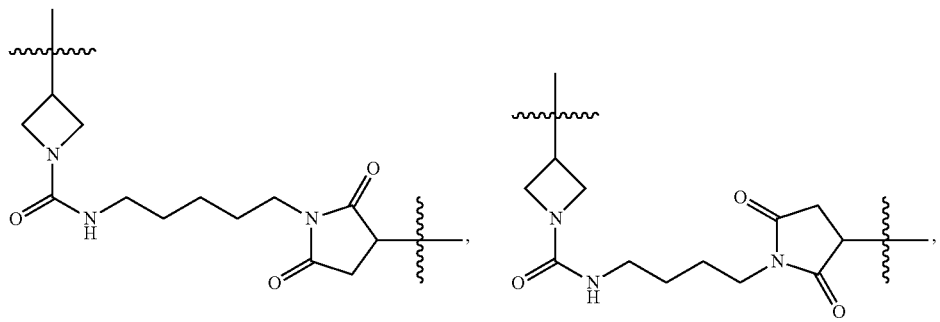
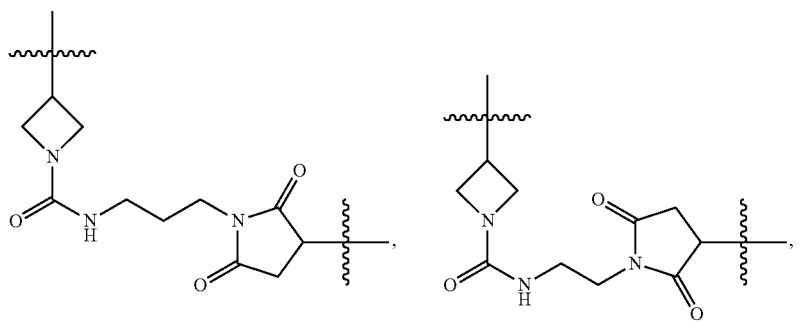
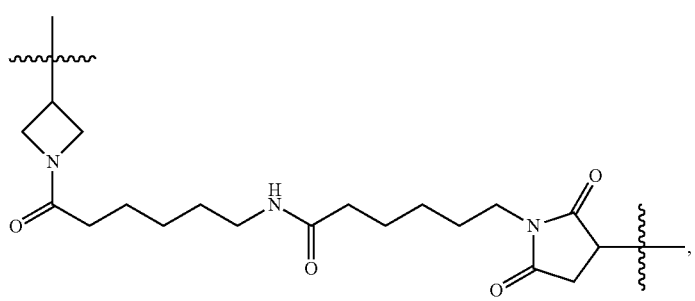
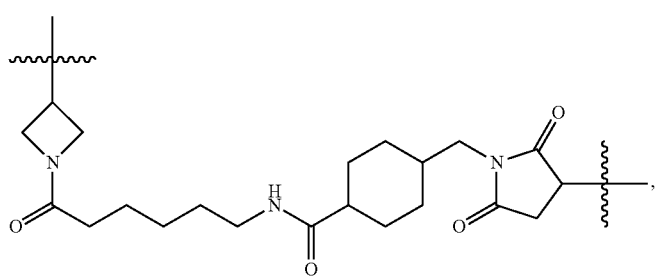
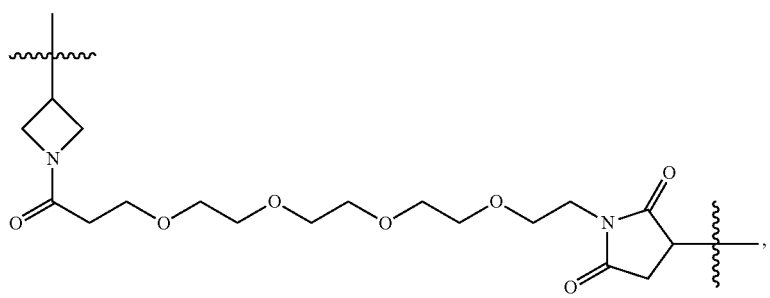

-continued
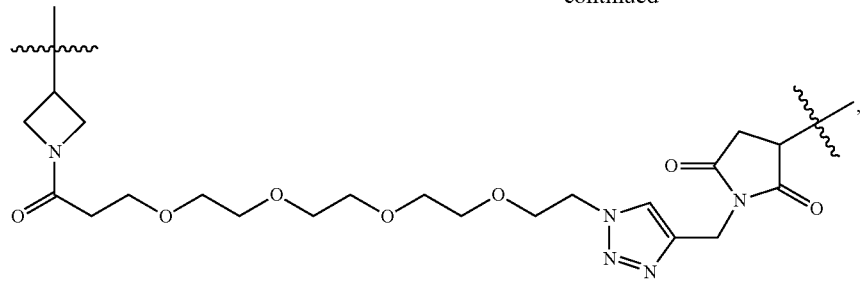
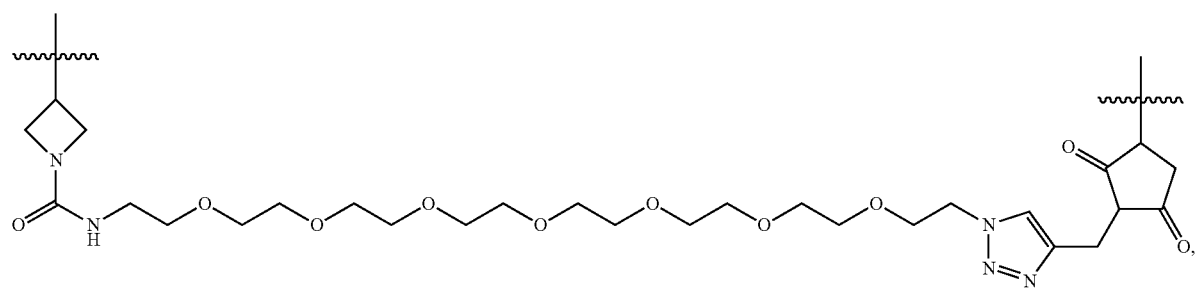
or
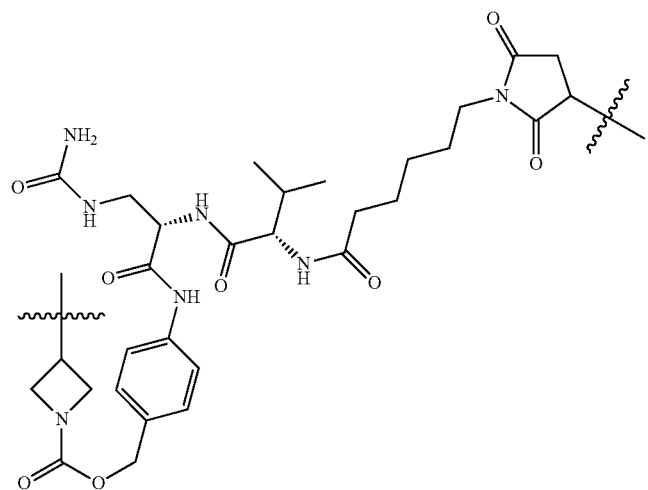 [SMILES: *C1CN(C(=O)OCc2ccc(NC(=O)[C@H](CNC(N)=O)NC(=O)[C@@H](NC(=O)CCCCCN3C(=O)CC(*)C3=O)C(C)C)cc2)C1]
19. The immunoconjugate of claim 13, wherein $R^{20}$ is
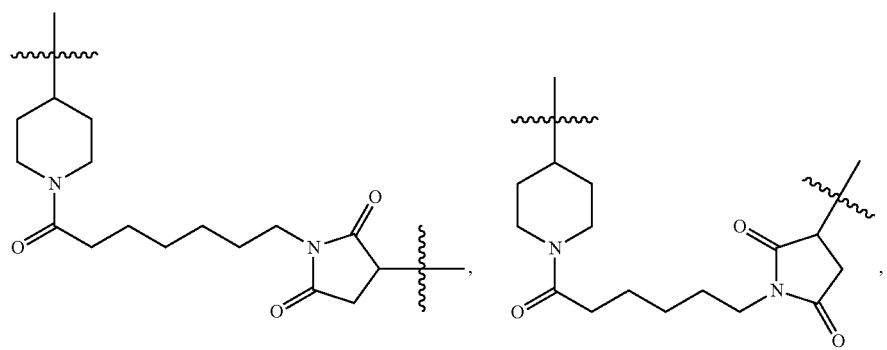

635
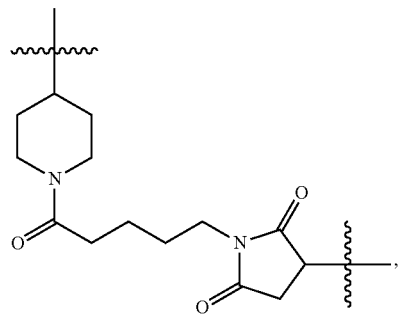
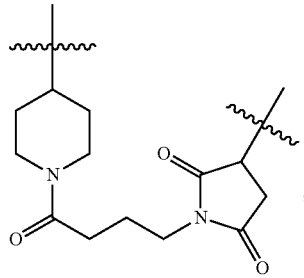
636
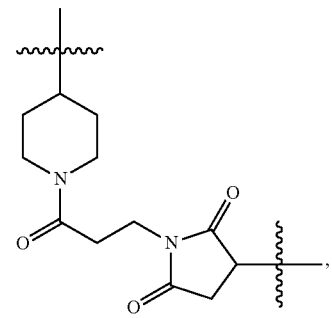
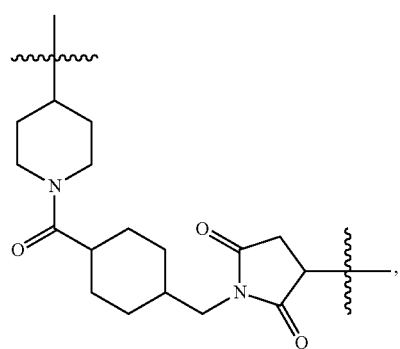
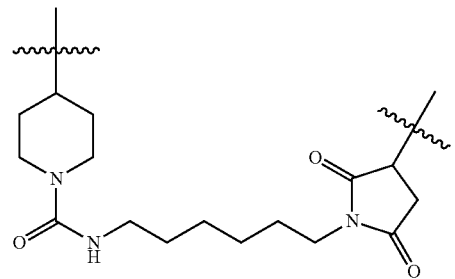
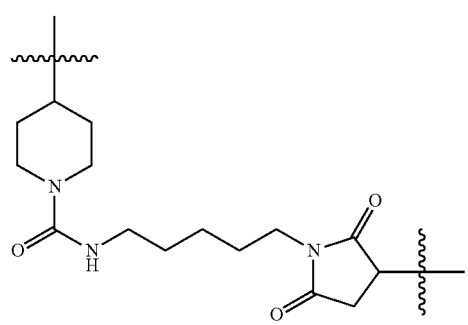
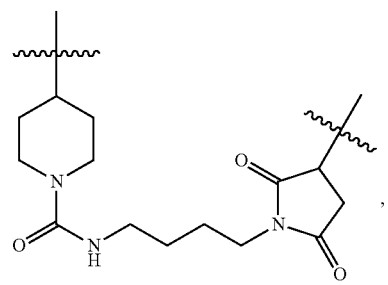
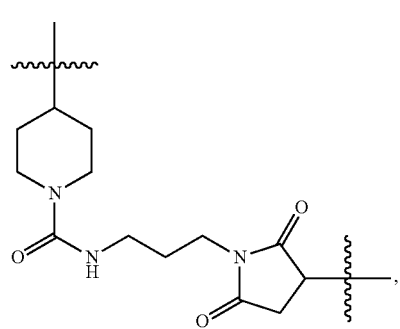
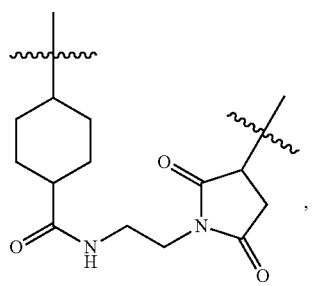
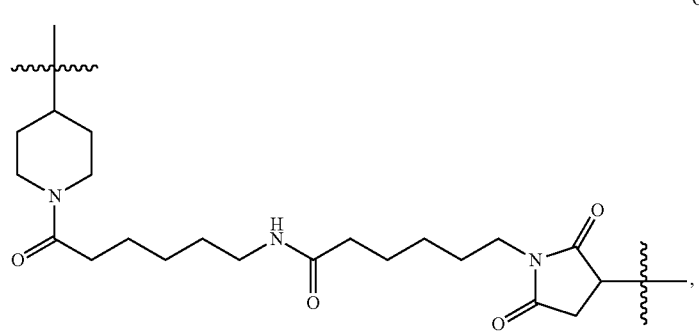

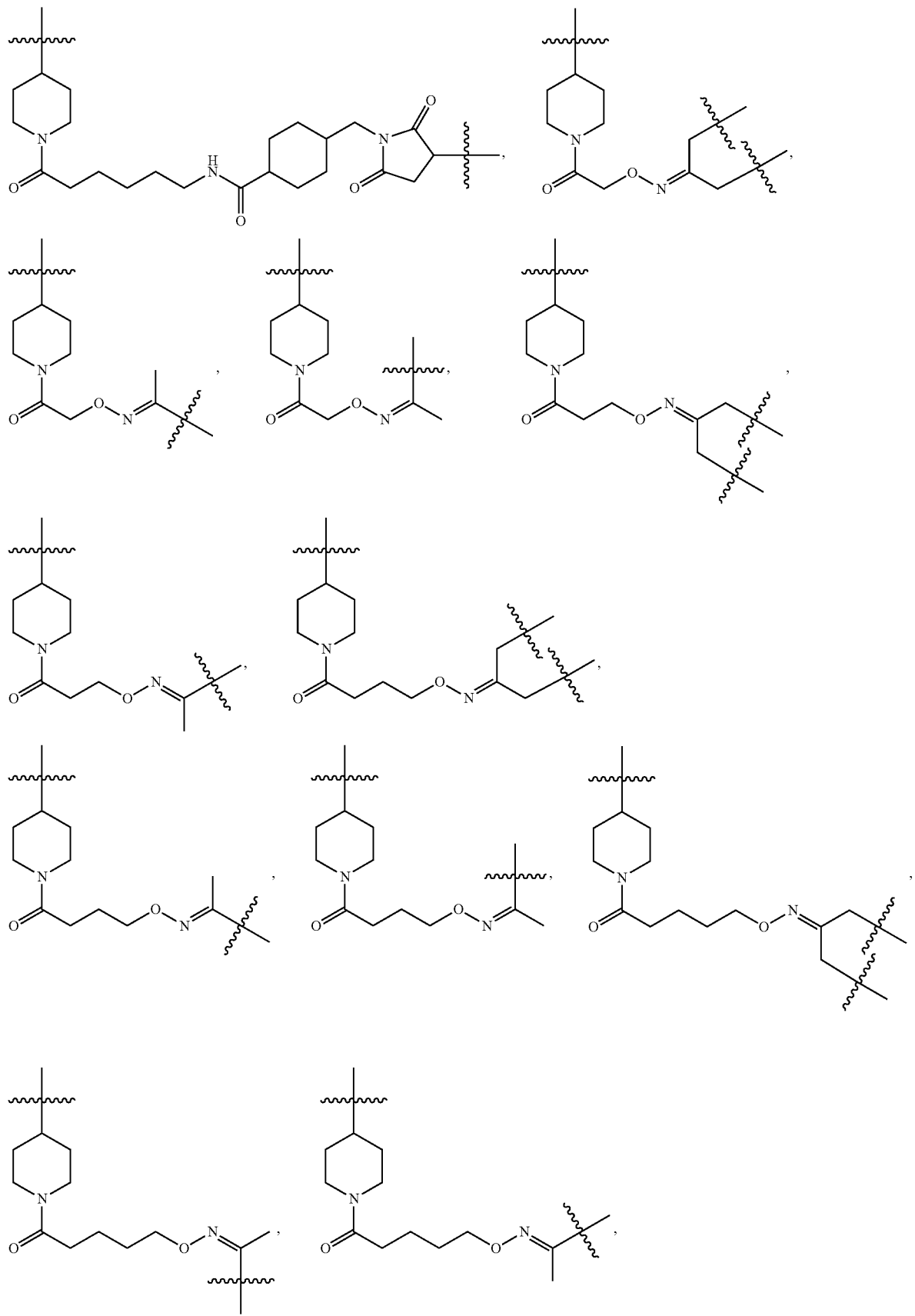

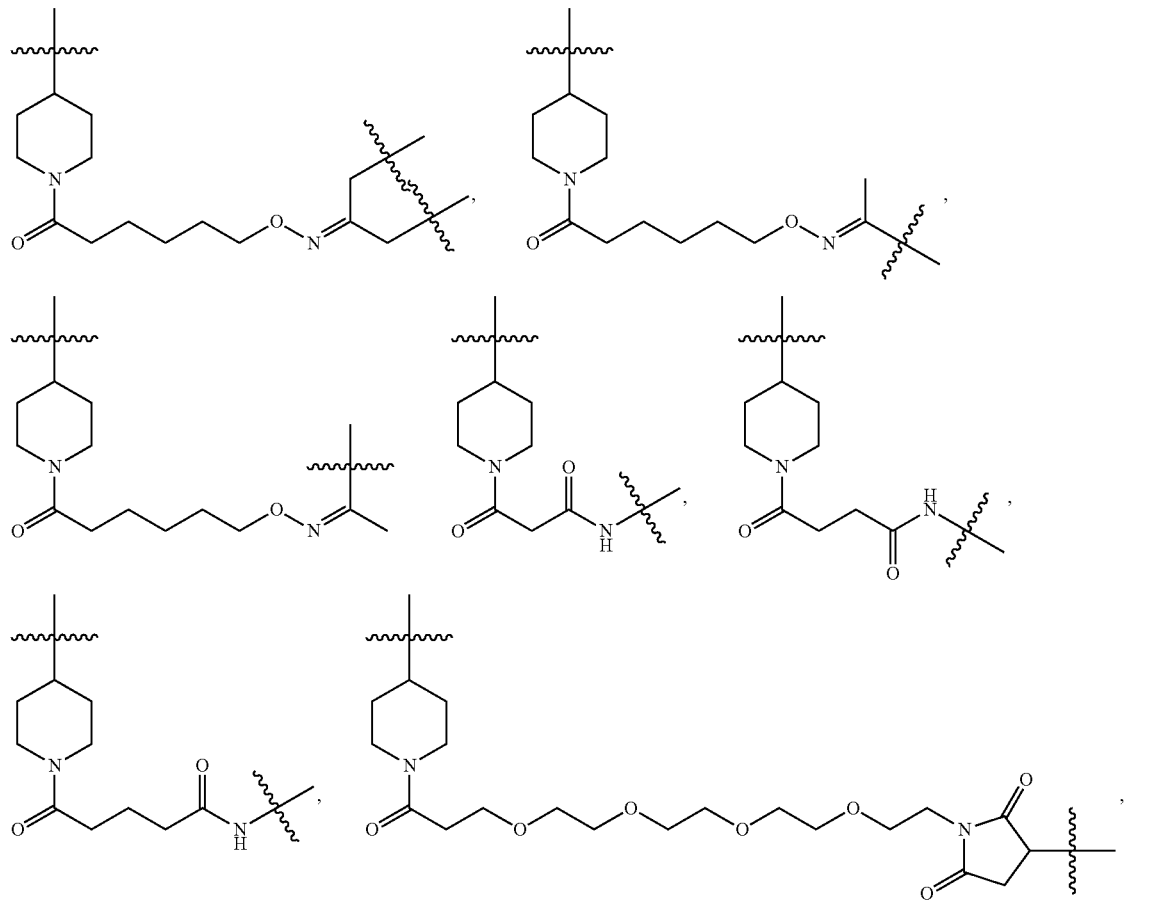
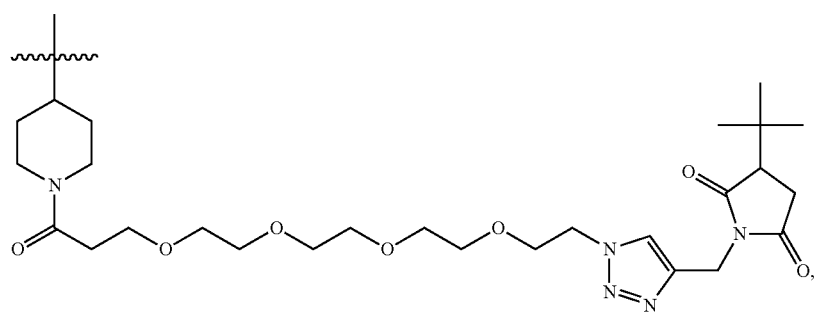
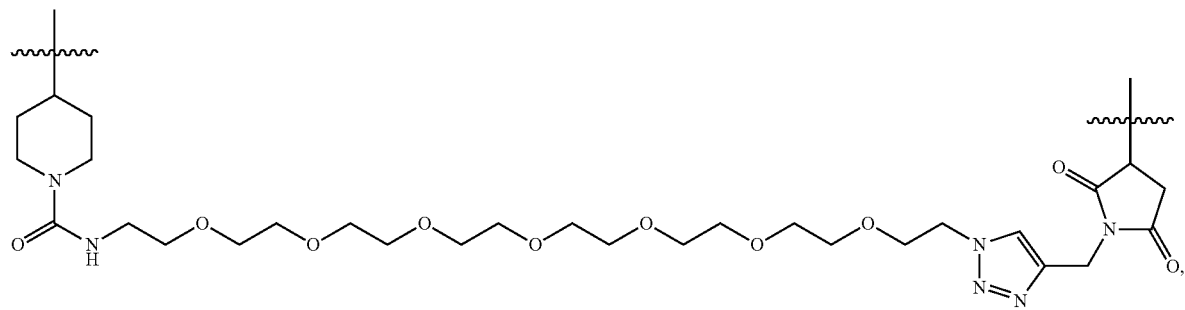

or
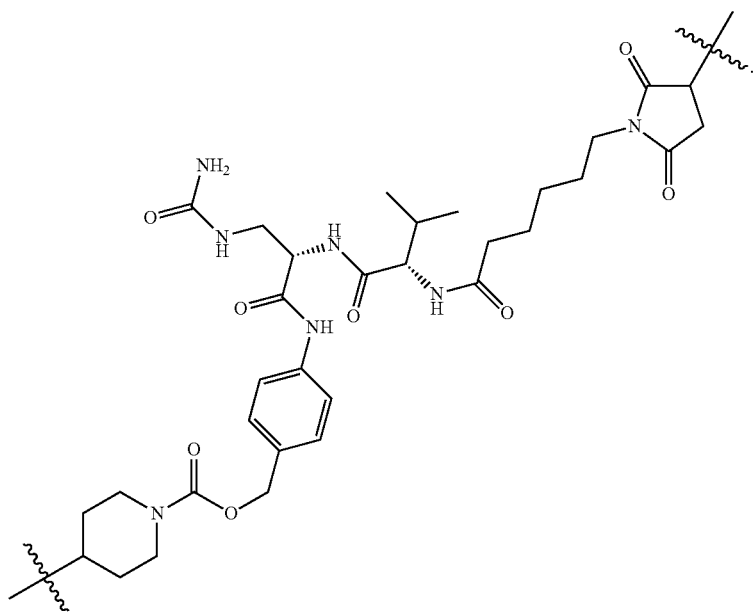
20. The immunoconjugate of claim 13, wherein $R^{20}$ is
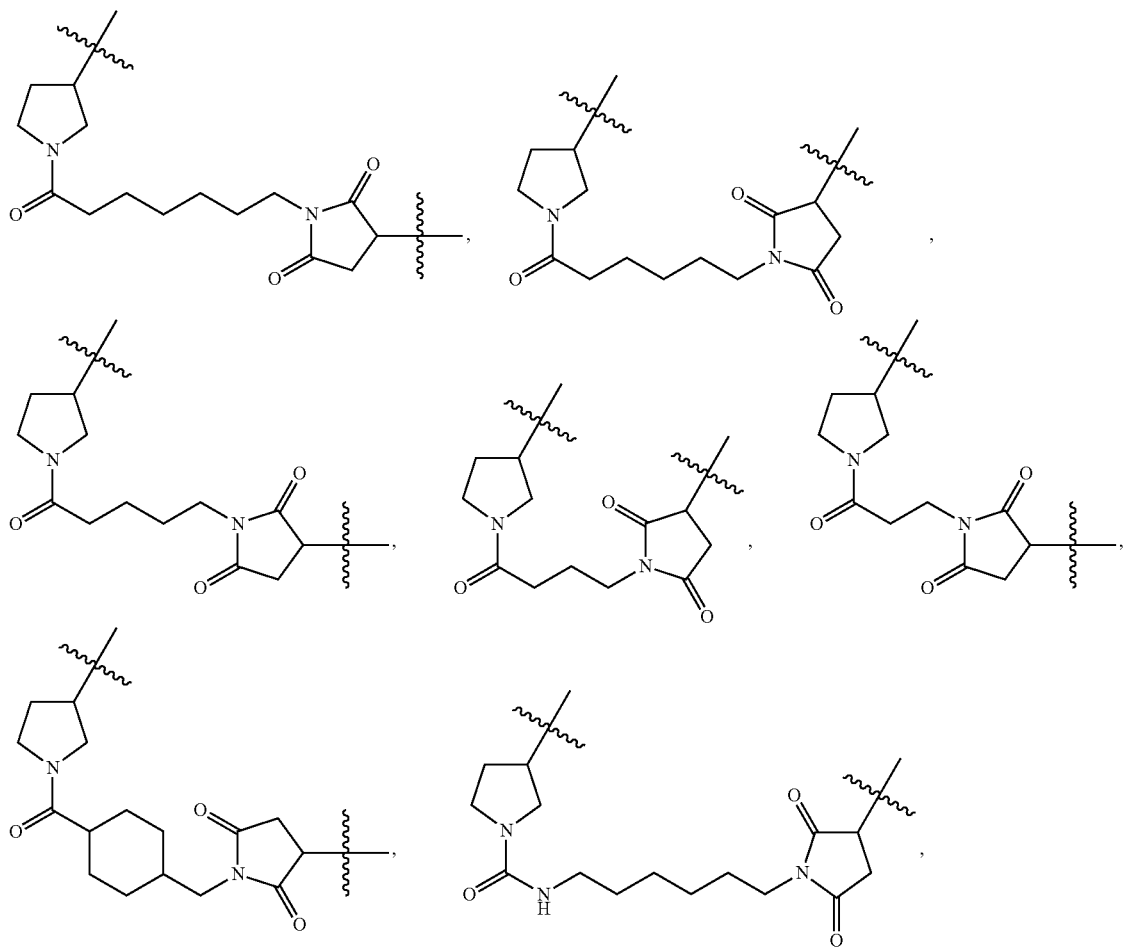

-continued
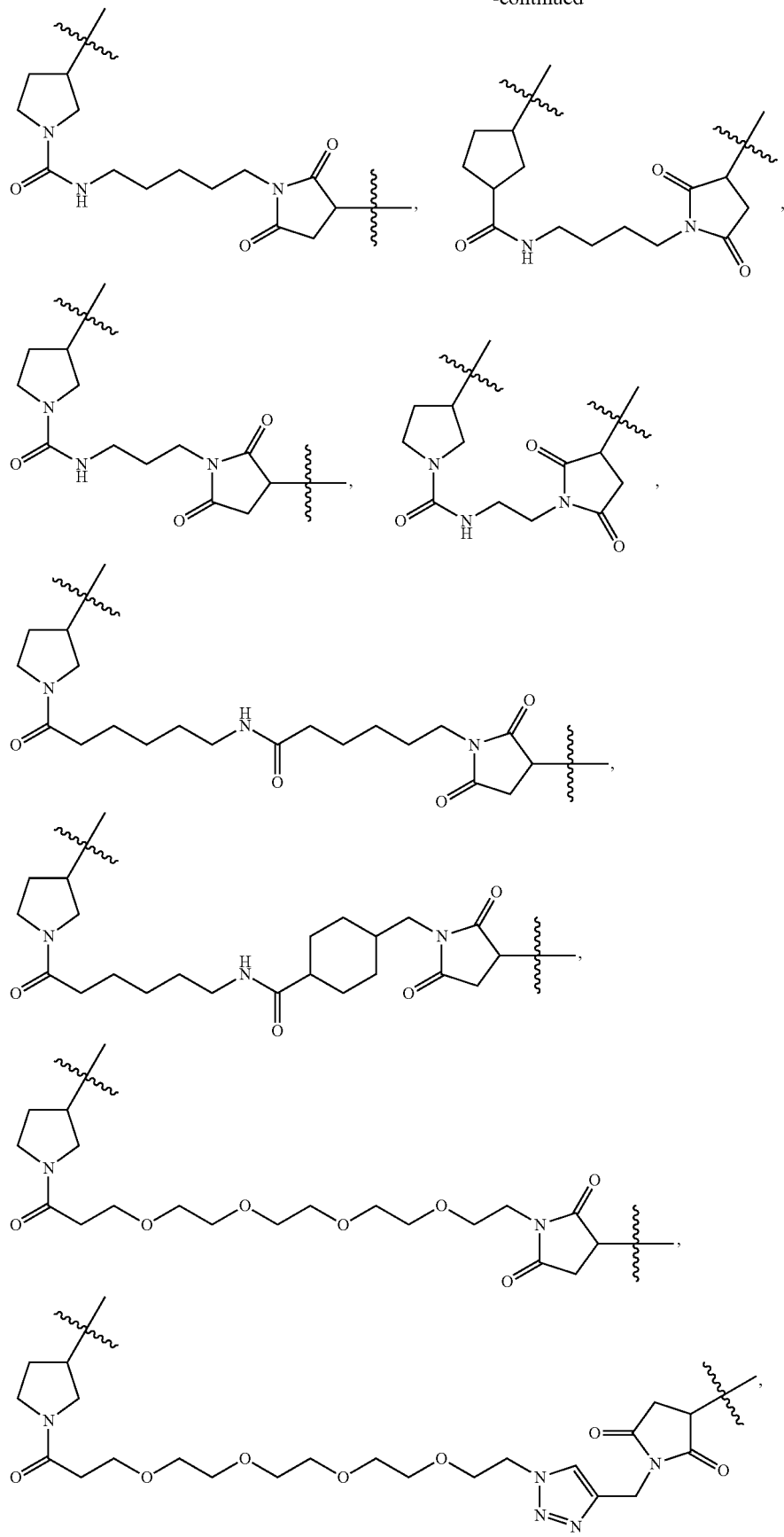

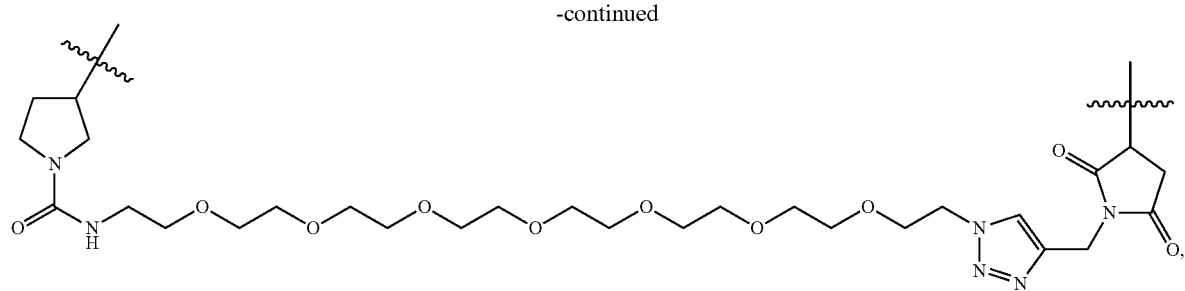
or
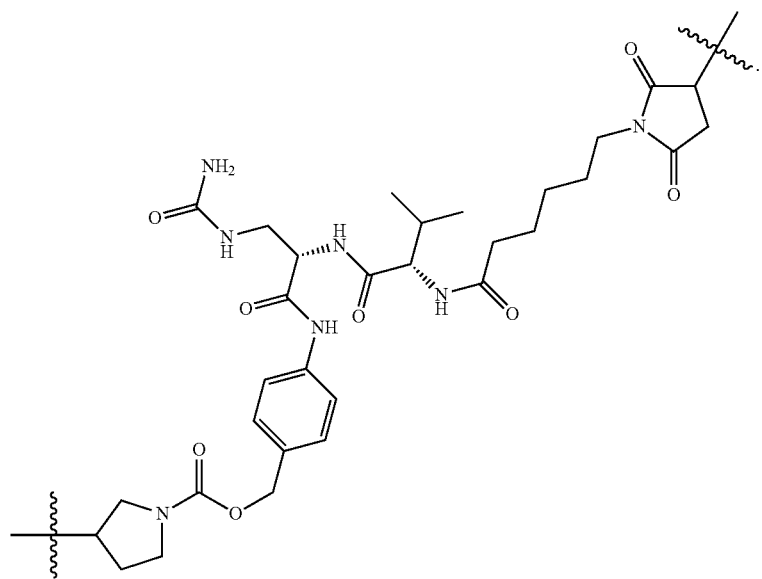 [SMILES: *C1CCN(C(=O)OCc2ccc(NC(=O)[C@H](CNC(N)=O)NC(=O)[C@@H](NC(=O)CCCCCN3C(=O)CC(*)C3=O)C(C)C)cc2)C1]
21. The immunoconjugate of claim 13, wherein $R^{20}$ is
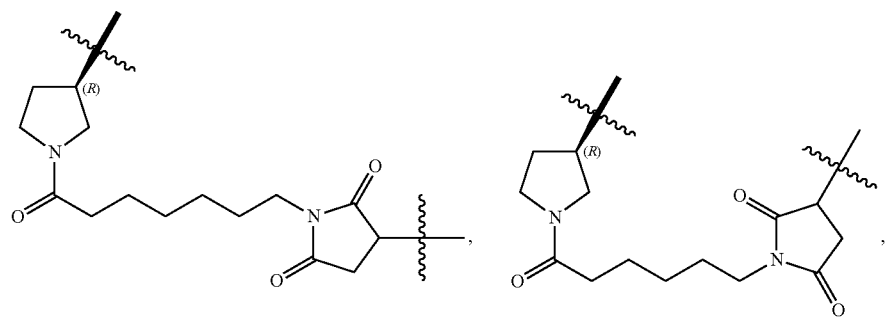
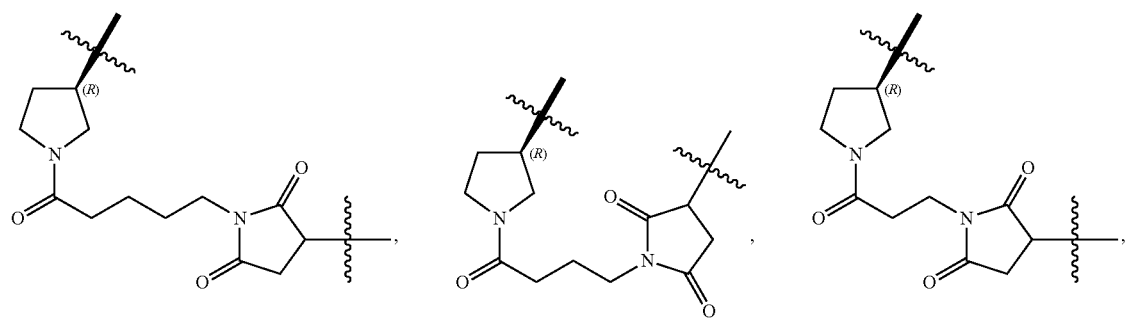

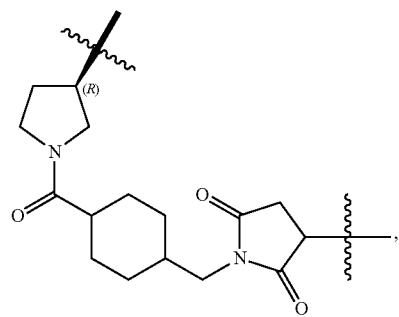 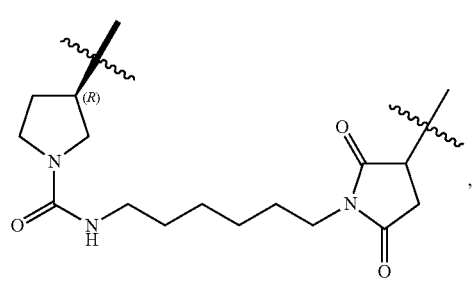
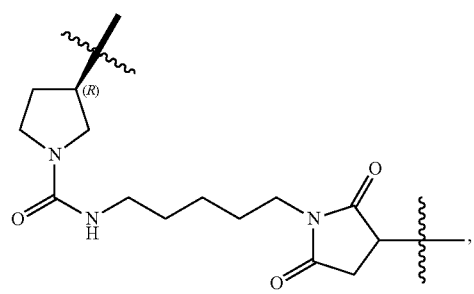 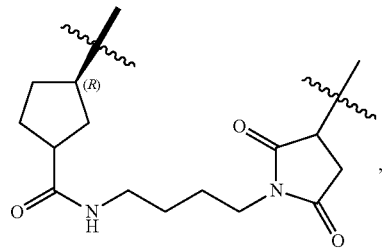
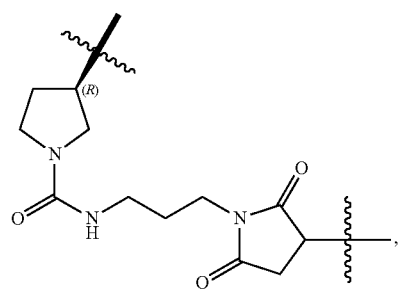 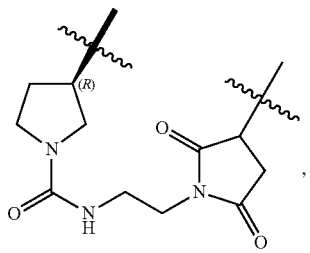
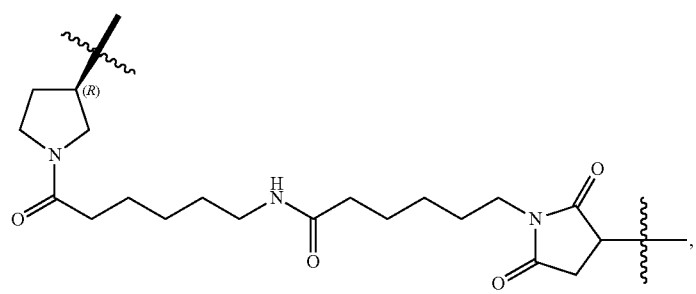
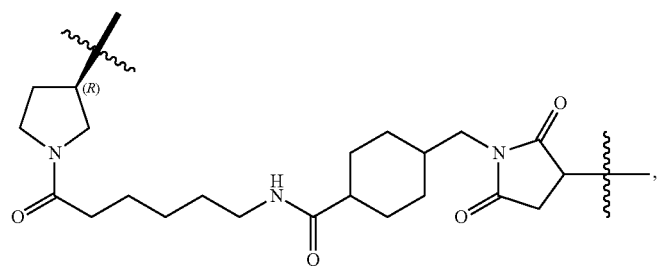

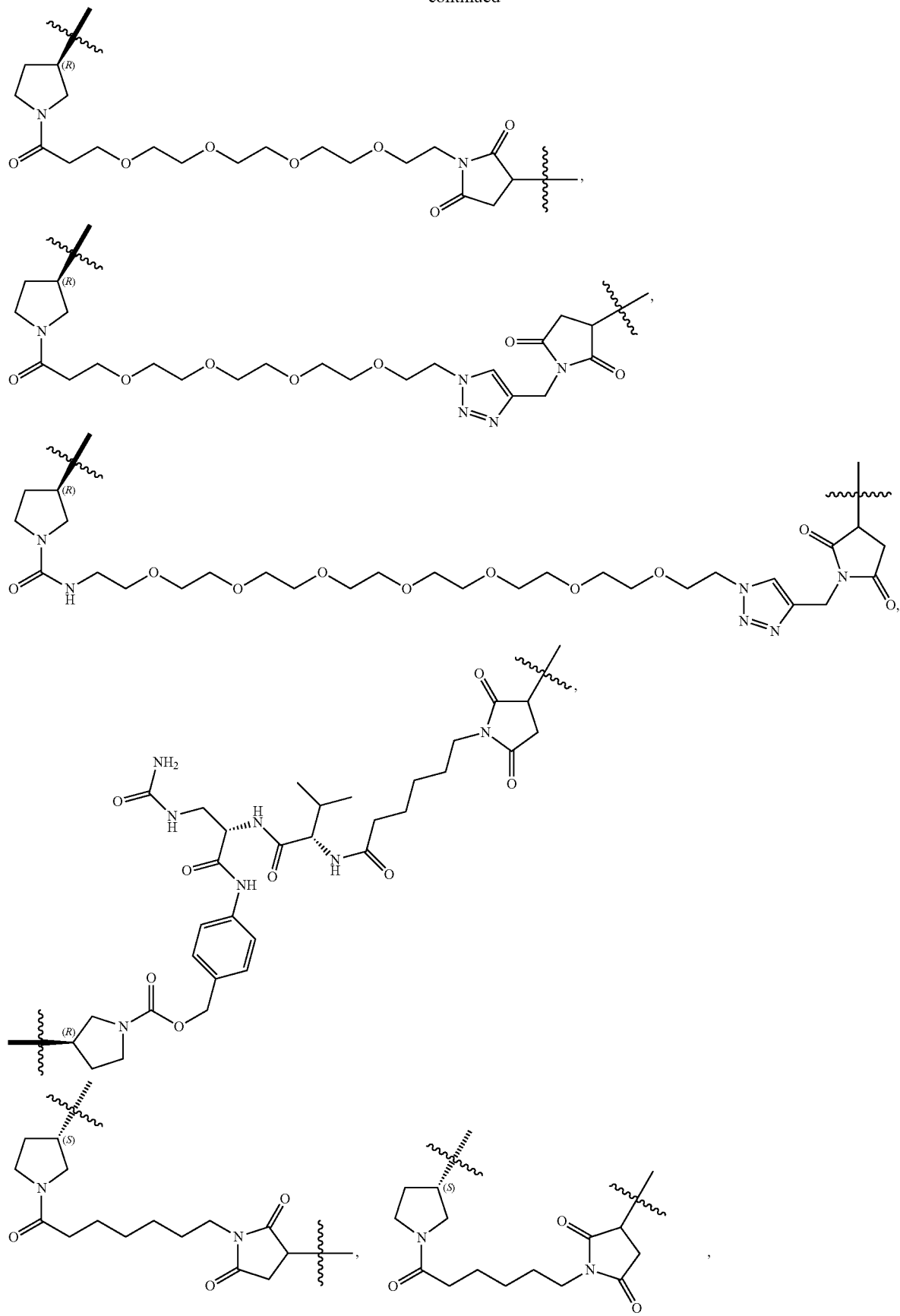

651
652
-continued
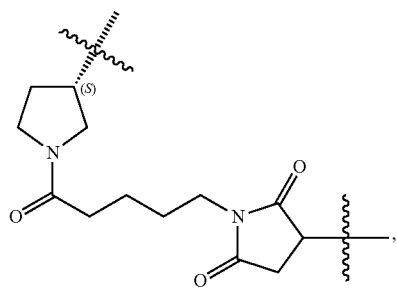
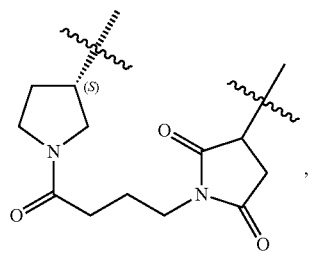
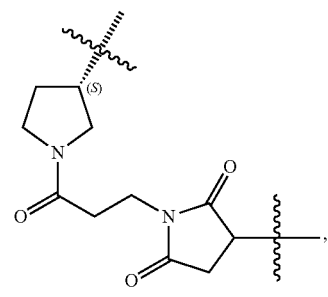
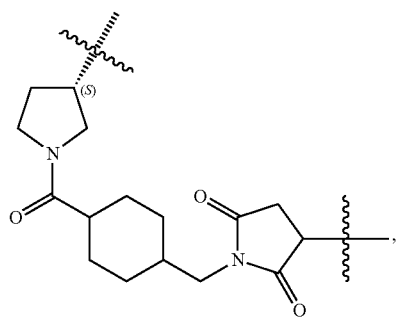
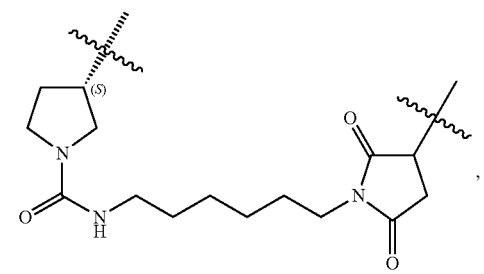
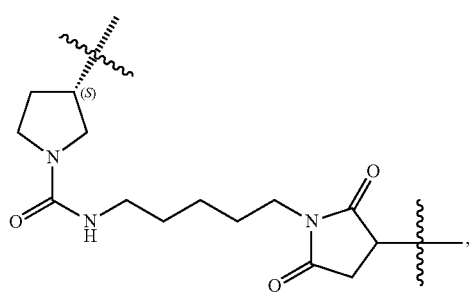
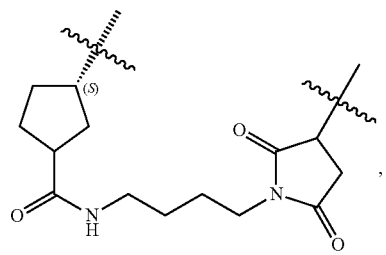
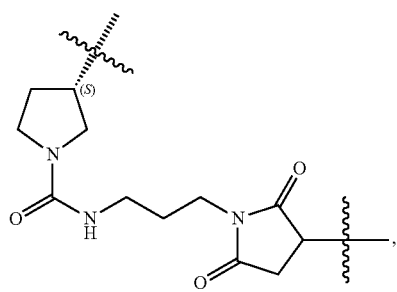
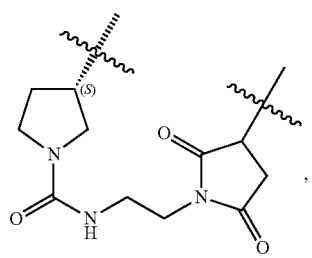
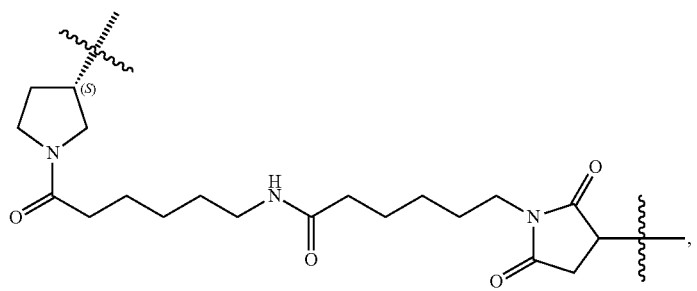

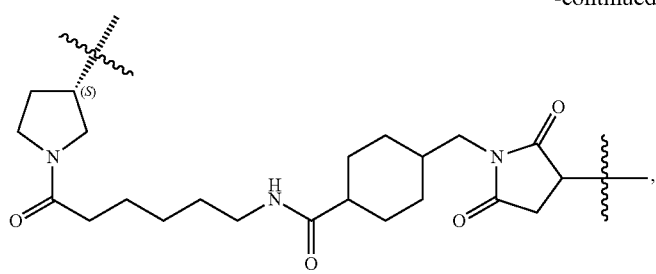
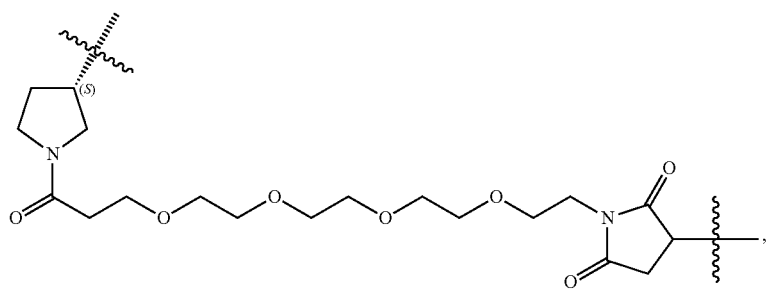
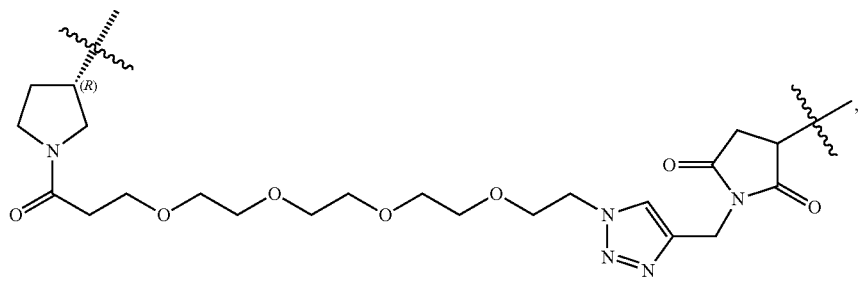
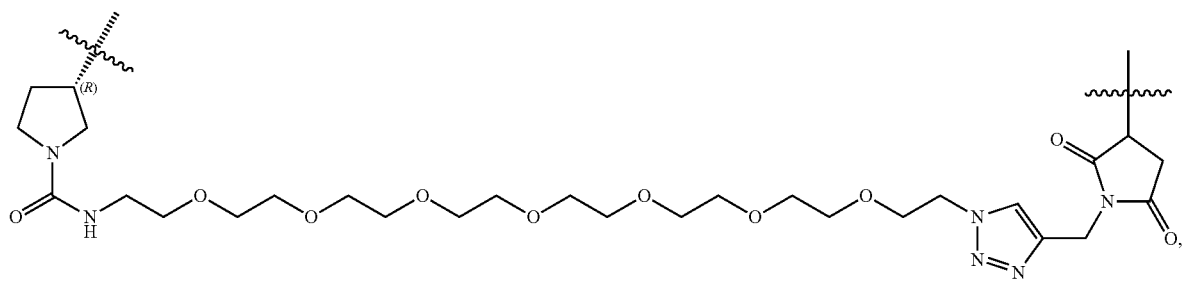

or
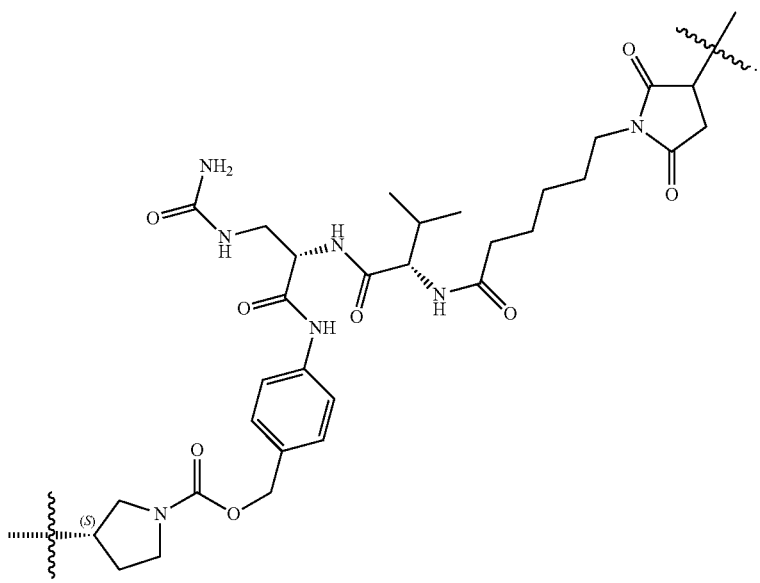
22. The immunoconjugate of claim 13, wherein:
R$^{20}$ is
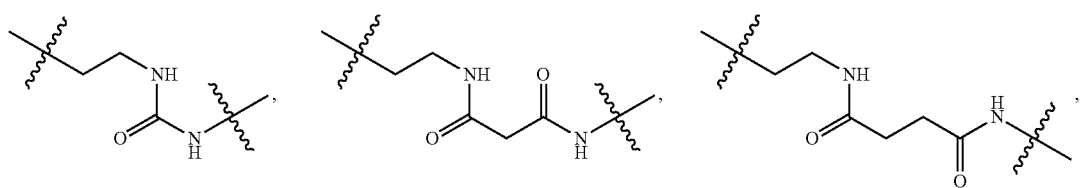
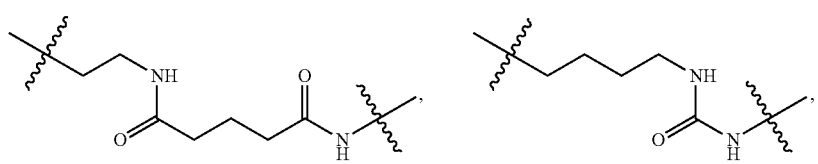
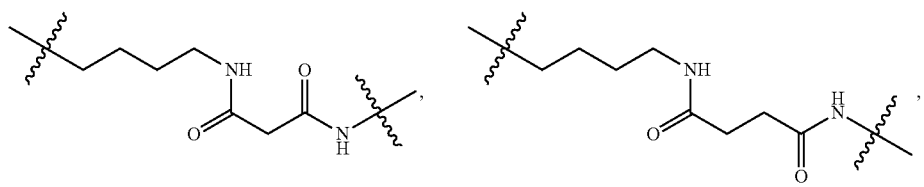
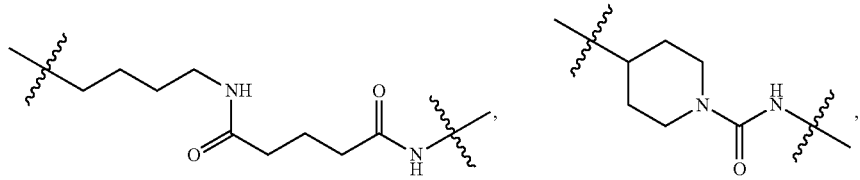 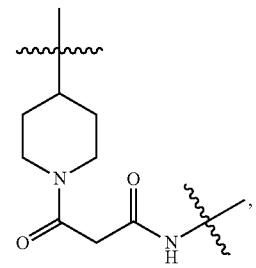

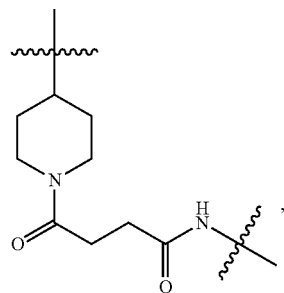
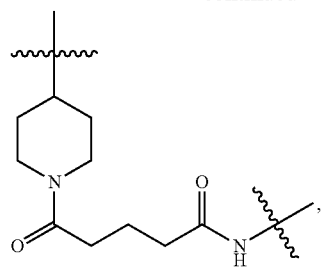
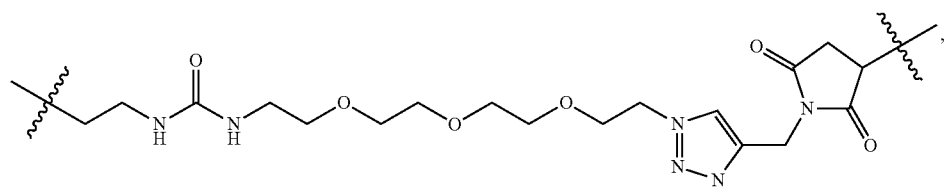
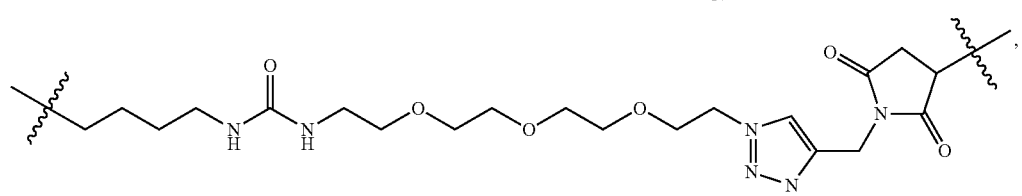
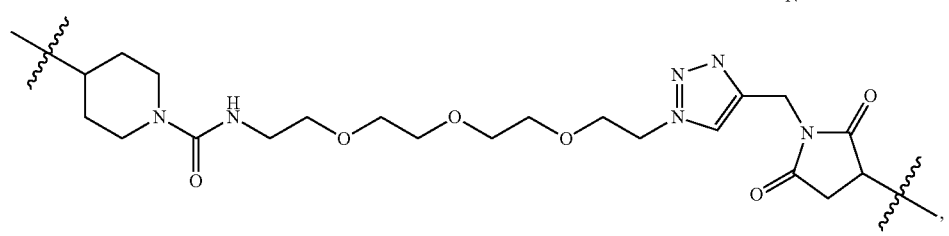
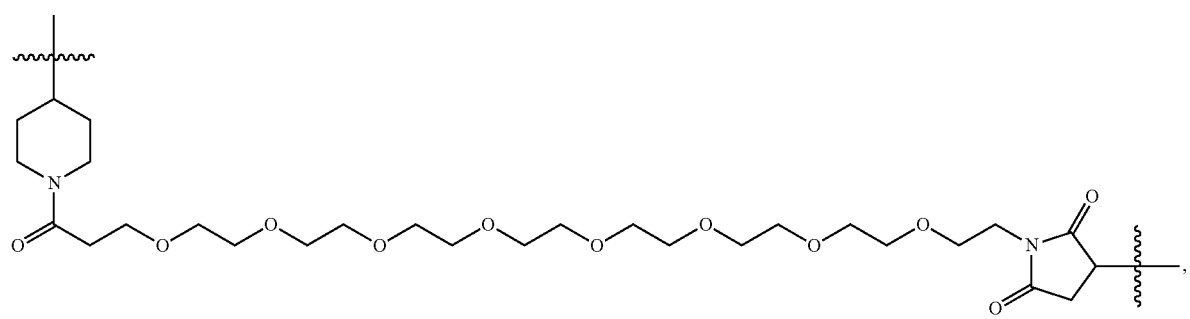
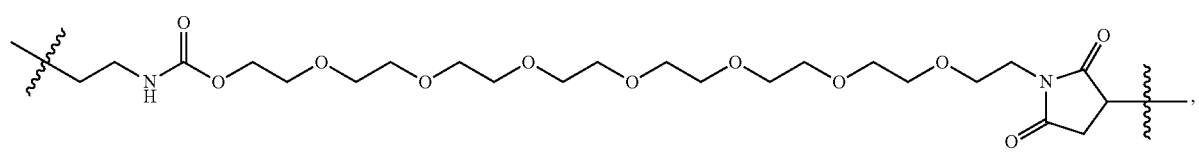
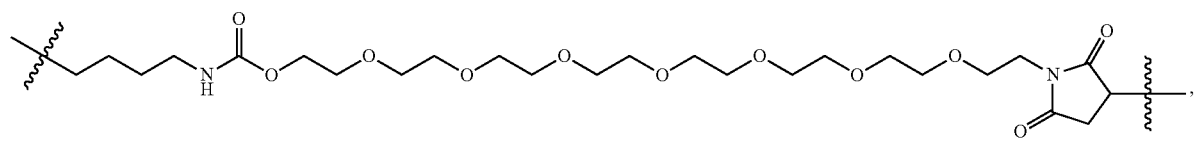

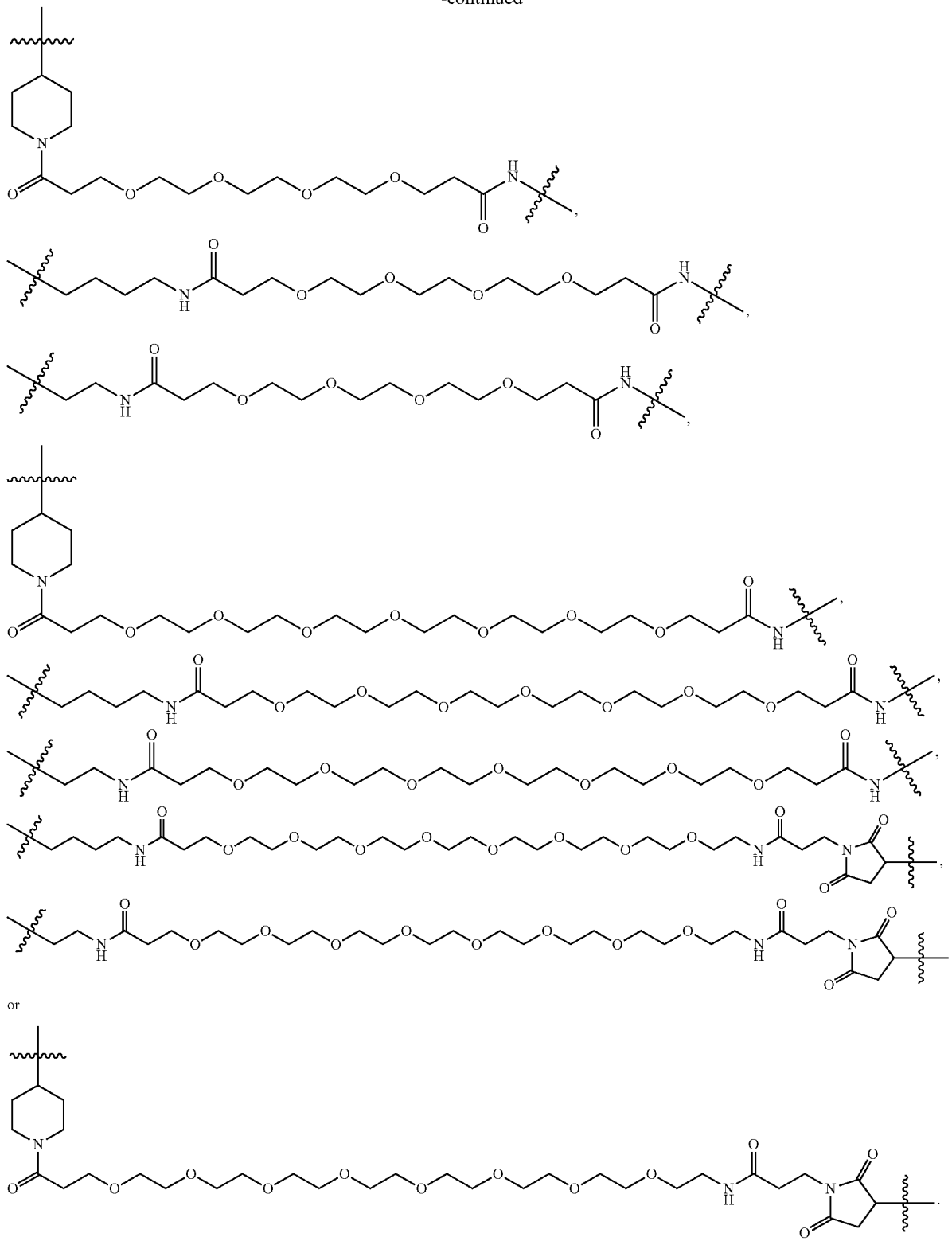
23. A pharmaceutical composition comprising an immunoconjugate of claim 13, and one or more pharmaceutically acceptable carriers.
* * * * *

SEQUENCE LISTING

<160> NUMBER OF SEQ ID NOS: 20

<210> SEQ ID NO 1
<211> LENGTH: 450
<212> TYPE: PRT
<213> ORGANISM: Artificial Sequence
<220> FEATURE:
<223> OTHER INFORMATION: anti-Her2 heavy chain wild-type

<400> SEQUENCE: 1

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                355                 360                 365
Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: anti-Her2 light chain wild-type

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 331
<212> TYPE: PRT
<213> ORGANISM: Artificial Sequence
<220> FEATURE:
<223> OTHER INFORMATION: constant region of the heavy chain wild-type of
``` anti-Her2

<400> SEQUENCE: 3

```
Ser Ala Ser Thr Lys Gly Pro Ser Val Phe Pro Leu Ala Pro Ser Ser
 1               5                  10                  15
Lys Ser Thr Ser Gly Gly Thr Ala Ala Leu Gly Cys Leu Val Lys Asp
            20                  25                  30
Tyr Phe Pro Glu Pro Val Thr Val Ser Trp Asn Ser Gly Ala Leu Thr
        35                  40                  45
Ser Gly Val His Thr Phe Pro Ala Val Leu Gln Ser Ser Gly Leu Tyr
    50                  55                  60
Ser Leu Ser Ser Val Val Thr Val Pro Ser Ser Leu Gly Thr Gln
 65                 70                  75                  80
Thr Tyr Ile Cys Asn Val Asn His Lys Pro Ser Asn Thr Lys Val Asp
                85                  90                  95
Lys Lys Val Glu Pro Lys Ser Cys Asp Lys Thr His Thr Cys Pro Pro
            100                 105                 110
Cys Pro Ala Pro Glu Leu Leu Gly Gly Pro Ser Val Phe Leu Phe Pro
        115                 120                 125
Pro Lys Pro Lys Asp Thr Leu Met Ile Ser Arg Thr Pro Glu Val Thr
    130                 135                 140
Cys Val Val Val Asp Val Ser His Glu Asp Pro Glu Val Lys Phe Asn
145                 150                 155                 160
Trp Tyr Val Asp Gly Val Glu Val His Asn Ala Lys Thr Lys Pro Arg
                165                 170                 175
Glu Glu Gln Tyr Asn Ser Thr Tyr Arg Val Val Ser Val Leu Thr Val
            180                 185                 190
Leu His Gln Asp Trp Leu Asn Gly Lys Glu Tyr Lys Cys Lys Val Ser
        195                 200                 205
Asn Lys Ala Leu Pro Ala Pro Ile Glu Lys Thr Ile Ser Lys Ala Lys
    210                 215                 220
Gly Gln Pro Arg Glu Pro Gln Val Tyr Thr Leu Pro Pro Ser Arg Glu
225                 230                 235                 240
Glu Met Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
            260                 265                 270
Asn Asn Tyr Lys Thr Thr Pro Pro Val Leu Asp Ser Asp Gly Ser Phe
        275                 280                 285
Phe Leu Tyr Ser Lys Leu Thr Val Asp Lys Ser Arg Trp Gln Gln Gly
    290                 295                 300
Asn Val Phe Ser Cys Ser Val Met His Glu Ala Leu His Asn His Tyr
305                 310                 315                 320
Thr Gln Lys Ser Leu Ser Leu Ser Pro Gly Lys
                325                 330
```

<210> SEQ ID NO 4
<211> LENGTH: 108
<212> TYPE: PRT
<213> ORGANISM: Artificial Sequence
<220> FEATURE:
<223> OTHER INFORMATION: constant region of the light chain wild-type of anti-Her2

<400> SEQUENCE: 4

Lys Arg Thr Val Ala Ala Pro Ser Val Phe Ile Phe Pro Pro Ser Asp

```
                1               5                   10                  15
            Glu Gln Leu Lys Ser Gly Thr Ala Ser Val Val Cys Leu Leu Asn Asn
                            20                  25                  30

Phe Tyr Pro Arg Glu Ala Lys Val Gln Trp Lys Val Asp Asn Ala Leu
                            35                  40                  45

Gln Ser Gly Asn Ser Gln Glu Ser Val Thr Glu Gln Asp Ser Lys Asp
                        50                  55                  60

Ser Thr Tyr Ser Leu Ser Ser Thr Leu Thr Leu Ser Lys Ala Asp Tyr
             65                  70                  75                  80

Glu Lys His Lys Val Tyr Ala Cys Glu Val Thr His Gln Gly Leu Ser
                            85                  90                  95

Ser Pro Val Thr Lys Ser Phe Asn Arg Gly Glu Cys
                            100                 105

<210> SEQ ID NO 5
<211> LENGTH: 108
<212> TYPE: PRT
<213> ORGANISM: Artificial Sequence
<220> FEATURE:
<223> OTHER INFORMATION: constant region of the mutant light chain of
      anti-Her2 LC-S159C

<400> SEQUENCE: 5

Lys Arg Thr Val Ala Ala Pro Ser Val Phe Ile Phe Pro Pro Ser Asp
             1               5                   10                  15

Glu Gln Leu Lys Ser Gly Thr Ala Ser Val Val Cys Leu Leu Asn Asn
                            20                  25                  30

Phe Tyr Pro Arg Glu Ala Lys Val Gln Trp Lys Val Asp Asn Ala Leu
                            35                  40                  45

Gln Ser Gly Asn Cys Gln Glu Ser Val Thr Glu Gln Asp Ser Lys Asp
                        50                  55                  60

Ser Thr Tyr Ser Leu Ser Ser Thr Leu Thr Leu Ser Lys Ala Asp Tyr
             65                  70                  75                  80

Glu Lys His Lys Val Tyr Ala Cys Glu Val Thr His Gln Gly Leu Ser
                            85                  90                  95

Ser Pro Val Thr Lys Ser Phe Asn Arg Gly Glu Cys
                            100                 105

<210> SEQ ID NO 6
<211> LENGTH: 342
<212> TYPE: PRT
<213> ORGANISM: Artificial Sequence
<220> FEATURE:
<223> OTHER INFORMATION: constant region of the mutant heavy chain of
      HC-E388-DSLEFIASKLA-N389 in anti-Her2

<400> SEQUENCE: 6

Ser Ala Ser Thr Lys Gly Pro Ser Val Phe Pro Leu Ala Pro Ser Ser
             1               5                   10                  15

Lys Ser Thr Ser Gly Gly Thr Ala Ala Leu Gly Cys Leu Val Lys Asp
                            20                  25                  30

Tyr Phe Pro Glu Pro Val Thr Val Ser Trp Asn Ser Gly Ala Leu Thr
                            35                  40                  45

Ser Gly Val His Thr Phe Pro Ala Val Leu Gln Ser Gly Leu Tyr
                        50                  55                  60

Ser Leu Ser Ser Val Val Thr Val Pro Ser Ser Ser Leu Gly Thr Gln
             65                  70                  75                  80

Thr Tyr Ile Cys Asn Val Asn His Lys Pro Ser Asn Thr Lys Val Asp
```

85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asp Ser Leu Glu Phe Ile Ala Ser Lys Leu Ala Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 7
<211> LENGTH: 11
<212> TYPE: PRT
<213> ORGANISM: Artificial Sequence
<220> FEATURE:
<223> OTHER INFORMATION: ybbR tag

<400> SEQUENCE: 7

Asp Ser Leu Glu Phe Ile Ala Ser Lys Leu Ala
1               5                   10

<210> SEQ ID NO 8
<211> LENGTH: 24
<212> TYPE: PRT
<213> ORGANISM: Artificial Sequence
<220> FEATURE:
<223> OTHER INFORMATION: signal sequence

<400> SEQUENCE: 8

Met Lys Thr Phe Ile Leu Leu Trp Val Leu Leu Trp Val Ile
1               5                   10                  15

Phe Leu Leu Pro Gly Ala Thr Ala
            20

<210> SEQ ID NO 9
<211> LENGTH: 450
<212> TYPE: PRT
<213> ORGANISM: Artificial Sequence
<220> FEATURE:
<223> OTHER INFORMATION: Full length sequence of the mutant heavy chain
of anti-Her HC-E152C-S375C

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Cys Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365
```

```
Thr Cys Leu Val Lys Gly Phe Tyr Pro Cys Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 10
<211> LENGTH: 41
<212> TYPE: DNA
<213> ORGANISM: Artificial Sequence
<220> FEATURE:
<223> OTHER INFORMATION: LC-S159C (Sense)

<400> SEQUENCE: 10
agcggcaact gtcaggagag cgtcaccgag caggacagca a                 41

<210> SEQ ID NO 11
<211> LENGTH: 40
<212> TYPE: DNA
<213> ORGANISM: Artificial Sequence
<220> FEATURE:
<223> OTHER INFORMATION: LC-S159C (anti-sense)

<400> SEQUENCE: 11
ctctcctgac agttgccgct ctgcagggcg ttgtccacct                   40

<210> SEQ ID NO 12
<211> LENGTH: 52
<212> TYPE: DNA
<213> ORGANISM: Artificial Sequence
<220> FEATURE:
<223> OTHER INFORMATION: HC-E388-DSLEFIASKLA-N389 (Sense)

<400> SEQUENCE: 12
ctggagttca tcgccagcaa gctggccaac aactacaaga ccacacctcc ag     52

<210> SEQ ID NO 13
<211> LENGTH: 46
<212> TYPE: DNA
<213> ORGANISM: Artificial Sequence
<220> FEATURE:
<223> OTHER INFORMATION: HC-E388-DSLEFIASKLA-N389 (anti-sense)

<400> SEQUENCE: 13
cttgctggcg atgaactcca ggctgtcctc gggctggccg ttgctc            46

<210> SEQ ID NO 14
<211> LENGTH: 45
<212> TYPE: DNA
<213> ORGANISM: Artificial Sequence
<220> FEATURE:
<223> OTHER INFORMATION: B. subtilis Sfp pET22b primer

<400> SEQUENCE: 14
gaaggagata tacatatgaa aatttatggg atttacatgg atcgc             45
```

<210> SEQ ID NO 15
<211> LENGTH: 44
<212> TYPE: DNA
<213> ORGANISM: Artificial Sequence
<220> FEATURE:
<223> OTHER INFORMATION: B. subtilis Sfp pET22b primer

<400> SEQUENCE: 15
gtggtggtgg tggtggtgca gcaattcttc ataggagacc atcg    44

<210> SEQ ID NO 16
<211> LENGTH: 22
<212> TYPE: DNA
<213> ORGANISM: Artificial Sequence
<220> FEATURE:
<223> OTHER INFORMATION: pET22b primer

<400> SEQUENCE: 16
caccaccacc accaccactg ag    22

<210> SEQ ID NO 17
<211> LENGTH: 41
<212> TYPE: DNA
<213> ORGANISM: Artificial Sequence
<220> FEATURE:
<223> OTHER INFORMATION: pET22b primer

<400> SEQUENCE: 17
catatgtata tctccttctt aaagttaaac aaaattattt c    41

<210> SEQ ID NO 18
<211> LENGTH: 43
<212> TYPE: DNA
<213> ORGANISM: Artificial Sequence
<220> FEATURE:
<223> OTHER INFORMATION: TEV into B. subtilis Sfp pET22b primer

<400> SEQUENCE: 18
gagaacctgt acttccaagg ccaccaccac caccaccact gag    43

<210> SEQ ID NO 19
<211> LENGTH: 47
<212> TYPE: DNA
<213> ORGANISM: Artificial Sequence
<220> FEATURE:
<223> OTHER INFORMATION: TEV into B. subtilis Sfp pET22b primer

<400> SEQUENCE: 19
gccttggaag tacaggttct ccagcaattc ttcataggag accatcg    47

<210> SEQ ID NO 20
<211> LENGTH: 237
<212> TYPE: PRT
<213> ORGANISM: Artificial Sequence
<220> FEATURE:
<223> OTHER INFORMATION: Bacillus subtilis Sfp PPTase with C-terminal
      TEV cleavage site and His6 tag

<400> SEQUENCE: 20

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

```
Val Leu Val Arg Ser Val Ile Ser Arg Gln Tyr Gln Leu Asp Lys Ser
    50              55              60

Asp Ile Arg Phe Ser Thr Gln Glu Tyr Gly Lys Pro Cys Ile Pro Asp
65              70              75              80

Leu Pro Asp Ala His Phe Asn Ile Ser His Ser Gly Arg Trp Val Ile
            85              90              95

Cys Ala Phe Asp Ser Gln Pro Ile Gly Ile Asp Ile Glu Lys Thr Lys
            100             105             110

Pro Ile Ser Leu Glu Ile Ala Lys Arg Phe Phe Ser Lys Thr Glu Tyr
        115             120             125

Ser Asp Leu Leu Ala Lys Asp Lys Asp Glu Gln Thr Asp Tyr Phe Tyr
    130             135             140

His Leu Trp Ser Met Lys Glu Ser Phe Ile Lys Gln Glu Gly Lys Gly
145             150             155             160

Leu Ser Leu Pro Leu Asp Ser Phe Ser Val Arg Leu His Gln Asp Gly
            165             170             175

Gln Val Ser Ile Glu Leu Pro Asp Ser His Ser Pro Cys Tyr Ile Lys
            180             185             190

Thr Tyr Glu Val Asp Pro Gly Tyr Lys Met Ala Val Cys Ala Ala His
            195             200             205

Pro Asp Phe Pro Glu Asp Ile Thr Met Val Ser Tyr Glu Glu Leu Leu
    210             215             220

Glu Asn Leu Tyr Phe Gln Gly His His His His His His
225             230             235
```